US012398430B2

(12) United States Patent
Kondou et al.

(10) Patent No.: US 12,398,430 B2
(45) Date of Patent: Aug. 26, 2025

(54) BREAST CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoshi Kondou, Kamakura (JP); Hitoshi Nobumasa, Kamakura (JP); Satoko Kozono, Kamakura (JP); Hiroko Sudo, Kamakura (JP); Junpei Kawauchi, Kamakura (JP); Takahiro Ochiya, Tokyo (JP); Nobuyoshi Kosaka, Tokyo (JP); Makiko Ono, Tokyo (JP); Kenji Tamura, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 63 days.

(21) Appl. No.: 18/514,603

(22) Filed: Nov. 20, 2023

(65) Prior Publication Data

US 2024/0093311 A1    Mar. 21, 2024

Related U.S. Application Data

(62) Division of application No. 17/944,779, filed on Sep. 14, 2022, now Pat. No. 11,859,255, which is a division of application No. 16/797,625, filed on Feb. 21, 2020, now Pat. No. 11,479,822, which is a division of application No. 15/318,328, filed as application No. PCT/JP2015/066986 on Jun. 12, 2015, now Pat. No. 10,597,726.

(30) Foreign Application Priority Data

Jun. 13, 2014   (JP) ................... 2014-122672
Mar. 30, 2015   (JP) ................... 2015-069321

(51) Int. Cl.
C12Q 1/68      (2018.01)
C12M 1/00      (2006.01)
C12P 19/34     (2006.01)
C12Q 1/6886    (2018.01)
C12N 15/09     (2006.01)

(52) U.S. Cl.
CPC ............ *C12Q 1/6886* (2013.01); *C12M 1/00* (2013.01); *C12Q 1/68* (2013.01); *C12N 15/09* (2013.01); *C12Q 2600/158* (2013.01); *C12Q 2600/16* (2013.01); *C12Q 2600/178* (2013.01)

(58) Field of Classification Search
CPC ............ C12Q 2600/158; C12Q 1/6886; C12Q 2600/178
See application file for complete search history.

(56) References Cited

U.S. PATENT DOCUMENTS

| | | |
|---|---|---|
| 8,603,744 B2 | 12/2013 | Croce et al. |
| 2001/0053519 A1 | 12/2001 | Fodor et al. |
| 2007/0299030 A1 | 12/2007 | Dmitrovsky et al. |
| 2008/0076674 A1 | 3/2008 | Litman et al. |
| 2011/0028332 A1 | 2/2011 | Kuroda et al. |
| 2012/0115139 A1 | 5/2012 | Kuroda et al. |
| 2013/0035251 A1 | 2/2013 | Keller et al. |

FOREIGN PATENT DOCUMENTS

| | | |
|---|---|---|
| CN | 101921760 A | 12/2010 |
| CN | 101988061 A | 3/2011 |
| CN | 101988064 A | 3/2011 |
| EP | 2 336 353 A1 | 6/2011 |
| EP | 2 354 246 A1 | 8/2011 |
| JP | 2008-500837 A | 1/2008 |
| JP | WO 2012-507300 A | 3/2012 |
| WO | WO 2005/118806 A2 | 12/2005 |
| WO | WO 2009/082744 A2 | 7/2009 |
| WO | WO 2009/119809 A1 | 10/2009 |
| WO | WO 2010/062706 A2 | 6/2010 |
| WO | WO 2010/100328 A1 | 9/2010 |
| WO | WO 2010/123043 A1 | 10/2010 |
| WO | WO 2012/048236 A1 | 4/2012 |
| WO | WO 2012/070037 A2 | 5/2012 |
| WO | WO 2013/057567 A1 | 4/2013 |
| WO | WO 2013/190091 A1 | 12/2013 |
| WO | WO 2014/048441 A1 | 4/2014 |
| WO | WO 2014/057279 A1 | 4/2014 |
| WO | WO 2014/081507 A1 | 5/2014 |

OTHER PUBLICATIONS

Wu, Qian, et al. "Next-Generation Sequencing of MicroRNAs for Breast Cancer Detection", BioMed Research International, 2011, 597145, pp. 1-7, 2011. (Year: 2011).*
Chinese Office Action and Search Report for Chinese Application No. 202110418361.8, dated Jun. 27, 2024.
American Cancer Society, "Breast Cancer", pp. 6-9, 13, 27-28, 41-46, 52-54, 63-64, and 106 (2013).
Berillo et al., "Binding of intronic miRNAs to the mRNAs of host genes encoding intronic miRNAs and proteins that participate in tumourigenesis," Computers in Biology and Medicine (2013), vol. 43, pp. 1374-1381.
Buffa et al. "microRNA-Associated Progression Pathways and Potential Therapeutic Targets identified by integrated mRNA and microRNA Expression Profiling in Breast Cancer," Cancer Res. Sep. 1, 2011; 71(17): 5635-45. (Year:2011).

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or a device for the detection of breast cancer and a method for detecting breast cancer. The present invention provides a kit or a device for the detection of breast cancer, comprising nucleic acid(s) capable of specifically binding to a miRNA in a sample of a subject, and a method for detecting breast cancer, comprising measuring the miRNA in vitro.

6 Claims, 4 Drawing Sheets

Specification includes a Sequence Listing.

(56) References Cited

OTHER PUBLICATIONS

Carson et al. "Breast Imaging in Coronal Planes with Simultaneous Pulse Echo and Transmission Ultrasound," Science 214.4525 (1981): 1141-1143. (Year: 1981).

Cheung, V. G. et al., "Natural variation in human gene expression assessed in lymphoblastoid cells," Nature Genetics (2003), vol. 33, pp. 422-425.

Cobb et al., "Sepsis gene expression profiling: Murine splendic compared with hepatic responses determined by using complementary DNA microarrays," Crit. Care Med. (2002), vol. 30, No. 12, pp. 2711-2721.

Communication Pursuant to Rule 164(1) EPC issued Jan. 2, 2018, in European Patent Application No. 15805922.0.

Cookson et al., "Circulating microRNA profiles reflect the presence of breast tumours but not the profiles of microRNAs within the tumours", Cellular Oncology, vol. 35, No. 4, 2012, pp. 301-308.

Cuk et al., "Circulating microRNAs in plasma as early detection markers for breast cancer.", Int. J. Cancer, vol. 132, No. 7, 2013, pp. 1602-1612.

Cuk et al., "Plasma microRNA panel for minimally invasive detection of breast cancer.", Plos One, vol. 8, No. 10, e76729, 2013, 10 pages.

Eto et al. "Prospect of microRNA toward laboratory medicine Gastrointestinal Cancer and microRNA," Clinical Chemistry, vol. 43, 2014, 99-105.

Fu et al., "miRNA Biomarkers in Breast Cancer Detection and Management," Journal of Cancer (2011), vol. 2, pp. 116-122.

Godfrey et al., "Serum microRNA expression as an early marker for breast cancer risk in prospectively collected samples from the Sister Study cohort," Breast Cancer Research, vol. 15, No. 3, 2013, 10 pages.

Guadagni et al., "A Re-Evaluation of Carcinoembryonic Antigen (CEA) as a Serum Marker for Breast Cancer: A Prospective Longitudinal Study," Clinical Cancer Research, vol. 7, 2001, p. 2357-2362.

Hoshikawa et al., "Hypoxia induces different genes in the lungs of rats compared with mice," Physiol. Genomics (2003), vol. 12, pp. 209-219.

Inazawa, "Gan ni Okeru Morateki miRNA Kaiseki to Shindan Chiryo eno Oyo," Journal of Clinical and Experimental Medicine, vol. 249, No. 10, 2014, pp. 1119-1124.

International Search Report for PCT/JP2015/066986 (PCT/ISA/210) mailed on Sep. 1, 2015.

Japanese Office Action for Japanese Application No. 2022-057348, dated Apr. 25, 2023.

Kojima et al., MicroRNA markers for the diagnosis of pancreatic and biliary-tract cancers, PLOS ONE (2015), vol. 10, No. 2, e0118220 (pp. 1-22).

Leidner et al., "Dampening Enthusiasm for Circulating MicroRNA in Breast Cancer," PloS One, vol. 8, No. 3, e57841, 2013, 11 pages.

MiScriptTM miRNA PCR Array (384-well, 384HC) Human miRBase Profiler HC Plate 4 from Qiagen, from https://b2b.quiagen.com/-/media/genetable/mi/hs/34/mihs-3404z (Year: 2012).

Mitchell et al., "Circulating microRNAs as stable blood-based markers for cancer detection.", Proc. Natl. Acad. Sci. USA, vol. 105, No. 30, 2008, pp. 10513-10518.

Ng et al., "Circulating microRNAs as specific biomarkers for breast cancer detection.", Plos One, vol. 8, No. 1, e53141, 2013, 10 pages.

Office Action issued Jun. 29, 2021, in Japanese Patent Application No. 2020-079623.

Office Action issued Sep. 24, 2021, in Republic of Korea Patent Application No. 10-2017-7000876.

Ono et al., E-2022 "Circulating microRNA markers for detection of breast cancer," Digital Abstract for The 73rd Annual Meeting of the Japanese Cancer Association, Published (online) Sep. 19, 2014.

Ono et al., E-2022 "Circulating microRNA markers for detection of breast cancer," English Oral Session for The 73rd Annual Meeting of the Japanese Cancer Association, Published (online) Sep. 26, 2014.

Perez-Sanchez et al., "Clinical utility of microRNAs in Exhaled Breath Condensate as Biomarkers for Lung Cancer," J. Pers. Med. (2021), vol. 11, 111, pp. 1-14.

Persson et al., "Identification of new microRNAs In paired normal and tumor breast tissue suggests a dual role for the ERBB2/Her2 gene," Cancer Res. (2011), vol. 71, No. 1, pp. 78-86.

Qiagen Product description "mi Script™ miRNA PCR Array (384-well, 384HC) Human miRBase Profiler HC Plate 5", document 1073798, Aug. 2012, from https://b2b.qiagen.com/-/media/genetable/mi/hs/34/mihs-3405z (Year: 2012).

Sato, "microRNA chip nl yoru Biomarker Kaihatsu," Molecular Targeted Therapy for Cancer (2015), vol. 12, No. 4, pp. 456-465.

Schrauder et al., "Circulating Micro-RNAs as Potential Blood-Based Markers for Early Stage Breast Cancer Detection," PloS One, vol. 7, No. 1, e29770, 2012, 9 pages.

Sobin et al., "TNM Classification of Malignant Tumours," 7th edition, 2010, pp. 171-181.

Song et al., "Bioinformatic Prediction of SNPs within miRNA Binding Sites of Inflammatory Genes Associated with Gastric Cancer," Asian Pac. J. Cancer Prev. (2014), vol. 15, pp. 937-943.

Tamaki et al., "The Challenge to Reduce Breast Cancer Mortality in Okinawa: Consensus of the first Okinawa Breast Oncology Meeting," Japanese Journal of Clinical Oncology, vol. 43, No. 2, 2013, pp. 208-213.

Wang et al., "Plasma miR-601 and miR-760 are novel biomarkers for the early detection of colorectal cancer.", Plos One, vol. 7, No. 9, e44398, 2012, 8 pages.

Written Opinion of the International Searching Authority for PCT/JP2015/066986 (PCT/ISA/237) mailed on Sep. 1, 2015.

U.S. Appl. No. 17/944,779, filed Sep. 14, 2022.

U.S. Appl. No. 16/797,625, filed Feb. 21, 2020.

U.S. Appl. No. 15/318,328, filed Dec. 12, 2016.

Extended European Search Report for European Application No. 24215251.0, dated Mar. 17, 2025.

Gao et al., "miR-615-5p is epigenetically inactivated and functions as a tumor suppressor in pancreatic ductal adenocarcinoma," Oncogene, vol. 34, No. 13, XP037748183, Apr. 28, 2014, pp. 1629-1640.

Tayebi et al., "miR-615-5p is restrictedly expressed in cirrhotic and cancerous liver tissues and its overexpression alleviates the tumorigenic effects in hepatocellular carcinoma," FEBS Letters, vol. 586, No. 19, XP071253316, Jul. 20, 2012, pp. 3309-3316.

* cited by examiner

```
                              SEQUENCE LISTING

Sequence total quantity: 871
SEQ ID NO: 1              moltype = RNA  length = 23
FEATURE                   Location/Qualifiers
source                    1..23
                          mol_type = unassigned RNA
                          organism = Homo sapiens
SEQUENCE: 1
ccccggtgtt ggggcgcgtc tgc                                            23

SEQ ID NO: 2              moltype = RNA  length = 23
FEATURE                   Location/Qualifiers
source                    1..23
                          mol_type = unassigned RNA
                          organism = Homo sapiens
SEQUENCE: 2
ctggcggagc ccattccatg cca                                            23

SEQ ID NO: 3              moltype = RNA  length = 22
FEATURE                   Location/Qualifiers
source                    1..22
                          mol_type = unassigned RNA
                          organism = Homo sapiens
SEQUENCE: 3
actcggcgtg gcgtcggtcg tg                                             22

SEQ ID NO: 4              moltype = RNA  length = 19
FEATURE                   Location/Qualifiers
source                    1..19
                          mol_type = unassigned RNA
                          organism = Homo sapiens
SEQUENCE: 4
cggcgcgacc ggcccgggg                                                 19

SEQ ID NO: 5              moltype = RNA  length = 22
FEATURE                   Location/Qualifiers
source                    1..22
                          mol_type = unassigned RNA
                          organism = Homo sapiens
SEQUENCE: 5
aggcggggcg ccgcgggacc gc                                             22

SEQ ID NO: 6              moltype = RNA  length = 17
FEATURE                   Location/Qualifiers
source                    1..17
                          mol_type = unassigned RNA
                          organism = Homo sapiens
SEQUENCE: 6
```

-continued

```
ccccggggag cccggcg                                                     17

SEQ ID NO: 7            moltype = RNA    length = 19
FEATURE                 Location/Qualifiers
source                  1..19
                        mol_type = unassigned RNA
                        organism = Homo sapiens
SEQUENCE: 7
cggggtcggc ggcgacgtg                                                   19

SEQ ID NO: 8            moltype = RNA    length = 17
FEATURE                 Location/Qualifiers
source                  1..17
                        mol_type = unassigned RNA
                        organism = Homo sapiens
SEQUENCE: 8
ggggcgcggc cggatcg                                                     17

SEQ ID NO: 9            moltype = RNA    length = 22
FEATURE                 Location/Qualifiers
source                  1..22
                        mol_type = unassigned RNA
                        organism = Homo sapiens
SEQUENCE: 9
tgggcgaggg cggctgagcg gc                                               22

SEQ ID NO: 10           moltype = RNA    length = 19
FEATURE                 Location/Qualifiers
source                  1..19
                        mol_type = unassigned RNA
                        organism = Homo sapiens
SEQUENCE: 10
ggggagcgag gggcggggc                                                   19

SEQ ID NO: 11           moltype = RNA    length = 23
FEATURE                 Location/Qualifiers
source                  1..23
                        mol_type = unassigned RNA
                        organism = Homo sapiens
SEQUENCE: 11
tgtagagcag ggagcaggaa gct                                              23

SEQ ID NO: 12           moltype = RNA    length = 24
FEATURE                 Location/Qualifiers
source                  1..24
                        mol_type = unassigned RNA
                        organism = Homo sapiens
SEQUENCE: 12
tgagggcct cagaccgagc tttt                                              24

SEQ ID NO: 13           moltype = RNA    length = 23
FEATURE                 Location/Qualifiers
source                  1..23
                        mol_type = unassigned RNA
                        organism = Homo sapiens
SEQUENCE: 13
ctcggggcag gcggctggga gcg                                              23

SEQ ID NO: 14           moltype = RNA    length = 20
FEATURE                 Location/Qualifiers
source                  1..20
                        mol_type = unassigned RNA
                        organism = Homo sapiens
SEQUENCE: 14
agagatgaag cggggggcg                                                   20

SEQ ID NO: 15           moltype = RNA    length = 21
FEATURE                 Location/Qualifiers
source                  1..21
                        mol_type = unassigned RNA
                        organism = Homo sapiens
SEQUENCE: 15
ctgggctcgg gacgcgcggc t                                                21

SEQ ID NO: 16           moltype = RNA    length = 22
FEATURE                 Location/Qualifiers
source                  1..22
                        mol_type = unassigned RNA
                        organism = Homo sapiens
```

-continued

```
SEQUENCE: 16
acctggcagc agggagcgtc gt                                              22

SEQ ID NO: 17           moltype = RNA  length = 22
FEATURE                 Location/Qualifiers
source                  1..22
                        mol_type = unassigned RNA
                        organism = Homo sapiens
SEQUENCE: 17
gcggggtgg cggcggcatc cc                                               22

SEQ ID NO: 18           moltype = RNA  length = 22
FEATURE                 Location/Qualifiers
source                  1..22
                        mol_type = unassigned RNA
                        organism = Homo sapiens
SEQUENCE: 18
ctcggcgcgg ggcgcgggct cc                                              22

SEQ ID NO: 19           moltype = RNA  length = 22
FEATURE                 Location/Qualifiers
source                  1..22
                        mol_type = unassigned RNA
                        organism = Homo sapiens
SEQUENCE: 19
acaggtgagg ttcttgggag cc                                              22

SEQ ID NO: 20           moltype = RNA  length = 22
FEATURE                 Location/Qualifiers
source                  1..22
                        mol_type = unassigned RNA
                        organism = Homo sapiens
SEQUENCE: 20
agtgggaggc cagggcacgg ca                                              22

SEQ ID NO: 21           moltype = RNA  length = 22
FEATURE                 Location/Qualifiers
source                  1..22
                        mol_type = unassigned RNA
                        organism = Homo sapiens
SEQUENCE: 21
aggcagcggg gtgtagtgga ta                                              22

SEQ ID NO: 22           moltype = RNA  length = 20
FEATURE                 Location/Qualifiers
source                  1..20
                        mol_type = unassigned RNA
                        organism = Homo sapiens
SEQUENCE: 22
ctaggtgggg ggcttgaagc                                                 20

SEQ ID NO: 23           moltype = RNA  length = 23
FEATURE                 Location/Qualifiers
source                  1..23
                        mol_type = unassigned RNA
                        organism = Homo sapiens
SEQUENCE: 23
gggggggcag gaggggctca ggg                                             23

SEQ ID NO: 24           moltype = RNA  length = 22
FEATURE                 Location/Qualifiers
source                  1..22
                        mol_type = unassigned RNA
                        organism = Homo sapiens
SEQUENCE: 24
tggcgggggt agagctggct gc                                              22

SEQ ID NO: 25           moltype = RNA  length = 23
FEATURE                 Location/Qualifiers
source                  1..23
                        mol_type = unassigned RNA
                        organism = Homo sapiens
SEQUENCE: 25
ggatggttgg gggcggtcgg cgt                                             23

SEQ ID NO: 26           moltype = RNA  length = 21
FEATURE                 Location/Qualifiers
source                  1..21
                        mol_type = unassigned RNA
```

```
                         organism = Homo sapiens
SEQUENCE: 26
tgagggaccc aggacaggag a                                              21

SEQ ID NO: 27           moltype = RNA   length = 19
FEATURE                 Location/Qualifiers
source                  1..19
                        mol_type = unassigned RNA
                        organism = Homo sapiens
SEQUENCE: 27
aatggatttt tggagcagg                                                 19

SEQ ID NO: 28           moltype = RNA   length = 22
FEATURE                 Location/Qualifiers
source                  1..22
                        mol_type = unassigned RNA
                        organism = Homo sapiens
SEQUENCE: 28
gctgcgggct gcggtcaggg cg                                             22

SEQ ID NO: 29           moltype = RNA   length = 22
FEATURE                 Location/Qualifiers
source                  1..22
                        mol_type = unassigned RNA
                        organism = Homo sapiens
SEQUENCE: 29
tagggatggg aggccaggat ga                                             22

SEQ ID NO: 30           moltype = RNA   length = 23
FEATURE                 Location/Qualifiers
source                  1..23
                        mol_type = unassigned RNA
                        organism = Homo sapiens
SEQUENCE: 30
agggtggggc tggaggtggg gct                                            23

SEQ ID NO: 31           moltype = RNA   length = 18
FEATURE                 Location/Qualifiers
source                  1..18
                        mol_type = unassigned RNA
                        organism = Homo sapiens
SEQUENCE: 31
agcaggtgcg gggcggcg                                                  18

SEQ ID NO: 32           moltype = RNA   length = 21
FEATURE                 Location/Qualifiers
source                  1..21
                        mol_type = unassigned RNA
                        organism = Homo sapiens
SEQUENCE: 32
atgcctcccc cggccccgca g                                              21

SEQ ID NO: 33           moltype = RNA   length = 23
FEATURE                 Location/Qualifiers
source                  1..23
                        mol_type = unassigned RNA
                        organism = Homo sapiens
SEQUENCE: 33
gtgcgtggtg gctcgaggcg ggg                                            23

SEQ ID NO: 34           moltype = RNA   length = 22
FEATURE                 Location/Qualifiers
source                  1..22
                        mol_type = unassigned RNA
                        organism = Homo sapiens
SEQUENCE: 34
taggggggcgg cttgtggagt gt                                            22

SEQ ID NO: 35           moltype = RNA   length = 23
FEATURE                 Location/Qualifiers
source                  1..23
                        mol_type = unassigned RNA
                        organism = Homo sapiens
SEQUENCE: 35
tgggagggga gaggcagcaa gca                                            23

SEQ ID NO: 36           moltype = RNA   length = 21
FEATURE                 Location/Qualifiers
source                  1..21
```

```
                       mol_type = unassigned RNA
                       organism = Homo sapiens
SEQUENCE: 36
cgggagctgg ggtctgcagg t                                              21

SEQ ID NO: 37          moltype = RNA  length = 23
FEATURE                Location/Qualifiers
source                 1..23
                       mol_type = unassigned RNA
                       organism = Homo sapiens
SEQUENCE: 37
cgggtagaga gggcagtggg agg                                            23

SEQ ID NO: 38          moltype = RNA  length = 21
FEATURE                Location/Qualifiers
source                 1..21
                       mol_type = unassigned RNA
                       organism = Homo sapiens
SEQUENCE: 38
agggagggac gggggctgtg c                                              21

SEQ ID NO: 39          moltype = RNA  length = 22
FEATURE                Location/Qualifiers
source                 1..22
                       mol_type = unassigned RNA
                       organism = Homo sapiens
SEQUENCE: 39
gtgcggaacg ctggccgggg cg                                             22

SEQ ID NO: 40          moltype = RNA  length = 22
FEATURE                Location/Qualifiers
source                 1..22
                       mol_type = unassigned RNA
                       organism = Homo sapiens
SEQUENCE: 40
caggaaggat ttagggacag gc                                             22

SEQ ID NO: 41          moltype = RNA  length = 22
FEATURE                Location/Qualifiers
source                 1..22
                       mol_type = unassigned RNA
                       organism = Homo sapiens
SEQUENCE: 41
gtgaggaggg gctggcaggg ac                                             22

SEQ ID NO: 42          moltype = RNA  length = 19
FEATURE                Location/Qualifiers
source                 1..19
                       mol_type = unassigned RNA
                       organism = Homo sapiens
SEQUENCE: 42
aggcacggtg tcagcaggc                                                 19

SEQ ID NO: 43          moltype = RNA  length = 24
FEATURE                Location/Qualifiers
source                 1..24
                       mol_type = unassigned RNA
                       organism = Homo sapiens
SEQUENCE: 43
aggcaggggc tggtgctggg cggg                                           24

SEQ ID NO: 44          moltype = RNA  length = 19
FEATURE                Location/Qualifiers
source                 1..19
                       mol_type = unassigned RNA
                       organism = Homo sapiens
SEQUENCE: 44
gagccagttg gacaggagc                                                 19

SEQ ID NO: 45          moltype = RNA  length = 22
FEATURE                Location/Qualifiers
source                 1..22
                       mol_type = unassigned RNA
                       organism = Homo sapiens
SEQUENCE: 45
ctcgggaggg catgggccag gc                                             22

SEQ ID NO: 46          moltype = RNA  length = 20
FEATURE                Location/Qualifiers
```

```
source                  1..20
                        mol_type = unassigned RNA
                        organism = Homo sapiens
SEQUENCE: 46
gtgtctgggc ggacagctgc                                                  20

SEQ ID NO: 47           moltype = RNA   length = 21
FEATURE                 Location/Qualifiers
source                  1..21
                        mol_type = unassigned RNA
                        organism = Homo sapiens
SEQUENCE: 47
ccggccgccg gctccgcccc g                                                21

SEQ ID NO: 48           moltype = RNA   length = 22
FEATURE                 Location/Qualifiers
source                  1..22
                        mol_type = unassigned RNA
                        organism = Homo sapiens
SEQUENCE: 48
ctggtacagg cctgggggac ag                                               22

SEQ ID NO: 49           moltype = RNA   length = 23
FEATURE                 Location/Qualifiers
source                  1..23
                        mol_type = unassigned RNA
                        organism = Homo sapiens
SEQUENCE: 49
acaggcggct gtagcaatgg ggg                                              23

SEQ ID NO: 50           moltype = RNA   length = 22
FEATURE                 Location/Qualifiers
source                  1..22
                        mol_type = unassigned RNA
                        organism = Homo sapiens
SEQUENCE: 50
gtgaacgggc gccatcccga gg                                               22

SEQ ID NO: 51           moltype = RNA   length = 20
FEATURE                 Location/Qualifiers
source                  1..20
                        mol_type = unassigned RNA
                        organism = Homo sapiens
SEQUENCE: 51
gtgggttggg gcgggctctg                                                  20

SEQ ID NO: 52           moltype = RNA   length = 23
FEATURE                 Location/Qualifiers
source                  1..23
                        mol_type = unassigned RNA
                        organism = Homo sapiens
SEQUENCE: 52
cgggctgtcc ggaggggtcg gct                                              23

SEQ ID NO: 53           moltype = RNA   length = 22
FEATURE                 Location/Qualifiers
source                  1..22
                        mol_type = unassigned RNA
                        organism = Homo sapiens
SEQUENCE: 53
caggcaggga ggtgggacca tg                                               22

SEQ ID NO: 54           moltype = RNA   length = 22
FEATURE                 Location/Qualifiers
source                  1..22
                        mol_type = unassigned RNA
                        organism = Homo sapiens
SEQUENCE: 54
gtgagtagtg gcgcgcggcg gc                                               22

SEQ ID NO: 55           moltype = RNA   length = 23
FEATURE                 Location/Qualifiers
source                  1..23
                        mol_type = unassigned RNA
                        organism = Homo sapiens
SEQUENCE: 55
ccggggcaga ttggtgtagg gtg                                              23

SEQ ID NO: 56           moltype = RNA   length = 22
```

```
FEATURE                 Location/Qualifiers
source                  1..22
                        mol_type = unassigned RNA
                        organism = Homo sapiens
SEQUENCE: 56
gggggtcccc ggtgctcgga tc                                                  22

SEQ ID NO: 57           moltype = RNA   length = 20
FEATURE                 Location/Qualifiers
source                  1..20
                        mol_type = unassigned RNA
                        organism = Homo sapiens
SEQUENCE: 57
ggcggcgggg aggtaggcag                                                     20

SEQ ID NO: 58           moltype = RNA   length = 23
FEATURE                 Location/Qualifiers
source                  1..23
                        mol_type = unassigned RNA
                        organism = Homo sapiens
SEQUENCE: 58
cggggccgta gcactgtctg aga                                                 23

SEQ ID NO: 59           moltype = RNA   length = 23
FEATURE                 Location/Qualifiers
source                  1..23
                        mol_type = unassigned RNA
                        organism = Homo sapiens
SEQUENCE: 59
gtgagtggga gccccagtgt gtg                                                 23

SEQ ID NO: 60           moltype = RNA   length = 23
FEATURE                 Location/Qualifiers
source                  1..23
                        mol_type = unassigned RNA
                        organism = Homo sapiens
SEQUENCE: 60
agggactttt gggggcagat gtg                                                 23

SEQ ID NO: 61           moltype = RNA   length = 21
FEATURE                 Location/Qualifiers
source                  1..21
                        mol_type = unassigned RNA
                        organism = Homo sapiens
SEQUENCE: 61
gctgggaagg caaagggacg t                                                   21

SEQ ID NO: 62           moltype = RNA   length = 17
FEATURE                 Location/Qualifiers
source                  1..17
                        mol_type = unassigned RNA
                        organism = Homo sapiens
SEQUENCE: 62
ggggctgggc gcgcgcc                                                        17

SEQ ID NO: 63           moltype = RNA   length = 22
FEATURE                 Location/Qualifiers
source                  1..22
                        mol_type = unassigned RNA
                        organism = Homo sapiens
SEQUENCE: 63
tgggagggcg tggatgatgg tg                                                  22

SEQ ID NO: 64           moltype = RNA   length = 23
FEATURE                 Location/Qualifiers
source                  1..23
                        mol_type = unassigned RNA
                        organism = Homo sapiens
SEQUENCE: 64
caggcagaag tggggctgac agg                                                 23

SEQ ID NO: 65           moltype = RNA   length = 21
FEATURE                 Location/Qualifiers
source                  1..21
                        mol_type = unassigned RNA
                        organism = Homo sapiens
SEQUENCE: 65
gggggggatgt gcatgctggt t                                                  21
```

```
SEQ ID NO: 66          moltype = RNA   length = 22
FEATURE                Location/Qualifiers
source                 1..22
                       mol_type = unassigned RNA
                       organism = Homo sapiens
SEQUENCE: 66
accttgcctt gctgcccggg cc                                          22

SEQ ID NO: 67          moltype = RNA   length = 19
FEATURE                Location/Qualifiers
source                 1..19
                       mol_type = unassigned RNA
                       organism = Homo sapiens
SEQUENCE: 67
tggggcggag cttccggag                                              19

SEQ ID NO: 68          moltype = RNA   length = 22
FEATURE                Location/Qualifiers
source                 1..22
                       mol_type = unassigned RNA
                       organism = Homo sapiens
SEQUENCE: 68
cagggcaggg aaggtgggag ag                                          22

SEQ ID NO: 69          moltype = RNA   length = 20
FEATURE                Location/Qualifiers
source                 1..20
                       mol_type = unassigned RNA
                       organism = Homo sapiens
SEQUENCE: 69
cctgagcccg ggccgcgcag                                             20

SEQ ID NO: 70          moltype = RNA   length = 22
FEATURE                Location/Qualifiers
source                 1..22
                       mol_type = unassigned RNA
                       organism = Homo sapiens
SEQUENCE: 70
ccgggagaag gaggtggcct gg                                          22

SEQ ID NO: 71          moltype = RNA   length = 22
FEATURE                Location/Qualifiers
source                 1..22
                       mol_type = unassigned RNA
                       organism = Homo sapiens
SEQUENCE: 71
gggacccagg gagagacgta ag                                          22

SEQ ID NO: 72          moltype = RNA   length = 22
FEATURE                Location/Qualifiers
source                 1..22
                       mol_type = unassigned RNA
                       organism = Homo sapiens
SEQUENCE: 72
ggtggcccgg ccgtgcctga gg                                          22

SEQ ID NO: 73          moltype = RNA   length = 22
FEATURE                Location/Qualifiers
source                 1..22
                       mol_type = unassigned RNA
                       organism = Homo sapiens
SEQUENCE: 73
agcccgcccc agccgaggtt ct                                          22

SEQ ID NO: 74          moltype = RNA   length = 21
FEATURE                Location/Qualifiers
source                 1..21
                       mol_type = unassigned RNA
                       organism = Homo sapiens
SEQUENCE: 74
caggcaggtg tagggtggag c                                           21

SEQ ID NO: 75          moltype = RNA   length = 22
FEATURE                Location/Qualifiers
source                 1..22
                       mol_type = unassigned RNA
                       organism = Homo sapiens
SEQUENCE: 75
ggggctgtga ttgaccagca gg                                          22
```

```
SEQ ID NO: 76            moltype = RNA   length = 21
FEATURE                  Location/Qualifiers
source                   1..21
                         mol_type = unassigned RNA
                         organism = Homo sapiens
SEQUENCE: 76
actcggctgc ggtggacaag t                                          21

SEQ ID NO: 77            moltype = RNA   length = 20
FEATURE                  Location/Qualifiers
source                   1..20
                         mol_type = unassigned RNA
                         organism = Homo sapiens
SEQUENCE: 77
cggggtgggt gaggtcgggc                                            20

SEQ ID NO: 78            moltype = RNA   length = 18
FEATURE                  Location/Qualifiers
source                   1..18
                         mol_type = unassigned RNA
                         organism = Homo sapiens
SEQUENCE: 78
tgaggcgggg gggcgagc                                              18

SEQ ID NO: 79            moltype = RNA   length = 23
FEATURE                  Location/Qualifiers
source                   1..23
                         mol_type = unassigned RNA
                         organism = Homo sapiens
SEQUENCE: 79
ctgggggacg cgtgagcgcg agc                                        23

SEQ ID NO: 80            moltype = RNA   length = 23
FEATURE                  Location/Qualifiers
source                   1..23
                         mol_type = unassigned RNA
                         organism = Homo sapiens
SEQUENCE: 80
gtgagtggga gccggtgggg ctg                                        23

SEQ ID NO: 81            moltype = RNA   length = 23
FEATURE                  Location/Qualifiers
source                   1..23
                         mol_type = unassigned RNA
                         organism = Homo sapiens
SEQUENCE: 81
tgggggaca gatggagagg aca                                         23

SEQ ID NO: 82            moltype = RNA   length = 22
FEATURE                  Location/Qualifiers
source                   1..22
                         mol_type = unassigned RNA
                         organism = Homo sapiens
SEQUENCE: 82
gtgggctggg ctgggctggg cc                                         22

SEQ ID NO: 83            moltype = RNA   length = 22
FEATURE                  Location/Qualifiers
source                   1..22
                         mol_type = unassigned RNA
                         organism = Homo sapiens
SEQUENCE: 83
cgcaggggcc gggtgctcac cg                                         22

SEQ ID NO: 84            moltype = RNA   length = 19
FEATURE                  Location/Qualifiers
source                   1..19
                         mol_type = unassigned RNA
                         organism = Homo sapiens
SEQUENCE: 84
ttgatctcgg aagctaagc                                             19

SEQ ID NO: 85            moltype = RNA   length = 23
FEATURE                  Location/Qualifiers
source                   1..23
                         mol_type = unassigned RNA
                         organism = Homo sapiens
SEQUENCE: 85
```

```
ctgggcccgc ggcgggcgtg ggg                                          23

SEQ ID NO: 87           moltype = RNA   length = 22
FEATURE                 Location/Qualifiers
source                  1..22
                        mol_type = unassigned RNA
                        organism = Homo sapiens
SEQUENCE: 86
ctcctggggc ccgcactctc gc                                           22

SEQ ID NO: 87           moltype = RNA   length = 23
FEATURE                 Location/Qualifiers
source                  1..23
                        mol_type = unassigned RNA
                        organism = Homo sapiens
SEQUENCE: 87
tggggaaggc ttggcaggga aga                                          23

SEQ ID NO: 88           moltype = RNA   length = 20
FEATURE                 Location/Qualifiers
source                  1..20
                        mol_type = unassigned RNA
                        organism = Homo sapiens
SEQUENCE: 88
aaaaggcggg agaagcccca                                              20

SEQ ID NO: 89           moltype = RNA   length = 22
FEATURE                 Location/Qualifiers
source                  1..22
                        mol_type = unassigned RNA
                        organism = Homo sapiens
SEQUENCE: 89
gagcaggcga ggctgggctg aa                                           22

SEQ ID NO: 90           moltype = RNA   length = 20
FEATURE                 Location/Qualifiers
source                  1..20
                        mol_type = unassigned RNA
                        organism = Homo sapiens
SEQUENCE: 90
aaaagctggg ctgagaggcg                                              20

SEQ ID NO: 91           moltype = RNA   length = 17
FEATURE                 Location/Qualifiers
source                  1..17
                        mol_type = unassigned RNA
                        organism = Homo sapiens
SEQUENCE: 91
gtggggccag gcggtgg                                                 17

SEQ ID NO: 92           moltype = RNA   length = 22
FEATURE                 Location/Qualifiers
source                  1..22
                        mol_type = unassigned RNA
                        organism = Homo sapiens
SEQUENCE: 92
tggggaaggc gtcagtgtcg gg                                           22

SEQ ID NO: 93           moltype = RNA   length = 22
FEATURE                 Location/Qualifiers
source                  1..22
                        mol_type = unassigned RNA
                        organism = Homo sapiens
SEQUENCE: 93
actgggtagg tggggctcca gg                                           22

SEQ ID NO: 94           moltype = RNA   length = 25
FEATURE                 Location/Qualifiers
source                  1..25
                        mol_type = unassigned RNA
                        organism = Homo sapiens
SEQUENCE: 94
atggggtgag atgggaggga gcagc                                        25

SEQ ID NO: 95           moltype = RNA   length = 23
FEATURE                 Location/Qualifiers
source                  1..23
                        mol_type = unassigned RNA
                        organism = Homo sapiens
```

-continued

```
SEQUENCE: 95
ggaggcgcag gctcggaaag gcg                                               23

SEQ ID NO: 96           moltype = RNA   length = 22
FEATURE                 Location/Qualifiers
source                  1..22
                        mol_type = unassigned RNA
                        organism = Homo sapiens
SEQUENCE: 96
ggggaactgt agatgaaaag gc                                                22

SEQ ID NO: 97           moltype = RNA   length = 23
FEATURE                 Location/Qualifiers
source                  1..23
                        mol_type = unassigned RNA
                        organism = Homo sapiens
SEQUENCE: 97
agaagaaggc ggtcggtctg cgg                                               23

SEQ ID NO: 98           moltype = RNA   length = 25
FEATURE                 Location/Qualifiers
source                  1..25
                        mol_type = unassigned RNA
                        organism = Homo sapiens
SEQUENCE: 98
agcggggagg aagtgggcgc tgctt                                             25

SEQ ID NO: 99           moltype = RNA   length = 17
FEATURE                 Location/Qualifiers
source                  1..17
                        mol_type = unassigned RNA
                        organism = Homo sapiens
SEQUENCE: 99
ctccgggacg gctgggc                                                      17

SEQ ID NO: 100          moltype = RNA   length = 23
FEATURE                 Location/Qualifiers
source                  1..23
                        mol_type = unassigned RNA
                        organism = Homo sapiens
SEQUENCE: 100
tcgaggactg gtggaagggc ctt                                               23

SEQ ID NO: 101          moltype = RNA   length = 24
FEATURE                 Location/Qualifiers
source                  1..24
                        mol_type = unassigned RNA
                        organism = Homo sapiens
SEQUENCE: 101
tgtaggcatg aggcagggcc cagg                                              24

SEQ ID NO: 102          moltype = RNA   length = 22
FEATURE                 Location/Qualifiers
source                  1..22
                        mol_type = unassigned RNA
                        organism = Homo sapiens
SEQUENCE: 102
ggctacaaca caggacccgg gc                                                22

SEQ ID NO: 103          moltype = RNA   length = 22
FEATURE                 Location/Qualifiers
source                  1..22
                        mol_type = unassigned RNA
                        organism = Homo sapiens
SEQUENCE: 103
tggggcggag cttccggagg cc                                                22

SEQ ID NO: 104          moltype = RNA   length = 23
FEATURE                 Location/Qualifiers
source                  1..23
                        mol_type = unassigned RNA
                        organism = Homo sapiens
SEQUENCE: 104
tggggctgg gatgggccat ggt                                                23

SEQ ID NO: 105          moltype = RNA   length = 19
FEATURE                 Location/Qualifiers
source                  1..19
                        mol_type = unassigned RNA
```

```
                              organism = Homo sapiens
SEQUENCE: 105
tgcggcagag ctggggtca                                                  19

SEQ ID NO: 106          moltype = RNA  length = 21
FEATURE                 Location/Qualifiers
source                  1..21
                        mol_type = unassigned RNA
                        organism = Homo sapiens
SEQUENCE: 106
gtaggtgaca gtcagggcg g                                                21

SEQ ID NO: 107          moltype = RNA  length = 22
FEATURE                 Location/Qualifiers
source                  1..22
                        mol_type = unassigned RNA
                        organism = Homo sapiens
SEQUENCE: 107
aggcgatgtg gggatgtaga ga                                              22

SEQ ID NO: 108          moltype = RNA  length = 24
FEATURE                 Location/Qualifiers
source                  1..24
                        mol_type = unassigned RNA
                        organism = Homo sapiens
SEQUENCE: 108
tgggggaca ggatgagagg ctgt                                             24

SEQ ID NO: 109          moltype = RNA  length = 23
FEATURE                 Location/Qualifiers
source                  1..23
                        mol_type = unassigned RNA
                        organism = Homo sapiens
SEQUENCE: 109
gagggcagcg tgggtgtggc gga                                             23

SEQ ID NO: 110          moltype = RNA  length = 20
FEATURE                 Location/Qualifiers
source                  1..20
                        mol_type = unassigned RNA
                        organism = Homo sapiens
SEQUENCE: 110
accaggaggc tgaggcccct                                                 20

SEQ ID NO: 111          moltype = RNA  length = 22
FEATURE                 Location/Qualifiers
source                  1..22
                        mol_type = unassigned RNA
                        organism = Homo sapiens
SEQUENCE: 111
agtgggagga caggaggcag gt                                              22

SEQ ID NO: 112          moltype = RNA  length = 23
FEATURE                 Location/Qualifiers
source                  1..23
                        mol_type = unassigned RNA
                        organism = Homo sapiens
SEQUENCE: 112
tgagcaccac acaggccggg cgc                                             23

SEQ ID NO: 113          moltype = RNA  length = 22
FEATURE                 Location/Qualifiers
source                  1..22
                        mol_type = unassigned RNA
                        organism = Homo sapiens
SEQUENCE: 113
ttgaggagac atggtggggg cc                                              22

SEQ ID NO: 114          moltype = RNA  length = 21
FEATURE                 Location/Qualifiers
source                  1..21
                        mol_type = unassigned RNA
                        organism = Homo sapiens
SEQUENCE: 114
gcagggacag caaagggtg c                                                21

SEQ ID NO: 115          moltype = RNA  length = 24
FEATURE                 Location/Qualifiers
source                  1..24
```

```
                       mol_type = unassigned RNA
                       organism = Homo sapiens
SEQUENCE: 115
ctgcaggcag aagtgggct gaca                                          24

SEQ ID NO: 116         moltype = RNA   length = 22
FEATURE                Location/Qualifiers
source                 1..22
                       mol_type = unassigned RNA
                       organism = Homo sapiens
SEQUENCE: 116
ctcgggcgga ggtggttgag tg                                           22

SEQ ID NO: 117         moltype = RNA   length = 18
FEATURE                Location/Qualifiers
source                 1..18
                       mol_type = unassigned RNA
                       organism = Homo sapiens
SEQUENCE: 117
gtgaaggccc ggcggaga                                                18

SEQ ID NO: 118         moltype = RNA   length = 23
FEATURE                Location/Qualifiers
source                 1..23
                       mol_type = unassigned RNA
                       organism = Homo sapiens
SEQUENCE: 118
gaacgcctgt tcttgccagg tgg                                          23

SEQ ID NO: 119         moltype = RNA   length = 21
FEATURE                Location/Qualifiers
source                 1..21
                       mol_type = unassigned RNA
                       organism = Homo sapiens
SEQUENCE: 119
tgggggtgtg gggagagaga g                                            21

SEQ ID NO: 120         moltype = RNA   length = 22
FEATURE                Location/Qualifiers
source                 1..22
                       mol_type = unassigned RNA
                       organism = Homo sapiens
SEQUENCE: 120
tgcggggcta gggctaacag ca                                           22

SEQ ID NO: 121         moltype = RNA   length = 21
FEATURE                Location/Qualifiers
source                 1..21
                       mol_type = unassigned RNA
                       organism = Homo sapiens
SEQUENCE: 121
aggtgggtat ggaggagccc t                                            21

SEQ ID NO: 122         moltype = RNA   length = 18
FEATURE                Location/Qualifiers
source                 1..18
                       mol_type = unassigned RNA
                       organism = Homo sapiens
SEQUENCE: 122
cggtgagcgc tcgctggc                                                18

SEQ ID NO: 123         moltype = RNA   length = 20
FEATURE                Location/Qualifiers
source                 1..20
                       mol_type = unassigned RNA
                       organism = Homo sapiens
SEQUENCE: 123
gggctggggc gcggggaggt                                              20

SEQ ID NO: 124         moltype = RNA   length = 23
FEATURE                Location/Qualifiers
source                 1..23
                       mol_type = unassigned RNA
                       organism = Homo sapiens
SEQUENCE: 124
ccaggggat gggcgagctt ggg                                           23

SEQ ID NO: 125         moltype = RNA   length = 21
FEATURE                Location/Qualifiers
```

```
source                  1..21
                        mol_type = unassigned RNA
                        organism = Homo sapiens
SEQUENCE: 125
cgggccggag gtcaagggcg t                                                  21

SEQ ID NO: 126          moltype = RNA   length = 18
FEATURE                 Location/Qualifiers
source                  1..18
                        mol_type = unassigned RNA
                        organism = Homo sapiens
SEQUENCE: 126
gaggctgaag gaagatgg                                                      18

SEQ ID NO: 127          moltype = RNA   length = 22
FEATURE                 Location/Qualifiers
source                  1..22
                        mol_type = unassigned RNA
                        organism = Homo sapiens
SEQUENCE: 127
cagggctggc agtgacatgg gt                                                 22

SEQ ID NO: 128          moltype = RNA   length = 22
FEATURE                 Location/Qualifiers
source                  1..22
                        mol_type = unassigned RNA
                        organism = Homo sapiens
SEQUENCE: 128
cagttgggtc tagggtcag ga                                                  22

SEQ ID NO: 129          moltype = RNA   length = 21
FEATURE                 Location/Qualifiers
source                  1..21
                        mol_type = unassigned RNA
                        organism = Homo sapiens
SEQUENCE: 129
gttggggtgc aggggtctgc t                                                  21

SEQ ID NO: 130          moltype = RNA   length = 21
FEATURE                 Location/Qualifiers
source                  1..21
                        mol_type = unassigned RNA
                        organism = Homo sapiens
SEQUENCE: 130
acggcccagg cggcattggt g                                                  21

SEQ ID NO: 131          moltype = RNA   length = 22
FEATURE                 Location/Qualifiers
source                  1..22
                        mol_type = unassigned RNA
                        organism = Homo sapiens
SEQUENCE: 131
gagggttggg tggaggctct cc                                                 22

SEQ ID NO: 132          moltype = RNA   length = 19
FEATURE                 Location/Qualifiers
source                  1..19
                        mol_type = unassigned RNA
                        organism = Homo sapiens
SEQUENCE: 132
taaggagggg gatgagggg                                                     19

SEQ ID NO: 133          moltype = RNA   length = 23
FEATURE                 Location/Qualifiers
source                  1..23
                        mol_type = unassigned RNA
                        organism = Homo sapiens
SEQUENCE: 133
tgagtggggc tcccgggacg gcg                                                23

SEQ ID NO: 134          moltype = RNA   length = 25
FEATURE                 Location/Qualifiers
source                  1..25
                        mol_type = unassigned RNA
                        organism = Homo sapiens
SEQUENCE: 134
tcggggcatg ggggagggag gctgg                                              25

SEQ ID NO: 135          moltype = RNA   length = 19
```

```
FEATURE                 Location/Qualifiers
source                  1..19
                        mol_type = unassigned RNA
                        organism = Homo sapiens
SEQUENCE: 135
tgggggagat gggggttga                                                          19

SEQ ID NO: 136          moltype = RNA   length = 20
FEATURE                 Location/Qualifiers
source                  1..20
                        mol_type = unassigned RNA
                        organism = Homo sapiens
SEQUENCE: 136
ggggagctgt ggaagcagta                                                         20

SEQ ID NO: 137          moltype = RNA   length = 18
FEATURE                 Location/Qualifiers
source                  1..18
                        mol_type = unassigned RNA
                        organism = Homo sapiens
SEQUENCE: 137
cccagcagga cgggagcg                                                           18

SEQ ID NO: 138          moltype = RNA   length = 22
FEATURE                 Location/Qualifiers
source                  1..22
                        mol_type = unassigned RNA
                        organism = Homo sapiens
SEQUENCE: 138
ttggggtgga gggccaagga gc                                                      22

SEQ ID NO: 139          moltype = RNA   length = 22
FEATURE                 Location/Qualifiers
source                  1..22
                        mol_type = unassigned RNA
                        organism = Homo sapiens
SEQUENCE: 139
tggggaggtg tggagtcagc at                                                      22

SEQ ID NO: 140          moltype = RNA   length = 21
FEATURE                 Location/Qualifiers
source                  1..21
                        mol_type = unassigned RNA
                        organism = Homo sapiens
SEQUENCE: 140
cgtggaggac gaggaggagg c                                                       21

SEQ ID NO: 141          moltype = RNA   length = 19
FEATURE                 Location/Qualifiers
source                  1..19
                        mol_type = unassigned RNA
                        organism = Homo sapiens
SEQUENCE: 141
ggctggtcag atgggagtg                                                          19

SEQ ID NO: 142          moltype = RNA   length = 21
FEATURE                 Location/Qualifiers
source                  1..21
                        mol_type = unassigned RNA
                        organism = Homo sapiens
SEQUENCE: 142
acaggagtgg gggtgggaca t                                                       21

SEQ ID NO: 143          moltype = RNA   length = 21
FEATURE                 Location/Qualifiers
source                  1..21
                        mol_type = unassigned RNA
                        organism = Homo sapiens
SEQUENCE: 143
gtgggcgggg gcaggtgtgt g                                                       21

SEQ ID NO: 144          moltype = RNA   length = 22
FEATURE                 Location/Qualifiers
source                  1..22
                        mol_type = unassigned RNA
                        organism = Homo sapiens
SEQUENCE: 144
aaggggcagg gacgggtggc cc                                                      22
```

```
SEQ ID NO: 145          moltype = RNA   length = 18
FEATURE                 Location/Qualifiers
source                  1..18
                        mol_type = unassigned RNA
                        organism = Homo sapiens
SEQUENCE: 145
cgggcgtggt ggtggggg                                                           18

SEQ ID NO: 146          moltype = RNA   length = 20
FEATURE                 Location/Qualifiers
source                  1..20
                        mol_type = unassigned RNA
                        organism = Homo sapiens
SEQUENCE: 146
gctcggactg agcaggtggg                                                         20

SEQ ID NO: 147          moltype = RNA   length = 21
FEATURE                 Location/Qualifiers
source                  1..21
                        mol_type = unassigned RNA
                        organism = Homo sapiens
SEQUENCE: 147
gcggtggggc cggaggggcg t                                                       21

SEQ ID NO: 148          moltype = RNA   length = 22
FEATURE                 Location/Qualifiers
source                  1..22
                        mol_type = unassigned RNA
                        organism = Homo sapiens
SEQUENCE: 148
cagaagggga gttgggagca ga                                                      22

SEQ ID NO: 149          moltype = RNA   length = 25
FEATURE                 Location/Qualifiers
source                  1..25
                        mol_type = unassigned RNA
                        organism = Homo sapiens
SEQUENCE: 149
agggatcgcg ggcgggtggc ggcct                                                   25

SEQ ID NO: 150          moltype = RNA   length = 22
FEATURE                 Location/Qualifiers
source                  1..22
                        mol_type = unassigned RNA
                        organism = Homo sapiens
SEQUENCE: 150
gtgggtgctg gtgggagccg tg                                                      22

SEQ ID NO: 151          moltype = RNA   length = 23
FEATURE                 Location/Qualifiers
source                  1..23
                        mol_type = unassigned RNA
                        organism = Homo sapiens
SEQUENCE: 151
tcggggagtc tggggtccgg aat                                                     23

SEQ ID NO: 152          moltype = RNA   length = 22
FEATURE                 Location/Qualifiers
source                  1..22
                        mol_type = unassigned RNA
                        organism = Homo sapiens
SEQUENCE: 152
gcccaggact ttgtgcgggg tg                                                      22

SEQ ID NO: 153          moltype = RNA   length = 22
FEATURE                 Location/Qualifiers
source                  1..22
                        mol_type = unassigned RNA
                        organism = Homo sapiens
SEQUENCE: 153
cagcagggga gagagaggag tc                                                      22

SEQ ID NO: 154          moltype = RNA   length = 23
FEATURE                 Location/Qualifiers
source                  1..23
                        mol_type = unassigned RNA
                        organism = Homo sapiens
SEQUENCE: 154
agaggctttg tgcggatacg ggg                                                     23
```

```
SEQ ID NO: 155          moltype = RNA   length = 22
FEATURE                 Location/Qualifiers
source                  1..22
                        mol_type = unassigned RNA
                        organism = Homo sapiens
SEQUENCE: 155
gaaatcaagc gtgggtgaga cc                                                  22

SEQ ID NO: 156          moltype = RNA   length = 24
FEATURE                 Location/Qualifiers
source                  1..24
                        mol_type = unassigned RNA
                        organism = Homo sapiens
SEQUENCE: 156
agggctggac tcagcggcgg agct                                                24

SEQ ID NO: 157          moltype = RNA   length = 20
FEATURE                 Location/Qualifiers
source                  1..20
                        mol_type = unassigned RNA
                        organism = Homo sapiens
SEQUENCE: 157
cgggcgtggt ggtggggtg                                                      20

SEQ ID NO: 158          moltype = RNA   length = 22
FEATURE                 Location/Qualifiers
source                  1..22
                        mol_type = unassigned RNA
                        organism = Homo sapiens
SEQUENCE: 158
tcggcctggg gaggaggaag gg                                                  22

SEQ ID NO: 159          moltype = RNA   length = 22
FEATURE                 Location/Qualifiers
source                  1..22
                        mol_type = unassigned RNA
                        organism = Homo sapiens
SEQUENCE: 159
gtagggagg ttgggccagg ga                                                   22

SEQ ID NO: 160          moltype = RNA   length = 20
FEATURE                 Location/Qualifiers
source                  1..20
                        mol_type = unassigned RNA
                        organism = Homo sapiens
SEQUENCE: 160
taggggtgg caggctggcc                                                      20

SEQ ID NO: 161          moltype = RNA   length = 20
FEATURE                 Location/Qualifiers
source                  1..20
                        mol_type = unassigned RNA
                        organism = Homo sapiens
SEQUENCE: 161
actcaaactg tgggggcact                                                     20

SEQ ID NO: 162          moltype = RNA   length = 20
FEATURE                 Location/Qualifiers
source                  1..20
                        mol_type = unassigned RNA
                        organism = Homo sapiens
SEQUENCE: 162
caggggact ggggtgagc                                                       20

SEQ ID NO: 163          moltype = RNA   length = 21
FEATURE                 Location/Qualifiers
source                  1..21
                        mol_type = unassigned RNA
                        organism = Homo sapiens
SEQUENCE: 163
ctgggagggg ctgggtttgg c                                                   21

SEQ ID NO: 164          moltype = RNA   length = 19
FEATURE                 Location/Qualifiers
source                  1..19
                        mol_type = unassigned RNA
                        organism = Homo sapiens
SEQUENCE: 164
```

```
gggggaagaa aaggtgggg                                                    19

SEQ ID NO: 165         moltype = RNA   length = 21
FEATURE                Location/Qualifiers
source                 1..21
                       mol_type = unassigned RNA
                       organism = Homo sapiens
SEQUENCE: 165
atccagttct ctgaggggc t                                                  21

SEQ ID NO: 166         moltype = RNA   length = 23
FEATURE                Location/Qualifiers
source                 1..23
                       mol_type = unassigned RNA
                       organism = Homo sapiens
SEQUENCE: 166
cggggccatg gagcagcctg tgt                                               23

SEQ ID NO: 167         moltype = RNA   length = 24
FEATURE                Location/Qualifiers
source                 1..24
                       mol_type = unassigned RNA
                       organism = Homo sapiens
SEQUENCE: 167
tggggagctg aggctctggg ggtg                                              24

SEQ ID NO: 168         moltype = RNA   length = 24
FEATURE                Location/Qualifiers
source                 1..24
                       mol_type = unassigned RNA
                       organism = Homo sapiens
SEQUENCE: 168
ccccgggaac gtcgagactg gagc                                              24

SEQ ID NO: 169         moltype = RNA   length = 23
FEATURE                Location/Qualifiers
source                 1..23
                       mol_type = unassigned RNA
                       organism = Homo sapiens
SEQUENCE: 169
acggggagtc aggcagtggt gga                                               23

SEQ ID NO: 170         moltype = RNA   length = 22
FEATURE                Location/Qualifiers
source                 1..22
                       mol_type = unassigned RNA
                       organism = Homo sapiens
SEQUENCE: 170
tgcagggtc gggtgggcca gg                                                 22

SEQ ID NO: 171         moltype = RNA   length = 17
FEATURE                Location/Qualifiers
source                 1..17
                       mol_type = unassigned RNA
                       organism = Homo sapiens
SEQUENCE: 171
ggcgggtgcg ggggtgg                                                      17

SEQ ID NO: 172         moltype = RNA   length = 22
FEATURE                Location/Qualifiers
source                 1..22
                       mol_type = unassigned RNA
                       organism = Homo sapiens
SEQUENCE: 172
tagggcagc agaggacctg gg                                                 22

SEQ ID NO: 173         moltype = RNA   length = 17
FEATURE                Location/Qualifiers
source                 1..17
                       mol_type = unassigned RNA
                       organism = Homo sapiens
SEQUENCE: 173
cgcgccgggc ccgggtt                                                      17

SEQ ID NO: 174         moltype = RNA   length = 24
FEATURE                Location/Qualifiers
source                 1..24
                       mol_type = unassigned RNA
                       organism = Homo sapiens
```

```
SEQUENCE: 174
cgggtgggag cagatcttat tgag                                              24

SEQ ID NO: 175          moltype = RNA   length = 17
FEATURE                 Location/Qualifiers
source                  1..17
                        mol_type = unassigned RNA
                        organism = Homo sapiens
SEQUENCE: 175
ggtggggct gttgttt                                                       17

SEQ ID NO: 176          moltype = RNA   length = 23
FEATURE                 Location/Qualifiers
source                  1..23
                        mol_type = unassigned RNA
                        organism = Homo sapiens
SEQUENCE: 176
tgggctgagg gcaggaggcc tgt                                               23

SEQ ID NO: 177          moltype = RNA   length = 21
FEATURE                 Location/Qualifiers
source                  1..21
                        mol_type = unassigned RNA
                        organism = Homo sapiens
SEQUENCE: 177
gtgtggccgg caggcgggtg g                                                 21

SEQ ID NO: 178          moltype = RNA   length = 23
FEATURE                 Location/Qualifiers
source                  1..23
                        mol_type = unassigned RNA
                        organism = Homo sapiens
SEQUENCE: 178
tggggacgta gctggccaga cag                                               23

SEQ ID NO: 179          moltype = RNA   length = 21
FEATURE                 Location/Qualifiers
source                  1..21
                        mol_type = unassigned RNA
                        organism = Homo sapiens
SEQUENCE: 179
accactgcac tccagcctga g                                                 21

SEQ ID NO: 180          moltype = RNA   length = 17
FEATURE                 Location/Qualifiers
source                  1..17
                        mol_type = unassigned RNA
                        organism = Homo sapiens
SEQUENCE: 180
gagactgggg tggggcc                                                      17

SEQ ID NO: 181          moltype = RNA   length = 19
FEATURE                 Location/Qualifiers
source                  1..19
                        mol_type = unassigned RNA
                        organism = Homo sapiens
SEQUENCE: 181
ggggcctggc ggtgggcgg                                                    19

SEQ ID NO: 182          moltype = RNA   length = 18
FEATURE                 Location/Qualifiers
source                  1..18
                        mol_type = unassigned RNA
                        organism = Homo sapiens
SEQUENCE: 182
cggggcggca ggggcctc                                                     18

SEQ ID NO: 183          moltype = RNA   length = 22
FEATURE                 Location/Qualifiers
source                  1..22
                        mol_type = unassigned RNA
                        organism = Homo sapiens
SEQUENCE: 183
agggccgaag ggtggaagct gc                                                22

SEQ ID NO: 184          moltype = RNA   length = 23
FEATURE                 Location/Qualifiers
source                  1..23
                        mol_type = unassigned RNA
```

```
                        organism = Homo sapiens
SEQUENCE: 184
tgaggatatg gcagggaagg gga                                               23

SEQ ID NO: 185          moltype = RNA   length = 17
FEATURE                 Location/Qualifiers
source                  1..17
                        mol_type = unassigned RNA
                        organism = Homo sapiens
SEQUENCE: 185
gccggacaag agggagg                                                      17

SEQ ID NO: 186          moltype = RNA   length = 24
FEATURE                 Location/Qualifiers
source                  1..24
                        mol_type = unassigned RNA
                        organism = Homo sapiens
SEQUENCE: 186
gtagggcgt cccgggcgcg cggg                                               24

SEQ ID NO: 187          moltype = RNA   length = 25
FEATURE                 Location/Qualifiers
source                  1..25
                        mol_type = unassigned RNA
                        organism = Homo sapiens
SEQUENCE: 187
tagggtggg ggaattcagg ggtgt                                              25

SEQ ID NO: 188          moltype = RNA   length = 21
FEATURE                 Location/Qualifiers
source                  1..21
                        mol_type = unassigned RNA
                        organism = Homo sapiens
SEQUENCE: 188
cggggcagct cagtacagga t                                                 21

SEQ ID NO: 189          moltype = RNA   length = 19
FEATURE                 Location/Qualifiers
source                  1..19
                        mol_type = unassigned RNA
                        organism = Homo sapiens
SEQUENCE: 189
aaggggctgg gggagcaca                                                    19

SEQ ID NO: 190          moltype = RNA   length = 21
FEATURE                 Location/Qualifiers
source                  1..21
                        mol_type = unassigned RNA
                        organism = Homo sapiens
SEQUENCE: 190
agcggtgctc ctgcgggccg a                                                 21

SEQ ID NO: 191          moltype = RNA   length = 22
FEATURE                 Location/Qualifiers
source                  1..22
                        mol_type = unassigned RNA
                        organism = Homo sapiens
SEQUENCE: 191
gctgggatta caggcatgag cc                                                22

SEQ ID NO: 192          moltype = RNA   length = 20
FEATURE                 Location/Qualifiers
source                  1..20
                        mol_type = unassigned RNA
                        organism = Homo sapiens
SEQUENCE: 192
gtgagtcagg gtggggctgg                                                   20

SEQ ID NO: 193          moltype = RNA   length = 22
FEATURE                 Location/Qualifiers
source                  1..22
                        mol_type = unassigned RNA
                        organism = Homo sapiens
SEQUENCE: 193
ctgggggtgg ggggctgggc gt                                                22

SEQ ID NO: 194          moltype = RNA   length = 22
FEATURE                 Location/Qualifiers
source                  1..22
```

```
                        mol_type = unassigned RNA
                        organism = Homo sapiens
SEQUENCE: 194
ctgggacagg aggaggaggc ag                                            22

SEQ ID NO: 195          moltype = RNA   length = 20
FEATURE                 Location/Qualifiers
source                  1..20
                        mol_type = unassigned RNA
                        organism = Homo sapiens
SEQUENCE: 195
ggatccgagt cacggcacca                                               20

SEQ ID NO: 196          moltype = RNA   length = 22
FEATURE                 Location/Qualifiers
source                  1..22
                        mol_type = unassigned RNA
                        organism = Homo sapiens
SEQUENCE: 196
ccaggaggcg gaggaggtgg ag                                            22

SEQ ID NO: 197          moltype = RNA   length = 18
FEATURE                 Location/Qualifiers
source                  1..18
                        mol_type = unassigned RNA
                        organism = Homo sapiens
SEQUENCE: 197
ctggcagggg gagaggta                                                 18

SEQ ID NO: 198          moltype = RNA   length = 22
FEATURE                 Location/Qualifiers
source                  1..22
                        mol_type = unassigned RNA
                        organism = Homo sapiens
SEQUENCE: 198
tggtggagga agagggcagc tc                                            22

SEQ ID NO: 199          moltype = RNA   length = 22
FEATURE                 Location/Qualifiers
source                  1..22
                        mol_type = unassigned RNA
                        organism = Homo sapiens
SEQUENCE: 199
cgtcccgggg ctgcgcgagg ca                                            22

SEQ ID NO: 200          moltype = RNA   length = 22
FEATURE                 Location/Qualifiers
source                  1..22
                        mol_type = unassigned RNA
                        organism = Homo sapiens
SEQUENCE: 200
tcaaaatcag gagtcggggc tt                                            22

SEQ ID NO: 201          moltype = RNA   length = 22
FEATURE                 Location/Qualifiers
source                  1..22
                        mol_type = unassigned RNA
                        organism = Homo sapiens
SEQUENCE: 201
caggaggcag tgggcgagca gg                                            22

SEQ ID NO: 202          moltype = RNA   length = 19
FEATURE                 Location/Qualifiers
source                  1..19
                        mol_type = unassigned RNA
                        organism = Homo sapiens
SEQUENCE: 202
agcagggctg gggattgca                                                19

SEQ ID NO: 203          moltype = RNA   length = 20
FEATURE                 Location/Qualifiers
source                  1..20
                        mol_type = unassigned RNA
                        organism = Homo sapiens
SEQUENCE: 203
tgggctgctg agaaggggca                                               20

SEQ ID NO: 204          moltype = RNA   length = 17
FEATURE                 Location/Qualifiers
```

```
source                      1..17
                            mol_type = unassigned RNA
                            organism = Homo sapiens
SEQUENCE: 204
gctgggcgag gctggca                                                              17

SEQ ID NO: 205              moltype = RNA  length = 23
FEATURE                     Location/Qualifiers
source                      1..23
                            mol_type = unassigned RNA
                            organism = Homo sapiens
SEQUENCE: 205
ttgctctgct cccccgcccc cag                                                       23

SEQ ID NO: 206              moltype = RNA  length = 23
FEATURE                     Location/Qualifiers
source                      1..23
                            mol_type = unassigned RNA
                            organism = Homo sapiens
SEQUENCE: 206
tcaataggaa agaggtggga cct                                                       23

SEQ ID NO: 207              moltype = RNA  length = 17
FEATURE                     Location/Qualifiers
source                      1..17
                            mol_type = unassigned RNA
                            organism = Homo sapiens
SEQUENCE: 207
gcggggctgg gcgcgcg                                                              17

SEQ ID NO: 208              moltype = RNA  length = 22
FEATURE                     Location/Qualifiers
source                      1..22
                            mol_type = unassigned RNA
                            organism = Homo sapiens
SEQUENCE: 208
tggggagcgg cccccgggtg gg                                                        22

SEQ ID NO: 209              moltype = RNA  length = 21
FEATURE                     Location/Qualifiers
source                      1..21
                            mol_type = unassigned RNA
                            organism = Homo sapiens
SEQUENCE: 209
tctgtggagt ggggtgcctg t                                                         21

SEQ ID NO: 210              moltype = RNA  length = 22
FEATURE                     Location/Qualifiers
source                      1..22
                            mol_type = unassigned RNA
                            organism = Homo sapiens
SEQUENCE: 210
caggcacggg agctcaggtg ag                                                        22

SEQ ID NO: 211              moltype = RNA  length = 25
FEATURE                     Location/Qualifiers
source                      1..25
                            mol_type = unassigned RNA
                            organism = Homo sapiens
SEQUENCE: 211
gtgaggcggg gccaggaggg tgtgt                                                     25

SEQ ID NO: 212              moltype = RNA  length = 21
FEATURE                     Location/Qualifiers
source                      1..21
                            mol_type = unassigned RNA
                            organism = Homo sapiens
SEQUENCE: 212
aagggacagg gagggtcgtg g                                                         21

SEQ ID NO: 213              moltype = RNA  length = 20
FEATURE                     Location/Qualifiers
source                      1..20
                            mol_type = unassigned RNA
                            organism = Homo sapiens
SEQUENCE: 213
ggcggcggcg gaggcggggg                                                           20

SEQ ID NO: 214              moltype = RNA  length = 22
```

```
                            -continued

FEATURE              Location/Qualifiers
source               1..22
                     mol_type = unassigned RNA
                     organism = Homo sapiens
SEQUENCE: 214
tcgggcctgg ggttggggga gc                                            22

SEQ ID NO: 215       moltype = RNA   length = 19
FEATURE              Location/Qualifiers
source               1..19
                     mol_type = unassigned RNA
                     organism = Homo sapiens
SEQUENCE: 215
atcccaccac tgccaccat                                                19

SEQ ID NO: 216       moltype = RNA   length = 20
FEATURE              Location/Qualifiers
source               1..20
                     mol_type = unassigned RNA
                     organism = Homo sapiens
SEQUENCE: 216
ggggaggtgt gcagggctgg                                               20

SEQ ID NO: 217       moltype = RNA   length = 24
FEATURE              Location/Qualifiers
source               1..24
                     mol_type = unassigned RNA
                     organism = Homo sapiens
SEQUENCE: 217
tgggggagcc atgagataag agca                                          24

SEQ ID NO: 218       moltype = RNA   length = 20
FEATURE              Location/Qualifiers
source               1..20
                     mol_type = unassigned RNA
                     organism = Homo sapiens
SEQUENCE: 218
gccggggctt tgggtgaggg                                               20

SEQ ID NO: 219       moltype = RNA   length = 22
FEATURE              Location/Qualifiers
source               1..22
                     mol_type = unassigned RNA
                     organism = Homo sapiens
SEQUENCE: 219
ttcagatccc agcggtgcct ct                                            22

SEQ ID NO: 220       moltype = RNA   length = 23
FEATURE              Location/Qualifiers
source               1..23
                     mol_type = unassigned RNA
                     organism = Homo sapiens
SEQUENCE: 220
tggtgggtgg ggaggagaag tgc                                           23

SEQ ID NO: 221       moltype = RNA   length = 21
FEATURE              Location/Qualifiers
source               1..21
                     mol_type = unassigned RNA
                     organism = Homo sapiens
SEQUENCE: 221
tggcagggag gctgggaggg g                                             21

SEQ ID NO: 222       moltype = RNA   length = 22
FEATURE              Location/Qualifiers
source               1..22
                     mol_type = unassigned RNA
                     organism = Homo sapiens
SEQUENCE: 222
agacacattt ggagagggaa cc                                            22

SEQ ID NO: 223       moltype = RNA   length = 18
FEATURE              Location/Qualifiers
source               1..18
                     mol_type = unassigned RNA
                     organism = Homo sapiens
SEQUENCE: 223
aggctgggct gggacgga                                                 18
```

```
SEQ ID NO: 224          moltype = RNA   length = 20
FEATURE                 Location/Qualifiers
source                  1..20
                        mol_type = unassigned RNA
                        organism = Homo sapiens
SEQUENCE: 224
tcagggagtc aggggagggc                                                    20

SEQ ID NO: 225          moltype = RNA   length = 23
FEATURE                 Location/Qualifiers
source                  1..23
                        mol_type = unassigned RNA
                        organism = Homo sapiens
SEQUENCE: 225
tgggcagggg cttattgtag gag                                                23

SEQ ID NO: 226          moltype = RNA   length = 22
FEATURE                 Location/Qualifiers
source                  1..22
                        mol_type = unassigned RNA
                        organism = Homo sapiens
SEQUENCE: 226
tgggggagga aggacaggcc at                                                 22

SEQ ID NO: 227          moltype = RNA   length = 22
FEATURE                 Location/Qualifiers
source                  1..22
                        mol_type = unassigned RNA
                        organism = Homo sapiens
SEQUENCE: 227
cccctggggc tgggcaggcg ga                                                 22

SEQ ID NO: 228          moltype = RNA   length = 21
FEATURE                 Location/Qualifiers
source                  1..21
                        mol_type = unassigned RNA
                        organism = Homo sapiens
SEQUENCE: 228
ctgggggag gagaccctgc t                                                   21

SEQ ID NO: 229          moltype = RNA   length = 17
FEATURE                 Location/Qualifiers
source                  1..17
                        mol_type = unassigned RNA
                        organism = Homo sapiens
SEQUENCE: 229
ccccgccacc gccttgg                                                       17

SEQ ID NO: 230          moltype = RNA   length = 20
FEATURE                 Location/Qualifiers
source                  1..20
                        mol_type = unassigned RNA
                        organism = Homo sapiens
SEQUENCE: 230
tctcttcatc taccccccag                                                    20

SEQ ID NO: 231          moltype = RNA   length = 23
FEATURE                 Location/Qualifiers
source                  1..23
                        mol_type = unassigned RNA
                        organism = Homo sapiens
SEQUENCE: 231
aggaggtggt actagggcc agc                                                 23

SEQ ID NO: 232          moltype = RNA   length = 20
FEATURE                 Location/Qualifiers
source                  1..20
                        mol_type = unassigned RNA
                        organism = Homo sapiens
SEQUENCE: 232
gcggaaggcg gagcggcgga                                                    20

SEQ ID NO: 233          moltype = RNA   length = 22
FEATURE                 Location/Qualifiers
source                  1..22
                        mol_type = unassigned RNA
                        organism = Homo sapiens
SEQUENCE: 233
tgcggggaca ggccagggca tc                                                 22
```

```
SEQ ID NO: 234          moltype = RNA   length = 23
FEATURE                 Location/Qualifiers
source                  1..23
                        mol_type = unassigned RNA
                        organism = Homo sapiens
SEQUENCE: 234
agggccagag gagcctggag tgg                                               23

SEQ ID NO: 235          moltype = RNA   length = 22
FEATURE                 Location/Qualifiers
source                  1..22
                        mol_type = unassigned RNA
                        organism = Homo sapiens
SEQUENCE: 235
agactgacgg ctggaggccc at                                                22

SEQ ID NO: 236          moltype = RNA   length = 20
FEATURE                 Location/Qualifiers
source                  1..20
                        mol_type = unassigned RNA
                        organism = Homo sapiens
SEQUENCE: 236
cggctctggg tctgtgggga                                                   20

SEQ ID NO: 237          moltype = RNA   length = 23
FEATURE                 Location/Qualifiers
source                  1..23
                        mol_type = unassigned RNA
                        organism = Homo sapiens
SEQUENCE: 237
gacacgggcg acagctgcgg ccc                                               23

SEQ ID NO: 238          moltype = RNA   length = 23
FEATURE                 Location/Qualifiers
source                  1..23
                        mol_type = unassigned RNA
                        organism = Homo sapiens
SEQUENCE: 238
tgagggcag agagcgagac ttt                                                23

SEQ ID NO: 239          moltype = RNA   length = 22
FEATURE                 Location/Qualifiers
source                  1..22
                        mol_type = unassigned RNA
                        organism = Homo sapiens
SEQUENCE: 239
gggtggggat ttgttgcatt ac                                                22

SEQ ID NO: 240          moltype = RNA   length = 22
FEATURE                 Location/Qualifiers
source                  1..22
                        mol_type = unassigned RNA
                        organism = Homo sapiens
SEQUENCE: 240
tagcagcacg taaatattgg cg                                                22

SEQ ID NO: 241          moltype = RNA   length = 22
FEATURE                 Location/Qualifiers
source                  1..22
                        mol_type = unassigned RNA
                        organism = Homo sapiens
SEQUENCE: 241
aaaccgttac cattactgag tt                                                22

SEQ ID NO: 242          moltype = RNA   length = 22
FEATURE                 Location/Qualifiers
source                  1..22
                        mol_type = unassigned RNA
                        organism = Homo sapiens
SEQUENCE: 242
tatagggatt ggagccgtgg cg                                                22

SEQ ID NO: 243          moltype = RNA   length = 22
FEATURE                 Location/Qualifiers
source                  1..22
                        mol_type = unassigned RNA
                        organism = Homo sapiens
SEQUENCE: 243
```

```
tcctgtactg agctgccccg ag                                              22

SEQ ID NO: 251          moltype = RNA   length = 18
FEATURE                 Location/Qualifiers
source                  1..18
                        mol_type = unassigned RNA
                        organism = Homo sapiens
SEQUENCE: 244
ccagaggtgg ggactgag                                                   18

SEQ ID NO: 245          moltype = RNA   length = 22
FEATURE                 Location/Qualifiers
source                  1..22
                        mol_type = unassigned RNA
                        organism = Homo sapiens
SEQUENCE: 245
agggacggga cgcggtgcag tg                                              22

SEQ ID NO: 246          moltype = RNA   length = 20
FEATURE                 Location/Qualifiers
source                  1..20
                        mol_type = unassigned RNA
                        organism = Homo sapiens
SEQUENCE: 246
ccccagggcg acgcggcggg                                                 20

SEQ ID NO: 247          moltype = RNA   length = 21
FEATURE                 Location/Qualifiers
source                  1..21
                        mol_type = unassigned RNA
                        organism = Homo sapiens
SEQUENCE: 247
cttccgcccc gccgggcgtc g                                               21

SEQ ID NO: 248          moltype = RNA   length = 21
FEATURE                 Location/Qualifiers
source                  1..21
                        mol_type = unassigned RNA
                        organism = Homo sapiens
SEQUENCE: 248
aaggcagggc ccccgctccc c                                               21

SEQ ID NO: 249          moltype = RNA   length = 21
FEATURE                 Location/Qualifiers
source                  1..21
                        mol_type = unassigned RNA
                        organism = Homo sapiens
SEQUENCE: 249
agggccccc ctcaatcctg t                                                21

SEQ ID NO: 250          moltype = RNA   length = 21
FEATURE                 Location/Qualifiers
source                  1..21
                        mol_type = unassigned RNA
                        organism = Homo sapiens
SEQUENCE: 250
atcacattgc cagggattac c                                               21

SEQ ID NO: 251          moltype = RNA   length = 22
FEATURE                 Location/Qualifiers
source                  1..22
                        mol_type = unassigned RNA
                        organism = Homo sapiens
SEQUENCE: 251
tattgcactt gtcccggcct gt                                              22

SEQ ID NO: 252          moltype = RNA   length = 25
FEATURE                 Location/Qualifiers
source                  1..25
                        mol_type = unassigned RNA
                        organism = Homo sapiens
SEQUENCE: 252
ggcgaggga agtaggtccg ttggt                                            25

SEQ ID NO: 253          moltype = RNA   length = 22
FEATURE                 Location/Qualifiers
source                  1..22
                        mol_type = unassigned RNA
                        organism = Homo sapiens
```

```
SEQUENCE: 253
tgggggtggt ctctagccaa gg                                                    22

SEQ ID NO: 254          moltype = RNA   length = 20
FEATURE                 Location/Qualifiers
source                  1..20
                        mol_type = unassigned RNA
                        organism = Homo sapiens
SEQUENCE: 254
gggaaaagga aggggagga                                                        20

SEQ ID NO: 255          moltype = RNA   length = 21
FEATURE                 Location/Qualifiers
source                  1..21
                        mol_type = unassigned RNA
                        organism = Homo sapiens
SEQUENCE: 255
tcacctggct ggcccgccca g                                                     21

SEQ ID NO: 256          moltype = RNA   length = 20
FEATURE                 Location/Qualifiers
source                  1..20
                        mol_type = unassigned RNA
                        organism = Homo sapiens
SEQUENCE: 256
tgggaggagg ggatcttggg                                                       20

SEQ ID NO: 257          moltype = RNA   length = 17
FEATURE                 Location/Qualifiers
source                  1..17
                        mol_type = unassigned RNA
                        organism = Homo sapiens
SEQUENCE: 257
ggatggagga ggggtct                                                          17

SEQ ID NO: 258          moltype = RNA   length = 22
FEATURE                 Location/Qualifiers
source                  1..22
                        mol_type = unassigned RNA
                        organism = Homo sapiens
SEQUENCE: 258
tattgcactc gtcccggcct cc                                                    22

SEQ ID NO: 259          moltype = RNA   length = 22
FEATURE                 Location/Qualifiers
source                  1..22
                        mol_type = unassigned RNA
                        organism = Homo sapiens
SEQUENCE: 259
ggctggagcg agtgcagtgg tg                                                    22

SEQ ID NO: 260          moltype = RNA   length = 21
FEATURE                 Location/Qualifiers
source                  1..21
                        mol_type = unassigned RNA
                        organism = Homo sapiens
SEQUENCE: 260
tggctgttgg aggggcagg c                                                      21

SEQ ID NO: 261          moltype = RNA   length = 22
FEATURE                 Location/Qualifiers
source                  1..22
                        mol_type = unassigned RNA
                        organism = Homo sapiens
SEQUENCE: 261
ggggctgggg ccggggccga gc                                                    22

SEQ ID NO: 262          moltype = RNA   length = 22
FEATURE                 Location/Qualifiers
source                  1..22
                        mol_type = unassigned RNA
                        organism = Homo sapiens
SEQUENCE: 262
gggaccatcc tgcctgctgt gg                                                    22

SEQ ID NO: 263          moltype = RNA   length = 22
FEATURE                 Location/Qualifiers
source                  1..22
                        mol_type = unassigned RNA
```

```
                          organism = Homo sapiens
SEQUENCE: 263
tggcggcggt agttatgggc tt                                            22

SEQ ID NO: 264            moltype = RNA   length = 23
FEATURE                   Location/Qualifiers
source                    1..23
                          mol_type = unassigned RNA
                          organism = Homo sapiens
SEQUENCE: 264
gtttgcacgg gtgggccttg tct                                           23

SEQ ID NO: 265            moltype = RNA   length = 21
FEATURE                   Location/Qualifiers
source                    1..21
                          mol_type = unassigned RNA
                          organism = Homo sapiens
SEQUENCE: 265
cgggggcggg gccgaagcgc g                                             21

SEQ ID NO: 266            moltype = RNA   length = 21
FEATURE                   Location/Qualifiers
source                    1..21
                          mol_type = unassigned RNA
                          organism = Homo sapiens
SEQUENCE: 266
cggcggggac ggcgattggt c                                             21

SEQ ID NO: 267            moltype = RNA   length = 17
FEATURE                   Location/Qualifiers
source                    1..17
                          mol_type = unassigned RNA
                          organism = Homo sapiens
SEQUENCE: 267
accccactcc tggtacc                                                  17

SEQ ID NO: 268            moltype = RNA   length = 25
FEATURE                   Location/Qualifiers
source                    1..25
                          mol_type = unassigned RNA
                          organism = Homo sapiens
SEQUENCE: 268
aggggggcac tgcgcaagca aagcc                                         25

SEQ ID NO: 269            moltype = RNA   length = 19
FEATURE                   Location/Qualifiers
source                    1..19
                          mol_type = unassigned RNA
                          organism = Homo sapiens
SEQUENCE: 269
ctggggagtg gctggggag                                                19

SEQ ID NO: 270            moltype = RNA   length = 82
FEATURE                   Location/Qualifiers
source                    1..82
                          mol_type = unassigned RNA
                          organism = Homo sapiens
SEQUENCE: 270
gggaaagcgg agggcgcgcc cagctcccgg gctgattgcg ctaacagtgg ccccggtgtt   60
ggggcgcgtc tgccgctgcc cc                                            82

SEQ ID NO: 271            moltype = RNA   length = 76
FEATURE                   Location/Qualifiers
source                    1..76
                          mol_type = unassigned RNA
                          organism = Homo sapiens
SEQUENCE: 271
cgcaggcctc tggcggagcc cattccatgc cagatgctga gcgatggctg gtgtgtgctg   60
ctccacaggc ctggtg                                                   76

SEQ ID NO: 272            moltype = RNA   length = 149
FEATURE                   Location/Qualifiers
source                    1..149
                          mol_type = unassigned RNA
                          organism = Homo sapiens
SEQUENCE: 272
catcaagacc cagctgagtc actgtcactg cctaccaatc tcgaccggac ctcgaccggc   60
tcgtctgtgt tgccaatcga ctcggcgtgg cgtcggtcgt ggtagatagg cggtcatgca  120
tacgaattttt cagctcttgt tctggtgac                                   149
```

```
SEQ ID NO: 273            moltype = RNA   length = 54
FEATURE                   Location/Qualifiers
source                    1..54
                          mol_type = unassigned RNA
                          organism = Homo sapiens
SEQUENCE: 273
ggacaagggc ggcgcgaccg gcccggggct cttgggcggc cgcgtttccc ctcc        54

SEQ ID NO: 274            moltype = RNA   length = 93
FEATURE                   Location/Qualifiers
source                    1..93
                          mol_type = unassigned RNA
                          organism = Homo sapiens
SEQUENCE: 274
ccttccggcg tcccaggcgg ggcgccgcgg gaccgccctc gtgtctgtgg cggtgggatc  60
ccgcggccgt gttttcctgg tggcccggcc atg                               93

SEQ ID NO: 275            moltype = RNA   length = 51
FEATURE                   Location/Qualifiers
source                    1..51
                          mol_type = unassigned RNA
                          organism = Homo sapiens
SEQUENCE: 275
acagaccccg gggagcccgg cggtgaagct cctggtatcc tgggtgtctg a           51

SEQ ID NO: 276            moltype = RNA   length = 59
FEATURE                   Location/Qualifiers
source                    1..59
                          mol_type = unassigned RNA
                          organism = Homo sapiens
SEQUENCE: 276
cggggtcggc ggcgacgtgc tcagcttggc acccaagttc tgccgctccg acgcccggc   59

SEQ ID NO: 277            moltype = RNA   length = 84
FEATURE                   Location/Qualifiers
source                    1..84
                          mol_type = unassigned RNA
                          organism = Homo sapiens
SEQUENCE: 277
gaggctgggc ggggcgcggc cggatcggtc gagagcgtcc tggctgatga cggtctcccg  60
tgcccacgcc ccaaacgcag tctc                                         84

SEQ ID NO: 278            moltype = RNA   length = 65
FEATURE                   Location/Qualifiers
source                    1..65
                          mol_type = unassigned RNA
                          organism = Homo sapiens
SEQUENCE: 278
gagggtgggc gagggcggct gagcggctcc atccccggc ctgctcatcc ccctcgccct   60
ctcag                                                              65

SEQ ID NO: 279            moltype = RNA   length = 60
FEATURE                   Location/Qualifiers
source                    1..60
                          mol_type = unassigned RNA
                          organism = Homo sapiens
SEQUENCE: 279
cgctgggtcc gcgcgccctg ggccgggcga tgtccgcttg ggggagcgag gggcggggcg  60

SEQ ID NO: 280            moltype = RNA   length = 76
FEATURE                   Location/Qualifiers
source                    1..76
                          mol_type = unassigned RNA
                          organism = Homo sapiens
SEQUENCE: 280
gagggagctg tagagcaggg agcaggaagc tgtgtgtgtc cagccctgac ctgtcctgtt  60
ctgccccag ccctc                                                    76

SEQ ID NO: 281            moltype = RNA   length = 75
FEATURE                   Location/Qualifiers
source                    1..75
                          mol_type = unassigned RNA
                          organism = Homo sapiens
SEQUENCE: 281
aagcaagact gagggcctc agaccgagct tttggaaaat agaaaagtct cgctctctgc   60
ccctcagcct aactt                                                   75

SEQ ID NO: 282            moltype = RNA   length = 65
```

```
FEATURE                 Location/Qualifiers
source                  1..65
                        mol_type = unassigned RNA
                        organism = Homo sapiens
SEQUENCE: 282
gggtgctcgg ggcaggcggc tgggagcggc cctcacattg atggctcctg ccacctcctc    60
cgcag                                                                65

SEQ ID NO: 283          moltype = RNA  length = 51
FEATURE                 Location/Qualifiers
source                  1..51
                        mol_type = unassigned RNA
                        organism = Homo sapiens
SEQUENCE: 283
agagatgaag cgggggggcg gggtcttgct ctattgccta cgctgatctc a              51

SEQ ID NO: 284          moltype = RNA  length = 87
FEATURE                 Location/Qualifiers
source                  1..87
                        mol_type = unassigned RNA
                        organism = Homo sapiens
SEQUENCE: 284
cccaggcgcc cgctcccgac ccacgccgcg ccgccgggtc cctcctcccc ggagaggctg    60
ggctcgggac gcgcggctca gctcggg                                        87

SEQ ID NO: 285          moltype = RNA  length = 72
FEATURE                 Location/Qualifiers
source                  1..72
                        mol_type = unassigned RNA
                        organism = Homo sapiens
SEQUENCE: 285
gatttcagtg acctggcagc agggagcgtc gtcagtgttt gactgtttat ggtatgtcag    60
ggagctggtt cc                                                        72

SEQ ID NO: 286          moltype = RNA  length = 84
FEATURE                 Location/Qualifiers
source                  1..84
                        mol_type = unassigned RNA
                        organism = Homo sapiens
SEQUENCE: 286
cggtccagac gtggcggggg tggcggcggc atcccggacg gcctgtgagg gatgcgccgc    60
ccactgcccc gcgccgcctg accg                                           84

SEQ ID NO: 287          moltype = RNA  length = 47
FEATURE                 Location/Qualifiers
source                  1..47
                        mol_type = unassigned RNA
                        organism = Homo sapiens
SEQUENCE: 287
ctcggcgcgg ggcgcgggct ccgggttggg gcgagccaac gccgggg                  47

SEQ ID NO: 288          moltype = RNA  length = 86
FEATURE                 Location/Qualifiers
source                  1..86
                        mol_type = unassigned RNA
                        organism = Homo sapiens
SEQUENCE: 288
tgccagtctc taggtccctg agaccctta acctgtgagg acatccaggg tcacaggtga    60
ggttcttggg agcctggcgt ctggcc                                         86

SEQ ID NO: 289          moltype = RNA  length = 82
FEATURE                 Location/Qualifiers
source                  1..82
                        mol_type = unassigned RNA
                        organism = Homo sapiens
SEQUENCE: 289
gtgagtggga ggccagggca cggcaggggg agctgcaggg ctatgggagg ggccccagcg    60
tctgagccct gtcctcccgc ag                                             82

SEQ ID NO: 290          moltype = RNA  length = 82
FEATURE                 Location/Qualifiers
source                  1..82
                        mol_type = unassigned RNA
                        organism = Homo sapiens
SEQUENCE: 290
gtgagtggga ggccagggca cggcaggggg agctgcaggg ctatgggagg ggccccagcg    60
tctgagccct gtcctcccgc ag                                             82

SEQ ID NO: 291          moltype = RNA  length = 74
```

```
FEATURE                 Location/Qualifiers
source                  1..74
                        mol_type = unassigned RNA
                        organism = Homo sapiens
SEQUENCE: 291
ccgcactctc tccattacac taccctgcct cttctccatg agaggcagcg gggtgtagtg    60
gatagagcac gggt                                                     74

SEQ ID NO: 292          moltype = RNA  length = 65
FEATURE                 Location/Qualifiers
source                  1..65
                        mol_type = unassigned RNA
                        organism = Homo sapiens
SEQUENCE: 292
gagggctagg tgggggcttt gaagccccga gatgcctcac gtcttcaccc ctctcaccta    60
agcag                                                               65

SEQ ID NO: 293          moltype = RNA  length = 75
FEATURE                 Location/Qualifiers
source                  1..75
                        mol_type = unassigned RNA
                        organism = Homo sapiens
SEQUENCE: 293
tggagtgggg gggcaggagg ggctcaggga gaaagtgcat acagccctg gccctctctg     60
cccttccgtc ccctg                                                    75

SEQ ID NO: 294          moltype = RNA  length = 61
FEATURE                 Location/Qualifiers
source                  1..61
                        mol_type = unassigned RNA
                        organism = Homo sapiens
SEQUENCE: 294
tcggctggcg ggggtagagc tggctgcagg cccggcccct ctcagctgct gccctctcca    60
g                                                                   61

SEQ ID NO: 295          moltype = RNA  length = 86
FEATURE                 Location/Qualifiers
source                  1..86
                        mol_type = unassigned RNA
                        organism = Homo sapiens
SEQUENCE: 295
cgcctgagcg tgcagcagga catcttcctg acctggtaat aattaggtga aaggatggt     60
tggggcggt cggcgtaact caggga                                         86

SEQ ID NO: 296          moltype = RNA  length = 72
FEATURE                 Location/Qualifiers
source                  1..72
                        mol_type = unassigned RNA
                        organism = Homo sapiens
SEQUENCE: 296
gagtctgagg gacccaggac aggagaaggc ctatggtgat ttgcattctt cctgccctgg    60
ctccatcctc ag                                                       72

SEQ ID NO: 297          moltype = RNA  length = 73
FEATURE                 Location/Qualifiers
source                  1..73
                        mol_type = unassigned RNA
                        organism = Homo sapiens
SEQUENCE: 297
tgtatccttg aatggatttt tggagcagga gtggacacct gacccaaagg aaatcaatcc    60
ataggctagc aat                                                      73

SEQ ID NO: 298          moltype = RNA  length = 70
FEATURE                 Location/Qualifiers
source                  1..70
                        mol_type = unassigned RNA
                        organism = Homo sapiens
SEQUENCE: 298
ctcgggcccg accgcgccgg cccgcacctc ccggcccgga gctgcgggct gcggtcaggg    60
cgatcccggg                                                          70

SEQ ID NO: 299          moltype = RNA  length = 69
FEATURE                 Location/Qualifiers
source                  1..69
                        mol_type = unassigned RNA
                        organism = Homo sapiens
SEQUENCE: 299
gggcttaggg atgggaggcc aggatgaaga ttaatccta atccccaaca ctggccttgc     60
tatccccag                                                           69
```

```
SEQ ID NO: 300              moltype = RNA   length = 63
FEATURE                     Location/Qualifiers
source                      1..63
                            mol_type = unassigned RNA
                            organism = Homo sapiens
SEQUENCE: 300
accctagggt ggggctggag gtggggctga ggctgagtct tcctcccctt cctccctgcc   60
cag                                                                 63

SEQ ID NO: 301              moltype = RNA   length = 105
FEATURE                     Location/Qualifiers
source                      1..105
                            mol_type = unassigned RNA
                            organism = Homo sapiens
SEQUENCE: 301
gcgggcggcg gcggcggcag cagcagcagg tgcggggcgg cggccgcgct ggccgctcga   60
ctccgcagct gctcgttctg cttctccagc ttgcgcacca gctcc                  105

SEQ ID NO: 302              moltype = RNA   length = 63
FEATURE                     Location/Qualifiers
source                      1..63
                            mol_type = unassigned RNA
                            organism = Homo sapiens
SEQUENCE: 302
ggctccgcag ggcctggcg caggcatcca gacagcgggc gaatgcctcc cccggccccg    60
cag                                                                 63

SEQ ID NO: 303              moltype = RNA   length = 74
FEATURE                     Location/Qualifiers
source                      1..74
                            mol_type = unassigned RNA
                            organism = Homo sapiens
SEQUENCE: 303
gtgcgtggtg gctcgaggcg ggggtggggg cctcgccctg cttgggccct ccctgacctc   60
tccgctccgc acag                                                     74

SEQ ID NO: 304              moltype = RNA   length = 62
FEATURE                     Location/Qualifiers
source                      1..62
                            mol_type = unassigned RNA
                            organism = Homo sapiens
SEQUENCE: 304
tggcctaggg ggcggcttgt ggagtgtatg ggctgagcct tgctctgctc ccccgccccc   60
ag                                                                  62

SEQ ID NO: 305              moltype = RNA   length = 67
FEATURE                     Location/Qualifiers
source                      1..67
                            mol_type = unassigned RNA
                            organism = Homo sapiens
SEQUENCE: 305
gtgggagggg agaggcagca agcacacagg gcctgggact agcatgctga cctccctcct   60
gccccag                                                             67

SEQ ID NO: 306              moltype = RNA   length = 61
FEATURE                     Location/Qualifiers
source                      1..61
                            mol_type = unassigned RNA
                            organism = Homo sapiens
SEQUENCE: 306
gggggcggga gctgggtct gcaggttcgc actgatgcct gctcgccctg tctccgcta    60
g                                                                   61

SEQ ID NO: 307              moltype = RNA   length = 75
FEATURE                     Location/Qualifiers
source                      1..75
                            mol_type = unassigned RNA
                            organism = Homo sapiens
SEQUENCE: 307
ggctgtgccg ggtagagagg gcagtgggag gtaagagctc ttcacccttc accaccttct   60
ccacccagca tggcc                                                    75

SEQ ID NO: 308              moltype = RNA   length = 89
FEATURE                     Location/Qualifiers
source                      1..89
                            mol_type = unassigned RNA
                            organism = Homo sapiens
SEQUENCE: 308
```

```
gccggcgccc gagctctggc tccgtgtctt cactcccgtg cttgtccgag gagggaggga    60
gggacggggg ctgtgctggg gcagctgga                                      89

SEQ ID NO: 309            moltype = RNA   length = 61
FEATURE                   Location/Qualifiers
source                    1..61
                          mol_type = unassigned RNA
                          organism = Homo sapiens
SEQUENCE: 309
gtgcggaacg ctggccgggg cgggagggga agggacgccc ggccggaacg ccgcactcac    60
g                                                                    61

SEQ ID NO: 310            moltype = RNA   length = 70
FEATURE                   Location/Qualifiers
source                    1..70
                          mol_type = unassigned RNA
                          organism = Homo sapiens
SEQUENCE: 310
aaaagcctgt ccctaagtcc ctcccagcct tccagagttg gtgccaggaa ggatttaggg    60
acaggctttg                                                           70

SEQ ID NO: 311            moltype = RNA   length = 67
FEATURE                   Location/Qualifiers
source                    1..67
                          mol_type = unassigned RNA
                          organism = Homo sapiens
SEQUENCE: 311
gtgaggaggg gctggcaggg acccctccaa gttggggacg gcagccagcc cctgctcacc    60
cctcgcc                                                              67

SEQ ID NO: 312            moltype = RNA   length = 94
FEATURE                   Location/Qualifiers
source                    1..94
                          mol_type = unassigned RNA
                          organism = Homo sapiens
SEQUENCE: 312
cgggcagcgg gtgccaggca cggtgtcagc aggcaacatg gccgagaggc cggggcctcc    60
gggcggcgcc gtgtccgcga ccgcgtaccc tgac                                94

SEQ ID NO: 313            moltype = RNA   length = 92
FEATURE                   Location/Qualifiers
source                    1..92
                          mol_type = unassigned RNA
                          organism = Homo sapiens
SEQUENCE: 313
cctgtccctc ctgccctgcg cctgccagc cctcctgctc tggtgactga ggaccgccag     60
gcaggggctg gtgctgggcg gggggcggcg gg                                  92

SEQ ID NO: 314            moltype = RNA   length = 94
FEATURE                   Location/Qualifiers
source                    1..94
                          mol_type = unassigned RNA
                          organism = Homo sapiens
SEQUENCE: 314
aattcagccc tgccactggc ttatgtcatg accttgggct actcaggctg tctgcacaat    60
gagccagttg gacaggagca gtgccactca actc                                94

SEQ ID NO: 315            moltype = RNA   length = 60
FEATURE                   Location/Qualifiers
source                    1..60
                          mol_type = unassigned RNA
                          organism = Homo sapiens
SEQUENCE: 315
ggtgcctcgg gagggcatgg gccaggccac ataatgagcc aaacccctgt ctacccgcag    60

SEQ ID NO: 316            moltype = RNA   length = 92
FEATURE                   Location/Qualifiers
source                    1..92
                          mol_type = unassigned RNA
                          organism = Homo sapiens
SEQUENCE: 316
gtcagtgtct gggcggacag ctgcaggaaa gggaagacca aggcttgctg tctgtccagt    60
ctgccaccct accctgtctg ttcttgccac ag                                  92

SEQ ID NO: 317            moltype = RNA   length = 80
FEATURE                   Location/Qualifiers
source                    1..80
                          mol_type = unassigned RNA
                          organism = Homo sapiens
```

```
SEQUENCE: 317
cgggaatgcc gcggcgggga cggcgattgg tccgtatgtg tggtgccacc ggccgccggc    60
tccgccccgg cccccgcccc                                                80

SEQ ID NO: 318          moltype = RNA   length = 84
FEATURE                 Location/Qualifiers
source                  1..84
                        mol_type = unassigned RNA
                        organism = Homo sapiens
SEQUENCE: 318
ctccccatgg ccctgtctcc caacccttgt accagtgctg ggctcagacc ctggtacagg    60
cctgggggac agggacctgg ggac                                           84

SEQ ID NO: 319          moltype = RNA   length = 106
FEATURE                 Location/Qualifiers
source                  1..106
                        mol_type = unassigned RNA
                        organism = Homo sapiens
SEQUENCE: 319
agaagaatgc ccaaccagcc ctcagttgct acagttccct gttgtttcag ctcgacaaca    60
acaggcggct gtagcaatgg ggggctggat gggcatctca atgtgc                   106

SEQ ID NO: 320          moltype = RNA   length = 79
FEATURE                 Location/Qualifiers
source                  1..79
                        mol_type = unassigned RNA
                        organism = Homo sapiens
SEQUENCE: 320
gtgcagatcc ttgggagccc tgttagactc tggattttac acttggagtg aacgggcgcc    60
atcccgaggc tttgcacag                                                 79

SEQ ID NO: 321          moltype = RNA   length = 102
FEATURE                 Location/Qualifiers
source                  1..102
                        mol_type = unassigned RNA
                        organism = Homo sapiens
SEQUENCE: 321
gcttatcgag gaaaagatcg aggtgggttg gggcgggctc tggggatttg gtctcacagc    60
ccggatccca gcccacttac cttggttact ctccttcctt ct                       102

SEQ ID NO: 322          moltype = RNA   length = 90
FEATURE                 Location/Qualifiers
source                  1..90
                        mol_type = unassigned RNA
                        organism = Homo sapiens
SEQUENCE: 322
cgggcggggc gggtccggcc gcctccgagc ccggccggca gccccggcc ttaaagcgcg     60
ggctgtccgg aggggtcggc tttcccaccg                                     90

SEQ ID NO: 323          moltype = RNA   length = 59
FEATURE                 Location/Qualifiers
source                  1..59
                        mol_type = unassigned RNA
                        organism = Homo sapiens
SEQUENCE: 323
ggggccaggc agggaggtgg gaccatgggg gccttgctgt gtgaccaccg ttcctgcag     59

SEQ ID NO: 324          moltype = RNA   length = 62
FEATURE                 Location/Qualifiers
source                  1..62
                        mol_type = unassigned RNA
                        organism = Homo sapiens
SEQUENCE: 324
gtgagtagtg gcgcgcggcg gctcggagta cctctgccgc gcgcgcatc ggctcagcat     60
gc                                                                   62

SEQ ID NO: 325          moltype = RNA   length = 85
FEATURE                 Location/Qualifiers
source                  1..85
                        mol_type = unassigned RNA
                        organism = Homo sapiens
SEQUENCE: 325
tctgaggtac ccggggcaga ttggtgtagg gtgcaaagcc tgcccgcccc ctaagccttc    60
tgcccccaac tccagcctgt cagga                                          85

SEQ ID NO: 326          moltype = RNA   length = 96
FEATURE                 Location/Qualifiers
source                  1..96
                        mol_type = unassigned RNA
```

```
                               organism = Homo sapiens
SEQUENCE: 326
ctcgggaggg gcgggagggg ggtccccggt gctcggatct cgagggtgct tattgttcgg    60
tccgagcctg ggtctccctc ttccccccaa cccccc                              96

SEQ ID NO: 327          moltype = RNA   length = 80
FEATURE                 Location/Qualifiers
source                  1..80
                        mol_type = unassigned RNA
                        organism = Homo sapiens
SEQUENCE: 327
gcgtcaagat ggcggcgggg aggtaggcag agcaggacgc cgctgctgcc gccgccaccg    60
ccgcctccgc tccagtcgcc                                                80

SEQ ID NO: 328          moltype = RNA   length = 82
FEATURE                 Location/Qualifiers
source                  1..82
                        mol_type = unassigned RNA
                        organism = Homo sapiens
SEQUENCE: 328
tgagctgttg gattcggggc cgtagcactg tctgagaggt ttacatttct cacagtgaac    60
cggtctcttt ttcagctgct tc                                             82

SEQ ID NO: 329          moltype = RNA   length = 83
FEATURE                 Location/Qualifiers
source                  1..83
                        mol_type = unassigned RNA
                        organism = Homo sapiens
SEQUENCE: 329
gtgagtggga gccccagtgt gtggttgggg ccatggcggg tgggcagccc agcctctgag    60
ccttcctcgt ctgtctgccc cag                                            83

SEQ ID NO: 330          moltype = RNA   length = 87
FEATURE                 Location/Qualifiers
source                  1..87
                        mol_type = unassigned RNA
                        organism = Homo sapiens
SEQUENCE: 330
accgcaggga aaatgaggga cttttggggg cagatgtgtt tccattccac tatcataatg    60
cccctaaaaa tccttattgc tcttgca                                        87

SEQ ID NO: 331          moltype = RNA   length = 110
FEATURE                 Location/Qualifiers
source                  1..110
                        mol_type = unassigned RNA
                        organism = Homo sapiens
SEQUENCE: 331
ggctacagtc tttcttcatg tgactcgtgg acttcccttt gtcatcctat gcctgagaat    60
atatgaagga ggctgggaag gcaaagggac gttcaattgt catcactggc              110

SEQ ID NO: 332          moltype = RNA   length = 80
FEATURE                 Location/Qualifiers
source                  1..80
                        mol_type = unassigned RNA
                        organism = Homo sapiens
SEQUENCE: 332
ctgcagcgtg cttctccagg ccccgcgcgc ggacagacac acggacaagt cccgccaggg    60
gctgggcgcg cgccagccgg                                                80

SEQ ID NO: 333          moltype = RNA   length = 81
FEATURE                 Location/Qualifiers
source                  1..81
                        mol_type = unassigned RNA
                        organism = Homo sapiens
SEQUENCE: 333
ctccctggga gggcgtggat gatggtggga gaggagcccc actgtggaag tctgaccccc    60
acatcgcccc accttcccca g                                              81

SEQ ID NO: 334          moltype = RNA   length = 67
FEATURE                 Location/Qualifiers
source                  1..67
                        mol_type = unassigned RNA
                        organism = Homo sapiens
SEQUENCE: 334
cctgcaggca gaagtggggc tgacagggca gagggttgcg cccctcacc atcccttctg     60
cctgcag                                                              67

SEQ ID NO: 335          moltype = RNA   length = 67
FEATURE                 Location/Qualifiers
```

```
source                          1..67
                                mol_type = unassigned RNA
                                organism = Homo sapiens
SEQUENCE: 335
cctgcaggca gaagtggggc tgacagggca gagggttgcg cccccctcacc atcccttctg    60
cctgcag                                                               67

SEQ ID NO: 336                  moltype = RNA   length = 67
FEATURE                         Location/Qualifiers
source                          1..67
                                mol_type = unassigned RNA
                                organism = Homo sapiens
SEQUENCE: 336
cctgcaggca gaagtggggc tgacagggca gagggttgcg cccccctcacc atcccttctg    60
cctgcag                                                               67

SEQ ID NO: 337                  moltype = RNA   length = 67
FEATURE                         Location/Qualifiers
source                          1..67
                                mol_type = unassigned RNA
                                organism = Homo sapiens
SEQUENCE: 337
cctgcaggca gaagtggggc tgacagggca gagggttgcg cccccctcacc atcccttctg    60
cctgcag                                                               67

SEQ ID NO: 338                  moltype = RNA   length = 75
FEATURE                         Location/Qualifiers
source                          1..75
                                mol_type = unassigned RNA
                                organism = Homo sapiens
SEQUENCE: 338
gtcagagggg ggatgtgcat gctggttggg gtgggctgcc tgtggaccaa tcagcgtgca    60
cttccccacc ctgaa                                                     75

SEQ ID NO: 339                  moltype = RNA   length = 80
FEATURE                         Location/Qualifiers
source                          1..80
                                mol_type = unassigned RNA
                                organism = Homo sapiens
SEQUENCE: 339
tgagaggccg caccttgcct tgctgcccgg gccgtgcacc cgtgggcccc agggcgacgc    60
ggcggggggcg gccctagcga                                               80

SEQ ID NO: 340                  moltype = RNA   length = 153
FEATURE                         Location/Qualifiers
source                          1..153
                                mol_type = unassigned RNA
                                organism = Homo sapiens
SEQUENCE: 340
gctccgcccc acgtcgcatg cgccccggga acgcgtgggg cggagcttcc ggaggccccg    60
ctctgctgcc gacccgtgg agcggagggt gaagcctccg gatgccagtc cctcatcgct    120
ggcctggtcg cgctgtggcg aaggggggcgg agc                                153

SEQ ID NO: 341                  moltype = RNA   length = 153
FEATURE                         Location/Qualifiers
source                          1..153
                                mol_type = unassigned RNA
                                organism = Homo sapiens
SEQUENCE: 341
gctccgcccc acgtcgcatg cgccccggga acgcgtgggg cggagcttcc ggaggccccg    60
ccctgctgcc gacccgtgg agcggagggt gaagcctccg gatgccagtc cctcatcgct    120
ggcccggtcg cgctgtggcg aaggggggcgg agc                                153

SEQ ID NO: 342                  moltype = RNA   length = 66
FEATURE                         Location/Qualifiers
source                          1..66
                                mol_type = unassigned RNA
                                organism = Homo sapiens
SEQUENCE: 342
cagagcaggg cagggaaggt gggagagggg cccagctgac cctcctgtca cccgctcctt    60
gcccag                                                               66

SEQ ID NO: 343                  moltype = RNA   length = 119
FEATURE                         Location/Qualifiers
source                          1..119
                                mol_type = unassigned RNA
                                organism = Homo sapiens
SEQUENCE: 343
agcctgcgcc ggagccgggg cctgagcccg ggccgcgcag gccgtgaact cgtcgagctg    60
```

```
cgcgtgcggc cggtgctcaa cctgccgggt cctggcccg cgctcccgcg cgccctgga      119

SEQ ID NO: 344         moltype = RNA   length = 63
FEATURE                Location/Qualifiers
source                 1..63
                       mol_type = unassigned RNA
                       organism = Homo sapiens
SEQUENCE: 344
cttgcccggg agaaggaggt ggcctggaga gctgctgtct ccagccgccg cctgtctcca      60
cag                                                                   63

SEQ ID NO: 345         moltype = RNA   length = 76
FEATURE                Location/Qualifiers
source                 1..76
                       mol_type = unassigned RNA
                       organism = Homo sapiens
SEQUENCE: 345
actgactttg agtctctcct cagggtgctg caggcaaagc tggggaccca gggagagacg      60
taagtgaggg gagatg                                                     76

SEQ ID NO: 346         moltype = RNA   length = 115
FEATURE                Location/Qualifiers
source                 1..115
                       mol_type = unassigned RNA
                       organism = Homo sapiens
SEQUENCE: 346
ggtgccgagg gccgtccggc atcctaggcg ggtcgctgcg gtacctccct cctgtctgtg      60
gcggtgggat cccgtggccg tgttttcctg gtggcccggc cgtgcctgag gtttc          115

SEQ ID NO: 347         moltype = RNA   length = 80
FEATURE                Location/Qualifiers
source                 1..80
                       mol_type = unassigned RNA
                       organism = Homo sapiens
SEQUENCE: 347
ggttccggag ccccggcgcg ggcgggttct ggggtgtaga cgctgctggc cagcccgccc      60
cagccgaggt tctcggcacc                                                 80

SEQ ID NO: 348         moltype = RNA   length = 69
FEATURE                Location/Qualifiers
source                 1..69
                       mol_type = unassigned RNA
                       organism = Homo sapiens
SEQUENCE: 348
ccgggcaggc aggtgtaggg tggagcccac tgtggctcct gactcagccc tgctgccttc      60
acctgccag                                                             69

SEQ ID NO: 349         moltype = RNA   length = 77
FEATURE                Location/Qualifiers
source                 1..77
                       mol_type = unassigned RNA
                       organism = Homo sapiens
SEQUENCE: 349
catgagaaat cctgctggtc aaccatagcc ctggtcagac tctccggggc tgtgattgac      60
cagcaggact tctcatg                                                    77

SEQ ID NO: 350         moltype = RNA   length = 68
FEATURE                Location/Qualifiers
source                 1..68
                       mol_type = unassigned RNA
                       organism = Homo sapiens
SEQUENCE: 350
gactcggctg cggtggacaa gtccggctcc agaacctgga caccgctcag ccggccgcgg      60
cagggtc                                                               68

SEQ ID NO: 351         moltype = RNA   length = 73
FEATURE                Location/Qualifiers
source                 1..73
                       mol_type = unassigned RNA
                       organism = Homo sapiens
SEQUENCE: 351
cggcgacggc ggggtgggtg aggtcgggcc ccaagactcg gggtttgccg ggcgcctcag      60
ttcaccgcgg ccg                                                        73

SEQ ID NO: 352         moltype = RNA   length = 49
FEATURE                Location/Qualifiers
source                 1..49
                       mol_type = unassigned RNA
                       organism = Homo sapiens
```

```
SEQUENCE: 352
ggtgaggcgg gggggcgagc cctgagggc tctcgcttct ggcgccaag                49

SEQ ID NO: 353          moltype = RNA   length = 79
FEATURE                 Location/Qualifiers
source                  1..79
                        mol_type = unassigned RNA
                        organism = Homo sapiens
SEQUENCE: 353
ctcgaggtgc tgggggacgc gtgagcgcga ccgcttcct cacggctcgg ccgcggcgcg    60
tagccccgc cacatcggg                                                 79

SEQ ID NO: 354          moltype = RNA   length = 71
FEATURE                 Location/Qualifiers
source                  1..71
                        mol_type = unassigned RNA
                        organism = Homo sapiens
SEQUENCE: 354
ggtgagtggg agccggtggg gctggagtaa gggcacgccc ggggctgccc cacctgctga   60
ccaccctccc c                                                        71

SEQ ID NO: 355          moltype = RNA   length = 65
FEATURE                 Location/Qualifiers
source                  1..65
                        mol_type = unassigned RNA
                        organism = Homo sapiens
SEQUENCE: 355
gagaatgggg ggacagatgg agaggacaca ggctggcact gaggtcccct ccactttcct   60
cctag                                                               65

SEQ ID NO: 356          moltype = RNA   length = 79
FEATURE                 Location/Qualifiers
source                  1..79
                        mol_type = unassigned RNA
                        organism = Homo sapiens
SEQUENCE: 356
gtgaggtggg ggccagcagg gagtgggctg ggctgggctg ggccaaggta caaggcctca   60
ccctgcatcc cgcacccag                                                79

SEQ ID NO: 357          moltype = RNA   length = 80
FEATURE                 Location/Qualifiers
source                  1..80
                        mol_type = unassigned RNA
                        organism = Homo sapiens
SEQUENCE: 357
catccaggac aatggtgagt gccggtgcct gccctggggc cgtccctgcg caggggccgg   60
gtgctcaccg catctgcccc                                               80

SEQ ID NO: 358          moltype = RNA   length = 61
FEATURE                 Location/Qualifiers
source                  1..61
                        mol_type = unassigned RNA
                        organism = Homo sapiens
SEQUENCE: 358
tctcgtttga tctcggaagc taagcagggt tgggcctggt tagtacttgg atgggaaact   60
t                                                                   61

SEQ ID NO: 359          moltype = RNA   length = 53
FEATURE                 Location/Qualifiers
source                  1..53
                        mol_type = unassigned RNA
                        organism = Homo sapiens
SEQUENCE: 359
gtttgatctc ggaagctaag cagggtcggg cctggttagt acttggatgg gag          53

SEQ ID NO: 360          moltype = RNA   length = 92
FEATURE                 Location/Qualifiers
source                  1..92
                        mol_type = unassigned RNA
                        organism = Homo sapiens
SEQUENCE: 360
cgctgcgctt ctgggcccgc ggcgggcgtg gggctgcccg ggccggtcga ccagcgcgcc   60
gtagctcccg aggcccgagc cgcgacccgc gg                                 92

SEQ ID NO: 361          moltype = RNA   length = 84
FEATURE                 Location/Qualifiers
source                  1..84
                        mol_type = unassigned RNA
                        organism = Homo sapiens
```

```
SEQUENCE: 361
gctggcgtcg gtgctgggga gcggcccccg ggtgggcctc tgctctggcc cctcctgggg    60
cccgcactct cgctctgggc ccgc                                          84

SEQ ID NO: 362            moltype = RNA   length = 79
FEATURE                   Location/Qualifiers
source                    1..79
                          mol_type = unassigned RNA
                          organism = Homo sapiens
SEQUENCE: 362
cagcctgggg aaggcttggc agggaagaca catgagcagt gcctccactt cacgcctctc    60
ccttgtctcc tttccctag                                                79

SEQ ID NO: 363            moltype = RNA   length = 83
FEATURE                   Location/Qualifiers
source                    1..83
                          mol_type = unassigned RNA
                          organism = Homo sapiens
SEQUENCE: 363
gggtttcctc tgccttttt tccaatgaaa ataacgaaac ctgttatttc ccattgaggg     60
ggaaaaaggc gggagaagcc cca                                           83

SEQ ID NO: 364            moltype = RNA   length = 60
FEATURE                   Location/Qualifiers
source                    1..60
                          mol_type = unassigned RNA
                          organism = Homo sapiens
SEQUENCE: 364
gagcaggcga ggctgggctg aacccgtggg tgaggagtgc agcccagctg aggcctctgc    60

SEQ ID NO: 365            moltype = RNA   length = 73
FEATURE                   Location/Qualifiers
source                    1..73
                          mol_type = unassigned RNA
                          organism = Homo sapiens
SEQUENCE: 365
agggagaaaa gctgggctga gaggcgactg gtgtctaatt tgtttgtctc tccaactcag    60
actgcctggc cca                                                      73

SEQ ID NO: 366            moltype = RNA   length = 88
FEATURE                   Location/Qualifiers
source                    1..88
                          mol_type = unassigned RNA
                          organism = Homo sapiens
SEQUENCE: 366
gtggggccag gcggtggtgg gcactgctgg ggtgggcaca gcagccatgc agagcgggca    60
tttgaccccg tgccacccct ttccccag                                      88

SEQ ID NO: 367            moltype = RNA   length = 90
FEATURE                   Location/Qualifiers
source                    1..90
                          mol_type = unassigned RNA
                          organism = Homo sapiens
SEQUENCE: 367
gtgtctctct ggagaccctg cagccttccc acccaccagg gagctttcca tgggctgtgg    60
ggaaggcgtc agtgtcgggt gagggaacac                                    90

SEQ ID NO: 368            moltype = RNA   length = 64
FEATURE                   Location/Qualifiers
source                    1..64
                          mol_type = unassigned RNA
                          organism = Homo sapiens
SEQUENCE: 368
gaggcactgg gtaggtgggg ctccagggct cctgacacct ggacctctcc tccccaggcc    60
caca                                                                64

SEQ ID NO: 369            moltype = RNA   length = 64
FEATURE                   Location/Qualifiers
source                    1..64
                          mol_type = unassigned RNA
                          organism = Homo sapiens
SEQUENCE: 369
tgaggatggg gtgagatggg gaggagcagc cagtcctgtc tcaccgctct tccctgacc    60
ccag                                                                64

SEQ ID NO: 370            moltype = RNA   length = 73
FEATURE                   Location/Qualifiers
source                    1..73
                          mol_type = unassigned RNA
```

```
                             organism = Homo sapiens
SEQUENCE: 370
ggcgagggga ggcgcaggct cggaaaggcg cgcgaggctc caggctcctt cccgatccac    60
cgctctcctc gct                                                       73

SEQ ID NO: 371           moltype = RNA   length = 81
FEATURE                  Location/Qualifiers
source                   1..81
                         mol_type = unassigned RNA
                         organism = Homo sapiens
SEQUENCE: 371
tacaggtgca ggggaactgt agatgaaaag gcttggcact tgagggaaag cctcagttca    60
ttctcatttt gctcacctgt t                                              81

SEQ ID NO: 372           moltype = RNA   length = 68
FEATURE                  Location/Qualifiers
source                   1..68
                         mol_type = unassigned RNA
                         organism = Homo sapiens
SEQUENCE: 372
gaatggaaga agaaggcggt cggtctgcgg gagccaggcc gcagagccat ccgccttctg    60
tccatgtc                                                             68

SEQ ID NO: 373           moltype = RNA   length = 82
FEATURE                  Location/Qualifiers
source                   1..82
                         mol_type = unassigned RNA
                         organism = Homo sapiens
SEQUENCE: 373
gctacgggga gcggggagga agtgggcgct gcttctgcgt tatctggaag gagcagccca    60
ctcctgtcct gggctctgtg gt                                             82

SEQ ID NO: 374           moltype = RNA   length = 89
FEATURE                  Location/Qualifiers
source                   1..89
                         mol_type = unassigned RNA
                         organism = Homo sapiens
SEQUENCE: 374
acctccggga cggctgggcg ccggcggccg ggagatccgc gcttcctgaa tcccggccgg    60
cccgcccggc gcccgtccgc ccgcgggtc                                      89

SEQ ID NO: 375           moltype = RNA   length = 63
FEATURE                  Location/Qualifiers
source                   1..63
                         mol_type = unassigned RNA
                         organism = Homo sapiens
SEQUENCE: 375
gagtcgagga ctggtggaag ggcctttccc ctcagaccaa ggccctggcc ccagcttctt    60
ctc                                                                  63

SEQ ID NO: 376           moltype = RNA   length = 64
FEATURE                  Location/Qualifiers
source                   1..64
                         mol_type = unassigned RNA
                         organism = Homo sapiens
SEQUENCE: 376
tgctctgtag gcatgaggca gggcccaggt tccatgtgat gctgaagctc tgacattcct    60
gcag                                                                 64

SEQ ID NO: 377           moltype = RNA   length = 109
FEATURE                  Location/Qualifiers
source                   1..109
                         mol_type = unassigned RNA
                         organism = Homo sapiens
SEQUENCE: 377
ggtcgggctc accatgacac agtgtgagac ctcgggctac aacacaggac ccgggcgctg    60
ctctgacccc tcgtgtcttg tgttgcagcc ggagggacgc aggtccgca              109

SEQ ID NO: 378           moltype = RNA   length = 94
FEATURE                  Location/Qualifiers
source                   1..94
                         mol_type = unassigned RNA
                         organism = Homo sapiens
SEQUENCE: 378
cagtgcgacg ggcggagctt ccagacgctc cgcccacgt cgcatgcgcc ccgggaaagc     60
gtgggcgga gcttccggag gccccgccct gctg                                 94

SEQ ID NO: 379           moltype = RNA   length = 88
FEATURE                  Location/Qualifiers
```

```
                        source          1..88
                                        mol_type = unassigned RNA
                                        organism = Homo sapiens
SEQUENCE: 379
gcgacgggcg gagcttccag acgctccgcc ccacgtcgca tgcgcccggg gaaagcgtgg    60
ggcggagctt ccggaggccc cgccctgc                                      88

SEQ ID NO: 380          moltype = RNA   length = 94
FEATURE                 Location/Qualifiers
source                  1..94
                        mol_type = unassigned RNA
                        organism = Homo sapiens
SEQUENCE: 380
cagtgcgacg ggcggagctt ccagacgctc gccccacgt cgcatgcgcc ccgggaaagc    60
gtggggcgga gcttccggag gccccgccct gctg                              94

SEQ ID NO: 381          moltype = RNA   length = 70
FEATURE                 Location/Qualifiers
source                  1..70
                        mol_type = unassigned RNA
                        organism = Homo sapiens
SEQUENCE: 381
gtccctgggg gctgggatgg gccatggtgt gctctgatcc ccctgtggtc tcttggcccc    60
caggaactcc                                                          70

SEQ ID NO: 382          moltype = RNA   length = 62
FEATURE                 Location/Qualifiers
source                  1..62
                        mol_type = unassigned RNA
                        organism = Homo sapiens
SEQUENCE: 382
ccttctgcgg cagagctggg gtcaccagcc ctcatgtact tgtgacttct ccctgccac    60
ag                                                                  62

SEQ ID NO: 383          moltype = RNA   length = 82
FEATURE                 Location/Qualifiers
source                  1..82
                        mol_type = unassigned RNA
                        organism = Homo sapiens
SEQUENCE: 383
acctgtaggt gacagtcagg ggcggggtgt ggtggggctg gggctggccc ctcctcaca    60
cctctcctgg catcgccccc ag                                            82

SEQ ID NO: 384          moltype = RNA   length = 73
FEATURE                 Location/Qualifiers
source                  1..73
                        mol_type = unassigned RNA
                        organism = Homo sapiens
SEQUENCE: 384
ctggtgtttg aggcgatgtg gggatgtaga gacaacttcc cagtctcatt tcctcatcct    60
gccaggccac cat                                                      73

SEQ ID NO: 385          moltype = RNA   length = 68
FEATURE                 Location/Qualifiers
source                  1..68
                        mol_type = unassigned RNA
                        organism = Homo sapiens
SEQUENCE: 385
agggttgggg ggacaggatg agaggctgtc ttcattccct cttgaccacc cctcgtttct    60
tccccccag                                                           68

SEQ ID NO: 386          moltype = RNA   length = 61
FEATURE                 Location/Qualifiers
source                  1..61
                        mol_type = unassigned RNA
                        organism = Homo sapiens
SEQUENCE: 386
gagggcagcg tgggtgtggc ggaggcaggc gtgaccgttt gccgccctct cgctgctcta    60
g                                                                   61

SEQ ID NO: 387          moltype = RNA   length = 72
FEATURE                 Location/Qualifiers
source                  1..72
                        mol_type = unassigned RNA
                        organism = Homo sapiens
SEQUENCE: 387
tctcctcgag gggtctctgc ctctacccag gactctttca tgaccaggag gctgaggccc    60
ctcacaggcg gc                                                       72
```

```
SEQ ID NO: 388            moltype = RNA   length = 73
FEATURE                   Location/Qualifiers
source                    1..73
                          mol_type = unassigned RNA
                          organism = Homo sapiens
SEQUENCE: 388
gttcaagtgg gaggacagga ggcaggtgtg gttggaggaa gcagcctgaa cctgcctccc    60
tgacattcca cag                                                      73

SEQ ID NO: 389            moltype = RNA   length = 97
FEATURE                   Location/Qualifiers
source                    1..97
                          mol_type = unassigned RNA
                          organism = Homo sapiens
SEQUENCE: 389
cccgggacct tggtccaggc gctggtctgc gtggtgctcg ggtggataag tctgatctga    60
gcaccacaca ggccgggcgc cgggaccaag ggggctc                             97

SEQ ID NO: 390            moltype = RNA   length = 70
FEATURE                   Location/Qualifiers
source                    1..70
                          mol_type = unassigned RNA
                          organism = Homo sapiens
SEQUENCE: 390
ggtttctcct tgaggagaca tggtgggggc cggtcaggca gcccatgcca tgtgtcctca    60
tggagaggcc                                                          70

SEQ ID NO: 391            moltype = RNA   length = 110
FEATURE                   Location/Qualifiers
source                    1..110
                          mol_type = unassigned RNA
                          organism = Homo sapiens
SEQUENCE: 391
tcacctggcc atgtgacttg tgggcttccc tttgtcatcc ttcgcctagg gctctgagca    60
gggcaggac agcaaagggg tgctcagttg tcacttccca cagcacggag               110

SEQ ID NO: 392            moltype = RNA   length = 85
FEATURE                   Location/Qualifiers
source                    1..85
                          mol_type = unassigned RNA
                          organism = Homo sapiens
SEQUENCE: 392
gggacggggc ctgcaggcag aagtgggggct gacagggcag agggttgcgc cccctcacca   60
cccttctgc ctgcagcggt gggct                                          85

SEQ ID NO: 393            moltype = RNA   length = 71
FEATURE                   Location/Qualifiers
source                    1..71
                          mol_type = unassigned RNA
                          organism = Homo sapiens
SEQUENCE: 393
ggggcctgca ggcagaagtg gggctgacag ggcagagggt tgcgcccct caccaccct    60
tctgcctgca g                                                        71

SEQ ID NO: 394            moltype = RNA   length = 56
FEATURE                   Location/Qualifiers
source                    1..56
                          mol_type = unassigned RNA
                          organism = Homo sapiens
SEQUENCE: 394
cgctcgggcg gaggtggttg agtgccgact ggcgcctgac ccaccccctc ccgcag        56

SEQ ID NO: 395            moltype = RNA   length = 89
FEATURE                   Location/Qualifiers
source                    1..89
                          mol_type = unassigned RNA
                          organism = Homo sapiens
SEQUENCE: 395
agcctgtggg aaagagaaga gcagggcagg gtgaaggccc ggcggagaca ctctgcccac    60
cccacaccct gcctatgggc cacacagct                                     89

SEQ ID NO: 396            moltype = RNA   length = 90
FEATURE                   Location/Qualifiers
source                    1..90
                          mol_type = unassigned RNA
                          organism = Homo sapiens
SEQUENCE: 396
tctaagaaac gcagtggtct ctgaagcctg caggggcagg ccagccctgc actgaacgcc    60
tgttcttgcc aggtggcaga aggttgctgc                                    90
```

```
SEQ ID NO: 397          moltype = RNA    length = 86
FEATURE                 Location/Qualifiers
source                  1..86
                        mol_type = unassigned RNA
                        organism = Homo sapiens
SEQUENCE: 397
ggggctgggg gtgtgggag agagagtgca cagccagctc agggattaaa gctctttctc    60
tctctctctc tcccacttcc ctgcag                                        86

SEQ ID NO: 398          moltype = RNA    length = 98
FEATURE                 Location/Qualifiers
source                  1..98
                        mol_type = unassigned RNA
                        organism = Homo sapiens
SEQUENCE: 398
ttgggcaagg tgcggggcta gggctaacag cagtcttact gaaggtttcc tggaaaccac    60
gcacatgctg ttgccactaa cctcaacctt actcggtc                            98

SEQ ID NO: 399          moltype = RNA    length = 73
FEATURE                 Location/Qualifiers
source                  1..73
                        mol_type = unassigned RNA
                        organism = Homo sapiens
SEQUENCE: 399
aggccaggtg ggtatggagg agccctcata tggcagttgg cgagggccca gtgagcccct    60
ctctgctctc cag                                                      73

SEQ ID NO: 400          moltype = RNA    length = 74
FEATURE                 Location/Qualifiers
source                  1..74
                        mol_type = unassigned RNA
                        organism = Homo sapiens
SEQUENCE: 400
gcagcccggt gagcgctcgc tggcctggca gtgcgtcgga agaacagggc gggtggggcc    60
gcgcacatct ctgc                                                     74

SEQ ID NO: 401          moltype = RNA    length = 55
FEATURE                 Location/Qualifiers
source                  1..55
                        mol_type = unassigned RNA
                        organism = Homo sapiens
SEQUENCE: 401
gggggctggg gcgcggggag gtgctaggtc ggcctcggct cccgcgccgc acccc          55

SEQ ID NO: 402          moltype = RNA    length = 67
FEATURE                 Location/Qualifiers
source                  1..67
                        mol_type = unassigned RNA
                        organism = Homo sapiens
SEQUENCE: 402
ggcagccagg gggatgggcg agcttgggcc cattcctttc cttaccctac cccccatccc    60
cctgtag                                                             67

SEQ ID NO: 403          moltype = RNA    length = 64
FEATURE                 Location/Qualifiers
source                  1..64
                        mol_type = unassigned RNA
                        organism = Homo sapiens
SEQUENCE: 403
aaccccgggc cggaggtcaa gggcgtcgct tctccctaat gttgcctctt ttccacggcc    60
tcag                                                                64

SEQ ID NO: 404          moltype = RNA    length = 68
FEATURE                 Location/Qualifiers
source                  1..68
                        mol_type = unassigned RNA
                        organism = Homo sapiens
SEQUENCE: 404
ctcaggctca gtggtgcatg cttatagtcc cagccactct ggaggctgaa ggaagatggc    60
ttgagcct                                                            68

SEQ ID NO: 405          moltype = RNA    length = 67
FEATURE                 Location/Qualifiers
source                  1..67
                        mol_type = unassigned RNA
                        organism = Homo sapiens
SEQUENCE: 405
ctggtccatt tccctgccat tcccttggct tcaatttact cccagggctg gcagtgacat    60
```

```
gggtcaa                                                                     67

SEQ ID NO: 406          moltype = RNA   length = 101
FEATURE                 Location/Qualifiers
source                  1..101
                        mol_type = unassigned RNA
                        organism = Homo sapiens
SEQUENCE: 406
gatgggcccc ttgtgtcctg aattgggtgg gggctctgag tggggaaagt gggggcctag           60
gggaggtcac agttgggtct aggggtcagg agggcccagg a                              101

SEQ ID NO: 407          moltype = RNA   length = 137
FEATURE                 Location/Qualifiers
source                  1..137
                        mol_type = unassigned RNA
                        organism = Homo sapiens
SEQUENCE: 407
agccagacaa gagggtcatg gggagtcact gtcaacccag agcaggcact gcccctgcga           60
ccagcctggg gcatcggttg gggtgcaggg gtctgctggt gatgctttcc atctctttgc          120
tttgtcctga ttgtagc                                                         137

SEQ ID NO: 408          moltype = RNA   length = 95
FEATURE                 Location/Qualifiers
source                  1..95
                        mol_type = unassigned RNA
                        organism = Homo sapiens
SEQUENCE: 408
gacaccacat gctcctccag gcctgcctgc cctccaggtc atgttccagt gtcccacaga           60
tgcagcacca cggcccaggc ggcattggtg tcacc                                      95

SEQ ID NO: 409          moltype = RNA   length = 80
FEATURE                 Location/Qualifiers
source                  1..80
                        mol_type = unassigned RNA
                        organism = Homo sapiens
SEQUENCE: 409
aggacccttc cagagggccc ccctcaatc ctgttgtgcc taattcagag ggttgggtgg            60
aggctctcct gaagggctct                                                       80

SEQ ID NO: 410          moltype = RNA   length = 93
FEATURE                 Location/Qualifiers
source                  1..93
                        mol_type = unassigned RNA
                        organism = Homo sapiens
SEQUENCE: 410
gtaaggaggg ggatgagggg tcatatctct tctcagggaa agcaggagcc cttcagcagg           60
gtcagggccc ctcatcttcc cctcctttcc cag                                        93

SEQ ID NO: 411          moltype = RNA   length = 62
FEATURE                 Location/Qualifiers
source                  1..62
                        mol_type = unassigned RNA
                        organism = Homo sapiens
SEQUENCE: 411
gtgagtgggg ctcccgggac ggcgcccgcc ctggccctgg cccggcgacg tctcacggtc           60
cc                                                                          62

SEQ ID NO: 412          moltype = RNA   length = 69
FEATURE                 Location/Qualifiers
source                  1..69
                        mol_type = unassigned RNA
                        organism = Homo sapiens
SEQUENCE: 412
gaacctcggg gcatgggga gggaggctgg acaggagagg gctcacccag gccctgtcct            60
ctgcccag                                                                    69

SEQ ID NO: 413          moltype = RNA   length = 60
FEATURE                 Location/Qualifiers
source                  1..60
                        mol_type = unassigned RNA
                        organism = Homo sapiens
SEQUENCE: 413
caaggtgggg gagatggggg ttgaacttca tttctcatgc tcatccccat ctcctttcag           60

SEQ ID NO: 414          moltype = RNA   length = 75
FEATURE                 Location/Qualifiers
source                  1..75
                        mol_type = unassigned RNA
                        organism = Homo sapiens
```

```
SEQUENCE: 414
gtagttgttc tacagaagac ctggatgtgt aggagctaag acacactcca ggggagctgt    60
ggaagcagta acacg                                                    75

SEQ ID NO: 415          moltype = RNA  length = 56
FEATURE                 Location/Qualifiers
source                  1..56
                        mol_type = unassigned RNA
                        organism = Homo sapiens
SEQUENCE: 415
cgaccgcacc cgcccgaagc tgggtcaagg agcccagcag gacgggagcg cggcgc        56

SEQ ID NO: 416          moltype = RNA  length = 61
FEATURE                 Location/Qualifiers
source                  1..61
                        mol_type = unassigned RNA
                        organism = Homo sapiens
SEQUENCE: 416
gagggttggg gtggagggcc aaggagctgg gtggggtgcc aagcctctgt ccccacccca    60
g                                                                   61

SEQ ID NO: 417          moltype = RNA  length = 66
FEATURE                 Location/Qualifiers
source                  1..66
                        mol_type = unassigned RNA
                        organism = Homo sapiens
SEQUENCE: 417
gggcatgggg aggtgtggag tcagcatggg gctaggaggc cccgcgctga cccgccttct    60
ccgcag                                                              66

SEQ ID NO: 418          moltype = RNA  length = 103
FEATURE                 Location/Qualifiers
source                  1..103
                        mol_type = unassigned RNA
                        organism = Homo sapiens
SEQUENCE: 418
gtgtcggctg tggcgtgact gtccctctgt gtcccccact aggcccactg ctcagtggag    60
cgtggaggac gaggaggagg ccgtccacga gcaatgccag cat                     103

SEQ ID NO: 419          moltype = RNA  length = 109
FEATURE                 Location/Qualifiers
source                  1..109
                        mol_type = unassigned RNA
                        organism = Homo sapiens
SEQUENCE: 419
tcccgcattc cctctgcttt ggtcaggtgg tgccctcctt ccatgggtag agccagagat    60
ggtgggttct ggctggtcag atgggagtgg acagagaccc ggggtcctc               109

SEQ ID NO: 420          moltype = RNA  length = 81
FEATURE                 Location/Qualifiers
source                  1..81
                        mol_type = unassigned RNA
                        organism = Homo sapiens
SEQUENCE: 420
catcctcctt acgtcccacc ccccactcct gtttctggtg aaatattcaa acaggagtgg    60
gggtgggaca taaggaggat a                                             81

SEQ ID NO: 421          moltype = RNA  length = 73
FEATURE                 Location/Qualifiers
source                  1..73
                        mol_type = unassigned RNA
                        organism = Homo sapiens
SEQUENCE: 421
gtgggcgggg gcaggtgtgt ggtgggtggt ggcctgcggt gagcagggcc ctcacacctg    60
cctcgccccc cag                                                      73

SEQ ID NO: 422          moltype = RNA  length = 71
FEATURE                 Location/Qualifiers
source                  1..71
                        mol_type = unassigned RNA
                        organism = Homo sapiens
SEQUENCE: 422
gggtaaaggg gcaggacgg gtggccccag gaagaagggc ctggtggagc cgctcttctc     60
cctgcccaca g                                                        71

SEQ ID NO: 423          moltype = RNA  length = 52
FEATURE                 Location/Qualifiers
source                  1..52
                        mol_type = unassigned RNA
```

```
                        organism = Homo sapiens
SEQUENCE: 423
tagccgggcg tggtggtggg ggcctgtggt cccagctact ttggaggctg ag            52

SEQ ID NO: 424          moltype = RNA   length = 93
FEATURE                 Location/Qualifiers
source                  1..93
                        mol_type = unassigned RNA
                        organism = Homo sapiens
SEQUENCE: 424
ggcgcttttg tgcgcgcccg ggtctgttgg tgctcagagt gtggtcaggc ggctcggact    60
gagcaggtgg gtgcggggct cggaggaggc ggc                                 93

SEQ ID NO: 425          moltype = RNA   length = 113
FEATURE                 Location/Qualifiers
source                  1..113
                        mol_type = unassigned RNA
                        organism = Homo sapiens
SEQUENCE: 425
gccgggtggg gcgggcggc ctcaggaggg gcccagctcc cctggatgtg ctgcggtggg     60
gccggagggg cgtcacgtgc acccaagtga cgccccttct gattctgcct cag          113

SEQ ID NO: 426          moltype = RNA   length = 84
FEATURE                 Location/Qualifiers
source                  1..84
                        mol_type = unassigned RNA
                        organism = Homo sapiens
SEQUENCE: 426
ggcccctcct tctcagcccc agctcccgct caccctgcc acgtcaaagg aggcagaagg     60
ggagttggga gcagagaggg gacc                                           84

SEQ ID NO: 427          moltype = RNA   length = 100
FEATURE                 Location/Qualifiers
source                  1..100
                        mol_type = unassigned RNA
                        organism = Homo sapiens
SEQUENCE: 427
gtgagcgggc gcggcaggga tcgcgggcgg gtggcggcct agggcgcgga gggcggaccg    60
ggaatggcgc gccgtgcgcc gccggcgtaa ctgcggcgct                         100

SEQ ID NO: 428          moltype = RNA   length = 63
FEATURE                 Location/Qualifiers
source                  1..63
                        mol_type = unassigned RNA
                        organism = Homo sapiens
SEQUENCE: 428
aatgggtggg tgctggtggg agccgtgccc tggccactca ttcggctctc tccctcaccc    60
tag                                                                  63

SEQ ID NO: 429          moltype = RNA   length = 59
FEATURE                 Location/Qualifiers
source                  1..59
                        mol_type = unassigned RNA
                        organism = Homo sapiens
SEQUENCE: 429
ctgtgtcggg gagtctgggg tccggaattc tccagagcct ctgtgccct acttcccag      59

SEQ ID NO: 430          moltype = RNA   length = 71
FEATURE                 Location/Qualifiers
source                  1..71
                        mol_type = unassigned RNA
                        organism = Homo sapiens
SEQUENCE: 430
tgaccacccc cgggcaaaga cctgcagatc ccctgttaga dacgggccca ggactttgtg    60
cggggtgccc a                                                         71

SEQ ID NO: 431          moltype = RNA   length = 54
FEATURE                 Location/Qualifiers
source                  1..54
                        mol_type = unassigned RNA
                        organism = Homo sapiens
SEQUENCE: 431
agcagcaggg gagagagagg agtcctctag acaccgactc tgtctcctgc agat          54

SEQ ID NO: 432          moltype = RNA   length = 85
FEATURE                 Location/Qualifiers
source                  1..85
                        mol_type = unassigned RNA
                        organism = Homo sapiens
```

```
SEQUENCE: 432
ggcgcctcct gctctgctgt gccgccaggg cctccctag cgcgccttct ggagaggctt    60
tgtgcggata cggggctgga ggcct                                         85

SEQ ID NO: 433          moltype = RNA   length = 96
FEATURE                 Location/Qualifiers
source                  1..96
                        mol_type = unassigned RNA
                        organism = Homo sapiens
SEQUENCE: 433
agatgtgctc tcctggccca tgaaatcaag cgtgggtgag acctggtgca gaacgggaag    60
gcgacccata cttggtttca gaggctgtga gaataa                              96

SEQ ID NO: 434          moltype = RNA   length = 100
FEATURE                 Location/Qualifiers
source                  1..100
                        mol_type = unassigned RNA
                        organism = Homo sapiens
SEQUENCE: 434
agctcagggc ggctgcgcag agggctggac tcagcggcgg agctggctgc tggcctcagt    60
tctgcctctg tccaggtcct tgtgacccgc ccgctctcct                         100

SEQ ID NO: 435          moltype = RNA   length = 50
FEATURE                 Location/Qualifiers
source                  1..50
                        mol_type = unassigned RNA
                        organism = Homo sapiens
SEQUENCE: 435
acccgggcgt ggtggtgggg gtgggtgcct gtaattccag ctagttggga               50

SEQ ID NO: 436          moltype = RNA   length = 80
FEATURE                 Location/Qualifiers
source                  1..80
                        mol_type = unassigned RNA
                        organism = Homo sapiens
SEQUENCE: 436
tgccgtcggc ctggggagga ggaagggcaa gtccaaaggt atacagttgg tctgttcatt    60
ctctcttttt ggcctacaag                                                80

SEQ ID NO: 437          moltype = RNA   length = 63
FEATURE                 Location/Qualifiers
source                  1..63
                        mol_type = unassigned RNA
                        organism = Homo sapiens
SEQUENCE: 437
gaggtgtagg ggaggttggg ccagggatgc cttcactgtg tctctctggt cttgccaccc    60
cag                                                                  63

SEQ ID NO: 438          moltype = RNA   length = 60
FEATURE                 Location/Qualifiers
source                  1..60
                        mol_type = unassigned RNA
                        organism = Homo sapiens
SEQUENCE: 438
aggcctaggg ggtggcaggc tggccatcag tgtgggctaa ccctgtcctc tccctcccag    60

SEQ ID NO: 439          moltype = RNA   length = 67
FEATURE                 Location/Qualifiers
source                  1..67
                        mol_type = unassigned RNA
                        organism = Homo sapiens
SEQUENCE: 439
gtggcactca aactgtgggg gcactttctg ctctctggtg aaagtgccgc catcttttga    60
gtgttac                                                              67

SEQ ID NO: 440          moltype = RNA   length = 68
FEATURE                 Location/Qualifiers
source                  1..68
                        mol_type = unassigned RNA
                        organism = Homo sapiens
SEQUENCE: 440
gggcgcaggg ggactggggg tgagcaggcc cagaacccag ctcgtgctca ctctcagtcc    60
ctccctag                                                             68

SEQ ID NO: 441          moltype = RNA   length = 64
FEATURE                 Location/Qualifiers
source                  1..64
                        mol_type = unassigned RNA
                        organism = Homo sapiens
```

```
SEQUENCE: 441
gagctctggg aggggctggg tttggcagga cagtttccaa gccctgtctc ctcccatctt    60
ccag                                                                 64

SEQ ID NO: 442           moltype = RNA   length = 67
FEATURE                  Location/Qualifiers
source                   1..67
                         mol_type = unassigned RNA
                         organism = Homo sapiens
SEQUENCE: 442
aaatctctct ccatatcttt cctgcagccc ccaggtgggg gggaagaaaa ggtggggaat    60
tagattc                                                              67

SEQ ID NO: 443           moltype = RNA   length = 115
FEATURE                  Location/Qualifiers
source                   1..115
                         mol_type = unassigned RNA
                         organism = Homo sapiens
SEQUENCE: 443
gagcaaaaac cagagaacaa catgggagcg ttcctaaccc ctaaggcaac tggatgggag    60
acctgaccca tccagttctc tgaggggct cttgtgtgtt ctacaaggtt gttca         115

SEQ ID NO: 444           moltype = RNA   length = 86
FEATURE                  Location/Qualifiers
source                   1..86
                         mol_type = unassigned RNA
                         organism = Homo sapiens
SEQUENCE: 444
agagccgggg ccatggagca gcctgtgtag acggggacct gccctgcatg ggcacccct    60
cactggctgc ttcccttggt ctccag                                         86

SEQ ID NO: 445           moltype = RNA   length = 82
FEATURE                  Location/Qualifiers
source                   1..82
                         mol_type = unassigned RNA
                         organism = Homo sapiens
SEQUENCE: 445
tgtgggcagg gccctgggga gctgaggctc tgggggtggc cggggctgac cctgggcctc    60
tgctccccag tgtctgaccg cg                                             82

SEQ ID NO: 446           moltype = RNA   length = 136
FEATURE                  Location/Qualifiers
source                   1..136
                         mol_type = unassigned RNA
                         organism = Homo sapiens
SEQUENCE: 446
ccgcttgcct cgcccagcgc agccccggcc gctgggcgca cccgtcccgt tcgtccccgg    60
acgttgctct ctaccccggg aacgtcgaga ctggagcgcc cgaactgagc caccttcgcg   120
gaccccgaga gcggcg                                                   136

SEQ ID NO: 447           moltype = RNA   length = 66
FEATURE                  Location/Qualifiers
source                   1..66
                         mol_type = unassigned RNA
                         organism = Homo sapiens
SEQUENCE: 447
tcaagacggg gagtcaggca gtggtggaga tggagagccc tgagcctcca ctctcctggc    60
ccccag                                                               66

SEQ ID NO: 448           moltype = RNA   length = 78
FEATURE                  Location/Qualifiers
source                   1..78
                         mol_type = unassigned RNA
                         organism = Homo sapiens
SEQUENCE: 448
ggcctcaggc aggcgcaccc gaccacatgc atggctggtg gcggcgtgca ggggtcggt    60
gggccaggct gtggggcg                                                  78

SEQ ID NO: 449           moltype = RNA   length = 69
FEATURE                  Location/Qualifiers
source                   1..69
                         mol_type = unassigned RNA
                         organism = Homo sapiens
SEQUENCE: 449
ctttcggcca gcgggacggc atccgaggtg ggctaggctc gggcccgtgg cgggtgcggg    60
ggtgggagg                                                            69

SEQ ID NO: 450           moltype = RNA   length = 83
FEATURE                  Location/Qualifiers
```

```
                               -continued source                1..83
                      mol_type = unassigned RNA
                      organism = Homo sapiens
SEQUENCE: 450
gtctactccc agggtgccaa gctgtttcgt gttccctccc taggggatcc caggtagggg     60
cagcagagga cctgggcctg gac                                             83

SEQ ID NO: 451        moltype = RNA   length = 84
FEATURE               Location/Qualifiers
source                1..84
                      mol_type = unassigned RNA
                      organism = Homo sapiens
SEQUENCE: 451
ccgcagccgc cgcgccgggc ccgggttggc cgctgacccc cgcggggccc ccggcggccg     60
gggcgggggc gggggctgcc ccgg                                            84

SEQ ID NO: 452        moltype = RNA   length = 72
FEATURE               Location/Qualifiers
source                1..72
                      mol_type = unassigned RNA
                      organism = Homo sapiens
SEQUENCE: 452
atgagcgggt gggagcagat cttattgaga gttccttctc ctgctcctga ttgtcttccc     60
ccaccctcac ag                                                         72

SEQ ID NO: 453        moltype = RNA   length = 91
FEATURE               Location/Qualifiers
source                1..91
                      mol_type = unassigned RNA
                      organism = Homo sapiens
SEQUENCE: 453
gttctagagc atggtttctc atcatttgca ctactgatac ttggggtcag ataattgttt     60
gtggtggggg ctgttgtttg cattgtagga t                                    91

SEQ ID NO: 454        moltype = RNA   length = 75
FEATURE               Location/Qualifiers
source                1..75
                      mol_type = unassigned RNA
                      organism = Homo sapiens
SEQUENCE: 454
aggctggcgt gggctgaggg caggaggcct gtggccggtc ccaggcctcc tgcttcctgg     60
gctcaggctc ggttt                                                      75

SEQ ID NO: 455        moltype = RNA   length = 87
FEATURE               Location/Qualifiers
source                1..87
                      mol_type = unassigned RNA
                      organism = Homo sapiens
SEQUENCE: 455
gtgtggccgg caggcgggtg ggcggggggcg gccggtggga acccgcccc gccccgcgcc      60
cgcactcacc cgcccgtctc cccacag                                         87

SEQ ID NO: 456        moltype = RNA   length = 76
FEATURE               Location/Qualifiers
source                1..76
                      mol_type = unassigned RNA
                      organism = Homo sapiens
SEQUENCE: 456
ggggtcacct ctctggccgt ctaccttcca cactgacaag ggccgtgggg acgtagctgg     60
ccagacaggt gacccc                                                     76

SEQ ID NO: 457        moltype = RNA   length = 100
FEATURE               Location/Qualifiers
source                1..100
                      mol_type = unassigned RNA
                      organism = Homo sapiens
SEQUENCE: 457
gaggtggag gattgcttga gtcagggtgg ttgaggctgc agtaagttgt gatcatacca      60
ctgcactcca gcctgagtga cagagcaaga ccttgtctca                          100

SEQ ID NO: 458        moltype = RNA   length = 67
FEATURE               Location/Qualifiers
source                1..67
                      mol_type = unassigned RNA
                      organism = Homo sapiens
SEQUENCE: 458
aatagattat tggtcaccac ctccagtttc tgaatttgtg agactggggt ggggcctgag     60
aatttgc                                                               67
```

```
SEQ ID NO: 459          moltype = RNA   length = 90
FEATURE                 Location/Qualifiers
source                  1..90
                        mol_type = unassigned RNA
                        organism = Homo sapiens
SEQUENCE: 459
ggcgcctctg cagctccggc tccccctggc ctctcgggaa ctacaagtcc caggggggcct    60
ggcggtgggc ggcgggcgga agaggcgggg                                     90

SEQ ID NO: 460          moltype = RNA   length = 64
FEATURE                 Location/Qualifiers
source                  1..64
                        mol_type = unassigned RNA
                        organism = Homo sapiens
SEQUENCE: 460
gggtggggggc ggggcggcag gggcctcccc cagtgccagg ccccattctg cttctctccc    60
agct                                                                 64

SEQ ID NO: 461          moltype = RNA   length = 64
FEATURE                 Location/Qualifiers
source                  1..64
                        mol_type = unassigned RNA
                        organism = Homo sapiens
SEQUENCE: 461
agttcagggc cgaagggtgg aagctgctgg tgctcatctc agcctctgcc cttggcctcc    60
ccag                                                                 64

SEQ ID NO: 462          moltype = RNA   length = 68
FEATURE                 Location/Qualifiers
source                  1..68
                        mol_type = unassigned RNA
                        organism = Homo sapiens
SEQUENCE: 462
cgtggtgagg atatggcagg gaagggagt ttccctctat tcccttcccc ccagtaatct     60
tcatcatg                                                             68

SEQ ID NO: 463          moltype = RNA   length = 67
FEATURE                 Location/Qualifiers
source                  1..67
                        mol_type = unassigned RNA
                        organism = Homo sapiens
SEQUENCE: 463
gcgccctccc tctctccccg gtgtgcaaat gtgtgtgtgc ggtgttatgc cggacaagag    60
ggaggtg                                                              67

SEQ ID NO: 464          moltype = RNA   length = 98
FEATURE                 Location/Qualifiers
source                  1..98
                        mol_type = unassigned RNA
                        organism = Homo sapiens
SEQUENCE: 464
cgaggtaggg gcgtcccggg cgcgcgggcg ggtcccaggc tgggcccctc ggaggccggg    60
tgctcactgc cccgtcccgg cgcccgtgtc tcctccag                            98

SEQ ID NO: 465          moltype = RNA   length = 69
FEATURE                 Location/Qualifiers
source                  1..69
                        mol_type = unassigned RNA
                        organism = Homo sapiens
SEQUENCE: 465
tggggtaggg gtgggggaat tcagggggtgt cgaactcatg gctgccacct ttgtgtcccc    60
atcctgcag                                                            69

SEQ ID NO: 466          moltype = RNA   length = 68
FEATURE                 Location/Qualifiers
source                  1..68
                        mol_type = unassigned RNA
                        organism = Homo sapiens
SEQUENCE: 466
gcatcctgta ctgagctgcc ccgaggccct tcatgctgcc cagctcgggg cagctcagta    60
caggatac                                                             68

SEQ ID NO: 467          moltype = RNA   length = 64
FEATURE                 Location/Qualifiers
source                  1..64
                        mol_type = unassigned RNA
                        organism = Homo sapiens
SEQUENCE: 467
tcctgtactg agctgccccg agctgggcag catgaagggc ctcggggcag ctcagtacag    60
```

```
gatg                                                                    64

SEQ ID NO: 468          moltype = RNA   length = 110
FEATURE                 Location/Qualifiers
source                  1..110
                        mol_type = unassigned RNA
                        organism = Homo sapiens
SEQUENCE: 468
gtctaccagg tgtgggccca gctttacata gttcatgctg aggccgggat ttcatgcaga         60
aaactggttg caaaaggtgc tgaagggct ggggagcac aagggagaag                    110

SEQ ID NO: 469          moltype = RNA   length = 71
FEATURE                 Location/Qualifiers
source                  1..71
                        mol_type = unassigned RNA
                        organism = Homo sapiens
SEQUENCE: 469
gtgtctgtgc cggtcccagg agaacctgca gaggcatcgg gtcagcggtg ctcctgcggg         60
ccgacactca c                                                             71

SEQ ID NO: 470          moltype = RNA   length = 99
FEATURE                 Location/Qualifiers
source                  1..99
                        mol_type = unassigned RNA
                        organism = Homo sapiens
SEQUENCE: 470
cgcccacctc agcctcccaa aatgctggga ttacaggcat gagccactgc ggtcgaccat         60
gacctggaca tgtttgtgcc cagtactgtc agtttgcag                               99

SEQ ID NO: 471          moltype = RNA   length = 86
FEATURE                 Location/Qualifiers
source                  1..86
                        mol_type = unassigned RNA
                        organism = Homo sapiens
SEQUENCE: 471
agcactgccc ccggtgagtc agggtggggc tggcccctg cttcgtgccc atccgcgctc          60
tgactctctg cccacctgca ggagct                                             86

SEQ ID NO: 472          moltype = RNA   length = 65
FEATURE                 Location/Qualifiers
source                  1..65
                        mol_type = unassigned RNA
                        organism = Homo sapiens
SEQUENCE: 472
ctcctctggg ggtgggggc tgggcgtggt ggacagcgat gcatccctcg ccttctcacc          60
ctcag                                                                    65

SEQ ID NO: 473          moltype = RNA   length = 73
FEATURE                 Location/Qualifiers
source                  1..73
                        mol_type = unassigned RNA
                        organism = Homo sapiens
SEQUENCE: 473
ggggaggtac ctgggacagg aggaggaggc agccttgcct cagaaaccaa actgtcaaaa         60
gtgtaggttc cac                                                           73

SEQ ID NO: 474          moltype = RNA   length = 55
FEATURE                 Location/Qualifiers
source                  1..55
                        mol_type = unassigned RNA
                        organism = Homo sapiens
SEQUENCE: 474
ccggatccga gtcacggcac caaatttcat gcgtgtccgt gtgaagagac cacca             55

SEQ ID NO: 475          moltype = RNA   length = 66
FEATURE                 Location/Qualifiers
source                  1..66
                        mol_type = unassigned RNA
                        organism = Homo sapiens
SEQUENCE: 475
acccaggagg cggaggaggt ggaggttgca gtgagccaag atcgtggcac tgactccagc         60
ctgggg                                                                   66

SEQ ID NO: 476          moltype = RNA   length = 94
FEATURE                 Location/Qualifiers
source                  1..94
                        mol_type = unassigned RNA
                        organism = Homo sapiens
SEQUENCE: 476
```

```
cacggtgtcc cctggtggaa cctggcaggg ggagaggtaa ggtctttcag cctctccaaa    60
gcccatggtc aggtactcag gtgggggagc cctg                                94

SEQ ID NO: 477          moltype = RNA   length = 62
FEATURE                 Location/Qualifiers
source                  1..62
                        mol_type = unassigned RNA
                        organism = Homo sapiens
SEQUENCE: 477
gagggtggtg gaggaagagg gcagctccca tgactgcctg accgccttct ctcctccccc    60
ag                                                                   62

SEQ ID NO: 478          moltype = RNA   length = 66
FEATURE                 Location/Qualifiers
source                  1..66
                        mol_type = unassigned RNA
                        organism = Homo sapiens
SEQUENCE: 478
agcagccctc ggcggcccgg ggggcgggcg gcggtgcccg tcccggggct gcgcgaggca    60
caggcg                                                               66

SEQ ID NO: 479          moltype = RNA   length = 81
FEATURE                 Location/Qualifiers
source                  1..81
                        mol_type = unassigned RNA
                        organism = Homo sapiens
SEQUENCE: 479
tagaggcagt ttcaacagat gtgtagactt ttgatatgag aaattggttt caaaatcagg    60
agtcggggct ttactgcttt t                                              81

SEQ ID NO: 480          moltype = RNA   length = 74
FEATURE                 Location/Qualifiers
source                  1..74
                        mol_type = unassigned RNA
                        organism = Homo sapiens
SEQUENCE: 480
cctgcaggag gcagtgggcg agcaggcggg gcagcccaat gccatgggcc tgatctcacc    60
gctgcctcct tccc                                                      74

SEQ ID NO: 481          moltype = RNA   length = 109
FEATURE                 Location/Qualifiers
source                  1..109
                        mol_type = unassigned RNA
                        organism = Homo sapiens
SEQUENCE: 481
tgctattgtc ttactgctac agcagggctg gggattgcag tatccgctgt tgctgctgct    60
cccagtcctg cccctgctgc tacctagtcc agcctcaccg catcccaga              109

SEQ ID NO: 482          moltype = RNA   length = 67
FEATURE                 Location/Qualifiers
source                  1..67
                        mol_type = unassigned RNA
                        organism = Homo sapiens
SEQUENCE: 482
cagcgtgggc tgctgagaag gggcagggtc ctccagctca ttcctcctgc ctcctccgtg    60
gcctcag                                                              67

SEQ ID NO: 483          moltype = RNA   length = 63
FEATURE                 Location/Qualifiers
source                  1..63
                        mol_type = unassigned RNA
                        organism = Homo sapiens
SEQUENCE: 483
gcatgctggg cgaggctggc atctagcaca ggcggtagat gcttgctctt gccattgcaa    60
tga                                                                  63

SEQ ID NO: 484          moltype = RNA   length = 98
FEATURE                 Location/Qualifiers
source                  1..98
                        mol_type = unassigned RNA
                        organism = Homo sapiens
SEQUENCE: 484
cttggtcaat aggaaagagg tgggacctcc tggcttttcc tctgcagcat ggctcggacc    60
tagtgcaatg tttaagctcc cctctctttc ctgttcag                            98

SEQ ID NO: 485          moltype = RNA   length = 70
FEATURE                 Location/Qualifiers
source                  1..70
                        mol_type = unassigned RNA
```

```
                        organism = Homo sapiens
SEQUENCE: 485
aggacccagc ggggctgggc gcgcggagca gcgctgggtg cagcgcctgc gccggcagct      60
gcaagggccg                                                            70

SEQ ID NO: 486          moltype = RNA   length = 61
FEATURE                 Location/Qualifiers
source                  1..61
                        mol_type = unassigned RNA
                        organism = Homo sapiens
SEQUENCE: 486
tccgctctgt ggagtggggt gcctgtcccc tgccactggg tgacccaccc ctctccacca      60
g                                                                     61

SEQ ID NO: 487          moltype = RNA   length = 83
FEATURE                 Location/Qualifiers
source                  1..83
                        mol_type = unassigned RNA
                        organism = Homo sapiens
SEQUENCE: 487
aatagagggt gcacaggcac gggagctcag gtgaggcagg gagctgagct cacctgacct      60
cccatgcctg tgcaccctct att                                             83

SEQ ID NO: 488          moltype = RNA   length = 87
FEATURE                 Location/Qualifiers
source                  1..87
                        mol_type = unassigned RNA
                        organism = Homo sapiens
SEQUENCE: 488
gtgaggcggg gccaggaggg tgtgtggcgt gggtgctgcg gggccgtcag ggtgcctgcg      60
ggacgctcac ctggctggcc cgcccag                                         87

SEQ ID NO: 489          moltype = RNA   length = 99
FEATURE                 Location/Qualifiers
source                  1..99
                        mol_type = unassigned RNA
                        organism = Homo sapiens
SEQUENCE: 489
gcaagggaca gggagggtcg tggcgacact cgcgccagct cccgggacgg ctgggctcgg      60
gctggtcgcc gacctccgac cctccactag atgcctggc                            99

SEQ ID NO: 490          moltype = RNA   length = 91
FEATURE                 Location/Qualifiers
source                  1..91
                        mol_type = unassigned RNA
                        organism = Homo sapiens
SEQUENCE: 490
ggcgccccgg ctccccgcgc ccccgatcgg ggccgccgct agtagtggcg gcggcggagg      60
cgggggcagc ggcggcggcg gcggaggcgc c                                    91

SEQ ID NO: 491          moltype = RNA   length = 69
FEATURE                 Location/Qualifiers
source                  1..69
                        mol_type = unassigned RNA
                        organism = Homo sapiens
SEQUENCE: 491
ggccctcggg cctgggggttg ggggagctct gtcctgtctc actcattgct cctcccctgc    60
ctggcccag                                                             69

SEQ ID NO: 492          moltype = RNA   length = 89
FEATURE                 Location/Qualifiers
source                  1..89
                        mol_type = unassigned RNA
                        organism = Homo sapiens
SEQUENCE: 492
tctccgttta tcccaccact gccaccatta ttgctactgt tcagcaggtg ctgctggtgg      60
tgatggtgat agtctggtgg gggcggtgg                                       89

SEQ ID NO: 493          moltype = RNA   length = 69
FEATURE                 Location/Qualifiers
source                  1..69
                        mol_type = unassigned RNA
                        organism = Homo sapiens
SEQUENCE: 493
gaggagggga ggtgtgcagg gctgggtca ctgactctgc ttcccctgcc ctgcatggtg       60
tccccacag                                                             69

SEQ ID NO: 494          moltype = RNA   length = 81
FEATURE                 Location/Qualifiers
```

```
source                  1..81
                        mol_type = unassigned RNA
                        organism = Homo sapiens
SEQUENCE: 494
agttggtggg ggagccatga gataagagca cctcctagag aatgttgaac taaaggtgcc    60
ctctctggct cctccccaaa g                                              81

SEQ ID NO: 495          moltype = RNA  length = 67
FEATURE                 Location/Qualifiers
source                  1..67
                        mol_type = unassigned RNA
                        organism = Homo sapiens
SEQUENCE: 495
tacaggccgg ggctttgggt gagggacccc cggagtctgt cacggtctca ccccaactct    60
gccccag                                                              67

SEQ ID NO: 496          moltype = RNA  length = 119
FEATURE                 Location/Qualifiers
source                  1..119
                        mol_type = unassigned RNA
                        organism = Homo sapiens
SEQUENCE: 496
ccatgaggag ctggcagtgg gatggcctgg gggtaggagc gtggcttctg gagctagacc    60
acatgggttc agatcccagc ggtgcctcta actggccaca ggaccttggg cagtcagct    119

SEQ ID NO: 497          moltype = RNA  length = 62
FEATURE                 Location/Qualifiers
source                  1..62
                        mol_type = unassigned RNA
                        organism = Homo sapiens
SEQUENCE: 497
cttcctggtg ggtggggagg agaagtgccg tcctcatgag ccctctctg tcccacccat     60
ag                                                                   62

SEQ ID NO: 498          moltype = RNA  length = 87
FEATURE                 Location/Qualifiers
source                  1..87
                        mol_type = unassigned RNA
                        organism = Homo sapiens
SEQUENCE: 498
gcagggctgg cagggaggct gggaggggct ggctgggtct ggtagtgggc atcagctggc    60
cctcatttct taagacagca cttctgt                                        87

SEQ ID NO: 499          moltype = RNA  length = 97
FEATURE                 Location/Qualifiers
source                  1..97
                        mol_type = unassigned RNA
                        organism = Homo sapiens
SEQUENCE: 499
atctgagttg ggagggtccc tctccaaatg tgtcttgggg tgggggatca agacacattt    60
ggagagggaa cctcccaact cggcctctgc catcatt                             97

SEQ ID NO: 500          moltype = RNA  length = 73
FEATURE                 Location/Qualifiers
source                  1..73
                        mol_type = unassigned RNA
                        organism = Homo sapiens
SEQUENCE: 500
ggaggctggg ctgggacgga cacccggcct ccactttctg tggcaggtac ctcctccatg    60
tcggcccgcc ttg                                                       73

SEQ ID NO: 501          moltype = RNA  length = 70
FEATURE                 Location/Qualifiers
source                  1..70
                        mol_type = unassigned RNA
                        organism = Homo sapiens
SEQUENCE: 501
acaaatagct tcagggagtc aggggagggc agaaatagat ggccttcccc tgctgggaag    60
aaagtgggtc                                                           70

SEQ ID NO: 502          moltype = RNA  length = 87
FEATURE                 Location/Qualifiers
source                  1..87
                        mol_type = unassigned RNA
                        organism = Homo sapiens
SEQUENCE: 502
ccctcatctc tggcaggggg cttattgtag gagtctctga agagagctgt ggactgacct    60
gctttaaccc ttccccaggt tcccatt                                        87
```

| SEQ ID NO: 503 | moltype = RNA   length = 72 |
| --- | --- |
| FEATURE | Location/Qualifiers |
| source | 1..72 |
| | mol_type = unassigned RNA |
| | organism = Homo sapiens |

SEQUENCE: 503
ctggggagg aaggacaggc catctgctat tcgtccacca acctgacttg atcctctctt   60
ccctcctccc ag                                                     72

| SEQ ID NO: 504 | moltype = RNA   length = 67 |
| --- | --- |
| FEATURE | Location/Qualifiers |
| source | 1..67 |
| | mol_type = unassigned RNA |
| | organism = Homo sapiens |

SEQUENCE: 504
ccagacccct gggctgggc aggcggaaag aggtctgaac tgcctctgcc tccttggtct   60
ccggcag                                                           67

| SEQ ID NO: 505 | moltype = RNA   length = 65 |
| --- | --- |
| FEATURE | Location/Qualifiers |
| source | 1..65 |
| | mol_type = unassigned RNA |
| | organism = Homo sapiens |

SEQUENCE: 505
gtctcctggg gggaggagac cctgctctcc ctggcagcaa gcctctcctg cccttccaga   60
ttagc                                                              65

| SEQ ID NO: 506 | moltype = RNA   length = 91 |
| --- | --- |
| FEATURE | Location/Qualifiers |
| source | 1..91 |
| | mol_type = unassigned RNA |
| | organism = Homo sapiens |

SEQUENCE: 506
acgcccccg cccgccacc gccttggagg ctgacctctt actttcggtc ggtcttcttc   60
cctgggcttg gtttggggc gggggagtgt c                                 91

| SEQ ID NO: 507 | moltype = RNA   length = 57 |
| --- | --- |
| FEATURE | Location/Qualifiers |
| source | 1..57 |
| | mol_type = unassigned RNA |
| | organism = Homo sapiens |

SEQUENCE: 507
cattggaggg tgtggaagac atctgggcca actctgatct cttcatctac cccccag     57

| SEQ ID NO: 508 | moltype = RNA   length = 67 |
| --- | --- |
| FEATURE | Location/Qualifiers |
| source | 1..67 |
| | mol_type = unassigned RNA |
| | organism = Homo sapiens |

SEQUENCE: 508
cagggaggag gtggtactag gggccagcaa cctgattacc cctctttggc cctttgtacc   60
cctccag                                                            67

| SEQ ID NO: 509 | moltype = RNA   length = 96 |
| --- | --- |
| FEATURE | Location/Qualifiers |
| source | 1..96 |
| | mol_type = unassigned RNA |
| | organism = Homo sapiens |

SEQUENCE: 509
gctctgggc gtgccgccgc cgtcgctgcc acctccccta ccgctagtgg aagaagatgg   60
cggaaggcgg agcggcggat ctggacaccc agcggt                            96

| SEQ ID NO: 510 | moltype = RNA   length = 61 |
| --- | --- |
| FEATURE | Location/Qualifiers |
| source | 1..61 |
| | mol_type = unassigned RNA |
| | organism = Homo sapiens |

SEQUENCE: 510
cctgcgggga caggccaggg catctaggct gtgcacagtg acgcccctcc tgcccccaca   60
g                                                                  61

| SEQ ID NO: 511 | moltype = RNA   length = 58 |
| --- | --- |
| FEATURE | Location/Qualifiers |
| source | 1..58 |
| | mol_type = unassigned RNA |
| | organism = Homo sapiens |

SEQUENCE: 511
agggccagag gagcctggag tggtcgggtc gactgaaccc aggttccctc tggccgca     58

| SEQ ID NO: 512 | moltype = RNA   length = 86 |
|---|---|
| FEATURE | Location/Qualifiers |
| source | 1..86 |
| | mol_type = unassigned RNA |
| | organism = Homo sapiens |

SEQUENCE: 512
attctaggtg gggagactga cggctggagg cccataagct gtctaaaact tcggcccca   60
gatttctggt ctccccactt cagaac                                        86

| SEQ ID NO: 513 | moltype = RNA   length = 80 |
|---|---|
| FEATURE | Location/Qualifiers |
| source | 1..80 |
| | mol_type = unassigned RNA |
| | organism = Homo sapiens |

SEQUENCE: 513
ggcgcgtcgc cccctcagt ccaccagagc ccggatacct cagaaattcg gctctgggtc    60
tgtggggagc gaaatgcaac                                                80

| SEQ ID NO: 514 | moltype = RNA   length = 98 |
|---|---|
| FEATURE | Location/Qualifiers |
| source | 1..98 |
| | mol_type = unassigned RNA |
| | organism = Homo sapiens |

SEQUENCE: 514
ttctcacccc cgcctgacac gggcgacagc tgcggcccgc tgtgttcact cgggccgagt   60
gcgtctcctg tcaggcaagg gagagcagag ccccctg                            98

| SEQ ID NO: 515 | moltype = RNA   length = 94 |
|---|---|
| FEATURE | Location/Qualifiers |
| source | 1..94 |
| | mol_type = unassigned RNA |
| | organism = Homo sapiens |

SEQUENCE: 515
ataaaggaag ttaggctgag gggcagagag cgagactttt ctattttcca aaagctcggt   60
ctgaggcccc tcagtcttgc ttcctaaccc gcgc                               94

| SEQ ID NO: 516 | moltype = RNA   length = 75 |
|---|---|
| FEATURE | Location/Qualifiers |
| source | 1..75 |
| | mol_type = unassigned RNA |
| | organism = Homo sapiens |

SEQUENCE: 516
tcatccctgg gtggggattt gttgcattac ttgtgttcta tataaagtat tgcacttgtc   60
ccggcctgtg gaaga                                                    75

| SEQ ID NO: 517 | moltype = RNA   length = 89 |
|---|---|
| FEATURE | Location/Qualifiers |
| source | 1..89 |
| | mol_type = unassigned RNA |
| | organism = Homo sapiens |

SEQUENCE: 517
gtcagcagtg ccttagcagc acgtaaatat tggcgttaag attctaaaat tatctccagt   60
attaactgtg ctgctgaagt aaggttgac                                     89

| SEQ ID NO: 518 | moltype = RNA   length = 81 |
|---|---|
| FEATURE | Location/Qualifiers |
| source | 1..81 |
| | mol_type = unassigned RNA |
| | organism = Homo sapiens |

SEQUENCE: 518
gttccactct agcagcacgt aaatattggc gtagtgaaat atatattaaa caccaatatt   60
actgtgctgc tttagtgtga c                                             81

| SEQ ID NO: 519 | moltype = RNA   length = 72 |
|---|---|
| FEATURE | Location/Qualifiers |
| source | 1..72 |
| | mol_type = unassigned RNA |
| | organism = Homo sapiens |

SEQUENCE: 519
cttgggaatg gcaaggaaac cgttaccatt actgagttta gtaatggtaa tggttctctt   60
gctataccca ga                                                       72

| SEQ ID NO: 520 | moltype = RNA   length = 90 |
|---|---|
| FEATURE | Location/Qualifiers |
| source | 1..90 |
| | mol_type = unassigned RNA |
| | organism = Homo sapiens |

SEQUENCE: 520
aggcctcgct gttctctatg gcttttatt cctatgtgat tctactgctc actcatatag    60

```
ggattggagc cgtggcgcac ggcggggaca                                          90

SEQ ID NO: 521         moltype = RNA   length = 86
FEATURE                Location/Qualifiers
source                 1..86
                       mol_type = unassigned RNA
                       organism = Homo sapiens
SEQUENCE: 521
ggcttagaaa cagtccctag gtaggatttg gggaggagct aagaagcccc tacagggccc         60
agaggtgggg actgagcctt agttgg                                              86

SEQ ID NO: 522         moltype = RNA   length = 96
FEATURE                Location/Qualifiers
source                 1..96
                       mol_type = unassigned RNA
                       organism = Homo sapiens
SEQUENCE: 522
cgggccccgg gcgggcggga gggacgggac gcggtgcagt gttgtttttt cccccgccaa         60
tattgcactc gtcccggcct ccggccccc cggccc                                    96

SEQ ID NO: 523         moltype = RNA   length = 70
FEATURE                Location/Qualifiers
source                 1..70
                       mol_type = unassigned RNA
                       organism = Homo sapiens
SEQUENCE: 523
ggccgcggcg cgcaagatgg cggcgggccc gggcaccgcc ccttccgccc cgccgggcgt         60
cgcacgaggc                                                                70

SEQ ID NO: 524         moltype = RNA   length = 94
FEATURE                Location/Qualifiers
source                 1..94
                       mol_type = unassigned RNA
                       organism = Homo sapiens
SEQUENCE: 524
gtgaggtgtg ggcccggccc caggagcggg gcctgggcag ccccgtgtgt tgaggaagga         60
aggcagggcc cccgctcccc gggcctgacc ccac                                     94

SEQ ID NO: 525         moltype = RNA   length = 97
FEATURE                Location/Qualifiers
source                 1..97
                       mol_type = unassigned RNA
                       organism = Homo sapiens
SEQUENCE: 525
ctcaggtgct ctggctgctt gggttcctgg catgctgatt tgtgacttaa gattaaaatc         60
acattgccag ggattaccac gcaaccacga ccttggc                                  97

SEQ ID NO: 526         moltype = RNA   length = 78
FEATURE                Location/Qualifiers
source                 1..78
                       mol_type = unassigned RNA
                       organism = Homo sapiens
SEQUENCE: 526
ctttctacac aggttgggat cggttgcaat gctgtgtttc tgtatggtat tgcacttgtc         60
ccggcctgtt gagtttgg                                                       78

SEQ ID NO: 527         moltype = RNA   length = 75
FEATURE                Location/Qualifiers
source                 1..75
                       mol_type = unassigned RNA
                       organism = Homo sapiens
SEQUENCE: 527
tcatccctgg gtgggatttt gttgcattac ttgtgttcta tataaagtat tgcacttgtc         60
ccggcctgtg gaaga                                                          75

SEQ ID NO: 528         moltype = RNA   length = 100
FEATURE                Location/Qualifiers
source                 1..100
                       mol_type = unassigned RNA
                       organism = Homo sapiens
SEQUENCE: 528
gctcggttgc cgtggttgcg ggccctgccc gcccgccagc tcgctgacag cacgactcag         60
ggcggaggga agtaggtccg ttggtcggtc gggaacgagg                              100

SEQ ID NO: 529         moltype = RNA   length = 65
FEATURE                Location/Qualifiers
source                 1..65
                       mol_type = unassigned RNA
                       organism = Homo sapiens
```

```
SEQUENCE: 529
agccctgggg gtggtctcta gccaaggctc tggggtctca cccttggctg gtctctgctc    60
cgcag                                                                65

SEQ ID NO: 530          moltype = RNA   length = 85
FEATURE                 Location/Qualifiers
source                  1..85
                        mol_type = unassigned RNA
                        organism = Homo sapiens
SEQUENCE: 530
ggggaggtag ggaaaaggaa ggggaggag aaggtgagac caatgtcctg ggtgccactc     60
ctgcccagtg cctcccttcc tcgtt                                          85

SEQ ID NO: 531          moltype = RNA   length = 87
FEATURE                 Location/Qualifiers
source                  1..87
                        mol_type = unassigned RNA
                        organism = Homo sapiens
SEQUENCE: 531
gtgaggcggg gccaggaggg tgtgtggcgt gggtgctgcg gggccgtcag ggtgcctgcg    60
ggacgctcac ctggctggcc cgcccag                                        87

SEQ ID NO: 532          moltype = RNA   length = 65
FEATURE                 Location/Qualifiers
source                  1..65
                        mol_type = unassigned RNA
                        organism = Homo sapiens
SEQUENCE: 532
gcttctggga ggagggatc ttgggagtga tcccaacagc tgagctccct gaatccctgt     60
cccag                                                                65

SEQ ID NO: 533          moltype = RNA   length = 60
FEATURE                 Location/Qualifiers
source                  1..60
                        mol_type = unassigned RNA
                        organism = Homo sapiens
SEQUENCE: 533
tgtgaatgac ccccttccag agccaaaatc accagggatg gaggaggggt cttgggtact    60

SEQ ID NO: 534          moltype = RNA   length = 68
FEATURE                 Location/Qualifiers
source                  1..68
                        mol_type = unassigned RNA
                        organism = Homo sapiens
SEQUENCE: 534
tgcccaggct ggagcgagtg cagtggtgca gtcagtccta gctcactgca gcctcgaact    60
cctgggct                                                             68

SEQ ID NO: 535          moltype = RNA   length = 80
FEATURE                 Location/Qualifiers
source                  1..80
                        mol_type = unassigned RNA
                        organism = Homo sapiens
SEQUENCE: 535
acctgaggag ccagccctcc tcccgcaccc aaacttggag cacttgacct ttggctgttg    60
gaggggcag gctcgcgggt                                                 80

SEQ ID NO: 536          moltype = RNA   length = 83
FEATURE                 Location/Qualifiers
source                  1..83
                        mol_type = unassigned RNA
                        organism = Homo sapiens
SEQUENCE: 536
ggcccggctc cgggtctcgg cccgtacagt ccggccggcc atgctggcgg ggctggggcc    60
ggggccgagc ccgcggcggg gcc                                            83

SEQ ID NO: 537          moltype = RNA   length = 83
FEATURE                 Location/Qualifiers
source                  1..83
                        mol_type = unassigned RNA
                        organism = Homo sapiens
SEQUENCE: 537
acggcatctt tgcactcagc aggcaggctg gtgcagcccg tggtggggga ccatcctgcc    60
tgctgtgggg taaggacggc tgt                                            83

SEQ ID NO: 538          moltype = RNA   length = 63
FEATURE                 Location/Qualifiers
source                  1..63
                        mol_type = unassigned RNA
```

```
                              organism  =  Homo sapiens
SEQUENCE: 538
tggtggcggc ggtagttatg ggcttctctt tctcaccagc agccctggg ccgccgcctc    60
cct                                                                 63

SEQ ID NO: 539            moltype = RNA   length = 98
FEATURE                   Location/Qualifiers
source                    1..98
                          mol_type = unassigned RNA
                          organism = Homo sapiens
SEQUENCE: 539
agaatgggca aatgaacagt aaatttggag gcctggggcc ctccctgctg ctggagaagt    60
gtttgcacgg gtgggccttg tctttgaaag gaggtgga                           98

SEQ ID NO: 540            moltype = RNA   length = 102
FEATURE                   Location/Qualifiers
source                    1..102
                          mol_type = unassigned RNA
                          organism = Homo sapiens
SEQUENCE: 540
gtgggagggc ccaggcgcgg gcaggggtgg gggtggcaga gcgctgtccc ggggcggg      60
ccgaagcgcg gcgaccgtaa ctccttctgc tccgtccccc ag                     102

SEQ ID NO: 541            moltype = RNA   length = 80
FEATURE                   Location/Qualifiers
source                    1..80
                          mol_type = unassigned RNA
                          organism = Homo sapiens
SEQUENCE: 541
cgggaatgcc gcggcgggga cggcgattgg tccgtatgtg tggtgccacc ggccgccggc    60
tccgccccgg ccccgcccc                                                80

SEQ ID NO: 542            moltype = RNA   length = 93
FEATURE                   Location/Qualifiers
source                    1..93
                          mol_type = unassigned RNA
                          organism = Homo sapiens
SEQUENCE: 542
tacttatggc accccactcc tggtaccata gtcataagtt aggagatgtt agagctgtga    60
gtaccatgac ttaagtgtgg tggcttaaac atg                                93

SEQ ID NO: 543            moltype = RNA   length = 66
FEATURE                   Location/Qualifiers
source                    1..66
                          mol_type = unassigned RNA
                          organism = Homo sapiens
SEQUENCE: 543
cctgaggggg ggcactgcgc aagcaaagcc agggaccctg agaggctttg cttcctgctc    60
ccctag                                                              66

SEQ ID NO: 544            moltype = RNA   length = 65
FEATURE                   Location/Qualifiers
source                    1..65
                          mol_type = unassigned RNA
                          organism = Homo sapiens
SEQUENCE: 544
ttctcctggg gagtggctgg ggagcagaca gacccaacct catgctcccc ggcctctgcc    60
cccag                                                               65

SEQ ID NO: 545            moltype = RNA   length = 22
FEATURE                   Location/Qualifiers
source                    1..22
                          mol_type = unassigned RNA
                          organism = Homo sapiens
SEQUENCE: 545
ccccggtgtt ggggcgcgtc tg                                            22

SEQ ID NO: 546            moltype = RNA   length = 21
FEATURE                   Location/Qualifiers
source                    1..21
                          mol_type = unassigned RNA
                          organism = Homo sapiens
SEQUENCE: 546
cccggtgttg gggcgcgtct g                                             21

SEQ ID NO: 547            moltype = RNA   length = 22
FEATURE                   Location/Qualifiers
source                    1..22
                          mol_type = unassigned RNA
```

```
                                  organism = Homo sapiens
SEQUENCE: 547
tggcggagcc cattccatgc ca                                                  22

SEQ ID NO: 548          moltype = RNA   length = 21
FEATURE                 Location/Qualifiers
source                  1..21
                        mol_type = unassigned RNA
                        organism = Homo sapiens
SEQUENCE: 548
ctggcggagc ccattccatg c                                                   21

SEQ ID NO: 549          moltype = RNA   length = 25
FEATURE                 Location/Qualifiers
source                  1..25
                        mol_type = unassigned RNA
                        organism = Homo sapiens
SEQUENCE: 549
actcggcgtg gcgtcggtcg tggta                                               25

SEQ ID NO: 550          moltype = RNA   length = 15
FEATURE                 Location/Qualifiers
source                  1..15
                        mol_type = unassigned RNA
                        organism = Homo sapiens
SEQUENCE: 550
actcggcgtg gcgtc                                                          15

SEQ ID NO: 551          moltype = RNA   length = 19
FEATURE                 Location/Qualifiers
source                  1..19
                        mol_type = unassigned RNA
                        organism = Homo sapiens
SEQUENCE: 551
cggcgcgacc ggcccgggg                                                      19

SEQ ID NO: 552          moltype = RNA   length = 19
FEATURE                 Location/Qualifiers
source                  1..19
                        mol_type = unassigned RNA
                        organism = Homo sapiens
SEQUENCE: 552
cggcgcgacc ggcccgggg                                                      19

SEQ ID NO: 553          moltype = RNA   length = 26
FEATURE                 Location/Qualifiers
source                  1..26
                        mol_type = unassigned RNA
                        organism = Homo sapiens
SEQUENCE: 553
cggtgggatc ccgcggccgt gttttc                                              26

SEQ ID NO: 554          moltype = RNA   length = 15
FEATURE                 Location/Qualifiers
source                  1..15
                        mol_type = unassigned RNA
                        organism = Homo sapiens
SEQUENCE: 554
ggggcgccgc gggac                                                          15

SEQ ID NO: 555          moltype = RNA   length = 20
FEATURE                 Location/Qualifiers
source                  1..20
                        mol_type = unassigned RNA
                        organism = Homo sapiens
SEQUENCE: 555
cccgggag cccggcggtg                                                       20

SEQ ID NO: 556          moltype = RNA   length = 15
FEATURE                 Location/Qualifiers
source                  1..15
                        mol_type = unassigned RNA
                        organism = Homo sapiens
SEQUENCE: 556
accccgggga gcccg                                                          15

SEQ ID NO: 557          moltype = RNA   length = 24
FEATURE                 Location/Qualifiers
source                  1..24
```

-continued

```
                              mol_type = unassigned RNA
                              organism = Homo sapiens
SEQUENCE: 557
gatcggtcga gagcgtcctg gctg                                            24

SEQ ID NO: 558                moltype = RNA  length = 15
FEATURE                       Location/Qualifiers
source                        1..15
                              mol_type = unassigned RNA
                              organism = Homo sapiens
SEQUENCE: 558
gctgggcggg gcgcg                                                      15

SEQ ID NO: 559                moltype = RNA  length = 23
FEATURE                       Location/Qualifiers
source                        1..23
                              mol_type = unassigned RNA
                              organism = Homo sapiens
SEQUENCE: 559
tgtagagcag ggagcaggaa gct                                             23

SEQ ID NO: 560                moltype = RNA  length = 15
FEATURE                       Location/Qualifiers
source                        1..15
                              mol_type = unassigned RNA
                              organism = Homo sapiens
SEQUENCE: 560
cagggagcag gaagc                                                      15

SEQ ID NO: 561                moltype = RNA  length = 15
FEATURE                       Location/Qualifiers
source                        1..15
                              mol_type = unassigned RNA
                              organism = Homo sapiens
SEQUENCE: 561
tgaagcgggg gggcg                                                      15

SEQ ID NO: 562                moltype = RNA  length = 15
FEATURE                       Location/Qualifiers
source                        1..15
                              mol_type = unassigned RNA
                              organism = Homo sapiens
SEQUENCE: 562
tgaagcgggg gggcg                                                      15

SEQ ID NO: 563                moltype = RNA  length = 22
FEATURE                       Location/Qualifiers
source                        1..22
                              mol_type = unassigned RNA
                              organism = Homo sapiens
SEQUENCE: 563
ctgggctcgg gacgcgcggc tc                                              22

SEQ ID NO: 564                moltype = RNA  length = 19
FEATURE                       Location/Qualifiers
source                        1..19
                              mol_type = unassigned RNA
                              organism = Homo sapiens
SEQUENCE: 564
ctgggctcgg gacgcgcgg                                                  19

SEQ ID NO: 565                moltype = RNA  length = 23
FEATURE                       Location/Qualifiers
source                        1..23
                              mol_type = unassigned RNA
                              organism = Homo sapiens
SEQUENCE: 565
cacaggtgag gttcttggga gcc                                             23

SEQ ID NO: 566                moltype = RNA  length = 15
FEATURE                       Location/Qualifiers
source                        1..15
                              mol_type = unassigned RNA
                              organism = Homo sapiens
SEQUENCE: 566
acaggtgagg ttctt                                                      15

SEQ ID NO: 567                moltype = RNA  length = 19
FEATURE                       Location/Qualifiers
```

```
source                  1..19
                        mol_type = unassigned RNA
                        organism = Homo sapiens
SEQUENCE: 567
agtgggaggc cagggcacg                                                    19

SEQ ID NO: 568          moltype = RNA   length = 15
FEATURE                 Location/Qualifiers
source                  1..15
                        mol_type = unassigned RNA
                        organism = Homo sapiens
SEQUENCE: 568
aggggagct gcagg                                                         15

SEQ ID NO: 569          moltype = RNA   length = 22
FEATURE                 Location/Qualifiers
source                  1..22
                        mol_type = unassigned RNA
                        organism = Homo sapiens
SEQUENCE: 569
aggcagcggg gtgtagtgga ta                                                22

SEQ ID NO: 570          moltype = RNA   length = 21
FEATURE                 Location/Qualifiers
source                  1..21
                        mol_type = unassigned RNA
                        organism = Homo sapiens
SEQUENCE: 570
aggcagcggg gtgtagtgga t                                                 21

SEQ ID NO: 571          moltype = RNA   length = 22
FEATURE                 Location/Qualifiers
source                  1..22
                        mol_type = unassigned RNA
                        organism = Homo sapiens
SEQUENCE: 571
gggggcagg aggggctcag gg                                                 22

SEQ ID NO: 572          moltype = RNA   length = 16
FEATURE                 Location/Qualifiers
source                  1..16
                        mol_type = unassigned RNA
                        organism = Homo sapiens
SEQUENCE: 572
gtggggggc aggagg                                                        16

SEQ ID NO: 573          moltype = RNA   length = 21
FEATURE                 Location/Qualifiers
source                  1..21
                        mol_type = unassigned RNA
                        organism = Homo sapiens
SEQUENCE: 573
gaatggattt ttggagcagg a                                                 21

SEQ ID NO: 574          moltype = RNA   length = 15
FEATURE                 Location/Qualifiers
source                  1..15
                        mol_type = unassigned RNA
                        organism = Homo sapiens
SEQUENCE: 574
gaatggattt ttgga                                                        15

SEQ ID NO: 575          moltype = RNA   length = 24
FEATURE                 Location/Qualifiers
source                  1..24
                        mol_type = unassigned RNA
                        organism = Homo sapiens
SEQUENCE: 575
gctgcgggct gcggtcaggg cgat                                              24

SEQ ID NO: 576          moltype = RNA   length = 20
FEATURE                 Location/Qualifiers
source                  1..20
                        mol_type = unassigned RNA
                        organism = Homo sapiens
SEQUENCE: 576
gctgcgggct gcggtcaggg                                                   20

SEQ ID NO: 577          moltype = RNA   length = 18
```

```
FEATURE              Location/Qualifiers
source               1..18
                     mol_type = unassigned RNA
                     organism = Homo sapiens
SEQUENCE: 577
gcggcggcgg cggcagca                                                       18

SEQ ID NO: 578       moltype = RNA   length = 15
FEATURE              Location/Qualifiers
source               1..15
                     mol_type = unassigned RNA
                     organism = Homo sapiens
SEQUENCE: 578
gcgggcggcg gcggc                                                          15

SEQ ID NO: 579       moltype = RNA   length = 22
FEATURE              Location/Qualifiers
source               1..22
                     mol_type = unassigned RNA
                     organism = Homo sapiens
SEQUENCE: 579
tgggagggga gaggcagcaa gc                                                  22

SEQ ID NO: 580       moltype = RNA   length = 22
FEATURE              Location/Qualifiers
source               1..22
                     mol_type = unassigned RNA
                     organism = Homo sapiens
SEQUENCE: 580
tgggagggga gaggcagcaa gc                                                  22

SEQ ID NO: 581       moltype = RNA   length = 26
FEATURE              Location/Qualifiers
source               1..26
                     mol_type = unassigned RNA
                     organism = Homo sapiens
SEQUENCE: 581
cgggtagaga gggcagtggg aggtaa                                              26

SEQ ID NO: 582       moltype = RNA   length = 15
FEATURE              Location/Qualifiers
source               1..15
                     mol_type = unassigned RNA
                     organism = Homo sapiens
SEQUENCE: 582
cgggtagaga gggca                                                          15

SEQ ID NO: 583       moltype = RNA   length = 23
FEATURE              Location/Qualifiers
source               1..23
                     mol_type = unassigned RNA
                     organism = Homo sapiens
SEQUENCE: 583
gagggaggga cggggctgt gct                                                  23

SEQ ID NO: 584       moltype = RNA   length = 15
FEATURE              Location/Qualifiers
source               1..15
                     mol_type = unassigned RNA
                     organism = Homo sapiens
SEQUENCE: 584
gaggagggag ggagg                                                          15

SEQ ID NO: 585       moltype = RNA   length = 25
FEATURE              Location/Qualifiers
source               1..25
                     mol_type = unassigned RNA
                     organism = Homo sapiens
SEQUENCE: 585
caggaaggat ttagggacag gcttt                                               25

SEQ ID NO: 586       moltype = RNA   length = 19
FEATURE              Location/Qualifiers
source               1..19
                     mol_type = unassigned RNA
                     organism = Homo sapiens
SEQUENCE: 586
caggaaggat ttagggaca                                                      19
```

| SEQ ID NO: 587 | moltype = RNA length = 18 | |
|---|---|---|
| FEATURE | Location/Qualifiers | |
| source | 1..18 | |
| | mol_type = unassigned RNA | |
| | organism = Homo sapiens | |
| SEQUENCE: 587 | | |
| ctccgggcgg cgccgtgt | | 18 |

| SEQ ID NO: 588 | moltype = RNA length = 18 | |
|---|---|---|
| FEATURE | Location/Qualifiers | |
| source | 1..18 | |
| | mol_type = unassigned RNA | |
| | organism = Homo sapiens | |
| SEQUENCE: 588 | | |
| ctccgggcgg cgccgtgt | | 18 |

| SEQ ID NO: 589 | moltype = RNA length = 24 | |
|---|---|---|
| FEATURE | Location/Qualifiers | |
| source | 1..24 | |
| | mol_type = unassigned RNA | |
| | organism = Homo sapiens | |
| SEQUENCE: 589 | | |
| aggcaggggc tggtgctggg cggg | | 24 |

| SEQ ID NO: 590 | moltype = RNA length = 15 | |
|---|---|---|
| FEATURE | Location/Qualifiers | |
| source | 1..15 | |
| | mol_type = unassigned RNA | |
| | organism = Homo sapiens | |
| SEQUENCE: 590 | | |
| gggcgggggg cggcg | | 15 |

| SEQ ID NO: 591 | moltype = RNA length = 21 | |
|---|---|---|
| FEATURE | Location/Qualifiers | |
| source | 1..21 | |
| | mol_type = unassigned RNA | |
| | organism = Homo sapiens | |
| SEQUENCE: 591 | | |
| ccggccgccg gctccgcccc g | | 21 |

| SEQ ID NO: 592 | moltype = RNA length = 17 | |
|---|---|---|
| FEATURE | Location/Qualifiers | |
| source | 1..17 | |
| | mol_type = unassigned RNA | |
| | organism = Homo sapiens | |
| SEQUENCE: 592 | | |
| ccggccgccg gctccgc | | 17 |

| SEQ ID NO: 593 | moltype = RNA length = 24 | |
|---|---|---|
| FEATURE | Location/Qualifiers | |
| source | 1..24 | |
| | mol_type = unassigned RNA | |
| | organism = Homo sapiens | |
| SEQUENCE: 593 | | |
| ctggtacagg cctgggggac aggg | | 24 |

| SEQ ID NO: 594 | moltype = RNA length = 18 | |
|---|---|---|
| FEATURE | Location/Qualifiers | |
| source | 1..18 | |
| | mol_type = unassigned RNA | |
| | organism = Homo sapiens | |
| SEQUENCE: 594 | | |
| ctggtacagg cctggggg | | 18 |

| SEQ ID NO: 595 | moltype = RNA length = 27 | |
|---|---|---|
| FEATURE | Location/Qualifiers | |
| source | 1..27 | |
| | mol_type = unassigned RNA | |
| | organism = Homo sapiens | |
| SEQUENCE: 595 | | |
| gtgaacgggc gccatcccga ggctttg | | 27 |

| SEQ ID NO: 596 | moltype = RNA length = 16 | |
|---|---|---|
| FEATURE | Location/Qualifiers | |
| source | 1..16 | |
| | mol_type = unassigned RNA | |
| | organism = Homo sapiens | |
| SEQUENCE: 596 | | |
| gtgaacgggc gccatc | | 16 |

| | | |
|---|---|---|
| SEQ ID NO: 597<br>FEATURE<br>source | moltype = RNA   length = 19<br>Location/Qualifiers<br>1..19<br>mol_type = unassigned RNA<br>organism = Homo sapiens | |
| SEQUENCE: 597<br>gtgggttggg gcgggctct | | 19 |
| SEQ ID NO: 598<br>FEATURE<br>source | moltype = RNA   length = 19<br>Location/Qualifiers<br>1..19<br>mol_type = unassigned RNA<br>organism = Homo sapiens | |
| SEQUENCE: 598<br>gtgggttggg gcgggctct | | 19 |
| SEQ ID NO: 599<br>FEATURE<br>source | moltype = RNA   length = 26<br>Location/Qualifiers<br>1..26<br>mol_type = unassigned RNA<br>organism = Homo sapiens | |
| SEQUENCE: 599<br>gcgggctgtc cggaggggtc ggcttt | | 26 |
| SEQ ID NO: 600<br>FEATURE<br>source | moltype = RNA   length = 16<br>Location/Qualifiers<br>1..16<br>mol_type = unassigned RNA<br>organism = Homo sapiens | |
| SEQUENCE: 600<br>gctgtccgga ggggtc | | 16 |
| SEQ ID NO: 601<br>FEATURE<br>source | moltype = RNA   length = 24<br>Location/Qualifiers<br>1..24<br>mol_type = unassigned RNA<br>organism = Homo sapiens | |
| SEQUENCE: 601<br>cccggggcag attggtgtag ggtg | | 24 |
| SEQ ID NO: 602<br>FEATURE<br>source | moltype = RNA   length = 17<br>Location/Qualifiers<br>1..17<br>mol_type = unassigned RNA<br>organism = Homo sapiens | |
| SEQUENCE: 602<br>cggggcagat tggtgta | | 17 |
| SEQ ID NO: 603<br>FEATURE<br>source | moltype = RNA   length = 23<br>Location/Qualifiers<br>1..23<br>mol_type = unassigned RNA<br>organism = Homo sapiens | |
| SEQUENCE: 603<br>gggggtcccc ggtgctcgga tct | | 23 |
| SEQ ID NO: 604<br>FEATURE<br>source | moltype = RNA   length = 16<br>Location/Qualifiers<br>1..16<br>mol_type = unassigned RNA<br>organism = Homo sapiens | |
| SEQUENCE: 604<br>tcgggagggg cgggag | | 16 |
| SEQ ID NO: 605<br>FEATURE<br>source | moltype = RNA   length = 23<br>Location/Qualifiers<br>1..23<br>mol_type = unassigned RNA<br>organism = Homo sapiens | |
| SEQUENCE: 605<br>cggggccgta gcactgtctg aga | | 23 |
| SEQ ID NO: 606<br>FEATURE<br>source | moltype = RNA   length = 20<br>Location/Qualifiers<br>1..20<br>mol_type = unassigned RNA<br>organism = Homo sapiens | |
| SEQUENCE: 606 | | |

```
cggggccgta gcactgtctg                                                   20

SEQ ID NO: 607         moltype = RNA   length = 27
FEATURE                Location/Qualifiers
source                 1..27
                       mol_type = unassigned RNA
                       organism = Homo sapiens
SEQUENCE: 607
tgagggactt ttgggggcag atgtgtt                                           27

SEQ ID NO: 608         moltype = RNA   length = 17
FEATURE                Location/Qualifiers
source                 1..17
                       mol_type = unassigned RNA
                       organism = Homo sapiens
SEQUENCE: 608
ggactttggg gggcaga                                                      17

SEQ ID NO: 609         moltype = RNA   length = 24
FEATURE                Location/Qualifiers
source                 1..24
                       mol_type = unassigned RNA
                       organism = Homo sapiens
SEQUENCE: 609
gaggctggga aggcaaaggg acgt                                              24

SEQ ID NO: 610         moltype = RNA   length = 15
FEATURE                Location/Qualifiers
source                 1..15
                       mol_type = unassigned RNA
                       organism = Homo sapiens
SEQUENCE: 610
gaaggaggct gggaa                                                        15

SEQ ID NO: 611         moltype = RNA   length = 17
FEATURE                Location/Qualifiers
source                 1..17
                       mol_type = unassigned RNA
                       organism = Homo sapiens
SEQUENCE: 611
aggggctggg cgcgcgc                                                      17

SEQ ID NO: 612         moltype = RNA   length = 15
FEATURE                Location/Qualifiers
source                 1..15
                       mol_type = unassigned RNA
                       organism = Homo sapiens
SEQUENCE: 612
caggggctgg gcgcg                                                        15

SEQ ID NO: 613         moltype = RNA   length = 25
FEATURE                Location/Qualifiers
source                 1..25
                       mol_type = unassigned RNA
                       organism = Homo sapiens
SEQUENCE: 613
tgcaggcaga agtggggctg acagg                                             25

SEQ ID NO: 614         moltype = RNA   length = 20
FEATURE                Location/Qualifiers
source                 1..20
                       mol_type = unassigned RNA
                       organism = Homo sapiens
SEQUENCE: 614
ctgcaggcag aagtggggct                                                   20

SEQ ID NO: 615         moltype = RNA   length = 23
FEATURE                Location/Qualifiers
source                 1..23
                       mol_type = unassigned RNA
                       organism = Homo sapiens
SEQUENCE: 615
gggggatgt gcatgctggt tgg                                                23

SEQ ID NO: 616         moltype = RNA   length = 15
FEATURE                Location/Qualifiers
source                 1..15
                       mol_type = unassigned RNA
                       organism = Homo sapiens
```

| | | |
|---|---|---|
| SEQUENCE: 616 | | |
| atcagcgtgc acttc | | 15 |
| | | |
| SEQ ID NO: 617 | moltype = RNA length = 23 | |
| FEATURE | Location/Qualifiers | |
| source | 1..23 | |
| | mol_type = unassigned RNA | |
| | organism = Homo sapiens | |
| SEQUENCE: 617 | | |
| caccttgcct tgctgcccgg gcc | | 23 |
| | | |
| SEQ ID NO: 618 | moltype = RNA length = 22 | |
| FEATURE | Location/Qualifiers | |
| source | 1..22 | |
| | mol_type = unassigned RNA | |
| | organism = Homo sapiens | |
| SEQUENCE: 618 | | |
| caccttgcct tgctgcccgg gc | | 22 |
| | | |
| SEQ ID NO: 619 | moltype = RNA length = 23 | |
| FEATURE | Location/Qualifiers | |
| source | 1..23 | |
| | mol_type = unassigned RNA | |
| | organism = Homo sapiens | |
| SEQUENCE: 619 | | |
| tggggcggag cttccggagg ccc | | 23 |
| | | |
| SEQ ID NO: 620 | moltype = RNA length = 17 | |
| FEATURE | Location/Qualifiers | |
| source | 1..17 | |
| | mol_type = unassigned RNA | |
| | organism = Homo sapiens | |
| SEQUENCE: 620 | | |
| tggggcggag cttccgg | | 17 |
| | | |
| SEQ ID NO: 621 | moltype = RNA length = 16 | |
| FEATURE | Location/Qualifiers | |
| source | 1..16 | |
| | mol_type = unassigned RNA | |
| | organism = Homo sapiens | |
| SEQUENCE: 621 | | |
| ggacccaggg agagac | | 16 |
| | | |
| SEQ ID NO: 622 | moltype = RNA length = 16 | |
| FEATURE | Location/Qualifiers | |
| source | 1..16 | |
| | mol_type = unassigned RNA | |
| | organism = Homo sapiens | |
| SEQUENCE: 622 | | |
| ggacccaggg agagac | | 16 |
| | | |
| SEQ ID NO: 623 | moltype = RNA length = 23 | |
| FEATURE | Location/Qualifiers | |
| source | 1..23 | |
| | mol_type = unassigned RNA | |
| | organism = Homo sapiens | |
| SEQUENCE: 623 | | |
| ggcccggccg tgcctgaggt ttc | | 23 |
| | | |
| SEQ ID NO: 624 | moltype = RNA length = 15 | |
| FEATURE | Location/Qualifiers | |
| source | 1..15 | |
| | mol_type = unassigned RNA | |
| | organism = Homo sapiens | |
| SEQUENCE: 624 | | |
| ggcggtggga tcccg | | 15 |
| | | |
| SEQ ID NO: 625 | moltype = RNA length = 23 | |
| FEATURE | Location/Qualifiers | |
| source | 1..23 | |
| | mol_type = unassigned RNA | |
| | organism = Homo sapiens | |
| SEQUENCE: 625 | | |
| cagcccgccc cagccgaggt tct | | 23 |
| | | |
| SEQ ID NO: 626 | moltype = RNA length = 17 | |
| FEATURE | Location/Qualifiers | |
| source | 1..17 | |
| | mol_type = unassigned RNA | |

```
                              organism = Homo sapiens
SEQUENCE: 626
agcccgcccc agccgag                                                              17

SEQ ID NO: 627          moltype = RNA  length = 22
FEATURE                 Location/Qualifiers
source                  1..22
                        mol_type = unassigned RNA
                        organism = Homo sapiens
SEQUENCE: 627
actcggctgc ggtggacaag tc                                                        22

SEQ ID NO: 628          moltype = RNA  length = 20
FEATURE                 Location/Qualifiers
source                  1..20
                        mol_type = unassigned RNA
                        organism = Homo sapiens
SEQUENCE: 628
actcggctgc ggtggacaag                                                           20

SEQ ID NO: 629          moltype = RNA  length = 23
FEATURE                 Location/Qualifiers
source                  1..23
                        mol_type = unassigned RNA
                        organism = Homo sapiens
SEQUENCE: 629
ggtgggtgag gtcgggcccc aag                                                       23

SEQ ID NO: 630          moltype = RNA  length = 20
FEATURE                 Location/Qualifiers
source                  1..20
                        mol_type = unassigned RNA
                        organism = Homo sapiens
SEQUENCE: 630
cggggtgggt gaggtcgggc                                                           20

SEQ ID NO: 631          moltype = RNA  length = 26
FEATURE                 Location/Qualifiers
source                  1..26
                        mol_type = unassigned RNA
                        organism = Homo sapiens
SEQUENCE: 631
gaggggctct cgcttctggc gccaag                                                    26

SEQ ID NO: 632          moltype = RNA  length = 15
FEATURE                 Location/Qualifiers
source                  1..15
                        mol_type = unassigned RNA
                        organism = Homo sapiens
SEQUENCE: 632
ggtgaggcgg ggggg                                                                15

SEQ ID NO: 633          moltype = RNA  length = 23
FEATURE                 Location/Qualifiers
source                  1..23
                        mol_type = unassigned RNA
                        organism = Homo sapiens
SEQUENCE: 633
ctgggggacg cgtgagcgcg agc                                                       23

SEQ ID NO: 634          moltype = RNA  length = 21
FEATURE                 Location/Qualifiers
source                  1..21
                        mol_type = unassigned RNA
                        organism = Homo sapiens
SEQUENCE: 634
ctgggggacg cgtgagcgcg a                                                         21

SEQ ID NO: 635          moltype = RNA  length = 24
FEATURE                 Location/Qualifiers
source                  1..24
                        mol_type = unassigned RNA
                        organism = Homo sapiens
SEQUENCE: 635
gtgagtggga gccggtgggg ctgg                                                      24

SEQ ID NO: 636          moltype = RNA  length = 15
FEATURE                 Location/Qualifiers
source                  1..15
```

```
                              mol_type = unassigned RNA
                              organism = Homo sapiens
SEQUENCE: 636
ggggctggag taagg                                                       15

SEQ ID NO: 637                moltype = RNA  length = 23
FEATURE                       Location/Qualifiers
source                        1..23
                              mol_type = unassigned RNA
                              organism = Homo sapiens
SEQUENCE: 637
gtgggctggg ctgggctggg cca                                              23

SEQ ID NO: 638                moltype = RNA  length = 15
FEATURE                       Location/Qualifiers
source                        1..15
                              mol_type = unassigned RNA
                              organism = Homo sapiens
SEQUENCE: 638
gggctgggct gggct                                                       15

SEQ ID NO: 639                moltype = RNA  length = 23
FEATURE                       Location/Qualifiers
source                        1..23
                              mol_type = unassigned RNA
                              organism = Homo sapiens
SEQUENCE: 639
tgcgcagggg ccgggtgctc acc                                              23

SEQ ID NO: 640                moltype = RNA  length = 19
FEATURE                       Location/Qualifiers
source                        1..19
                              mol_type = unassigned RNA
                              organism = Homo sapiens
SEQUENCE: 640
cgcaggggcc gggtgctca                                                   19

SEQ ID NO: 641                moltype = RNA  length = 25
FEATURE                       Location/Qualifiers
source                        1..25
                              mol_type = unassigned RNA
                              organism = Homo sapiens
SEQUENCE: 641
ttctgggccc gcggcgggcg tgggg                                            25

SEQ ID NO: 642                moltype = RNA  length = 15
FEATURE                       Location/Qualifiers
source                        1..15
                              mol_type = unassigned RNA
                              organism = Homo sapiens
SEQUENCE: 642
cgcggcgggc gtggg                                                       15

SEQ ID NO: 643                moltype = RNA  length = 23
FEATURE                       Location/Qualifiers
source                        1..23
                              mol_type = unassigned RNA
                              organism = Homo sapiens
SEQUENCE: 643
ctcctggggc ccgcactctc gct                                              23

SEQ ID NO: 644                moltype = RNA  length = 18
FEATURE                       Location/Qualifiers
source                        1..18
                              mol_type = unassigned RNA
                              organism = Homo sapiens
SEQUENCE: 644
ctcctggggc ccgcactc                                                    18

SEQ ID NO: 645                moltype = RNA  length = 22
FEATURE                       Location/Qualifiers
source                        1..22
                              mol_type = unassigned RNA
                              organism = Homo sapiens
SEQUENCE: 645
gaaaaaggcg ggagaagccc ca                                               22

SEQ ID NO: 646                moltype = RNA  length = 15
FEATURE                       Location/Qualifiers
```

```
source                  1..15
                        mol_type = unassigned RNA
                        organism = Homo sapiens
SEQUENCE: 646
gaaaaaggcg ggaga                                                        15

SEQ ID NO: 647          moltype = RNA   length = 19
FEATURE                 Location/Qualifiers
source                  1..19
                        mol_type = unassigned RNA
                        organism = Homo sapiens
SEQUENCE: 647
gcaggcgagg ctgggctga                                                    19

SEQ ID NO: 648          moltype = RNA   length = 16
FEATURE                 Location/Qualifiers
source                  1..16
                        mol_type = unassigned RNA
                        organism = Homo sapiens
SEQUENCE: 648
aggcgaggct gggctg                                                       16

SEQ ID NO: 649          moltype = RNA   length = 22
FEATURE                 Location/Qualifiers
source                  1..22
                        mol_type = unassigned RNA
                        organism = Homo sapiens
SEQUENCE: 649
aaaagctggg ctgagaggcg ac                                                22

SEQ ID NO: 650          moltype = RNA   length = 15
FEATURE                 Location/Qualifiers
source                  1..15
                        mol_type = unassigned RNA
                        organism = Homo sapiens
SEQUENCE: 650
aaagctgggc tgaga                                                        15

SEQ ID NO: 651          moltype = RNA   length = 23
FEATURE                 Location/Qualifiers
source                  1..23
                        mol_type = unassigned RNA
                        organism = Homo sapiens
SEQUENCE: 651
tggggaaggc gtcagtgtcg ggt                                               23

SEQ ID NO: 652          moltype = RNA   length = 16
FEATURE                 Location/Qualifiers
source                  1..16
                        mol_type = unassigned RNA
                        organism = Homo sapiens
SEQUENCE: 652
tggggaaggc gtcagt                                                       16

SEQ ID NO: 653          moltype = RNA   length = 23
FEATURE                 Location/Qualifiers
source                  1..23
                        mol_type = unassigned RNA
                        organism = Homo sapiens
SEQUENCE: 653
ggaggcgcag gctcggaaag gcg                                               23

SEQ ID NO: 654          moltype = RNA   length = 15
FEATURE                 Location/Qualifiers
source                  1..15
                        mol_type = unassigned RNA
                        organism = Homo sapiens
SEQUENCE: 654
gcaggctcgg aaagg                                                        15

SEQ ID NO: 655          moltype = RNA   length = 23
FEATURE                 Location/Qualifiers
source                  1..23
                        mol_type = unassigned RNA
                        organism = Homo sapiens
SEQUENCE: 655
agaagaaggc ggtcggtctg cgg                                               23

SEQ ID NO: 656          moltype = RNA   length = 21
```

```
                           FEATURE              Location/Qualifiers
                           source               1..21
                                                mol_type = unassigned RNA
                                                organism = Homo sapiens
SEQUENCE: 656
aagaaggcgg tcggtctgcg g                                                        21

SEQ ID NO: 657            moltype = RNA   length = 25
FEATURE                   Location/Qualifiers
source                    1..25
                          mol_type = unassigned RNA
                          organism = Homo sapiens
SEQUENCE: 657
agcggggagg aagtgggcgc tgctt                                                    25

SEQ ID NO: 658            moltype = RNA   length = 21
FEATURE                   Location/Qualifiers
source                    1..21
                          mol_type = unassigned RNA
                          organism = Homo sapiens
SEQUENCE: 658
agcggggagg aagtgggcgc t                                                        21

SEQ ID NO: 659            moltype = RNA   length = 17
FEATURE                   Location/Qualifiers
source                    1..17
                          mol_type = unassigned RNA
                          organism = Homo sapiens
SEQUENCE: 659
cctccgggac ggctggg                                                             17

SEQ ID NO: 660            moltype = RNA   length = 15
FEATURE                   Location/Qualifiers
source                    1..15
                          mol_type = unassigned RNA
                          organism = Homo sapiens
SEQUENCE: 660
ctccgggacg gctgg                                                               15

SEQ ID NO: 661            moltype = RNA   length = 24
FEATURE                   Location/Qualifiers
source                    1..24
                          mol_type = unassigned RNA
                          organism = Homo sapiens
SEQUENCE: 661
tcgaggactg gtggaagggc cttt                                                     24

SEQ ID NO: 662            moltype = RNA   length = 16
FEATURE                   Location/Qualifiers
source                    1..16
                          mol_type = unassigned RNA
                          organism = Homo sapiens
SEQUENCE: 662
tcgaggactg gtggaa                                                              16

SEQ ID NO: 663            moltype = RNA   length = 23
FEATURE                   Location/Qualifiers
source                    1..23
                          mol_type = unassigned RNA
                          organism = Homo sapiens
SEQUENCE: 663
ggctacaaca caggacccgg gcg                                                      23

SEQ ID NO: 664            moltype = RNA   length = 21
FEATURE                   Location/Qualifiers
source                    1..21
                          mol_type = unassigned RNA
                          organism = Homo sapiens
SEQUENCE: 664
ggctacaaca caggacccgg g                                                        21

SEQ ID NO: 665            moltype = RNA   length = 23
FEATURE                   Location/Qualifiers
source                    1..23
                          mol_type = unassigned RNA
                          organism = Homo sapiens
SEQUENCE: 665
tggggcggag cttccggagg ccc                                                      23
```

| | | |
|---|---|---|
| SEQ ID NO: 666<br>FEATURE<br>source | moltype = RNA   length = 15<br>Location/Qualifiers<br>1..15<br>mol_type = unassigned RNA<br>organism = Homo sapiens | |
| SEQUENCE: 666<br>gccccgggaa agcgt | | 15 |
| SEQ ID NO: 667<br>FEATURE<br>source | moltype = RNA   length = 21<br>Location/Qualifiers<br>1..21<br>mol_type = unassigned RNA<br>organism = Homo sapiens | |
| SEQUENCE: 667<br>gaggcgatgt ggggatgtag a | | 21 |
| SEQ ID NO: 668<br>FEATURE<br>source | moltype = RNA   length = 20<br>Location/Qualifiers<br>1..20<br>mol_type = unassigned RNA<br>organism = Homo sapiens | |
| SEQUENCE: 668<br>cccagtctca tttcctcatc | | 20 |
| SEQ ID NO: 669<br>FEATURE<br>source | moltype = RNA   length = 21<br>Location/Qualifiers<br>1..21<br>mol_type = unassigned RNA<br>organism = Homo sapiens | |
| SEQUENCE: 669<br>gagggcagcg tgggtgtggc g | | 21 |
| SEQ ID NO: 670<br>FEATURE<br>source | moltype = RNA   length = 21<br>Location/Qualifiers<br>1..21<br>mol_type = unassigned RNA<br>organism = Homo sapiens | |
| SEQUENCE: 670<br>gagggcagcg tgggtgtggc g | | 21 |
| SEQ ID NO: 671<br>FEATURE<br>source | moltype = RNA   length = 22<br>Location/Qualifiers<br>1..22<br>mol_type = unassigned RNA<br>organism = Homo sapiens | |
| SEQUENCE: 671<br>accaggaggc tgaggcccct ca | | 22 |
| SEQ ID NO: 672<br>FEATURE<br>source | moltype = RNA   length = 15<br>Location/Qualifiers<br>1..15<br>mol_type = unassigned RNA<br>organism = Homo sapiens | |
| SEQUENCE: 672<br>accaggaggc tgagg | | 15 |
| SEQ ID NO: 673<br>FEATURE<br>source | moltype = RNA   length = 21<br>Location/Qualifiers<br>1..21<br>mol_type = unassigned RNA<br>organism = Homo sapiens | |
| SEQUENCE: 673<br>ttgaggagac atggtggggg c | | 21 |
| SEQ ID NO: 674<br>FEATURE<br>source | moltype = RNA   length = 15<br>Location/Qualifiers<br>1..15<br>mol_type = unassigned RNA<br>organism = Homo sapiens | |
| SEQUENCE: 674<br>ttgaggagac atggt | | 15 |
| SEQ ID NO: 675<br>FEATURE<br>source | moltype = RNA   length = 22<br>Location/Qualifiers<br>1..22<br>mol_type = unassigned RNA<br>organism = Homo sapiens | |
| SEQUENCE: 675<br>ggcagggaca gcaaaggggt gc | | 22 |

```
SEQ ID NO: 676            moltype = RNA   length = 18
FEATURE                   Location/Qualifiers
source                    1..18
                          mol_type = unassigned RNA
                          organism = Homo sapiens
SEQUENCE: 676
gcagggacag caaaggg                                                         18

SEQ ID NO: 677            moltype = RNA   length = 25
FEATURE                   Location/Qualifiers
source                    1..25
                          mol_type = unassigned RNA
                          organism = Homo sapiens
SEQUENCE: 677
ctgcaggcag aagtggggct gacag                                                25

SEQ ID NO: 678            moltype = RNA   length = 19
FEATURE                   Location/Qualifiers
source                    1..19
                          mol_type = unassigned RNA
                          organism = Homo sapiens
SEQUENCE: 678
caggcagaag tggggctga                                                       19

SEQ ID NO: 679            moltype = RNA   length = 24
FEATURE                   Location/Qualifiers
source                    1..24
                          mol_type = unassigned RNA
                          organism = Homo sapiens
SEQUENCE: 679
cgctcgggcg gaggtggttg agtg                                                 24

SEQ ID NO: 680            moltype = RNA   length = 17
FEATURE                   Location/Qualifiers
source                    1..17
                          mol_type = unassigned RNA
                          organism = Homo sapiens
SEQUENCE: 680
tcggcggag gtggttg                                                          17

SEQ ID NO: 681            moltype = RNA   length = 16
FEATURE                   Location/Qualifiers
source                    1..16
                          mol_type = unassigned RNA
                          organism = Homo sapiens
SEQUENCE: 681
gtgaaggccc ggcgga                                                          16

SEQ ID NO: 682            moltype = RNA   length = 15
FEATURE                   Location/Qualifiers
source                    1..15
                          mol_type = unassigned RNA
                          organism = Homo sapiens
SEQUENCE: 682
gtgaaggccc ggcgg                                                           15

SEQ ID NO: 683            moltype = RNA   length = 17
FEATURE                   Location/Qualifiers
source                    1..17
                          mol_type = unassigned RNA
                          organism = Homo sapiens
SEQUENCE: 683
tgcaggggca ggccagc                                                         17

SEQ ID NO: 684            moltype = RNA   length = 17
FEATURE                   Location/Qualifiers
source                    1..17
                          mol_type = unassigned RNA
                          organism = Homo sapiens
SEQUENCE: 684
tgcaggggca ggccagc                                                         17

SEQ ID NO: 685            moltype = RNA   length = 25
FEATURE                   Location/Qualifiers
source                    1..25
                          mol_type = unassigned RNA
                          organism = Homo sapiens
SEQUENCE: 685
```

```
tgcggggcta gggctaacag cagtc                                              25

SEQ ID NO: 686          moltype = RNA   length = 15
FEATURE                 Location/Qualifiers
source                  1..15
                        mol_type = unassigned RNA
                        organism = Homo sapiens
SEQUENCE: 686
tgcggggcta gggct                                                         15

SEQ ID NO: 687          moltype = RNA   length = 17
FEATURE                 Location/Qualifiers
source                  1..17
                        mol_type = unassigned RNA
                        organism = Homo sapiens
SEQUENCE: 687
ggtgagcgct cgctggc                                                       17

SEQ ID NO: 688          moltype = RNA   length = 15
FEATURE                 Location/Qualifiers
source                  1..15
                        mol_type = unassigned RNA
                        organism = Homo sapiens
SEQUENCE: 688
cggtgagcgc tcgct                                                         15

SEQ ID NO: 689          moltype = RNA   length = 15
FEATURE                 Location/Qualifiers
source                  1..15
                        mol_type = unassigned RNA
                        organism = Homo sapiens
SEQUENCE: 689
ggcgcgggga ggtgc                                                         15

SEQ ID NO: 690          moltype = RNA   length = 15
FEATURE                 Location/Qualifiers
source                  1..15
                        mol_type = unassigned RNA
                        organism = Homo sapiens
SEQUENCE: 690
ggcgcgggga ggtgc                                                         15

SEQ ID NO: 691          moltype = RNA   length = 18
FEATURE                 Location/Qualifiers
source                  1..18
                        mol_type = unassigned RNA
                        organism = Homo sapiens
SEQUENCE: 691
gaggctgaag gaagatgg                                                      18

SEQ ID NO: 692          moltype = RNA   length = 15
FEATURE                 Location/Qualifiers
source                  1..15
                        mol_type = unassigned RNA
                        organism = Homo sapiens
SEQUENCE: 692
gaggctgaag gaaga                                                         15

SEQ ID NO: 693          moltype = RNA   length = 23
FEATURE                 Location/Qualifiers
source                  1..23
                        mol_type = unassigned RNA
                        organism = Homo sapiens
SEQUENCE: 693
ccagggctgg cagtgacatg ggt                                                23

SEQ ID NO: 694          moltype = RNA   length = 19
FEATURE                 Location/Qualifiers
source                  1..19
                        mol_type = unassigned RNA
                        organism = Homo sapiens
SEQUENCE: 694
cagggctggc agtgacatg                                                     19

SEQ ID NO: 695          moltype = RNA   length = 16
FEATURE                 Location/Qualifiers
source                  1..16
                        mol_type = unassigned RNA
                        organism = Homo sapiens
```

```
SEQUENCE: 695
tgctggtgat gctttc                                                          16

SEQ ID NO: 696           moltype = RNA   length = 16
FEATURE                  Location/Qualifiers
source                   1..16
                         mol_type = unassigned RNA
                         organism = Homo sapiens
SEQUENCE: 696
tgctggtgat gctttc                                                          16

SEQ ID NO: 697           moltype = RNA   length = 22
FEATURE                  Location/Qualifiers
source                   1..22
                         mol_type = unassigned RNA
                         organism = Homo sapiens
SEQUENCE: 697
gagggttggg tggaggctct cc                                                   22

SEQ ID NO: 698           moltype = RNA   length = 15
FEATURE                  Location/Qualifiers
source                   1..15
                         mol_type = unassigned RNA
                         organism = Homo sapiens
SEQUENCE: 698
gagggttggg tggag                                                           15

SEQ ID NO: 699           moltype = RNA   length = 20
FEATURE                  Location/Qualifiers
source                   1..20
                         mol_type = unassigned RNA
                         organism = Homo sapiens
SEQUENCE: 699
tgagtggggc tcccgggacg                                                      20

SEQ ID NO: 700           moltype = RNA   length = 20
FEATURE                  Location/Qualifiers
source                   1..20
                         mol_type = unassigned RNA
                         organism = Homo sapiens
SEQUENCE: 700
tgagtggggc tcccgggacg                                                      20

SEQ ID NO: 701           moltype = RNA   length = 21
FEATURE                  Location/Qualifiers
source                   1..21
                         mol_type = unassigned RNA
                         organism = Homo sapiens
SEQUENCE: 701
cccagcagga cgggagcgcg g                                                    21

SEQ ID NO: 702           moltype = RNA   length = 16
FEATURE                  Location/Qualifiers
source                   1..16
                         mol_type = unassigned RNA
                         organism = Homo sapiens
SEQUENCE: 702
aagctgggtc aaggag                                                          16

SEQ ID NO: 703           moltype = RNA   length = 20
FEATURE                  Location/Qualifiers
source                   1..20
                         mol_type = unassigned RNA
                         organism = Homo sapiens
SEQUENCE: 703
ggctggtcag atgggagtgg                                                      20

SEQ ID NO: 704           moltype = RNA   length = 20
FEATURE                  Location/Qualifiers
source                   1..20
                         mol_type = unassigned RNA
                         organism = Homo sapiens
SEQUENCE: 704
ggctggtcag atgggagtgg                                                      20

SEQ ID NO: 705           moltype = RNA   length = 23
FEATURE                  Location/Qualifiers
source                   1..23
                         mol_type = unassigned RNA
```

```
                              organism = Homo sapiens
SEQUENCE: 705
acaggagtgg gggtgggaca taa                                              23

SEQ ID NO: 706          moltype = RNA  length = 20
FEATURE                 Location/Qualifiers
source                  1..20
                        mol_type = unassigned RNA
                        organism = Homo sapiens
SEQUENCE: 706
acaggagtgg gggtgggaca                                                  20

SEQ ID NO: 707          moltype = RNA  length = 22
FEATURE                 Location/Qualifiers
source                  1..22
                        mol_type = unassigned RNA
                        organism = Homo sapiens
SEQUENCE: 707
gtgggcgggg gcaggtgtgt gg                                               22

SEQ ID NO: 708          moltype = RNA  length = 15
FEATURE                 Location/Qualifiers
source                  1..15
                        mol_type = unassigned RNA
                        organism = Homo sapiens
SEQUENCE: 708
cggggcagg tgtgt                                                        15

SEQ ID NO: 709          moltype = RNA  length = 21
FEATURE                 Location/Qualifiers
source                  1..21
                        mol_type = unassigned RNA
                        organism = Homo sapiens
SEQUENCE: 709
gccgggcgtg gtggtggggg c                                                21

SEQ ID NO: 710          moltype = RNA  length = 15
FEATURE                 Location/Qualifiers
source                  1..15
                        mol_type = unassigned RNA
                        organism = Homo sapiens
SEQUENCE: 710
tagccgggcg tggtg                                                       15

SEQ ID NO: 711          moltype = RNA  length = 29
FEATURE                 Location/Qualifiers
source                  1..29
                        mol_type = unassigned RNA
                        organism = Homo sapiens
SEQUENCE: 711
ggtcaggcgg ctcggactga gcaggtggg                                        29

SEQ ID NO: 712          moltype = RNA  length = 15
FEATURE                 Location/Qualifiers
source                  1..15
                        mol_type = unassigned RNA
                        organism = Homo sapiens
SEQUENCE: 712
agagtgtggt caggc                                                       15

SEQ ID NO: 713          moltype = RNA  length = 22
FEATURE                 Location/Qualifiers
source                  1..22
                        mol_type = unassigned RNA
                        organism = Homo sapiens
SEQUENCE: 713
cagaagggga gttgggagca ga                                               22

SEQ ID NO: 714          moltype = RNA  length = 16
FEATURE                 Location/Qualifiers
source                  1..16
                        mol_type = unassigned RNA
                        organism = Homo sapiens
SEQUENCE: 714
gaagggagt tgggag                                                       16

SEQ ID NO: 715          moltype = RNA  length = 16
FEATURE                 Location/Qualifiers
source                  1..16
```

```
                            mol_type = unassigned RNA
                            organism = Homo sapiens
SEQUENCE: 715
ggcgcggagg gcggac                                                        16

SEQ ID NO: 716              moltype = RNA   length = 15
FEATURE                     Location/Qualifiers
source                      1..15
                            mol_type = unassigned RNA
                            organism = Homo sapiens
SEQUENCE: 716
ggcgcggagg gcgga                                                         15

SEQ ID NO: 717              moltype = RNA   length = 21
FEATURE                     Location/Qualifiers
source                      1..21
                            mol_type = unassigned RNA
                            organism = Homo sapiens
SEQUENCE: 717
cagcagggga gagagaggag t                                                  21

SEQ ID NO: 718              moltype = RNA   length = 20
FEATURE                     Location/Qualifiers
source                      1..20
                            mol_type = unassigned RNA
                            organism = Homo sapiens
SEQUENCE: 718
cagcagggga gagagaggag                                                    20

SEQ ID NO: 719              moltype = RNA   length = 26
FEATURE                     Location/Qualifiers
source                      1..26
                            mol_type = unassigned RNA
                            organism = Homo sapiens
SEQUENCE: 719
ccttctggag aggctttgtg cggata                                             26

SEQ ID NO: 720              moltype = RNA   length = 15
FEATURE                     Location/Qualifiers
source                      1..15
                            mol_type = unassigned RNA
                            organism = Homo sapiens
SEQUENCE: 720
ccttctggag aggct                                                         15

SEQ ID NO: 721              moltype = RNA   length = 23
FEATURE                     Location/Qualifiers
source                      1..23
                            mol_type = unassigned RNA
                            organism = Homo sapiens
SEQUENCE: 721
gaaatcaagc gtgggtgaga cct                                                23

SEQ ID NO: 722              moltype = RNA   length = 20
FEATURE                     Location/Qualifiers
source                      1..20
                            mol_type = unassigned RNA
                            organism = Homo sapiens
SEQUENCE: 722
gaaatcaagc gtgggtgaga                                                    20

SEQ ID NO: 723              moltype = RNA   length = 26
FEATURE                     Location/Qualifiers
source                      1..26
                            mol_type = unassigned RNA
                            organism = Homo sapiens
SEQUENCE: 723
agggctggac tcagcggcgg agctgg                                             26

SEQ ID NO: 724              moltype = RNA   length = 17
FEATURE                     Location/Qualifiers
source                      1..17
                            mol_type = unassigned RNA
                            organism = Homo sapiens
SEQUENCE: 724
gcggcggagc tggctgc                                                       17

SEQ ID NO: 725              moltype = RNA   length = 24
FEATURE                     Location/Qualifiers
```

```
source                  1..24
                        mol_type = unassigned RNA
                        organism = Homo sapiens
SEQUENCE: 725
cgggcgtggt ggtggggtg ggtg                                                24

SEQ ID NO: 726          moltype = RNA   length = 15
FEATURE                 Location/Qualifiers
source                  1..15
                        mol_type = unassigned RNA
                        organism = Homo sapiens
SEQUENCE: 726
cgggcgtggt ggtgg                                                         15

SEQ ID NO: 727          moltype = RNA   length = 22
FEATURE                 Location/Qualifiers
source                  1..22
                        mol_type = unassigned RNA
                        organism = Homo sapiens
SEQUENCE: 727
actcaaactg tgggggcact tt                                                 22

SEQ ID NO: 728          moltype = RNA   length = 19
FEATURE                 Location/Qualifiers
source                  1..19
                        mol_type = unassigned RNA
                        organism = Homo sapiens
SEQUENCE: 728
actcaaactg tgggggcac                                                     19

SEQ ID NO: 729          moltype = RNA   length = 16
FEATURE                 Location/Qualifiers
source                  1..16
                        mol_type = unassigned RNA
                        organism = Homo sapiens
SEQUENCE: 729
tgggggggaa gaaaag                                                        16

SEQ ID NO: 730          moltype = RNA   length = 16
FEATURE                 Location/Qualifiers
source                  1..16
                        mol_type = unassigned RNA
                        organism = Homo sapiens
SEQUENCE: 730
tgggggggaa gaaaag                                                        16

SEQ ID NO: 731          moltype = RNA   length = 21
FEATURE                 Location/Qualifiers
source                  1..21
                        mol_type = unassigned RNA
                        organism = Homo sapiens
SEQUENCE: 731
atccagttct ctgagggggc t                                                  21

SEQ ID NO: 732          moltype = RNA   length = 21
FEATURE                 Location/Qualifiers
source                  1..21
                        mol_type = unassigned RNA
                        organism = Homo sapiens
SEQUENCE: 732
atccagttct ctgagggggc t                                                  21

SEQ ID NO: 733          moltype = RNA   length = 24
FEATURE                 Location/Qualifiers
source                  1..24
                        mol_type = unassigned RNA
                        organism = Homo sapiens
SEQUENCE: 733
tggggagctg aggctctggg ggtg                                               24

SEQ ID NO: 734          moltype = RNA   length = 15
FEATURE                 Location/Qualifiers
source                  1..15
                        mol_type = unassigned RNA
                        organism = Homo sapiens
SEQUENCE: 734
ggccctgggg agctg                                                         15

SEQ ID NO: 735          moltype = RNA   length = 22
```

```
FEATURE              Location/Qualifiers
source               1..22
                     mol_type = unassigned RNA
                     organism = Homo sapiens
SEQUENCE: 735
ccgggaacgt cgagactgga gc                                           22

SEQ ID NO: 736       moltype = RNA   length = 15
FEATURE              Location/Qualifiers
source               1..15
                     mol_type = unassigned RNA
                     organism = Homo sapiens
SEQUENCE: 736
cgggaacgtc gagac                                                   15

SEQ ID NO: 737       moltype = RNA   length = 19
FEATURE              Location/Qualifiers
source               1..19
                     mol_type = unassigned RNA
                     organism = Homo sapiens
SEQUENCE: 737
tggcgggtgc gggggtggg                                               19

SEQ ID NO: 738       moltype = RNA   length = 15
FEATURE              Location/Qualifiers
source               1..15
                     mol_type = unassigned RNA
                     organism = Homo sapiens
SEQUENCE: 738
tggcgggtgc ggggg                                                   15

SEQ ID NO: 739       moltype = RNA   length = 23
FEATURE              Location/Qualifiers
source               1..23
                     mol_type = unassigned RNA
                     organism = Homo sapiens
SEQUENCE: 739
taggggcagc agaggacctg ggc                                          23

SEQ ID NO: 740       moltype = RNA   length = 20
FEATURE              Location/Qualifiers
source               1..20
                     mol_type = unassigned RNA
                     organism = Homo sapiens
SEQUENCE: 740
taggggcagc agaggacctg                                              20

SEQ ID NO: 741       moltype = RNA   length = 17
FEATURE              Location/Qualifiers
source               1..17
                     mol_type = unassigned RNA
                     organism = Homo sapiens
SEQUENCE: 741
ggggcggggg cggggc                                                  17

SEQ ID NO: 742       moltype = RNA   length = 15
FEATURE              Location/Qualifiers
source               1..15
                     mol_type = unassigned RNA
                     organism = Homo sapiens
SEQUENCE: 742
cgcgccgggc ccggg                                                   15

SEQ ID NO: 743       moltype = RNA   length = 23
FEATURE              Location/Qualifiers
source               1..23
                     mol_type = unassigned RNA
                     organism = Homo sapiens
SEQUENCE: 743
tggggacgta gctggccaga cag                                          23

SEQ ID NO: 744       moltype = RNA   length = 20
FEATURE              Location/Qualifiers
source               1..20
                     mol_type = unassigned RNA
                     organism = Homo sapiens
SEQUENCE: 744
tggggacgta gctggccaga                                              20
```

```
SEQ ID NO: 745            moltype = RNA  length = 21
FEATURE                   Location/Qualifiers
source                    1..21
                          mol_type = unassigned RNA
                          organism = Homo sapiens
SEQUENCE: 745
cagcctgagt gacagagcaa g                                                  21

SEQ ID NO: 746            moltype = RNA  length = 15
FEATURE                   Location/Qualifiers
source                    1..15
                          mol_type = unassigned RNA
                          organism = Homo sapiens
SEQUENCE: 746
actgcactcc agcct                                                         15

SEQ ID NO: 747            moltype = RNA  length = 18
FEATURE                   Location/Qualifiers
source                    1..18
                          mol_type = unassigned RNA
                          organism = Homo sapiens
SEQUENCE: 747
gagactgggg tggggcct                                                      18

SEQ ID NO: 748            moltype = RNA  length = 16
FEATURE                   Location/Qualifiers
source                    1..16
                          mol_type = unassigned RNA
                          organism = Homo sapiens
SEQUENCE: 748
agactggggt ggggcc                                                        16

SEQ ID NO: 749            moltype = RNA  length = 16
FEATURE                   Location/Qualifiers
source                    1..16
                          mol_type = unassigned RNA
                          organism = Homo sapiens
SEQUENCE: 749
ggcggtgggc ggcggg                                                        16

SEQ ID NO: 750            moltype = RNA  length = 15
FEATURE                   Location/Qualifiers
source                    1..15
                          mol_type = unassigned RNA
                          organism = Homo sapiens
SEQUENCE: 750
ggcctctcgg gaact                                                         15

SEQ ID NO: 751            moltype = RNA  length = 17
FEATURE                   Location/Qualifiers
source                    1..17
                          mol_type = unassigned RNA
                          organism = Homo sapiens
SEQUENCE: 751
gcggggcggc aggggcc                                                       17

SEQ ID NO: 752            moltype = RNA  length = 15
FEATURE                   Location/Qualifiers
source                    1..15
                          mol_type = unassigned RNA
                          organism = Homo sapiens
SEQUENCE: 752
gggggcgggg cggca                                                         15

SEQ ID NO: 753            moltype = RNA  length = 23
FEATURE                   Location/Qualifiers
source                    1..23
                          mol_type = unassigned RNA
                          organism = Homo sapiens
SEQUENCE: 753
tgaggatatg gcagggaagg gga                                                23

SEQ ID NO: 754            moltype = RNA  length = 19
FEATURE                   Location/Qualifiers
source                    1..19
                          mol_type = unassigned RNA
                          organism = Homo sapiens
SEQUENCE: 754
tgaggatatg gcagggaag                                                     19
```

```
SEQ ID NO: 755           moltype = RNA  length = 20
FEATURE                  Location/Qualifiers
source                   1..20
                         mol_type = unassigned RNA
                         organism = Homo sapiens
SEQUENCE: 755
ctccccggtg tgcaaatgtg                                                      20

SEQ ID NO: 756           moltype = RNA  length = 15
FEATURE                  Location/Qualifiers
source                   1..15
                         mol_type = unassigned RNA
                         organism = Homo sapiens
SEQUENCE: 756
gtgtgcggtg ttatg                                                           15

SEQ ID NO: 757           moltype = RNA  length = 23
FEATURE                  Location/Qualifiers
source                   1..23
                         mol_type = unassigned RNA
                         organism = Homo sapiens
SEQUENCE: 757
cggggcagct cagtacagga tac                                                  23

SEQ ID NO: 758           moltype = RNA  length = 15
FEATURE                  Location/Qualifiers
source                   1..15
                         mol_type = unassigned RNA
                         organism = Homo sapiens
SEQUENCE: 758
agctcagtac aggat                                                           15

SEQ ID NO: 759           moltype = RNA  length = 24
FEATURE                  Location/Qualifiers
source                   1..24
                         mol_type = unassigned RNA
                         organism = Homo sapiens
SEQUENCE: 759
cccaaaatgc tgggattaca ggca                                                 24

SEQ ID NO: 760           moltype = RNA  length = 15
FEATURE                  Location/Qualifiers
source                   1..15
                         mol_type = unassigned RNA
                         organism = Homo sapiens
SEQUENCE: 760
gcccacctca gcctc                                                           15

SEQ ID NO: 761           moltype = RNA  length = 21
FEATURE                  Location/Qualifiers
source                   1..21
                         mol_type = unassigned RNA
                         organism = Homo sapiens
SEQUENCE: 761
gtgagtcagg gtggggctgg c                                                    21

SEQ ID NO: 762           moltype = RNA  length = 21
FEATURE                  Location/Qualifiers
source                   1..21
                         mol_type = unassigned RNA
                         organism = Homo sapiens
SEQUENCE: 762
gtgagtcagg gtggggctgg c                                                    21

SEQ ID NO: 763           moltype = RNA  length = 15
FEATURE                  Location/Qualifiers
source                   1..15
                         mol_type = unassigned RNA
                         organism = Homo sapiens
SEQUENCE: 763
aggaggagga ggcag                                                           15

SEQ ID NO: 764           moltype = RNA  length = 15
FEATURE                  Location/Qualifiers
source                   1..15
                         mol_type = unassigned RNA
                         organism = Homo sapiens
SEQUENCE: 764
```

```
aggaggagga ggcag                                                        15

SEQ ID NO: 765          moltype = RNA   length = 21
FEATURE                 Location/Qualifiers
source                  1..21
                        mol_type = unassigned RNA
                        organism = Homo sapiens
SEQUENCE: 765
cggatccgag tcacggcacc a                                                 21

SEQ ID NO: 766          moltype = RNA   length = 15
FEATURE                 Location/Qualifiers
source                  1..15
                        mol_type = unassigned RNA
                        organism = Homo sapiens
SEQUENCE: 766
ggatccgagt cacgg                                                        15

SEQ ID NO: 767          moltype = RNA   length = 23
FEATURE                 Location/Qualifiers
source                  1..23
                        mol_type = unassigned RNA
                        organism = Homo sapiens
SEQUENCE: 767
ccaggaggcg gaggaggtgg agg                                               23

SEQ ID NO: 768          moltype = RNA   length = 15
FEATURE                 Location/Qualifiers
source                  1..15
                        mol_type = unassigned RNA
                        organism = Homo sapiens
SEQUENCE: 768
acccaggagg cggag                                                        15

SEQ ID NO: 769          moltype = RNA   length = 26
FEATURE                 Location/Qualifiers
source                  1..26
                        mol_type = unassigned RNA
                        organism = Homo sapiens
SEQUENCE: 769
gtcccggggc tgcgcgaggc acaggc                                            26

SEQ ID NO: 770          moltype = RNA   length = 15
FEATURE                 Location/Qualifiers
source                  1..15
                        mol_type = unassigned RNA
                        organism = Homo sapiens
SEQUENCE: 770
ggcccggggg gcggg                                                        15

SEQ ID NO: 771          moltype = RNA   length = 21
FEATURE                 Location/Qualifiers
source                  1..21
                        mol_type = unassigned RNA
                        organism = Homo sapiens
SEQUENCE: 771
aggaggcagt gggcgagcag g                                                 21

SEQ ID NO: 772          moltype = RNA   length = 21
FEATURE                 Location/Qualifiers
source                  1..21
                        mol_type = unassigned RNA
                        organism = Homo sapiens
SEQUENCE: 772
aggaggcagt gggcgagcag g                                                 21

SEQ ID NO: 773          moltype = RNA   length = 23
FEATURE                 Location/Qualifiers
source                  1..23
                        mol_type = unassigned RNA
                        organism = Homo sapiens
SEQUENCE: 773
acagcagggc tggggattgc agt                                               23

SEQ ID NO: 774          moltype = RNA   length = 19
FEATURE                 Location/Qualifiers
source                  1..19
                        mol_type = unassigned RNA
                        organism = Homo sapiens
```

-continued

```
SEQUENCE: 774
tgctgctccc agtcctgcc                                                          19

SEQ ID NO: 775          moltype = RNA   length = 19
FEATURE                 Location/Qualifiers
source                  1..19
                        mol_type = unassigned RNA
                        organism = Homo sapiens
SEQUENCE: 775
gctgggcgag gctggcatc                                                          19

SEQ ID NO: 776          moltype = RNA   length = 17
FEATURE                 Location/Qualifiers
source                  1..17
                        mol_type = unassigned RNA
                        organism = Homo sapiens
SEQUENCE: 776
gctgggcgag gctggca                                                            17

SEQ ID NO: 777          moltype = RNA   length = 18
FEATURE                 Location/Qualifiers
source                  1..18
                        mol_type = unassigned RNA
                        organism = Homo sapiens
SEQUENCE: 777
cagcggggct gggcgcgc                                                           18

SEQ ID NO: 778          moltype = RNA   length = 15
FEATURE                 Location/Qualifiers
source                  1..15
                        mol_type = unassigned RNA
                        organism = Homo sapiens
SEQUENCE: 778
cagcggggct gggcg                                                              15

SEQ ID NO: 779          moltype = RNA   length = 22
FEATURE                 Location/Qualifiers
source                  1..22
                        mol_type = unassigned RNA
                        organism = Homo sapiens
SEQUENCE: 779
caggcacggg agctcaggtg ag                                                      22

SEQ ID NO: 780          moltype = RNA   length = 17
FEATURE                 Location/Qualifiers
source                  1..17
                        mol_type = unassigned RNA
                        organism = Homo sapiens
SEQUENCE: 780
caggcacggg agctcag                                                            17

SEQ ID NO: 781          moltype = RNA   length = 18
FEATURE                 Location/Qualifiers
source                  1..18
                        mol_type = unassigned RNA
                        organism = Homo sapiens
SEQUENCE: 781
ggcagcggcg gcggcggc                                                           18

SEQ ID NO: 782          moltype = RNA   length = 15
FEATURE                 Location/Qualifiers
source                  1..15
                        mol_type = unassigned RNA
                        organism = Homo sapiens
SEQUENCE: 782
gctccccgcg ccccc                                                              15

SEQ ID NO: 783          moltype = RNA   length = 20
FEATURE                 Location/Qualifiers
source                  1..20
                        mol_type = unassigned RNA
                        organism = Homo sapiens
SEQUENCE: 783
atcccaccac tgccaccatt                                                         20

SEQ ID NO: 784          moltype = RNA   length = 15
FEATURE                 Location/Qualifiers
source                  1..15
                        mol_type = unassigned RNA
```

```
                        organism = Homo sapiens
SEQUENCE: 784
atcccaccac tgcca                                                          15

SEQ ID NO: 785          moltype = RNA  length = 25
FEATURE                 Location/Qualifiers
source                  1..25
                        mol_type = unassigned RNA
                        organism = Homo sapiens
SEQUENCE: 785
gggggagcca tgagataaga gcacc                                               25

SEQ ID NO: 786          moltype = RNA  length = 20
FEATURE                 Location/Qualifiers
source                  1..20
                        mol_type = unassigned RNA
                        organism = Homo sapiens
SEQUENCE: 786
tgggggagcc atgagataag                                                     20

SEQ ID NO: 787          moltype = RNA  length = 17
FEATURE                 Location/Qualifiers
source                  1..17
                        mol_type = unassigned RNA
                        organism = Homo sapiens
SEQUENCE: 787
gatcccagcg gtgcctc                                                        17

SEQ ID NO: 788          moltype = RNA  length = 15
FEATURE                 Location/Qualifiers
source                  1..15
                        mol_type = unassigned RNA
                        organism = Homo sapiens
SEQUENCE: 788
gatcccagcg gtgcc                                                          15

SEQ ID NO: 789          moltype = RNA  length = 24
FEATURE                 Location/Qualifiers
source                  1..24
                        mol_type = unassigned RNA
                        organism = Homo sapiens
SEQUENCE: 789
agacacattt ggagagggaa cctc                                                24

SEQ ID NO: 790          moltype = RNA  length = 16
FEATURE                 Location/Qualifiers
source                  1..16
                        mol_type = unassigned RNA
                        organism = Homo sapiens
SEQUENCE: 790
agacacattt ggagag                                                         16

SEQ ID NO: 791          moltype = RNA  length = 30
FEATURE                 Location/Qualifiers
source                  1..30
                        mol_type = unassigned RNA
                        organism = Homo sapiens
SEQUENCE: 791
gctgggctgg gacggacacc cggcctccac                                          30

SEQ ID NO: 792          moltype = RNA  length = 19
FEATURE                 Location/Qualifiers
source                  1..19
                        mol_type = unassigned RNA
                        organism = Homo sapiens
SEQUENCE: 792
gaggctgggc tgggacgga                                                      19

SEQ ID NO: 793          moltype = RNA  length = 25
FEATURE                 Location/Qualifiers
source                  1..25
                        mol_type = unassigned RNA
                        organism = Homo sapiens
SEQUENCE: 793
tgggcagggg cttattgtag gagtc                                               25

SEQ ID NO: 794          moltype = RNA  length = 19
FEATURE                 Location/Qualifiers
source                  1..19
```

```
                              mol_type = unassigned RNA
                              organism = Homo sapiens
SEQUENCE: 794
tgggcagggg cttattgta                                              19

SEQ ID NO: 795                moltype = RNA   length = 21
FEATURE                       Location/Qualifiers
source                        1..21
                              mol_type = unassigned RNA
                              organism = Homo sapiens
SEQUENCE: 795
caactctgat ctcttcatct a                                           21

SEQ ID NO: 796                moltype = RNA   length = 20
FEATURE                       Location/Qualifiers
source                        1..20
                              mol_type = unassigned RNA
                              organism = Homo sapiens
SEQUENCE: 796
tctcttcatc tacccccag                                              20

SEQ ID NO: 797                moltype = RNA   length = 23
FEATURE                       Location/Qualifiers
source                        1..23
                              mol_type = unassigned RNA
                              organism = Homo sapiens
SEQUENCE: 797
ctagtggaag aagatggcgg aag                                         23

SEQ ID NO: 798                moltype = RNA   length = 15
FEATURE                       Location/Qualifiers
source                        1..15
                              mol_type = unassigned RNA
                              organism = Homo sapiens
SEQUENCE: 798
tagtggaaga agatg                                                  15

SEQ ID NO: 799                moltype = RNA   length = 24
FEATURE                       Location/Qualifiers
source                        1..24
                              mol_type = unassigned RNA
                              organism = Homo sapiens
SEQUENCE: 799
ctgcggggac aggccagggc atct                                        24

SEQ ID NO: 800                moltype = RNA   length = 20
FEATURE                       Location/Qualifiers
source                        1..20
                              mol_type = unassigned RNA
                              organism = Homo sapiens
SEQUENCE: 800
ctgcggggac aggccagggc                                             20

SEQ ID NO: 801                moltype = RNA   length = 27
FEATURE                       Location/Qualifiers
source                        1..27
                              mol_type = unassigned RNA
                              organism = Homo sapiens
SEQUENCE: 801
agggccagag gagcctggag tggtcgg                                     27

SEQ ID NO: 802                moltype = RNA   length = 23
FEATURE                       Location/Qualifiers
source                        1..23
                              mol_type = unassigned RNA
                              organism = Homo sapiens
SEQUENCE: 802
agggccagag gagcctggag tgg                                         23

SEQ ID NO: 803                moltype = RNA   length = 18
FEATURE                       Location/Qualifiers
source                        1..18
                              mol_type = unassigned RNA
                              organism = Homo sapiens
SEQUENCE: 803
tctaggtggg gagactga                                               18

SEQ ID NO: 804                moltype = RNA   length = 16
FEATURE                       Location/Qualifiers
```

```
source                  1..16
                        mol_type = unassigned RNA
                        organism = Homo sapiens
SEQUENCE: 804
gtggggagac tgacgg                                                       16

SEQ ID NO: 805          moltype = RNA   length = 23
FEATURE                 Location/Qualifiers
source                  1..23
                        mol_type = unassigned RNA
                        organism = Homo sapiens
SEQUENCE: 805
tcggctctgg gtctgtgggg agc                                               23

SEQ ID NO: 806          moltype = RNA   length = 15
FEATURE                 Location/Qualifiers
source                  1..15
                        mol_type = unassigned RNA
                        organism = Homo sapiens
SEQUENCE: 806
gcccggatac ctcag                                                        15

SEQ ID NO: 807          moltype = RNA   length = 30
FEATURE                 Location/Qualifiers
source                  1..30
                        mol_type = unassigned RNA
                        organism = Homo sapiens
SEQUENCE: 807
tgagggcag agagcgagac ttttctattt                                         30

SEQ ID NO: 808          moltype = RNA   length = 15
FEATURE                 Location/Qualifiers
source                  1..15
                        mol_type = unassigned RNA
                        organism = Homo sapiens
SEQUENCE: 808
tgagggcag agagc                                                         15

SEQ ID NO: 809          moltype = RNA   length = 25
FEATURE                 Location/Qualifiers
source                  1..25
                        mol_type = unassigned RNA
                        organism = Homo sapiens
SEQUENCE: 809
gggtggggat tgttgcatt acttg                                              25

SEQ ID NO: 810          moltype = RNA   length = 20
FEATURE                 Location/Qualifiers
source                  1..20
                        mol_type = unassigned RNA
                        organism = Homo sapiens
SEQUENCE: 810
gggtggggat tgttgcatt                                                    20

SEQ ID NO: 811          moltype = RNA   length = 27
FEATURE                 Location/Qualifiers
source                  1..27
                        mol_type = unassigned RNA
                        organism = Homo sapiens
SEQUENCE: 811
tagcagcacg taaatattgg cgttaag                                           27

SEQ ID NO: 812          moltype = RNA   length = 15
FEATURE                 Location/Qualifiers
source                  1..15
                        mol_type = unassigned RNA
                        organism = Homo sapiens
SEQUENCE: 812
tagcagcacg taaat                                                        15

SEQ ID NO: 813          moltype = RNA   length = 27
FEATURE                 Location/Qualifiers
source                  1..27
                        mol_type = unassigned RNA
                        organism = Homo sapiens
SEQUENCE: 813
aaaccgttac cattactgag tttagta                                           27

SEQ ID NO: 814          moltype = RNA   length = 15
```

```
FEATURE                 Location/Qualifiers
source                  1..15
                        mol_type = unassigned RNA
                        organism = Homo sapiens
SEQUENCE: 814
gaaaccgtta ccatt                                                          15

SEQ ID NO: 815          moltype = RNA   length = 22
FEATURE                 Location/Qualifiers
source                  1..22
                        mol_type = unassigned RNA
                        organism = Homo sapiens
SEQUENCE: 815
atatagggat tggagccgtg gc                                                  22

SEQ ID NO: 816          moltype = RNA   length = 20
FEATURE                 Location/Qualifiers
source                  1..20
                        mol_type = unassigned RNA
                        organism = Homo sapiens
SEQUENCE: 816
atatagggat tggagccgtg                                                     20

SEQ ID NO: 817          moltype = RNA   length = 25
FEATURE                 Location/Qualifiers
source                  1..25
                        mol_type = unassigned RNA
                        organism = Homo sapiens
SEQUENCE: 817
tcctgtactg agctgccccg aggcc                                               25

SEQ ID NO: 818          moltype = RNA   length = 15
FEATURE                 Location/Qualifiers
source                  1..15
                        mol_type = unassigned RNA
                        organism = Homo sapiens
SEQUENCE: 818
tcctgtactg agctg                                                          15

SEQ ID NO: 819          moltype = RNA   length = 26
FEATURE                 Location/Qualifiers
source                  1..26
                        mol_type = unassigned RNA
                        organism = Homo sapiens
SEQUENCE: 819
agggacggga cgcggtgcag tgttgt                                              26

SEQ ID NO: 820          moltype = RNA   length = 15
FEATURE                 Location/Qualifiers
source                  1..15
                        mol_type = unassigned RNA
                        organism = Homo sapiens
SEQUENCE: 820
ggcgggcggg aggga                                                          15

SEQ ID NO: 821          moltype = RNA   length = 20
FEATURE                 Location/Qualifiers
source                  1..20
                        mol_type = unassigned RNA
                        organism = Homo sapiens
SEQUENCE: 821
ccccagggcg acgcggcggg                                                     20

SEQ ID NO: 822          moltype = RNA   length = 15
FEATURE                 Location/Qualifiers
source                  1..15
                        mol_type = unassigned RNA
                        organism = Homo sapiens
SEQUENCE: 822
cgcggcgggg gcggc                                                          15

SEQ ID NO: 823          moltype = RNA   length = 15
FEATURE                 Location/Qualifiers
source                  1..15
                        mol_type = unassigned RNA
                        organism = Homo sapiens
SEQUENCE: 823
ggcggcgggc ccggg                                                          15
```

| | | |
|---|---|---|
| SEQ ID NO: 824<br>FEATURE<br>source | moltype = RNA   length = 15<br>Location/Qualifiers<br>1..15<br>mol_type = unassigned RNA<br>organism = Homo sapiens | |
| SEQUENCE: 824<br>ggcggcgggc ccggg | | 15 |
| SEQ ID NO: 825<br>FEATURE<br>source | moltype = RNA   length = 25<br>Location/Qualifiers<br>1..25<br>mol_type = unassigned RNA<br>organism = Homo sapiens | |
| SEQUENCE: 825<br>aaggcagggc ccccgctccc cgggc | | 25 |
| SEQ ID NO: 826<br>FEATURE<br>source | moltype = RNA   length = 15<br>Location/Qualifiers<br>1..15<br>mol_type = unassigned RNA<br>organism = Homo sapiens | |
| SEQUENCE: 826<br>gtgtgttgag gaagg | | 15 |
| SEQ ID NO: 827<br>FEATURE<br>source | moltype = RNA   length = 23<br>Location/Qualifiers<br>1..23<br>mol_type = unassigned RNA<br>organism = Homo sapiens | |
| SEQUENCE: 827<br>gagggccccc cctcaatcct gtt | | 23 |
| SEQ ID NO: 828<br>FEATURE<br>source | moltype = RNA   length = 16<br>Location/Qualifiers<br>1..16<br>mol_type = unassigned RNA<br>organism = Homo sapiens | |
| SEQUENCE: 828<br>agggccccccc ctcaat | | 16 |
| SEQ ID NO: 829<br>FEATURE<br>source | moltype = RNA   length = 26<br>Location/Qualifiers<br>1..26<br>mol_type = unassigned RNA<br>organism = Homo sapiens | |
| SEQUENCE: 829<br>aaaatcacat tgccagggat taccac | | 26 |
| SEQ ID NO: 830<br>FEATURE<br>source | moltype = RNA   length = 15<br>Location/Qualifiers<br>1..15<br>mol_type = unassigned RNA<br>organism = Homo sapiens | |
| SEQUENCE: 830<br>aatcacattg ccagg | | 15 |
| SEQ ID NO: 831<br>FEATURE<br>source | moltype = RNA   length = 28<br>Location/Qualifiers<br>1..28<br>mol_type = unassigned RNA<br>organism = Homo sapiens | |
| SEQUENCE: 831<br>gtatggtatt gcacttgtcc cggcctgt | | 28 |
| SEQ ID NO: 832<br>FEATURE<br>source | moltype = RNA   length = 15<br>Location/Qualifiers<br>1..15<br>mol_type = unassigned RNA<br>organism = Homo sapiens | |
| SEQUENCE: 832<br>tattgcactt gtccc | | 15 |
| SEQ ID NO: 833<br>FEATURE<br>source | moltype = RNA   length = 22<br>Location/Qualifiers<br>1..22<br>mol_type = unassigned RNA<br>organism = Homo sapiens | |
| SEQUENCE: 833<br>gcacgactca gggcggaggg aa | | 22 |

```
SEQ ID NO: 834           moltype = RNA   length = 15
FEATURE                  Location/Qualifiers
source                   1..15
                         mol_type = unassigned RNA
                         organism = Homo sapiens
SEQUENCE: 834
agggcggagg gaagt                                                         15

SEQ ID NO: 835           moltype = RNA   length = 18
FEATURE                  Location/Qualifiers
source                   1..18
                         mol_type = unassigned RNA
                         organism = Homo sapiens
SEQUENCE: 835
aaaaggaagg gggaggag                                                      18

SEQ ID NO: 836           moltype = RNA   length = 16
FEATURE                  Location/Qualifiers
source                   1..16
                         mol_type = unassigned RNA
                         organism = Homo sapiens
SEQUENCE: 836
aaggaagggg gaggag                                                        16

SEQ ID NO: 837           moltype = RNA   length = 24
FEATURE                  Location/Qualifiers
source                   1..24
                         mol_type = unassigned RNA
                         organism = Homo sapiens
SEQUENCE: 837
aatattgcac tcgtcccggc ctcc                                               24

SEQ ID NO: 838           moltype = RNA   length = 15
FEATURE                  Location/Qualifiers
source                   1..15
                         mol_type = unassigned RNA
                         organism = Homo sapiens
SEQUENCE: 838
tattgcactc gtccc                                                         15

SEQ ID NO: 839           moltype = RNA   length = 21
FEATURE                  Location/Qualifiers
source                   1..21
                         mol_type = unassigned RNA
                         organism = Homo sapiens
SEQUENCE: 839
cccaggctgg agcgagtgca g                                                  21

SEQ ID NO: 840           moltype = RNA   length = 15
FEATURE                  Location/Qualifiers
source                   1..15
                         mol_type = unassigned RNA
                         organism = Homo sapiens
SEQUENCE: 840
agctcactgc agcct                                                         15

SEQ ID NO: 841           moltype = RNA   length = 20
FEATURE                  Location/Qualifiers
source                   1..20
                         mol_type = unassigned RNA
                         organism = Homo sapiens
SEQUENCE: 841
tggctgttgg aggggcagg                                                     20

SEQ ID NO: 842           moltype = RNA   length = 15
FEATURE                  Location/Qualifiers
source                   1..15
                         mol_type = unassigned RNA
                         organism = Homo sapiens
SEQUENCE: 842
ggaggggca ggctc                                                          15

SEQ ID NO: 843           moltype = RNA   length = 25
FEATURE                  Location/Qualifiers
source                   1..25
                         mol_type = unassigned RNA
                         organism = Homo sapiens
SEQUENCE: 843
```

```
tggcggcggt agttatgggc ttctc                                           25

SEQ ID NO: 844         moltype = RNA   length = 25
FEATURE                Location/Qualifiers
source                 1..25
                       mol_type = unassigned RNA
                       organism = Homo sapiens
SEQUENCE: 844
tggcggcggt agttatgggc ttctc                                           25

SEQ ID NO: 845         moltype = RNA   length = 15
FEATURE                Location/Qualifiers
source                 1..15
                       mol_type = unassigned RNA
                       organism = Homo sapiens
SEQUENCE: 845
tggcagagcg ctgtc                                                      15

SEQ ID NO: 846         moltype = RNA   length = 15
FEATURE                Location/Qualifiers
source                 1..15
                       mol_type = unassigned RNA
                       organism = Homo sapiens
SEQUENCE: 846
tggcagagcg ctgtc                                                      15

SEQ ID NO: 847         moltype = RNA   length = 22
FEATURE                Location/Qualifiers
source                 1..22
                       mol_type = unassigned RNA
                       organism = Homo sapiens
SEQUENCE: 847
cgcggcgggg acggcgattg gt                                              22

SEQ ID NO: 848         moltype = RNA   length = 17
FEATURE                Location/Qualifiers
source                 1..17
                       mol_type = unassigned RNA
                       organism = Homo sapiens
SEQUENCE: 848
cggcggggac ggcgatt                                                    17

SEQ ID NO: 849         moltype = RNA   length = 22
FEATURE                Location/Qualifiers
source                 1..22
                       mol_type = unassigned RNA
                       organism = Homo sapiens
SEQUENCE: 849
accccactcc tggtaccata gt                                              22

SEQ ID NO: 850         moltype = RNA   length = 15
FEATURE                Location/Qualifiers
source                 1..15
                       mol_type = unassigned RNA
                       organism = Homo sapiens
SEQUENCE: 850
accccactcc tggta                                                      15

SEQ ID NO: 851         moltype = RNA   length = 24
FEATURE                Location/Qualifiers
source                 1..24
                       mol_type = unassigned RNA
                       organism = Homo sapiens
SEQUENCE: 851
ggaggccggg gtgggcggg gcgg                                             24

SEQ ID NO: 852         moltype = RNA   length = 21
FEATURE                Location/Qualifiers
source                 1..21
                       mol_type = unassigned RNA
                       organism = Homo sapiens
SEQUENCE: 852
tggggcgggg caggtccctg c                                               21

SEQ ID NO: 853         moltype = RNA   length = 18
FEATURE                Location/Qualifiers
source                 1..18
                       mol_type = unassigned RNA
                       organism = Homo sapiens
```

```
SEQUENCE: 853
gggtgcgggc cggcgggg                                                    18

SEQ ID NO: 854         moltype = RNA  length = 18
FEATURE                Location/Qualifiers
source                 1..18
                       mol_type = unassigned RNA
                       organism = Homo sapiens
SEQUENCE: 854
aggggcggg ctccggcg                                                     18

SEQ ID NO: 855         moltype = RNA  length = 22
FEATURE                Location/Qualifiers
source                 1..22
                       mol_type = unassigned RNA
                       organism = Homo sapiens
SEQUENCE: 855
gggggtgtg gagccagggg gc                                                22

SEQ ID NO: 856         moltype = RNA  length = 25
FEATURE                Location/Qualifiers
source                 1..25
                       mol_type = unassigned RNA
                       organism = Homo sapiens
SEQUENCE: 856
aagggaggag gagcggaggg gccct                                            25

SEQ ID NO: 857         moltype = RNA  length = 64
FEATURE                Location/Qualifiers
source                 1..64
                       mol_type = unassigned RNA
                       organism = Homo sapiens
SEQUENCE: 857
ccccgggccc ggcgttccct ccccttccgt gcgccagtgg aggccggggt ggggcggggc      60
gggg                                                                   64

SEQ ID NO: 858         moltype = RNA  length = 64
FEATURE                Location/Qualifiers
source                 1..64
                       mol_type = unassigned RNA
                       organism = Homo sapiens
SEQUENCE: 858
ccccgggccc ggcgttccct ccccttccgt gcgccagtgg aggccggggt ggggcggggc      60
gggg                                                                   64

SEQ ID NO: 859         moltype = RNA  length = 66
FEATURE                Location/Qualifiers
source                 1..66
                       mol_type = unassigned RNA
                       organism = Homo sapiens
SEQUENCE: 859
ccgagtgggg cggggcaggt ccctgcaggg actgtgacac tgaaggacct gcaccttcgc      60
ccacag                                                                 66

SEQ ID NO: 860         moltype = RNA  length = 54
FEATURE                Location/Qualifiers
source                 1..54
                       mol_type = unassigned RNA
                       organism = Homo sapiens
SEQUENCE: 860
acgcgggtgc gggccggcgg ggtagaagcc acccggcccg gcccggcccg gcga             54

SEQ ID NO: 861         moltype = RNA  length = 62
FEATURE                Location/Qualifiers
source                 1..62
                       mol_type = unassigned RNA
                       organism = Homo sapiens
SEQUENCE: 861
ggtaggggc gggctccggc gctgggaccc cactagggtg gcgccttggc cccgcccgc        60
cc                                                                     62

SEQ ID NO: 862         moltype = RNA  length = 71
FEATURE                Location/Qualifiers
source                 1..71
                       mol_type = unassigned RNA
                       organism = Homo sapiens
SEQUENCE: 862
atggagggg gtgtggagcc aggggggccca ggtctacagc ttctcccgc tccctgcccc       60
catactccca g                                                           71
```

```
SEQ ID NO: 863            moltype = RNA  length = 74
FEATURE                   Location/Qualifiers
source                    1..74
                          mol_type = unassigned RNA
                          organism = Homo sapiens
SEQUENCE: 863
gggaggaaga agggaggagg agcggagggg cccttgtctt cccagagcct ctcccttcct    60
ccctccccc tccc                                                       74

SEQ ID NO: 864            moltype = RNA  length = 16
FEATURE                   Location/Qualifiers
source                    1..16
                          mol_type = unassigned RNA
                          organism = Homo sapiens
SEQUENCE: 864
cgggcccggc gttccc                                                    16

SEQ ID NO: 865            moltype = RNA  length = 15
FEATURE                   Location/Qualifiers
source                    1..15
                          mol_type = unassigned RNA
                          organism = Homo sapiens
SEQUENCE: 865
ccgggcccgg cgttc                                                     15

SEQ ID NO: 866            moltype = RNA  length = 19
FEATURE                   Location/Qualifiers
source                    1..19
                          mol_type = unassigned RNA
                          organism = Homo sapiens
SEQUENCE: 866
gggtgcgggc cggcggggt                                                 19

SEQ ID NO: 867            moltype = RNA  length = 15
FEATURE                   Location/Qualifiers
source                    1..15
                          mol_type = unassigned RNA
                          organism = Homo sapiens
SEQUENCE: 867
tgcgggccgg cgggg                                                     15

SEQ ID NO: 868            moltype = RNA  length = 19
FEATURE                   Location/Qualifiers
source                    1..19
                          mol_type = unassigned RNA
                          organism = Homo sapiens
SEQUENCE: 868
aggggcggg ctccggcgc                                                  19

SEQ ID NO: 869            moltype = RNA  length = 15
FEATURE                   Location/Qualifiers
source                    1..15
                          mol_type = unassigned RNA
                          organism = Homo sapiens
SEQUENCE: 869
gtaggggcg ggctc                                                      15

SEQ ID NO: 870            moltype = RNA  length = 23
FEATURE                   Location/Qualifiers
source                    1..23
                          mol_type = unassigned RNA
                          organism = Homo sapiens
SEQUENCE: 870
aagggaggag gagcggaggg gcc                                            23

SEQ ID NO: 871            moltype = RNA  length = 15
FEATURE                   Location/Qualifiers
source                    1..15
                          mol_type = unassigned RNA
                          organism = Homo sapiens
SEQUENCE: 871
gggaggagga gcgga                                                     15
```

BREAST CANCER DETECTION KIT OR DEVICE, AND DETECTION METHOD

CROSS-REFERENCE TO RELATED APPLICATIONS

This application is a Divisional of U.S. application Ser. No. 17/944,779 filed Sep. 14, 2022, which is a Divisional of U.S. application Ser. No. 16/797,625 filed Feb. 21, 2020 (now U.S. Pat. No. 11,479,822), which is a Divisional of U.S. application Ser. No. 15/318,328, filed on Dec. 12, 2016 (now U.S. Pat. No. 10,597,726), which is the National Phase under 35 U.S.C. § 371 of International Application No. PCT/JP2015/066986 filed on Jun. 12, 2015, which claims the benefit under 35 U.S.C. § 119(a) to Japanese Patent Application Nos. 2014-122672 filed Jun. 13, 2014, and 2015-069321 filed Mar. 30, 2015, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Sep. 12, 2022, is named "PH-6234-PCT-US-DIV1-DIV1 Sequence Listing ST26" and is 784,115 bytes in size. The sequence listing contained in this .XML file is part of the specification and is hereby incorporated by reference herein in its entirety.

TECHNICAL FIELD

The present invention relates to a kit or a device for the detection of breast cancer, comprising nucleic acid(s) capable of specifically binding to a particular miRNA, which is used for examining the presence or absence of breast cancer in a subject, and a method for detecting breast cancer, comprising measuring an expression level of the miRNA using the nucleic acid.

BACKGROUND ART

The breast is constituted by a mammary gland which produces mother milk, lobules which arise from the mammary gland, mammary ducts which arise from the lobules and deliver milk, and fat which supports these constituents, etc. Approximately 90% of breast cancer cases originate in the mammary ducts, while approximately 5 to 10% of the breast cancer cases originate in the lobules (Non-Patent Literature 1). According to the 2011 statistics of cancer type-specific mortality in Japan disclosed by the Center for Cancer Control and Information Services, National Cancer Center, the number of breast cancer deaths climbed to 12,731 people. It is estimated that one out of 14 Japanese females will experience breast cancer. The number of incidences of this cancer in females takes the 1st place by cancer type. It is estimated that one out of 8 American females will experience breast cancer. The estimated number of American individuals affected by breast cancer climbed to 232,670 people in 2014, among which approximately 40,000 people reportedly died (Non-Patent Literature 1).

The stages of breast cancer progression are defined in Non-Patent Literature 2 and classified into stages 0, IA, IB, IIA, IIB, IIIA, IIIB, IIIC, and IV according to tumor size, infiltration, lymph node metastasis, distant metastasis, etc. The 5-year relative survival rate of breast cancer largely depends on the stages of cancer progression and is reportedly 100% for stage 0 and stage I, 93% for stage 11, 72% for stage 111, and 22% for stage IV (Non-Patent Literature 1). Thus, the early detection of breast cancer leads to improvement in the survival rate. Therefore, an approach that permits the early detection is strongly desired.

The treatment of breast cancer is basically surgical treatment, which is used in combination with drug therapy or radiotherapy depending on the progressed stage, metastasis, general health conditions, and breast cancer classification. Particularly, for early breast cancer of stage 1 or 2, breast conservation therapy may be selected with a combined use with radiotherapy (Non-Patent Literature 1).

According to Non-Patent Literature 1, initial diagnostic tests of breast cancer include inspection and palpation as well as imaging tests such as mammography, which is breast-dedicated X-ray examination, and ultrasonography (echo examination). When there are findings on suspected breast cancer by the initial test, pathological examination which involves inserting a needle into a lesion and collecting cells or tissues to be examined under a microscope, is carried out as a secondary test. If necessary, imaging tests such as CT, MRI, abdominal ultrasonography, bone scintigraphy, and PET are also carried out in order to examine the state or spread of the lesion.

For example, CEA, CA-15-3, and CA27-29 are known as tumor markers for the detection of breast cancer. These tumor markers in blood have been reported to elevate when breast cancer has metastasized to other organs such as the bone or the liver. However, these tumor markers do not elevate in some patients and may thus be limited by their usefulness (Non-Patent Literature 1).

As shown in Patent Literatures 1 to 4, there are reports, albeit at a research stage, on the detection of breast cancer using the expression levels of microRNAs (miRNAs) or combinations of the expression levels of miRNAs and the expression levels of additional protein markers in biological samples including blood.

Specifically, Patent Literature 1 discloses a method for detecting prostate cancer or other cancers including breast cancer by combining hsa-miR-602 or hsa-miR-135a-3p with known protein markers in blood.

Patent Literature 2 discloses a method for detecting various cancers including breast cancer by combining hsa-miR-23b-3p or hsa-miR-135a-3p with 5 or more other miRNAs in blood or tissues.

Patent Literature 3 discloses a method for detecting breast cancer using hsa-miR-92a-3p, hsa-miR-92a-2-5p, hsa-miR-92b-5p, and the like in blood cells.

Patent Literature 4 discloses a method for detecting breast cancer using hsa-miR-451a, hsa-miR-296-5p, hsa-miR-16-5p, and the like in tissues.

Non-Patent Literature 3 discloses that hsa-miR-760 and the like in blood are significantly expressed in breast cancer patients.

Non-Patent Literature 4 discloses that hsa-miR-423-5p, hsa-miR-486-5p, and the like in blood are decreased after surgery of breast cancer.

Non-Patent Literature 5 discloses that hsa-miR-4257, hsa-miR-1915-3p, hsa-miR-718, and the like in blood are significantly expressed in breast cancer patients.

Non-Patent Literature 6 discloses that hsa-miR-940 and the like in blood are significantly expressed in breast cancer patients.

CITATION LIST

Patent Literature

Patent Literature 1: JP Patent Publication (Kohyo) No. 2012-507300 A (2012)
Patent Literature 2: JP Patent Publication (Kohyo) No. 2008-500837 A (2008)
Patent Literature 3: International Publication No. WO 10/123043
Patent Literature 4: Published U.S. Patent Application No. 2008/0076674

Non-Patent Literature

Non-Patent Literature 1: American Cancer Society, "Breast Cancer", 2013, p. 6-9, 13, 27-28, 41-46, 52-54, 63-64, and 106
Non-Patent Literature 2: Sobin, L. et al., "TNM Classification of Malignant Tumours, the 7th edition", 2010, p. 171 to 181
Non-Patent Literature 3: Godfrey, A C. et al., 2013, Breast Cancer Research, Vol. 15 (3), p. R42
Non-Patent Literature 4: Cookson, V J. et al., 2012, Cellular Oncology, Vol. 35 (4), p. 301-8
Non-Patent Literature 5: Schrauder, M G. et al., 2012, PLoS One, Vol. 7 (1), p. e29770
Non-Patent Literature 6: Leidner, R S. et al., 2013, PLoS One, Vol. 8 (3), p. e57841
Non-Patent Literature 7: Tamaki, K. et al., 2013, Japanese Journal of Clinical Oncology, Vol. 43 (2), p. 208-213
Non-Patent Literature 8: Guadagni, F. et al., 2001, Clinical Cancer Research, Vol. 7, p. 2357 to 2362

SUMMARY OF INVENTION

Problem to be Solved by Invention

An object of the present invention is to find novel tumor markers for breast cancer and to provide a method that can effectively detect breast cancer using nucleic acid(s) capable of specifically binding to the markers. As described in Non-Patent Literature 1, initial diagnostic tests of breast cancer include inspection and palpation as well as imaging tests such as mammography, which is breast-dedicated X-ray examination, and ultrasonography. The mammography is reportedly effective as breast cancer examination targeting women aged 40 or older, and the American Cancer Society recommends that women in this age range take mammography every year (Non-Patent Literature 1). The mammography, however, has been reported to have limitations in the visualization of breast cancer present in the dense breast before menopause or a very small tumor of early breast cancer (Non-Patent Literature 1). In Japan, the mammography rate was only 24.3% in 2010, and a challenge to improvement in breast cancer survival rate will be to increase this mammography rate (Non-Patent Literature 7).

For example, CEA, CA-15-3, and CA27-29 mentioned above are known as tumor markers for the detection of breast cancer. These tumor markers, however, are helpful in confirming therapeutic effects on recurrent breast cancer, but rarely elevate in early breast cancer. Therefore, the tumor markers may not be useful for the purpose of breast cancer examination (Non-Patent Literature 1). According to Non-Patent Literature 8, the specific sensitivity of CEA and CA15-3 is uselessly 6.4% and 12.2%, respectively, for stage 1 and is only 25.0% and 62.5%, respectively, even for stage 4. Thus, the tumor marker measurement is less significant as a preoperative test. Since these blood tumor markers may elevate for reasons other than breast cancer, the presence or absence of breast cancer is difficult to determine. The false diagnosis of other cancers as breast cancer wastes appropriate therapeutic opportunity or places unnecessary economical and physical burdens on patients due to the application of wrong medicine.

As described below, there are reports, albeit at a research stage, on the determination of breast cancer using the expression levels of microRNAs (miRNAs) in biological samples including blood, none of which, however, have yet been brought into practical use.

Patent Literature 1 discloses a method for detecting prostate cancer or other cancers including breast cancer by combining hsa-miR-602 or hsa-miR-135a-3p with known protein markers in blood. The measurement of both miRNA and protein markers, however, brings about increase in examination costs and a complicated process and is therefore not favorable. This detection method does not describe specific detection performance such as accuracy, sensitivity, or specificity for determining breast cancer and is thus industrially less practical.

Patent Literature 2 discloses a method for detecting various cancers including breast cancer by combining hsa-miR-23b-3p or hsa-miR-135a-3p with 5 or more other miRNAs in blood or tissues. This detection method does not describe specific detection performance such as accuracy, sensitivity, or specificity for determining breast cancer and is thus industrially less practical.

Patent Literature 3 describes a method for detecting breast cancer using hsa-miR-92a-3p, hsa-miR-92a-2-5p, hsa-miR-92b-5p, and the like. This detection method does not describe specific detection performance such as accuracy, sensitivity, or specificity for determining breast cancer and is thus industrially less practical. In addition, these miRNA markers were not validated in an independent sample group and are therefore less reliable.

Patent Literature 4 discloses a method for detecting breast cancer using hsa-miR-451a, hsa-miR-296-5p, hsa-miR-16-5p, and the like in tissues. For this detection method, however, tissue resection by surgical operation is essential for obtaining samples, and this step places a heavy physical burden on patients. Therefore, this method is not favorable as an examination method. In addition, this detection method does not describe specific detection performance such as accuracy, sensitivity, or specificity for determining breast cancer and is thus industrially less practical.

Non-Patent Literature 3 discloses that hsa-miR-760 and the like in blood are significantly expressed in breast cancer patients. This literature, however, neither describes detection performance such as accuracy, sensitivity, or specificity for determining breast cancer nor describes a specific method for detecting breast cancer. Therefore, this approach is industrially less practical.

Non-Patent Literature 4 discloses that hsa-miR-423-5p, hsa-miR-486-5p, and the like in blood are decreased after surgery of breast cancer. This literature, however, neither describes detection performance such as accuracy, sensitivity, or specificity for determining breast cancer nor describes a specific method for detecting breast cancer. Therefore, this approach is industrially less practical.

Non-Patent Literature 5 discloses that hsa-miR-4257, hsa-miR-1915-3p, hsa-miR-718, and the like in blood are significantly expressed in breast cancer patients. This approach, however, employed as many as 240 miRNAs for detecting breast cancer and might cause increase in examination cost and complicated discriminant algorithms. Thus, this approach is not industrially practical.

Non-Patent Literature 6 discloses that hsa-miR-940 and the like in blood are significantly expressed in breast cancer patients. The authors, however, concluded that this marker is less reproducible, and finally abandoned the marker in the study. In addition, this literature neither describes detection performance such as accuracy, sensitivity, or specificity for determining breast cancer nor describes a specific method for detecting breast cancer. Therefore, this approach is industrially less practical.

As mentioned above, the existing tumor markers exhibit low performance in the detection of breast cancer, or neither performance nor detection methods are specifically shown as to the markers at a research stage. Therefore, use of these markers might impose implementation of needless extra examination due to the false detection of healthy subjects as being breast cancer patients, or might waste therapeutic opportunity because of overlooking breast cancer patients. In addition, the measurement of dozens of miRNAs increases examination cost and is therefore difficult to use in large-scale screening such as medical checkup. Furthermore, the collection of breast tissues for measuring the tumor markers is highly invasive to patients and is not favorable. Hence, there is a demand for a highly accurate breast cancer marker that is detectable from blood, which can be collected with limitedly invasiveness, and is capable of correctly determining a breast cancer patient as a breast cancer patient and a healthy subject as a healthy subject. Particularly, the early detection and treatment of breast cancer can drastically reduce the risk of recurrence and also permit breast conservation therapy. Therefore, a highly sensitive breast cancer marker capable of detecting breast cancer even at a low progressed stage is desired. Moreover, the mammography rate is presumably increased by providing a more convenient initial screening of breast cancer.

Solution to Problem

The present inventors have conducted diligent studies to attain the object and consequently completed the present invention by finding several genes usable as markers for the detection of breast cancer from blood, which can be collected with limitedly invasiveness, and finding that breast cancer can be significantly detected by using nucleic acids capable of specifically binding to any of these markers.

SUMMARY OF INVENTION

The present invention has the following features:

(1) A kit for the detection of breast cancer, comprising nucleic acid(s) capable of specifically binding to at least one polynucleotide selected from the group consisting of the following breast cancer markers: miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739.

(2) The kit according to (1), wherein miR-4783-3p is hsa-miR-4783-3p, miR-4730 is hsa-miR-4730, miR-1307-3p is hsa-miR-1307-3p, miR-4634 is hsa-miR-4634, miR-663a is hsa-miR-663a, miR-4532 is hsa-miR-4532, miR-7704 is hsa-miR-7704, miR-3178 is hsa-miR-3178, miR-6729-5p is hsa-miR-6729-5p, miR-6090 is hsa-miR-6090, miR-4732-5p is hsa-miR-4732-5p, miR-3184-5p is hsa-miR-3184-5p, miR-6727-5p is hsa-miR-6727-5p, miR-6088 is hsa-miR-6088, miR-4674 is hsa-miR-4674, miR-8073 is hsa-miR-8073, miR-4787-5p is hsa-miR-4787-5p, miR-1469 is hsa-miR-1469, miR-125a-3p is hsa-miR-125a-3p, miR-1233-5p is hsa-miR-1233-5p, miR-885-3p is hsa-miR-885-3p, miR-6802-5p is hsa-miR-6802-5p, miR-328-5p is hsa-miR-328-5p, miR-6787-5p is hsa-miR-6787-5p, miR-8069 is hsa-miR-8069, miR-6875-5p is hsa-miR-6875-5p, miR-1246 is hsa-miR-1246, miR-4734 is hsa-miR-4734, miR-6757-5p is hsa-miR-6757-5p, miR-6756-5p is hsa-miR-6756-5p, miR-3665 is hsa-miR-3665, miR-6836-3p is hsa-miR-6836-3p, miR-6821-5p is hsa-miR-6821-5p, miR-6805-5p is hsa-miR-6805-5p, miR-4728-5p is hsa-miR-4728-5p, miR-6726-5p is hsa-miR-6726-5p, miR-197-5p is hsa-miR-197-5p, miR-149-3p is hsa-miR-149-3p, miR-6850-5p is hsa-miR-6850-5p, miR-4476 is hsa-miR-4476, miR-6858-5p is hsa-miR-6858-5p, miR-564 is hsa-miR-564, miR-4763-3p is hsa-miR-4763-3p, miR-575 is hsa-miR-575, miR-6771-5p is hsa-miR-6771-5p, miR-1231 is hsa-miR-1231, miR-1908-3p is hsa-miR-1908-3p, miR-150-3p is hsa-miR-150-3p, miR-3937 is hsa-miR-3937, miR-887-3p is hsa-miR-887-3p, miR-3940-5p is hsa-miR-3940-5p, miR-4741 is hsa-miR-4741, miR-6808-5p is hsa-miR-6808-5p, miR-6869-5p is hsa-miR-6869-5p, miR-5090 is hsa-miR-5090, miR-615-5p is hsa-miR-615-5p, miR-8072 is hsa-miR-8072, miR-128-1-5p is hsa-miR-128-1-5p, miR-1238-5p is hsa-miR-1238-5p, miR-365a-5p is hsa-miR-365a-5p, miR-204-3p is hsa-miR-204-3p, miR-4492 is hsa-miR-4492, miR-6785-5p is hsa-miR-6785-5p, miR-6511a-5p is hsa-miR-6511a-5p, miR-4525 is hsa-miR-4525, miR-1915-5p is hsa-miR-1915-5p, miR-3180 is hsa-miR-3180, miR-6879-5p is hsa-miR-6879-5p, miR-1199-5p is hsa-miR-1199-5p, miR-6746-5p is hsa-miR-6746-5p, 711 is hsa-miR-711, miR-663b is hsa-miR-663b, miR-4707-3p is hsa-miR-4707-3p, miR-6893-5p is hsa-miR-6893-5p, miR-4675 is hsa-miR-4675, miR-4638-5p is hsa-miR-4638-5p, miR-4651 is hsa-miR-4651, miR-6087 is hsa-miR-6087, miR-4665-5p is hsa-miR-4665-5p, miR-4758-5p is hsa-miR-4758-5p, miR-6887-5p is hsa-miR-6887-5p, miR-3620-5p is hsa-miR-3620-5p, miR-1909-3p is hsa-miR-1909-3p, miR-7641 is hsa-miR-7641, miR-6724-5p is hsa-miR-6724-5p, miR-1343-3p is hsa-miR-1343-3p, miR-6780b-5p is hsa-miR-6780b-5p, miR-4484 is hsa-miR-4484, miR-4690-5p is hsa-miR-4690-5p, miR-4429 is hsa-miR-4429, miR-1227-5p is hsa-miR-1227-5p, miR-4725-3p is hsa-miR-4725-3p, miR-6861-5p is hsa-miR-6861-5p, miR-6812-5p is hsa-miR-6812-5p, miR-3197 is hsa-miR-3197, miR-8059 is hsa-miR-8059, miR-3185 is hsa-miR-3185, miR-4706 is hsa-miR-4706, miR-4497 is hsa-miR-4497, miR-3131 is hsa-miR-3131, miR-6806-5p is hsa-miR-6806-5p, miR-187-5p is hsa-miR-187-5p, miR-3180-3p is hsa-miR-3180-3p, miR-6848-5p is hsa-miR-6848-5p, miR-6820-5p is hsa-miR-6820-5p, miR-6800-5p is hsa-miR-6800-5p, miR-6717-5p is hsa-miR-6717-5p, miR-6795-5p is hsa-miR-6795-5p, miR-4632-5p is hsa-miR-4632-5p, miR-665 is hsa-miR-665, miR-6778-5p is hsa-miR-6778-5p, miR-3663-3p is hsa-miR-3663-3p, miR-4689 is hsa-miR-4689, miR-211-3p is hsa-miR-211-3p, miR-6511b-5p is hsa-miR-6511b-5p, miR-4750-5p is hsa-miR-4750-5p, miR-6126 is hsa-miR-6126, miR-614 is hsa-miR-614, miR-7110-5p is hsa-miR-7110-5p, miR-744-5p is hsa-miR-744-5p, miR-6769a-5p is hsa-miR-6769a-5p, miR-4792 is hsa-miR-4792, miR-5787 is hsa-miR-5787, miR-6798-5p is hsa-miR-6798-5p, miR-6781-5p is hsa-miR-6781-5p, miR-4419b hsa-miR-4419b, miR-4446-3p is hsa-miR-4446-3p, miR-4259 is hsa-miR-4259, miR-5572 is hsa-miR-5572, miR-6075 is hsa-miR-6075, miR-296-3p is hsa-miR-296-3p, miR-6891-5p is hsa-miR-6891-5p, miR-4745-5p is hsa-miR-4745-5p, miR-6775-5p is hsa-miR-6775-5p, miR-6870-5p is hsa-miR-6870-5p, miR-920 is hsa-miR-920, miR-4530 is hsa-miR-4530, miR-6819-5p is hsa-miR-6819-5p, miR-6825-5p is hsa-miR-6825-5p, miR-7847-3p is hsa-miR-7847-3p, miR-6131 is hsa-miR-6131, miR-4433-3p is hsa-miR-4433-3p, miR-1228-5p is hsa-miR-1228-5p, miR-6743-5p is hsa-miR-6743-5p, miR-1268a is hsa-miR-1268a, miR-3917 is hsa-miR-3917, miR-6786-5p is hsa-miR-6786-5p, miR-3154 is hsa-miR-3154, miR-638 is hsa-miR-638, miR-6741-5p is hsa-miR-6741-5p, miR-6889-5p is hsa-miR-6889-5p, miR-6840-3p is hsa-miR-6840-3p, miR-6510-5p is hsa-miR-6510-5p, miR-3188 is hsa-miR-3188, miR-551b-5p is hsa-miR-551b-5p, miR-5001-5p is hsa-miR-5001-5p, miR-1268b is hsa-miR-1268b, miR-7107-5p is hsa-miR-7107-5p, miR-6824-5p is hsa-miR-6824-5p, miR-6732-5p is hsa-miR-6732-5p, miR-371a-5p is hsa-miR-371a-5p, miR-6794-5p is hsa-miR-6794-5p, miR-6779-5p is hsa-miR-6779-5p, miR-4271 is hsa-miR-4271, miR-5195-3p is hsa-miR-5195-3p, miR-6762-5p is hsa-miR-6762-5p, miR-939-5p is hsa-miR-939-5p, miR-1247-3p is hsa-miR-1247-3p, miR-6777-5p is hsa-miR-6777-5p, miR-6722-3p is hsa-miR-6722-3p, miR-3656 is hsa-miR-3656, miR-4688 is hsa-miR-4688, miR-3195 is hsa-miR-3195, miR-6766-5p is hsa-miR-6766-5p, miR-4447 is hsa-miR-4447, miR-4656 is hsa-miR-4656, miR-7108-5p is hsa-miR-7108-5p, miR-3191-3p is hsa-miR-3191-3p, miR-1273g-3p is hsa-miR-1273g-3p, miR-4463 is hsa-miR-4463, miR-2861 is hsa-miR-2861, miR-3196 is hsa-miR-3196, miR-6877-5p is hsa-miR-6877-5p, miR-3679-5p is hsa-miR-3679-5p, miR-4442 is hsa-miR-4442, miR-6789-5p is hsa-miR-6789-5p, miR-6782-5p is hsa-miR-6782-5p, miR-486-3p is hsa-miR-486-3p, miR-6085 is hsa-miR-6085, miR-4746-3p is hsa-miR-4746-3p, miR-619-5p is hsa-miR-619-5p, miR-937-5p is hsa-miR-937-5p, miR-6803-5p is hsa-miR-6803-5p, miR-4298 is hsa-miR-4298, miR-4454 is hsa-miR-4454, miR-4459 is hsa-miR-4459, miR-7150 is hsa-miR-7150, miR-6880-5p is hsa-miR-6880-5p, miR-4449 is hsa-miR-4449, miR-8063 is hsa-miR-8063, miR-4695-5p is hsa-miR-4695-5p, miR-6132 is hsa-miR-6132, miR-6829-5p is hsa-miR-6829-5p, miR-4486 is hsa-miR-4486, miR-6805-3p is hsa-miR-6805-3p, miR-6826-5p is hsa-miR-6826-5p, miR-4508 is hsa-miR-4508, miR-1343-5p is hsa-miR-1343-5p, miR-7114-5p is hsa-miR-7114-5p, miR-3622a-5p is hsa-miR-3622a-5p, miR-6765-5p is hsa-miR-6765-5p, miR-7845-5p is hsa-miR-7845-5p, miR-3960 is hsa-miR-3960, miR-6749-5p is hsa-miR-6749-5p, miR-1260b is hsa-miR-1260b, miR-6799-5p is hsa-miR-6799-5p, miR-4723-5p is hsa-miR-4723-5p, miR-6784-5p is hsa-miR-6784-5p, miR-5100 is hsa-miR-5100, miR-6769b-5p is hsa-miR-6769b-5p, miR-1207-5p is hsa-miR-1207-5p, miR-642a-3p is hsa-miR-642a-3p, miR-4505 is hsa-miR-4505, miR-4270 is hsa-miR-4270, miR-6721-5p is hsa-miR-6721-5p, miR-7111-5p is hsa-miR-7111-5p, miR-6791-5p is hsa-miR-6791-5p, miR-7109-5p is hsa-miR-7109-5p, miR-4258 is hsa-miR-4258, miR-6515-3p is hsa-miR-6515-3p, miR-6851-5p is hsa-miR-6851-5p, miR-6125 is hsa-miR-6125, miR-4749-5p is hsa-miR-4749-5p, miR-4726-5p is hsa-miR-4726-5p, miR-4513 is hsa-miR-4513, miR-6089 is hsa-miR-6089, miR-6816-5p is hsa-miR-6816-5p, miR-4466 is hsa-miR-4466, miR-4488 is hsa-miR-4488, miR-6752-5p is hsa-miR-6752-5p, and miR-4739 is hsa-miR-4739.

(3) The kit according to (1) or (2), wherein the nucleic acid is a polynucleotide selected from the group consisting of the following polynucleotides (a) to (e):
(a) a polynucleotide consisting of a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 235 and 851 to 856 or a nucleotide sequence derived from the nucleotide sequence by the replacement of u with t,
(c) a polynucleotide consisting of a nucleotide sequence complementary to a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 235 and 851 to 856 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises nucleic acid(s) capable of specifically binding to at least one polynucleotide selected from the group consisting of other breast cancer markers miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

(5) The kit according to (4), wherein miR-760 is hsa-miR-760, miR-602 is hsa-miR-602, miR-423-5p is hsa-miR-423-5p, miR-92a-2-5p is hsa-miR-92a-2-5p, miR-16-5p is hsa-miR-16-5p, miR-451a is hsa-miR-451a, miR-135a-3p is hsa-miR-135a-3p, miR-486-5p is hsa-miR-486-5p, miR-4257 is hsa-miR-4257, miR-92b-5p is hsa-miR-92b-5p, miR-1915-3p is hsa-miR-1915-3p, miR-718 is hsa-miR-718, miR-940 is hsa-miR-940, miR-296-5p is hsa-miR-296-5p, miR-23b-3p is hsa-miR-23b-3p, and miR-92a-3p is hsa-miR-92a-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 236 to 251, (h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 236 to 251 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises nucleic acid(s) capable of specifically binding to at least one polynucleotide selected from the group consisting of other breast cancer markers miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

(8) The kit according to (7), wherein miR-658 is hsa-miR-658, miR-6842-5p is hsa-miR-6842-5p, miR-6124 is hsa-miR-6124, miR-6765-3p is hsa-miR-6765-3p, miR-7106-5p is hsa-miR-7106-5p, miR-4534 is hsa-miR-4534, miR-92b-3p is hsa-miR-92b-3p, miR-3135b is hsa-miR-3135b, miR-4687-3p is hsa-miR-4687-3p, miR-762 is hsa-miR-762, miR-3619-3p is hsa-miR-3619-3p, miR-4467 is hsa-miR-4467, miR-557 is hsa-miR-557, miR-1237-5p is hsa-miR-1237-5p, miR-1908-5p is hsa-miR-1908-5p, miR-4286 is hsa-miR-4286, miR-6885-5p is hsa-miR-6885-5p, and miR-6763-5p is hsa-miR-6763-5p.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 252 to 269, (m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 252 to 269 or a nucleotide sequence derived from the nucleotide sequence by the replacement of u with t, and (o) a polynucleotide hybridizing under stringent conditions to any of the polynucleotides (k) to (n).

(10) The kit according to any of (1) to (9), wherein the kit comprises at least two nucleic acids capable of specifically binding to at least two polynucleotides, respectively, selected from the group consisting of all of the breast cancer markers according to (1) or (2).

(11) A device for the detection of breast cancer, comprising nucleic acid(s) capable of specifically binding to at least one polynucleotide selected from the group consisting of the following breast cancer markers: miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-6089, miR-6816-5p, miR-4466, miR-4488, miR-6752-5p and miR-4739.

(12) The device according to (11), wherein miR-4783-3p is hsa-miR-4783-3p, miR-4730 is hsa-miR-4730, miR-1307-3p is hsa-miR-1307-3p, miR-4634 is hsa-miR-4634, miR-663a is hsa-miR-663a, miR-4532 is hsa-miR-4532, miR-7704 is hsa-miR-7704, miR-3178 is hsa-miR-3178, miR-6729-5p is hsa-miR-6729-5p, miR-6090 is hsa-miR-6090, miR-4732-5p is hsa-miR-4732-5p, miR-3184-5p is hsa-miR-3184-5p, miR-6727-5p is hsa-miR-6727-5p, miR-6088 is hsa-miR-6088, miR-4674 is hsa-miR-4674, miR-8073 is hsa-miR-8073, miR-4787-5p is hsa-miR-4787-5p, miR-1469 is hsa-miR-1469, miR-125a-3p is hsa-miR-125a-3p, miR-1233-5p is hsa-miR-1233-5p, miR-885-3p is hsa-miR-885-3p, miR-6802-5p is hsa-miR-6802-5p, miR-328-5p is hsa-miR-328-5p, miR-6787-5p is hsa-miR-6787-5p, miR-8069 is hsa-miR-8069, miR-6875-5p is hsa-miR-6875-5p, miR-1246 is hsa-miR-1246, miR-4734 is hsa-miR-4734, miR-6757-5p is hsa-miR-6757-5p, miR-6756-5p is hsa-miR-6756-5p, miR-3665 is hsa-miR-3665, miR-6836-3p is hsa-miR-6836-3p, miR-6821-5p is hsa-miR-6821-5p, miR-6805-5p is hsa-miR-6805-5p, miR-4728-5p is hsa-miR-4728-5p, miR-6726-5p is hsa-miR-6726-5p, miR-197-5p is hsa-miR-197-5p, miR-149-3p is hsa-miR-149-3p, miR-6850-5p is hsa-miR-6850-5p, miR-4476 is hsa-miR-4476, miR-6858-5p is hsa-miR-6858-5p, miR-564 is hsa-miR-564, miR-4763-3p is hsa-miR-4763-3p, miR-575 is hsa-miR-575, miR-6771-5p is hsa-miR-6771-5p, miR-1231 is hsa-miR-1231, miR-1908-3p is hsa-miR-1908-3p, miR-150-3p is hsa-miR-150-3p, miR-3937 is hsa-miR-3937, miR-887-3p is hsa-miR-887-3p, miR-3940-5p is hsa-miR-3940-5p, miR-4741 is hsa-miR-4741, miR-6808-5p is hsa-miR-6808-5p, miR-6869-5p is hsa-miR-6869-5p, miR-5090 is hsa-miR-5090, miR-615-5p is hsa-miR-615-5p, miR-8072 is hsa-miR-8072, miR-128-1-5p is hsa-miR-128-1-5p, miR-1238-5p is hsa-miR-1238-5p, miR-365a-5p is hsa-miR-365a-5p, miR-204-3p is hsa-miR-204-3p, miR-4492 is hsa-miR-4492, miR-6785-5p is hsa-miR-6785-5p, miR-6511a-5p is hsa-miR-6511a-5p, miR-4525 is hsa-miR-4525, miR-1915-5p is hsa-miR-1915-5p, miR-3180 is hsa-miR-3180, miR-6879-5p is hsa-miR-6879-5p, miR-1199-5p is hsa-miR-1199-5p, miR-6746-5p is hsa-miR-6746-5p, miR-711 is hsa-miR-711, miR-663b is hsa-miR-663b, miR-4707-3p is hsa-miR-4707-3p, miR-6893-5p is hsa-miR-6893-5p, miR-4675 is hsa-miR-4675, miR-4638-5p is hsa-miR-4638-5p, miR-4651 is hsa-miR-4651, miR-6087 is hsa-miR-6087, miR-4665-5p is hsa-miR-4665-5p, miR-4758-5p is hsa-miR-4758-5p, miR-6887-5p is hsa-miR-6887-5p, miR-3620-5p is hsa-miR-3620-5p, miR-1909-3p is hsa-miR-1909-3p, miR-7641 is hsa-miR-7641, miR-6724-5p is hsa-miR-6724-5p, miR-1343-3p is hsa-miR-1343-3p, miR-6780b-5p is hsa-miR-6780b-5p, miR-4484 is hsa-miR-4484, miR-4690-5p is hsa-miR-4690-5p, miR-4429 is hsa-miR-4429, miR-1227-5p is hsa-miR-1227-5p, miR-4725-3p is hsa-miR-4725-3p, miR-6861-5p is hsa-miR-6861-5p, miR-6812-5p is hsa-miR-6812-5p, miR-3197 is hsa-miR-3197, miR-8059 is hsa-miR-8059, miR-3185 is hsa-miR-3185, miR-4706 is hsa-miR-4706, miR-4497 is hsa-miR-4497, miR-3131 is hsa-miR-3131, miR-6806-5p is hsa-miR-6806-5p, miR-187-5p is hsa-miR-187-5p, miR-3180-3p is hsa-miR-3180-3p, miR-6848-5p is hsa-miR-6848-5p, miR-6820-5p is hsa-miR-6820-5p, miR-6800-5p is hsa-miR-6800-5p, miR-6717-5p is hsa-miR-6717-5p, miR-6795-5p is hsa-miR-6795-5p, miR-4632-5p is hsa-miR-4632-5p, miR-665 is hsa-miR-665, miR-6778-5p is hsa-miR-6778-5p, miR-3663-3p is hsa-miR-3663-3p, miR-4689 is hsa-miR-4689, miR-211-3p is hsa-miR-211-3p, miR-6511b-5p is hsa-miR-6511b-5p, miR-4750-5p is hsa-miR-4750-5p, miR-6126 is hsa-miR-6126, miR-614 is hsa-miR-614, miR-7110-5p is hsa-miR-7110-5p, miR-744-5p is hsa-miR-744-5p, miR-6769a-5p is hsa-miR-6769a-5p, miR-4792 is hsa-miR-4792, miR-5787 is hsa-miR-5787, miR-6798-5p is hsa-miR-6798-5p, miR-6781-5p is hsa-miR-6781-5p, miR-4419b is hsa-miR-4419b, miR-4446-3p is hsa-miR-4446-3p, miR-4259 is hsa-miR-4259, miR-5572 is hsa-miR-5572, miR-6075 is hsa-miR-6075, miR-296-3p is hsa-miR-296-3p, miR-6891-5p is hsa-miR-6891-5p, miR-4745-5p is hsa-miR-4745-5p, miR-6775-5p is hsa-miR-6775-5p, miR-6870-5p is hsa-miR-6870-5p, miR-920 is hsa-miR-920, miR-4530 is hsa-miR-4530, miR-6819-5p is hsa-miR-6819-5p, miR-6825-5p is hsa-miR-6825-5p, miR-7847-3p is hsa-miR-7847-3p, miR-6131 is hsa-miR-6131, miR-4433-3p is hsa-miR-4433-3p, miR-1228-5p is hsa-miR-1228-5p, miR-6743-5p is hsa-miR-6743-5p, miR-1268a is hsa-miR-1268a, miR-3917 is hsa-miR-3917, miR-6786-5p is hsa-miR-6786-5p, miR-3154 is hsa-miR-3154, miR-638 is hsa-miR-638, miR-6741-5p is hsa-miR-6741-5p, miR-6889-5p is hsa-miR-6889-5p, miR-6840-3p is hsa-miR-6840-3p, miR-6510-5p is hsa-miR-6510-5p, miR-3188 is hsa-miR-3188, miR-551b-5p is hsa-miR-551b-5p, miR-5001-5p is hsa-miR-5001-5p, miR-1268b is hsa-miR-1268b, miR-7107-5p is hsa-miR-7107-5p, miR-6824-5p is hsa-miR-6824-5p, miR-6732-5p is hsa-miR-6732-5p, miR-371a-5p is hsa-miR-371a-5p, miR-6794-5p is hsa-miR-6794-5p, miR-6779-5p is hsa-miR-6779-5p, miR-4271 is hsa-miR-4271, miR-5195-3p is hsa-miR-5195-3p, miR-6762-5p is hsa-miR-6762-5p, miR-939-5p is hsa-miR-939-5p, miR-1247-3p is hsa-miR-1247-3p, miR-6777-5p is hsa-miR-6777-5p, miR-6722-3p is hsa-miR-6722-3p, miR-3656 is hsa-miR-3656, miR-4688 is hsa-miR-4688, miR-3195 is hsa-miR-3195, miR-6766-5p is hsa-miR-6766-5p, miR-4447 is hsa-miR-4447, miR-4656 is hsa-miR-4656, miR-7108-5p is hsa-miR-7108-5p, miR-3191-3p is hsa-miR-3191-3p, miR-1273g-3p is hsa-miR-1273g-3p, miR-4463 is hsa-miR-4463, miR-2861 is hsa-miR-2861, miR-3196 is hsa-miR-3196, miR-6877-5p is hsa-miR-6877-5p, miR-3679-5p is hsa-miR-3679-5p, miR-4442 is hsa-miR-4442, miR-6789-5p is hsa-miR-6789-5p, miR-6782-5p is hsa-miR-6782-5p, miR-486-3p is hsa-miR-486-3p, miR-6085 is hsa-miR-6085, miR-4746-3p is hsa-miR-4746-3p, miR-619-5p is hsa-miR-619-5p, miR-937-5p is hsa-miR-937-5p, miR-6803-5p is hsa-miR-6803-5p, miR-4298 is hsa-miR-4298, miR-4454 is hsa-miR-4454, miR-4459 is hsa-miR-4459, miR-7150 is hsa-miR-7150, miR-6880-5p is hsa-miR-6880-5p, miR-4449 is hsa-miR-4449, miR-8063 is hsa-miR-8063, miR-4695-5p is hsa-miR-4695-5p, miR-6132 is hsa-miR-6132, miR-6829-5p is hsa-miR-6829-5p, miR-4486 is hsa-miR-4486, miR-6805-3p is hsa-miR-6805-3p, miR-6826-5p is hsa-miR-6826-5p, miR-4508 is hsa-miR-4508, miR-1343-5p is hsa-miR-1343-5p, miR-7114-5p is hsa-miR-7114-5p, miR-3622a-5p is hsa-miR-3622a-5p, miR-6765-5p is hsa-miR-6765-5p, miR-7845-5p is hsa-miR-7845-5p, miR-3960 is hsa-miR-3960, miR-6749-5p is hsa-miR-6749-5p, miR-1260b is hsa-miR-1260b, miR-6799-5p is hsa-miR-6799-5p, miR-4723-5p is hsa-miR-4723-5p, miR-6784-5p is hsa-miR-6784-5p, miR-5100 is hsa-miR-5100, miR-6769b-5p is hsa-miR-6769b-5p, miR-1207-5p is hsa-miR-1207-5p, miR-642a-3p is hsa-miR-642a-3p, miR-4505 is hsa-miR-4505, miR-4270 is hsa-miR-4270, miR-6721-5p is hsa-miR-6721-5p, miR-7111-5p is hsa-miR-7111-5p, miR-6791-5p is hsa-miR-6791-5p, miR-7109-5p is hsa-miR-7109-5p, miR-4258 is hsa-miR-4258, miR-6515-3p is hsa-miR-6515-3p, miR-6851-5p is hsa-miR-6851-5p, miR-6125 is hsa-miR-6125, miR-4749-5p is hsa-miR-4749-5p, miR-4726-5p is hsa-miR-4726-5p, miR-4513 is hsa-miR-4513, miR-6089 is hsa-miR-6089, miR-6816-5p is hsa-miR-6816-5p, miR-4466 is hsa-miR-4466, miR-4488 is hsa-miR-4488, miR-6752-5p is hsa-miR-6752-5p, and miR-4739 is hsa-miR-4739.

(13) The device according to (11) or (12), wherein the nucleic acid is a polynucleotide selected from the group consisting of the following polynucleotides (a) to (e):
 (a) a polynucleotide consisting of a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
 (b) a polynucleotide comprising a nucleotide sequence represented by any of SEQ ID NOs: 1 to 235 and 851 to 856 or a nucleotide sequence derived from the nucleotide sequence by the replacement of u with t,
 (c) a polynucleotide consisting of a nucleotide sequence complementary to a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
 (d) a polynucleotide comprising a nucleotide sequence complementary to a nucleotide sequence represented by any of SEQ ID NOs: 1 to 235 and 851 to 856 or a nucleotide sequence derived from the nucleotide sequence by the replacement of u with t, and
 (e) a polynucleotide hybridizing under stringent conditions to any of the polynucleotides (a) to (d).

(14) The device according to any of (11) to (13), wherein the device further comprises nucleic acid(s) capable of specifically binding to at least one polynucleotide selected from the group consisting of other breast cancer markers miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

(15) The device according to (14), wherein miR-760 is hsa-miR-760, miR-602 is hsa-miR-602, miR-423-5p is hsa-miR-423-5p, miR-92a-2-5p is hsa-miR-92a-2-5p, miR-16-5p is hsa-miR-16-5p, miR-451a is hsa-miR-451a, miR-135a-3p is hsa-miR-135a-3p, miR-486-5p is hsa-miR-486-5p, miR-4257 is hsa-miR-4257, miR-92b-5p is hsa-miR-92b-5p, miR-1915-3p is hsa-miR-1915-3p, miR-718 is hsa-miR-718, miR-940 is hsa-miR-940, miR-296-5p is hsa-miR-296-5p, miR-23b-3p is hsa-miR-23b-3p, and miR-92a-3p is hsa-miR-92a-3p.

(16) The device according to (14) or (15), wherein the nucleic acid is a polynucleotide selected from the group consisting of the following polynucleotides (f) to (j):
 (f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
 (g) a polynucleotide comprising a nucleotide sequence represented by any of SEQ ID NOs: 236 to 251,
 (h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
 (i) a polynucleotide comprising a nucleotide sequence complementary to a nucleotide sequence represented by any of SEQ ID NOs: 236 to 251 or a nucleotide sequence derived from the nucleotide sequence by the replacement of u with t, and
 (j) a polynucleotide hybridizing under stringent conditions to any of the polynucleotides (f) to (i).

(17) The device according to any of (11) to (16), wherein the device further comprises nucleic acid(s) capable of specifically binding to at least one polynucleotide selected from the group consisting of other breast cancer markers miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

(18) The device according to (17), wherein miR-658 is hsa-miR-658, miR-6842-5p is hsa-miR-6842-5p, miR-6124 is hsa-miR-6124, miR-6765-3p is hsa-miR-6765-3p, miR-7106-5p is hsa-miR-7106-5p, miR-4534 is hsa-miR-4534, miR-92b-3p is hsa-miR-92b-3p, miR-3135b is hsa-miR-3135b, miR-4687-3p is hsa-miR-4687-3p, miR-762 is hsa-miR-762, miR-3619-3p is hsa-miR-3619-3p, miR-4467 is hsa-miR-4467, miR-557 is hsa-miR-557, miR-1237-5p is hsa-miR-1237-5p, miR-1908-5p is hsa-miR-1908-5p, miR-4286 is hsa-miR-4286, miR-6885-5p is hsa-miR-6885-5p, and miR-6763-5p is hsa-miR-6763-5p.

(19) The device according to (17) or (18), wherein the nucleic acid is a polynucleotide selected from the group consisting of the following polynucleotides (k) to (o):
 (k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides,
 (l) a polynucleotide comprising a nucleotide sequence represented by any of SEQ ID NOs: 252 to 269,
 (m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 252 to 269 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any one of (11) to (21), wherein the device comprises at least two nucleic acids capable of specifically binding to at least two polynucleotides, respectively, selected from all of the breast cancer markers according to (11) or (12).

(23) A method for detecting breast cancer, comprising measuring an expression level(s) of a target nucleic acid(s) in a sample from a subject using a kit according to any one of (1) to (10) or a device according to any one of (11) to (22), and evaluating in vitro whether or not the subject has breast cancer using both of the measured expression level(s) and a control expression level(s) in a sample from a healthy subject measured in the same way.

(24) The method according to (23), wherein the subject is a human.

(25) The method according to (23) or (24), wherein the sample is blood, serum, or plasma.

DEFINITION OF TERMS

The terms used herein are defined as described below.

Abbreviations or terms such as nucleotide, polynucleotide, DNA, and RNA used herein abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. The "synthetic DNA" and the "synthetic RNA" used herein refer to DNA and RNA artificially prepared using, for example, an automatic nucleic acid synthesizer, on the basis of predetermined nucleotide sequences (which may be any of natural and non-natural sequences). The "non-natural sequence" used herein is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. The term "polynucleotide" used herein is used interchangeably with the term "nucleic acid".

The term "fragment" used herein refers to a polynucleotide (including oligonucleotides) having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) constituting the duplex. The gene is not particularly limited by its length. Thus, The "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but also "nucleic acids" encoding RNAs having biological functions equivalent to an RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 871 or a nucleotide sequence derived from the nucleotide sequence by the replacement of u with t. Regardless whether or not there is a difference in functional region, the "gene(s)" can comprise, for example, expression regulatory region(s), coding region(s), exon(s), or intron(s). The "gene" may be contained in a cell or may exist alone after being released into the outside of a cell. Alternatively, the "gene" may be in a state enclosed in a vesicle called exosome.

The term "exosome" used herein refers to a vesicle that is encapsulated by a lipid bilayer and secreted from a cell. The exosome is derived from a multivesicular endosome and may incorporate biomaterials such as "gene(s)" (e.g., RNA or DNA) or protein(s) when released into an extracellular environment. The exosome is known to be contained in a body fluid such as blood, serum, plasma, or lymph.

The term "transcript" used herein refers to RNA synthesized with the DNA sequence of a gene as a template. RNA polymerase binds to a site called a promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a polyA sequence, including expression regultory region(s), coding region(s), exon(s), or intron(s).

Unless otherwise specified, the term "microRNA (miRNA)" used herein is intended to mean a 15- to 25-nucleotide non-coding RNA that is transcribed as an RNA precursor which has a hairpin-like structure, cleaved by a dsRNA-cleaving enzyme which has RNase III cleavage activity, and integrated into a protein complex called RISC, and is involved in the suppression of translation of mRNA. The term "miRNA" used herein includes not only a "miRNA" represented by a particular nucleotide sequence (or SEQ ID NO) but also a precursor of the "miRNA" (pre-miRNA or pri-miRNA), and miRNAs that have biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 871. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto. In this context, the "complementary polynucleotide (complementary strand or reverse strand)" means a polynucleotide in a complementary relationship of A:T (U) and G:C base pairs with the full-length sequence of a polynucleotide consisting of a nucleotide sequence defined by any of SEQ ID NOs: 1 to 871 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 871 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "multiple" used herein means an integer of approximately 10, 9, 8, 7, 6, 5, 4, 3, or 2.

The "variant" used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

The "nucleic acid" used herein capable of specifically binding to a polynucleotide selected from the breast cancer marker miRNAs described above is a synthesized or prepared nucleic acid and specifically includes a "nucleic acid probe" or a "primer". The "nucleic acid" is utilized directly or indirectly for detecting the presence or absence of breast cancer in a subject, for diagnosing the presence or absence of breast cancer, or the severity of breast cancer, the presence or absence of amelioration of breast cancer, or the degree of amelioration of breast cancer, or the therapeutic sensitivity of breast cancer, or for screening for a candidate substance useful in the prevention, amelioration, or treatment of breast cancer. The "nucleic acid" includes a nucleotide, an oligonucleotide, and a polynucleotide capable of specifically recognizing and binding to a transcript represented by any of SEQ ID NOs:1 to 871 or a synthetic cDNA nucleic acid thereof in vivo, particularly, in a sample such as a body fluid (e.g., blood or urine), in relation to the development of breast cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", or "detection or decision support". The term "evaluation" used herein is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that is actually calculated from data under a null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows breast cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects who might have been misjudged as being breast cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

The "sample" used herein, that is subjected to determination, detection, or diagnosis refers to a tissue and a biological material in which the expression of the gene of the present invention varies as breast cancer develops, as breast cancer progresses, or as therapeutic effects on breast cancer are exerted. Specifically, the "sample" refers to a breast tissue, a perimammary vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4783-3p gene" or "hsa-miR-4783-3p" used herein includes the hsa-miR-4783-3p gene (miRBase Accession No. MIMAT0019947) described in SEQ ID NO: 1, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 270) having a hairpin-like structure is known as a precursor of "hsa-miR-4783-3p".

The term "hsa-miR-4730 gene" or "hsa-miR-4730" used herein includes the hsa-miR-4730 gene (miRBase Accession No. MIMAT0019852) described in SEQ ID NO: 2, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 271) having a hairpin-like structure is known as a precursor of "hsa-miR-4730".

The term "hsa-miR-1307-3p gene" or "hsa-miR-1307-3p" used herein includes the hsa-miR-1307-3p gene (miRBase Accession No. MIMAT0005951) described in SEQ ID NO: 3, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI006444, SEQ ID NO: 272) having a hairpin-like structure is known as a precursor of "hsa-miR-1307-3p".

The term "hsa-miR-4634 gene" or "hsa-miR-4634" used herein includes the hsa-miR-4634 gene (miRBase Accession No. MIMAT0019691) described in SEQ ID NO: 4, a homolog or an ortholog of a different organism species, and the like. The hsa-miR-4634 gene can be obtained by a method described in Persson H et al., 2011, Cancer Res, Vol. 71, p. 78-86. Also, "hsa-mir-4634" (miRBase Accession No. MI0017261, SEQ ID NO: 273) having a hairpin-like structure is known as a precursor of "hsa-miR-4634".

The term "hsa-miR-663a gene" or "hsa-miR-663a" used herein includes the hsa-miR-663a gene (miRBase Accession No. MIMAT0003326) described in SEQ ID NO: 5, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 274) having a hairpin-like structure is known as a precursor of "hsa-miR-663a".

The term "hsa-miR-4532 gene" or "hsa-miR-4532" used herein includes the hsa-miR-4532 gene (miRBase Accession No. MIMAT0019071) described in SEQ ID NO: 6, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 275) having a hairpin-like structure is known as a precursor of "hsa-miR-4532".

The term "hsa-miR-7704 gene" or "hsa-miR-7704" used herein includes the hsa-miR-7704 gene (miRBase Accession No. MIMAT0030019) described in SEQ ID NO: 7, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 276) having a hairpin-like structure is known as a precursor of "hsa-miR-7704".

The term "hsa-miR-3178 gene" or "hsa-miR-3178" used herein includes the hsa-miR-3178 gene (miRBase Accession No. MIMAT0015055) described in SEQ ID NO: 8, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 277) having a hairpin-like structure is known as a precursor of "hsa-miR-3178".

The term "hsa-miR-6729-5p gene" or "hsa-miR-6729-5p" used herein includes the hsa-miR-6729-5p gene (miRBase Accession No. MIMAT0027359) described in SEQ ID NO: 9, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 278) having a hairpin-like structure is known as a precursor of "hsa-miR-6729-5p".

The term "hsa-miR-6090 gene" or "hsa-miR-6090" used in herein includes the hsa-miR-6090 gene (miRBase Accession No. MIMAT0023715) described in SEQ ID NO: 10, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 279) having a hairpin-like structure is known as a precursor of "hsa-miR-6090".

The term "hsa-miR-4732-5p gene" or "hsa-miR-4732-5p" used in herein includes the hsa-miR-4732-5p gene (miRBase Accession No. MIMAT0019855) described in SEQ ID NO: 11, a homolog or an ortholog of a different organism species, and the like. The hsa-miR-4732-5p gene can be obtained by a method described in Persson H et al., 2011, Cancer Res, Vol. 71, p. 78-86. Also, "hsa-mir-4732" (miRBase Accession No. MI0017369, SEQ ID NO: 280) having a hairpin-like structure is known as a precursor of "hsa-miR-4732-5p".

The term "hsa-miR-3184-5p gene" or "hsa-miR-3184-5p" used herein includes the hsa-miR-3184-5p gene (miRBase Accession No. MIMAT0015064) described in SEQ ID NO: 12, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 281) having a hairpin-like structure is known as a precursor of "hsa-miR-3184-5p".

The term "hsa-miR-6727-5p gene" or "hsa-miR-6727-5p" used herein includes the hsa-miR-6727-5p gene (miRBase Accession No. MIMAT0027355) described in SEQ ID NO: 13, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 282) having a hairpin-like structure is known as a precursor of "hsa-miR-6727-5p".

The term "hsa-miR-6088 gene" or "hsa-miR-6088" used herein includes the hsa-miR-6088 gene (miRBase Accession No. MIMAT0023713) described in SEQ ID NO: 14, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 283) having a hairpin-like structure is known as a precursor of "hsa-miR-6088".

The term "hsa-miR-4674 gene" or "hsa-miR-4674" used herein includes the hsa-miR-4674 gene (miRBase Accession No. MIMAT0019756) described in SEQ ID NO: 15, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 284) having a hairpin-like structure is known as a precursor of "hsa-miR-4674".

The term "hsa-miR-8073 gene" or "hsa-miR-8073" used herein includes the hsa-miR-8073 gene (miRBase Accession No. MIMAT0031000) described in SEQ ID NO: 16, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 285) having a hairpin-like structure is known as a precursor of "hsa-miR-8073".

The term "hsa-miR-4787-5p gene" or "hsa-miR-4787-5p" used herein includes the hsa-miR-4787-5p gene (miRBase Accession No. MIMAT0019956) described in SEQ ID NO: 17, a homolog or an ortholog of a different organism species, and the like. The hsa-miR-4787-5p gene can be obtained by a method described in Persson H et al., 2011, Cancer Res, Vol. 71, p. 78-86. Also, "hsa-mir-4787" (miRBase Accession No. MI0017434, SEQ ID NO: 286) having a hairpin-like structure is known as a precursor of "hsa-miR-4787-5p".

The term "hsa-miR-1469 gene" or "hsa-miR-1469" used herein includes the hsa-miR-1469 gene (miRBase Accession No. MIMAT0007347) described in SEQ ID NO: 18, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 287) having a hairpin-like structure is known as a precursor of "hsa-miR-1469".

The term "hsa-miR-125a-3p gene" or "hsa-miR-125a-3p" used herein includes the hsa-miR-125a-3p gene (miRBase Accession No. MIMAT0004602) described in SEQ ID NO: 19, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 288) having a hairpin-like structure is known as a precursor of "hsa-miR-125a-3p".

The term "hsa-miR-1233-5p gene" or "hsa-miR-1233-5p" used herein includes the hsa-miR-1233-5p gene (miRBase Accession No. MIMAT0022943) described in SEQ ID NO: 20, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 289 and 290) having a hairpin-like structure are known as precursors of "hsa-miR-1233-5p".

The term "hsa-miR-885-3p gene" or "hsa-miR-885-3p" used herein includes the hsa-miR-885-3p gene (miRBase Accession No. MIMAT0004948) described in SEQ ID NO: 21, a homolog or an ortholog of a different organism species, and the like. The hsa-miR-885-3p gene can be obtained by a method described in Berezikov E et al., 2006, Genome Res, Vol. 16, p. 1289-1298. Also, "hsa-mir-885" (miRBase Accession No. MI0005560, SEQ ID NO: 291) having a hairpin-like structure is known as a precursor of "hsa-miR-885-3p".

The term "hsa-miR-6802-5p gene" or "hsa-miR-6802-5p" used herein includes the hsa-miR-6802-5p gene (miRBase Accession No. MIMAT0027504) described in SEQ ID NO: 22, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 292) having a hairpin-like structure is known as a precursor of "hsa-miR-6802-5p".

The term "hsa-miR-328-5p gene" or "hsa-miR-328-5p" used herein includes the hsa-miR-328-5p gene (miRBase Accession No. MIMAT0026486) described in SEQ ID NO: 23, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 293) having a hairpin-like structure is known as a precursor of "hsa-miR-328-5p".

The term "hsa-miR-6787-5p gene" or "hsa-miR-6787-5p" used herein includes the hsa-miR-6787-5p gene (miRBase Accession No. MIMAT0027474) described in SEQ ID NO: 24, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 294) having a hairpin-like structure is known as a precursor of "hsa-miR-6787-5p".

The term "hsa-miR-8069 gene" or "hsa-miR-8069" used herein includes the hsa-miR-8069 gene (miRBase Accession No. MIMAT0030996) described in SEQ ID NO: 25, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 295) having a hairpin-like structure is known as a precursor of "hsa-miR-8069".

The term "hsa-miR-6875-5p gene" or "hsa-miR-6875-5p" used herein includes the hsa-miR-6875-5p gene (miRBase Accession No. MIMAT0027650) described in SEQ ID NO: 26, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 296) having a hairpin-like structure is known as a precursor of "hsa-miR-6875-5p".

The term "hsa-miR-1246 gene" or "hsa-miR-1246" used herein includes the hsa-miR-1246 gene (miRBase Accession No. MIMAT0005898) described in SEQ ID NO: 27, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 297) having a hairpin-like structure is known as a precursor of "hsa-miR-1246".

The term "hsa-miR-4734 gene" or "hsa-miR-4734" used herein includes the hsa-miR-4734 gene (miRBase Accession No. MIMAT0019859) described in SEQ ID NO: 28, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 298) having a hairpin-like structure is known as a precursor of "hsa-miR-4734".

The term "hsa-miR-6757-5p gene" or "hsa-miR-6757-5p" used herein includes the hsa-miR-6757-5p gene (miRBase Accession No. MIMAT0027414) described in SEQ ID NO: 29, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 299) having a hairpin-like structure is known as a precursor of "hsa-miR-6757-5p".

The term "hsa-miR-6756-5p gene" or "hsa-miR-6756-5p" used herein includes the hsa-miR-6756-5p gene (miRBase Accession No. MIMAT0027412) described in SEQ ID NO: 30, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 300) having a hairpin-like structure is known as a precursor of "hsa-miR-6756-5p".

The term "hsa-miR-3665 gene" or "hsa-miR-3665" used herein includes the hsa-miR-3665 gene (miRBase Accession No. MIMAT0018087) described in SEQ ID NO: 31, a homolog or an ortholog of a different organism species, and the like. The hsa-miR-3665 gene can be obtained by a method described in Xie X et al., 2005, Nature, Vol. 434, p. 338-345. Also, "hsa-mir-3665" (miRBase Accession No. MI0016066, SEQ ID NO: 301) having a hairpin-like structure is known as a precursor of "hsa-miR-3665".

The term "hsa-miR-6836-3p gene" or "hsa-miR-6836-3p" used herein includes the hsa-miR-6836-3p gene (miRBase Accession No. MIMAT0027575) described in SEQ ID NO: 32, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 302) having a hairpin-like structure is known as a precursor of "hsa-miR-6836-3p".

The term "hsa-miR-6821-5p gene" or "hsa-miR-6821-5p" used herein includes the hsa-miR-6821-5p gene (miRBase Accession No. MIMAT0027542) described in SEQ ID NO: 33, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 303) having a hairpin-like structure is known as a precursor of "hsa-miR-6821-5p".

The term "hsa-miR-6805-5p gene" or "hsa-miR-6805-5p" used herein includes the hsa-miR-6805-5p gene (miRBase Accession No. MIMAT0027510) described in SEQ ID NO: 34, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 304) having a hairpin-like structure is known as a precursor of "hsa-miR-6805-5p".

The term "hsa-miR-4728-5p gene" or "hsa-miR-4728-5p" used herein includes the hsa-miR-4728-5p gene (miRBase Accession No. MIMAT0019849) described in SEQ ID NO: 35, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 305) having a hairpin-like structure is known as a precursor of "hsa-miR-4728-5p".

The term "hsa-miR-6726-5p gene" or "hsa-miR-6726-5p" used herein includes the hsa-miR-6726-5p gene (miRBase Accession No. MIMAT0027353) described in SEQ ID NO: 36, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 306) having a hairpin-like structure is known as a precursor of "hsa-miR-6726-5p".

The term "hsa-miR-197-5p gene" or "hsa-miR-197-5p" used herein includes the hsa-miR-197-5p gene (miRBase Accession No. MIMAT0022691) described in SEQ ID NO: 37, a homolog or an ortholog of a different organism species, and the like. The hsa-miR-197-5p gene can be obtained by a method described in Lagos-Quintana M et al., 2003, RNA, Vol. 9, p. 175-179. Also, "hsa-mir-197" (miRBase Accession No. MI0000239, SEQ ID NO: 307) having a hairpin-like structure is known as a precursor of "hsa-miR-197-5p".

The term "hsa-miR-149-3p gene" or "hsa-miR-149-3p" used herein includes the hsa-miR-149-3p gene (miRBase Accession No. MIMAT0004609) described in SEQ ID NO: 38, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 308) having a hairpin-like structure is known as a precursor of "hsa-miR-149-3p".

The term "hsa-miR-6850-5p gene" or "hsa-miR-6850-5p" used herein includes the hsa-miR-6850-5p gene (miRBase Accession No. MIMAT0027600) described in SEQ ID NO: 39, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 309) having a hairpin-like structure is known as a precursor of "hsa-miR-6850-5p".

The term "hsa-miR-4476 gene" or "hsa-miR-4476" used herein includes the hsa-miR-4476 gene (miRBase Accession No. MIMAT0019003) described in SEQ ID NO: 40, a homolog or an ortholog of a different organism species, and the like. The hsa-miR-4476 gene can be obtained by a method described in lima D D et al., 2010, Blood, Vol. 116, e118-e127. Also, "hsa-mir-4476" (miRBase Accession No. MI0016828, SEQ ID NO: 310) having a hairpin-like structure is known as a precursor of "hsa-miR-4476".

The term "hsa-miR-6858-5p gene" or "hsa-miR-6858-5p" used herein includes the hsa-miR-6858-5p gene (miRBase Accession No. MIMAT0027616) described in SEQ ID NO: 41, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 311) having a hairpin-like structure is known as a precursor of "hsa-miR-6858-5p".

The term "hsa-miR-564 gene" or "hsa-miR-564" used herein includes the hsa-miR-564 gene (miRBase Accession No. MIMAT0003228) described in SEQ ID NO: 42, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 312) having a hairpin-like structure is known as a precursor of "hsa-miR-564".

The term "hsa-miR-4763-3p gene" or "hsa-miR-4763-3p" used herein includes the hsa-miR-4763-3p gene (miRBase Accession No. MIMAT0019913) described in SEQ ID NO: 43, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 313) having a hairpin-like structure is known as a precursor of "hsa-miR-4763-3p".

The term "hsa-miR-575 gene" or "hsa-miR-575" used herein includes the hsa-miR-575 gene (miRBase Accession No. MIMAT0003240) described in SEQ ID NO: 44, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 314) having a hairpin-like structure is known as a precursor of "hsa-miR-575".

The term "hsa-miR-6771-5p gene" or "hsa-miR-6771-5p" used herein includes the hsa-miR-6771-5p gene (miRBase Accession No. MIMAT0027442) described in SEQ ID NO: 45, a homolog or an ortholog of a different organism species, and the like. The hsa-miR-6771-5p gene can be obtained by a method described in Ladewig E et al., 2012, Genome Res, Vol. 22, p. 1634-1645. Also, "hsa-mir-6771" (miRBase Accession No. MI0022616, SEQ ID NO: 315) having a hairpin-like structure is known as a precursor of "hsa-miR-6771-5p".

The term "hsa-miR-1231 gene" or "hsa-miR-1231" used herein includes the hsa-miR-1231 gene (miRBase Accession No. MIMAT0005586) described in SEQ ID NO: 46, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 316) having a hairpin-like structure is known as a precursor of "hsa-miR-1231".

The term "hsa-miR-1908-3p gene" or "hsa-miR-1908-3p" used herein includes the hsa-miR-1908-3p gene (miRBase Accession No. MIMAT0026916) described in SEQ ID NO: 47, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 317) having a hairpin-like structure is known as a precursor of "hsa-miR-1908-3p".

The term "hsa-miR-150-3p gene" or "hsa-miR-150-3p" used herein includes the hsa-miR-150-3p gene (miRBase Accession No. MIMAT0004610) described in SEQ ID NO: 48, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 318) having a hairpin-like structure is known as a precursor of "hsa-miR-150-3p".

The term "hsa-miR-3937 gene" or "hsa-miR-3937" used herein includes the hsa-miR-3937 gene (miRBase Accession No. MIMAT0018352) described in SEQ ID NO: 49, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 319) having a hairpin-like structure is known as a precursor of "hsa-miR-3937".

The term "hsa-miR-887-3p gene" or "hsa-miR-887-3p" used herein includes the hsa-miR-887-3p gene (miRBase Accession No. MIMAT0004951) described in SEQ ID NO: 50, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 320) having a hairpin-like structure is known as a precursor of "hsa-miR-887-3p".

The term "hsa-miR-3940-5p gene" or "hsa-miR-3940-5p" used herein includes the hsa-miR-3940-5p gene (miRBase Accession No. MIMAT0019229) described in SEQ ID NO: 51, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 321) having a hairpin-like structure is known as a precursor of "hsa-miR-3940-5p".

The term "hsa-miR-4741 gene" or "hsa-miR-4741" used herein includes the hsa-miR-4741 gene (miRBase Accession No. MIMAT0019871) described in SEQ ID NO: 52, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 322) having a hairpin-like structure is known as a precursor of "hsa-miR-4741".

The term "hsa-miR-6808-5p gene" or "hsa-miR-6808-5p" used herein includes the hsa-miR-6808-5p gene (miRBase Accession No. MIMAT0027516) described in SEQ ID NO: 53, a homolog or an ortholog of a different organism species, and the like. The hsa-miR-6808-5p gene can be obtained by a method described in Ladewig E et al., 2012, Genome Res, Vol. 22, p. 1634-1645. Also, "hsa-mir-6808" (miRBase Accession No. MI0022653, SEQ ID NO: 323) having a hairpin-like structure is known as a precursor of "hsa-miR-6808-5p".

The term "hsa-miR-6869-5p gene" or "hsa-miR-6869-5p" used herein includes the hsa-miR-6869-5p gene (miRBase Accession No. MIMAT0027638) described in SEQ ID NO: 54, a homolog or an ortholog of a different organism species, and the like. The hsa-miR-6869-5p gene can be obtained by a method described in Ladewig E et al., 2012, Genome Res, Vol. 22, p. 1634-1645. Also, "hsa-mir-6869" (miRBase Accession No. MI0022716, SEQ ID NO: 324) having a hairpin-like structure is known as a precursor of "hsa-miR-6869-5p".

The term "hsa-miR-5090 gene" or "hsa-miR-5090" used herein includes the hsa-miR-5090 gene (miRBase Accession No. MIMAT0021082) described in SEQ ID NO: 55, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 325) having a hairpin-like structure is known as a precursor of "hsa-miR-5090".

The term "hsa-miR-615-5p gene" or "hsa-miR-615-5p" used herein includes the hsa-miR-615-5p gene (miRBase Accession No. MIMAT0004804) described in SEQ ID NO: 56, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 326) having a hairpin-like structure is known as a precursor of "hsa-miR-615-5p".

The term "hsa-miR-8072 gene" or "hsa-miR-8072" used herein includes the hsa-miR-8072 gene (miRBase Accession No. MIMAT0030999) described in SEQ ID NO: 57, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 327) having a hairpin-like structure is known as a precursor of "hsa-miR-8072".

The term "hsa-miR-128-1-5p gene" or "hsa-miR-128-1-5p" used herein includes the hsa-miR-128-1-5p gene (miRBase Accession No. MIMAT0026477) described in SEQ ID NO: 58, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 328) having a hairpin-like structure is known as a precursor of "hsa-miR-128-1-5p".

The term "hsa-miR-1238-5p gene" or "hsa-miR-1238-5p" used herein includes the hsa-miR-1238-5p gene (miRBase Accession No. MIMAT0022947) described in SEQ ID NO: 59, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 329) having a hairpin-like structure is known as a precursor of "hsa-miR-1238-5p".

The term "hsa-miR-365a-5p gene" or "hsa-miR-365a-5p" used herein includes the hsa-miR-365a-5p gene (miRBase Accession No. MIMAT0009199) described in SEQ ID NO: 60, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 330) having a hairpin-like structure is known as a precursor of "hsa-miR-365a-5p".

The term "hsa-miR-204-3p gene" or "hsa-miR-204-3p" used herein includes the hsa-miR-204-3p gene (miRBase Accession No. MIMAT0022693) described in SEQ ID NO: 61, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 331) having a hairpin-like structure is known as a precursor of "hsa-miR-204-3p".

The term "hsa-miR-4492 gene" or "hsa-miR-4492" used herein includes the hsa-miR-4492 gene (miRBase Accession No. MIMAT0019027) described in SEQ ID NO: 62, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 332) having a hairpin-like structure is known as a precursor of "hsa-miR-4492".

The term "hsa-miR-6785-5p gene" or "hsa-miR-6785-5p" used herein includes the hsa-miR-6785-5p gene (miRBase Accession No. MIMAT0027470) described in SEQ ID NO: 63, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 333) having a hairpin-like structure is known as a precursor of "hsa-miR-6785-5p".

The term "hsa-miR-6511a-5p gene" or "hsa-miR-6511a-5p" used herein includes the hsa-miR-6511a-5p gene (miRBase Accession No. MIMAT0025478) described in SEQ ID NO: 64, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3, and hsa-mir-6511a-4" (miRBase Accession Nos. MI0022223, MI0023564, MI0023565, and MI0023566, SEQ ID NOs: 334, 335, 336, and 337) having a hairpin-like structure are known as precursors of "hsa-miR-6511a-5p".

The term "hsa-miR-4525 gene" or "hsa-miR-4525" used herein includes the hsa-miR-4525 gene (miRBase Accession No. MIMAT0019064) described in SEQ ID NO: 65, a homolog or an ortholog of a different organism species, and the like. The hsa-miR-4525 gene can be obtained by a method described in lima D D et al., 2010, Blood, Vol. 116, e118-e127. Also, "hsa-mir-4525" (miRBase Accession No. MI0016892, SEQ ID NO: 338) having a hairpin-like structure is known as a precursor of "hsa-miR-4525".

The term "hsa-miR-1915-5p gene" or "hsa-miR-1915-5p" used herein includes the hsa-miR-1915-5p gene (miRBase Accession No. MIMAT0007891) described in SEQ ID NO: 66, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 339) having a hairpin-like structure is known as a precursor of "hsa-miR-1915-5p".

The term "hsa-miR-3180 gene" or "hsa-miR-3180" used herein includes the hsa-miR-3180 gene (miRBase Accession No. MIMAT0018178) described in SEQ ID NO: 67, a homolog or an ortholog of a different organism species, and the like. The hsa-miR-3180 gene can be obtained by a method described in Creighton Cl et al., 2010, PLoS One, Vol. 5, e9637. Also, "hsa-mir-3180-4 and hsa-mir-3180-5" (miRBase Accession Nos. MI0016408 and MI0016409, SEQ ID NOs: 340 and 341) having a hairpin-like structure are known as precursors of "hsa-miR-3180".

The term "hsa-miR-6879-5p gene" or "hsa-miR-6879-5p" used herein includes the hsa-miR-6879-5p gene (miRBase Accession No. MIMAT0027658) described in SEQ ID NO: 68, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 342) having a hairpin-like structure is known as a precursor of "hsa-miR-6879-5p".

The term "hsa-miR-1199-5p gene" or "hsa-miR-1199-5p" used herein includes the hsa-miR-1199-5p gene (miRBase Accession No. MIMAT0031119) described in SEQ ID NO: 69, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 343) having a hairpin-like structure is known as a precursor of "hsa-miR-1199-5p".

The term "hsa-miR-6746-5p gene" or "hsa-miR-6746-5p" used herein includes the hsa-miR-6746-5p gene (miRBase Accession No. MIMAT0027392) described in SEQ ID NO: 70, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 344) having a hairpin-like structure is known as a precursor of "hsa-miR-6746-5p".

The term "hsa-miR-711 gene" or "hsa-miR-711" used herein includes the hsa-miR-711 gene (miRBase Accession No. MIMAT0012734) described in SEQ ID NO: 71, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 345) having a hairpin-like structure is known as a precursor of "hsa-miR-711".

The term "hsa-miR-663b gene" or "hsa-miR-663b" used herein includes the hsa-miR-663b gene (miRBase Accession No. MIMAT0005867) described in SEQ ID NO: 72, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 346) having a hairpin-like structure is known as a precursor of "hsa-miR-663b".

The term "hsa-miR-4707-3p gene" or "hsa-miR-4707-3p" used herein includes the hsa-miR-4707-3p gene (miRBase Accession No. MIMAT0019808) described in SEQ ID NO: 73, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 347) having a hairpin-like structure is known as a precursor of "hsa-miR-4707-3p".

The term "hsa-miR-6893-5p gene" or "hsa-miR-6893-5p" used herein includes the hsa-miR-6893-5p gene (miRBase Accession No. MIMAT0027686) described in SEQ ID NO: 74, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 348) having a hairpin-like structure is known as a precursor of "hsa-miR-6893-5p".

The term "hsa-miR-4675 gene" or "hsa-miR-4675" used herein includes the hsa-miR-4675 gene (miRBase Accession No. MIMAT0019757) described in SEQ ID NO: 75, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 349) having a hairpin-like structure is known as a precursor of "hsa-miR-4675".

The term "hsa-miR-4638-5p gene" or "hsa-miR-4638-5p" used herein includes the hsa-miR-4638-5p gene (miRBase Accession No. MIMAT0019695) described in SEQ ID NO: 76, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 350) having a hairpin-like structure is known as a precursor of "hsa-miR-4638-5p".

The term "hsa-miR-4651 gene" or "hsa-miR-4651" used herein includes the hsa-miR-4651 gene (miRBase Accession No. MIMAT0019715) described in SEQ ID NO: 77, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 351) having a hairpin-like structure is known as a precursor of "hsa-miR-4651".

The term "hsa-miR-6087 gene" or "hsa-miR-6087" used herein includes the hsa-miR-6087 gene (miRBase Accession No. MIMAT0023712) described in SEQ ID NO: 78, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 352) having a hairpin-like structure is known as a precursor of "hsa-miR-6087".

The term "hsa-miR-4665-5p gene" or "hsa-miR-4665-5p" used herein includes the hsa-miR-4665-5p gene (miRBase Accession No. MIMAT0019739) described in SEQ ID NO: 79, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 353) having a hairpin-like structure is known as a precursor of "hsa-miR-4665-5p".

The term "hsa-miR-4758-5p gene" or "hsa-miR-4758-5p" used herein includes the hsa-miR-4758-5p gene (miRBase Accession No. MIMAT0019903) described in SEQ ID NO: 80, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 354) having a hairpin-like structure is known as a precursor of "hsa-miR-4758-5p".

The term "hsa-miR-6887-5p gene" or "hsa-miR-6887-5p" used herein includes the hsa-miR-6887-5p gene (miRBase Accession No. MIMAT0027674) described in SEQ ID NO: 81, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 355) having a hairpin-like structure is known as a precursor of "hsa-miR-6887-5p".

The term "hsa-miR-3620-5p gene" or "hsa-miR-3620-5p" used herein includes the hsa-miR-3620-5p gene (miRBase Accession No. MIMAT0022967) described in SEQ ID NO: 82, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 356) having a hairpin-like structure is known as a precursor of "hsa-miR-3620-5p".

The term "hsa-miR-1909-3p gene" or "hsa-miR-1909-3p" used herein includes the hsa-miR-1909-3p gene (miRBase Accession No. MIMAT0007883) described in SEQ ID NO: 83, a homolog or an ortholog of a different organism species, and the like. The hsa-miR-1909-3p gene can be obtained by a method described in Bar M et al., 2008, Stem Cells, Vol. 26, p. 2496-2505. Also, "hsa-mir-1909" (miRBase Accession No. MI0008330, SEQ ID NO: 357) having a hairpin-like structure is known as a precursor of "hsa-miR-1909-3p".

The term "hsa-miR-7641 gene" or "hsa-miR-7641" used herein includes the hsa-miR-7641 gene (miRBase Accession No. MIMAT0029782) described in SEQ ID NO: 84, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 358 and 359) having a hairpin-like structure are known as precursors of "hsa-miR-7641".

The term "hsa-miR-6724-5p gene" or "hsa-miR-6724-5p" used herein includes the hsa-miR-6724-5p gene (miRBase Accession No. MIMAT0025856) described in SEQ ID NO: 85, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 360) having a hairpin-like structure is known as a precursor of "hsa-miR-6724-5p".

The term "hsa-miR-1343-3p gene" or "hsa-miR-1343-3p" used herein includes the hsa-miR-1343-3p gene (miRBase Accession No. MIMAT0019776) described in SEQ ID NO: 86, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 361) having a hairpin-like structure is known as a precursor of "hsa-miR-1343-3p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 87, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 362) having a hairpin-like structure is known as a precursor of "hsa-miR-6780b-5p".

The term "hsa-miR-4484 gene" or "hsa-miR-4484" used herein includes the hsa-miR-4484 gene (miRBase Accession No. MIMAT0019018) described in SEQ ID NO: 88, a homolog or an ortholog of a different organism species, and the like. The hsa-miR-4484 gene can be obtained by a method described in Jima D D et al., 2010, Blood, Vol. 116, e118-e127. Also, "hsa-mir-4484" (miRBase Accession No. MI0016845, SEQ ID NO: 363) having a hairpin-like structure is known as a precursor of "hsa-miR-4484".

The term "hsa-miR-4690-5p gene" or "hsa-miR-4690-5p" used herein includes the hsa-miR-4690-5p gene (miRBase Accession No. MIMAT0019779) described in SEQ ID NO: 89, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 364) having a hairpin-like structure is known as a precursor of "hsa-miR-4690-5p".

The term "hsa-miR4429 gene" or "hsa-miR-4429" used herein includes the hsa-miR-4429 gene (miRBase Accession No. MIMAT0018944) described in SEQ ID NO: 90, a homolog or an ortholog of a different organism species, and the like. The hsa-miR-4429 gene can be obtained by a method described in Jima D D et al., 2010, Blood, Vol. 116, e118-e127. Also, "hsa-mir-4429" (miRBase Accession No. MI0016768, SEQ ID NO: 365) having a hairpin-like structure is known as a precursor of "hsa-miR4429".

The term "hsa-miR-1227-5p gene" or "hsa-miR-1227-5p" used herein includes the hsa-miR-1227-5p gene (miRBase Accession No. MIMAT0022941) described in SEQ ID NO: 91, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 366) having a hairpin-like structure is known as a precursor of "hsa-miR-1227-5p".

The term "hsa-miR-4725-3p gene" or "hsa-miR-4725-3p" used herein includes the hsa-miR-4725-3p gene (miRBase Accession No. MIMAT0019844) described in SEQ ID NO: 92, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 367) having a hairpin-like structure is known as a precursor of "hsa-miR-4725-3p".

The term "hsa-miR-6861-5p gene" or "hsa-miR-6861-5p" used herein includes the hsa-miR-6861-5p gene (miRBase Accession No. MIMAT0027623) described in SEQ ID NO: 93, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 368) having a hairpin-like structure is known as a precursor of "hsa-miR-6861-5p".

The term "hsa-miR-6812-5p gene" or "hsa-miR-6812-5p" used herein includes the hsa-miR-6812-5p gene (miRBase Accession No. MIMAT0027524) described in SEQ ID NO: 94, a homolog or an ortholog of a different organism species, and the like. The hsa-miR-6812-5p gene can be obtained by a method described in Ladewig E et al., 2012, Genome Res, Vol. 22, p. 1634-1645. Also, "hsa-mir-6812" (miRBase Accession No. MI0022657, SEQ ID NO: 369) having a hairpin-like structure is known as a precursor of "hsa-miR-6812-5p".

The term "hsa-miR-3197 gene" or "hsa-miR-3197" used herein includes the hsa-miR-3197 gene (miRBase Accession No. MIMAT0015082) described in SEQ ID NO: 95, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No.

MI0014245, SEQ ID NO: 370) having a hairpin-like structure is known as a precursor of "hsa-miR-3197".

The term "hsa-miR-8059 gene" or "hsa-miR-8059" used herein includes the hsa-miR-8059 gene (miRBase Accession No. MIMAT0030986) described in SEQ ID NO: 96, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 371) having a hairpin-like structure is known as a precursor of "hsa-miR-8059".

The term "hsa-miR-3185 gene" or "hsa-miR-3185" used herein includes the hsa-miR-3185 gene (miRBase Accession No. MIMAT0015065) described in SEQ ID NO: 97, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 372) having a hairpin-like structure is known as a precursor of "hsa-miR-3185".

The term "hsa-miR-4706 gene" or "hsa-miR-4706" used herein includes the hsa-miR-4706 gene (miRBase Accession No. MIMAT0019806) described in SEQ ID NO: 98, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 373) having a hairpin-like structure is known as a precursor of "hsa-miR-4706".

The term "hsa-miR-4497 gene" or "hsa-miR-4497" used herein includes the hsa-miR-4497 gene (miRBase Accession No. MIMAT0019032) described in SEQ ID NO: 99, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 374) having a hairpin-like structure is known as a precursor of "hsa-miR-4497".

The term "hsa-miR-3131 gene" or "hsa-miR-3131" used herein includes the hsa-miR-3131 gene (miRBase Accession No. MIMAT0014996) described in SEQ ID NO: 100, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 375) having a hairpin-like structure is known as a precursor of "hsa-miR-3131".

The term "hsa-miR-6806-5p gene" or "hsa-miR-6806-5p" used herein includes the hsa-miR-6806-5p gene (miRBase Accession No. MIMAT0027512) described in SEQ ID NO: 101, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 376) having a hairpin-like structure is known as a precursor of "hsa-miR-6806-5p".

The term "hsa-miR-187-5p gene" or "hsa-miR-187-5p" used herein includes the hsa-miR-187-5p gene (miRBase Accession No. MIMAT0004561) described in SEQ ID NO: 102, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 377) having a hairpin-like structure is known as a precursor of "hsa-miR-187-5p".

The term "hsa-miR-3180-3p gene" or "hsa-miR-3180-3p" used herein includes the hsa-miR-3180-3p gene (miRBase Accession No. MIMAT0015058) described in SEQ ID NO: 103, a homolog or an ortholog of a different organism species, and the like. The hsa-miR-3180-3p gene can be obtained by a method described in Creighton C J et al., 2010, PLoS One, Vol. 5, e9637. Also, "hsa-mir-3180-1, hsa-mir-3180-2, and hsa-mir-3180-3" (miRBase Accession Nos. MI0014214, MI0014215, and MI0014217, SEQ ID NOs: 378, 379, and 380) having a hairpin-like structure are known as precursors of "hsa-miR-3180-3p".

The term "hsa-miR-6848-5p gene" or "hsa-miR-6848-5p" used herein includes the hsa-miR-6848-5p gene (miRBase Accession No. MIMAT0027596) described in SEQ ID NO: 104, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 381) having a hairpin-like structure is known as a precursor of "hsa-miR-6848-5p".

The term "hsa-miR-6820-5p gene" or "hsa-miR-6820-5p" used herein includes the hsa-miR-6820-5p gene (miRBase Accession No. MIMAT0027540) described in SEQ ID NO: 105, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 382) having a hairpin-like structure is known as a precursor of "hsa-miR-6820-5p".

The term "hsa-miR-6800-5p gene" or "hsa-miR-6800-5p" used herein includes the hsa-miR-6800-5p gene (miRBase Accession No. MIMAT0027500) described in SEQ ID NO: 106, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 383) having a hairpin-like structure is known as a precursor of "hsa-miR-6800-5p".

The term "hsa-miR-6717-5p gene" or "hsa-miR-6717-5p" used herein includes the hsa-miR-6717-5p gene (miRBase Accession No. MIMAT0025846) described in SEQ ID NO: 107, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 384) having a hairpin-like structure is known as a precursor of "hsa-miR-6717-5p".

The term "hsa-miR-6795-5p gene" or "hsa-miR-6795-5p" used herein includes the hsa-miR-6795-5p gene (miRBase Accession No. MIMAT0027490) described in SEQ ID NO: 108, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795" (miRBase Accession No. MI0022640, SEQ ID NO: 385) having a hairpin-like structure is known as a precursor of "hsa-miR-6795-5p".

The term "hsa-miR-4632-5p gene" or "hsa-miR-4632-5p" used herein includes the hsa-miR-4632-5p gene (miRBase Accession No. MIMAT0022977) described in SEQ ID NO: 109, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 386) having a hairpin-like structure is known as a precursor of "hsa-miR-4632-5p".

The term "hsa-miR-665 gene" or "hsa-miR-665" used herein includes the hsa-miR-665 gene (miRBase Accession No. MIMAT0004952) described in SEQ ID NO: 110, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 387) having a hairpin-like structure is known as a precursor of "hsa-miR-665".

The term "hsa-miR-6778-5p gene" or "hsa-miR-6778-5p" used herein includes the hsa-miR-6778-5p gene (miRBase Accession No. MIMAT0027456) described in SEQ ID NO: 111, a homolog or an ortholog of a different organism species, and the like. The hsa-miR-6778-5p gene can be obtained by a method described in Ladewig E et al., 2012, Genome Res, Vol. 22, p. 1634-1645. Also, "hsa-mir-6778" (miRBase Accession No. MI0022623, SEQ ID NO: 388) having a hairpin-like structure is known as a precursor of "hsa-miR-6778-5p".

The term "hsa-miR-3663-3p gene" or "hsa-miR-3663-3p" used herein includes the hsa-miR-3663-3p gene (miRBase Accession No. MIMAT0018085) described in SEQ ID NO: 112, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 389) having a hairpin-like structure is known as a precursor of "hsa-miR-3663-3p".

The term "hsa-miR-4689 gene" or "hsa-miR-4689" used herein includes the hsa-miR-4689 gene (miRBase Accession No. MIMAT0019778) described in SEQ ID NO: 113, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 390) having a hairpin-like structure is known as a precursor of "hsa-miR-4689".

The term "hsa-miR-211-3p gene" or "hsa-miR-211-3p" used herein includes the hsa-miR-211-3p gene (miRBase Accession No. MIMAT0022694) described in SEQ ID NO: 114, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 391) having a hairpin-like structure is known as a precursor of "hsa-miR-211-3p".

The term "hsa-miR-6511b-5p gene" or "hsa-miR-6511b-5p" used herein includes the hsa-miR-6511b-5p gene (miRBase Accession No. MIMAT0025847) described in SEQ ID NO: 115, a homolog or an ortholog of a different organism species, and the like. The hsa-miR-6511b-5p gene can be obtained by a method described in Li Y et al., 2012, Gene, Vol. 497, p. 330-335. Also, "hsa-mir-6511b-1 and hsa-mir-6511b-2" (miRBase Accession Nos. MI0022552 and MI0023431, SEQ ID NOs: 392 and 393) having a hairpin-like structure are known as precursors of "hsa-miR-6511b-5p".

The term "hsa-miR-4750-5p gene" or "hsa-miR-4750-5p" used herein includes the hsa-miR-4750-5p gene (miRBase Accession No. MIMAT0019887) described in SEQ ID NO: 116, a homolog or an ortholog of a different organism species, and the like. The hsa-miR-4750-5p gene can be obtained by a method described in Persson H et al., 2011, Cancer Res, Vol. 71, p. 78-86. Also, "hsa-mir-4750" (miRBase Accession No. MI0017389, SEQ ID NO: 394) having a hairpin-like structure is known as a precursor of "hsa-miR-4750-5p".

The term "hsa-miR-6126 gene" or "hsa-miR-6126" used herein includes the hsa-miR-6126 gene (miRBase Accession No. MIMAT0024599) described in SEQ ID NO: 117, a homolog or an ortholog of a different organism species, and the like. The hsa-miR-6126 gene can be obtained by a method described in Smith J L et al., 2012, J Virol. Vol. 86, p. 5278-5287. Also, "hsa-mir-6126" (miRBase Accession No. MI0021260, SEQ ID NO: 395) having a hairpin-like structure is known as a precursor of "hsa-miR-6126".

The term "hsa-miR-614 gene" or "hsa-miR-614" used herein includes the hsa-miR-614 gene (miRBase Accession No. MIMAT0003282) described in SEQ ID NO: 118, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 396) having a hairpin-like structure is known as a precursor of "hsa-miR-614".

The term "hsa-miR-7110-5p gene" or "hsa-miR-7110-5p" used herein includes the hsa-miR-7110-5p gene (miRBase Accession No. MIMAT0028117) described in SEQ ID NO: 119, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 397) having a hairpin-like structure is known as a precursor of "hsa-miR-7110-5p".

The term "hsa-miR-744-5p gene" or "hsa-miR-744-5p" used herein includes the hsa-miR-744-5p gene (miRBase Accession No. MIMAT0004945) described in SEQ ID NO: 120, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 398) having a hairpin-like structure is known as a precursor of "hsa-miR-744-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 121, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 399) having a hairpin-like structure is known as a precursor of "hsa-miR-6769a-5p".

The term "hsa-miR-4792 gene" or "hsa-miR-4792" used herein includes the hsa-miR-4792 gene (miRBase Accession No. MIMAT0019964) described in SEQ ID NO: 122, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 400) having a hairpin-like structure is known as a precursor of "hsa-miR-4792".

The term "hsa-miR-5787 gene" or "hsa-miR-5787" used herein includes the hsa-miR-5787 gene (miRBase Accession No. MIMAT0023252) described in SEQ ID NO: 123, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 401) having a hairpin-like structure is known as a precursor of "hsa-miR-5787".

The term "hsa-miR-6798-5p gene" or "hsa-miR-6798-5p" used herein includes the hsa-miR-6798-5p gene (miRBase Accession No. MIMAT0027496) described in SEQ ID NO: 124, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 402) having a hairpin-like structure is known as a precursor of "hsa-miR-6798-5p".

The term "hsa-miR-6781-5p gene" or "hsa-miR-6781-5p" used herein includes the hsa-miR-6781-5p gene (miRBase Accession No. MIMAT0027462) described in SEQ ID NO: 125, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 403) having a hairpin-like structure is known as a precursor of "hsa-miR-6781-5p".

The term "hsa-miR-4419b gene" or "hsa-miR-4419b" used herein includes the hsa-miR-4419b gene (miRBase Accession No. MIMAT0019034) described in SEQ ID NO: 126, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 404) having a hairpin-like structure is known as a precursor of "hsa-miR-4419b".

The term "hsa-miR-4446-3p gene" or "hsa-miR-4446-3p" used herein includes the hsa-miR-4446-3p gene (miRBase Accession No. MIMAT0018965) described in SEQ ID NO: 127, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 405) having a hairpin-like structure is known as a precursor of "hsa-miR-4446-3p".

The term "hsa-miR-4259 gene" or "hsa-miR-4259" used herein includes the hsa-miR-4259 gene (miRBase Accession No. MIMAT0016880) described in SEQ ID NO: 128, a homolog or an ortholog of a different organism species, and the like. The hsa-miR-4259 gene can be obtained by a method described in Goff L A et al., 2009, PLoS One, Vol. 4, e7192. Also, "hsa-mir-4259" (miRBase Accession No. MI0015858, SEQ ID NO: 406) having a hairpin-like structure is known as a precursor of "hsa-miR-4259".

The term "hsa-miR-5572 gene" or "hsa-miR-5572" used herein includes the hsa-miR-5572 gene (miRBase Accession No. MIMAT0022260) described in SEQ ID NO: 129, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 407) having a hairpin-like structure is known as a precursor of "hsa-miR-5572".

The term "hsa-miR-6075 gene" or "hsa-miR-6075" used herein includes the hsa-miR-6075 gene (miRBase Accession No. MIMAT0023700) described in SEQ ID NO: 130, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 408) having a hairpin-like structure is known as a precursor of "hsa-miR-6075".

The term "hsa-miR-296-3p gene" or "hsa-miR-296-3p" used herein includes the hsa-miR-296-3p gene (miRBase Accession No. MIMAT0004679) described in SEQ ID NO: 131, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 409) having a hairpin-like structure is known as a precursor of "hsa-miR-296-3p".

The term "hsa-miR-6891-5p gene" or "hsa-miR-6891-5p" used herein includes the hsa-miR-6891-5p gene (miRBase Accession No. MIMAT0027682) described in SEQ ID NO: 132, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 410) having a hairpin-like structure is known as a precursor of "hsa-miR-6891-5p".

The term "hsa-miR-4745-5p gene" or "hsa-miR-4745-5p" used herein includes the hsa-miR-4745-5p gene (miRBase Accession No. MIMAT0019878) described in SEQ ID NO: 133, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 411) having a hairpin-like structure is known as a precursor of "hsa-miR-4745-5p".

The term "hsa-miR-6775-5p gene" or "hsa-miR-6775-5p" used herein includes the hsa-miR-6775-5p gene (miRBase Accession No. MIMAT0027450) described in SEQ ID NO: 134, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 412) having a hairpin-like structure is known as a precursor of "hsa-miR-6775-5p".

The term "hsa-miR-6870-5p gene" or "hsa-miR-6870-5p" used herein includes the hsa-miR-6870-5p gene (miRBase Accession No. MIMAT0027640) described in SEQ ID NO: 135, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 413) having a hairpin-like structure is known as a precursor of "hsa-miR-6870-5p".

The term "hsa-miR-920 gene" or "hsa-miR-920" used herein includes the hsa-miR-920 gene (miRBase Accession No. MIMAT0004970) described in SEQ ID NO: 136, a homolog or an ortholog of a different organism species, and the like. The hsa-miR-920 gene can be obtained by a method described in Novotny G W et al., 2007, Int J Androl, Vol. 30, p. 316-326. Also, "hsa-mir-920" (miRBase Accession No. MI0005712, SEQ ID NO: 414) having a hairpin-like structure is known as a precursor of "hsa-miR-920".

The term "hsa-miR-4530 gene" or "hsa-miR-4530" used herein includes the hsa-miR-4530 gene (miRBase Accession No. MIMAT0019069) described in SEQ ID NO: 137, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 415) having a hairpin-like structure is known as a precursor of "hsa-miR-4530".

The term "hsa-miR-6819-5p gene" or "hsa-miR-6819-5p" used herein includes the hsa-miR-6819-5p gene (miRBase Accession No. MIMAT0027538) described in SEQ ID NO: 138, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 416) having a hairpin-like structure is known as a precursor of "hsa-miR-6819-5p".

The term "hsa-miR-6825-5p gene" or "hsa-miR-6825-5p" used herein includes the hsa-miR-6825-5p gene (miRBase Accession No. MIMAT0027550) described in SEQ ID NO: 139, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 417) having a hairpin-like structure is known as a precursor of "hsa-miR-6825-5p".

The term "hsa-miR-7847-3p gene" or "hsa-miR-7847-3p" used herein includes the hsa-miR-7847-3p gene (miRBase Accession No. MIMAT0030422) described in SEQ ID NO: 140, a homolog or an ortholog of a different organism species, and the like. The hsa-miR-7847-3p gene can be obtained by a method described in Pie H et al., 2012, PLoS One, Vol. 7, e50746. Also, "hsa-mir-7847" (miRBase Accession No. MI0025517, SEQ ID NO: 418) having a hairpin-like structure is known as a precursor of "hsa-miR-7847-3p".

The term "hsa-miR-6131 gene" or "hsa-miR-6131" used herein includes the hsa-miR-6131 gene (miRBase Accession No. MIMAT0024615) described in SEQ ID NO: 141, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 419) having a hairpin-like structure is known as a precursor of "hsa-miR-6131".

The term "hsa-miR-4433-3p gene" or "hsa-miR-4433-3p" used herein includes the hsa-miR-4433-3p gene (miRBase Accession No. MIMAT0018949) described in SEQ ID NO: 142, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 420) having a hairpin-like structure is known as a precursor of "hsa-miR-4433-3p".

The term "hsa-miR-1228-5p gene" or "hsa-miR-1228-5p" used herein includes the hsa-miR-1228-5p gene (miRBase Accession No. MIMAT0005582) described in SEQ ID NO: 143, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 421) having a hairpin-like structure is known as a precursor of "hsa-miR-1228-5p".

The term "hsa-miR-6743-5p gene" or "hsa-miR-6743-5p" used herein includes the hsa-miR-6743-5p gene (miRBase Accession No. MIMAT0027387) described in SEQ ID NO: 144, a homolog or an ortholog of a different organism species, and the like. The hsa-miR-6743-5p gene can be obtained by a method described in Ladewig E et al., 2012, Genome Res, Vol. 22, p. 1634-1645. Also, "hsa-mir-6743" (miRBase Accession No. MI0022588, SEQ ID NO: 422) having a hairpin-like structure is known as a precursor of "hsa-miR-6743-5p".

The term "hsa-miR-1268a gene" or "hsa-miR-1268a" used herein includes the hsa-miR-1268a gene (miRBase Accession No. MIMAT0005922) described in SEQ ID NO: 145, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 423) having a hairpin-like structure is known as a precursor of "hsa-miR-1268a".

The term "hsa-miR-3917 gene" or "hsa-miR-3917" used herein includes the hsa-miR-3917 gene (miRBase Accession No. MIMAT0018191) described in SEQ ID NO: 146, a homolog or an ortholog of a different organism species, and the like. The hsa-miR-3917 gene can be obtained by a method described in Creighton C) et al., 2010, PLoS One, Vol. 5, e9637. Also, "hsa-mir-3917" (miRBase Accession No. MI0016423, SEQ ID NO: 424) having a hairpin-like structure is known as a precursor of "hsa-miR-3917".

The term "hsa-miR-6786-5p gene" or "hsa-miR-6786-5p" used herein includes the hsa-miR-6786-5p gene (miRBase Accession No. MIMAT0027472) described in SEQ ID NO: 147, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 425) having a hairpin-like structure is known as a precursor of "hsa-miR-6786-5p".

The term "hsa-miR-3154 gene" or "hsa-miR-3154" used herein includes the hsa-miR-3154 gene (miRBase Accession No. MIMAT0015028) described in SEQ ID NO: 148, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 426) having a hairpin-like structure is known as a precursor of "hsa-miR-3154".

The term "hsa-miR-638 gene" or "hsa-miR-638" used herein includes the hsa-miR-638 gene (miRBase Accession No. MIMAT0003308) described in SEQ ID NO: 149, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 427) having a hairpin-like structure is known as a precursor of "hsa-miR-638".

The term "hsa-miR-6741-5p gene" or "hsa-miR-6741-5p" used herein includes the hsa-miR-6741-5p gene (miRBase Accession No. MIMAT0027383) described in SEQ ID NO: 150, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 428) having a hairpin-like structure is known as a precursor of "hsa-miR-6741-5p".

The term "hsa-miR-6889-5p gene" or "hsa-miR-6889-5p" used herein includes the hsa-miR-6889-5p gene (miRBase Accession No. MIMAT0027678) described in SEQ ID NO: 151, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 429) having a hairpin-like structure is known as a precursor of "hsa-miR-6889-5p".

The term "hsa-miR-6840-3p gene" or "hsa-miR-6840-3p" used herein includes the hsa-miR-6840-3p gene (miRBase Accession No. MIMAT0027583) described in SEQ ID NO: 152, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 430) having a hairpin-like structure is known as a precursor of "hsa-miR-6840-3p".

The term "hsa-miR-6510-5p gene" or "hsa-miR-6510-5p" used herein includes the hsa-miR-6510-5p gene (miRBase Accession No. MIMAT0025476) described in SEQ ID NO: 153, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 431) having a hairpin-like structure is known as a precursor of "hsa-miR-6510-5p".

The term "hsa-miR-3188 gene" or "hsa-miR-3188" used herein includes the hsa-miR-3188 gene (miRBase Accession No. MIMAT0015070) described in SEQ ID NO: 154, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 432) having a hairpin-like structure is known as a precursor of "hsa-miR-3188".

The term "hsa-miR-551b-5p gene" or "hsa-miR-551b-5p" used herein includes the hsa-miR-551b-5p gene (miRBase Accession No. MIMAT0004794) described in SEQ ID NO: 155, a homolog or an ortholog of a different organism species, and the like. The hsa-miR-551b-5p gene can be obtained by a method described in Cummins J M et al., 2006, Proc Natl Acad Sci USA, Vol. 103, p. 3687-3692. Also, "hsa-mir-551b" (miRBase Accession No. MI0003575, SEQ ID NO: 433) having a hairpin-like structure is known as a precursor of "hsa-miR-551b-5p".

The term "hsa-miR-5001-5p gene" or "hsa-miR-5001-5p" used herein includes the hsa-miR-5001-5p gene (miRBase Accession No. MIMAT0021021) described in SEQ ID NO: 156, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 434) having a hairpin-like structure is known as a precursor of "hsa-miR-5001-5p".

The term "hsa-miR-1268b gene" or "hsa-miR-1268b" used herein includes the hsa-miR-1268b gene (miRBase Accession No. MIMAT0018925) described in SEQ ID NO: 157, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 435) having a hairpin-like structure is known as a precursor of "hsa-miR-1268b".

The term "hsa-miR-7107-5p gene" or "hsa-miR-7107-5p" used herein includes the hsa-miR-7107-5p gene (miRBase Accession No. MIMAT0028111) described in SEQ ID NO: 158, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 436) having a hairpin-like structure is known as a precursor of "hsa-miR-7107-5p".

The term "hsa-miR-6824-5p gene" or "hsa-miR-6824-5p" used herein includes the hsa-miR-6824-5p gene (miRBase Accession No. MIMAT0027548) described in SEQ ID NO: 159, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 437) having a hairpin-like structure is known as a precursor of "hsa-miR-6824-5p".

The term "hsa-miR-6732-5p gene" or "hsa-miR-6732-5p" used herein includes the hsa-miR-6732-5p gene (miRBase Accession No. MIMAT0027365) described in SEQ ID NO: 160, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 438) having a hairpin-like structure is known as a precursor of "hsa-miR-6732-5p".

The term "hsa-miR-371a-5p gene" or "hsa-miR-371a-5p" used herein includes the hsa-miR-371a-5p gene (miRBase Accession No. MIMAT0004687) described in SEQ ID NO: 161, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 439) having a hairpin-like structure is known as a precursor of "hsa-miR-371a-5p".

The term "hsa-miR-6794-5p gene" or "hsa-miR-6794-5p" used herein includes the hsa-miR-6794-5p gene (miRBase Accession No. MIMAT0027488) described in SEQ ID NO: 162, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 440) having a hairpin-like structure is known as a precursor of "hsa-miR-6794-5p".

The term "hsa-miR-6779-5p gene" or "hsa-miR-6779-5p" used herein includes the hsa-miR-6779-5p gene (miRBase Accession No. MIMAT0027458) described in SEQ ID NO: 163, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 441) having a hairpin-like structure is known as a precursor of "hsa-miR-6779-5p".

The term "hsa-miR-4271 gene" or "hsa-miR-4271" used herein includes the hsa-miR-4271 gene (miRBase Accession No. MIMAT0016901) described in SEQ ID NO: 164, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 442) having a hairpin-like structure is known as a precursor of "hsa-miR-4271".

The term "hsa-miR-5195-3p gene" or "hsa-miR-5195-3p" used herein includes the hsa-miR-5195-3p gene (miRBase Accession No. MIMAT0021127) described in SEQ ID NO: 165, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 443) having a hairpin-like structure is known as a precursor of "hsa-miR-5195-3p".

The term "hsa-miR-6762-5p gene" or "hsa-miR-6762-5p" used herein includes the hsa-miR-6762-5p gene (miRBase Accession No. MIMAT0027424) described in SEQ ID NO: 166, a homolog or an ortholog of a different organism species, and the like. The hsa-miR-6762-5p gene can be obtained by a method described in Ladewig E et al., 2012, Genome Res, Vol. 22, p. 1634-1645. Also, "hsa-mir-6762" (miRBase Accession No. MI0022607, SEQ ID NO: 444) having a hairpin-like structure is known as a precursor of "hsa-miR-6762-5p".

The term "hsa-miR-939-5p gene" or "hsa-miR-939-5p" used herein includes the hsa-miR-939-5p gene (miRBase Accession No. MIMAT0004982) described in SEQ ID NO: 167, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 445) having a hairpin-like structure is known as a precursor of "hsa-miR-939-5p".

The term "hsa-miR-1247-3p gene" or "hsa-miR-1247-3p" used herein includes the hsa-miR-1247-3p gene (miRBase Accession No. MIMAT0022721) described in SEQ ID NO: 168, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 446) having a hairpin-like structure is known as a precursor of "hsa-miR-1247-3p".

The term "hsa-miR-6777-5p gene" or "hsa-miR-6777-5p" used herein includes the hsa-miR-6777-5p gene (miRBase Accession No. MIMAT0027454) described in SEQ ID NO: 169, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 447) having a hairpin-like structure is known as a precursor of "hsa-miR-6777-5p".

The term "hsa-miR-6722-3p gene" or "hsa-miR-6722-3p" used herein includes the hsa-miR-6722-3p gene (miRBase Accession No. MIMAT0025854) described in SEQ ID NO: 170, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 448) having a hairpin-like structure is known as a precursor of "hsa-miR-6722-3p".

The term "hsa-miR-3656 gene" or "hsa-miR-3656" used herein includes the hsa-miR-3656 gene (miRBase Accession No. MIMAT0018076) described in SEQ ID NO: 171, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 449) having a hairpin-like structure is known as a precursor of "hsa-miR-3656".

The term "hsa-miR-4688 gene" or "hsa-miR-4688" used herein includes the hsa-miR-4688 gene (miRBase Accession No. MIMAT0019777) described in SEQ ID NO: 172, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 450) having a hairpin-like structure is known as a precursor of "hsa-miR-4688".

The term "hsa-miR-3195 gene" or "hsa-miR-3195" used herein includes the hsa-miR-3195 gene (miRBase Accession No. MIMAT0015079) described in SEQ ID NO: 173, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 451) having a hairpin-like structure is known as a precursor of "hsa-miR-3195".

The term "hsa-miR-6766-5p gene" or "hsa-miR-6766-5p" used herein includes the hsa-miR-6766-5p gene (miRBase Accession No. MIMAT0027432) described in SEQ ID NO: 174, a homolog or an ortholog of a different organism species, and the like. The hsa-miR-6766-5p gene can be obtained by a method described in Ladewig E et al., 2012, Genome Res, Vol. 22, p. 1634-1645. Also, "hsa-mir-6766" (miRBase Accession No. MI0022611, SEQ ID NO: 452) having a hairpin-like structure is known as a precursor of "hsa-miR-6766-5p".

The term "hsa-miR-4447 gene" or "hsa-miR-4447" used herein includes the hsa-miR-4447 gene (miRBase Accession No. MIMAT0018966) described in SEQ ID NO: 175, a homolog or an ortholog of a different organism species, and the like. The hsa-miR-4447 gene can be obtained by a method described in Jima D D et al., 2010, Blood, Vol. 116, e118-e127. Also, "hsa-mir-4447" (miRBase Accession No. MI0016790, SEQ ID NO: 453) having a hairpin-like structure is known as a precursor of "hsa-miR-4447".

The term "hsa-miR-4656 gene" or "hsa-miR-4656" used herein includes the hsa-miR-4656 gene (miRBase Accession No. MIMAT0019723) described in SEQ ID NO: 176, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miRBase Accession No. MI0017284, SEQ ID NO: 454) having a hairpin-like structure is known as a precursor of "hsa-miR-4656".

The term "hsa-miR-7108-5p gene" or "hsa-miR-7108-5p" used herein includes the hsa-miR-7108-5p gene (miRBase Accession No. MIMAT0028113) described in SEQ ID NO: 177, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108"

(miRBase Accession No. MI0022959, SEQ ID NO: 455) having a hairpin-like structure is known as a precursor of "hsa-miR-7108-5p".

The term "hsa-miR-3191-3p gene" or "hsa-miR-3191-3p" used herein includes the hsa-miR-3191-3p gene (miRBase Accession No. MIMAT0015075) described in SEQ ID NO: 178, a homolog or an ortholog of a different organism species, and the like. The hsa-miR-3191-3p gene can be obtained by a method described in Stark M S et al., 2010, PLoS One, Vol. 5, e9685. Also, "hsa-mir-3191" (miRBase Accession No. MI0014236, SEQ ID NO: 456) having a hairpin-like structure is known as a precursor of "hsa-miR-3191-3p".

The term "hsa-miR-1273g-3p gene" or "hsa-miR-1273g-3p" used herein includes the hsa-miR-1273g-3p gene (miR-Base Accession No. MIMAT0022742) described in SEQ ID NO: 179, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 457) having a hairpin-like structure is known as a precursor of "hsa-miR-1273g-3p".

The term "hsa-miR-4463 gene" or "hsa-miR-4463" used herein includes the hsa-miR-4463 gene (miRBase Accession No. MIMAT0018987) described in SEQ ID NO: 180, a homolog or an ortholog of a different organism species, and the like. The hsa-miR-4463 gene can be obtained by a method described in lima D D et al., 2010, Blood, Vol. 116, e118-e127. Also, "hsa-mir-4463" (miRBase Accession No. MI0016811, SEQ ID NO: 458) having a hairpin-like structure is known as a precursor of "hsa-miR-4463".

The term "hsa-miR-2861 gene" or "hsa-miR-2861" used herein includes the hsa-miR-2861 gene (miRBase Accession No. MIMAT0013802) described in SEQ ID NO: 181, a homolog or an ortholog of a different organism species, and the like. The hsa-miR-2861 gene can be obtained by a method described in Li H et al., 2009, 1 Clin Invest, Vol. 119, p. 3666-3677. Also, "hsa-mir-2861" (miRBase Accession No. MI0013006, SEQ ID NO: 459) having a hairpin-like structure is known as a precursor of "hsa-miR-2861".

The term "hsa-miR-3196 gene" or "hsa-miR-3196" used herein includes the hsa-miR-3196 gene (miRBase Accession No. MIMAT0015080) described in SEQ ID NO: 182, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 460) having a hairpin-like structure is known as a precursor of "hsa-miR-3196".

The term "hsa-miR-6877-5p gene" or "hsa-miR-6877-5p" used herein includes the hsa-miR-6877-5p gene (miRBase Accession No. MIMAT0027654) described in SEQ ID NO: 183, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 461) having a hairpin-like structure is known as a precursor of "hsa-miR-6877-5p".

The term "hsa-miR-3679-5p gene" or "hsa-miR-3679-5p" used herein includes the hsa-miR-3679-5p gene (miRBase Accession No. MIMAT0018104) described in SEQ ID NO: 184, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 462) having a hairpin-like structure is known as a precursor of "hsa-miR-3679-5p".

The term "hsa-miR-4442 gene" or "hsa-miR-4442" used herein includes the hsa-miR-4442 gene (miRBase Accession No. MIMAT0018960) described in SEQ ID NO: 185, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 463) having a hairpin-like structure is known as a precursor of "hsa-miR-4442".

The term "hsa-miR-6789-5p gene" or "hsa-miR-6789-5p" used herein includes the hsa-miR-6789-5p gene (miRBase Accession No. MIMAT0027478) described in SEQ ID NO: 186, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 464) having a hairpin-like structure is known as a precursor of "hsa-miR-6789-5p".

The term "hsa-miR-6782-5p gene" or "hsa-miR-6782-5p" used herein includes the hsa-miR-6782-5p gene (miRBase Accession No. MIMAT0027464) described in SEQ ID NO: 187, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 465) having a hairpin-like structure is known as a precursor of "hsa-miR-6782-5p".

The term "hsa-miR-486-3p gene" or "hsa-miR-486-3p" used herein includes the hsa-miR-486-3p gene (miRBase Accession No. MIMAT0004762) described in SEQ ID NO: 188, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 466 and 467) having a hairpin-like structure are known as precursors of "hsa-miR-486-3p".

The term "hsa-miR-6085 gene" or "hsa-miR-6085" used herein includes the hsa-miR-6085 gene (miRBase Accession No. MIMAT0023710) described in SEQ ID NO: 189, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 468) having a hairpin-like structure is known as a precursor of "hsa-miR-6085".

The term "hsa-miR-4746-3p gene" or "hsa-miR-4746-3p" used herein includes the hsa-miR-4746-3p gene (miRBase Accession No. MIMAT0019881) described in SEQ ID NO: 190, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 469) having a hairpin-like structure is known as a precursor of "hsa-miR-4746-3p".

The term "hsa-miR-619-5p gene" or "hsa-miR-619-5p" used herein includes the hsa-miR-619-5p gene (miRBase Accession No. MIMAT0026622) described in SEQ ID NO: 191, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 470) having a hairpin-like structure is known as a precursor of "hsa-miR-619-5p".

The term "hsa-miR-937-5p gene" or "hsa-miR-937-5p" used herein includes the hsa-miR-937-5p gene (miRBase Accession No. MIMAT0022938) described in SEQ ID NO: 192, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 471) having a hairpin-like structure is known as a precursor of "hsa-miR-937-5p".

The term "hsa-miR-6803-5p gene" or "hsa-miR-6803-5p" used herein includes the hsa-miR-6803-5p gene (miRBase Accession No. MIMAT0027506) described in SEQ ID NO: 193, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 472) having a hairpin-like structure is known as a precursor of "hsa-miR-6803-5p".

The term "hsa-miR-4298 gene" or "hsa-miR-4298" used herein includes the hsa-miR-4298 gene (miRBase Accession No. MIMAT0016852) described in SEQ ID NO: 194, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 473) having a hairpin-like structure is known as a precursor of "hsa-miR-4298".

The term "hsa-miR-4454 gene" or "hsa-miR-4454" used herein includes the hsa-miR-4454 gene (miRBase Accession No. MIMAT0018976) described in SEQ ID NO: 195, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 474) having a hairpin-like structure is known as a precursor of "hsa-miR-4454".

The term "hsa-miR-4459 gene" or "hsa-miR-4459" used herein includes the hsa-miR-4459 gene (miRBase Accession No. MIMAT0018981) described in SEQ ID NO: 196, a homolog or an ortholog of a different organism species, and the like. The hsa-miR-4459 gene can be obtained by a method described in lima D D et al., 2010, Blood, Vol. 116, e118-e127. Also, "hsa-mir-4459" (miRBase Accession No. MI0016805, SEQ ID NO: 475) having a hairpin-like structure is known as a precursor of "hsa-miR-4459".

The term "hsa-miR-7150 gene" or "hsa-miR-7150" used herein includes the hsa-miR-7150 gene (miRBase Accession No. MIMAT0028211) described in SEQ ID NO: 197, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 476) having a hairpin-like structure is known as a precursor of "hsa-miR-7150".

The term "hsa-miR-6880-5p gene" or "hsa-miR-6880-5p" used herein includes the hsa-miR-6880-5p gene (miRBase Accession No. MIMAT0027660) described in SEQ ID NO: 198, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 477) having a hairpin-like structure is known as a precursor of "hsa-miR-6880-5p".

The term "hsa-miR-4449 gene" or "hsa-miR-4449" used herein includes the hsa-miR-4449 gene (miRBase Accession No. MIMAT0018968) described in SEQ ID NO: 199, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 478) having a hairpin-like structure is known as a precursor of "hsa-miR-4449".

The term "hsa-miR-8063 gene" or "hsa-miR-8063" used herein includes the hsa-miR-8063 gene (miRBase Accession No. MIMAT0030990) described in SEQ ID NO: 200, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 479) having a hairpin-like structure is known as a precursor of "hsa-miR-8063".

The term "hsa-miR-4695-5p gene" or "hsa-miR-4695-5p" used herein includes the hsa-miR-4695-5p gene (miRBase Accession No. MIMAT0019788) described in SEQ ID NO: 201, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 480) having a hairpin-like structure is known as a precursor of "hsa-miR-4695-5p".

The term "hsa-miR-6132 gene" or "hsa-miR-6132" used herein includes the hsa-miR-6132 gene (miRBase Accession No. MIMAT0024616) described in SEQ ID NO: 202, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 481) having a hairpin-like structure is known as a precursor of "hsa-miR-6132".

The term "hsa-miR-6829-5p gene" or "hsa-miR-6829-5p" used herein includes the hsa-miR-6829-5p gene (miRBase Accession No. MIMAT0027558) described in SEQ ID NO: 203, a homolog or an ortholog of a different organism species, and the like. The hsa-miR-6829-5p gene can be obtained by a method described in Ladewig E et al., 2012, Genome Res, Vol. 22, p. 1634-1645. Also, "hsa-mir-6829" (miRBase Accession No. MI0022674, SEQ ID NO: 482) having a hairpin-like structure is known as a precursor of "hsa-miR-6829-5p".

The term "hsa-miR-4486 gene" or "hsa-miR-4486" used herein includes the hsa-miR-4486 gene (miRBase Accession No. MIMAT0019020) described in SEQ ID NO: 204, a homolog or an ortholog of a different organism species, and the like. The hsa-miR-4486 gene can be obtained by a method described in lima D D et al., 2010, Blood, Vol. 116, e118-e127. Also, "hsa-mir-4486" (miRBase Accession No. MI0016847, SEQ ID NO: 483) having a hairpin-like structure is known as a precursor of "hsa-miR-4486".

The term "hsa-miR-6805-3p gene" or "hsa-miR-6805-3p" used herein includes the hsa-miR-6805-3p gene (miRBase Accession No. MIMAT0027511) described in SEQ ID NO: 205, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 304) having a hairpin-like structure is known as a precursor of "hsa-miR-6805-3p".

The term "hsa-miR-6826-5p gene" or "hsa-miR-6826-5p" used herein includes the hsa-miR-6826-5p gene (miRBase Accession No. MIMAT0027552) described in SEQ ID NO: 206, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 484) having a hairpin-like structure is known as a precursor of "hsa-miR-6826-5p".

The term "hsa-miR-4508 gene" or "hsa-miR-4508" used herein includes the hsa-miR-4508 gene (miRBase Accession No. MIMAT0019045) described in SEQ ID NO: 207, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 485) having a hairpin-like structure is known as a precursor of "hsa-miR-4508".

The term "hsa-miR-1343-5p gene" or "hsa-miR-1343-5p" used herein includes the hsa-miR-1343-5p gene (miRBase Accession No. MIMAT0027038) described in SEQ ID NO: 208, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 361) having a hairpin-like structure is known as a precursor of "hsa-miR-1343-5p".

The term "hsa-miR-7114-5p gene" or "hsa-miR-7114-5p" used herein includes the hsa-miR-7114-5p gene (miRBase Accession No. MIMAT0028125) described in SEQ ID NO: 209, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 486) having a hairpin-like structure is known as a precursor of "hsa-miR-7114-5p".

The term "hsa-miR-3622a-5p gene" or "hsa-miR-3622a-5p" used herein includes the hsa-miR-3622a-5p gene (miRBase Accession No. MIMAT0018003) described in SEQ ID NO: 210, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 487) having a hairpin-like structure is known as a precursor of "hsa-miR-3622a-5p".

The term "hsa-miR-6765-5p gene" or "hsa-miR-6765-5p" used herein includes the hsa-miR-6765-5p gene (miRBase Accession No. MIMAT0027430) described in SEQ ID NO: 211, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 488) having a hairpin-like structure is known as a precursor of "hsa-miR-6765-5p".

The term "hsa-miR-7845-5p gene" or "hsa-miR-7845-5p" used herein includes the hsa-miR-7845-5p gene (miRBase Accession No. MIMAT0030420) described in SEQ ID NO: 212, a homolog or an ortholog of a different organism species, and the like. The hsa-miR-7845-5p gene can be obtained by a method described in Pie H et al., 2012, PLoS One, Vol. 7, e50746. Also, "hsa-mir-7845" (miRBase Accession No. MI0025515, SEQ ID NO: 489) having a hairpin-like structure is known as a precursor of "hsa-miR-7845-5p".

The term "hsa-miR-3960 gene" or "hsa-miR-3960" used herein includes the hsa-miR-3960 gene (miRBase Accession No. MIMAT0019337) described in SEQ ID NO: 213, a homolog or an ortholog of a different organism species, and the like. The hsa-miR-3960 gene can be obtained by a method described in Hu R et al., 2011, J Biol Chem, Vol. 286, p. 12328-12339. Also, "hsa-mir-3960" (miRBase Accession No. MI0016964, SEQ ID NO: 490) having a hairpin-like structure is known as a precursor of "hsa-miR-3960".

The term "hsa-miR-6749-5p gene" or "hsa-miR-6749-5p" used herein includes the hsa-miR-6749-5p gene (miRBase Accession No. MIMAT0027398) described in SEQ ID NO: 214, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 491) having a hairpin-like structure is known as a precursor of "hsa-miR-6749-5p".

The term "hsa-miR-1260b gene" or "hsa-miR-1260b" used herein includes the hsa-miR-1260b gene (miRBase Accession No. MIMAT0015041) described in SEQ ID NO: 215, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 492) having a hairpin-like structure is known as a precursor of "hsa-miR-1260b".

The term "hsa-miR-6799-5p gene" or "hsa-miR-6799-5p" used herein includes the hsa-miR-6799-5p gene (miRBase Accession No. MIMAT0027498) described in SEQ ID NO: 216, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 493) having a hairpin-like structure is known as a precursor of "hsa-miR-6799-5p".

The term "hsa-miR-4723-5p gene" or "hsa-miR-4723-5p" used herein includes the hsa-miR-4723-5p gene (miRBase Accession No. MIMAT0019838) described in SEQ ID NO: 217, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 494) having a hairpin-like structure is known as a precursor of "hsa-miR-4723-5p".

The term "hsa-miR-6784-5p gene" or "hsa-miR-6784-5p" used herein includes the hsa-miR-6784-5p gene (miRBase Accession No. MIMAT0027468) described in SEQ ID NO: 218, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 495) having a hairpin-like structure is known as a precursor of "hsa-miR-6784-5p".

The term "hsa-miR-5100 gene" or "hsa-miR-5100" used herein includes the hsa-miR-5100 gene (miRBase Accession No. MIMAT0022259) described in SEQ ID NO: 219, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 496) having a hairpin-like structure is known as a precursor of "hsa-miR-5100".

The term "hsa-miR-6769b-5p gene" or "hsa-miR-6769b-5p" used herein includes the hsa-miR-6769b-5p gene (miRBase Accession No. MIMAT0027620) described in SEQ ID NO: 220, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 497) having a hairpin-like structure is known as a precursor of "hsa-miR-6769b-5p".

The term "hsa-miR-1207-5p gene" or "hsa-miR-1207-5p" used herein includes the hsa-miR-1207-5p gene (miRBase Accession No. MIMAT0005871) described in SEQ ID NO: 221, a homolog or an ortholog of a different organism species, and the like. The hsa-miR-1207-5p gene can be obtained by a method described in Huppi K et al., 2008, Mol Cancer Res, Vol. 6, p. 212-221. Also, "hsa-mir-1207" (miRBase Accession No. MI0006340, SEQ ID NO: 498) having a hairpin-like structure is known as a precursor of "hsa-miR-1207-5p".

The term "hsa-miR-642a-3p gene" or "hsa-miR-642a-3p" used herein includes the hsa-miR-642a-3p gene (miRBase Accession No. MIMAT0020924) described in SEQ ID NO: 222, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 499) having a hairpin-like structure is known as a precursor of "hsa-miR-642a-3p".

The term "hsa-miR-4505 gene" or "hsa-miR-4505" used herein includes the hsa-miR-4505 gene (miRBase Accession No. MIMAT0019041) described in SEQ ID NO: 223, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 500) having a hairpin-like structure is known as a precursor of "hsa-miR-4505".

The term "hsa-miR-4270 gene" or "hsa-miR-4270" used herein includes the hsa-miR-4270 gene (miRBase Accession No. MIMAT0016900) described in SEQ ID NO: 224, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 501) having a hairpin-like structure is known as a precursor of "hsa-miR-4270".

The term "hsa-miR-6721-5p gene" or "hsa-miR-6721-5p" used herein includes the hsa-miR-6721-5p gene (miRBase Accession No. MIMAT0025852) described in SEQ ID NO: 225, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 502) having a hairpin-like structure is known as a precursor of "hsa-miR-6721-5p".

The term "hsa-miR-7111-5p gene" or "hsa-miR-7111-5p" used herein includes the hsa-miR-7111-5p gene (miRBase Accession No. MIMAT0028119) described in SEQ ID NO: 226, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 503) having a hairpin-like structure is known as a precursor of "hsa-miR-7111-5p".

The term "hsa-miR-6791-5p gene" or "hsa-miR-6791-5p" used herein includes the hsa-miR-6791-5p gene (miRBase Accession No. MIMAT0027482) described in SEQ ID NO: 227, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 504) having a hairpin-like structure is known as a precursor of "hsa-miR-6791-5p".

The term "hsa-miR-7109-5p gene" or "hsa-miR-7109-5p" used herein includes the hsa-miR-7109-5p gene (miRBase Accession No. MIMAT0028115) described in SEQ ID NO: 228, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 505) having a hairpin-like structure is known as a precursor of "hsa-miR-7109-5p".

The term "hsa-miR-4258 gene" or "hsa-miR-4258" used herein includes the hsa-miR-4258 gene (miRBase Accession No. MIMAT0016879) described in SEQ ID NO: 229, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 506) having a hairpin-like structure is known as a precursor of "hsa-miR-4258".

The term "hsa-miR-6515-3p gene" or "hsa-miR-6515-3p" used herein includes the hsa-miR-6515-3p gene (miRBase Accession No. MIMAT0025487) described in SEQ ID NO: 230, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 507) having a hairpin-like structure is known as a precursor of "hsa-miR-6515-3p".

The term "hsa-miR-6851-5p gene" or "hsa-miR-6851-5p" used herein includes the hsa-miR-6851-5p gene (miRBase Accession No. MIMAT0027602) described in SEQ ID NO: 231, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 508) having a hairpin-like structure is known as a precursor of "hsa-miR-6851-5p".

The term "hsa-miR-6125 gene" or "hsa-miR-6125" used herein includes the hsa-miR-6125 gene (miRBase Accession No. MIMAT0024598) described in SEQ ID NO: 232, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 509) having a hairpin-like structure is known as a precursor of "hsa-miR-6125".

The term "hsa-miR-4749-5p gene" or "hsa-miR-4749-5p" used herein includes the hsa-miR-4749-5p gene (miRBase Accession No. MIMAT0019885) described in SEQ ID NO: 233, a homolog or an ortholog of a different organism species, and the like. The hsa-miR-4749-5p gene can be obtained by a method described in Persson H et al., 2011, Cancer Res, Vol. 71, p. 78-86. Also, "hsa-mir-4749" (miRBase Accession No. MI0017388, SEQ ID NO: 510) having a hairpin-like structure is known as a precursor of "hsa-miR-4749-5p".

The term "hsa-miR-4726-5p gene" or "hsa-miR-4726-5p" used herein includes the hsa-miR-4726-5p gene (miRBase Accession No. MIMAT0019845) described in SEQ ID NO: 234, a homolog or an ortholog of a different organism species, and the like. The hsa-miR-4726-5p gene can be obtained by a method described in Persson H et al., 2011, Cancer Res, Vol. 71, p. 78-86. Also, "hsa-mir-4726" (miRBase Accession No. MI0017363, SEQ ID NO: 511) having a hairpin-like structure is known as a precursor of "hsa-miR-4726-5p".

The term "hsa-miR-4513 gene" or "hsa-miR-4513" used herein includes the hsa-miR-4513 gene (miRBase Accession No. MIMAT0019050) described in SEQ ID NO: 235, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 512) having a hairpin-like structure is known as a precursor of "hsa-miR-4513".

The term "hsa-miR-760 gene" or "hsa-miR-760" used herein includes the hsa-miR-760 gene (miRBase Accession No. MIMAT0004957) described in SEQ ID NO: 236, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 513) having a hairpin-like structure is known as a precursor of "hsa-miR-760".

The term "hsa-miR-602 gene" or "hsa-miR-602" used herein includes the hsa-miR-602 gene (miRBase Accession No. MIMAT0003270) described in SEQ ID NO: 237, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 514) having a hairpin-like structure is known as a precursor of "hsa-miR-602".

The term "hsa-miR-423-5p gene" or "hsa-miR-423-5p" used herein includes the hsa-miR-423-5p gene (miRBase Accession No. MIMAT0004748) described in SEQ ID NO: 238, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 515) having a hairpin-like structure is known as a precursor of "hsa-miR-423-5p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 239, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 516) having a hairpin-like structure is known as a precursor of "hsa-miR-92a-2-5p".

The term "hsa-miR-16-5p gene" or "hsa-miR-16-5p" used herein includes the hsa-miR-16-5p gene (miRBase Accession No. MIMAT0000069) described in SEQ ID NO: 240, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1 and hsa-mir-16-2" (miRBase Accession Nos. MI0000070 and MI0000115, SEQ ID NOs: 517 and 518) having a hairpin-like structure are known as precursors of "hsa-miR-16-5p".

The term "hsa-miR-451a gene" or "hsa-miR-451a" used herein includes the hsa-miR-451a gene (miRBase Accession No. MIMAT0001631) described in SEQ ID NO: 241, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 519) having a hairpin-like structure is known as a precursor of "hsa-miR-451a".

The term "hsa-miR-135a-3p gene" or "hsa-miR-135a-3p" used herein includes the hsa-miR-135a-3p gene (miRBase Accession No. MIMAT0004595) described in SEQ ID NO: 242, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a" (miRBase Accession No. MI0000452, SEQ ID NO: 520) having a hairpin-like structure is known as a precursor of "hsa-miR-135a-3p".

The term "hsa-miR-486-5p gene" or "hsa-miR-486-5p" used herein includes the hsa-miR-486-5p gene (miRBase Accession No. MIMAT0002177) described in SEQ ID NO: 243, a homolog or an ortholog of a different organism species, and the like. The hsa-miR-486-5p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 466 and 467) having a hairpin-like structure are known as precursors of "hsa-miR-486-5p".

The term "hsa-miR-4257 gene" or "hsa-miR-4257" used herein includes the hsa-miR-4257 gene (miRBase Accession No. MIMAT0016878) described in SEQ ID NO: 244, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 521) having a hairpin-like structure is known as a precursor of "hsa-miR-4257".

The term "hsa-miR-92b-5p gene" or "hsa-miR-92b-5p" used herein includes the hsa-miR-92b-5p gene (miRBase Accession No. MIMAT0004792) described in SEQ ID NO: 245, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 522) having a hairpin-like structure is known as a precursor of "hsa-miR-92b-5p".

The term "hsa-miR-1915-3p gene" or "hsa-miR-1915-3p" used herein includes the hsa-miR-1915-3p gene (miRBase Accession No. MIMAT0007892) described in SEQ ID NO: 246, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 339) having a hairpin-like structure is known as a precursor of "hsa-miR-1915-3p".

The term "hsa-miR-718 gene" or "hsa-miR-718" used herein includes the hsa-miR-718 gene (miRBase Accession No. MIMAT0012735) described in SEQ ID NO: 247, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 523) having a hairpin-like structure is known as a precursor of "hsa-miR-718".

The term "hsa-miR-940 gene" or "hsa-miR-940" used herein includes the hsa-miR-940 gene (miRBase Accession No. MIMAT0004983) described in SEQ ID NO: 248, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 524) having a hairpin-like structure is known as a precursor of "hsa-miR-940".

The term "hsa-miR-296-5p gene" or "hsa-miR-296-5p" used herein includes the hsa-miR-296-5p gene (miRBase Accession No. MIMAT0000690) described in SEQ ID NO: 249, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 409) having a hairpin-like structure is known as a precursor of "hsa-miR-296-5p".

The term "hsa-miR-23b-3p gene" or "hsa-miR-23b-3p" used herein includes the hsa-miR-23b-3p gene (miRBase Accession No. MIMAT0000418) described in SEQ ID NO: 250, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 525) having a hairpin-like structure is known as a precursor of "hsa-miR-23b-3p".

The term "hsa-miR-92a-3p gene" or "hsa-miR-92a-3p" used herein includes the hsa-miR-92a-3p gene (miRBase Accession No. MIMAT0000092) described in SEQ ID NO: 251, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 526 and 527) having a hairpin-like structure are known as precursors of "hsa-miR-92a-3p".

The term "hsa-miR-658 gene" or "hsa-miR-658" used herein includes the hsa-miR-658 gene (miRBase Accession No. MIMAT0003336) described in SEQ ID NO: 252, a homolog or an ortholog of a different organism species, and the like. The hsa-miR-658 gene can be obtained by a method described in Cummins J M et al., 2006, Proc Natl Acad Sci USA, Vol. 103, p. 3687-3692. Also, "hsa-mir-658" (miRBase Accession No. MI0003682, SEQ ID NO: 528) having a hairpin-like structure is known as a precursor of "hsa-miR-658".

The term "hsa-miR-6842-5p gene" or "hsa-miR-6842-5p" used herein includes the hsa-miR-6842-5p gene (miRBase Accession No. MIMAT0027586) described in SEQ ID NO: 253, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 529) having a hairpin-like structure is known as a precursor of "hsa-miR-6842-5p".

The term "hsa-miR-6124 gene" or "hsa-miR-6124" used herein includes the hsa-miR-6124 gene (miRBase Accession No. MIMAT0024597) described in SEQ ID NO: 254, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 530) having a hairpin-like structure is known as a precursor of "hsa-miR-6124".

The term "hsa-miR-6765-3p gene" or "hsa-miR-6765-3p" used herein includes the hsa-miR-6765-3p gene (miRBase Accession No. MIMAT0027431) described in SEQ ID NO: 255, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 531) having a hairpin-like structure is known as a precursor of "hsa-miR-6765-3p".

The term "hsa-miR-7106-5p gene" or "hsa-miR-7106-5p" used herein includes the hsa-miR-7106-5p gene (miRBase Accession No. MIMAT0028109) described in SEQ ID NO: 256, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 532) having a hairpin-like structure is known as a precursor of "hsa-miR-7106-5p".

The term "hsa-miR-4534 gene" or "hsa-miR-4534" used herein includes the hsa-miR-4534 gene (miRBase Accession No. MIMAT0019073) described in SEQ ID NO: 257, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 533) having a hairpin-like structure is known as a precursor of "hsa-miR-4534".

The term "hsa-miR-92b-3p gene" or "hsa-miR-92b-3p" used herein includes the hsa-miR-92b-3p gene (miRBase Accession No. MIMAT0003218) described in SEQ ID NO: 258, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 522) having a hairpin-like structure is known as a precursor of "hsa-miR-92b-3p".

The term "hsa-miR-3135b gene" or "hsa-miR-3135b" used herein includes the hsa-miR-3135b gene (miRBase Accession No. MIMAT0018985) described in SEQ ID NO: 259, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 534) having a hairpin-like structure is known as a precursor of "hsa-miR-3135b".

The term "hsa-miR-4687-3p gene" or "hsa-miR-4687-3p" used herein includes the hsa-miR-4687-3p gene (miRBase Accession No. MIMAT0019775) described in SEQ ID NO: 260, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 535) having a hairpin-like structure is known as a precursor of "hsa-miR-4687-3p".

The term "hsa-miR-762 gene" or "hsa-miR-762" used herein includes the hsa-miR-762 gene (miRBase Accession No. MIMAT0010313) described in SEQ ID NO: 261, a homolog or an ortholog of a different organism species, and the like. The hsa-miR-762 gene can be obtained by a method described in Berezikov E et al., 2006, Genome Res, Vol. 16, p. 1289-1298. Also, "hsa-mir-762" (miRBase Accession No. MI0003892, SEQ ID NO: 536) having a hairpin-like structure is known as a precursor of "hsa-miR-762".

The term "hsa-miR-3619-3p gene" or "hsa-miR-3619-3p" used herein includes the hsa-miR-3619-3p gene (miRBase Accession No. MIMAT0019219) described in SEQ ID NO: 262, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 537) having a hairpin-like structure is known as a precursor of "hsa-miR-3619-3p".

The term "hsa-miR-4467 gene" or "hsa-miR-4467" used herein includes the hsa-miR-4467 gene (miRBase Accession No. MIMAT0018994) described in SEQ ID NO: 263, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 538) having a hairpin-like structure is known as a precursor of "hsa-miR-4467".

The term "hsa-miR-557 gene" or "hsa-miR-557" used herein includes the hsa-miR-557 gene (miRBase Accession No. MIMAT0003221) described in SEQ ID NO: 264, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 539) having a hairpin-like structure is known as a precursor of "hsa-miR-557".

The term "hsa-miR-1237-5p gene" or "hsa-miR-1237-5p" used herein includes the hsa-miR-1237-5p gene (miRBase Accession No. MIMAT0022946) described in SEQ ID NO: 265, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 540) having a hairpin-like structure is known as a precursor of "hsa-miR-1237-5p".

The term "hsa-miR-1908-5p gene" or "hsa-miR-1908-5p" used herein includes the hsa-miR-1908-5p gene (miRBase Accession No. MIMAT0007881) described in SEQ ID NO: 266, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 541) having a hairpin-like structure is known as a precursor of "hsa-miR-1908-5p".

The term "hsa-miR-4286 gene" or "hsa-miR-4286" used herein includes the hsa-miR-4286 gene (miRBase Accession No. MIMAT0016916) described in SEQ ID NO: 267, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 542) having a hairpin-like structure is known as a precursor of "hsa-miR-4286".

The term "hsa-miR-6885-5p gene" or "hsa-miR-6885-5p" used herein includes the hsa-miR-6885-5p gene (miRBase Accession No. MIMAT0027670) described in SEQ ID NO: 268, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 543) having a hairpin-like structure is known as a precursor of "hsa-miR-6885-5p".

The term "hsa-miR-6763-5p gene" or "hsa-miR-6763-5p" used herein includes the hsa-miR-6763-5p gene (miRBase Accession No. MIMAT0027426) described in SEQ ID NO: 269, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 544) having a hairpin-like structure is known as a precursor of "hsa-miR-6763-5p".

The term "hsa-miR-6089 gene" or "hsa-miR-6089" used herein includes the hsa-miR-6089 gene (miRBase Accession No. MIMAT0023714) described in SEQ ID NO: 851, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 857 and 858) having a hairpin-like structure are known as precursors of "hsa-miR-6089".

The term "hsa-miR-6816-5p gene" or "hsa-miR-6816-5p" used herein includes the hsa-miR-6816-5p gene (miRBase Accession No. MIMAT0027532) described in SEQ ID NO: 852, a homolog or an ortholog of a different organism species, and the like. The hsa-miR-6816-5p gene can be obtained by a method described in Ladewig E et al., 2012, Genome Res., Vol. 22, p. 1634-1645. Also, "hsa-mir-6816" (miRBase Accession No. MI0022661, SEQ ID NO: 859) having a hairpin-like structure is known as a precursor of "hsa-miR-6816-5p".

The term "hsa-miR-4466 gene" or "hsa-miR-4466" used herein includes the hsa-miR-4466 gene (miRBase Accession No. MIMAT0018993) described in SEQ ID NO: 853, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817, SEQ ID NO: 860) having a hairpin-like structure is known as a precursor of "hsa-miR-4466".

The term "hsa-miR-4488 gene" or "hsa-miR-4488" used herein includes the hsa-miR-4488 gene (miRBase Accession No. MIMAT0019022) described in SEQ ID NO: 854, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 861) having a hairpin-like structure is known as a precursor of "hsa-miR-4488".

The term "hsa-miR-6752-5p gene" or "hsa-miR-6752-5p" used herein includes the hsa-miR-6752-5p gene (miRBase Accession No. MIMAT0027404) described in SEQ ID NO: 855, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 862) having a hairpin-like structure is known as a precursor of "hsa-miR-6752-5p".

The term "hsa-miR-4739 gene" or "hsa-miR-4739" used herein includes the hsa-miR-4739 gene (miRBase Accession No. MIMAT0019868) described in SEQ ID NO: 856, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 863) having a hairpin-like structure is known as a precursor of "hsa-miR-4739".

A mature miRNA may become a variant due to the sequence cleaved shorter or longer by one to several upstream or downstream nucleotide(s) substitution when cleaved as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 269 and 851 to 856 as well as a large number of the nucleotide sequence variants and fragments represented by SEQ ID NOs: 545 to 850 and 864 to 871, called isomiRs. These variants can also be obtained as miRNAs that have a nucleotide sequence represented by any of SEQ ID NOs: 1 to 269 and 851 to 856. Specifically, among the variants of polynucleotides consisting of a nucleotide sequence represented by any of SEQ ID NOs: 1, 2, 3, 4, 5, 6, 8, 11, 14, 15, 19, 20, 21, 23, 27, 28, 31, 35, 37, 38, 40, 42, 43, 47, 48, 50, 51, 52, 55, 56, 58, 60, 61, 62, 64, 65, 66, 67, 71, 72, 73, 76, 77, 78, 79, 80, 82, 83, 85, 86, 88, 89, 90, 92, 95, 97, 98, 99, 100, 102, 103, 107, 109, 110, 113, 114, 115, 116, 117, 118, 120, 122, 123, 126, 127, 129, 131, 133, 137, 141, 142, 143, 145, 146, 148, 149, 153, 154, 155, 156, 157, 161, 164, 165, 167, 168, 171, 172, 173, 178, 179, 180, 181, 182, 184, 185, 188, 191, 192, 194, 195, 196, 199, 201, 202, 204, 207, 210, 213, 215, 217, 219, 222, 223, 225, 230, 232, 233, 234, 235, 236, 238, 239, 240, 241, 242, 243, 245, 246, 247, 248, 249, 250, 251, 252, 254, 258, 259, 260, 263, 265, 266, 267, 851,853, 854 and 856, or a nucleotide sequence derived from the nucleotide sequence by the replacement of u with t according to the present invention, examples of the longest variants registered in miRBase Release 20 include polynucleotides represented by SEQ ID NOs: 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, 775, 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 864, 866, 868 and 870, respectively. Also, among the variants of polynucleotides consisting of a nucleotide sequence represented by any of SEQ ID NOs: 1, 2, 3, 4, 5, 6, 8, 11, 14, 15, 19, 20, 21, 23, 27, 28, 31, 35, 37, 38, 40, 42, 43, 47, 48, 50, 51, 52, 55, 56, 58, 60, 61, 62, 64, 65, 66, 67, 71, 72, 73, 76, 77, 78, 79, 80, 82, 83, 85, 86, 88, 89, 90, 92, 95, 97, 98, 99, 100, 102, 103, 107, 109, 110, 113, 114, 115, 116, 117, 118, 120, 122, 123, 126, 127, 129, 131, 133, 137, 141, 142, 143, 145, 146, 148, 149, 153, 154, 155, 156, 157, 161, 164, 165, 167, 168, 171, 172, 173, 178, 179, 180, 181, 182, 184, 185, 188, 191, 192, 194, 195, 196, 199, 201, 202, 204, 207, 210, 213, 215, 217, 219, 222, 223, 225, 230, 232, 233, 234, 235, 236, 238, 239, 240, 241, 242, 243, 245, 246, 247, 248, 249, 250, 251, 252, 254, 258, 259, 260, 263, 265, 266, 267, 851,853, 854 and 856, or a nucleotide sequence derived from the nucleotide sequence by the replacement of u with t according to the present invention, examples of the shortest variants registered in miRBase Release 20 include polynucleotides having sequences represented by SEQ ID NOs: 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 865, 867, 869 and 871, respectively. In addition to these variants and fragments, examples thereof include a large number of isomiR polynucleotides of SEQ ID NOs: 1 to 269 and 851 to 856 registered in miRBase. Examples of the polynucleotide comprising a nucleotide sequence represented by any of SEQ ID NOs: 1 to 269 and 851 to 856 include a polynucleotide represented by any of SEQ ID NOs: 270 to 544, and 857 to 863, which are their respective precursors.

The names and miRBase Accession Nos. (registration numbers) of the genes represented by SEQ ID NOs: 1 to 871 are shown in Table 1.

The term "capable of specifically binding" used herein means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-4783-3p | MIMAT0019947 |
| 2 | hsa-miR-4730 | MIMAT0019852 |
| 3 | hsa-miR-1307-3p | MIMAT0005951 |
| 4 | hsa-miR-4634 | MIMAT0019691 |
| 5 | hsa-miR-663a | MIMAT0003326 |
| 6 | hsa-miR-4532 | MIMAT0019071 |
| 7 | hsa-miR-7704 | MIMAT0030019 |
| 8 | hsa-miR-3178 | MIMAT0015055 |
| 9 | hsa-miR-6729-5p | MIMAT0027359 |
| 10 | hsa-miR-6090 | MIMAT0023715 |
| 11 | hsa-miR-4732-5p | MIMAT0019855 |
| 12 | hsa-miR-3184-5p | MIMAT0015064 |
| 13 | hsa-miR-6727-5p | MIMAT0027355 |
| 14 | hsa-miR-6088 | MIMAT0023713 |
| 15 | hsa-miR-4674 | MIMAT0019756 |
| 16 | hsa-miR-8073 | MIMAT0031000 |
| 17 | hsa-miR-4787-5p | MIMAT0019956 |
| 18 | hsa-miR-1469 | MIMAT0007347 |
| 19 | hsa-miR-125a-3p | MIMAT0004602 |
| 20 | hsa-miR-1233-5p | MIMAT0022943 |
| 21 | hsa-miR-885-3p | MIMAT0004948 |
| 22 | hsa-miR-6802-5p | MIMAT0027504 |

TABLE 1-continued

| SEQ ID NO: | Gene name | miRBase registration No. |
|---|---|---|
| 23 | hsa-miR-328-5p | MIMAT0026486 |
| 24 | hsa-miR-6787-5p | MIMAT0027474 |
| 25 | hsa-miR-8069 | MIMAT0030996 |
| 26 | hsa-miR-6875-5p | MIMAT0027650 |
| 27 | hsa-miR-1246 | MIMAT0005898 |
| 28 | hsa-miR-4734 | MIMAT0019859 |
| 29 | hsa-miR-6757-5p | MIMAT0027414 |
| 30 | hsa-miR-6756-5p | MIMAT0027412 |
| 31 | hsa-miR-3665 | MIMAT0018087 |
| 32 | hsa-miR-6836-3p | MIMAT0027575 |
| 33 | hsa-miR-6821-5p | MIMAT0027542 |
| 34 | hsa-miR-6805-5p | MIMAT0027510 |
| 35 | hsa-miR-4728-5p | MIMAT0019849 |
| 36 | hsa-miR-6726-5p | MIMAT0027353 |
| 37 | hsa-miR-197-5p | MIMAT0022691 |
| 38 | hsa-miR-149-3p | MIMAT0004609 |
| 39 | hsa-miR-6850-5p | MIMAT0027600 |
| 40 | hsa-miR-4476 | MIMAT0019003 |
| 41 | hsa-miR-6858-5p | MIMAT0027616 |
| 42 | hsa-miR-564 | MIMAT0003228 |
| 43 | hsa-miR-4763-3p | MIMAT0019913 |
| 44 | hsa-miR-575 | MIMAT0003240 |
| 45 | hsa-miR-6771-5p | MIMAT0027442 |
| 46 | hsa-miR-1231 | MIMAT0005586 |
| 47 | hsa-miR-1908-3p | MIMAT0026916 |
| 48 | hsa-miR-150-3p | MIMAT0004610 |
| 49 | hsa-miR-3937 | MIMAT0018352 |
| 50 | hsa-miR-887-3p | MIMAT0004951 |
| 51 | hsa-miR-3940-5p | MIMAT0019229 |
| 52 | hsa-miR-4741 | MIMAT0019871 |
| 53 | hsa-miR-6808-5p | MIMAT0027516 |
| 54 | hsa-miR-6869-5p | MIMAT0027638 |
| 55 | hsa-miR-5090 | MIMAT0021082 |
| 56 | hsa-miR-615-5p | MIMAT0004804 |
| 57 | hsa-miR-8072 | MIMAT0030999 |
| 58 | hsa-miR-128-1-5p | MIMAT0026477 |
| 59 | hsa-miR-1238-5p | MIMAT0022947 |
| 60 | hsa-miR-365a-5p | MIMAT0009199 |
| 61 | hsa-miR-204-3p | MIMAT0022693 |
| 62 | hsa-miR-4492 | MIMAT0019027 |
| 63 | hsa-miR-6785-5p | MIMAT0027470 |
| 64 | hsa-miR-6511a-5p | MIMAT0025478 |
| 65 | hsa-miR-4525 | MIMAT0019064 |
| 66 | hsa-miR-1915-5p | MIMAT0007891 |
| 67 | hsa-miR-3180 | MIMAT0018178 |
| 68 | hsa-miR-6879-5p | MIMAT0027658 |
| 69 | hsa-miR-1199-5p | MIMAT0031119 |
| 70 | hsa-miR-6746-5p | MIMAT0027392 |
| 71 | hsa-miR-711 | MIMAT0012734 |
| 72 | hsa-miR-663b | MIMAT0005867 |
| 73 | hsa-miR-4707-3p | MIMAT0019808 |
| 74 | hsa-miR-6893-5p | MIMAT0027686 |
| 75 | hsa-miR-4675 | MIMAT0019757 |
| 76 | hsa-miR-4638-5p | MIMAT0019695 |
| 77 | hsa-miR-4651 | MIMAT0019715 |
| 78 | hsa-miR-6087 | MIMAT0023712 |
| 79 | hsa-miR-4665-5p | MIMAT0019739 |
| 80 | hsa-miR-4758-5p | MIMAT0019903 |
| 81 | hsa-miR-6887-5p | MIMAT0027674 |
| 82 | hsa-miR-3620-5p | MIMAT0022967 |
| 83 | hsa-miR-1909-3p | MIMAT0007883 |
| 84 | hsa-miR-7641 | MIMAT0029782 |
| 85 | hsa-miR-6724-5p | MIMAT0025856 |
| 86 | hsa-miR-1343-3p | MIMAT0019776 |
| 87 | hsa-miR-6780b-5p | MIMAT0027572 |
| 88 | hsa-miR-4484 | MIMAT0019018 |
| 89 | hsa-miR-4690-5p | MIMAT0019779 |
| 90 | hsa-miR-4429 | MIMAT0018944 |
| 91 | hsa-miR-1227-5p | MIMAT0022941 |
| 92 | hsa-miR-4725-3p | MIMAT0019844 |
| 93 | hsa-miR-6861-5p | MIMAT0027623 |
| 94 | hsa-miR-6812-5p | MIMAT0027524 |
| 95 | hsa-miR-3197 | MIMAT0015082 |
| 96 | hsa-miR-8059 | MIMAT0030986 |
| 97 | hsa-miR-3185 | MIMAT0015065 |
| 98 | hsa-miR-4706 | MIMAT0019806 |
| 99 | hsa-miR-4497 | MIMAT0019032 |
| 100 | hsa-miR-3131 | MIMAT0014996 |
| 101 | hsa-miR-6806-5p | MIMAT0027512 |
| 102 | hsa-miR-187-5p | MIMAT0004561 |
| 103 | hsa-miR-3180-3p | MIMAT0015058 |
| 104 | hsa-miR-6848-5p | MIMAT0027596 |
| 105 | hsa-miR-6820-5p | MIMAT0027540 |
| 106 | hsa-miR-6800-5p | MIMAT0027500 |
| 107 | hsa-miR-6717-5p | MIMAT0025846 |
| 108 | hsa-miR-6795-5p | MIMAT0027490 |
| 109 | hsa-miR-4632-5p | MIMAT0022977 |
| 110 | hsa-miR-665 | MIMAT0004952 |
| 111 | hsa-miR-6778-5p | MIMAT0027456 |
| 112 | hsa-miR-3663-3p | MIMAT0018085 |
| 113 | hsa-miR-4689 | MIMAT0019778 |
| 114 | hsa-miR-211-3p | MIMAT0022694 |
| 115 | hsa-miR-6511b-5p | MIMAT0025847 |
| 116 | hsa-miR-4750-5p | MIMAT0019887 |
| 117 | hsa-miR-6126 | MIMAT0024599 |
| 118 | hsa-miR-614 | MIMAT0003282 |
| 119 | hsa-miR-7110-5p | MIMAT0028117 |
| 120 | hsa-miR-744-5p | MIMAT0004945 |
| 121 | hsa-miR-6769a-5p | MIMAT0027438 |
| 122 | hsa-miR-4792 | MIMAT0019964 |
| 123 | hsa-miR-5787 | MIMAT0023252 |
| 124 | hsa-miR-6798-5p | MIMAT0027496 |
| 125 | hsa-miR-6781-5p | MIMAT0027462 |
| 126 | hsa-miR-4419b | MIMAT0019034 |
| 127 | hsa-miR-4446-3p | MIMAT0018965 |
| 128 | hsa-miR-4259 | MIMAT0016880 |
| 129 | hsa-miR-5572 | MIMAT0022260 |
| 130 | hsa-miR-6075 | MIMAT0023700 |
| 131 | hsa-miR-296-3p | MIMAT0004679 |
| 132 | hsa-miR-6891-5p | MIMAT0027682 |
| 133 | hsa-miR-4745-5p | MIMAT0019878 |
| 134 | hsa-miR-6775-5p | MIMAT0027450 |
| 135 | hsa-miR-6870-5p | MIMAT0027640 |
| 136 | hsa-miR-920 | MIMAT0004970 |
| 137 | hsa-miR-4530 | MIMAT0019069 |
| 138 | hsa-miR-6819-5p | MIMAT0027538 |
| 139 | hsa-miR-6825-5p | MIMAT0027550 |
| 140 | hsa-miR-7847-3p | MIMAT0030422 |
| 141 | hsa-miR-6131 | MIMAT0024615 |
| 142 | hsa-miR-4433-3p | MIMAT0018949 |
| 143 | hsa-miR-1228-5p | MIMAT0005582 |
| 144 | hsa-miR-6743-5p | MIMAT0027387 |
| 145 | hsa-miR-1268a | MIMAT0005922 |
| 146 | hsa-miR-3917 | MIMAT0018191 |
| 147 | hsa-miR-6786-5p | MIMAT0027472 |
| 148 | hsa-miR-3154 | MIMAT0015028 |
| 149 | hsa-miR-638 | MIMAT0003308 |
| 150 | hsa-miR-6741-5p | MIMAT0027383 |
| 151 | hsa-miR-6889-5p | MIMAT0027678 |
| 152 | hsa-miR-6840-3p | MIMAT0027583 |
| 153 | hsa-miR-6510-5p | MIMAT0025476 |
| 154 | hsa-miR-3188 | MIMAT0015070 |
| 155 | hsa-miR-551b-5p | MIMAT0004794 |
| 156 | hsa-miR-5001-5p | MIMAT0021021 |
| 157 | hsa-miR-1268b | MIMAT0018925 |
| 158 | hsa-miR-7107-5p | MIMAT0028111 |
| 159 | hsa-miR-6824-5p | MIMAT0027548 |
| 160 | hsa-miR-6732-5p | MIMAT0027365 |
| 161 | hsa-miR-371a-5p | MIMAT0004687 |
| 162 | hsa-miR-6794-5p | MIMAT0027488 |
| 163 | hsa-miR-6779-5p | MIMAT0027458 |
| 164 | hsa-miR-4271 | MIMAT0016901 |
| 165 | hsa-miR-5195-3p | MIMAT0021127 |
| 166 | hsa-miR-6762-5p | MIMAT0027424 |
| 167 | hsa-miR-939-5p | MIMAT0004982 |
| 168 | hsa-miR-1247-3p | MIMAT0022721 |
| 169 | hsa-miR-6777-5p | MIMAT0027454 |
| 170 | hsa-miR-6722-3p | MIMAT0025854 |
| 171 | hsa-miR-3656 | MIMAT0018076 |
| 172 | hsa-miR-4688 | MIMAT0019777 |
| 173 | hsa-miR-3195 | MIMAT0015079 |
| 174 | hsa-miR-6766-5p | MIMAT0027432 |
| 175 | hsa-miR-4447 | MIMAT0018966 |
| 176 | hsa-miR-4656 | MIMAT0019723 |

TABLE 1-continued

| SEQ ID NO: | Gene name | miRBase registration No. |
|---|---|---|
| 177 | hsa-miR-7108-5p | MIMAT0028113 |
| 178 | hsa-miR-3191-3p | MIMAT0015075 |
| 179 | hsa-miR-1273g-3p | MIMAT0022742 |
| 180 | hsa-miR-4463 | MIMAT0018987 |
| 181 | hsa-miR-2861 | MIMAT0013802 |
| 182 | hsa-miR-3196 | MIMAT0015080 |
| 183 | hsa-miR-6877-5p | MIMAT0027654 |
| 184 | hsa-miR-3679-5p | MIMAT0018104 |
| 185 | hsa-miR-4442 | MIMAT0018960 |
| 186 | hsa-miR-6789-5p | MIMAT0027478 |
| 187 | hsa-miR-6782-5p | MIMAT0027464 |
| 188 | hsa-miR-486-3p | MIMAT0004762 |
| 189 | hsa-miR-6085 | MIMAT0023710 |
| 190 | hsa-miR-4746-3p | MIMAT0019881 |
| 191 | hsa-miR-619-5p | MIMAT0026622 |
| 192 | hsa-miR-937-5p | MIMAT0022938 |
| 193 | hsa-miR-6803-5p | MIMAT0027506 |
| 194 | hsa-miR-4298 | MIMAT0016852 |
| 195 | hsa-miR-4454 | MIMAT0018976 |
| 196 | hsa-miR-4459 | MIMAT0018981 |
| 197 | hsa-miR-7150 | MIMAT0028211 |
| 198 | hsa-miR-6880-5p | MIMAT0027660 |
| 199 | hsa-miR-4449 | MIMAT0018968 |
| 200 | hsa-miR-8063 | MIMAT0030990 |
| 201 | hsa-miR-4695-5p | MIMAT0019788 |
| 202 | hsa-miR-6132 | MIMAT0024616 |
| 203 | hsa-miR-6829-5p | MIMAT0027558 |
| 204 | hsa-miR-4486 | MIMAT0019020 |
| 205 | hsa-miR-6805-3p | MIMAT0027511 |
| 206 | hsa-miR-6826-5p | MIMAT0027552 |
| 207 | hsa-miR-4508 | MIMAT0019045 |
| 208 | hsa-miR-1343-5p | MIMAT0027038 |
| 209 | hsa-miR-7114-5p | MIMAT0028125 |
| 210 | hsa-miR-3622a-5p | MIMAT0018003 |
| 211 | hsa-miR-6765-5p | MIMAT0027430 |
| 212 | hsa-miR-7845-5p | MIMAT0030420 |
| 213 | hsa-miR-3960 | MIMAT0019337 |
| 214 | hsa-miR-6749-5p | MIMAT0027398 |
| 215 | hsa-miR-1260b | MIMAT0015041 |
| 216 | hsa-miR-6799-5p | MIMAT0027498 |
| 217 | hsa-miR-4723-5p | MIMAT0019838 |
| 218 | hsa-miR-6784-5p | MIMAT0027468 |
| 219 | hsa-miR-5100 | MIMAT0022259 |
| 220 | hsa-miR-6769b-5p | MIMAT0027620 |
| 221 | hsa-miR-1207-5p | MIMAT0005871 |
| 222 | hsa-miR-642a-3p | MIMAT0020924 |
| 223 | hsa-miR-4505 | MIMAT0019041 |
| 224 | hsa-miR-4270 | MIMAT0016900 |
| 225 | hsa-miR-6721-5p | MIMAT0025852 |
| 226 | hsa-miR-7111-5p | MIMAT0028119 |
| 227 | hsa-miR-6791-5p | MIMAT0027482 |
| 228 | hsa-miR-7109-5p | MIMAT0028115 |
| 229 | hsa-miR-4258 | MIMAT0016879 |
| 230 | hsa-miR-6515-3p | MIMAT0025487 |
| 231 | hsa-miR-6851-5p | MIMAT0027602 |
| 232 | hsa-miR-6125 | MIMAT0024598 |
| 233 | hsa-miR-4749-5p | MIMAT0019885 |
| 234 | hsa-miR-4726-5p | MIMAT0019845 |
| 235 | hsa-miR-4513 | MIMAT0019050 |
| 236 | hsa-miR-760 | MIMAT0004957 |
| 237 | hsa-miR-602 | MIMAT0003270 |
| 238 | hsa-miR-423-5p | MIMAT0004748 |
| 239 | hsa-miR-92a-2-5p | MIMAT0004508 |
| 240 | hsa-miR-16-5p | MIMAT0000069 |
| 241 | hsa-miR-451a | MIMAT0001631 |
| 242 | hsa-miR-135a-3p | MIMAT0004595 |
| 243 | hsa-miR-486-5p | MIMAT0002177 |
| 244 | hsa-miR-4257 | MIMAT0016878 |
| 245 | hsa-miR-92b-5p | MIMAT0004792 |
| 246 | hsa-miR-1915-3p | MIMAT0007892 |
| 247 | hsa-miR-718 | MIMAT0012735 |
| 248 | hsa-miR-940 | MIMAT0004983 |
| 249 | hsa-miR-296-5p | MIMAT0000690 |
| 250 | hsa-miR-23b-3p | MIMAT0000418 |
| 251 | hsa-miR-92a-3p | MIMAT0000092 |
| 252 | hsa-miR-658 | MIMAT0003336 |
| 253 | hsa-miR-6842-5p | MIMAT0027586 |
| 254 | hsa-miR-6124 | MIMAT0024597 |
| 255 | hsa-miR-6765-3p | MIMAT0027431 |
| 256 | hsa-miR-7106-5p | MIMAT0028109 |
| 257 | hsa-miR-4534 | MIMAT0019073 |
| 258 | hsa-miR-92b-3p | MIMAT0003218 |
| 259 | hsa-miR-3135b | MIMAT0018985 |
| 260 | hsa-miR-4687-3p | MIMAT0019775 |
| 261 | hsa-miR-762 | MIMAT0010313 |
| 262 | hsa-miR-3619-3p | MIMAT0019219 |
| 263 | hsa-miR-4467 | MIMAT0018994 |
| 264 | hsa-miR-557 | MIMAT0003221 |
| 265 | hsa-miR-1237-5p | MIMAT0022946 |
| 266 | hsa-miR-1908-5p | MIMAT0007881 |
| 267 | hsa-miR-4286 | MIMAT0016916 |
| 268 | hsa-miR-6885-5p | MIMAT0027670 |
| 269 | hsa-miR-6763-5p | MIMAT0027426 |
| 270 | hsa-mir-4783 | MI0017428 |
| 271 | hsa-mir-4730 | MI0017367 |
| 272 | hsa-mir-1307 | MI0006444 |
| 273 | hsa-mir-4634 | MI0017261 |
| 274 | hsa-mir-663a | MI0003672 |
| 275 | hsa-mir-4532 | MI0016899 |
| 276 | hsa-mir-7704 | MI0025240 |
| 277 | hsa-mir-3178 | MI0014212 |
| 278 | hsa-mir-6729 | MI0022574 |
| 279 | hsa-mir-6090 | MI0020367 |
| 280 | hsa-mir-4732 | MI0017369 |
| 281 | hsa-mir-3184 | MI0014226 |
| 282 | hsa-mir-6727 | MI0022572 |
| 283 | hsa-mir-6088 | MI0020365 |
| 284 | hsa-mir-4674 | MI0017305 |
| 285 | hsa-mir-8073 | MI0025909 |
| 286 | hsa-mir-4787 | MI0017434 |
| 287 | hsa-mir-1469 | MI0007074 |
| 288 | hsa-mir-125a | MI0000469 |
| 289 | hsa-mir-1233-1 | MI0006323 |
| 290 | hsa-mir-1233-2 | MI0015973 |
| 291 | hsa-mir-885 | MI0005560 |
| 292 | hsa-mir-6802 | MI0022647 |
| 293 | hsa-mir-328 | MI0000804 |
| 294 | hsa-mir-6787 | MI0022632 |
| 295 | hsa-mir-8069 | MI0025905 |
| 296 | hsa-mir-6875 | MI0022722 |
| 297 | hsa-mir-1246 | MI0006381 |
| 298 | hsa-mir-4734 | MI0017371 |
| 299 | hsa-mir-6757 | MI0022602 |
| 300 | hsa-mir-6756 | MI0022601 |
| 301 | hsa-mir-3665 | MI0016066 |
| 302 | hsa-mir-6836 | MI0022682 |
| 303 | hsa-mir-6821 | MI0022666 |
| 304 | hsa-mir-6805 | MI0022650 |
| 305 | hsa-mir-4728 | MI0017365 |
| 306 | hsa-mir-6726 | MI0022571 |
| 307 | hsa-mir-197 | MI0000239 |
| 308 | hsa-mir-149 | MI0000478 |
| 309 | hsa-mir-6850 | MI0022696 |
| 310 | hsa-mir-4476 | MI0016828 |
| 311 | hsa-mir-6858 | MI0022704 |
| 312 | hsa-mir-564 | MI0003570 |
| 313 | hsa-mir-4763 | MI0017404 |
| 314 | hsa-mir-575 | MI0003582 |
| 315 | hsa-mir-6771 | MI0022616 |
| 316 | hsa-mir-1231 | MI0006321 |
| 317 | hsa-mir-1908 | MI0008329 |
| 318 | hsa-mir-150 | MI0000479 |
| 319 | hsa-mir-3937 | MI0016593 |
| 320 | hsa-mir-887 | MI0005562 |
| 321 | hsa-mir-3940 | MI0016597 |
| 322 | hsa-mir-4741 | MI0017379 |
| 323 | hsa-mir-6808 | MI0022653 |
| 324 | hsa-mir-6869 | MI0022716 |
| 325 | hsa-mir-5090 | MI0017979 |
| 326 | hsa-mir-615 | MI0003628 |
| 327 | hsa-mir-8072 | MI0025908 |
| 328 | hsa-mir-128-1 | MI0000447 |
| 329 | hsa-mir-1238 | MI0006328 |
| 330 | hsa-mir-365a | MI0000767 |

TABLE 1-continued

| SEQ ID NO: | Gene name | miRBase registration No. |
|---|---|---|
| 331 | hsa-mir-204 | MI0000284 |
| 332 | hsa-mir-4492 | MI0016854 |
| 333 | hsa-mir-6785 | MI0022630 |
| 334 | hsa-mir-6511a-1 | MI0022223 |
| 335 | hsa-mir-6511a-2 | MI0023564 |
| 336 | hsa-mir-6511a-3 | MI0023565 |
| 337 | hsa-mir-6511a-4 | MI0023566 |
| 338 | hsa-mir-4525 | MI0016892 |
| 339 | hsa-mir-1915 | MI0008336 |
| 340 | hsa-mir-3180-4 | MI0016408 |
| 341 | hsa-mir-3180-5 | MI0016409 |
| 342 | hsa-mir-6879 | MI0022726 |
| 343 | hsa-mir-1199 | MI0020340 |
| 344 | hsa-mir-6746 | MI0022591 |
| 345 | hsa-mir-711 | MI0012488 |
| 346 | hsa-mir-663b | MI0006336 |
| 347 | hsa-mir-4707 | MI0017340 |
| 348 | hsa-mir-6893 | MI0022740 |
| 349 | hsa-mir-4675 | MI0017306 |
| 350 | hsa-mir-4638 | MI0017265 |
| 351 | hsa-mir-4651 | MI0017279 |
| 352 | hsa-mir-6087 | MI0020364 |
| 353 | hsa-mir-4665 | MI0017295 |
| 354 | hsa-mir-4758 | MI0017399 |
| 355 | hsa-mir-6887 | MI0022734 |
| 356 | hsa-mir-3620 | MI0016011 |
| 357 | hsa-mir-1909 | MI0008330 |
| 358 | hsa-mir-7641-1 | MI0024975 |
| 359 | hsa-mir-7641-2 | MI0024976 |
| 360 | hsa-mir-6724 | MI0022559 |
| 361 | hsa-mir-1343 | MI0017320 |
| 362 | hsa-mir-6780b | MI0022681 |
| 363 | hsa-mir-4484 | MI0016845 |
| 364 | hsa-mir-4690 | MI0017323 |
| 365 | hsa-mir-4429 | MI0016768 |
| 366 | hsa-mir-1227 | MI0006316 |
| 367 | hsa-mir-4725 | MI0017362 |
| 368 | hsa-mir-6861 | MI0022708 |
| 369 | hsa-mir-6812 | MI0022657 |
| 370 | hsa-mir-3197 | MI0014245 |
| 371 | hsa-mir-8059 | MI0025895 |
| 372 | hsa-mir-3185 | MI0014227 |
| 373 | hsa-mir-4706 | MI0017339 |
| 374 | hsa-mir-4497 | MI0016859 |
| 375 | hsa-mir-3131 | MI0014151 |
| 376 | hsa-mir-6806 | MI0022651 |
| 377 | hsa-mir-187 | MI0000274 |
| 378 | hsa-mir-3180-1 | MI0014214 |
| 379 | hsa-mir-3180-2 | MI0014215 |
| 380 | hsa-mir-3180-3 | MI0014217 |
| 381 | hsa-mir-6848 | MI0022694 |
| 382 | hsa-mir-6820 | MI0022665 |
| 383 | hsa-mir-6800 | MI0022645 |
| 384 | hsa-mir-6717 | MI0022551 |
| 385 | hsa-mir-6795 | MI0022640 |
| 386 | hsa-mir-4632 | MI0017259 |
| 387 | hsa-mir-665 | MI0005563 |
| 388 | hsa-mir-6778 | MI0022623 |
| 389 | hsa-mir-3663 | MI0016064 |
| 390 | hsa-mir-4689 | MI0017322 |
| 391 | hsa-mir-211 | MI0000287 |
| 392 | hsa-mir-6511b-1 | MI0022552 |
| 393 | hsa-mir-6511b-2 | MI0023431 |
| 394 | hsa-mir-4750 | MI0017389 |
| 395 | hsa-mir-6126 | MI0021260 |
| 396 | hsa-mir-614 | MI0003627 |
| 397 | hsa-mir-7110 | MI0022961 |
| 398 | hsa-mir-744 | MI0005559 |
| 399 | hsa-mir-6769a | MI0022614 |
| 400 | hsa-mir-4792 | MI0017439 |
| 401 | hsa-mir-5787 | MI0019797 |
| 402 | hsa-mir-6798 | MI0022643 |
| 403 | hsa-mir-6781 | MI0022626 |
| 404 | hsa-mir-4419b | MI0016861 |
| 405 | hsa-mir-4446 | MI0016789 |
| 406 | hsa-mir-4259 | MI0015858 |
| 407 | hsa-mir-5572 | MI0019117 |
| 408 | hsa-mir-6075 | MI0020352 |
| 409 | hsa-mir-296 | MI0000747 |
| 410 | hsa-mir-6891 | MI0022738 |
| 411 | hsa-mir-4745 | MI0017384 |
| 412 | hsa-mir-6775 | MI0022620 |
| 413 | hsa-mir-6870 | MI0022717 |
| 414 | hsa-mir-920 | MI0005712 |
| 415 | hsa-mir-4530 | MI0016897 |
| 416 | hsa-mir-6819 | MI0022664 |
| 417 | hsa-mir-6825 | MI0022670 |
| 418 | hsa-mir-7847 | MI0025517 |
| 419 | hsa-mir-6131 | MI0021276 |
| 420 | hsa-mir-4433 | MI0016773 |
| 421 | hsa-mir-1228 | MI0006318 |
| 422 | hsa-mir-6743 | MI0022588 |
| 423 | hsa-mir-1268a | MI0006405 |
| 424 | hsa-mir-3917 | MI0016423 |
| 425 | hsa-mir-6786 | MI0022631 |
| 426 | hsa-mir-3154 | MI0014182 |
| 427 | hsa-mir-638 | MI0003653 |
| 428 | hsa-mir-6741 | MI0022586 |
| 429 | hsa-mir-6889 | MI0022736 |
| 430 | hsa-mir-6840 | MI0022686 |
| 431 | hsa-mir-6510 | MI0022222 |
| 432 | hsa-mir-3188 | MI0014232 |
| 433 | hsa-mir-551b | MI0003575 |
| 434 | hsa-mir-5001 | MI0017867 |
| 435 | hsa-mir-1268b | MI0016748 |
| 436 | hsa-mir-7107 | MI0022958 |
| 437 | hsa-mir-6824 | MI0022669 |
| 438 | hsa-mir-6732 | MI0022577 |
| 439 | hsa-mir-371a | MI0000779 |
| 440 | hsa-mir-6794 | MI0022639 |
| 441 | hsa-mir-6779 | MI0022624 |
| 442 | hsa-mir-4271 | MI0015879 |
| 443 | hsa-mir-5195 | MI0018174 |
| 444 | hsa-mir-6762 | MI0022607 |
| 445 | hsa-mir-939 | MI0005761 |
| 446 | hsa-mir-1247 | MI0006382 |
| 447 | hsa-mir-6777 | MI0022622 |
| 448 | hsa-mir-6722 | MI0022557 |
| 449 | hsa-mir-3656 | MI0016056 |
| 450 | hsa-mir-4688 | MI0017321 |
| 451 | hsa-mir-3195 | MI0014240 |
| 452 | hsa-mir-6766 | MI0022611 |
| 453 | hsa-mir-4447 | MI0016790 |
| 454 | hsa-mir-4656 | MI0017284 |
| 455 | hsa-mir-7108 | MI0022959 |
| 456 | hsa-mir-3191 | MI0014236 |
| 457 | hsa-mir-1273g | MI0018003 |
| 458 | hsa-mir-4463 | MI0016811 |
| 459 | hsa-mir-2861 | MI0013006 |
| 460 | hsa-mir-3196 | MI0014241 |
| 461 | hsa-mir-6877 | MI0022724 |
| 462 | hsa-mir-3679 | MI0016080 |
| 463 | hsa-mir-4442 | MI0016785 |
| 464 | hsa-mir-6789 | MI0022634 |
| 465 | hsa-mir-6782 | MI0022627 |
| 466 | hsa-mir-486 | MI0002470 |
| 467 | hsa-mir-486-2 | MI0023622 |
| 468 | hsa-mir-6085 | MI0020362 |
| 469 | hsa-mir-4746 | MI0017385 |
| 470 | hsa-mir-619 | MI0003633 |
| 471 | hsa-mir-937 | MI0005759 |
| 472 | hsa-mir-6803 | MI0022648 |
| 473 | hsa-mir-4298 | MI0015830 |
| 474 | hsa-mir-4454 | MI0016800 |
| 475 | hsa-mir-4459 | MI0016805 |
| 476 | hsa-mir-7150 | MI0023610 |
| 477 | hsa-mir-6880 | MI0022727 |
| 478 | hsa-mir-4449 | MI0016792 |
| 479 | hsa-mir-8063 | MI0025899 |
| 480 | hsa-mir-4695 | MI0017328 |
| 481 | hsa-mir-6132 | MI0021277 |
| 482 | hsa-mir-6829 | MI0022674 |
| 483 | hsa-mir-4486 | MI0016847 |
| 484 | hsa-mir-6826 | MI0022671 |

TABLE 1-continued

| SEQ ID NO: | Gene name | miRBase registration No. |
|---|---|---|
| 485 | hsa-mir-4508 | MI0016872 |
| 486 | hsa-mir-7114 | MI0022965 |
| 487 | hsa-mir-3622a | MI0016013 |
| 488 | hsa-mir-6765 | MI0022610 |
| 489 | hsa-mir-7845 | MI0025515 |
| 490 | hsa-mir-3960 | MI0016964 |
| 491 | hsa-mir-6749 | MI0022594 |
| 492 | hsa-mir-1260b | MI0014197 |
| 493 | hsa-mir-6799 | MI0022644 |
| 494 | hsa-mir-4723 | MI0017359 |
| 495 | hsa-mir-6784 | MI0022629 |
| 496 | hsa-mir-5100 | MI0019116 |
| 497 | hsa-mir-6769b | MI0022706 |
| 498 | hsa-mir-1207 | MI0006340 |
| 499 | hsa-mir-642a | MI0003657 |
| 500 | hsa-mir-4505 | MI0016868 |
| 501 | hsa-mir-4270 | MI0015878 |
| 502 | hsa-mir-6721 | MI0022556 |
| 503 | hsa-mir-7111 | MI0022962 |
| 504 | hsa-mir-6791 | MI0022636 |
| 505 | hsa-mir-7109 | MI0022960 |
| 506 | hsa-mir-4258 | MI0015857 |
| 507 | hsa-mir-6515 | MI0022227 |
| 508 | hsa-mir-6851 | MI0022697 |
| 509 | hsa-mir-6125 | MI0021259 |
| 510 | hsa-mir-4749 | MI0017388 |
| 511 | hsa-mir-4726 | MI0017363 |
| 512 | hsa-mir-4513 | MI0016879 |
| 513 | hsa-mir-760 | MI0005567 |
| 514 | hsa-mir-602 | MI0003615 |
| 515 | hsa-mir-423 | MI0001445 |
| 516 | hsa-mir-92a-2 | MI0000094 |
| 517 | hsa-mir-16-1 | MI0000070 |
| 518 | hsa-mir-16-2 | MI0000115 |
| 519 | hsa-mir-451a | MI0001729 |
| 520 | hsa-mir-135a | MI0000452 |
| 521 | hsa-mir-4257 | MI0015856 |
| 522 | hsa-mir-92b | MI0003560 |
| 523 | hsa-mir-718 | MI0012489 |
| 524 | hsa-mir-940 | MI0005762 |
| 525 | hsa-mir-23b | MI0000439 |
| 526 | hsa-mir-92a-1 | MI0000093 |
| 527 | hsa-mir-92a-2 | MI0000094 |
| 528 | hsa-mir-658 | MI0003682 |
| 529 | hsa-mir-6842 | MI0022688 |
| 530 | hsa-mir-6124 | MI0021258 |
| 531 | hsa-mir-6765 | MI0022610 |
| 532 | hsa-mir-7106 | MI0022957 |
| 533 | hsa-mir-4534 | MI0016901 |
| 534 | hsa-mir-3135b | MI0016809 |
| 535 | hsa-mir-4687 | MI0017319 |
| 536 | hsa-mir-762 | MI0003892 |
| 537 | hsa-mir-3619 | MI0016009 |
| 538 | hsa-mir-4467 | MI0016818 |
| 539 | hsa-mir-557 | MI0003563 |
| 540 | hsa-mir-1237 | MI0006327 |
| 541 | hsa-mir-1908 | MI0008329 |
| 542 | hsa-mir-4286 | MI0015894 |
| 543 | hsa-mir-6885 | MI0022732 |
| 544 | hsa-mir-6763 | MI0022608 |
| 545 | isomiR example 1 of SEQ ID NO: 1 | — |
| 546 | isomiR example 2 of SEQ ID NO: 1 | — |
| 547 | isomiR example 1 of SEQ ID NO: 2 | — |
| 548 | isomiR example 2 of SEQ ID NO: 2 | — |
| 549 | isomiR example 1 of SEQ ID NO: 3 | — |
| 550 | isomiR example 2 of SEQ ID NO: 3 | — |
| 551 | isomiR example 1 of SEQ ID NO: 4 | — |
| 552 | isomiR example 2 of SEQ ID NO: 4 | — |
| 553 | isomiR example 1 of SEQ ID NO: 5 | — |
| 554 | isomiR example 2 of SEQ ID NO: 5 | — |
| 555 | isomiR example 1 of SEQ ID NO: 6 | — |
| 556 | isomiR example 2 of SEQ ID NO: 6 | — |
| 557 | isomiR example 1 of SEQ ID NO: 8 | — |
| 558 | isomiR example 2 of SEQ ID NO: 8 | — |
| 559 | isomiR example 1 of SEQ ID NO: 11 | — |
| 560 | isomiR example 2 of SEQ ID NO: 11 | — |
| 561 | isomiR example 1 of SEQ ID NO: 14 | — |
| 562 | isomiR example 2 of SEQ ID NO: 14 | — |
| 563 | isomiR example 1 of SEQ ID NO: 15 | — |
| 564 | isomiR example 2 of SEQ ID NO: 15 | — |
| 565 | isomiR example 1 of SEQ ID NO: 19 | — |
| 566 | isomiR example 2 of SEQ ID NO: 19 | — |
| 567 | isomiR example 1 of SEQ ID NO: 20 | — |
| 568 | isomiR example 2 of SEQ ID NO: 20 | — |
| 569 | isomiR example 1 of SEQ ID NO: 21 | — |
| 570 | isomiR example 2 of SEQ ID NO: 21 | — |
| 571 | isomiR example 1 of SEQ ID NO: 23 | — |
| 572 | isomiR example 2 of SEQ ID NO: 23 | — |
| 573 | isomiR example 1 of SEQ ID NO: 27 | — |
| 574 | isomiR example 2 of SEQ ID NO: 27 | — |
| 575 | isomiR example 1 of SEQ ID NO: 28 | — |
| 576 | isomiR example 2 of SEQ ID NO: 28 | — |
| 577 | isomiR example 1 of SEQ ID NO: 31 | — |
| 578 | isomiR example 2 of SEQ ID NO: 31 | — |
| 579 | isomiR example 1 of SEQ ID NO: 35 | — |
| 580 | isomiR example 2 of SEQ ID NO: 35 | — |
| 581 | isomiR example 1 of SEQ ID NO: 37 | — |
| 582 | isomiR example 2 of SEQ ID NO: 37 | — |
| 583 | isomiR example 1 of SEQ ID NO: 38 | — |
| 584 | isomiR example 2 of SEQ ID NO: 38 | — |
| 585 | isomiR example 1 of SEQ ID NO: 40 | — |
| 586 | isomiR example 2 of SEQ ID NO: 40 | — |
| 587 | isomiR example 1 of SEQ ID NO: 42 | — |
| 588 | isomiR example 2 of SEQ ID NO: 42 | — |
| 589 | isomiR example 1 of SEQ ID NO: 43 | — |
| 590 | isomiR example 2 of SEQ ID NO: 43 | — |
| 591 | isomiR example 1 of SEQ ID NO: 47 | — |
| 592 | isomiR example 2 of SEQ ID NO: 47 | — |
| 593 | isomiR example 1 of SEQ ID NO: 48 | — |
| 594 | isomiR example 2 of SEQ ID NO: 48 | — |
| 595 | isomiR example 1 of SEQ ID NO: 50 | — |
| 596 | isomiR example 2 of SEQ ID NO: 50 | — |
| 597 | isomiR example 1 of SEQ ID NO: 51 | — |
| 598 | isomiR example 2 of SEQ ID NO: 51 | — |
| 599 | isomiR example 1 of SEQ ID NO: 52 | — |
| 600 | isomiR example 2 of SEQ ID NO: 52 | — |
| 601 | isomiR example 1 of SEQ ID NO: 55 | — |
| 602 | isomiR example 2 of SEQ ID NO: 55 | — |
| 603 | isomiR example 1 of SEQ ID NO: 56 | — |
| 604 | isomiR example 2 of SEQ ID NO: 56 | — |
| 605 | isomiR example 1 of SEQ ID NO: 58 | — |
| 606 | isomiR example 2 of SEQ ID NO: 58 | — |
| 607 | isomiR example 1 of SEQ ID NO: 60 | — |
| 608 | isomiR example 2 of SEQ ID NO: 60 | — |
| 609 | isomiR example 1 of SEQ ID NO: 61 | — |
| 610 | isomiR example 2 of SEQ ID NO: 61 | — |
| 611 | isomiR example 1 of SEQ ID NO: 62 | — |
| 612 | isomiR example 2 of SEQ ID NO: 62 | — |
| 613 | isomiR example 1 of SEQ ID NO: 64 | — |
| 614 | isomiR example 2 of SEQ ID NO: 64 | — |
| 615 | isomiR example 1 of SEQ ID NO: 65 | — |
| 616 | isomiR example 2 of SEQ ID NO: 65 | — |
| 617 | isomiR example 1 of SEQ ID NO: 66 | — |
| 618 | isomiR example 2 of SEQ ID NO: 66 | — |
| 619 | isomiR example 1 of SEQ ID NO: 67 | — |
| 620 | isomiR example 2 of SEQ ID NO: 67 | — |
| 621 | isomiR example 1 of SEQ ID NO: 71 | — |
| 622 | isomiR example 2 of SEQ ID NO: 71 | — |
| 623 | isomiR example 1 of SEQ ID NO: 72 | — |
| 624 | isomiR example 2 of SEQ ID NO: 72 | — |
| 625 | isomiR example 1 of SEQ ID NO: 73 | — |
| 626 | isomiR example 2 of SEQ ID NO: 73 | — |
| 627 | isomiR example 1 of SEQ ID NO: 76 | — |
| 628 | isomiR example 2 of SEQ ID NO: 76 | — |
| 629 | isomiR example 1 of SEQ ID NO: 77 | — |
| 630 | isomiR example 2 of SEQ ID NO: 77 | — |
| 631 | isomiR example 1 of SEQ ID NO: 78 | — |
| 632 | isomiR example 2 of SEQ ID NO: 78 | — |
| 633 | isomiR example 1 of SEQ ID NO: 79 | — |
| 634 | isomiR example 2 of SEQ ID NO: 79 | — |
| 635 | isomiR example 1 of SEQ ID NO: 80 | — |
| 636 | isomiR example 2 of SEQ ID NO: 80 | — |
| 637 | isomiR example 1 of SEQ ID NO: 82 | — |
| 638 | isomiR example 2 of SEQ ID NO: 82 | — |

TABLE 1-continued

| SEQ ID NO: | Gene name | miRBase registration No. |
|---|---|---|
| 639 | isomiR example 1 of SEQ ID NO: 83 | — |
| 640 | isomiR example 2 of SEQ ID NO: 83 | — |
| 641 | isomiR example 1 of SEQ ID NO: 85 | — |
| 642 | isomiR example 2 of SEQ ID NO: 85 | — |
| 643 | isomiR example 1 of SEQ ID NO: 86 | — |
| 644 | isomiR example 2 of SEQ ID NO: 86 | — |
| 645 | isomiR example 1 of SEQ ID NO: 88 | — |
| 646 | isomiR example 2 of SEQ ID NO: 88 | — |
| 647 | isomiR example 1 of SEQ ID NO: 89 | — |
| 648 | isomiR example 2 of SEQ ID NO: 89 | — |
| 649 | isomiR example 1 of SEQ ID NO: 90 | — |
| 650 | isomiR example 2 of SEQ ID NO: 90 | — |
| 651 | isomiR example 1 of SEQ ID NO: 92 | — |
| 652 | isomiR example 2 of SEQ ID NO: 92 | — |
| 653 | isomiR example 1 of SEQ ID NO: 95 | — |
| 654 | isomiR example 2 of SEQ ID NO: 95 | — |
| 655 | isomiR example 1 of SEQ ID NO: 97 | — |
| 656 | isomiR example 2 of SEQ ID NO: 97 | — |
| 657 | isomiR example 1 of SEQ ID NO: 98 | — |
| 658 | isomiR example 2 of SEQ ID NO: 98 | — |
| 659 | isomiR example 1 of SEQ ID NO: 99 | — |
| 660 | isomiR example 2 of SEQ ID NO: 99 | — |
| 661 | isomiR example 1 of SEQ ID NO: 100 | — |
| 662 | isomiR example 2 of SEQ ID NO: 100 | — |
| 663 | isomiR example 1 of SEQ ID NO: 102 | — |
| 664 | isomiR example 2 of SEQ ID NO: 102 | — |
| 665 | isomiR example 1 of SEQ ID NO: 103 | — |
| 666 | isomiR example 2 of SEQ ID NO: 103 | — |
| 667 | isomiR example 1 of SEQ ID NO: 107 | — |
| 668 | isomiR example 2 of SEQ ID NO: 107 | — |
| 669 | isomiR example 1 of SEQ ID NO: 109 | — |
| 670 | isomiR example 2 of SEQ ID NO: 109 | — |
| 671 | isomiR example 1 of SEQ ID NO: 110 | — |
| 672 | isomiR example 2 of SEQ ID NO: 110 | — |
| 673 | isomiR example 1 of SEQ ID NO: 113 | — |
| 674 | isomiR example 2 of SEQ ID NO: 113 | — |
| 675 | isomiR example 1 of SEQ ID NO: 114 | — |
| 676 | isomiR example 2 of SEQ ID NO: 114 | — |
| 677 | isomiR example 1 of SEQ ID NO: 115 | — |
| 678 | isomiR example 2 of SEQ ID NO: 115 | — |
| 679 | isomiR example 1 of SEQ ID NO: 116 | — |
| 680 | isomiR example 2 of SEQ ID NO: 116 | — |
| 681 | isomiR example 1 of SEQ ID NO: 117 | — |
| 682 | isomiR example 2 of SEQ ID NO: 117 | — |
| 683 | isomiR example 1 of SEQ ID NO: 118 | — |
| 684 | isomiR example 2 of SEQ ID NO: 118 | — |
| 685 | isomiR example 1 of SEQ ID NO: 120 | — |
| 686 | isomiR example 2 of SEQ ID NO: 120 | — |
| 687 | isomiR example 1 of SEQ ID NO: 122 | — |
| 688 | isomiR example 2 of SEQ ID NO: 122 | — |
| 689 | isomiR example 1 of SEQ ID NO: 123 | — |
| 690 | isomiR example 2 of SEQ ID NO: 123 | — |
| 691 | isomiR example 1 of SEQ ID NO: 126 | — |
| 692 | isomiR example 2 of SEQ ID NO: 126 | — |
| 693 | isomiR example 1 of SEQ ID NO: 127 | — |
| 694 | isomiR example 2 of SEQ ID NO: 127 | — |
| 695 | isomiR example 1 of SEQ ID NO: 129 | — |
| 696 | isomiR example 2 of SEQ ID NO: 129 | — |
| 697 | isomiR example 1 of SEQ ID NO: 131 | — |
| 698 | isomiR example 2 of SEQ ID NO: 131 | — |
| 699 | isomiR example 1 of SEQ ID NO: 133 | — |
| 700 | isomiR example 2 of SEQ ID NO: 133 | — |
| 701 | isomiR example 1 of SEQ ID NO: 137 | — |
| 702 | isomiR example 2 of SEQ ID NO: 137 | — |
| 703 | isomiR example 1 of SEQ ID NO: 141 | — |
| 704 | isomiR example 2 of SEQ ID NO: 141 | — |
| 705 | isomiR example 1 of SEQ ID NO: 142 | — |
| 706 | isomiR example 2 of SEQ ID NO: 142 | — |
| 707 | isomiR example 1 of SEQ ID NO: 143 | — |
| 708 | isomiR example 2 of SEQ ID NO: 143 | — |
| 709 | isomiR example 1 of SEQ ID NO: 145 | — |
| 710 | isomiR example 2 of SEQ ID NO: 145 | — |
| 711 | isomiR example 1 of SEQ ID NO: 146 | — |
| 712 | isomiR example 2 of SEQ ID NO: 146 | — |
| 713 | isomiR example 1 of SEQ ID NO: 148 | — |
| 714 | isomiR example 2 of SEQ ID NO: 148 | — |
| 715 | isomiR example 1 of SEQ ID NO: 149 | — |
| 716 | isomiR example 2 of SEQ ID NO: 149 | — |
| 717 | isomiR example 1 of SEQ ID NO: 153 | — |
| 718 | isomiR example 2 of SEQ ID NO: 153 | — |
| 719 | isomiR example 1 of SEQ ID NO: 154 | — |
| 720 | isomiR example 2 of SEQ ID NO: 154 | — |
| 721 | isomiR example 1 of SEQ ID NO: 155 | — |
| 722 | isomiR example 2 of SEQ ID NO: 155 | — |
| 723 | isomiR example 1 of SEQ ID NO: 156 | — |
| 724 | isomiR example 2 of SEQ ID NO: 156 | — |
| 725 | isomiR example 1 of SEQ ID NO: 157 | — |
| 726 | isomiR example 2 of SEQ ID NO: 157 | — |
| 727 | isomiR example 1 of SEQ ID NO: 161 | — |
| 728 | isomiR example 2 of SEQ ID NO: 161 | — |
| 729 | isomiR example 1 of SEQ ID NO: 164 | — |
| 730 | isomiR example 2 of SEQ ID NO: 164 | — |
| 731 | isomiR example 1 of SEQ ID NO: 165 | — |
| 732 | isomiR example 2 of SEQ ID NO: 165 | — |
| 733 | isomiR example 1 of SEQ ID NO: 167 | — |
| 734 | isomiR example 2 of SEQ ID NO: 167 | — |
| 735 | isomiR example 1 of SEQ ID NO: 168 | — |
| 736 | isomiR example 2 of SEQ ID NO: 168 | — |
| 737 | isomiR example 1 of SEQ ID NO: 171 | — |
| 738 | isomiR example 2 of SEQ ID NO: 171 | — |
| 739 | isomiR example 1 of SEQ ID NO: 172 | — |
| 740 | isomiR example 2 of SEQ ID NO: 172 | — |
| 741 | isomiR example 1 of SEQ ID NO: 173 | — |
| 742 | isomiR example 2 of SEQ ID NO: 173 | — |
| 743 | isomiR example 1 of SEQ ID NO: 178 | — |
| 744 | isomiR example 2 of SEQ ID NO: 178 | — |
| 745 | isomiR example 1 of SEQ ID NO: 179 | — |
| 746 | isomiR example 2 of SEQ ID NO: 179 | — |
| 747 | isomiR example 1 of SEQ ID NO: 180 | — |
| 748 | isomiR example 2 of SEQ ID NO: 180 | — |
| 749 | isomiR example 1 of SEQ ID NO: 181 | — |
| 750 | isomiR example 2 of SEQ ID NO: 181 | — |
| 751 | isomiR example 1 of SEQ ID NO: 182 | — |
| 752 | isomiR example 2 of SEQ ID NO: 182 | — |
| 753 | isomiR example 1 of SEQ ID NO: 184 | — |
| 754 | isomiR example 2 of SEQ ID NO: 184 | — |
| 755 | isomiR example 1 of SEQ ID NO: 185 | — |
| 756 | isomiR example 2 of SEQ ID NO: 185 | — |
| 757 | isomiR example 1 of SEQ ID NO: 188 | — |
| 758 | isomiR example 2 of SEQ ID NO: 188 | — |
| 759 | isomiR example 1 of SEQ ID NO: 191 | — |
| 760 | isomiR example 2 of SEQ ID NO: 191 | — |
| 761 | isomiR example 1 of SEQ ID NO: 192 | — |
| 762 | isomiR example 2 of SEQ ID NO: 192 | — |
| 763 | isomiR example 1 of SEQ ID NO: 194 | — |
| 764 | isomiR example 2 of SEQ ID NO: 194 | — |
| 765 | isomiR example 1 of SEQ ID NO: 195 | — |
| 766 | isomiR example 2 of SEQ ID NO: 195 | — |
| 767 | isomiR example 1 of SEQ ID NO: 196 | — |
| 768 | isomiR example 2 of SEQ ID NO: 196 | — |
| 769 | isomiR example 1 of SEQ ID NO: 199 | — |
| 770 | isomiR example 2 of SEQ ID NO: 199 | — |
| 771 | isomiR example 1 of SEQ ID NO: 201 | — |
| 772 | isomiR example 2 of SEQ ID NO: 201 | — |
| 773 | isomiR example 1 of SEQ ID NO: 202 | — |
| 774 | isomiR example 2 of SEQ ID NO: 202 | — |
| 775 | isomiR example 1 of SEQ ID NO: 204 | — |
| 776 | isomiR example 2 of SEQ ID NO: 204 | — |
| 777 | isomiR example 1 of SEQ ID NO: 207 | — |
| 778 | isomiR example 2 of SEQ ID NO: 207 | — |
| 779 | isomiR example 1 of SEQ ID NO: 210 | — |
| 780 | isomiR example 2 of SEQ ID NO: 210 | — |
| 781 | isomiR example 1 of SEQ ID NO: 213 | — |
| 782 | isomiR example 2 of SEQ ID NO: 213 | — |
| 783 | isomiR example 1 of SEQ ID NO: 215 | — |
| 784 | isomiR example 2 of SEQ ID NO: 215 | — |
| 785 | isomiR example 1 of SEQ ID NO: 217 | — |
| 786 | isomiR example 2 of SEQ ID NO: 217 | — |
| 787 | isomiR example 1 of SEQ ID NO: 219 | — |
| 788 | isomiR example 2 of SEQ ID NO: 219 | — |
| 789 | isomiR example 1 of SEQ ID NO: 222 | — |
| 790 | isomiR example 2 of SEQ ID NO: 222 | — |
| 791 | isomiR example 1 of SEQ ID NO: 223 | — |
| 792 | isomiR example 2 of SEQ ID NO: 223 | — |

TABLE 1-continued

| SEQ ID NO: | Gene name | miRBase registration No. |
|---|---|---|
| 793 | isomiR example 1 of SEQ ID NO: 225 | — |
| 794 | isomiR example 2 of SEQ ID NO: 225 | — |
| 795 | isomiR example 1 of SEQ ID NO: 230 | — |
| 796 | isomiR example 2 of SEQ ID NO: 230 | — |
| 797 | isomiR example 1 of SEQ ID NO: 232 | — |
| 798 | isomiR example 2 of SEQ ID NO: 232 | — |
| 799 | isomiR example 1 of SEQ ID NO: 233 | — |
| 800 | isomiR example 2 of SEQ ID NO: 233 | — |
| 801 | isomiR example 1 of SEQ ID NO: 234 | — |
| 802 | isomiR example 2 of SEQ ID NO: 234 | — |
| 803 | isomiR example 1 of SEQ ID NO: 235 | — |
| 804 | isomiR example 2 of SEQ ID NO: 235 | — |
| 805 | isomiR example 1 of SEQ ID NO: 236 | — |
| 806 | isomiR example 2 of SEQ ID NO: 236 | — |
| 807 | isomiR example 1 of SEQ ID NO: 238 | — |
| 808 | isomiR example 2 of SEQ ID NO: 238 | — |
| 809 | isomiR example 1 of SEQ ID NO: 239 | — |
| 810 | isomiR example 2 of SEQ ID NO: 239 | — |
| 811 | isomiR example 1 of SEQ ID NO: 240 | — |
| 812 | isomiR example 2 of SEQ ID NO: 240 | — |
| 813 | isomiR example 1 of SEQ ID NO: 241 | — |
| 814 | isomiR example 2 of SEQ ID NO: 241 | — |
| 815 | isomiR example 1 of SEQ ID NO: 242 | — |
| 816 | isomiR example 2 of SEQ ID NO: 242 | — |
| 817 | isomiR example 1 of SEQ ID NO: 243 | — |
| 818 | isomiR example 2 of SEQ ID NO: 243 | — |
| 819 | isomiR example 1 of SEQ ID NO: 245 | — |
| 820 | isomiR example 2 of SEQ ID NO: 245 | — |
| 821 | isomiR example 1 of SEQ ID NO: 246 | — |
| 822 | isomiR example 2 of SEQ ID NO: 246 | — |
| 823 | isomiR example 1 of SEQ ID NO: 247 | — |
| 824 | isomiR example 2 of SEQ ID NO: 247 | — |
| 825 | isomiR example 1 of SEQ ID NO: 248 | — |
| 826 | isomiR example 2 of SEQ ID NO: 248 | — |
| 827 | isomiR example 1 of SEQ ID NO: 249 | — |
| 828 | isomiR example 2 of SEQ ID NO: 249 | — |
| 829 | isomiR example 1 of SEQ ID NO: 250 | — |
| 830 | isomiR example 2 of SEQ ID NO: 250 | — |
| 831 | isomiR example 1 of SEQ ID NO: 251 | — |
| 832 | isomiR example 2 of SEQ ID NO: 251 | — |
| 833 | isomiR example 1 of SEQ ID NO: 252 | — |
| 834 | isomiR example 2 of SEQ ID NO: 252 | — |
| 835 | isomiR example 1 of SEQ ID NO: 254 | — |
| 836 | isomiR example 2 of SEQ ID NO: 254 | — |
| 837 | isomiR example 1 of SEQ ID NO: 258 | — |
| 838 | isomiR example 2 of SEQ ID NO: 258 | — |
| 839 | isomiR example 1 of SEQ ID NO: 259 | — |
| 840 | isomiR example 2 of SEQ ID NO: 259 | — |
| 841 | isomiR example 1 of SEQ ID NO: 260 | — |
| 842 | isomiR example 2 of SEQ ID NO: 260 | — |
| 843 | isomiR example 1 of SEQ ID NO: 263 | — |
| 844 | isomiR example 2 of SEQ ID NO: 263 | — |
| 845 | isomiR example 1 of SEQ ID NO: 265 | — |
| 846 | isomiR example 2 of SEQ ID NO: 265 | — |
| 847 | isomiR example 1 of SEQ ID NO: 266 | — |
| 848 | isomiR example 2 of SEQ ID NO: 266 | — |
| 849 | isomiR example 1 of SEQ ID NO: 267 | — |
| 850 | isomiR example 2 of SEQ ID NO: 267 | — |
| 851 | hsa-miR-6089 | MIMAT0023714 |
| 852 | hsa-miR-6816-5p | MIMAT0027532 |
| 853 | hsa-miR-4466 | MIMAT0018993 |
| 854 | hsa-miR-4488 | MIMAT0019022 |
| 855 | hsa-miR-6752-5p | MIMAT0027404 |
| 856 | hsa-miR-4739 | MIMAT0019868 |
| 857 | hsa-mir-6089-1 | MI0020366 |
| 858 | hsa-mir-6089-2 | MI0023563 |
| 859 | hsa-mir-6816 | MI0022661 |
| 860 | hsa-mir-4466 | MI0016817 |
| 861 | hsa-mir-4488 | MI0016849 |
| 862 | hsa-mir-6752 | MI0022597 |
| 863 | hsa-mir-4739 | MI0017377 |
| 864 | isomiR example 1 of SEQ ID NO: 851 | — |
| 865 | isomiR example 2 of SEQ ID NO: 851 | — |
| 866 | isomiR example 1 of SEQ ID NO: 853 | — |
| 867 | isomiR example 2 of SEQ ID NO: 853 | — |
| 868 | isomiR example 1 of SEQ ID NO: 854 | — |
| 869 | isomiR example 2 of SEQ ID NO: 854 | — |
| 870 | isomiR example 1 of SEQ ID NO: 856 | — |
| 871 | isomiR example 2 of SEQ ID NO: 856 | — |

The present specification encompasses the contents described in the specifications and/or drawings of Japanese Patent Application No. 2014-122672 and No. 2015-069321 from which the present application claims priorities.

Advantageous Effect of Invention

According to the present invention, breast cancer can be detected easily and in high accuracy. For example, the presence or absence of breast cancer in patients can be easily detected by using, as indicators, the measurement values of several miRNAs in bloods, sera, and/or plasmas of the patients, which can be collected with limitedly invasiveness.

DESCRIPTION OF EMBODIMENTS

Figure 1:
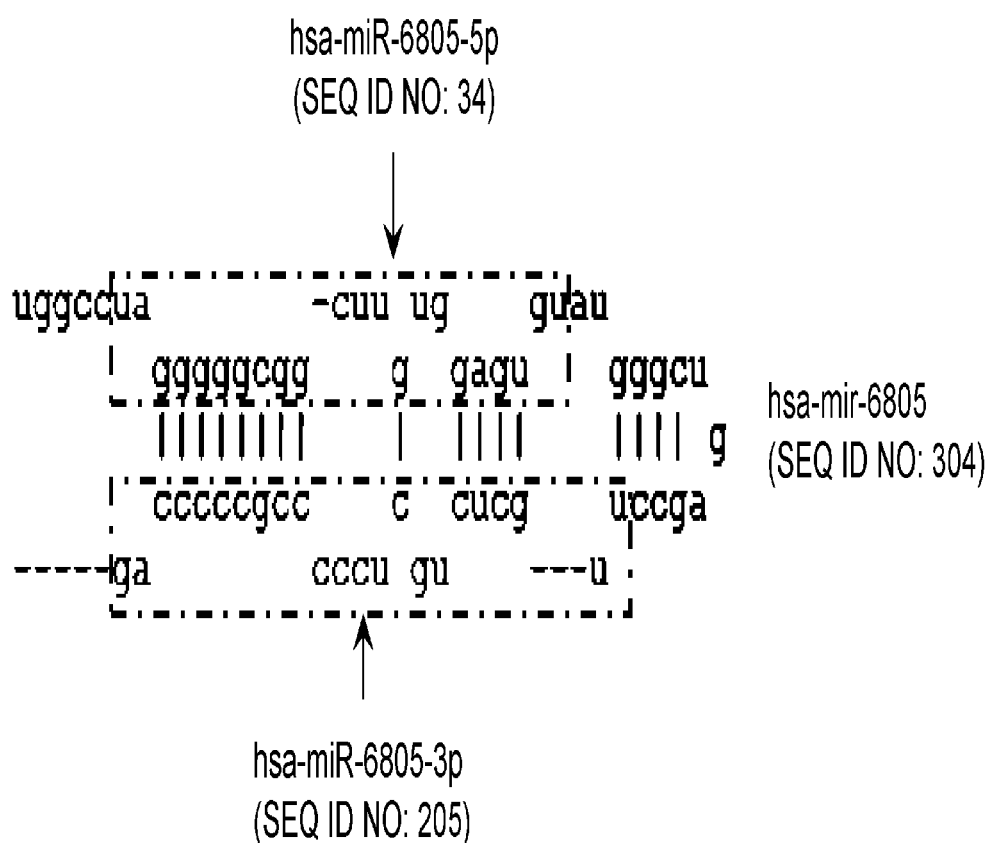
FIG. 1 This figure shows the relationship between the nucleotide sequences of hsa-miR-6805-5p represented by SEQ ID NO: 34 and hsa-miR-6805-3p represented by SEQ ID NO: 205, which are produced from a precursor hsa-mir-6805 represented by SEQ ID NO: 304.

Hereinafter, the present invention will be further described in detail.

1. Target Nucleic Acid for Breast Cancer

Primary target nucleic acids as breast cancer markers for detecting the presence and/or absence of breast cancer or breast cancer cells using the nucleic acid probes or the primers for the detection of breast cancer defined above according to the present invention, at least one miRNA selected from the group consisting of the following miR-NAs: hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p and hsa-miR-4739 can be used. Furthermore, at least one miRNA selected from the group consisting of the following other breast cancer markers that can be combined with these miRNAs, i.e., hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p and hsa-miR-92a-3p can also be preferably used as a target nucleic acid. Moreover, at least one miRNA selected from the group consisting of the following other breast cancer markers that can be combined with these miRNAs, i.e., hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p can also be preferably used as target nucleic acids.

These miRNAs include, for example, a human gene comprising a nucleotide sequence represented by any of SEQ ID NOs: 1 to 269, and 851 to 856 (i.e., hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p, hsa-miR-4739, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p, hsa-miR-92a-3p, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p, respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 871 or a transcript thereof, more preferably the transcript, i.e., a miRNA or its precursor RNA (pri-miRNA or pre-miRNA).

The first target gene is the hsa-miR-4783-3p gene, a congener thereof, a transcript thereof, or a variant or a derivative thereof. None of the previously known reports show that change in the expression of the gene or the transcript thereof can serve as a marker for breast cancer.

The second target gene is the hsa-miR-4730 gene, a congener thereof, a transcript thereof, or a variant or a derivative thereof. None of the previously known reports show that change in the expression of the gene or the transcript thereof can serve as a marker for breast cancer.

The third target gene is the hsa-miR-1307-3p gene, a congener thereof, a transcript thereof, or a variant or a derivative thereof. None of the previously known reports show that change in the expression of the gene or the transcript thereof can serve as a marker for breast cancer.

The fourth target gene is the hsa-miR-4634 gene, a congener thereof, a transcript thereof, or a variant or a derivative thereof. None of the previously known reports show that change in the expression of the gene or the transcript thereof can serve as a marker for breast cancer.

The fifth target gene is the hsa-miR-663a gene, a congener thereof, a transcript thereof, or a variant or a derivative thereof. None of the previously known reports show that change in the expression of the gene or the transcript thereof can serve as a marker for breast cancer.

The sixth target gene is the hsa-miR-4532 gene, a congener thereof, a transcript thereof, or a variant or a derivative thereof. None of the previously known reports show that change in the expression of the gene or the transcript thereof can serve as a marker for breast cancer.

The seventh target gene is the hsa-miR-7704 gene, a congener thereof, a transcript thereof, or a variant or a derivative thereof. None of the previously known reports show that change in the expression of the gene or the transcript thereof can serve as a marker for breast cancer.

The eighth target gene is the hsa-miR-3178 gene, a congener thereof, a transcript thereof, or a variant or a derivative thereof. None of the previously known reports show that change in the expression of the gene or the transcript thereof can serve as a marker for breast cancer.

The ninth target gene is the hsa-miR-6729-5p gene, a congener thereof, a transcript thereof, or a variant or a derivative thereof. None of the previously known reports show that change in the expression of the gene or the transcript thereof can serve as a marker for breast cancer.

The 10th target gene is the hsa-miR-6090 gene, a congener thereof, a transcript thereof, or a variant or a derivative thereof. None of the previously known reports show that change in the expression of the gene or the transcript thereof can serve as a marker for breast cancer.

The 11th target gene is the hsa-miR-4732-5p gene, a congener thereof, a transcript thereof, or a variant or a derivative thereof. None of the previously known reports show that change in the expression of the gene or the transcript thereof can serve as a marker for breast cancer.

The 12th target gene is the hsa-miR-3184-5p gene, a congener thereof, a transcript thereof, or a variant or a derivative thereof. None of the previously known reports show that change in the expression of the gene or the transcript thereof can serve as a marker for breast cancer.

The 13th target gene is the hsa-miR-6727-5p gene, a congener thereof, a transcript thereof, or a variant or a derivative thereof. None of the previously known reports show that change in the expression of the gene or the transcript thereof can serve as a marker for breast cancer.

The 14th target gene is the hsa-miR-6088 gene, a congener thereof, a transcript thereof, or a variant or a derivative thereof. None of the previously known reports show that change in the expression of the gene or the transcript thereof can serve as a marker for breast cancer.

The 15th target gene is the hsa-miR-4674 gene, a congener thereof, a transcript thereof, or a variant or a derivative thereof. None of the previously known reports show that change in the expression of the gene or the transcript thereof can serve as a marker for breast cancer.

The 16th target gene is the hsa-miR-8073 gene, a congener thereof, a transcript thereof, or a variant or a derivative thereof. None of the previously known reports show that change in the expression of the gene or the transcript thereof can serve as a marker for breast cancer.

The 17th target gene is the hsa-miR-4787-5p gene, a congener thereof, a transcript thereof, or a variant or a derivative thereof. None of the previously known reports show that change in the expression of the gene or the transcript thereof can serve as a marker for breast cancer.

The 18th target gene is the hsa-miR-1469 gene, a congener thereof, a transcript thereof, or a variant or a derivative thereof. None of the previously known reports show that change in the expression of the gene or the transcript thereof can serve as a marker for breast cancer.

The 19th target gene is the hsa-miR-125a-3p gene, a congener thereof, a transcript thereof, or a variant or a derivative thereof. None of the previously known reports show that change in the expression of the gene or the transcript thereof can serve as a marker for breast cancer.

The 20th target gene is the hsa-miR-1233-5p gene, a congener thereof, a transcript thereof, or a variant or a derivative thereof. None of the previously known reports show that change in the expression of the gene or the transcript thereof can serve as a marker for breast cancer.

The 21st target gene is the hsa-miR-885-3p gene, a congener thereof, a transcript thereof, or a variant or a derivative thereof. None of the previously known reports show that change in the expression of the gene or the transcript thereof can serve as a marker for breast cancer.

The 22nd target gene is the hsa-miR-6802-5p gene, a congener thereof, a transcript thereof, or a variant or a derivative thereof. None of the previously known reports show that change in the expression of the gene or the transcript thereof can serve as a marker for breast cancer.

The 23rd target gene is the hsa-miR-328-5p gene, a congener thereof, a transcript thereof, or a variant or a derivative thereof. None of the previously known reports show that change in the expression of the gene or the transcript thereof can serve as a marker for breast cancer.

The 24th target gene is the hsa-miR-6787-5p gene, a congener thereof, a transcript thereof, or a variant or a derivative thereof. None of the previously known reports show that change in the expression of the gene or the transcript thereof can serve as a marker for breast cancer.

The 25th target gene is the hsa-miR-8069 gene, a congener thereof, a transcript thereof, or a variant or a derivative thereof. None of the previously known reports show that change in the expression of the gene or the transcript thereof can serve as a marker for breast cancer.

The 26th target gene is the hsa-miR-6875-5p gene, a congener thereof, a transcript thereof, or a variant or a derivative thereof. None of the previously known reports show that change in the expression of the gene or the transcript thereof can serve as a marker for breast cancer.

The 27th target gene is the hsa-miR-1246 gene, a congener thereof, a transcript thereof, or a variant or a derivative thereof. None of the previously known reports show that change in the expression of the gene or the transcript thereof can serve as a marker for breast cancer.

The 28th target gene is the hsa-miR-4734 gene, a congener thereof, a transcript thereof, or a variant or a derivative thereof. None of the previously known reports show that change in the expression of the gene or the transcript thereof can serve as a marker for breast cancer.

The 29th target gene is the hsa-miR-6757-5p gene, a congener thereof, a transcript thereof, or a variant or a derivative thereof. None of the previously known reports show that change in the expression of the gene or the transcript thereof can serve as a marker The 30th target gene is the hsa-miR-6756-5p gene, a congener thereof, a transcript thereof, or a variant or a derivative thereof. None of the previously known reports show that change in the expression of the gene or the transcript thereof can serve as a marker for breast cancer.

The 31st target gene is the hsa-miR-3665 gene, a congener thereof, a transcript thereof, or a variant or a derivative thereof. None of the previously known reports show that change in the expression of the gene or the transcript thereof can serve as a marker for breast cancer.

The 32nd target gene is the hsa-miR-6836-3p gene, a congener thereof, a transcript thereof, or a variant or a derivative thereof. None of the previously known reports show that change in the expression of the gene or the transcript thereof can serve as a marker for breast cancer.

The 33rd target gene is the hsa-miR-6821-5p gene, a congener thereof, a transcript thereof, or a variant or a derivative thereof. None of the previously known reports show that change in the expression of the gene or the transcript thereof can serve as a marker for breast cancer.

The 34th target gene is the hsa-miR-6805-5p gene, a congener thereof, a transcript thereof, or a variant or a derivative thereof. None of the previously known reports show that change in the expression of the gene or the transcript thereof can serve as a marker for breast cancer.

The 35th target gene is the hsa-miR-4728-5p gene, a congener thereof, a transcript thereof, or a variant or a derivative thereof. None of the previously known reports show that change in the expression of the gene or the transcript thereof can serve as a marker for breast cancer.

The 36th target gene is the hsa-miR-6726-5p gene, a congener thereof, a transcript thereof, or a variant or a derivative thereof. None of the previously known reports show that change in the expression of the gene or the transcript thereof can serve as a marker for breast cancer.

The 37th target gene is the hsa-miR-197-5p gene, a congener thereof, a transcript thereof, or a variant or a derivative thereof. None of the previously known reports show that change in the expression of the gene or the transcript thereof can serve as a marker for breast cancer.

The 38th target gene is the hsa-miR-149-3p gene, a congener thereof, a transcript thereof, or a variant or a derivative thereof. None of the previously known reports show that change in the expression of the gene or the transcript thereof can serve as a marker for breast cancer.

The 39th target gene is the hsa-miR-6850-5p gene, a congener thereof, a transcript thereof, or a variant or a derivative thereof. None of the previously known reports show that change in the expression of the gene or the transcript thereof can serve as a marker for breast cancer.

The 40th target gene is the hsa-miR-4476 gene, a congener thereof, a transcript thereof, or a variant or a derivative thereof. None of the previously known reports show that change in the expression of the gene or the transcript thereof can serve as a marker for breast cancer.

The 41st target gene is the hsa-miR-6858-5p gene, a congener thereof, a transcript thereof, or a variant or a derivative thereof. None of the previously known reports show that change in the expression of the gene or the transcript thereof can serve as a marker for breast cancer.

The 42nd target gene is the hsa-miR-564 gene, a congener thereof, a transcript thereof, or a variant or a derivative thereof. None of the previously known reports show that change in the expression of the gene or the transcript thereof can serve as a marker for breast cancer.

The 43rd target gene is the hsa-miR-4763-3p gene, a congener thereof, a transcript thereof, or a variant or a derivative thereof. None of the previously known reports show that change in the expression of the gene or the transcript thereof can serve as a marker for breast cancer.

The 44th target gene is the hsa-miR-575 gene, a congener thereof, a transcript thereof, or a variant or a derivative thereof. None of the previously known reports show that change in the expression of the gene or the transcript thereof can serve as a marker for breast cancer.

The 45th target gene is the hsa-miR-6771-5p gene, a congener thereof, a transcript thereof, or a variant or a derivative thereof. None of the previously known reports show that change in the expression of the gene or the transcript thereof can serve as a marker for breast cancer.

The 46th target gene is the hsa-miR-1231 gene, a congener thereof, a transcript thereof, or a variant or a derivative thereof. None of the previously known reports show that change in the expression of the gene or the transcript thereof can serve as a marker for breast cancer.

The 47th target gene is the hsa-miR-1908-3p gene, a congener thereof, a transcript thereof, or a variant or a derivative thereof. None of the previously known reports show that change in the expression of the gene or the transcript thereof can serve as a marker for breast cancer.

The 48th target gene is the hsa-miR-150-3p gene, a congener thereof, a transcript thereof, or a variant or a derivative thereof. None of the previously known reports show that change in the expression of the gene or the transcript thereof can serve as a marker for breast cancer.

The 49th target gene is the hsa-miR-3937 gene, a congener thereof, a transcript thereof, or a variant or a derivative thereof. None of the previously known reports show that change in the expression of the gene or the transcript thereof can serve as a marker for breast cancer.

The 50th target gene is the hsa-miR-887-3p gene, a congener thereof, a transcript thereof, or a variant or a derivative thereof. None of the previously known reports show that change in the expression of the gene or the transcript thereof can serve as a marker for breast cancer.

The 51st target gene is the hsa-miR-3940-5p gene, a congener thereof, a transcript thereof, or a variant or a derivative thereof. None of the previously known reports show that change in the expression of the gene or the transcript thereof can serve as a marker for breast cancer.

The 52nd target gene is the hsa-miR-4741 gene, a congener thereof, a transcript thereof, or a variant or a derivative thereof. None of the previously known reports show that change in the expression of the gene or the transcript thereof can serve as a marker for breast cancer.

The 53rd target gene is the hsa-miR-6808-5p gene, a congener thereof, a transcript thereof, or a variant or a derivative thereof. None of the previously known reports show that change in the expression of the gene or the transcript thereof can serve as a marker for breast cancer.

The 54th target gene is the hsa-miR-6869-5p gene, a congener thereof, a transcript thereof, or a variant or a derivative thereof. None of the previously known reports show that change in the expression of the gene or the transcript thereof can serve as a marker for breast cancer.

The 55th target gene is the hsa-miR-5090 gene, a congener thereof, a transcript thereof, or a variant or a derivative thereof. None of the previously known reports show that change in the expression of the gene or the transcript thereof can serve as a marker for breast cancer.

The 56th target gene is the hsa-miR-615-5p gene, a congener thereof, a transcript thereof, or a variant or a derivative thereof. None of the previously known reports show that change in the expression of the gene or the transcript thereof can serve as a marker for breast cancer.

The 57th target gene is the hsa-miR-8072 gene, a congener thereof, a transcript thereof, or a variant or a derivative thereof. None of the previously known reports show that change in the expression of the gene or the transcript thereof can serve as a marker for breast cancer.

The 58th target gene is the hsa-miR-128-1-5p gene, a congener thereof, a transcript thereof, or a variant or a derivative thereof. None of the previously known reports show that change in the expression of the gene or the transcript thereof can serve as a marker for breast cancer.

The 59th target gene is the hsa-miR-1238-5p gene, a congener thereof, a transcript thereof, or a variant or a derivative thereof. None of the previously known reports show that change in the expression of the gene or the transcript thereof can serve as a marker for breast cancer.

The 60th target gene is the hsa-miR-365a-5p gene, a congener thereof, a transcript thereof, or a variant or a derivative thereof. None of the previously known reports show that change in the expression of the gene or the transcript thereof can serve as a marker for breast cancer.

The 61st target gene is the hsa-miR-204-3p gene, a congener thereof, a transcript thereof, or a variant or a derivative thereof. None of the previously known reports show that change in the expression of the gene or the transcript thereof can serve as a marker for breast cancer.

The 62nd target gene is the hsa-miR-4492 gene, a congener thereof, a transcript thereof, or a variant or a derivative thereof. None of the previously known reports show that change in the expression of the gene or the transcript thereof can serve as a marker for breast cancer.

The 63rd target gene is the hsa-miR-6785-5p gene, a congener thereof, a transcript thereof, or a variant or a derivative thereof. None of the previously known reports show that change in the expression of the gene or the transcript thereof can serve as a marker for breast cancer.

The 64th target gene is the hsa-miR-6511a-5p gene, a congener thereof, a transcript thereof, or a variant or a derivative thereof. None of the previously known reports show that change in the expression of the gene or the transcript thereof can serve as a marker for breast cancer.

The 65th target gene is the hsa-miR-4525 gene, a congener thereof, a transcript thereof, or a variant or a derivative thereof. None of the previously known reports show that change in the expression of the gene or the transcript thereof can serve as a marker for breast cancer.

The 66th target gene is the hsa-miR-1915-5p gene, a congener thereof, a transcript thereof, or a variant or a derivative thereof. None of the previously known reports show that change in the expression of the gene or the transcript thereof can serve as a marker for breast cancer.

The 67th target gene is the hsa-miR-3180 gene, a congener thereof, a transcript thereof, or a variant or a derivative thereof. None of the previously known reports show that change in the expression of the gene or the transcript thereof can serve as a marker for breast cancer.

The 68th target gene is the hsa-miR-6879-5p gene, a congener thereof, a transcript thereof, or a variant or a derivative thereof. None of the previously known reports show that change in the expression of the gene or the transcript thereof can serve as a marker for breast cancer.

The 69th target gene is the hsa-miR-1199-5p gene, a congener thereof, a transcript thereof, or a variant or a derivative thereof. None of the previously known reports show that change in the expression of the gene or the transcript thereof can serve as a marker for breast cancer.

The 70th target gene is the hsa-miR-6746-5p gene, a congener thereof, a transcript thereof, or a variant or a derivative thereof. None of the previously known reports show that change in the expression of the gene or the transcript thereof can serve as a marker for breast cancer.

The 71st target gene is the hsa-miR-711 gene, a congener thereof, a transcript thereof, or a variant or a derivative thereof. None of the previously known reports show that change in the expression of the gene or the transcript thereof can serve as a marker for breast cancer.

The 72nd target gene is the hsa-miR-663b gene, a congener thereof, a transcript thereof, or a variant or a derivative thereof. None of the previously known reports show that change in the expression of the gene or the transcript thereof can serve as a marker for breast cancer.

The 73rd target gene is the hsa-miR-4707-3p gene, a congener thereof, a transcript thereof, or a variant or a derivative thereof. None of the previously known reports show that change in the expression of the gene or the transcript thereof can serve as a marker for breast cancer.

The 74th target gene is the hsa-miR-6893-5p gene, a congener thereof, a transcript thereof, or a variant or a derivative thereof. None of the previously known reports show that change in the expression of the gene or the transcript thereof can serve as a marker for breast cancer.

The 75th target gene is the hsa-miR-4675 gene, a congener thereof, a transcript thereof, or a variant or a derivative thereof. None of the previously known reports show that change in the expression of the gene or the transcript thereof can serve as a marker for breast cancer.

The 76th target gene is the hsa-miR-4638-5p gene, a congener thereof, a transcript thereof, or a variant or a derivative thereof. None of the previously known reports show that change in the expression of the gene or the transcript thereof can serve as a marker for breast cancer.

The 77th target gene is the hsa-miR-4651 gene, a congener thereof, a transcript thereof, or a variant or a derivative thereof. None of the previously known reports show that change in the expression of the gene or the transcript thereof can serve as a marker for breast cancer.

The 78th target gene is the hsa-miR-6087 gene, a congener thereof, a transcript thereof, or a variant or a derivative thereof. None of the previously known reports show that change in the expression of the gene or the transcript thereof can serve as a marker for breast cancer.

The 79th target gene is the hsa-miR-4665-5p gene, a congener thereof, a transcript thereof, or a variant or a derivative thereof. None of the previously known reports show that change in the expression of the gene or the transcript thereof can serve as a marker for breast cancer.

The 80th target gene is the hsa-miR-4758-5p gene, a congener thereof, a transcript thereof, or a variant or a derivative thereof. None of the previously known reports show that change in the expression of the gene or the transcript thereof can serve as a marker for breast cancer.

The 81st target gene is the hsa-miR-6887-5p gene, a congener thereof, a transcript thereof, or a variant or a derivative thereof. None of the previously known reports show that change in the expression of the gene or the transcript thereof can serve as a marker for breast cancer.

The 82nd target gene is the hsa-miR-3620-5p gene, a congener thereof, a transcript thereof, or a variant or a derivative thereof. None of the previously known reports show that change in the expression of the gene or the transcript thereof can serve as a marker for breast cancer.

The 83rd target gene is the hsa-miR-1909-3p gene, a congener thereof, a transcript thereof, or a variant or a derivative thereof. None of the previously known reports show that change in the expression of the gene or the transcript thereof can serve as a marker for breast cancer.

The 84th target gene is the hsa-miR-7641 gene, a congener thereof, a transcript thereof, or a variant or a derivative thereof. None of the previously known reports show that change in the expression of the gene or the transcript thereof can serve as a marker for breast cancer.

The 85th target gene is the hsa-miR-6724-5p gene, a congener thereof, a transcript thereof, or a variant or a derivative thereof. None of the previously known reports show that change in the expression of the gene or the transcript thereof can serve as a marker for breast cancer.

The 86th target gene is the hsa-miR-1343-3p gene, a congener thereof, a transcript thereof, or a variant or a derivative thereof. None of the previously known reports show that change in the expression of the gene or the transcript thereof can serve as a marker for breast cancer.

The 87th target gene is the hsa-miR-6780b-5p gene, a congener thereof, a transcript thereof, or a variant or a derivative thereof. None of the previously known reports show that change in the expression of the gene or the transcript thereof can serve as a marker for breast cancer.

The 88th target gene is the hsa-miR-4484 gene, a congener thereof, a transcript thereof, or a variant or a derivative thereof. None of the previously known reports show that change in the expression of the gene or the transcript thereof can serve as a marker for breast cancer.

The 89th target gene is the hsa-miR-4690-5p gene, a congener thereof, a transcript thereof, or a variant or a derivative thereof. None of the previously known reports show that change in the expression of the gene or the transcript thereof can serve as a marker for breast cancer.

The 90th target gene is the hsa-miR-4429 gene, a congener thereof, a transcript thereof, or a variant or a derivative thereof. None of the previously known reports show that change in the expression of the gene or the transcript thereof can serve as a marker for breast cancer.

The 91st target gene is the hsa-miR-1227-5p gene, a congener thereof, a transcript thereof, or a variant or a derivative thereof. None of the previously known reports show that change in the expression of the gene or the transcript thereof can serve as a marker for breast cancer.

The 92nd target gene is the hsa-miR-4725-3p gene, a congener thereof, a transcript thereof, or a variant or a derivative thereof. None of the previously known reports show that change in the expression of the gene or the transcript thereof can serve as a marker for breast cancer.

The 93rd target gene is the hsa-miR-6861-5p gene, a congener thereof, a transcript thereof, or a variant or a derivative thereof. None of the previously known reports show that change in the expression of the gene or the transcript thereof can serve as a marker for breast cancer.

The 94th target gene is the hsa-miR-6812-5p gene, a congener thereof, a transcript thereof, or a variant or a derivative thereof. None of the previously known reports show that change in the expression of the gene or the transcript thereof can serve as a marker for breast cancer.

The 95th target gene is the hsa-miR-3197 gene, a congener thereof, a transcript thereof, or a variant or a derivative thereof. None of the previously known reports show that change in the expression of the gene or the transcript thereof can serve as a marker for breast cancer.

The 96th target gene is the hsa-miR-8059 gene, a congener thereof, a transcript thereof, or a variant or a derivative thereof. None of the previously known reports show that change in the expression of the gene or the transcript thereof can serve as a marker for breast cancer.

The 97th target gene is the hsa-miR-3185 gene, a congener thereof, a transcript thereof, or a variant or a derivative thereof. None of the previously known reports show that change in the expression of the gene or the transcript thereof can serve as a marker for breast cancer.

The 98th target gene is the hsa-miR-4706 gene, a congener thereof, a transcript thereof, or a variant or a derivative thereof. None of the previously known reports show that change in the expression of the gene or the transcript thereof can serve as a marker for breast cancer.

The 99th target gene is the hsa-miR-4497 gene, a congener thereof, a transcript thereof, or a variant or a derivative thereof. None of the previously known reports show that change in the expression of the gene or the transcript thereof can serve as a marker for breast cancer.

The 100th target gene is the hsa-miR-3131 gene, a congener thereof, a transcript thereof, or a variant or a derivative thereof. None of the previously known reports show that change in the expression of the gene or the transcript thereof can serve as a marker for breast cancer.

The 101st target gene is the hsa-miR-6806-5p gene, a congener thereof, a transcript thereof, or a variant or a derivative thereof. None of the previously known reports show that change in the expression of the gene or the transcript thereof can serve as a marker for breast cancer.

The 102nd target gene is the hsa-miR-187-5p gene, a congener thereof, a transcript thereof, or a variant or a derivative thereof. None of the previously known reports show that change in the expression of the gene or the transcript thereof can serve as a marker for breast cancer.

The 103rd target gene is the hsa-miR-3180-3p gene, a congener thereof, a transcript thereof, or a variant or a derivative thereof. None of the previously known reports show that change in the expression of the gene or the transcript thereof can serve as a marker for breast cancer.

The 104th target gene is the hsa-miR-6848-5p gene, a congener thereof, a transcript thereof, or a variant or a derivative thereof. None of the previously known reports show that change in the expression of the gene or the transcript thereof can serve as a marker for breast cancer.

The 105th target gene is the hsa-miR-6820-5p gene, a congener thereof, a transcript thereof, or a variant or a derivative thereof. None of the previously known reports show that change in the expression of the gene or the transcript thereof can serve as a marker for breast cancer.

The 106th target gene is the hsa-miR-6800-5p gene, a congener thereof, a transcript thereof, or a variant or a derivative thereof. None of the previously known reports show that change in the expression of the gene or the transcript thereof can serve as a marker for breast cancer.

The 107th target gene is the hsa-miR-6717-5p gene, a congener thereof, a transcript thereof, or a variant or a derivative thereof. None of the previously known reports show that change in the expression of the gene or the transcript thereof can serve as a marker for breast cancer.

The 108th target gene is the hsa-miR-6795-5p gene, a congener thereof, a transcript thereof, or a variant or a derivative thereof. None of the previously known reports show that change in the expression of the gene or the transcript thereof can serve as a marker for breast cancer.

The 109th target gene is the hsa-miR-4632-5p gene, a congener thereof, a transcript thereof, or a variant or a derivative thereof. None of the previously known reports show that change in the expression of the gene or the transcript thereof can serve as a marker for breast cancer.

The 110th target gene is the hsa-miR-665 gene, a congener thereof, a transcript thereof, or a variant or a derivative thereof. None of the previously known reports show that change in the expression of the gene or the transcript thereof can serve as a marker for breast cancer.

The 111th target gene is the hsa-miR-6778-5p gene, a congener thereof, a transcript thereof, or a variant or a derivative thereof. None of the previously known reports show that change in the expression of the gene or the transcript thereof can serve as a marker for breast cancer.

The 112th target gene is the hsa-miR-3663-3p gene, a congener thereof, a transcript thereof, or a variant or a derivative thereof. None of the previously known reports show that change in the expression of the gene or the transcript thereof can serve as a marker for breast cancer.

The 113th target gene is the hsa-miR-4689 gene, a congener thereof, a transcript thereof, or a variant or a derivative thereof. None of the previously known reports show that change in the expression of the gene or the transcript thereof can serve as a marker for breast cancer.

The 114th target gene is the hsa-miR-211-3p gene, a congener thereof, a transcript thereof, or a variant or a derivative thereof. None of the previously known reports show that change in the expression of the gene or the transcript thereof can serve as a marker for breast cancer.

The 115th target gene is the hsa-miR-6511b-5p gene, a congener thereof, a transcript thereof, or a variant or a derivative thereof. None of the previously known reports show that change in the expression of the gene or the transcript thereof can serve as a marker for breast cancer.

The 116th target gene is the hsa-miR-4750-5p gene, a congener thereof, a transcript thereof, or a variant or a derivative thereof. None of the previously known reports show that change in the expression of the gene or the transcript thereof can serve as a marker for breast cancer.

The 117th target gene is the hsa-miR-6126 gene, a congener thereof, a transcript thereof, or a variant or a derivative thereof. None of the previously known reports show that change in the expression of the gene or the transcript thereof can serve as a marker for breast cancer.

The 118th target gene is the hsa-miR-614 gene, a congener thereof, a transcript thereof, or a variant or a derivative thereof. None of the previously known reports show that change in the expression of the gene or the transcript thereof can serve as a marker for breast cancer.

The 119th target gene is the hsa-miR-7110-5p gene, a congener thereof, a transcript thereof, or a variant or a derivative thereof. None of the previously known reports show that change in the expression of the gene or the transcript thereof can serve as a marker for breast cancer.

The 120th target gene is the hsa-miR-744-5p gene, a congener thereof, a transcript thereof, or a variant or a derivative thereof. None of the previously known reports show that change in the expression of the gene or the transcript thereof can serve as a marker for breast cancer.

The 121st target gene is the hsa-miR-6769a-5p gene, a congener thereof, a transcript thereof, or a variant or a derivative thereof. None of the previously known reports show that change in the expression of the gene or the transcript thereof can serve as a marker for breast cancer.

The 122nd target gene is the hsa-miR-4792 gene, a congener thereof, a transcript thereof, or a variant or a derivative thereof. None of the previously known reports show that change in the expression of the gene or the transcript thereof can serve as a marker for breast cancer.

The 123rd target gene is the hsa-miR-5787 gene, a congener thereof, a transcript thereof, or a variant or a derivative thereof. None of the previously known reports show that change in the expression of the gene or the transcript thereof can serve as a marker for breast cancer.

The 124th target gene is the hsa-miR-6798-5p gene, a congener thereof, a transcript thereof, or a variant or a derivative thereof. None of the previously known reports show that change in the expression of the gene or the transcript thereof can serve as a marker for breast cancer.

The 125th target gene is the hsa-miR-6781-5p gene, a congener thereof, a transcript thereof, or a variant or a derivative thereof. None of the previously known reports show that change in the expression of the gene or the transcript thereof can serve as a marker for breast cancer.

The 126th target gene is the hsa-miR-4419b gene, a congener thereof, a transcript thereof, or a variant or a derivative thereof. None of the previously known reports show that change in the expression of the gene or the transcript thereof can serve as a marker for breast cancer.

The 127th target gene is the hsa-miR-4446-3p gene, a congener thereof, a transcript thereof, or a variant or a derivative thereof. None of the previously known reports show that change in the expression of the gene or the transcript thereof can serve as a marker for breast cancer.

The 128th target gene is the hsa-miR-4259 gene, a congener thereof, a transcript thereof, or a variant or a derivative thereof. None of the previously known reports show that change in the expression of the gene or the transcript thereof can serve as a marker for breast cancer.

The 129th target gene is the hsa-miR-5572 gene, a congener thereof, a transcript thereof, or a variant or a derivative thereof. None of the previously known reports show that change in the expression of the gene or the transcript thereof can serve as a marker for breast cancer.

The 130th target gene is the hsa-miR-6075 gene, a congener thereof, a transcript thereof, or a variant or a derivative thereof. None of the previously known reports show that change in the expression of the gene or the transcript thereof can serve as a marker for breast cancer.

The 131st target gene is the hsa-miR-296-3p gene, a congener thereof, a transcript thereof, or a variant or a derivative thereof. None of the previously known reports show that change in the expression of the gene or the transcript thereof can serve as a marker for breast cancer.

The 132nd target gene is the hsa-miR-6891-5p gene, a congener thereof, a transcript thereof, or a variant or a derivative thereof. None of the previously known reports show that change in the expression of the gene or the transcript thereof can serve as a marker for breast cancer.

The 133rd target gene is the hsa-miR-4745-5p gene, a congener thereof, a transcript thereof, or a variant or a derivative thereof. None of the previously known reports show that change in the expression of the gene or the transcript thereof can serve as a marker for breast cancer.

The 134th target gene is the hsa-miR-6775-5p gene, a congener thereof, a transcript thereof, or a variant or a derivative thereof. None of the previously known reports show that change in the expression of the gene or the transcript thereof can serve as a marker for breast cancer.

The 135th target gene is the hsa-miR-6870-5p gene, a congener thereof, a transcript thereof, or a variant or a derivative thereof. None of the previously known reports show that change in the expression of the gene or the transcript thereof can serve as a marker for breast cancer.

The 136th target gene is the hsa-miR-920 gene, a congener thereof, a transcript thereof, or a variant or a derivative thereof. None of the previously known reports show that change in the expression of the gene or the transcript thereof can serve as a marker for breast cancer.

The 137th target gene is the hsa-miR-4530 gene, a congener thereof, a transcript thereof, or a variant or a derivative thereof. None of the previously known reports show that change in the expression of the gene or the transcript thereof can serve as a marker for breast cancer.

The 138th target gene is the hsa-miR-6819-5p gene, a congener thereof, a transcript thereof, or a variant or a derivative thereof. None of the previously known reports show that change in the expression of the gene or the transcript thereof can serve as a marker for breast cancer.

The 139th target gene is the hsa-miR-6825-5p gene, a congener thereof, a transcript thereof, or a variant or a derivative thereof. None of the previously known reports show that change in the expression of the gene or the transcript thereof can serve as a marker for breast cancer.

The 140th target gene is the hsa-miR-7847-3p gene, a congener thereof, a transcript thereof, or a variant or a derivative thereof. None of the previously known reports show that change in the expression of the gene or the transcript thereof can serve as a marker for breast cancer.

The 141st target gene is the hsa-miR-6131 gene, a congener thereof, a transcript thereof, or a variant or a derivative thereof. None of the previously known reports show that change in the expression of the gene or the transcript thereof can serve as a marker for breast cancer.

The 142nd target gene is the hsa-miR-4433-3p gene, a congener thereof, a transcript thereof, or a variant or a derivative thereof. None of the previously known reports show that change in the expression of the gene or the transcript thereof can serve as a marker for breast cancer.

The 143rd target gene is the hsa-miR-1228-5p gene, a congener thereof, a transcript thereof, or a variant or a derivative thereof. None of the previously known reports show that change in the expression of the gene or the transcript thereof can serve as a marker for breast cancer.

The 144th target gene is the hsa-miR-6743-5p gene, a congener thereof, a transcript thereof, or a variant or a derivative thereof. None of the previously known reports show that change in the expression of the gene or the transcript thereof can serve as a marker for breast cancer.

The 145th target gene is the hsa-miR-1268a gene, a congener thereof, a transcript thereof, or a variant or a derivative thereof. None of the previously known reports show that change in the expression of the gene or the transcript thereof can serve as a marker for breast cancer.

The 146th target gene is the hsa-miR-3917 gene, a congener thereof, a transcript thereof, or a variant or a derivative thereof. None of the previously known reports show that change in the expression of the gene or the transcript thereof can serve as a marker for breast cancer.

The 147th target gene is the hsa-miR-6786-5p gene, a congener thereof, a transcript thereof, or a variant or a derivative thereof. None of the previously known reports show that change in the expression of the gene or the transcript thereof can serve as a marker for breast cancer.

The 148th target gene is the hsa-miR-3154 gene, a congener thereof, a transcript thereof, or a variant or a derivative thereof. None of the previously known reports show that change in the expression of the gene or the transcript thereof can serve as a marker for breast cancer.

The 149th target gene is the hsa-miR-638 gene, a congener thereof, a transcript thereof, or a variant or a derivative thereof. None of the previously known reports show that change in the expression of the gene or the transcript thereof can serve as a marker for breast cancer.

The 150th target gene is the hsa-miR-6741-5p gene, a congener thereof, a transcript thereof, or a variant or a derivative thereof. None of the previously known reports show that change in the expression of the gene or the transcript thereof can serve as a marker for breast cancer.

The 151st target gene is the hsa-miR-6889-5p gene, a congener thereof, a transcript thereof, or a variant or a derivative thereof. None of the previously known reports show that change in the expression of the gene or the transcript thereof can serve as a marker for breast cancer.

The 152nd target gene is the hsa-miR-6840-3p gene, a congener thereof, a transcript thereof, or a variant or a derivative thereof. None of the previously known reports show that change in the expression of the gene or the transcript thereof can serve as a marker for breast cancer.

The 153rd target gene is the hsa-miR-6510-5p gene, a congener thereof, a transcript thereof, or a variant or a derivative thereof. None of the previously known reports show that change in the expression of the gene or the transcript thereof can serve as a marker for breast cancer.

The 154th target gene is the hsa-miR-3188 gene, a congener thereof, a transcript thereof, or a variant or a derivative thereof. None of the previously known reports show that change in the expression of the gene or the transcript thereof can serve as a marker for breast cancer.

The 155th target gene is the hsa-miR-551b-5p gene, a congener thereof, a transcript thereof, or a variant or a derivative thereof. None of the previously known reports show that change in the expression of the gene or the transcript thereof can serve as a marker for breast cancer.

The 156th target gene is the hsa-miR-5001-5p gene, a congener thereof, a transcript thereof, or a variant or a derivative thereof. None of the previously known reports show that change in the expression of the gene or the transcript thereof can serve as a marker for breast cancer.

The 157th target gene is the hsa-miR-1268b gene, a congener thereof, a transcript thereof, or a variant or a derivative thereof. None of the previously known reports show that change in the expression of the gene or the transcript thereof can serve as a marker for breast cancer.

The 158th target gene is the hsa-miR-7107-5p gene, a congener thereof, a transcript thereof, or a variant or a derivative thereof. None of the previously known reports show that change in the expression of the gene or the transcript thereof can serve as a marker for breast cancer.

The 159th target gene is the hsa-miR-6824-5p gene, a congener thereof, a transcript thereof, or a variant or a derivative thereof. None of the previously known reports show that change in the expression of the gene or the transcript thereof can serve as a marker for breast cancer.

The 160th target gene is the hsa-miR-6732-5p gene, a congener thereof, a transcript thereof, or a variant or a derivative thereof. None of the previously known reports show that change in the expression of the gene or the transcript thereof can serve as a marker for breast cancer.

The 161st target gene is the hsa-miR-371a-5p gene, a congener thereof, a transcript thereof, or a variant or a derivative thereof. None of the previously known reports show that change in the expression of the gene or the transcript thereof can serve as a marker for breast cancer.

The 162nd target gene is the hsa-miR-6794-5p gene, a congener thereof, a transcript thereof, or a variant or a derivative thereof. None of the previously known reports show that change in the expression of the gene or the transcript thereof can serve as a marker for breast cancer.

The 163rd target gene is the hsa-miR-6779-5p gene, a congener thereof, a transcript thereof, or a variant or a derivative thereof. None of the previously known reports show that change in the expression of the gene or the transcript thereof can serve as a marker for breast cancer.

The 164th target gene is the hsa-miR-4271 gene, a congener thereof, a transcript thereof, or a variant or a derivative thereof. None of the previously known reports show that change in the expression of the gene or the transcript thereof can serve as a marker for breast cancer.

The 165th target gene is the hsa-miR-5195-3p gene, a congener thereof, a transcript thereof, or a variant or a derivative thereof. None of the previously known reports show that change in the expression of the gene or the transcript thereof can serve as a marker for breast cancer.

The 166th target gene is the hsa-miR-6762-5p gene, a congener thereof, a transcript thereof, or a variant or a derivative thereof. None of the previously known reports show that change in the expression of the gene or the transcript thereof can serve as a marker for breast cancer.

The 167th target gene is the hsa-miR-939-5p gene, a congener thereof, a transcript thereof, or a variant or a derivative thereof. None of the previously known reports show that change in the expression of the gene or the transcript thereof can serve as a marker for breast cancer.

The 168th target gene is the hsa-miR-1247-3p gene, a congener thereof, a transcript thereof, or a variant or a derivative thereof. None of the previously known reports show that change in the expression of the gene or the transcript thereof can serve as a marker for breast cancer.

The 169th target gene is the hsa-miR-6777-5p gene, a congener thereof, a transcript thereof, or a variant or a derivative thereof. None of the previously known reports show that change in the expression of the gene or the transcript thereof can serve as a marker for breast cancer.

The 170th target gene is the hsa-miR-6722-3p gene, a congener thereof, a transcript thereof, or a variant or a derivative thereof. None of the previously known reports show that change in the expression of the gene or the transcript thereof can serve as a marker for breast cancer.

The 171st target gene is the hsa-miR-3656 gene, a congener thereof, a transcript thereof, or a variant or a derivative thereof. None of the previously known reports show that change in the expression of the gene or the transcript thereof can serve as a marker for breast cancer.

The 172nd target gene is the hsa-miR-4688 gene, a congener thereof, a transcript thereof, or a variant or a derivative thereof. None of the previously known reports show that change in the expression of the gene or the transcript thereof can serve as a marker for breast cancer.

The 173rd target gene is the hsa-miR-3195 gene, a congener thereof, a transcript thereof, or a variant or a derivative thereof. None of the previously known reports show that change in the expression of the gene or the transcript thereof can serve as a marker for breast cancer.

The 174th target gene is the hsa-miR-6766-5p gene, a congener thereof, a transcript thereof, or a variant or a derivative thereof. None of the previously known reports show that change in the expression of the gene or the transcript thereof can serve as a marker for breast cancer.

The 175th target gene is the hsa-miR-4447 gene, a congener thereof, a transcript thereof, or a variant or a derivative thereof. None of the previously known reports show that change in the expression of the gene or the transcript thereof can serve as a marker for breast cancer.

The 176th target gene is the hsa-miR-4656 gene, a congener thereof, a transcript thereof, or a variant or a derivative thereof. None of the previously known reports show that change in the expression of the gene or the transcript thereof can serve as a marker for breast cancer.

The 177th target gene is the hsa-miR-7108-5p gene, a congener thereof, a transcript thereof, or a variant or a derivative thereof. None of the previously known reports show that change in the expression of the gene or the transcript thereof can serve as a marker for breast cancer.

The 178th target gene is the hsa-miR-3191-3p gene, a congener thereof, a transcript thereof, or a variant or a derivative thereof. None of the previously known reports show that change in the expression of the gene or the transcript thereof can serve as a marker for breast cancer.

The 179th target gene is the hsa-miR-1273g-3p gene, a congener thereof, a transcript thereof, or a variant or a derivative thereof. None of the previously known reports show that change in the expression of the gene or the transcript thereof can serve as a marker for breast cancer.

The 180th target gene is the hsa-miR-4463 gene, a congener thereof, a transcript thereof, or a variant or a derivative thereof. None of the previously known reports show that change in the expression of the gene or the transcript thereof can serve as a marker for breast cancer.

The 181st target gene is the hsa-miR-2861 gene, a congener thereof, a transcript thereof, or a variant or a derivative thereof. None of the previously known reports show that change in the expression of the gene or the transcript thereof can serve as a marker for breast cancer.

The 182nd target gene is the hsa-miR-3196 gene, a congener thereof, a transcript thereof, or a variant or a derivative thereof. None of the previously known reports show that change in the expression of the gene or the transcript thereof can serve as a marker for breast cancer.

The 183rd target gene is the hsa-miR-6877-5p gene, a congener thereof, a transcript thereof, or a variant or a derivative thereof. None of the previously known reports show that change in the expression of the gene or the transcript thereof can serve as a marker for breast cancer.

The 184th target gene is the hsa-miR-3679-5p gene, a congener thereof, a transcript thereof, or a variant or a derivative thereof. None of the previously known reports show that change in the expression of the gene or the transcript thereof can serve as a marker for breast cancer.

The 185th target gene is the hsa-miR-4442 gene, a congener thereof, a transcript thereof, or a variant or a derivative thereof. None of the previously known reports show that change in the expression of the gene or the transcript thereof can serve as a marker for breast cancer.

The 186th target gene is the hsa-miR-6789-5p gene, a congener thereof, a transcript thereof, or a variant or a derivative thereof. None of the previously known reports show that change in the expression of the gene or the transcript thereof can serve as a marker for breast cancer.

The 187th target gene is the hsa-miR-6782-5p gene, a congener thereof, a transcript thereof, or a variant or a derivative thereof. None of the previously known reports show that change in the expression of the gene or the transcript thereof can serve as a marker for breast cancer.

The 188th target gene is the hsa-miR-486-3p gene, a congener thereof, a transcript thereof, or a variant or a derivative thereof. None of the previously known reports show that change in the expression of the gene or the transcript thereof can serve as a marker for breast cancer.

The 189th target gene is the hsa-miR-6085 gene, a congener thereof, a transcript thereof, or a variant or a derivative thereof. None of the previously known reports show that change in the expression of the gene or the transcript thereof can serve as a marker for breast cancer.

The 190th target gene is the hsa-miR-4746-3p gene, a congener thereof, a transcript thereof, or a variant or a derivative thereof. None of the previously known reports show that change in the expression of the gene or the transcript thereof can serve as a marker for breast cancer.

The 191st target gene is the hsa-miR-619-5p gene, a congener thereof, a transcript thereof, or a variant or a derivative thereof. None of the previously known reports show that change in the expression of the gene or the transcript thereof can serve as a marker for breast cancer.

The 192nd target gene is the hsa-miR-937-5p gene, a congener thereof, a transcript thereof, or a variant or a derivative thereof. None of the previously known reports show that change in the expression of the gene or the transcript thereof can serve as a marker for breast cancer.

The 193rd target gene is the hsa-miR-6803-5p gene, a congener thereof, a transcript thereof, or a variant or a derivative thereof. None of the previously known reports show that change in the expression of the gene or the transcript thereof can serve as a marker for breast cancer.

The 194th target gene is the hsa-miR-4298 gene, a congener thereof, a transcript thereof, or a variant or a derivative thereof. None of the previously known reports show that change in the expression of the gene or the transcript thereof can serve as a marker for breast cancer.

The 195th target gene is the hsa-miR-4454 gene, a congener thereof, a transcript thereof, or a variant or a derivative thereof. None of the previously known reports show that change in the expression of the gene or the transcript thereof can serve as a marker for breast cancer.

The 196th target gene is the hsa-miR-4459 gene, a congener thereof, a transcript thereof, or a variant or a derivative thereof. None of the previously known reports show that change in the expression of the gene or the transcript thereof can serve as a marker for breast cancer.

The 197th target gene is the hsa-miR-7150 gene, a congener thereof, a transcript thereof, or a variant or a derivative thereof. None of the previously known reports show that change in the expression of the gene or the transcript thereof can serve as a marker for breast cancer.

The 198th target gene is the hsa-miR-6880-5p gene, a congener thereof, a transcript thereof, or a variant or a derivative thereof. None of the previously known reports show that change in the expression of the gene or the transcript thereof can serve as a marker for breast cancer.

The 199th target gene is the hsa-miR-4449 gene, a congener thereof, a transcript thereof, or a variant or a derivative thereof. None of the previously known reports show that change in the expression of the gene or the transcript thereof can serve as a marker for breast cancer.

The 200th target gene is the hsa-miR-8063 gene, a congener thereof, a transcript thereof, or a variant or a derivative thereof. None of the previously known reports show that change in the expression of the gene or the transcript thereof can serve as a marker for breast cancer.

The 201st target gene is the hsa-miR-4695-5p gene, a congener thereof, a transcript thereof, or a variant or a derivative thereof. None of the previously known reports show that change in the expression of the gene or the transcript thereof can serve as a marker for breast cancer.

The 202nd target gene is the hsa-miR-6132 gene, a congener thereof, a transcript thereof, or a variant or a derivative thereof. None of the previously known reports show that change in the expression of the gene or the transcript thereof can serve as a marker for breast cancer.

The 203rd target gene is the hsa-miR-6829-5p gene, a congener thereof, a transcript thereof, or a variant or a derivative thereof. None of the previously known reports show that change in the expression of the gene or the transcript thereof can serve as a marker for breast cancer.

The 204th target gene is the hsa-miR-4486 gene, a congener thereof, a transcript thereof, or a variant or a derivative thereof. None of the previously known reports show that change in the expression of the gene or the transcript thereof can serve as a marker for breast cancer.

The 205th target gene is the hsa-miR-6805-3p gene, a congener thereof, a transcript thereof, or a variant or a derivative thereof. None of the previously known reports show that change in the expression of the gene or the transcript thereof can serve as a marker for breast cancer.

The 206th target gene is the hsa-miR-6826-5p gene, a congener thereof, a transcript thereof, or a variant or a derivative thereof. None of the previously known reports show that change in the expression of the gene or the transcript thereof can serve as a marker for breast cancer.

The 207th target gene is the hsa-miR-4508 gene, a congener thereof, a transcript thereof, or a variant or a derivative thereof. None of the previously known reports show that change in the expression of the gene or the transcript thereof can serve as a marker for breast cancer.

The 208th target gene is the hsa-miR-1343-5p gene, a congener thereof, a transcript thereof, or a variant or a derivative thereof. None of the previously known reports show that change in the expression of the gene or the transcript thereof can serve as a marker for breast cancer.

The 209th target gene is the hsa-miR-7114-5p gene, a congener thereof, a transcript thereof, or a variant or a derivative thereof. None of the previously known reports show that change in the expression of the gene or the transcript thereof can serve as a marker for breast cancer.

The 210th target gene is the hsa-miR-3622a-5p gene, a congener thereof, a transcript thereof, or a variant or a derivative thereof. None of the previously known reports show that change in the expression of the gene or the transcript thereof can serve as a marker for breast cancer.

The 211th target gene is the hsa-miR-6765-5p gene, a congener thereof, a transcript thereof, or a variant or a derivative thereof. None of the previously known reports show that change in the expression of the gene or the transcript thereof can serve as a marker for breast cancer.

The 212th target gene is the hsa-miR-7845-5p gene, a congener thereof, a transcript thereof, or a variant or a derivative thereof. None of the previously known reports show that change in the expression of the gene or the transcript thereof can serve as a marker for breast cancer.

The 213th target gene is the hsa-miR-3960 gene, a congener thereof, a transcript thereof, or a variant or a derivative thereof. None of the previously known reports show that change in the expression of the gene or the transcript thereof can serve as a marker for breast cancer.

The 214th target gene is the hsa-miR-6749-5p gene, a congener thereof, a transcript thereof, or a variant or a derivative thereof. None of the previously known reports show that change in the expression of the gene or the transcript thereof can serve as a marker for breast cancer.

The 215th target gene is the hsa-miR-1260b gene, a congener thereof, a transcript thereof, or a variant or a derivative thereof. None of the previously known reports show that change in the expression of the gene or the transcript thereof can serve as a marker for breast cancer.

The 216th target gene is the hsa-miR-6799-5p gene, a congener thereof, a transcript thereof, or a variant or a derivative thereof. None of the previously known reports show that change in the expression of the gene or the transcript thereof can serve as a marker for breast cancer.

The 217th target gene is the hsa-miR-4723-5p gene, a congener thereof, a transcript thereof, or a variant or a derivative thereof. None of the previously known reports show that change in the expression of the gene or the transcript thereof can serve as a marker for breast cancer.

The 218th target gene is the hsa-miR-6784-5p gene, a congener thereof, a transcript thereof, or a variant or a derivative thereof. None of the previously known reports show that change in the expression of the gene or the transcript thereof can serve as a marker for breast cancer.

The 219th target gene is the hsa-miR-5100 gene, a congener thereof, a transcript thereof, or a variant or a derivative thereof. None of the previously known reports show that change in the expression of the gene or the transcript thereof can serve as a marker for breast cancer.

The 220th target gene is the hsa-miR-6769b-5p gene, a congener thereof, a transcript thereof, or a variant or a derivative thereof. None of the previously known reports show that change in the expression of the gene or the transcript thereof can serve as a marker for breast cancer.

The 221st target gene is the hsa-miR-1207-5p gene, a congener thereof, a transcript thereof, or a variant or a derivative thereof. None of the previously known reports show that change in the expression of the gene or the transcript thereof can serve as a marker for breast cancer.

The 222nd target gene is the hsa-miR-642a-3p gene, a congener thereof, a transcript thereof, or a variant or a derivative thereof. None of the previously known reports show that change in the expression of the gene or the transcript thereof can serve as a marker for breast cancer.

The 223rd target gene is the hsa-miR-4505 gene, a congener thereof, a transcript thereof, or a variant or a derivative thereof. None of the previously known reports show that change in the expression of the gene or the transcript thereof can serve as a marker for breast cancer.

The 224th target gene is the hsa-miR-4270 gene, a congener thereof, a transcript thereof, or a variant or a derivative thereof. None of the previously known reports show that change in the expression of the gene or the transcript thereof can serve as a marker for breast cancer.

The 225th target gene is the hsa-miR-6721-5p gene, a congener thereof, a transcript thereof, or a variant or a derivative thereof. None of the previously known reports show that change in the expression of the gene or the transcript thereof can serve as a marker for breast cancer.

The 226th target gene is the hsa-miR-7111-5p gene, a congener thereof, a transcript thereof, or a variant or a derivative thereof. None of the previously known reports show that change in the expression of the gene or the transcript thereof can serve as a marker for breast cancer.

The 227th target gene is the hsa-miR-6791-5p gene, a congener thereof, a transcript thereof, or a variant or a derivative thereof. None of the previously known reports show that change in the expression of the gene or the transcript thereof can serve as a marker for breast cancer.

The 228th target gene is the hsa-miR-7109-5p gene, a congener thereof, a transcript thereof, or a variant or a derivative thereof. None of the previously known reports show that change in the expression of the gene or the transcript thereof can serve as a marker for breast cancer.

The 229th target gene is the hsa-miR-4258 gene, a congener thereof, a transcript thereof, or a variant or a derivative thereof. None of the previously known reports show that change in the expression of the gene or the transcript thereof can serve as a marker for breast cancer.

The 230th target gene is the hsa-miR-6515-3p gene, a congener thereof, a transcript thereof, or a variant or a derivative thereof. None of the previously known reports show that change in the expression of the gene or the transcript thereof can serve as a marker for breast cancer.

The 231st target gene is the hsa-miR-6851-5p gene, a congener thereof, a transcript thereof, or a variant or a derivative thereof. None of the previously known reports show that change in the expression of the gene or the transcript thereof can serve as a marker for breast cancer.

The 232nd target gene is the hsa-miR-6125 gene, a congener thereof, a transcript thereof, or a variant or a derivative thereof. None of the previously known reports show that change in the expression of the gene or the transcript thereof can serve as a marker for breast cancer.

The 233rd target gene is the hsa-miR-4749-5p gene, a congener thereof, a transcript thereof, or a variant or a derivative thereof. None of the previously known reports show that change in the expression of the gene or the transcript thereof can serve as a marker for breast cancer.

The 234th target gene is the hsa-miR-4726-5p gene, a congener thereof, a transcript thereof, or a variant or a derivative thereof. None of the previously known reports show that change in the expression of the gene or the transcript thereof can serve as a marker for breast cancer.

The 235th target gene is the hsa-miR-4513 gene, a congener thereof, a transcript thereof, or a variant or a derivative thereof. None of the previously known reports show that change in the expression of the gene or the transcript thereof can serve as a marker for breast cancer.

The 236th target gene is the hsa-miR-760 gene, a congener thereof, a transcript thereof, or a variant or a derivative thereof. The previously known report shows that change in the expression of the gene or the transcript thereof can serve as a marker for breast cancer (Non-Patent Literature 3 described above).

The 237th target gene is the hsa-miR-602 gene, a congener thereof, a transcript thereof, or a variant or a derivative thereof. The previously known report shows that change in the expression of the gene or the transcript thereof can serve as a marker for breast cancer (Patent Literature 1 described above).

The 238th target gene is the hsa-miR-423-5p gene, a congener thereof, a transcript thereof, or a variant or a derivative thereof. The previously known report shows that change in the expression of the gene or the transcript thereof can serve as a marker for breast cancer (Non-Patent Literature 4 described above).

The 239th target gene is the hsa-miR-92a-2-5p gene, a congener thereof, a transcript thereof, or a variant or a derivative thereof. The previously known report shows that change in the expression of the gene or the transcript thereof can serve as a marker for breast cancer (Patent Literature 3 described above).

The 240th target gene is the hsa-miR-16-5p gene, a congener thereof, a transcript thereof, or a variant or a derivative thereof. The previously known report shows that change in the expression of the gene or the transcript thereof can serve as a marker for breast cancer (Patent Literature 4 described above).

The 241st target gene is the hsa-miR-451a gene, a congener thereof, a transcript thereof, or a variant or a derivative thereof. The previously known report shows that change in the expression of the gene or the transcript thereof can serve as a marker for breast cancer (Patent Literature 4 described above).

The 242nd target gene is the hsa-miR-135a-3p gene, a congener thereof, a transcript thereof, or a variant or a derivative thereof. The previously known report shows that change in the expression of the gene or the transcript thereof can serve as a marker for breast cancer (Patent Literatures 1 and 2 described above).

The 243rd target gene is the hsa-miR-486-5p gene, a congener thereof, a transcript thereof, or a variant or a derivative thereof. The previously known report shows that change in the expression of the gene or the transcript thereof can serve as a marker for breast cancer (Non-Patent Literature 4 described above).

The 244th target gene is the hsa-miR-4257 gene, a congener thereof, a transcript thereof, or a variant or a derivative thereof. The previously known report shows that change in the expression of the gene or the transcript thereof can serve as a marker for breast cancer (Non-Patent Literature 5 described above).

The 245th target gene is the hsa-miR-92b-5p gene, a congener thereof, a transcript thereof, or a variant or a derivative thereof. The previously known report shows that change in the expression of the gene or the transcript thereof can serve as a marker for breast cancer (Patent Literature 3 described above).

The 246th target gene is the hsa-miR-1915-3p gene, a congener thereof, a transcript thereof, or a variant or a derivative thereof. The previously known report shows that change in the expression of the gene or the transcript thereof can serve as a marker for breast cancer (Non-Patent Literature 5 described above).

The 247th target gene is the hsa-miR-718 gene, a congener thereof, a transcript thereof, or a variant or a derivative thereof. The previously known report shows that change in the expression of the gene or the transcript thereof can serve as a marker for breast cancer (Non-Patent Literature 5 described above).

The 248th target gene is the hsa-miR-940 gene, a congener thereof, a transcript thereof, or a variant or a derivative thereof. The previously known report shows that change in the expression of the gene or the transcript thereof can serve as a marker for breast cancer (Non-Patent Literature 6 described above).

The 249th target gene is the hsa-miR-296-5p gene, a congener thereof, a transcript thereof, or a variant or a derivative thereof. The previously known report shows that change in the expression of the gene or the transcript thereof can serve as a marker for breast cancer (Patent Literature 4 described above).

The 250th target gene is the hsa-miR-23b-3p gene, a congener thereof, a transcript thereof, or a variant or a derivative thereof. The previously known report shows that change in the expression of the gene or the transcript thereof can serve as a marker for breast cancer (Patent Literature 2 described above).

The 251st target gene is the hsa-miR-92a-3p gene, a congener thereof, a transcript thereof, or a variant or a derivative thereof. The previously known report shows that change in the expression of the gene or the transcript thereof can serve as a marker for breast cancer (Patent Literature 3 described above).

The 252nd target gene is the hsa-miR-658 gene, a congener thereof, a transcript thereof, or a variant or a derivative thereof. None of the previously known reports show that change in the expression of the gene or the transcript thereof can serve as a marker for breast cancer.

The 253rd target gene is the hsa-miR-6842-5p gene, a congener thereof, a transcript thereof, or a variant or a derivative thereof. None of the previously known reports show that change in the expression of the gene or the transcript thereof can serve as a marker for breast cancer.

The 254th target gene is the hsa-miR-6124 gene, a congener thereof, a transcript thereof, or a variant or a derivative thereof. None of the previously known reports show that change in the expression of the gene or the transcript thereof can serve as a marker for breast cancer.

The 255th target gene is the hsa-miR-6765-3p gene, a congener thereof, a transcript thereof, or a variant or a derivative thereof. None of the previously known reports show that change in the expression of the gene or the transcript thereof can serve as a marker for breast cancer.

The 256th target gene is the hsa-miR-7106-5p gene, a congener thereof, a transcript thereof, or a variant or a derivative thereof. None of the previously known reports show that change in the expression of the gene or the transcript thereof can serve as a marker for breast cancer.

The 257th target gene is the hsa-miR-4534 gene, a congener thereof, a transcript thereof, or a variant or a derivative thereof. None of the previously known reports show that change in the expression of the gene or the transcript thereof can serve as a marker for breast cancer.

The 258th target gene is the hsa-miR-92b-3p gene, a congener thereof, a transcript thereof, or a variant or a derivative thereof. None of the previously known reports show that change in the expression of the gene or the transcript thereof can serve as a marker for breast cancer.

The 259th target gene is the hsa-miR-3135b gene, a congener thereof, a transcript thereof, or a variant or a derivative thereof. None of the previously known reports show that change in the expression of the gene or the transcript thereof can serve as a marker for breast cancer.

The 260th target gene is the hsa-miR-4687-3p gene, a congener thereof, a transcript thereof, or a variant or a derivative thereof. None of the previously known reports show that change in the expression of the gene or the transcript thereof can serve as a marker for breast cancer.

The 261st target gene is the hsa-miR-762 gene, a congener thereof, a transcript thereof, or a variant or a derivative thereof. None of the previously known reports show that change in the expression of the gene or the transcript thereof can serve as a marker for breast cancer.

The 262nd target gene is the hsa-miR-3619-3p gene, a congener thereof, a transcript thereof, or a variant or a derivative thereof. None of the previously known reports show that change in the expression of the gene or the transcript thereof can serve as a marker for breast cancer.

The 263rd target gene is the hsa-miR-4467 gene, a congener thereof, a transcript thereof, or a variant or a derivative thereof. None of the previously known reports show that change in the expression of the gene or the transcript thereof can serve as a marker for breast cancer.

The 264th target gene is the hsa-miR-557 gene, a congener thereof, a transcript thereof, or a variant or a derivative thereof. None of the previously known reports show that change in the expression of the gene or the transcript thereof can serve as a marker for breast cancer.

The 265th target gene is the hsa-miR-1237-5p gene, a congener thereof, a transcript thereof, or a variant or a derivative thereof. None of the previously known reports show that change in the expression of the gene or the transcript thereof can serve as a marker for breast cancer.

The 266th target gene is the hsa-miR-1908-5p gene, a congener thereof, a transcript thereof, or a variant or a derivative thereof. None of the previously known reports show that change in the expression of the gene or the transcript thereof can serve as a marker for breast cancer.

The 267th target gene is the hsa-miR-4286 gene, a congener thereof, a transcript thereof, or a variant or a derivative thereof. None of the previously known reports show that change in the expression of the gene or the transcript thereof can serve as a marker for breast cancer.

The 268th target gene is the hsa-miR-6885-5p gene, a congener thereof, a transcript thereof, or a variant or a derivative thereof. None of the previously known reports show that change in the expression of the gene or the transcript thereof can serve as a marker for breast cancer.

The 269th target gene is the hsa-miR-6763-5p gene, a congener thereof, a transcript thereof, or a variant or a derivative thereof. None of the previously known reports show that change in the expression of the gene or the transcript thereof can serve as a marker for breast cancer.

The 270th target gene is the hsa-miR-6089 gene, a congener thereof, a transcript thereof, or a variant or a derivative thereof. None of the previously known reports show that change in the expression of the gene or the transcript thereof can serve as a marker for breast cancer.

The 271st target gene is the hsa-miR-6816-5p gene, a congener thereof, a transcript thereof, or a variant or a derivative thereof. None of the previously known reports show that change in the expression of the gene or the transcript thereof can serve as a marker for breast cancer.

The 272nd target gene is the hsa-miR-4466 gene, a congener thereof, a transcript thereof, or a variant or a derivative thereof. None of the previously known reports show that change in the expression of the gene or the transcript thereof can serve as a marker for breast cancer.

The 273rd target gene is the hsa-miR-4488 gene, a congener thereof, a transcript thereof, or a variant or a derivative thereof. None of the previously known reports show that change in the expression of the gene or the transcript thereof can serve as a marker for breast cancer.

The 274th target gene is the hsa-miR-6752-5p gene, a congener thereof, a transcript thereof, or a variant or a derivative thereof. None of the previously known reports show that change in the expression of the gene or the transcript thereof can serve as a marker for breast cancer.

The 275th target gene is the hsa-miR-4739 gene, a congener thereof, a transcript thereof, or a variant or a derivative thereof. None of the previously known reports show that change in the expression of the gene or the transcript thereof can serve as a marker for breast cancer.

2. Nucleic Acid Probe or Primer for Detection of Breast Cancer

In the present invention, nucleic acid(s) capable of specifically binding to any of the target nucleic acids as the breast cancer markers described above can be used as a nucleic acid, for example, a nucleic acid probe or a primer, for the detection or diagnosis of breast cancer.

In the present invention, the nucleic acid probes or the primers that can be used for detecting breast cancer or for diagnosing breast cancer enables qualitative and/or quantitative measurement of the presence, expression level, or existing amount (abundance) of any of the target nucleic acids as the breast cancer markers described above, for example, human-derived hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p and hsa-miR-4739 or a combination thereof, congeners thereof, transcripts thereof, or variants or derivatives thereof; and, optionally in combination therewith, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p and hsa-miR-92a-3p or a combination thereof, transcripts thereof, or variants or derivatives thereof; and, optionally in combination therewith, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p or a combination thereof; congeners thereof; transcripts thereof; or variants or derivatives thereof.

The expression level of the target nucleic acids described above are increased or decreased (hereinafter, referred to as "increased/decreased") depending on the types of the target nucleic acids in subjects who have breast cancer, as compared with healthy subjects. Hence, the nucleic acid of the present invention can be effectively used for measuring expression levels of the target nucleic acids in body fluids derived from subjects (e.g., humans) suspected of having breast cancer and body fluids derived from healthy subjects and thereby detecting breast cancer through the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 235 and 851 to 856, or a primer for amplifying a polynucleotide consisting of a nucleotide sequence represented by at least one of SEQ ID NOs: 1 to 235 and 851 to 856.

The nucleic acid probe or the primer that can be used in the present invention may further comprise a nucleic acid probe capable of specifically binding to a polynucleotide consisting of a nucleotide sequence represented by at least one of SEQ ID NOs: 236 to 251, or a primer for amplifying a polynucleotide consisting of a nucleotide sequence represented by at least one of SEQ ID NOs: 236 to 251.

The nucleic acid probe or the primer that can be used in the present invention may further comprise a nucleic acid probe capable of specifically binding to a polynucleotide that consists of a nucleotide sequence represented by at least one of SEQ ID NOs: 252 to 269, or a primer for amplifying a polynucleotide that consists of a nucleotide sequence represented by at least one of SEQ ID NOs: 252 to 269.

Specifically, these nucleic acid probes or primers comprise a combination of one or more polynucleotides selected from: a group of polynucleotides that comprise nucleotide sequences represented by any of SEQ ID NOs: 1 to 871 or nucleotide sequences derived from the nucleotide sequences by the replacement of u with t, and a group of complementary polynucleotides thereof, a group of polynucleotides that respectively hybridize under stringent conditions (mentioned later) to DNAs consisting of nucleotide sequences complementary to these nucleotide sequences; and a group of complementary polynucleotides thereof, and a group of polynucleotide comprising 15 or more, preferably 17 or more consecutive nucleotides in the nucleotide sequences of these polynucleotides. These polynucleotides can be used as nucleic acid probes and primers for detecting the breast cancer markers as target nucleic acids.

More specifically, examples of the nucleic acid probes or the primers that can be used in the present invention include one or more polynucleotides selected from the group consisting of the following polynucleotides (a) to (e):

(a) a polynucleotide consisting of a nucleotide sequence represented by any of SEQ ID NOs: 1 to 235, and 851 to 856 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence complementary to a nucleotide sequence represented by any of SEQ ID NOs: 1 to 235, and 851 to 856 or a nucleotide sequence derived from the nucleotide sequence by the replacement of u with t, (c) a polynucleotide consisting of a nucleotide sequence complementary to a nucleotide sequence represented by any of SEQ ID NOs: 1 to 235, and 851 to 856 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 235, and 851 to 856 or a nucleotide sequence derived from the nucleotide sequence by the replacement of u with t, and (e) a polynucleotide hybridizing under stringent conditions to any of the polynucleotides (a) to (d).

In addition to at least one polynucleotide selected from the group consisting of the polynucleotides (a) to (e), the nucleic acid probes or the primers that can be used in the present invention may further comprise a polynucleotide selected from the group consisting of the following polynucleotides (f) to (j):

(f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 236 to 251, (h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 236 to 251 or a nucleotide sequence derived from the nucleotide sequence by the replacement of u with t, and (j) a polynucleotide hybridizing under stringent conditions to any of the polynucleotides (f) to (i).

In addition to at least one polynucleotide selected from the group consisting of (a) to (j) described above, the nucleic acid probes or the primesr that can be used in the present invention may further comprise a polynucleotide selected from the group consisting of the following polynucleotides (k) to (o):

(k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 252 to 269, (m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 252 to 269 or a nucleotide sequence derived from the nucleotide sequence by the replacement of u with t, and (o) a polynucleotide hybridizing under stringent conditions to any of the polynucleotides (k) to (n).

For these polynucleotides, the "fragment thereof comprising 15 or more consecutive nucleotides" can comprise, but is not limited to, the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

These polynucleotides or fragments thereof used in the present invention may each be DNA or may each be RNA.

The polynucleotides that can be used in the present invention can each be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p, hsa-miR-4739, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p, hsa-miR-92a-3p, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p represented by SEQ ID NOs: 1 to 269, and 851 to 856 are known in the art, and their acquisition methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by a cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 269, and 851 to 856 do not exist as miRNAs or precursors thereof in the living body or in vivo. For example, the nucleotide sequences represented by SEQ ID NO: 34 and SEQ ID NO: 205 are produced from the precursor represented by SEQ ID NO: 304. This precursor has a hairpin-like structure as shown in FIG. 1, and the nucleotide sequences represented by SEQ ID NO: 34 and SEQ ID NO: 205 have mismatch sequences with each other. As such, a nucleotide sequence completely complementary to the nucleotide sequence represented by SEQ ID NO: 34 or SEQ ID NO: 205 is not naturally produced in vivo. Likewise, the nucleic acid probe and the primer for detecting the nucleotide sequence represented by any of SEQ ID NOs: 1 to 269, and 851 to 856 have artificial nucleotide sequences that do not exist in the living body or in vivo.

3. Kit or Device for Detection of Breast Cancer

The present invention also provides a kit or a device for the detection of breast cancer, comprising one or more polynucleotides (which may include a variant, a fragment, or a derivative thereof; hereinafter, also referred to as polynucleotide for detection) that can be used as nucleic acid probes or primers in the present invention for measuring target nucleic acids as breast cancer markers.

The target nucleic acid as a breast cancer marker according to the present invention is selected from the following group 1:

miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739.

An additional target nucleic acid(s) that may be optionally used in the measurement is selected from the following group 2:

miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

An additional target nucleic acid(s) that may be optionally used in the measurement is further selected from the following group 3:

miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

The kit or the device of the present invention comprises nucleic acid(s) capable of specifically binding to any of the target nucleic acids as the breast cancer markers described above, preferably one or more polynucleotides selected from the nucleic acid probes or the primers described in the preceding Section 2, specifically, the polynucleotides described in the preceding Section 2, or variants thereof, etc.

Specifically, the kit or the device of the present invention can comprise at least one polynucleotides comprising (or consisting of) a nucleotide sequence represented by any of SEQ ID NOs: 1 to 235, and 851 to 856 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 236 to 251 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 252 to 269 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment(s) that can be comprised in the kit or the device of the present invention is/are, for example, one or more polynucleotides, preferably two or more polynucleotides selected from the group consisting of the following polynucleotides (1) to (3):

(1) a polynucleotide comprising 15 or more consecutive nucleotides in a nucleotide sequence that is derived from a nucleotide sequence represented by any of SEQ ID NOs: 1 to 235, and 851 to 856 by the replacement of u with t, or a complementary sequence thereof;

(2) a polynucleotide comprising 15 or more consecutive nucleotides in a nucleotide sequence that is derived from a nucleotide sequence represented by any of SEQ ID NOs: 236 to 251 by the replacement of u with t, or a complementary sequence thereof; and (3) a polynucleotide comprising 15 or more consecutive nucleotides in a nucleotide sequence that is derived from a nucleotide sequence represented by any of SEQ ID NOs: 252 to 269 by the replacement of u with t, or a complementary sequence thereof.

In a preferred embodiment, the polynucleotide is a polynucleotide consisting of a nucleotide sequence represented by any of SEQ ID NOs: 1 to 235, and 851 to 856 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 236 to 251 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 252 to 269 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned polynucleotide combination that constitutes the kit or the device of the present invention can include combinations of 1, 2, 3, 4, 5, 6, 7, 8, 9, 10 or more of the polynucleotides consisting of the nucleotide sequences represented by SEQ ID NOs: 1 to 269 and 851 to 856 shown in Table 1 described above. However, these are given merely for illustrative purposes, and all of various other possible combinations are included in the present invention.

The aforementioned combination constituting the kit or the device for discriminating a breast cancer patient from a healthy subject according to the present invention is desirably, for example, a combination of two or more polynucleotides consisting of the nucleotide sequences represented by SEQ ID NOs shown in Table 1. Usually, a combination of two of these polynucleotides can produce adequate performance. Specifically, any two of the aforementioned polynucleotides that consist of the aforementioned nucleotide sequences represented by SEQ ID NOs: 1 to 269 and 851 to 856 may be combined. For such a combination, it is preferred to select at least one of the newly found polynucleotides consisting of the nucleotide sequences represented by SEQ ID NOs: 1 to 235 and 851 to 856. More specifically, the combination is more preferably a combination comprising at least one of polynucleotides consisting of the nucleotide sequences represented by SEQ ID NOs: 20, 24, 26, 27, 30, 33, 182, 194, 206, and 208, among the combinations of the polynucleotides consisting of the nucleotide sequences represented by SEQ ID NOs: 1 to 269 and 851 to 856.

The combination of polynucleotides with cancer type specificity capable of discriminating a breast cancer patient not only from a healthy subject but also from other cancer patients is preferably, for example, a combination of multiple polynucleotides comprising at least one polynucleotide selected from the group consisting of polynucleotides consisting of the nucleotide sequences represented by SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 53, 54, 55, 58, 59, 60, 62, 63, 64, 65, 67, 68, 69, 70, 71, 72, 73, 75, 77, 79, 80, 81, 82, 83, 86, 88, 89, 90, 92, 93, 94, 96, 98, 99, 100, 103, 104, 106, 107, 108, 110, 111, 113, 114, 115, 116, 118, 119, 121, 122, 124, 125, 126, 127, 128, 129, 130, 131, 132, 133, 135, 136, 139, 140, 143, 145, 146, 147, 149, 150, 155, 157, 160, 161, 165, 167, 171, 173, 174, 175, 177, 178, 181, 182, 186, 190, 193, 194, 199, 204, 205, 206, 208, 211, 218, 225, 232, 236, 237, 238, 239, 242, 243, 244, 246, 247, 252, 260, 265, 266, 851, 852, 853, 854, 855, 856 (hereinafter, this group is referred to as "cancer type-specific polynucleotide group 1"), with any of the polynucleotides consisting of nucleotide sequences represented by the other SEQ ID NOs.

The combination of polynucleotides with cancer type specificity capable of discriminating a breast cancer patient not only from a healthy subject but also from other cancer patients is more preferably a combination of multiple polynucleotides, any of which are selected from the cancer type-specific polynucleotide group 1 described above.

The combination of polynucleotides with cancer type specificity capable of discriminating a breast cancer patient not only from a healthy subject but also from other cancer patients is more preferably a combination comprising at least one polynucleotide selected from, particularly, the group consisting of polynucleotides of SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 53, 54, 55, 58, 59, 60, 62, 63, 64, 65, 67, 68, 69, 71, 72, 73, 75, 77, 79, 80, 82, 83, 86, 88, 92, 93, 96, 99, 103, 104, 106, 110, 111, 114, 116, 118, 119, 122, 124, 125, 127, 130, 132, 133, 135, 139, 143, 145, 147, 149, 157, 160, 173, 177, 181, 182, 186, 211, 218, 232, 236, 237, 238, 239, 242, 243, 246, 247, 260, 266, 851, 852, 853, 854 (hereinafter, this group is referred to as "cancer type-specific polynucleotide group 2"), among the combinations of multiple polynucleotides selected from the cancer type-specific polynucleotide group 1 described above.

The number of the polynucleotides with cancer type specificity in the combination described above can be 1, 2, 3, 4, 5, 6, 7, 8, 9, 10 or more and is preferably 2 or more for the combination.

Non-limiting examples of the combination of two polynucleotides that consist of one polynucleotide that consists of a nucleotide sequence selected from the cancer type-specific polynucleotide group 2 or a complementary sequence thereof and one polynucleotide that consists of a nucleotide sequence selected from the cancer type-specific polynucleotide group 1 or a complementary sequence thereof are listed below.

(1-1) a combination of SEQ ID NOs: 2 and 1 (markers: hsa-miR-4730 and hsa-miR-4783-3p);
    (1-2) a combination of SEQ ID NOs: 2 and 237 (markers: hsa-miR-4730 and hsa-miR-602);
    (1-3) a combination of SEQ ID NOs: 2 and 4 (markers: hsa-miR-4730 and hsa-miR-4634);
    (1-4) a combination of SEQ ID NOs: 2 and 3 (markers: hsa-miR-4730 and hsa-miR-1307-3p);
    (1-5) a combination of SEQ ID NOs: 2 and 51 (markers: hsa-miR-4730 and hsa-miR-3940-5p);
    (2-1) a combination of SEQ ID NOs: 1 and 237 (markers: hsa-miR-4783-3p and hsa-miR-602);
    (2-2) a combination of SEQ ID NOs: 1 and 4 (markers: hsa-miR-4783-3p and hsa-miR-4634);
    (2-3) a combination of SEQ ID NOs: 1 and 3 (markers: hsa-miR-4783-3p and hsa-miR-1307-3p);
    (2-4) a combination of SEQ ID NOs: 1 and 51 (markers: hsa-miR-4783-3p and hsa-miR-3940-5p);
    (2-5) a combination of SEQ ID NOs: 1 and 6 (markers: hsa-miR-4783-3p and hsa-miR-4532);
    (3-1) a combination of SEQ ID NOs: 4 and 237 (markers: hsa-miR-4634 and hsa-miR-602);

(3-2) a combination of SEQ ID NOs: 3 and 237 (markers: hsa-miR-1307-3p and hsa-miR-602);
(3-3) a combination of SEQ ID NOs: 51 and 237 (markers: hsa-miR-3940-5p and hsa-miR-602);
(3-4) a combination of SEQ ID NOs: 237 and 6 (markers: hsa-miR-602 and hsa-miR-4532);
(3-5) a combination of SEQ ID NOs: 237 and 12 (markers: hsa-miR-602 and hsa-miR-3184-5p);
(4-1) a combination of SEQ ID NOs: 3 and 4 (markers: hsa-miR-1307-3p and hsa-miR-4634);
(4-2) a combination of SEQ ID NOs: 4 and 51 (markers: hsa-miR-4634 and hsa-miR-3940-5p);
(4-3) a combination of SEQ ID NOs: 4 and 6 (markers: hsa-miR-4634 and hsa-miR-4532);
(4-4) a combination of SEQ ID NOs: 4 and 12 (markers: hsa-miR-4634 and hsa-miR-3184-5p);
(4-5) a combination of SEQ ID NOs: 4 and 15 (markers: hsa-miR-4634 and hsa-miR-4674);
(5-1) a combination of SEQ ID NOs: 3 and 51 (markers: hsa-miR-1307-3p and hsa-miR-3940-5p);
(5-2) a combination of SEQ ID NOs: 3 and 6 (markers: hsa-miR-1307-3p and hsa-miR-4532);
(5-3) a combination of SEQ ID NOs: 3 and 12 (markers: hsa-miR-1307-3p and hsa-miR-3184-5p);
(5-4) a combination of SEQ ID NOs: 3 and 15 (markers: hsa-miR-1307-3p and hsa-miR-4674);
(5-5) a combination of SEQ ID NOs: 3 and 8 (markers: hsa-miR-1307-3p and hsa-miR-3178);
(6-1) a combination of SEQ ID NOs: 51 and 6 (markers: hsa-miR-3940-5p and hsa-miR-4532);
(6-2) a combination of SEQ ID NOs: 51 and 12 (markers: hsa-miR-3940-5p and hsa-miR-3184-5p);
(6-3) a combination of SEQ ID NOs: 51 and 15 (markers: hsa-miR-3940-5p and hsa-miR-4674);
(6-4) a combination of SEQ ID NOs: 51 and 8 (markers: hsa-miR-3940-5p and hsa-miR-3178);
(6-5) a combination of SEQ ID NOs: 51 and 34 (markers: hsa-miR-3940-5p and hsa-miR-6805-5p);
(7-1) a combination of SEQ ID NOs: 2 and 6 (markers: hsa-miR-4730 and hsa-miR-4532);
(7-2) a combination of SEQ ID NOs: 12 and 6 (markers: hsa-miR-3184-5p and hsa-miR-4532);
(7-3) a combination of SEQ ID NOs: 15 and 6 (markers: hsa-miR-4674 and hsa-miR-4532);
(7-4) a combination of SEQ ID NOs: 8 and 6 (markers: hsa-miR-3178 and hsa-miR-4532);
(7-5) a combination of SEQ ID NOs: 6 and 34 (markers: hsa-miR-4532 and hsa-miR-6805-5p);
(8-1) a combination of SEQ ID NOs: 2 and 12 (markers: hsa-miR-4730 and hsa-miR-3184-5p);
(8-2) a combination of SEQ ID NOs: 1 and 12 (markers: hsa-miR-4783-3p and hsa-miR-3184-5p);
(8-3) a combination of SEQ ID NOs: 12 and 15 (markers: hsa-miR-3184-5p and hsa-miR-4674);
(8-4) a combination of SEQ ID NOs: 8 and 12 (markers: hsa-miR-3178 and hsa-miR-3184-5p);
(8-5) a combination of SEQ ID NOs: 12 and 34 (markers: hsa-miR-3184-5p and hsa-miR-6805-5p);
(9-1) a combination of SEQ ID NOs: 2 and 15 (markers: hsa-miR-4730 and hsa-miR-4674);
(9-2) a combination of SEQ ID NOs: 1 and 15 (markers: hsa-miR-4783-3p and hsa-miR-4674);
(9-3) a combination of SEQ ID NOs: 237 and 15 (markers: hsa-miR-602 and hsa-miR-4674);
(9-4) a combination of SEQ ID NOs: 8 and 15 (markers: hsa-miR-3178 and hsa-miR-4674);
(9-5) a combination of SEQ ID NOs: 15 and 34 (markers: hsa-miR-4674 and hsa-miR-6805-5p);
(10-1) a combination of SEQ ID NOs: 2 and 8 (markers: hsa-miR-4730 and hsa-miR-3178);
(10-2) a combination of SEQ ID NOs: 1 and 8 (markers: hsa-miR-4783-3p and hsa-miR-3178);
(10-3) a combination of SEQ ID NOs: 237 and 8 (markers: hsa-miR-602 and hsa-miR-3178);
(10-4) a combination of SEQ ID NOs: 4 and 8 (markers: hsa-miR-4634 and hsa-miR-3178);
(10-5) a combination of SEQ ID NOs:8 and 34 (markers: hsa-miR-3178 and hsa-miR-6805-5p);
(11-1) a combination of SEQ ID NOs: 2 and 34 (markers: hsa-miR-4730 and hsa-miR-6805-5p);
(11-2) a combination of SEQ ID NOs: 1 and 34 (markers: hsa-miR-4783-3p and hsa-miR-6805-5p);
(11-3) a combination of SEQ ID NOs: 237 and 34 (markers: hsa-miR-602 and hsa-miR-6805-5p);
(11-4) a combination of SEQ ID NOs: 4 and 34 (markers: hsa-miR-4634 and hsa-miR-6805-5p);
(11-5) a combination of SEQ ID NOs: 3 and 34 (markers: hsa-miR-1307-3p and hsa-miR-6805-5p);
(12-1) a combination of SEQ ID NOs: 2 and 9 (markers: hsa-miR-4730 and hsa-miR-6729-5p);
(12-2) a combination of SEQ ID NOs: 1 and 9 (markers: hsa-miR-4783-3p and hsa-miR-6729-5p);
(12-3) a combination of SEQ ID NOs: 9 and 237 (markers: hsa-miR-6729-5p and hsa-miR-602);
(12-4) a combination of SEQ ID NOs: 4 and 9 (markers: hsa-miR-4634 and hsa-miR-6729-5p);
(12-5) a combination of SEQ ID NOs: 3 and 9 (markers: hsa-miR-1307-3p and hsa-miR-6729-5p);
(13-1) a combination of SEQ ID NOs: 2 and 143 (markers: hsa-miR-4730 and hsa-miR-1228-5p);
(13-2) a combination of SEQ ID NOs: 1 and 143 (markers: hsa-miR-4783-3p and hsa-miR-1228-5p);
(13-3) a combination of SEQ ID NOs: 237 and 143 (markers: hsa-miR-602 and hsa-miR-1228-5p);
(13-4) a combination of SEQ ID NOs: 4 and 143 (markers: hsa-miR-4634 and hsa-miR-1228-5p);
(13-5) a combination of SEQ ID NOs: 3 and 143 (markers: hsa-miR-1307-3p and hsa-miR-1228-5p);
(14-1) a combination of SEQ ID NOs: 2 and 13 (markers: hsa-miR-4730 and hsa-miR-6727-5p);
(14-2) a combination of SEQ ID NOs: 1 and 13 (markers: hsa-miR-4783-3p and hsa-miR-6727-5p);
(14-3) a combination of SEQ ID NOs: 237 and 13 (markers: hsa-miR-602 and hsa-miR-6727-5p);
(14-4) a combination of SEQ ID NOs: 4 and 13 (markers: hsa-miR-4634 and hsa-miR-6727-5p);
(14-5) a combination of SEQ ID NOs: 3 and 13 (markers: hsa-miR-1307-3p and hsa-miR-6727-5p);
(15-1) a combination of SEQ ID NOs: 2 and 125 (markers: hsa-miR-4730 and hsa-miR-6781-5p);
(15-2) a combination of SEQ ID NOs: 1 and 125 (markers: hsa-miR-4783-3p and hsa-miR-6781-5p);
(15-3) a combination of SEQ ID NOs: 237 and 125 (markers: hsa-miR-602 and hsa-miR-6781-5p);
(15-4) a combination of SEQ ID NOs: 4 and 125 (markers: hsa-miR-4634 and hsa-miR-6781-5p);
(15-5) a combination of SEQ ID NOs: 3 and 125 (markers: hsa-miR-1307-3p and hsa-miR-6781-5p);
(16-1) a combination of SEQ ID NOs: 2 and 236 (markers: hsa-miR-4730 and hsa-miR-760);
(16-2) a combination of SEQ ID NOs: 1 and 236 (markers: hsa-miR-4783-3p and hsa-miR-760);

(16-3) a combination of SEQ ID NOs: 237 and 236 (markers: hsa-miR-602 and hsa-miR-760);
(16-4) a combination of SEQ ID NOs: 4 and 236 (markers: hsa-miR-4634 and hsa-miR-760);
(16-5) a combination of SEQ ID NOs: 3 and 236 (markers: hsa-miR-1307-3p and hsa-miR-760);
(17-1) a combination of SEQ ID NOs: 2 and 46 (markers: hsa-miR-4730 and hsa-miR-1231);
(17-2) a combination of SEQ ID NOs: 1 and 46 (markers: hsa-miR-4783-3p and hsa-miR-1231);
(17-3) a combination of SEQ ID NOs: 237 and 46 (markers: hsa-miR-602 and hsa-miR-1231);
(17-4) a combination of SEQ ID NOs: 4 and 46 (markers: hsa-miR-4634 and hsa-miR-1231);
(17-5) a combination of SEQ ID NOs: 3 and 46 (markers: hsa-miR-1307-3p and hsa-miR-1231);
(18-1) a combination of SEQ ID NOs: 2 and 32 (markers: hsa-miR-4730 and hsa-miR-6836-3p);
(18-2) a combination of SEQ ID NOs: 1 and 32 (markers: hsa-miR-4783-3p and hsa-miR-6836-3p);
(18-3) a combination of SEQ ID NOs: 237 and 32 (markers: hsa-miR-602 and hsa-miR-6836-3p);
(18-4) a combination of SEQ ID NOs: 4 and 32 (markers: hsa-miR-4634 and hsa-miR-6836-3p);
(18-5) a combination of SEQ ID NOs: 3 and 32 (markers: hsa-miR-1307-3p and hsa-miR-6836-3p);
(19-1) a combination of SEQ ID NOs: 2 and 62 (markers: hsa-miR-4730 and hsa-miR-4492);
(19-2) a combination of SEQ ID NOs: 1 and 62 (markers: hsa-miR-4783-3p and hsa-miR-4492);
(19-3) a combination of SEQ ID NOs: 237 and 62 (markers: hsa-miR-602 and hsa-miR-4492);
(19-4) a combination of SEQ ID NOs: 4 and 62 (markers: hsa-miR-4634 and hsa-miR-4492);
(19-5) a combination of SEQ ID NOs: 3 and 62 (markers: hsa-miR-1307-3p and hsa-miR-4492);
(20-1) a combination of SEQ ID NOs: 2 and 88 (markers: hsa-miR-4730 and hsa-miR-4484);
(20-2) a combination of SEQ ID NOs: 1 and 88 (markers: hsa-miR-4783-3p and hsa-miR-4484);
(20-3) a combination of SEQ ID NOs: 237 and 88 (markers: hsa-miR-602 and hsa-miR-4484);
(20-4) a combination of SEQ ID NOs: 4 and 88 (markers: hsa-miR-4634 and hsa-miR-4484);
(20-5) a combination of SEQ ID NOs: 3 and 88 (markers: hsa-miR-1307-3p and hsa-miR-4484);
(21-1) a combination of SEQ ID NOs: 2 and 52 (markers: hsa-miR-4730 and hsa-miR-4741);
(21-2) a combination of SEQ ID NOs: 1 and 52 (markers: hsa-miR-4783-3p and hsa-miR-4741);
(21-3) a combination of SEQ ID NOs: 237 and 52 (markers: hsa-miR-602 and hsa-miR-4741);
(21-4) a combination of SEQ ID NOs: 4 and 52 (markers: hsa-miR-4634 and hsa-miR-4741);
(21-5) a combination of SEQ ID NOs: 3 and 52 (markers: hsa-miR-1307-3p and hsa-miR-4741);
(22-1) a combination of SEQ ID NOs: 2 and 7 (markers: hsa-miR-4730 and hsa-miR-7704);
(22-2) a combination of SEQ ID NOs: 1 and 7 (markers: hsa-miR-4783-3p and hsa-miR-7704);
(22-3) a combination of SEQ ID NOs: 237 and 7 (markers: hsa-miR-602 and hsa-miR-7704);
(22-4) a combination of SEQ ID NOs: 4 and 7 (markers: hsa-miR-4634 and hsa-miR-7704);
(22-5) a combination of SEQ ID NOs: 3 and 7 (markers: hsa-miR-1307-3p and hsa-miR-7704);
(23-1) a combination of SEQ ID NOs: 2 and 26 (markers: hsa-miR-4730 and hsa-miR-6875-5p);
(23-2) a combination of SEQ ID NOs: 1 and 26 (markers: hsa-miR-4783-3p and hsa-miR-6875-5p);
(23-3) a combination of SEQ ID NOs: 237 and 26 (markers: hsa-miR-602 and hsa-miR-6875-5p);
(23-4) a combination of SEQ ID NOs: 4 and 26 (markers: hsa-miR-4634 and hsa-miR-6875-5p);
(23-5) a combination of SEQ ID NOs: 3 and 26 (markers: hsa-miR-1307-3p and hsa-miR-6875-5p);
(24-1) a combination of SEQ ID NOs: 2 and 25 (markers: hsa-miR-4730 and hsa-miR-8069);
(24-2) a combination of SEQ ID NOs: 1 and 25 (markers: hsa-miR-4783-3p and hsa-miR-8069);
(24-3) a combination of SEQ ID NOs: 237 and 25 (markers: hsa-miR-602 and hsa-miR-8069);
(24-4) a combination of SEQ ID NOs: 4 and 25 (markers: hsa-miR-4634 and hsa-miR-8069);
(24-5) a combination of SEQ ID NOs: 3 and 25 (markers: hsa-miR-1307-3p and hsa-miR-8069);
(25-1) a combination of SEQ ID NOs: 2 and 54 (markers: hsa-miR-4730 and hsa-miR-6869-5p);
(25-2) a combination of SEQ ID NOs: 1 and 54 (markers: hsa-miR-4783-3p and hsa-miR-6869-5p);
(25-3) a combination of SEQ ID NOs: 237 and 54 (markers: hsa-miR-602 and hsa-miR-6869-5p);
(25-4) a combination of SEQ ID NOs: 4 and 54 (markers: hsa-miR-4634 and hsa-miR-6869-5p);
(25-5) a combination of SEQ ID NOs: 3 and 54 (markers: hsa-miR-1307-3p and hsa-miR-6869-5p);
(26-1) a combination of SEQ ID NOs: 2 and 92 (markers: hsa-miR-4730 and hsa-miR-4725-3p);
(26-2) a combination of SEQ ID NOs: 1 and 92 (markers: hsa-miR-4783-3p and hsa-miR-4725-3p);
(26-3) a combination of SEQ ID NOs: 237 and 92 (markers: hsa-miR-602 and hsa-miR-4725-3p);
(26-4) a combination of SEQ ID NOs: 4 and 92 (markers: hsa-miR-4634 and hsa-miR-4725-3p);
(26-5) a combination of SEQ ID NOs: 3 and 92 (markers: hsa-miR-1307-3p and hsa-miR-4725-3p);
(27-1) a combination of SEQ ID NOs: 2 and 14 (markers: hsa-miR-4730 and hsa-miR-6088);
(27-2) a combination of SEQ ID NOs: 1 and 14 (markers: hsa-miR-4783-3p and hsa-miR-6088);
(27-3) a combination of SEQ ID NOs: 237 and 14 (markers: hsa-miR-602 and hsa-miR-6088);
(27-4) a combination of SEQ ID NOs: 4 and 14 (markers: hsa-miR-4634 and hsa-miR-6088);
(27-5) a combination of SEQ ID NOs: 3 and 14 (markers: hsa-miR-1307-3p and hsa-miR-6088);
(28-1) a combination of SEQ ID NOs: 2 and 242 (markers: hsa-miR-4730 and hsa-miR-135a-3p);
(28-2) a combination of SEQ ID NOs: 1 and 242 (markers: hsa-miR-4783-3p and hsa-miR-135a-3p);
(28-3) a combination of SEQ ID NOs: 237 and 242 (markers: hsa-miR-602 and hsa-miR-135a-3p);
(28-4) a combination of SEQ ID NOs: 4 and 242 (markers: hsa-miR-4634 and hsa-miR-135a-3p);
(28-5) a combination of SEQ ID NOs: 3 and 242 (markers: hsa-miR-1307-3p and hsa-miR-135a-3p);
(29-1) a combination of SEQ ID NOs: 2 and 47 (markers: hsa-miR-4730 and hsa-miR-1908-3p);
(29-2) a combination of SEQ ID NOs: 1 and 47 (markers: hsa-miR-4783-3p and hsa-miR-1908-3p);
(29-3) a combination of SEQ ID NOs: 237 and 47 (markers: hsa-miR-602 and hsa-miR-1908-3p);

(29-4) a combination of SEQ ID NOs: 4 and 47 (markers: hsa-miR-4634 and hsa-miR-1908-3p);
(29-5) a combination of SEQ ID NOs: 3 and 47 (markers: hsa-miR-1307-3p and hsa-miR-1908-3p);
(30-1) a combination of SEQ ID NOs: 2 and 45 (markers: hsa-miR-4730 and hsa-miR-6771-5p);
(30-2) a combination of SEQ ID NOs: 1 and 45 (markers: hsa-miR-4783-3p and hsa-miR-6771-5p);
(30-3) a combination of SEQ ID NOs: 237 and 45 (markers: hsa-miR-602 and hsa-miR-6771-5p);
(30-4) a combination of SEQ ID NOs: 4 and 45 (markers: hsa-miR-4634 and hsa-miR-6771-5p);
(30-5) a combination of SEQ ID NOs: 3 and 45 (markers: hsa-miR-1307-3p and hsa-miR-6771-5p);
(31-1) a combination of SEQ ID NOs: 2 and 39 (markers: hsa-miR-4730 and hsa-miR-6850-5p);
(31-2) a combination of SEQ ID NOs: 1 and 39 (markers: hsa-miR-4783-3p and hsa-miR-6850-5p);
(31-3) a combination of SEQ ID NOs: 237 and 39 (markers: hsa-miR-602 and hsa-miR-6850-5p);
(31-4) a combination of SEQ ID NOs: 4 and 39 (markers: hsa-miR-4634 and hsa-miR-6850-5p);
(31-5) a combination of SEQ ID NOs: 3 and 39 (markers: hsa-miR-1307-3p and hsa-miR-6850-5p);
(32-1) a combination of SEQ ID NOs: 2 and 21 (markers: hsa-miR-4730 and hsa-miR-885-3p);
(32-2) a combination of SEQ ID NOs: 1 and 21 (markers: hsa-miR-4783-3p and hsa-miR-885-3p);
(32-3) a combination of SEQ ID NOs: 237 and 21 (markers: hsa-miR-602 and hsa-miR-885-3p);
(32-4) a combination of SEQ ID NOs: 4 and 21 (markers: hsa-miR-4634 and hsa-miR-885-3p);
(32-5) a combination of SEQ ID NOs: 3 and 21 (markers: hsa-miR-1307-3p and hsa-miR-885-3p);
(33-1) a combination of SEQ ID NOs: 2 and 17 (markers: hsa-miR-4730 and hsa-miR-4787-5p);
(33-2) a combination of SEQ ID NOs: 1 and 17 (markers: hsa-miR-4783-3p and hsa-miR-4787-5p);
(33-3) a combination of SEQ ID NOs: 237 and 17 (markers: hsa-miR-602 and hsa-miR-4787-5p);
(33-4) a combination of SEQ ID NOs: 4 and 17 (markers: hsa-miR-4634 and hsa-miR-4787-5p);
(33-5) a combination of SEQ ID NOs: 3 and 17 (markers: hsa-miR-1307-3p and hsa-miR-4787-5p);
(34-1) a combination of SEQ ID NOs: 2 and 83 (markers: hsa-miR-4730 and hsa-miR-1909-3p);
(34-2) a combination of SEQ ID NOs: 1 and 83 (markers: hsa-miR-4783-3p and hsa-miR-1909-3p);
(34-3) a combination of SEQ ID NOs: 237 and 83 (markers: hsa-miR-602 and hsa-miR-1909-3p);
(34-4) a combination of SEQ ID NOs: 4 and 83 (markers: hsa-miR-4634 and hsa-miR-1909-3p);
(34-5) a combination of SEQ ID NOs: 3 and 83 (markers: hsa-miR-1307-3p and hsa-miR-1909-3p);
(35-1) a combination of SEQ ID NOs: 2 and 149 (markers: hsa-miR-4730 and hsa-miR-638);
(35-2) a combination of SEQ ID NOs: 1 and 149 (markers: hsa-miR-4783-3p and hsa-miR-638);
(35-3) a combination of SEQ ID NOs: 237 and 149 (markers: hsa-miR-602 and hsa-miR-638);
(35-4) a combination of SEQ ID NOs: 4 and 149 (markers: hsa-miR-4634 and hsa-miR-638);
(35-5) a combination of SEQ ID NOs: 3 and 149 (markers: hsa-miR-1307-3p and hsa-miR-638);
(36-1) a combination of SEQ ID NOs: 2 and 246 (markers: hsa-miR-4730 and hsa-miR-1915-3p);
(36-2) a combination of SEQ ID NOs: 1 and 246 (markers: hsa-miR-4783-3p and hsa-miR-1915-3p);
(36-3) a combination of SEQ ID NOs: 237 and 246 (markers: hsa-miR-602 and hsa-miR-1915-3p);
(36-4) a combination of SEQ ID NOs: 4 and 246 (markers: hsa-miR-4634 and hsa-miR-1915-3p);
(36-5) a combination of SEQ ID NOs: 3 and 246 (markers: hsa-miR-1307-3p and hsa-miR-1915-3p);
(37-1) a combination of SEQ ID NOs: 2 and 22 (markers: hsa-miR-4730 and hsa-miR-6802-5p);
(37-2) a combination of SEQ ID NOs: 1 and 22 (markers: hsa-miR-4783-3p and hsa-miR-6802-5p);
(37-3) a combination of SEQ ID NOs: 237 and 22 (markers: hsa-miR-602 and hsa-miR-6802-5p);
(37-4) a combination of SEQ ID NOs: 4 and 22 (markers: hsa-miR-4634 and hsa-miR-6802-5p);
(37-5) a combination of SEQ ID NOs: 3 and 22 (markers: hsa-miR-1307-3p and hsa-miR-6802-5p);
(38-1) a combination of SEQ ID NOs: 2 and 55 (markers: hsa-miR-4730 and hsa-miR-5090);
(38-2) a combination of SEQ ID NOs: 1 and 55 (markers: hsa-miR-4783-3p and hsa-miR-5090);
(38-3) a combination of SEQ ID NOs: 237 and 55 (markers: hsa-miR-602 and hsa-miR-5090);
(38-4) a combination of SEQ ID NOs: 4 and 55 (markers: hsa-miR-4634 and hsa-miR-5090);
(38-5) a combination of SEQ ID NOs: 3 and 55 (markers: hsa-miR-1307-3p and hsa-miR-5090);
(39-1) a combination of SEQ ID NOs: 2 and 182 (markers: hsa-miR-4730 and hsa-miR-3196);
(39-2) a combination of SEQ ID NOs: 1 and 182 (markers: hsa-miR-4783-3p and hsa-miR-3196);
(39-3) a combination of SEQ ID NOs: 237 and 182 (markers: hsa-miR-602 and hsa-miR-3196);
(39-4) a combination of SEQ ID NOs: 4 and 182 (markers: hsa-miR-4634 and hsa-miR-3196);
(39-5) a combination of SEQ ID NOs: 3 and 182 (markers: hsa-miR-1307-3p and hsa-miR-3196);
(40-1) a combination of SEQ ID NOs: 2 and 73 (markers: hsa-miR-4730 and hsa-miR-4707-3p);
(40-2) a combination of SEQ ID NOs: 1 and 73 (markers: hsa-miR-4783-3p and hsa-miR-4707-3p);
(40-3) a combination of SEQ ID NOs: 237 and 73 (markers: hsa-miR-602 and hsa-miR-4707-3p);
(40-4) a combination of SEQ ID NOs: 4 and 73 (markers: hsa-miR-4634 and hsa-miR-4707-3p);
(40-5) a combination of SEQ ID NOs: 3 and 73 (markers: hsa-miR-1307-3p and hsa-miR-4707-3p);
(41-1) a combination of SEQ ID NOs: 2 and 77 (markers: hsa-miR-4730 and hsa-miR-4651);
(41-2) a combination of SEQ ID NOs: 1 and 77 (markers: hsa-miR-4783-3p and hsa-miR-4651);
(41-3) a combination of SEQ ID NOs: 237 and 77 (markers: hsa-miR-602 and hsa-miR-4651);
(41-4) a combination of SEQ ID NOs: 4 and 77 (markers: hsa-miR-4634 and hsa-miR-4651);
(41-5) a combination of SEQ ID NOs: 3 and 77 (markers: hsa-miR-1307-3p and hsa-miR-4651);
(42-1) a combination of SEQ ID NOs: 2 and 24 (markers: hsa-miR-4730 and hsa-miR-6787-5p);
(42-2) a combination of SEQ ID NOs: 1 and 24 (markers: hsa-miR-4783-3p and hsa-miR-6787-5p);
(42-3) a combination of SEQ ID NOs: 237 and 24 (markers: hsa-miR-602 and hsa-miR-6787-5p);
(42-4) a combination of SEQ ID NOs: 4 and 24 (markers: hsa-miR-4634 and hsa-miR-6787-5p);

(42-5) a combination of SEQ ID NOs: 3 and 24 (markers: hsa-miR-1307-3p and hsa-miR-6787-5p);
(43-1) a combination of SEQ ID NOs: 2 and 103 (markers: hsa-miR-4730 and hsa-miR-3180-3p);
(43-2) a combination of SEQ ID NOs: 1 and 103 (markers: hsa-miR-4783-3p and hsa-miR-3180-3p);
(43-3) a combination of SEQ ID NOs: 237 and 103 (markers: hsa-miR-602 and hsa-miR-3180-3p);
(43-4) a combination of SEQ ID NOs: 4 and 103 (markers: hsa-miR-4634 and hsa-miR-3180-3p);
(43-5) a combination of SEQ ID NOs: 3 and 103 (markers: hsa-miR-1307-3p and hsa-miR-3180-3p);
(44-1) a combination of SEQ ID NOs: 2 and 49 (markers: hsa-miR-4730 and hsa-miR-3937);
(44-2) a combination of SEQ ID NOs: 1 and 49 (markers: hsa-miR-4783-3p and hsa-miR-3937);
(44-3) a combination of SEQ ID NOs: 237 and 49 (markers: hsa-miR-602 and hsa-miR-3937);
(44-4) a combination of SEQ ID NOs: 4 and 49 (markers: hsa-miR-4634 and hsa-miR-3937);
(44-5) a combination of SEQ ID NOs: 3 and 49 (markers: hsa-miR-1307-3p and hsa-miR-3937);
(45-1) a combination of SEQ ID NOs: 2 and 239 (markers: hsa-miR-4730 and hsa-miR-92a-2-5p);
(45-2) a combination of SEQ ID NOs: 1 and 239 (markers: hsa-miR-4783-3p and hsa-miR-92a-2-5p);
(45-3) a combination of SEQ ID NOs: 237 and 239 (markers: hsa-miR-602 and hsa-miR-92a-2-5p);
(45-4) a combination of SEQ ID NOs: 4 and 239 (markers: hsa-miR-4634 and hsa-miR-92a-2-5p);
(45-5) a combination of SEQ ID NOs: 3 and 239 (markers: hsa-miR-1307-3p and hsa-miR-92a-2-5p);
(46-1) a combination of SEQ ID NOs: 2 and 23 (markers: hsa-miR-4730 and hsa-miR-328-5p);
(46-2) a combination of SEQ ID NOs: 1 and 23 (markers: hsa-miR-4783-3p and hsa-miR-328-5p);
(46-3) a combination of SEQ ID NOs: 237 and 23 (markers: hsa-miR-602 and hsa-miR-328-5p);
(46-4) a combination of SEQ ID NOs: 4 and 23 (markers: hsa-miR-4634 and hsa-miR-328-5p);
(46-5) a combination of SEQ ID NOs: 3 and 23 (markers: hsa-miR-1307-3p and hsa-miR-328-5p);
(47-1) a combination of SEQ ID NOs: 2 and 58 (markers: hsa-miR-4730 and hsa-miR-128-1-5p);
(47-2) a combination of SEQ ID NOs: 1 and 58 (markers: hsa-miR-4783-3p and hsa-miR-128-1-5p);
(47-3) a combination of SEQ ID NOs: 237 and 58 (markers: hsa-miR-602 and hsa-miR-128-1-5p);
(47-4) a combination of SEQ ID NOs: 4 and 58 (markers: hsa-miR-4634 and hsa-miR-128-1-5p);
(47-5) a combination of SEQ ID NOs: 3 and 58 (markers: hsa-miR-1307-3p and hsa-miR-128-1-5p);
(48-1) a combination of SEQ ID NOs: 2 and 211 (markers: hsa-miR-4730 and hsa-miR-6765-5p);
(48-2) a combination of SEQ ID NOs: 1 and 211 (markers: hsa-miR-4783-3p and hsa-miR-6765-5p);
(48-3) a combination of SEQ ID NOs: 237 and 211 (markers: hsa-miR-602 and hsa-miR-6765-5p);
(48-4) a combination of SEQ ID NOs: 4 and 211 (markers: hsa-miR-4634 and hsa-miR-6765-5p);
(48-5) a combination of SEQ ID NOs: 3 and 211 (markers: hsa-miR-1307-3p and hsa-miR-6765-5p);
(49-1) a combination of SEQ ID NOs: 2 and 147 (markers: hsa-miR-4730 and hsa-miR-6786-5p);
(49-2) a combination of SEQ ID NOs: 1 and 147 (markers: hsa-miR-4783-3p and hsa-miR-6786-5p);
(49-3) a combination of SEQ ID NOs: 237 and 147 (markers: hsa-miR-602 and hsa-miR-6786-5p);
(49-4) a combination of SEQ ID NOs: 4 and 147 (markers: hsa-miR-4634 and hsa-miR-6786-5p);
(49-5) a combination of SEQ ID NOs: 3 and 147 (markers: hsa-miR-1307-3p and hsa-miR-6786-5p);
(50-1) a combination of SEQ ID NOs: 2 and 65 (markers: hsa-miR-4730 and hsa-miR-4525);
(50-2) a combination of SEQ ID NOs: 1 and 65 (markers: hsa-miR-4783-3p and hsa-miR-4525);
(50-3) a combination of SEQ ID NOs: 237 and 65 (markers: hsa-miR-602 and hsa-miR-4525);
(50-4) a combination of SEQ ID NOs: 4 and 65 (markers: hsa-miR-4634 and hsa-miR-4525);
(50-5) a combination of SEQ ID NOs: 3 and 65 (markers: hsa-miR-1307-3p and hsa-miR-4525);
(51-1) a combination of SEQ ID NOs: 2 and 31 (markers: hsa-miR-4730 and hsa-miR-3665);
(51-2) a combination of SEQ ID NOs: 1 and 31 (markers: hsa-miR-4783-3p and hsa-miR-3665);
(51-3) a combination of SEQ ID NOs: 237 and 31 (markers: hsa-miR-602 and hsa-miR-3665);
(51-4) a combination of SEQ ID NOs: 4 and 31 (markers: hsa-miR-4634 and hsa-miR-3665);
(51-5) a combination of SEQ ID NOs: 3 and 31 (markers: hsa-miR-1307-3p and hsa-miR-3665);
(52-1) a combination of SEQ ID NOs: 2 and 72 (markers: hsa-miR-4730 and hsa-miR-663b);
(52-2) a combination of SEQ ID NOs: 1 and 72 (markers: hsa-miR-4783-3p and hsa-miR-663b);
(52-3) a combination of SEQ ID NOs: 237 and 72 (markers: hsa-miR-602 and hsa-miR-663b);
(52-4) a combination of SEQ ID NOs: 4 and 72 (markers: hsa-miR-4634 and hsa-miR-663b);
(52-5) a combination of SEQ ID NOs: 3 and 72 (markers: hsa-miR-1307-3p and hsa-miR-663b);
(53-1) a combination of SEQ ID NOs: 2 and 63 (markers: hsa-miR-4730 and hsa-miR-6785-5p);
(53-2) a combination of SEQ ID NOs: 1 and 63 (markers: hsa-miR-4783-3p and hsa-miR-6785-5p);
(53-3) a combination of SEQ ID NOs: 237 and 63 (markers: hsa-miR-602 and hsa-miR-6785-5p);
(53-4) a combination of SEQ ID NOs: 4 and 63 (markers: hsa-miR-4634 and hsa-miR-6785-5p);
(53-5) a combination of SEQ ID NOs: 3 and 63 (markers: hsa-miR-1307-3p and hsa-miR-6785-5p);
(54-1) a combination of SEQ ID NOs: 2 and 80 (markers: hsa-miR-4730 and hsa-miR-4758-5p);
(54-2) a combination of SEQ ID NOs: 1 and 80 (markers: hsa-miR-4783-3p and hsa-miR-4758-5p);
(54-3) a combination of SEQ ID NOs: 237 and 80 (markers: hsa-miR-602 and hsa-miR-4758-5p);
(54-4) a combination of SEQ ID NOs: 4 and 80 (markers: hsa-miR-4634 and hsa-miR-4758-5p);
(54-5) a combination of SEQ ID NOs: 3 and 80 (markers: hsa-miR-1307-3p and hsa-miR-4758-5p);
(55-1) a combination of SEQ ID NOs: 2 and 37 (markers: hsa-miR-4730 and hsa-miR-197-5p);
(55-2) a combination of SEQ ID NOs: 1 and 37 (markers: hsa-miR-4783-3p and hsa-miR-197-5p);
(55-3) a combination of SEQ ID NOs: 237 and 37 (markers: hsa-miR-602 and hsa-miR-197-5p);
(55-4) a combination of SEQ ID NOs: 4 and 37 (markers: hsa-miR-4634 and hsa-miR-197-5p);
(55-5) a combination of SEQ ID NOs: 3 and 37 (markers: hsa-miR-1307-3p and hsa-miR-197-5p);

(56-1) a combination of SEQ ID NOs: 2 and 67 (markers: hsa-miR-4730 and hsa-miR-3180);
(56-2) a combination of SEQ ID NOs: 1 and 67 (markers: hsa-miR-4783-3p and hsa-miR-3180);
(56-3) a combination of SEQ ID NOs: 237 and 67 (markers: hsa-miR-602 and hsa-miR-3180);
(56-4) a combination of SEQ ID NOs: 4 and 67 (markers: hsa-miR-4634 and hsa-miR-3180);
(56-5) a combination of SEQ ID NOs: 3 and 67 (markers: hsa-miR-1307-3p and hsa-miR-3180);
(57-1) a combination of SEQ ID NOs: 2 and 232 (markers: hsa-miR-4730 and hsa-miR-6125);
(57-2) a combination of SEQ ID NOs: 1 and 232 (markers: hsa-miR-4783-3p and hsa-miR-6125);
(57-3) a combination of SEQ ID NOs: 237 and 232 (markers: hsa-miR-602 and hsa-miR-6125);
(57-4) a combination of SEQ ID NOs: 4 and 232 (markers: hsa-miR-4634 and hsa-miR-6125);
(57-5) a combination of SEQ ID NOs: 3 and 232 (markers: hsa-miR-1307-3p and hsa-miR-6125);
(58-1) a combination of SEQ ID NOs: 2 and 127 (markers: hsa-miR-4730 and hsa-miR-4446-3p);
(58-2) a combination of SEQ ID NOs: 1 and 127 (markers: hsa-miR-4783-3p and hsa-miR-4446-3p);
(58-3) a combination of SEQ ID NOs: 237 and 127 (markers: hsa-miR-602 and hsa-miR-4446-3p);
(58-4) a combination of SEQ ID NOs: 4 and 127 (markers: hsa-miR-4634 and hsa-miR-4446-3p);
(58-5) a combination of SEQ ID NOs: 3 and 127 (markers: hsa-miR-1307-3p and hsa-miR-4446-3p);
(59-1) a combination of SEQ ID NOs: 2 and 145 (markers: hsa-miR-4730 and hsa-miR-1268a);
(59-2) a combination of SEQ ID NOs: 1 and 145 (markers: hsa-miR-4783-3p and hsa-miR-1268a);
(59-3) a combination of SEQ ID NOs: 237 and 145 (markers: hsa-miR-602 and hsa-miR-1268a);
(59-4) a combination of SEQ ID NOs: 4 and 145 (markers: hsa-miR-4634 and hsa-miR-1268a);
(59-5) a combination of SEQ ID NOs: 3 and 145 (markers: hsa-miR-1307-3p and hsa-miR-1268a);
(60-1) a combination of SEQ ID NOs: 2 and 16 (markers: hsa-miR-4730 and hsa-miR-8073);
(60-2) a combination of SEQ ID NOs: 1 and 16 (markers: hsa-miR-4783-3p and hsa-miR-8073);
(60-3) a combination of SEQ ID NOs: 237 and 16 (markers: hsa-miR-602 and hsa-miR-8073);
(60-4) a combination of SEQ ID NOs: 4 and 16 (markers: hsa-miR-4634 and hsa-miR-8073);
(60-5) a combination of SEQ ID NOs: 3 and 16 (markers: hsa-miR-1307-3p and hsa-miR-8073);
(61-1) a combination of SEQ ID NOs: 2 and 11 (markers: hsa-miR-4730 and hsa-miR-4732-5p);
(61-2) a combination of SEQ ID NOs: 1 and 11 (markers: hsa-miR-4783-3p and hsa-miR-4732-5p);
(61-3) a combination of SEQ ID NOs: 237 and 11 (markers: hsa-miR-602 and hsa-miR-4732-5p);
(61-4) a combination of SEQ ID NOs: 4 and 11 (markers: hsa-miR-4634 and hsa-miR-4732-5p);
(61-5) a combination of SEQ ID NOs: 3 and 11 (markers: hsa-miR-1307-3p and hsa-miR-4732-5p);
(62-1) a combination of SEQ ID NOs: 2 and 186 (markers: hsa-miR-4730 and hsa-miR-6789-5p);
(62-2) a combination of SEQ ID NOs: 1 and 186 (markers: hsa-miR-4783-3p and hsa-miR-6789-5p);
(62-3) a combination of SEQ ID NOs: 237 and 186 (markers: hsa-miR-602 and hsa-miR-6789-5p);
(62-4) a combination of SEQ ID NOs: 4 and 186 (markers: hsa-miR-4634 and hsa-miR-6789-5p);
(62-5) a combination of SEQ ID NOs: 3 and 186 (markers: hsa-miR-1307-3p and hsa-miR-6789-5p);
(63-1) a combination of SEQ ID NOs: 2 and 50 (markers: hsa-miR-4730 and hsa-miR-887-3p);
(63-2) a combination of SEQ ID NOs: 1 and 50 (markers: hsa-miR-4783-3p and hsa-miR-887-3p);
(63-3) a combination of SEQ ID NOs: 237 and 50 (markers: hsa-miR-602 and hsa-miR-887-3p);
(63-4) a combination of SEQ ID NOs: 4 and 50 (markers: hsa-miR-4634 and hsa-miR-887-3p);
(63-5) a combination of SEQ ID NOs: 3 and 50 (markers: hsa-miR-1307-3p and hsa-miR-887-3p);
(64-1) a combination of SEQ ID NOs: 2 and 69 (markers: hsa-miR-4730 and hsa-miR-1199-5p);
(64-2) a combination of SEQ ID NOs: 1 and 69 (markers: hsa-miR-4783-3p and hsa-miR-1199-5p);
(64-3) a combination of SEQ ID NOs: 237 and 69 (markers: hsa-miR-602 and hsa-miR-1199-5p);
(64-4) a combination of SEQ ID NOs: 4 and 69 (markers: hsa-miR-4634 and hsa-miR-1199-5p);
(64-5) a combination of SEQ ID NOs: 3 and 69 (markers: hsa-miR-1307-3p and hsa-miR-1199-5p);
(65-1) a combination of SEQ ID NOs: 2 and 33 (markers: hsa-miR-4730 and hsa-miR-6821-5p);
(65-2) a combination of SEQ ID NOs: 1 and 33 (markers: hsa-miR-4783-3p and hsa-miR-6821-5p);
(65-3) a combination of SEQ ID NOs: 237 and 33 (markers: hsa-miR-602 and hsa-miR-6821-5p);
(65-4) a combination of SEQ ID NOs: 4 and 33 (markers: hsa-miR-4634 and hsa-miR-6821-5p);
(65-5) a combination of SEQ ID NOs: 3 and 33 (markers: hsa-miR-1307-3p and hsa-miR-6821-5p);
(66-1) a combination of SEQ ID NOs: 2 and 247 (markers: hsa-miR-4730 and hsa-miR-718);
(66-2) a combination of SEQ ID NOs: 1 and 247 (markers: hsa-miR-4783-3p and hsa-miR-718);
(66-3) a combination of SEQ ID NOs: 237 and 247 (markers: hsa-miR-602 and hsa-miR-718);
(66-4) a combination of SEQ ID NOs: 4 and 247 (markers: hsa-miR-4634 and hsa-miR-718);
(66-5) a combination of SEQ ID NOs: 3 and 247 (markers: hsa-miR-1307-3p and hsa-miR-718);
(67-1) a combination of SEQ ID NOs: 2 and 36 (markers: hsa-miR-4730 and hsa-miR-6726-5p);
(67-2) a combination of SEQ ID NOs: 1 and 36 (markers: hsa-miR-4783-3p and hsa-miR-6726-5p);
(67-3) a combination of SEQ ID NOs: 237 and 36 (markers: hsa-miR-602 and hsa-miR-6726-5p);
(67-4) a combination of SEQ ID NOs: 4 and 36 (markers: hsa-miR-4634 and hsa-miR-6726-5p);
(67-5) a combination of SEQ ID NOs: 3 and 36 (markers: hsa-miR-1307-3p and hsa-miR-6726-5p);
(68-1) a combination of SEQ ID NOs: 2 and 218 (markers: hsa-miR-4730 and hsa-miR-6784-5p);
(68-2) a combination of SEQ ID NOs: 1 and 218 (markers: hsa-miR-4783-3p and hsa-miR-6784-5p);
(68-3) a combination of SEQ ID NOs: 237 and 218 (markers: hsa-miR-602 and hsa-miR-6784-5p);
(68-4) a combination of SEQ ID NOs: 4 and 218 (markers: hsa-miR-4634 and hsa-miR-6784-5p);
(68-5) a combination of SEQ ID NOs: 3 and 218 (markers: hsa-miR-1307-3p and hsa-miR-6784-5p);
(69-1) a combination of SEQ ID NOs: 2 and 43 (markers: hsa-miR-4730 and hsa-miR-4763-3p);

(69-2) a combination of SEQ ID NOs: 1 and 43 (markers: hsa-miR-4783-3p and hsa-miR-4763-3p);
(69-3) a combination of SEQ ID NOs: 237 and 43 (markers: hsa-miR-602 and hsa-miR-4763-3p);
(69-4) a combination of SEQ ID NOs: 4 and 43 (markers: hsa-miR-4634 and hsa-miR-4763-3p);
(69-5) a combination of SEQ ID NOs: 3 and 43 (markers: hsa-miR-1307-3p and hsa-miR-4763-3p);
(70-1) a combination of SEQ ID NOs: 2 and 29 (markers: hsa-miR-4730 and hsa-miR-6757-5p);
(70-2) a combination of SEQ ID NOs: 1 and 29 (markers: hsa-miR-4783-3p and hsa-miR-6757-5p);
(70-3) a combination of SEQ ID NOs: 237 and 29 (markers: hsa-miR-602 and hsa-miR-6757-5p);
(70-4) a combination of SEQ ID NOs: 4 and 29 (markers: hsa-miR-4634 and hsa-miR-6757-5p);
(70-5) a combination of SEQ ID NOs: 3 and 29 (markers: hsa-miR-1307-3p and hsa-miR-6757-5p);
(71-1) a combination of SEQ ID NOs: 2 and 110 (markers: hsa-miR-4730 and hsa-miR-665);
(71-2) a combination of SEQ ID NOs: 1 and 110 (markers: hsa-miR-4783-3p and hsa-miR-665);
(71-3) a combination of SEQ ID NOs: 237 and 110 (markers: hsa-miR-602 and hsa-miR-665);
(71-4) a combination of SEQ ID NOs: 4 and 110 (markers: hsa-miR-4634 and hsa-miR-665);
(71-5) a combination of SEQ ID NOs: 3 and 110 (markers: hsa-miR-1307-3p and hsa-miR-665);
(72-1) a combination of SEQ ID NOs: 2 and 20 (markers: hsa-miR-4730 and hsa-miR-1233-5p);
(72-2) a combination of SEQ ID NOs: 1 and 20 (markers: hsa-miR-4783-3p and hsa-miR-1233-5p);
(72-3) a combination of SEQ ID NOs: 237 and 20 (markers: hsa-miR-602 and hsa-miR-1233-5p);
(72-4) a combination of SEQ ID NOs: 4 and 20 (markers: hsa-miR-4634 and hsa-miR-1233-5p);
(72-5) a combination of SEQ ID NOs: 3 and 20 (markers: hsa-miR-1307-3p and hsa-miR-1233-5p);
(73-1) a combination of SEQ ID NOs: 2 and 157 (markers: hsa-miR-4730 and hsa-miR-1268b);
(73-2) a combination of SEQ ID NOs: 1 and 157 (markers: hsa-miR-4783-3p and hsa-miR-1268b);
(73-3) a combination of SEQ ID NOs: 237 and 157 (markers: hsa-miR-602 and hsa-miR-1268b);
(73-4) a combination of SEQ ID NOs: 4 and 157 (markers: hsa-miR-4634 and hsa-miR-1268b);
(73-5) a combination of SEQ ID NOs: 3 and 157 (markers: hsa-miR-1307-3p and hsa-miR-1268b);
(74-1) a combination of SEQ ID NOs: 2 and 75 (markers: hsa-miR-4730 and hsa-miR-4675);
(74-2) a combination of SEQ ID NOs: 1 and 75 (markers: hsa-miR-4783-3p and hsa-miR-4675);
(74-3) a combination of SEQ ID NOs: 237 and 75 (markers: hsa-miR-602 and hsa-miR-4675);
(74-4) a combination of SEQ ID NOs: 4 and 75 (markers: hsa-miR-4634 and hsa-miR-4675);
(74-5) a combination of SEQ ID NOs: 3 and 75 (markers: hsa-miR-1307-3p and hsa-miR-4675);
(75-1) a combination of SEQ ID NOs: 2 and 82 (markers: hsa-miR-4730 and hsa-miR-3620-5p);
(75-2) a combination of SEQ ID NOs: 1 and 82 (markers: hsa-miR-4783-3p and hsa-miR-3620-5p);
(75-3) a combination of SEQ ID NOs: 237 and 82 (markers: hsa-miR-602 and hsa-miR-3620-5p);
(75-4) a combination of SEQ ID NOs: 4 and 82 (markers: hsa-miR-4634 and hsa-miR-3620-5p);
(75-5) a combination of SEQ ID NOs: 3 and 82 (markers: hsa-miR-1307-3p and hsa-miR-3620-5p);
(76-1) a combination of SEQ ID NOs: 2 and 106 (markers: hsa-miR-4730 and hsa-miR-6800-5p);
(76-2) a combination of SEQ ID NOs: 1 and 106 (markers: hsa-miR-4783-3p and hsa-miR-6800-5p);
(76-3) a combination of SEQ ID NOs: 237 and 106 (markers: hsa-miR-602 and hsa-miR-6800-5p);
(76-4) a combination of SEQ ID NOs: 4 and 106 (markers: hsa-miR-4634 and hsa-miR-6800-5p);
(76-5) a combination of SEQ ID NOs: 3 and 106 (markers: hsa-miR-1307-3p and hsa-miR-6800-5p);
(77-1) a combination of SEQ ID NOs: 2 and 111 (markers: hsa-miR-4730 and hsa-miR-6778-5p);
(77-2) a combination of SEQ ID NOs: 1 and 111 (markers: hsa-miR-4783-3p and hsa-miR-6778-5p);
(77-3) a combination of SEQ ID NOs: 237 and 111 (markers: hsa-miR-602 and hsa-miR-6778-5p);
(77-4) a combination of SEQ ID NOs: 4 and 111 (markers: hsa-miR-4634 and hsa-miR-6778-5p);
(77-5) a combination of SEQ ID NOs: 3 and 111 (markers: hsa-miR-1307-3p and hsa-miR-6778-5p);
(78-1) a combination of SEQ ID NOs: 2 and 96 (markers: hsa-miR-4730 and hsa-miR-8059);
(78-2) a combination of SEQ ID NOs: 1 and 96 (markers: hsa-miR-4783-3p and hsa-miR-8059);
(78-3) a combination of SEQ ID NOs: 237 and 96 (markers: hsa-miR-602 and hsa-miR-8059);
(78-4) a combination of SEQ ID NOs: 4 and 96 (markers: hsa-miR-4634 and hsa-miR-8059);
(78-5) a combination of SEQ ID NOs: 3 and 96 (markers: hsa-miR-1307-3p and hsa-miR-8059);
(79-1) a combination of SEQ ID NOs: 2 and 266 (markers: hsa-miR-4730 and hsa-miR-1908-5p);
(79-2) a combination of SEQ ID NOs: 1 and 266 (markers: hsa-miR-4783-3p and hsa-miR-1908-5p);
(79-3) a combination of SEQ ID NOs: 237 and 266 (markers: hsa-miR-602 and hsa-miR-1908-5p);
(79-4) a combination of SEQ ID NOs: 4 and 266 (markers: hsa-miR-4634 and hsa-miR-1908-5p);
(79-5) a combination of SEQ ID NOs: 3 and 266 (markers: hsa-miR-1307-3p and hsa-miR-1908-5p);
(80-1) a combination of SEQ ID NOs: 2 and 124 (markers: hsa-miR-4730 and hsa-miR-6798-5p);
(80-2) a combination of SEQ ID NOs: 1 and 124 (markers: hsa-miR-4783-3p and hsa-miR-6798-5p);
(80-3) a combination of SEQ ID NOs: 237 and 124 (markers: hsa-miR-602 and hsa-miR-6798-5p);
(80-4) a combination of SEQ ID NOs: 4 and 124 (markers: hsa-miR-4634 and hsa-miR-6798-5p);
(80-5) a combination of SEQ ID NOs: 3 and 124 (markers: hsa-miR-1307-3p and hsa-miR-6798-5p);
(81-1) a combination of SEQ ID NOs: 2 and 68 (markers: hsa-miR-4730 and hsa-miR-6879-5p);
(81-2) a combination of SEQ ID NOs: 1 and 68 (markers: hsa-miR-4783-3p and hsa-miR-6879-5p);
(81-3) a combination of SEQ ID NOs: 237 and 68 (markers: hsa-miR-602 and hsa-miR-6879-5p);
(81-4) a combination of SEQ ID NOs: 4 and 68 (markers: hsa-miR-4634 and hsa-miR-6879-5p);
(81-5) a combination of SEQ ID NOs: 3 and 68 (markers: hsa-miR-1307-3p and hsa-miR-6879-5p);
(82-1) a combination of SEQ ID NOs: 2 and 71 (markers: hsa-miR-4730 and hsa-miR-711);
(82-2) a combination of SEQ ID NOs: 1 and 71 (markers: hsa-miR-4783-3p and hsa-miR-711);

(82-3) a combination of SEQ ID NOs: 237 and 71 (markers: hsa-miR-602 and hsa-miR-711);
(82-4) a combination of SEQ ID NOs: 4 and 71 (markers: hsa-miR-4634 and hsa-miR-711);
(82-5) a combination of SEQ ID NOs: 3 and 71 (markers: hsa-miR-1307-3p and hsa-miR-711);
(83-1) a combination of SEQ ID NOs: 2 and 35 (markers: hsa-miR-4730 and hsa-miR-4728-5p);
(83-2) a combination of SEQ ID NOs: 1 and 35 (markers: hsa-miR-4783-3p and hsa-miR-4728-5p);
(83-3) a combination of SEQ ID NOs: 237 and 35 (markers: hsa-miR-602 and hsa-miR-4728-5p);
(83-4) a combination of SEQ ID NOs: 4 and 35 (markers: hsa-miR-4634 and hsa-miR-4728-5p);
(83-5) a combination of SEQ ID NOs: 3 and 35 (markers: hsa-miR-1307-3p and hsa-miR-4728-5p);
(84-1) a combination of SEQ ID NOs: 2 and 173 (markers: hsa-miR-4730 and hsa-miR-3195);
(84-2) a combination of SEQ ID NOs: 1 and 173 (markers: hsa-miR-4783-3p and hsa-miR-3195);
(84-3) a combination of SEQ ID NOs: 237 and 173 (markers: hsa-miR-602 and hsa-miR-3195);
(84-4) a combination of SEQ ID NOs: 4 and 173 (markers: hsa-miR-4634 and hsa-miR-3195);
(84-5) a combination of SEQ ID NOs: 3 and 173 (markers: hsa-miR-1307-3p and hsa-miR-3195);
(85-1) a combination of SEQ ID NOs: 2 and 5 (markers: hsa-miR-4730 and hsa-miR-663a);
(85-2) a combination of SEQ ID NOs: 1 and 5 (markers: hsa-miR-4783-3p and hsa-miR-663a);
(85-3) a combination of SEQ ID NOs: 237 and 5 (markers: hsa-miR-602 and hsa-miR-663a);
(85-4) a combination of SEQ ID NOs: 4 and 5 (markers: hsa-miR-4634 and hsa-miR-663a);
(85-5) a combination of SEQ ID NOs: 3 and 5 (markers: hsa-miR-1307-3p and hsa-miR-663a);
(86-1) a combination of SEQ ID NOs: 2 and 851 (markers: hsa-miR-4730 and hsa-miR-6089);
(86-2) a combination of SEQ ID NOs: 1 and 851 (markers: hsa-miR-4783-3p and hsa-miR-6089);
(86-3) a combination of SEQ ID NOs: 237 and 851 (markers: hsa-miR-602 and hsa-miR-6089);
(86-4) a combination of SEQ ID NOs: 4 and 851 (markers: hsa-miR-4634 and hsa-miR-6089);
(86-5) a combination of SEQ ID NOs: 3 and 851 (markers: hsa-miR-1307-3p and hsa-miR-6089);
(87-1) a combination of SEQ ID NOs: 2 and 852 (markers: hsa-miR-4730 and hsa-miR-6816-5p);
(87-2) a combination of SEQ ID NOs: 1 and 852 (markers: hsa-miR-4783-3p and hsa-miR-6816-5p);
(87-3) a combination of SEQ ID NOs: 237 and 852 (markers: hsa-miR-602 and hsa-miR-6816-5p);
(87-4) a combination of SEQ ID NOs: 4 and 852 (markers: hsa-miR-4634 and hsa-miR-6816-5p);
(87-5) a combination of SEQ ID NOs: 3 and 852 (markers: hsa-miR-1307-3p and hsa-miR-6816-5p);
(88-1) a combination of SEQ ID NOs: 2 and 30 (markers: hsa-miR-4730 and hsa-miR-6756-5p);
(88-2) a combination of SEQ ID NOs: 1 and 30 (markers: hsa-miR-4783-3p and hsa-miR-6756-5p);
(88-3) a combination of SEQ ID NOs: 237 and 30 (markers: hsa-miR-602 and hsa-miR-6756-5p);
(88-4) a combination of SEQ ID NOs: 4 and 30 (markers: hsa-miR-4634 and hsa-miR-6756-5p);
(88-5) a combination of SEQ ID NOs: 3 and 30 (markers: hsa-miR-1307-3p and hsa-miR-6756-5p);
(89-1) a combination of SEQ ID NOs: 2 and 93 (markers: hsa-miR-4730 and hsa-miR-6861-5p);
(89-2) a combination of SEQ ID NOs: 1 and 93 (markers: hsa-miR-4783-3p and hsa-miR-6861-5p);
(89-3) a combination of SEQ ID NOs: 237 and 93 (markers: hsa-miR-602 and hsa-miR-6861-5p);
(89-4) a combination of SEQ ID NOs: 4 and 93 (markers: hsa-miR-4634 and hsa-miR-6861-5p);
(89-5) a combination of SEQ ID NOs: 3 and 93 (markers: hsa-miR-1307-3p and hsa-miR-6861-5p);
(90-1) a combination of SEQ ID NOs: 2 and 27 (markers: hsa-miR-4730 and hsa-miR-1246);
(90-2) a combination of SEQ ID NOs: 1 and 27 (markers: hsa-miR-4783-3p and hsa-miR-1246);
(90-3) a combination of SEQ ID NOs: 237 and 27 (markers: hsa-miR-602 and hsa-miR-1246);
(90-4) a combination of SEQ ID NOs: 4 and 27 (markers: hsa-miR-4634 and hsa-miR-1246);
(90-5) a combination of SEQ ID NOs: 27 and 208 (markers: hsa-miR-1246 and hsa-miR-1343-5p);
(91-1) a combination of SEQ ID NOs: 2 and 853 (markers: hsa-miR-4730 and hsa-miR-4466);
(91-2) a combination of SEQ ID NOs: 1 and 853 (markers: hsa-miR-4783-3p and hsa-miR-4466);
(91-3) a combination of SEQ ID NOs: 237 and 853 (markers: hsa-miR-602 and hsa-miR-4466);
(91-4) a combination of SEQ ID NOs: 4 and 853 (markers: hsa-miR-4634 and hsa-miR-4466);
(91-5) a combination of SEQ ID NOs: 3 and 853 (markers: hsa-miR-1307-3p and hsa-miR-4466);
(92-1) a combination of SEQ ID NOs: 2 and 238 (markers: hsa-miR-4730 and hsa-miR-423-5p);
(92-2) a combination of SEQ ID NOs: 1 and 238 (markers: hsa-miR-4783-3p and hsa-miR-423-5p);
(92-3) a combination of SEQ ID NOs: 237 and 238 (markers: hsa-miR-602 and hsa-miR-423-5p);
(92-4) a combination of SEQ ID NOs: 4 and 238 (markers: hsa-miR-4634 and hsa-miR-423-5p);
(92-5) a combination of SEQ ID NOs: 3 and 238 (markers: hsa-miR-1307-3p and hsa-miR-423-5p);
(93-1) a combination of SEQ ID NOs: 2 and 130 (markers: hsa-miR-4730 and hsa-miR-6075);
(93-2) a combination of SEQ ID NOs: 1 and 130 (markers: hsa-miR-4783-3p and hsa-miR-6075);
(93-3) a combination of SEQ ID NOs: 237 and 130 (markers: hsa-miR-602 and hsa-miR-6075);
(93-4) a combination of SEQ ID NOs: 4 and 130 (markers: hsa-miR-4634 and hsa-miR-6075);
(93-5) a combination of SEQ ID NOs: 3 and 130 (markers: hsa-miR-1307-3p and hsa-miR-6075);
(94-1) a combination of SEQ ID NOs: 2 and 177 (markers: hsa-miR-4730 and hsa-miR-7108-5p);
(94-2) a combination of SEQ ID NOs: 1 and 177 (markers: hsa-miR-4783-3p and hsa-miR-7108-5p);
(94-3) a combination of SEQ ID NOs: 237 and 177 (markers: hsa-miR-602 and hsa-miR-7108-5p);
(94-4) a combination of SEQ ID NOs: 4 and 177 (markers: hsa-miR-4634 and hsa-miR-7108-5p);
(94-5) a combination of SEQ ID NOs: 3 and 177 (markers: hsa-miR-1307-3p and hsa-miR-7108-5p);
(95-1) a combination of SEQ ID NOs: 2 and 64 (markers: hsa-miR-4730 and hsa-miR-6511a-5p);
(95-2) a combination of SEQ ID NOs: 1 and 64 (markers: hsa-miR-4783-3p and hsa-miR-6511a-5p);
(95-3) a combination of SEQ ID NOs: 237 and 64 (markers: hsa-miR-602 and hsa-miR-6511a-5p);

(95-4) a combination of SEQ ID NOs: 4 and 64 (markers: hsa-miR-4634 and hsa-miR-6511a-5p);
(95-5) a combination of SEQ ID NOs: 3 and 64 (markers: hsa-miR-1307-3p and hsa-miR-6511a-5p);
(96-1) a combination of SEQ ID NOs: 2 and 114 (markers: hsa-miR-4730 and hsa-miR-211-3p);
(96-2) a combination of SEQ ID NOs: 1 and 114 (markers: hsa-miR-4783-3p and hsa-miR-211-3p);
(96-3) a combination of SEQ ID NOs: 237 and 114 (markers: hsa-miR-602 and hsa-miR-211-3p);
(96-4) a combination of SEQ ID NOs: 4 and 114 (markers: hsa-miR-4634 and hsa-miR-211-3p);
(96-5) a combination of SEQ ID NOs: 3 and 114 (markers: hsa-miR-1307-3p and hsa-miR-211-3p);
(97-1) a combination of SEQ ID NOs: 2 and 119 (markers: hsa-miR-4730 and hsa-miR-7110-5p);
(97-2) a combination of SEQ ID NOs: 1 and 119 (markers: hsa-miR-4783-3p and hsa-miR-7110-5p);
(97-3) a combination of SEQ ID NOs: 237 and 119 (markers: hsa-miR-602 and hsa-miR-7110-5p);
(97-4) a combination of SEQ ID NOs: 4 and 119 (markers: hsa-miR-4634 and hsa-miR-7110-5p);
(97-5) a combination of SEQ ID NOs: 3 and 119 (markers: hsa-miR-1307-3p and hsa-miR-7110-5p);
(98-1) a combination of SEQ ID NOs: 2 and 135 (markers: hsa-miR-4730 and hsa-miR-6870-5p);
(98-2) a combination of SEQ ID NOs: 1 and 135 (markers: hsa-miR-4783-3p and hsa-miR-6870-5p);
(98-3) a combination of SEQ ID NOs: 237 and 135 (markers: hsa-miR-602 and hsa-miR-6870-5p);
(98-4) a combination of SEQ ID NOs: 4 and 135 (markers: hsa-miR-4634 and hsa-miR-6870-5p);
(98-5) a combination of SEQ ID NOs: 3 and 135 (markers: hsa-miR-1307-3p and hsa-miR-6870-5p);
(99-1) a combination of SEQ ID NOs: 2 and 243 (markers: hsa-miR-4730 and hsa-miR-486-5p);
(99-2) a combination of SEQ ID NOs: 1 and 243 (markers: hsa-miR-4783-3p and hsa-miR-486-5p);
(99-3) a combination of SEQ ID NOs: 237 and 243 (markers: hsa-miR-602 and hsa-miR-486-5p);
(99-4) a combination of SEQ ID NOs: 4 and 243 (markers: hsa-miR-4634 and hsa-miR-486-5p);
(99-5) a combination of SEQ ID NOs: 3 and 243 (markers: hsa-miR-1307-3p and hsa-miR-486-5p);
(100-1) a combination of SEQ ID NOs: 2 and 122 (markers: hsa-miR-4730 and hsa-miR-4792);
(100-2) a combination of SEQ ID NOs: 1 and 122 (markers: hsa-miR-4783-3p and hsa-miR-4792);
(100-3) a combination of SEQ ID NOs: 237 and 122 (markers: hsa-miR-602 and hsa-miR-4792);
(100-4) a combination of SEQ ID NOs: 4 and 122 (markers: hsa-miR-4634 and hsa-miR-4792);
(100-5) a combination of SEQ ID NOs: 3 and 122 (markers: hsa-miR-1307-3p and hsa-miR-4792);
(101-1) a combination of SEQ ID NOs: 2 and 260 (markers: hsa-miR-4730 and hsa-miR-4687-3p);
(101-2) a combination of SEQ ID NOs: 1 and 260 (markers: hsa-miR-4783-3p and hsa-miR-4687-3p);
(101-3) a combination of SEQ ID NOs: 237 and 260 (markers: hsa-miR-602 and hsa-miR-4687-3p);
(101-4) a combination of SEQ ID NOs: 4 and 260 (markers: hsa-miR-4634 and hsa-miR-4687-3p);
(101-5) a combination of SEQ ID NOs: 3 and 260 (markers: hsa-miR-1307-3p and hsa-miR-4687-3p);
(102-1) a combination of SEQ ID NOs: 2 and 59 (markers: hsa-miR-4730 and hsa-miR-1238-5p);
(102-2) a combination of SEQ ID NOs: 1 and 59 (markers: hsa-miR-4783-3p and hsa-miR-1238-5p);
(102-3) a combination of SEQ ID NOs: 237 and 59 (markers: hsa-miR-602 and hsa-miR-1238-5p);
(102-4) a combination of SEQ ID NOs: 4 and 59 (markers: hsa-miR-4634 and hsa-miR-1238-5p);
(102-5) a combination of SEQ ID NOs: 3 and 59 (markers: hsa-miR-1307-3p and hsa-miR-1238-5p);
(103-1) a combination of SEQ ID NOs: 2 and 854 (markers: hsa-miR-4730 and hsa-miR-4488);
(103-2) a combination of SEQ ID NOs: 1 and 854 (markers: hsa-miR-4783-3p and hsa-miR-4488);
(103-3) a combination of SEQ ID NOs: 237 and 854 (markers: hsa-miR-602 and hsa-miR-4488);
(103-4) a combination of SEQ ID NOs: 4 and 854 (markers: hsa-miR-4634 and hsa-miR-4488);
(103-5) a combination of SEQ ID NOs: 3 and 854 (markers: hsa-miR-1307-3p and hsa-miR-4488);
(104-1) a combination of SEQ ID NOs: 2 and 132 (markers: hsa-miR-4730 and hsa-miR-6891-5p);
(104-2) a combination of SEQ ID NOs: 1 and 132 (markers: hsa-miR-4783-3p and hsa-miR-6891-5p);
(104-3) a combination of SEQ ID NOs: 237 and 132 (markers: hsa-miR-602 and hsa-miR-6891-5p);
(104-4) a combination of SEQ ID NOs: 4 and 132 (markers: hsa-miR-4634 and hsa-miR-6891-5p);
(104-5) a combination of SEQ ID NOs: 3 and 132 (markers: hsa-miR-1307-3p and hsa-miR-6891-5p);
(105-1) a combination of SEQ ID NOs: 2 and 181 (markers: hsa-miR-4730 and hsa-miR-2861);
(105-2) a combination of SEQ ID NOs: 1 and 181 (markers: hsa-miR-4783-3p and hsa-miR-2861);
(105-3) a combination of SEQ ID NOs: 237 and 181 (markers: hsa-miR-602 and hsa-miR-2861);
(105-4) a combination of SEQ ID NOs: 4 and 181 (markers: hsa-miR-4634 and hsa-miR-2861);
(105-5) a combination of SEQ ID NOs: 3 and 181 (markers: hsa-miR-1307-3p and hsa-miR-2861);
(106-1) a combination of SEQ ID NOs: 2 and 79 (markers: hsa-miR-4730 and hsa-miR-4665-5p);
(106-2) a combination of SEQ ID NOs: 1 and 79 (markers: hsa-miR-4783-3p and hsa-miR-4665-5p);
(106-3) a combination of SEQ ID NOs: 237 and 79 (markers: hsa-miR-602 and hsa-miR-4665-5p);
(106-4) a combination of SEQ ID NOs: 4 and 79 (markers: hsa-miR-4634 and hsa-miR-4665-5p);
(106-5) a combination of SEQ ID NOs: 3 and 79 (markers: hsa-miR-1307-3p and hsa-miR-4665-5p);
(107-1) a combination of SEQ ID NOs: 2 and 133 (markers: hsa-miR-4730 and hsa-miR-4745-5p);
(107-2) a combination of SEQ ID NOs: 1 and 133 (markers: hsa-miR-4783-3p and hsa-miR-4745-5p);
(107-3) a combination of SEQ ID NOs: 237 and 133 (markers: hsa-miR-602 and hsa-miR-4745-5p);
(107-4) a combination of SEQ ID NOs: 4 and 133 (markers: hsa-miR-4634 and hsa-miR-4745-5p);
(107-5) a combination of SEQ ID NOs: 3 and 133 (markers: hsa-miR-1307-3p and hsa-miR-4745-5p);
(108-1) a combination of SEQ ID NOs: 2 and 41 (markers: hsa-miR-4730 and hsa-miR-6858-5p);
(108-2) a combination of SEQ ID NOs: 1 and 41 (markers: hsa-miR-4783-3p and hsa-miR-6858-5p);
(108-3) a combination of SEQ ID NOs: 237 and 41 (markers: hsa-miR-602 and hsa-miR-6858-5p);
(108-4) a combination of SEQ ID NOs: 4 and 41 (markers: hsa-miR-4634 and hsa-miR-6858-5p);

(108-5) a combination of SEQ ID NOs: 3 and 41 (markers: hsa-miR-1307-3p and hsa-miR-6858-5p);
(109-1) a combination of SEQ ID NOs: 2 and 139 (markers: hsa-miR-4730 and hsa-miR-6825-5p);
(109-2) a combination of SEQ ID NOs: 1 and 139 (markers: hsa-miR-4783-3p and hsa-miR-6825-5p);
(109-3) a combination of SEQ ID NOs: 237 and 139 (markers: hsa-miR-602 and hsa-miR-6825-5p);
(109-4) a combination of SEQ ID NOs: 4 and 139 (markers: hsa-miR-4634 and hsa-miR-6825-5p);
(109-5) a combination of SEQ ID NOs: 3 and 139 (markers: hsa-miR-1307-3p and hsa-miR-6825-5p);
(110-1) a combination of SEQ ID NOs: 2 and 118 (markers: hsa-miR-4730 and hsa-miR-614);
(110-2) a combination of SEQ ID NOs: 1 and 118 (markers: hsa-miR-4783-3p and hsa-miR-614);
(110-3) a combination of SEQ ID NOs: 237 and 118 (markers: hsa-miR-602 and hsa-miR-614);
(110-4) a combination of SEQ ID NOs: 4 and 118 (markers: hsa-miR-4634 and hsa-miR-614);
(110-5) a combination of SEQ ID NOs: 3 and 118 (markers: hsa-miR-1307-3p and hsa-miR-614);
(111-1) a combination of SEQ ID NOs: 2 and 86 (markers: hsa-miR-4730 and hsa-miR-1343-3p);
(111-2) a combination of SEQ ID NOs: 1 and 86 (markers: hsa-miR-4783-3p and hsa-miR-1343-3p);
(111-3) a combination of SEQ ID NOs: 237 and 86 (markers: hsa-miR-602 and hsa-miR-1343-3p);
(111-4) a combination of SEQ ID NOs: 4 and 86 (markers: hsa-miR-4634 and hsa-miR-1343-3p);
(111-5) a combination of SEQ ID NOs: 3 and 86 (markers: hsa-miR-1307-3p and hsa-miR-1343-3p);
(112-1) a combination of SEQ ID NOs: 2 and 60 (markers: hsa-miR-4730 and hsa-miR-365a-5p);
(112-2) a combination of SEQ ID NOs: 1 and 60 (markers: hsa-miR-4783-3p and hsa-miR-365a-5p);
(112-3) a combination of SEQ ID NOs: 237 and 60 (markers: hsa-miR-602 and hsa-miR-365a-5p);
(112-4) a combination of SEQ ID NOs: 4 and 60 (markers: hsa-miR-4634 and hsa-miR-365a-5p);
(112-5) a combination of SEQ ID NOs: 3 and 60 (markers: hsa-miR-1307-3p and hsa-miR-365a-5p);
(113-1) a combination of SEQ ID NOs: 2 and 116 (markers: hsa-miR-4730 and hsa-miR-4750-5p);
(113-2) a combination of SEQ ID NOs: 1 and 116 (markers: hsa-miR-4783-3p and hsa-miR-4750-5p);
(113-3) a combination of SEQ ID NOs: 237 and 116 (markers: hsa-miR-602 and hsa-miR-4750-5p);
(113-4) a combination of SEQ ID NOs: 4 and 116 (markers: hsa-miR-4634 and hsa-miR-4750-5p);
(113-5) a combination of SEQ ID NOs: 3 and 116 (markers: hsa-miR-1307-3p and hsa-miR-4750-5p);
(114-1) a combination of SEQ ID NOs: 2 and 160 (markers: hsa-miR-4730 and hsa-miR-6732-5p);
(114-2) a combination of SEQ ID NOs: 1 and 160 (markers: hsa-miR-4783-3p and hsa-miR-6732-5p);
(114-3) a combination of SEQ ID NOs: 237 and 160 (markers: hsa-miR-602 and hsa-miR-6732-5p);
(114-4) a combination of SEQ ID NOs: 4 and 160 (markers: hsa-miR-4634 and hsa-miR-6732-5p);
(114-5) a combination of SEQ ID NOs: 3 and 160 (markers: hsa-miR-1307-3p and hsa-miR-6732-5p);
(115-1) a combination of SEQ ID NOs: 2 and 38 (markers: hsa-miR-4730 and hsa-miR-149-3p);
(115-2) a combination of SEQ ID NOs: 1 and 38 (markers: hsa-miR-4783-3p and hsa-miR-149-3p);
(115-3) a combination of SEQ ID NOs: 237 and 38 (markers: hsa-miR-602 and hsa-miR-149-3p);
(115-4) a combination of SEQ ID NOs: 4 and 38 (markers: hsa-miR-4634 and hsa-miR-149-3p);
(115-5) a combination of SEQ ID NOs: 3 and 38 (markers: hsa-miR-1307-3p and hsa-miR-149-3p);
(116-1) a combination of SEQ ID NOs: 2 and 99 (markers: hsa-miR-4730 and hsa-miR-4497);
(116-2) a combination of SEQ ID NOs: 1 and 99 (markers: hsa-miR-4783-3p and hsa-miR-4497);
(116-3) a combination of SEQ ID NOs: 237 and 99 (markers: hsa-miR-602 and hsa-miR-4497);
(116-4) a combination of SEQ ID NOs: 4 and 99 (markers: hsa-miR-4634 and hsa-miR-4497);
(116-5) a combination of SEQ ID NOs: 3 and 99 (markers: hsa-miR-1307-3p and hsa-miR-4497);
(117-1) a combination of SEQ ID NOs: 2 and 104 (markers: hsa-miR-4730 and hsa-miR-6848-5p);
(117-2) a combination of SEQ ID NOs: 1 and 104 (markers: hsa-miR-4783-3p and hsa-miR-6848-5p);
(117-3) a combination of SEQ ID NOs: 237 and 104 (markers: hsa-miR-602 and hsa-miR-6848-5p);
(117-4) a combination of SEQ ID NOs: 4 and 104 (markers: hsa-miR-4634 and hsa-miR-6848-5p); and
(117-5) a combination of SEQ ID NOs: 3 and 104 (markers: hsa-miR-1307-3p and hsa-miR-6848-5p).

The kit or the device of the present invention may also comprise a polynucleotide(s) that is/are already known or that will be found in the future, to enable detection of breast cancer, in addition to the polynucleotide(s) (which may include variant(s), fragment(s), or derivative(s)) according to the present invention The kit of the present invention may also comprise an antibody for measuring marker(s) for breast cancer examination known in the art, such as CEA, CA-15-3, and CA27-29, in addition to the polynucleotide(s) as described above.

The polynucleotides described above contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are bound or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves binding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group; a method of spraying the nucleic acids onto the solid phase using an inkjet which injects very small liquid droplets by a piezoelectric element or the like from a nozzle; or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one, preferably at least two, more preferably at least three, most preferably at least five to all of the breast cancer marker miRNAs, respectively, of the group 1 described above. The kit or the device of the present invention may optionally further comprise nucleic acids capable of specifically binding to the polynucleotides of at least one, preferably at least two, more preferably at least three, most preferably at least five to all of the breast cancer marker miRNAs, respectively, of the group 2 described above. The kit or the device of the present invention may optionally further comprise nucleic acids capable of specifically binding to the polynucleotides of at least one, preferably at least two, more preferably at least three, most preferably at least five to all of the breast cancer marker miRNAs, respectively, of the group 3 described above. The kit or the device of the present invention can be used for detecting breast cancer as described in Section 4 below.

4. Method for Detecting Breast Cancer

The present invention further provides a method for detecting breast cancer, comprising using the kit or the device of the present invention (comprising the aforementioned nucleic acid(s) that can be used in the present invention) as described in Section "3. Kit or device for detection of breast cancer" to measure an expression level of one or more breast cancer-derived genes represented by: expression level(s) of breast cancer-derived genes selected from the following group of miRNAs, i.e., miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739; and optionally expression level(s) of breast cancer-derived gene(s) selected from the following group of miRNA: i.e., miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p, and optionally expression level(s) of breast cancer-derived gene(s) selected from the following group of miRNA: i.e., miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p, and miR-6763-5p in a sample in vitro, further comparing, for example, the expression level(s) of the aforementioned gene(s) in the sample (e.g., blood, serum, or plasma) collected from a subject suspected of having breast cancer with a control expression level in the sample collected from a healthy subject (including a non-breast cancer patient(s)), and evaluating the subject as having breast cancer when the expression level(s) of the target nucleic acid(s) is different between the samples.

This method of the present invention enables limitedly-invasive early diagnosis of the breast cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the breast cancer-derived gene from the sample such as blood, serum, or plasma according to the present invention is particularly preferably a method in which the breast cancer-derived gene is prepared by the addition of a reagent for RNA extraction in 3D-Gener™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The breast cancer-derived gene(s) may be prepared by the addition of a reagent for RNA extraction containing acidic phenol, such as Trizol (Life Technologies Corp.) or Isogen (Nippon Gene Co., Ltd., Japan). Alternatively, a kit such as miRNeasy® Mini Kit (Qiagen N.V.) can be used, though the method is not limited thereto.

The present invention also provides use of the kit or the device of the present invention for detecting in vitro an expression product(s) of a breast cancer-derived miRNA gene in a sample derived from a subject.

In the method of the present invention, the used kit or the device comprises a single polynucleotide or any possible combination of polynucleotides that can be used in the present invention as described above.

In the detection or (genetic) diagnosis of breast cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of breast or the detection of the presence or absence of breast cancer. Specifically, the detection of breast cancer using the kit or the device can be performed by detecting in vitro an expression level of a gene using the nucleic acid probe or the primer contained in the kit or the device in a sample such as blood, serum, plasma, or urine from a subject suspected of having breast cancer. The subject suspected of having breast cancer can be evaluated as having breast cancer when the expression level(s) of a target miRNA marker(s) measured using a polynucleotide(s) (including variant(s), fragment(s), or derivative(s) thereof) consisting of a nucleotide sequence(s) represented by at least one of SEQ ID NOs: 1 to 235, and 851 to 856 or a complementary sequence(s) thereof, and optionally a nucleotide sequence(s) represented by one or more of SEQ ID NOs: 236 to 251 or a complementary sequence(s) thereof, and optionally a nucleotide sequence(s) represented by one or more of SEQ ID NOs: 252 to 269 or a complementary sequence thereof in the sample such as blood, serum, plasma, or urine of the subject has a statistically significantly higher or lower than the expression level(s) thereof in the sample such as blood, serum, or plasma, or urine of a healthy subject.

The method of the present invention can be combined with a diagnostic imaging method such as mammography, ultrasonography (echo examination), CT, MRI, abdominal ultrasonography, bone scintigraphy, or PET, or pathological examination which involves analyzing a lesion tissue under a microscope. The method of the present invention is capable of specifically detecting breast cancer and can substantially discriminate breast cancer from the other cancers.

The method for detecting the absence of an expression product(s) of a breast cancer-derived gene(s) or the presence of the expression product(s) of a breast cancer-derived gene in a sample using the kit or the device of the present invention comprises; collecting a body fluid such as blood, serum, plasma, or urine of a subject; measuring the expression level(s) of the target gene(s) contained therein using one or more polynucleotides (including variant(s), fragment(s), or derivative(s)) selected from the polynucleotide group of the present invention; and evaluating the presence or absence of breast cancer or to detect breast cancer. The method for detecting breast cancer according to the present invention can also evaluate or diagnose, for example, the presence or absence of amelioration of the disease or the degree of amelioration thereof in a breast cancer patient in the case that a therapeutic drug is administered to the patient for amelioration of the disease.

The method of the present invention can comprise, for example, the following steps (a), (b), and (c):

(a) a step of contacting in vitro a sample from a subject with a polynucleotide(s) contained in the kit or the device of the present invention in vitro;

(b) a step of measuring an expression level(s) of the target nucleic acid(s) in the sample using the polynucleotide (s) as a nucleic acid probe(s) or a primer(s); and (c) a step of evaluating the presence or absence of breast cancer (cells) in the subject on the basis of the measurement results in the step (b).

Specifically, the present invention provides a method for detecting breast cancer, comprising measuring an expression level(s) of a target nucleic acid(s) in a sample of a subject using nucleic acid(s) capable of specifically binding to at least one (preferably at least two) polynucleotides selected from the group consisting of miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739 and evaluating in vitro whether or not the subject has breast cancer in the subject using the above-measured expression levels and control expression levels of healthy subjects measured in the same way as above.

The term "evaluation" used herein is evaluation support based on results of in vitro examination, not physician's judgment.

As described above, in a preferred embodiment of the method of the present invention, specifically, miR-4783-3p is hsa-miR-4783-3p, miR-4730 is hsa-miR-4730, miR-1307-3p is hsa-miR-1307-3p, miR-4634 is hsa-miR-4634, miR-663a is hsa-miR-663a, miR-4532 is hsa-miR-4532, miR-7704 is hsa-miR-7704, miR-3178 is hsa-miR-3178, miR-6729-5p is hsa-miR-6729-5p, miR-6090 is hsa-miR-6090, miR-4732-5p is hsa-miR-4732-5p, miR-3184-5p is hsa-miR-3184-5p, miR-6727-5p is hsa-miR-6727-5p, miR-6088 is hsa-miR-6088, miR-4674 is hsa-miR-4674, miR-8073 is hsa-miR-8073, miR-4787-5p is hsa-miR-4787-5p, miR-1469 is hsa-miR-1469, miR-125a-3p is hsa-miR-125a-3p, miR-1233-5p is hsa-miR-1233-5p, miR-885-3p is hsa-miR-885-3p, miR-6802-5p is hsa-miR-6802-5p, miR-328-5p is hsa-miR-328-5p, miR-6787-5p is hsa-miR-6787-5p, miR-8069 is hsa-miR-8069, miR-6875-5p is hsa-miR-6875-5p, miR-1246 is hsa-miR-1246, miR-4734 is hsa-miR-4734, miR-6757-5p is hsa-miR-6757-5p, miR-6756-5p is hsa-miR-6756-5p, miR-3665 is hsa-miR-3665, miR-6836-3p is hsa-miR-6836-3p, miR-6821-5p is hsa-miR-6821-5p, miR-6805-5p is hsa-miR-6805-5p, miR-4728-5p is hsa-miR-4728-5p, miR-6726-5p is hsa-miR-6726-5p, miR-197-5p is hsa-miR-197-5p, miR-149-3p is hsa-miR-149-3p, miR-6850-5p is hsa-miR-6850-5p, miR-4476 is hsa-miR-4476, miR-6858-5p is hsa-miR-6858-5p, miR-564 is hsa-miR-564, miR-4763-3p is hsa-miR-4763-3p, miR-575 is hsa-miR-575, miR-6771-5p is hsa-miR-6771-5p, miR-1231 is hsa-miR-1231, miR-1908-3p is hsa-miR-1908-3p, miR-150-3p is hsa-miR-150-3p, miR-3937 is hsa-miR-3937, miR-887-3p is hsa-miR-887-3p, miR-3940-5p is hsa-miR-3940-5p, miR-4741 is hsa-miR-4741, miR-6808-5p is hsa-miR-6808-5p, miR-6869-5p is hsa-miR-6869-5p, miR-5090 is hsa-miR-5090, miR-615-5p is hsa-miR-615-5p, miR-8072 is hsa-miR-8072, miR-128-1-5p is hsa-miR-128-1-5p, miR-1238-5p is hsa-miR-1238-5p, miR-365a-5p is hsa-miR-365a-5p, miR-204-3p is hsa-miR-204-3p, miR-4492 is hsa-miR-4492, miR-6785-5p is hsa-miR-6785-5p, miR-6511a-5p is hsa-miR-6511a-5p, miR-4525 is hsa-miR-4525, miR-1915-5p is hsa-miR-1915-5p, miR-3180 is hsa-miR-3180, miR-6879-5p is hsa-miR-6879-5p, miR-1199-5p is hsa-miR-1199-5p, miR-6746-5p is hsa-miR-6746-5p, miR-711 is hsa-miR-711, miR-663b is hsa-miR-663b, miR-4707-3p is hsa-miR-4707-3p, miR-6893-5p is hsa-miR-6893-5p, miR-4675 is hsa-miR-4675, miR-4638-5p is hsa-miR-4638-5p, miR-4651 is hsa-miR-4651, miR-6087 is hsa-miR-6087, miR-4665-5p is hsa-miR-4665-5p, miR-4758-5p is hsa-miR-4758-5p, miR-6887-5p is hsa-miR-6887-5p, miR-3620-5p is hsa-miR-3620-5p, miR-1909-3p is hsa-miR-1909-3p, miR-7641 is hsa-miR-7641, miR-6724-5p is hsa-miR-6724-5p, miR-1343-3p is hsa-miR-1343-3p, miR-6780b-5p is hsa-miR-6780b-5p, miR-4484 is hsa-miR-4484, miR-4690-5p is hsa-miR-4690-5p, miR-4429 is hsa-miR-4429, miR-1227-5p is hsa-miR-1227-5p, miR-4725-3p is hsa-miR-4725-3p, miR-6861-5p is hsa-miR-6861-5p, miR-6812-5p is hsa-miR-6812-5p, miR-3197 is hsa-miR-3197, miR-8059 is hsa-miR-8059, miR-3185 is hsa-miR-3185, miR-4706 is hsa-miR-4706, miR-4497 is hsa-miR-4497, miR-3131 is hsa-miR-3131, miR-6806-5p is hsa-miR-6806-5p, miR-187-5p is hsa-miR-187-5p, miR-3180-3p is hsa-miR-3180-3p, miR-6848-5p is hsa-miR-6848-5p, miR-6820-5p is hsa-miR-6820-5p, miR-6800-5p is hsa-miR-6800-5p, miR-6717-5p is hsa-miR-6717-5p, miR-6795-5p is hsa-miR-6795-5p, miR-4632-5p is hsa-miR-4632-5p, miR-665 is hsa-miR-665, miR-6778-5p is hsa-miR-6778-5p, miR-3663-3p is hsa-miR-3663-3p, miR-4689 is hsa-miR-4689, miR-211-3p is hsa-miR-211-3p, miR-6511b-5p is hsa-miR-6511b-5p, miR-4750-5p is hsa-miR-4750-5p, miR-6126 is hsa-miR-6126, miR-614 is hsa-miR-614, miR-7110-5p is hsa-miR-7110-5p, miR-744-5p is hsa-miR-744-5p, miR-6769a-5p is hsa-miR-6769a-5p, miR-4792 is hsa-miR-4792, miR-5787 is hsa-miR-5787, miR-6798-5p is hsa-miR-6798-5p, miR-6781-5p is hsa-miR-6781-5p, miR-4419b is hsa-miR-4419b, miR-4446-3p is hsa-miR-4446-3p, miR-4259 is hsa-miR-4259, miR-5572 is hsa-miR-5572, miR-6075 is hsa-miR-6075, miR-296-3p is hsa-miR-296-3p, miR-6891-5p is hsa-miR-6891-5p, miR-4745-5p is hsa-miR-4745-5p, miR-6775-5p is hsa-miR-6775-5p, miR-6870-5p is hsa-miR-6870-5p, miR-920 is hsa-miR-920, miR-4530 is hsa-miR-4530, miR-6819-5p is hsa-miR-6819-5p, miR-6825-5p is hsa-miR-6825-5p, miR-7847-3p is hsa-miR-7847-3p, miR-6131 is hsa-miR-6131, miR-4433-3p is hsa-miR-4433-3p, miR-1228-5p is hsa-miR-1228-5p, miR-6743-5p is hsa-miR-6743-5p, miR-1268a is hsa-miR-1268a, miR-3917 is hsa-miR-3917, miR-6786-5p is hsa-miR-6786-5p, miR-3154 is hsa-miR-3154, miR-638 is hsa-miR-638, miR-6741-5p is hsa-miR-6741-5p, miR-6889-5p is hsa-miR-6889-5p, miR-6840-3p is hsa-miR-6840-3p, miR-6510-5p is hsa-miR-6510-5p, miR-3188 is hsa-miR-3188, miR-551b-5p is hsa-miR-551b-5p, miR-5001-5p is hsa-miR-5001-5p, miR-1268b is hsa-miR-1268b, miR-7107-5p is hsa-miR-7107-5p, miR-6824-5p is hsa-miR-6824-5p, miR-6732-5p is hsa-miR-6732-5p, miR-371a-5p is hsa-miR-371a-5p, miR-6794-5p is hsa-miR-6794-5p, miR-6779-5p is hsa-miR-6779-5p, miR-4271 is hsa-miR-4271, miR-5195-3p is hsa-miR-5195-3p, miR-6762-5p is hsa-miR-6762-5p, miR-939-5p is hsa-miR-939-5p, miR-1247-3p is hsa-miR-1247-3p, miR-6777-5p is hsa-miR-6777-5p, miR-6722-3p is hsa-miR-6722-3p, miR-3656 is hsa-miR-3656, miR-4688 is hsa-miR-4688, miR-3195 is hsa-miR-3195, miR-6766-5p is hsa-miR-6766-5p, miR-4447 is hsa-miR-4447, miR-4656 is hsa-miR-4656, miR-7108-5p is hsa-miR-7108-5p, miR-3191-3p is hsa-miR-3191-3p, miR-1273g-3p is hsa-miR-1273g-3p, miR-4463 is hsa-miR-4463, miR-2861 is hsa-miR-2861, miR-3196 is hsa-miR-3196, miR-6877-5p is hsa-miR-6877-5p, miR-3679-5p is hsa-miR-3679-5p, miR-4442 is hsa-miR-4442, miR-6789-5p is hsa-miR-6789-5p, miR-6782-5p is hsa-miR-6782-5p, miR-486-3p is hsa-miR-486-3p, miR-6085 is hsa-miR-6085, miR-4746-3p is hsa-miR-4746-3p, miR-619-5p is hsa-miR-619-5p, miR-937-5p is hsa-miR-937-5p, miR-6803-5p is hsa-miR-6803-5p, miR-4298 is hsa-miR-4298, miR-4454 is hsa-miR-4454, miR-4459 is hsa-miR-4459, miR-7150 is hsa-miR-7150, miR-6880-5p is hsa-miR-6880-5p, miR-4449 is hsa-miR-4449, miR-8063 is hsa-miR-8063, miR-4695-5p is hsa-miR-4695-5p, miR-6132 is hsa-miR-6132, miR-6829-5p is hsa-miR-6829-5p, miR-4486 is hsa-miR-4486, miR-6805-3p is hsa-miR-6805-3p, miR-6826-5p is hsa-miR-6826-5p, miR-4508 is hsa-miR-4508, miR-1343-5p is hsa-miR-1343-5p, miR-7114-5p is hsa-miR-7114-5p, miR-3622a-5p is hsa-miR-3622a-5p, miR-6765-5p is hsa-miR-6765-5p, miR-7845-5p is hsa-miR-7845-5p, miR-3960 is hsa-miR-3960, miR-6749-5p is hsa-miR-6749-5p, miR-1260b is hsa-miR-1260b, miR-6799-5p is hsa-miR-6799-5p, miR-4723-5p is hsa-miR-4723-5p, miR-6784-5p is hsa-miR-6784-5p, miR-5100 is hsa-miR-5100, miR-6769b-5p is hsa-miR-6769b-5p, miR-1207-5p is hsa-miR-1207-5p, miR-642a-3p is hsa-miR-642a-3p, miR-4505 is hsa-miR-4505, miR-4270 is hsa-miR-4270, miR-6721-5p is hsa-miR-6721-5p, miR-7111-5p is hsa-miR-7111-5p, miR-6791-5p is hsa-miR-6791-5p, miR-7109-5p is hsa-miR-7109-5p, miR-4258 is hsa-miR-4258, miR-6515-3p is hsa-miR-6515-3p, miR-6851-5p is hsa-miR-6851-5p, miR-6125 is hsa-miR-6125, miR-4749-5p is hsa-miR-4749-5p, miR-4726-5p is hsa-miR-4726-5p, miR-4513 is hsa-miR-4513, miR-6089 is hsa-miR-6089, miR-6816-5p is hsa-miR-6816-5p, miR-4466 is hsa-miR-4466, miR-4488 is hsa-miR-4488, miR-6752-5p is hsa-miR-6752-5p, and miR-4739 is hsa-miR-4739.

In a preferred embodiment of the method of the present invention, specifically, the nucleic acid (specifically, probe (s) or primer(s)) is selected from the group consisting of the following polynucleotides (a) to (e):
 (a) a polynucleotide consisting of a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
 (b) a polynucleotide comprising a nucleotide sequence represented by any of SEQ ID NOs: 1 to 235 and 851 to 856,
 (c) a polynucleotide consisting of a nucleotide sequence complementary to a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
 (d) a polynucleotide comprising a nucleotide sequence complementary to a nucleotide sequence represented by any of SEQ ID NOs: 1 to 235 and 851 to 856 or a nucleotide sequence derived from the nucleotide sequence by the replacement of u with t, and
 (e) a polynucleotide hybridizing under stringent conditions to any of the polynucleotides (a) to (d).

The method of the present invention can further employ nucleic acid(s) capable of specifically binding to at least one polynucleotide selected from the group consisting of miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

As for such a nucleic acid, specifically, miR-760 is hsa-miR-760, miR-602 is hsa-miR-602, miR-423-5p is hsa-miR-423-5p, miR-92a-2-5p is hsa-miR-92a-2-5p, miR-16-5p is hsa-miR-16-5p, miR-451a is hsa-miR-451a, miR-135a-3p is hsa-miR-135a-3p, miR-486-5p is hsa-miR-486-5p, miR-4257 is hsa-miR-4257, miR-92b-5p is hsa-miR-92b-5p, miR-1915-3p is hsa-miR-1915-3p, miR-718 is hsa-miR-718, miR-940 is hsa-miR-940, miR-296-5p is hsa-miR-296-5p, miR-23b-3p is hsa-miR-23b-3p, and miR-92a-3p is hsa-miR-92a-3p.

In a preferred embodiment, such a nucleic acid is specifically selected from the group consisting of the following polynucleotides (f) to (j):
 (f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
 (g) a polynucleotide comprising a nucleotide sequence represented by any of SEQ ID NOs: 236 to 251,
 (h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
 (i) a polynucleotide comprising a nucleotide sequence complementary to a nucleotide sequence represented by any of SEQ ID NOs: 236 to 251 or a nucleotide sequence derived from the nucleotide sequence by the replacement of u with t, and
 (j) a polynucleotide hybridizing under stringent conditions to any of the polynucleotides (f) to (i).

The nucleic acid(s) further used in the method of the present invention can comprise nucleic acid(s) capable of specifically binding to at least one polynucleotide selected from the group consisting of miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

Specifically, miR-658 is hsa-miR-658, miR-6842-5p is hsa-miR-6842-5p, miR-6124 is hsa-miR-6124, miR-6765-3p is hsa-miR-6765-3p, miR-7106-5p is hsa-miR-7106-5p, miR-4534 is hsa-miR-4534, miR-92b-3p is hsa-miR-92b-3p, miR-3135b is hsa-miR-3135b, miR-4687-3p is hsa-miR-4687-3p, miR-762 is hsa-miR-762, miR-3619-3p is hsa-miR-3619-3p, miR-4467 is hsa-miR-4467, miR-557 is hsa-miR-557, miR-1237-5p is hsa-miR-1237-5p, miR-1908-5p is hsa-miR-1908-5p, miR-4286 is hsa-miR-4286, miR-6885-5p is hsa-miR-6885-5p, and miR-6763-5p is hsa-miR-6763-5p.

Further, in a preferred embodiment, such nucleic acid(s) is/are specifically a polynucleotide selected from the group consisting of the following polynucleotides (k) to (o):
 (k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides,
 (l) a polynucleotide comprising a nucleotide sequence represented by any of SEQ ID NOs: 252 to 269,
 (m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 252 to 269 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from living tissues (preferably breast tissues) or body fluids such as blood, serum, plasma, and urine from the subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse or a rat, and is preferably a human.

The steps of the method of the present invention can be changed according to the type of the sample to be assayed.

In the case of using RNA as an analyte, the detection of breast cancer (cells) can comprise, for example, the following steps (a), (b), and (c):

(a) a step of binding RNA prepared from a sample from a subject or complementary polynucleotides (cDNAs) transcribed from the RNA to a polynucleotide(s) in the kit or the device of the present invention;

(b) a step of measuring the sample-derived RNA or the cDNAs synthesized from the RNA, which is/are bound to the polynucleotide(s) by hybridization using the polynucleotide(s) as nucleic acid probe(s) or by quantitative RT-PCR using the polynucleotide(s) as primer (s); and (c) a step of evaluating the presence or absence of breast cancer (or breast cancer-derived gene expression) on the basis of the measurement results of the step (b).

For example, various hybridization methods can be used for detecting, examining, evaluating, or diagnosing breast cancer (or breast cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}$P, $^{33}$P, $^{35}$S, etc.), a fluorescent material, or the like, that hybridizes the labeled product with the tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises; preparing cDNAs from the tissue-derived RNA of a subject according to a routine procedure; hybridizing a pair of primers (consisting of a plus strand and a reverse strand that bind to the cDNA) of the present invention with the cDNA such that the region of each target gene can be amplified with the cDNA as a template; and performing PCR according to a routine method to detect the obtained double-stranded DNA. The method for detecting the double-stranded DNA can include; a method of performing the PCR using the primers labeled in advance with a radioisotope or a fluorescent material; a method of electrophoresing the PCR product on an agarose gel and staining the double-stranded DNA with ethidium bromide or the like for detection; and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) are attached to a substrate (solid phase) is used. Regions having the attached nucleic acid probes are referred to as probe spots, and regions having no attached nucleic acid probe are referred to as blank spots. A gene group immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probe using an image detector (examples thereof can include Typhoon 9410 (GE Healthcare) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than "(a mean of background measurement values)+(a standard deviation of the background measurement values)×2") than that for other sequences.

The stringent conditions are defined by hybridization and subsequent washing conditions. Examples of the hybridization conditions include, but not limited to 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by the washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments contained in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.); LNA™-based MicroRNA PCR (Exiqon); or Ncode™ miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene that shows a gene expression level of $2^6$, preferably $2^8$, more preferably $2^{10}$, or larger, in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring target genes or gene expression levels in a sample from a subject using the polynucleotide, the kit, or the device (e.g., chip) for detection of the present invention, or a combination thereof, preparing a discriminant (discriminant function) with gene expression levels in a sample from a breast cancer patient and a sample from a healthy subject as supervising samples, and determining or evaluating the presence and/or absence of the breast cancer-derived genes in the sample.

Specifically, the present invention further provides the method comprising: a first step of measuring in vitro expression levels of target genes in multiple samples known to determine or evaluate the presence and/or absence of the breast cancer-derived genes in the samples, using the polynucleotides, the kit, or the device (e.g., chip) for detection of the present invention, or a combination thereof; a second step of preparing a discriminant with the measurement values of the expression levels of the target genes (target nucleic acid) obtained in the first step as supervising samples; a third step of measuring in vitro expression levels of the target genes in a sample derived from a subject in the same way as in the first step; and a fourth step of assigning the measurement values of the expression levels of the target genes obtained in the third step to the discriminant obtained in the second step, and determining or evaluating the presence and/or absence of the breast cancer-derived gene in the sample on the basis of the results obtained from the discriminant, wherein the target genes can be detected using the polynucleotides or using polynucleotides for detection contained in the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this formula, x represents an explanatory variable, w represents a coefficient of the explanatory variable, and wo represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimension reduction method for selecting a dimension suitable for classification, and constructs a highly discriminating synthetic variable by focusing on the variance of synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this formula, µ represents an average input, ng represents the number of data associated to class g, and µg represents an average input of the data associated to class g. The numerator and the denominator are the interclass variance and the intraclass variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)}$$  Formula 2

$$\text{subject to } \mu = \sum_{i=1}^{n} \frac{x_i}{n}, \mu_g = \sum_{i:u_l=g}^{n} \frac{x_l}{n_g}$$

The Mahalanobis' distance is calculated according to Formula 3 in consideration of data correlation and can be used as nonlinear discriminant analysis for determining a cluster to which a data point is associated, based on a short Mahalanobis' distance from the data point to that cluster. In this formula, μ represents a central vector of each cluster, and S−1 represents an inverse matrix of the variance-covariance matrix of the cluster. The central vector is calculated from explanatory variable x, and an average vector, a median value vector, or the like can be used.

$$D(x,\mu) = \{(x-\mu)^t S^{-1}(x-\mu)\}^{1/2}$$  Formula 3

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be the associated classe, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a breast cancer patient group and a healthy subject group. For example, breast tissue examination can be used for a reference under which each subject is confirmed either as a breast cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by explanatory variables that are genes found to differ clearly in their gene expression levels between the two groups, and objective variables (e.g., −1 and +1) that are the grouping. An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a$$  Formula 4 subject to $y^T a = 0, 0 \leq a_i \leq C, i = 1, \ldots, l,$

Formula 5 is a finally obtained discriminant, and a group to which the data point is associated can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right)$$  Formula 5

For example, a RBF kernel defined by Formula 6 can be used as the kernel function. In this formula, x represents a support vector, and y represents a kernel parameter for adjusting the complexity of the hyperplane.

$$K(x_i, x_j) = \exp(-r\|x_i - x_j\|^2), r < 0$$  Formula 6

In addition, an approach such as neural network, k-nearest neighbor algorithms, decision trees, or logistic regression analysis can be selected as a method for determining or evaluating the presence and/or absence of expression of a breast cancer-derived target gene in a sample derived from a subject, or for evaluating the expression level thereof by comparison with a control derived from a healthy subject.

The method of the present invention can comprise, for example, the following steps (a), (b), and (c):

(a) a step of measuring expression level(s) of target gene(s) in tissues containing breast cancer-derived genes derived from breast cancer patients and/or samples already known to be tissues containing no breast cancer-derived gene(s) derived from healthy subjects, using the polynucleotide(s), the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring expression level(s) of the target gene(s) in a sample derived from a subject using the polynucleotide(s), the kit, or the device (e.g., DNA chip) for diagnosis (detection) according to the present invention, substituting the obtained measurement valuec into the discriminants prepared in the step (b), and determining or evaluating the presence and/or absence of the breast cancer-derived target gene in the sample, or evaluating the expression levels thereof by comparison with a healthy subject-derived control, on the basis of the obtained results. In this context, in the discriminants of Formulas 1 to 3, 5, and 6, x represents an explanatory variable and includes a value obtained by measuring polynucleotide(s) selected from the polynucleotides described in the Section 2 above, or any fragment thereof. Specifically, the explanatory variable for discriminating a breast cancer patient from a healthy subject according to the present invention is gene expression level(s) selected from, for example, the following expression levels (1) to (3):

(1) gene expression level(s) in the serum of a breast cancer patient or a healthy subject measured by any DNA comprising 15 or more consecutive nucleotides in a nucleotide sequence represented by any of SEQ ID NOs: 1 to 235 and 851 to 856 or a complementary sequence thereof, (2) gene expression level(s) in the serum of a breast cancer patient or a healthy subject measured by any DNA comprising 15 or more consecutive nucleotides in a nucleotide sequence represented by any of SEQ ID NOs: 236 to 251 or a complementary sequence thereof, (3) gene expression level(s) in the serum of a breast cancer patient or a healthy subject measured by any DNA comprising 15 or more consecutive nucleotides in a nucleotide sequence represented by any of SEQ ID NOs: 252 to 269 or a complementary sequence thereof.

As described above, for the method for determining or evaluating the presence and/or absence of breast cancer-derived gene(s) in a sample derived from a subject, the preparation of a discriminant requires a discriminant prepared from a training cohort. For enhancing the accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a breast cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a breast cancer patient group and gene expression levels of a healthy subject group may be calculated to select a gene that is used for an explanatory variable in a discriminant. Alternatively, ROC curves may be prepared using gene expression levels of a breast cancer patient group and a healthy subject group, and a gene that is used for an explanatory variable in a discriminant can be selected on the basis of an AUROC value.

Next, a discriminant that can be calculated by various methods described above is prepared using any number of genes that show large difference in their gene expression levels determined here. Examples of the method for constructing a discriminant that produces the largest discriminant accuracy include a method of constructing a discriminant in every combination of genes that satisfy the significance level of P value, and a method of repetitively evaluating the genes for use in the construction of a discriminant while increasing the number of genes one by one in a descending order of the difference in gene expression level (Furey T S. et al., 2000, Bioinformatics., Vol. 16, p. 906-14). A gene expression level of another independent breast cancer patient or healthy subject is assigned as an explanatory variable to this discriminant to calculate discriminant results of the group to which this independent breast cancer patient or healthy subject is associated. Specifically, the found gene set for diagnosis and the discriminant constructed using the gene set for diagnosis can be evaluated in an independent sample cohort to find a more universal gene set for diagnosis capable of detecting breast cancer and a more universal method for discriminating breast cancer.

Split-sample method is preferably used for evaluating the performance (generality) of the discriminant. Specifically, a data set is divided into a training cohort and a validation cohort, and gene selection by a statistical test and discriminant construction are performed using the training cohort. Accuracy, sensitivity, and specificity are calculated using results of discriminant analysis in the validation cohort according to the discriminant constructed and a true group to which the validation cohort is associated, to evaluate the discriminant performance of the discriminant. On the other hand, instead of dividing a data set, gene selection by a statistical test and discriminant construction may be performed using all of samples, and accuracy, sensitivity, and specificity can be calculated by the discriminat analysis using a newly prepared cohorts for evaluation of the performance of the discriminant.

The present invention provides polynucleotides for detection and disease diagnosis useful in the diagnosis and treatment of breast cancer, a method for detecting breast cancer using the polynucleotide(s), and a kit and a device for the detection of breast cancer, comprising the polynucleotide(s). Particularly, in order to select gene(s) for diagnosis and prepare a discriminant so as to exhibit accuracy beyond the breast cancer diagnosis method using an existing tumor marker CEA, a gene set for diagnosis and a discriminant for the method of the present invention can be constructed, which exhibit accuracy beyond CEA, for example, by comparing expressed genes in serum from a patient confirmed to be negative using CEA but finally found to have breast cancer by detailed examination such as computed tomography using a contrast medium, with genes expressed in serum from a patient having no breast cancer.

For example, the gene set for diagnosis is set to any combination selected from one or two or more of the polynucleotides based on a nucleotide sequence represented by any of SEQ ID NOs: 1 to 235, and 851 to 856, or a complementary sequence thereof as described above; and optionally one or two or more of the polynucleotides based on a nucleotide sequence represented by any of SEQ ID NOs: 236 to 251, or a complementary sequence thereof; and optionally one or two or more of the polynucleotides based on a nucleotide sequence represented by any of SEQ ID NOs: 252 to 269, or a complementary sequence thereof. Further, a discriminant is constructed using expression levels of the gene set for diagnosis in samples from class I breast cancer patients as a result of tissue diagnosis and samples from class II healthy subjects as a result of tissue diagnosis. As a result, the presence or absence of breast cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples from Breast Cancer Patients and Healthy Subjects>

Sera were collected using VENOJECT II vacuum blood collecting tube VP-AS109K60 (Terumo Corp.) from 100 healthy subjects (92 males and 8 females) and 62 breast cancer patients (20 cases with stage I, 24 cases with stage IIA, 7 cases with stage IIB, 2 cases with stage IIIA, 3 cases with stage IIIB, 1 case with stage IIIC, and 5 cases with stage IV) who were confirmed to have no primary cancer other than breast cancer after acquisition of informed consent, and used as a training cohort. Likewise, Sera were collected using VENOJECT II vacuum blood collecting tube VP-AS109K60 (Terumo Corp.) from 50 healthy subjects (44 males and 6 females) and 31 breast cancer patients (9 cases with stage I, 13 cases with stage IIA, 5 cases with stage IIB, 1 case with stage IIIA, 1 case with stage IIIB, 1 case with stage IIIC, and 1 case with stage IV) who were confirmed to have no primary cancer other than breast cancer after acquisition of informed consent, and used as a validation cohort.

<Extraction of Total RNA>

Total RNA was obtained from 300 μL of the serum sample obtained from each of 243 persons in total of 150 healthy subjects and 93 breast cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum samples of each of 243 persons in total of 150 healthy subjects and 93 breast cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miR-Base Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value with a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 93 breast cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-projectorg/) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancer Other than Breast Cancer>

Sera were collected using VENOJECT II vacuum blood collecting tube VP-AS109K60 (Terumo Corp.) from each of 33 prostate cancer patients confirmed to have no cancer in other organs after acquisition of informed consent, and used as a training cohort together with the samples of 62 breast cancer patients and 102 healthy subjects of Reference Example 1. Likewise, sera were collected using VENOJECT 11 vacuum blood collecting tube VP-AS109K60 (Terumo Corp.) from each of 19 prostate cancer patients confirmed to have no cancer in other organs after acquisition of informed consent, and used as a validation cohort together with the samples of 31 breast cancer patients confirmed to have no cancer in organs other than the breast and 48 healthy subjects of Reference Example 1. Subsequent operations were conducted in the same way as in Reference Example 1.

Example 1

<Selection of Gene Marker Using the Training Cohort, and Method for Evaluating Breast Cancer Discriminant Performance of the Single Gene Marker Using the Validation Cohort>

In this Example, a gene marker for discriminating a breast cancer patient from a healthy subject was selected from the training cohort and studied in the validation cohort independent of the training cohort, for a method for evaluating the breast cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes that show the gene expression level of $2^6$ or higher in 50% or more of the samples in either of the breast cancer patient group in the training cohort or the healthy subject group in the training cohort were selected. In order to further acquire statistically significant genes for discriminating a breast cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The obtained genes are described in Table 2.

In this way, hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p and hsa-miR-92a-3p genes, and polynucleotides consisting of the nucleotide sequences of SEQ ID NOs: 1 to 251 related thereto were found.

Among them, genes newly found as markers for examining the presence or absence of breast cancer are polynucleotides consisting of the nucleotide sequences represented by SEQ ID NOs: 1 to 235.

A discriminant for determining the presence or absence of breast cancer was further prepared by Fisher's discriminant analysis with the expression levels of these genes as indicators. Specifically, any newly found polynucleotide consisting of a nucleotide sequence represented by any of SEQ ID NOs: 1 to 251 in the training cohort was applied for Formula 2 above to prepare a discriminant. Calculated accuracy, sensitivity, and specificity are shown in Table 3. In this respect, a discriminant coefficient and a constant term are shown in Table 4. Here, all of the polynucleotides consisting of the nucleotide sequences represented by SEQ ID NOs: 1 to 251 were selected as markers capable of determining not only invasive ductal breast cancer (56 cases), which is a main type of breast cancer, but also invasive lobular cancer (3 cases) and unusual metastatic carcinoma with poor prognosis (1 case).

Figure 2:
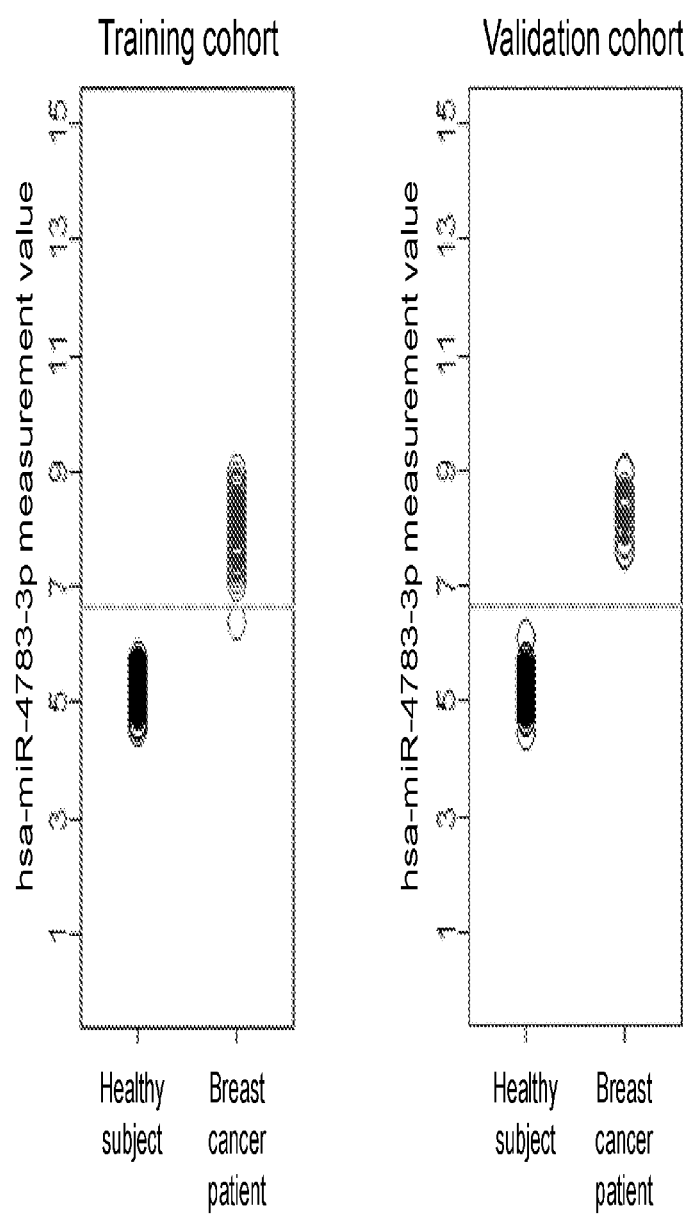
FIG. 2 Left diagram: the expression level measurement values of hsa-miR-4783-3p (SEQ ID NO: 1) in healthy subjects (100 persons) and breast cancer patients (62 persons) selected as a training cohort were each plotted on the ordinate. The horizontal line in the diagram depicts a threshold (6.63) that was optimized by Fisher's discriminant analysis and discriminated between the two groups. Right diagram: the expression level measurement values of hsa-miR-4783-3p (SEQ ID NO: 1) in healthy subjects (50 persons) and breast cancer patients (31 persons) selected as a validation cohort were each plotted on the ordinate. The horizontal line in the diagram depicts the threshold (6.63) that was set in the training cohort and discriminated between the two groups.

Accuracy, sensitivity, and specificity in the validation cohort were calculated using the discriminant thus prepared, and the discriminant performance of the selected polynucleotides was validated using the independent samples (Table 3). For example, the expression level measurement value of the gene that consists of the nucleotide sequence represented by SEQ ID NO: 1 was compared between the healthy subjects (100 persons) and the breast cancer patients (62 persons) in the training cohort. As a result, the expression level measurement values were found to be significantly lower in the breast cancer patient group than in the healthy subject group (see the left diagram of FIG. 2). These results were also reproducible for the healthy subjects (50 persons) and the breast cancer patients (31 persons) in the validation cohort (see the right diagram of FIG. 2). Likewise, the results obtained about the other polynucleotides shown in SEQ ID NOs: 2 to 251 showed that the expression level measurement values were significantly lower (−) or higher (+) in the breast cancer patient group than in the healthy subject group (Table 2). These results were able to be validated in the validation cohort. For example, as for this nucleotide sequence represented by SEQ ID NO: 1, the number of correctly or incorrectly identified samples in the detection of breast cancer was calculated using the threshold (6.63) that was set in the training cohort and discriminated between the two groups. As a result, 31 true positives, 50 true negatives, 0 false positives, and 0 false negatives were obtained. From these values, 100% accuracy, 100% sensitivity, and 100% specificity were obtained as the detection performance. In this way, the detection performance was calculated as to all of the polynucleotides shown in SEQ ID NOs: 1 to 251, and described in Table 3. Likewise, the polynucleotides consisting of the nucleotide sequences represented by SEQ ID NOs: 2 to 251 shown in Table 2 exhibited sensitivity of 100%, 100%, 90.3%, 96.8%, 100%, 100%, 96.8%, 96.8%, 100%, 100%, 100%, 100%, 96.8%, 96.8%, 100%, 100%, 96.8%, 100%, 93.5%, 96.8%, 96.8%, 100%, 96.8%, 96.8%, 93.5%, 96.8%, 93.5%, 87.1%, 83.9%, 96.8%, 96.8%, 96.8%, 100%, 80.6%, 87.1%, 87.1%, 100%, 90.3%, 90.3%, 90.3%, 100%, 96.8%, 100%, 87.1%, 87.1%, 96.8%, 96.8%, 90.3%, 96.8%, 83.9%, 77.4%, 90%, 83.9%, 96.8%, 93.5%, 80.6%, 96.8%, 90.3%, 93.5%, 90.3%, 87.1%, 87.1%, 96.8%, 83.9%, 87.1%, 77.4%, 90.3%, 77.4%, 90.3%, 83.9%, 74.2%, 93.5%, 87.1%, 93.5%, 93.5%, 77.4%, 90.3%, 87.1%, 87.1%, 83.9%, 87.1%, 93.5%, 77.4%, 93.5%, 74.2%, 83.9%, 100%, 90.3%, 74.2%, 83.9%, 80.6%, 87.1%, 77.4%, 83.9%, 71%, 96.8%, 77.4%, 87.1%, 77.4%, 71%, 90.3%, 80.6%, 67.7%, 77.4%, 87.1%, 74.2%, 83.9%, 77.4%, 71%, 87.1%, 74.2%, 90.3%, 80.6%, 74.2%, 83.9%, 83.9%, 71%, 87.1%, 61.3%, 61.3%, 83.9%, 61.3%, 90.3%, 80.6%, 61.3%, 64.5%, 80.6%, 74.2%, 80.6%, 71%, 71%, 77.4%, 64.5%, 71%, 71%, 83.9%, 74.2%, 83.9%, 63.3%, 64.5%, 71%, 67.7%, 71%, 71%, 74.2%, 71%, 64.5%, 83.9%, 71%, 83.9%, 61.3%, 61.3%, 67.7%, 64.5%, 64.5%, 54.8%, 64.5%, 74.2%, 58.1%, 58.1%, 58.1%, 58.1%, 61.3%, 67.7%, 61.3%, 67.7%, 58.1%, 58.1%, 54.8%, 67.7%, 58.1%, 64.5%, 61.3%, 67.7%, 58.1%, 58.1%, 48.4%, 61.3%, 54.8%, 38.7%, 35.5%, 64.5%, 54.8%, 64.5%, 54.8%, 61.3%, 35.5%, 48.4%, 61.3%, 61.3%, 54.8%, 71%, 61.3%, 45.2%, 48.4%, 29%, 54.8%, 41.9%, 67.7%, 29%, 29%, 53.3%, 51.6%, 45.2%, 35.5%, 41.9%, 41.9%, 48.4%, 41.9%, 35.5%, 41.9%, 35.5%, 48.4%, 32.3%, 41.9%, 41.9%, 41.9%, 35.5%, 35.5%, 41.9%, 61.3%, 32.3%, 45.2%, 38.7%, 51.6%, 29%, 35.5%, 38.7%, 54.8%, 58.1%, 51.6%, 29%, 41.9%, 38.7%, 96.8%, 96.8%, 96.8%, 100%, 96.8%, 87.1%, 80.6%, 100%, 87.1%, 93.5%, 67.7%, 67.7%, 61.3%, 67.7%, 38.7% and 54.8%, respectively, in the validation cohort (Table 3). As seen from Comparative Example mentioned later, the existing marker CEA had sensitivity of 19.4% in the validation cohort (Table 5-2), demonstrating that all of the polynucleotides consisting of the nucleotide sequences represented by SEQ ID Nos: 1 to 251 can discriminate, each alone, breast cancer in the validation cohort with sensitivity beyond CEA.

For example, the 83 polynucleotides consisting of the nucleotide sequences represented by SEQ ID NOs: 1, 2, 3, 4, 6, 7, 8, 9, 10, 11, 12, 13, 14, 15, 16, 17, 19, 20, 21, 22, 23, 24, 25, 26, 27, 28, 31, 32, 33, 34, 35, 36, 38, 40, 42, 44, 45, 47, 48, 49, 50, 55, 59, 64, 65, 66, 68, 70, 73, 75, 78, 79, 80, 81, 84, 88, 92, 93, 95, 97, 98, 99, 102, 109, 113, 119, 122, 124, 128, 130, 133, 145, 149, 169, 236, 237, 238, 239, 240, 241, 242, 243, 244 were able to correctly determine breast cancer in the 9 breast cancer samples of stage 1 contained in the validation cohort. Thus, these polynucleotides can detect even early breast cancer and contributes to the early diagnosis of breast cancer.

Example 2

<Method a for Evaluating Breast Cancer Discriminant Performance by Combination of Multiple Gene Markers Using the Samples in the Validation Cohort>

In this Example, a method for evaluating breast cancer discriminant performance by a combination of the gene markers selected in Example 1 was studied. Specifically, Fisher's discriminant analysis was conducted as to 31,255 polynucleotide combinations comprising at least one of the newly found polynucleotides consisting of the nucleotide sequences represented by SEQ ID NOs: 1 to 235 among the polynucleotides consisting of the nucleotide sequences represented by SEQ ID NOs: 1 to 251 selected in Example 1, to construct a discriminant for determining the presence or absence of breast cancer. Next, accuracy, sensitivity, and specificity in the validation cohort were calculated using the discriminant thus prepared, and the discriminant performance of the selected polynucleotides was validated using the independent samples.

Figure 3:
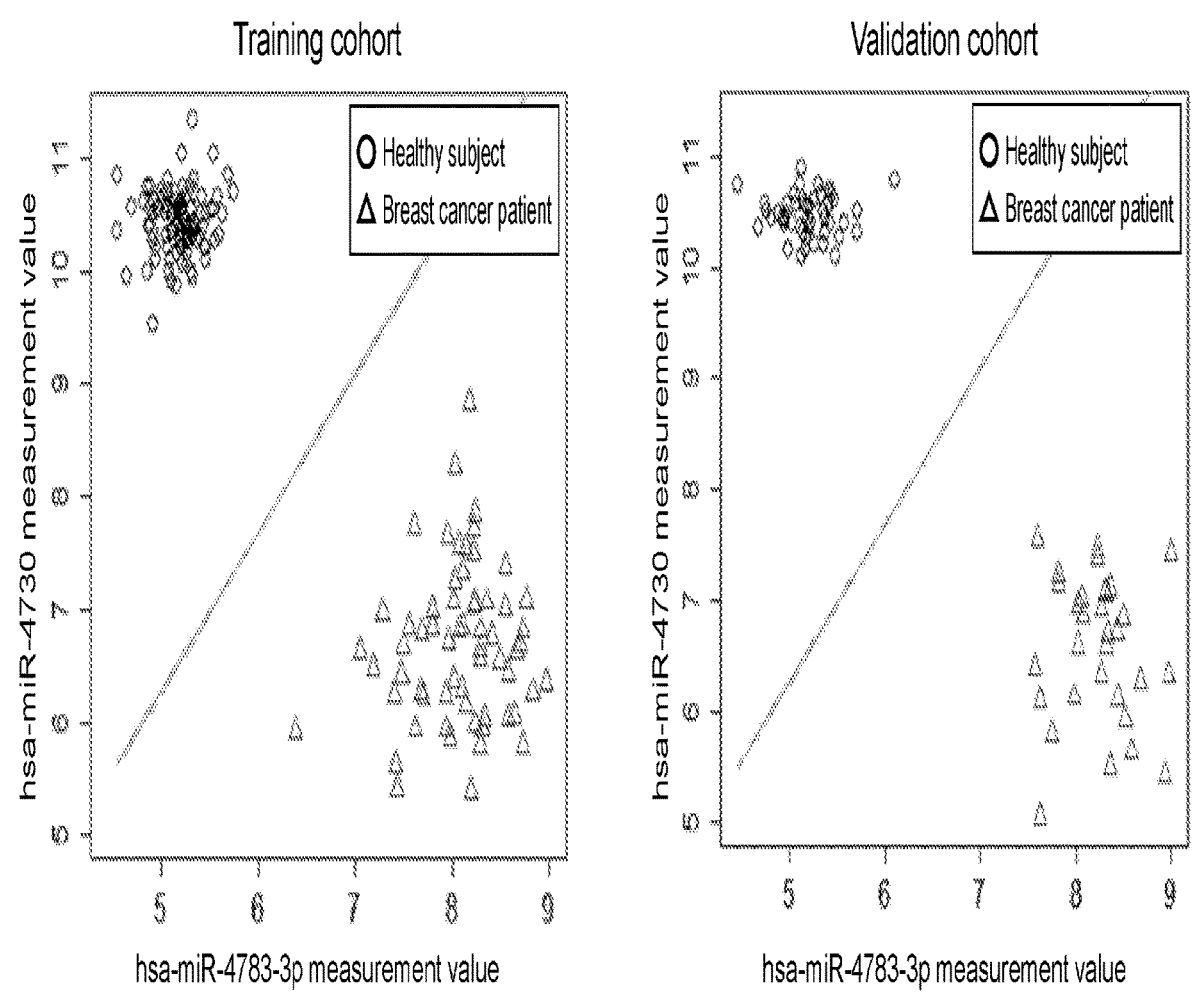
FIG. 3 Left diagram: the expression level measurement values of hsa-miR-4783-3p (SEQ ID NO: 1) in healthy subjects (100 persons, circles) and breast cancer patients (62 persons, triangles) selected as a training cohort were each plotted on the abscissa against their expression level measurement values of hsa-miR-4730 (SEQ ID NO: 2) on the ordinate. The line in the diagram depicts a discriminant function (0=1.41x+y+0.77) that was optimized by Fisher's discriminant analysis and discriminated between the two groups. Right diagram: the expression level measurement values of hsa-miR-4783-3p (SEQ ID NO: 1) in healthy subjects (50 persons, circles) and breast cancer patients (31 persons, triangles) selected as a validation cohort were each plotted on the abscissa against their expression level measurement values of hsa-miR-4730 (SEQ ID NO: 2) on the ordinate. The line in the diagram depicts the threshold (0=1.41x+y+0.77) that was set for the training cohort and discriminated between the two groups.

For example, the gene expression level measurement values of the nucleotide sequences represented by SEQ ID NO: 1 and SEQ ID NO: 2 were compared between the healthy subjects and the breast cancer patients. As a result, a scatter diagram that significantly separated the expression level measurement values of the breast cancer patient group from those of the healthy subject group was obtained (see the left diagram of FIG. 3). These results were also reproducible for the healthy subjects (50 persons) and the breast cancer patients (31 persons) in the validation cohort (see the right diagram of FIG. 3). Likewise, a scatter diagram that significantly separated the expression level measurement values of the breast cancer patient group from those of the healthy subject group was also obtained as to the other polynucleotide combinations comprising at least one of the newly found polynucleotides consisting of the nucleotide sequences represented by SEQ ID NOs: 1 to 235 among the polynucleotides consisting of the nucleotide sequences represented by SEQ ID NOs: 1 to 251. These results were able to be validated in the validation cohort. For example, as for these nucleotide sequences represented by SEQ ID NO: 1 and SEQ ID NO: 2, the number of samples that were correctly or incorrectly identified breast cancer was calculated using the discriminant function (0=1.41x+y+0.77) that was set in the training cohort and discriminated between the two groups. As a result, 31 true positives, 50 true negatives, 0 false positives, and 0 false negatives were obtained. From these values, 100% accuracy, 100% sensitivity, and 100% specificity were obtained as the detection performance. In this way, the detection performance was calculated as to all of the polynucleotide combinations comprising at least one of the newly found polynucleotides consisting of the nucleotide sequences represented by SEQ ID NOs: 1 to 235 among the polynucleotides consisting of the nucleotide sequences represented by SEQ ID NOs: 1 to 251. Among them, 250 combinations comprising the expression level measurement value of the polynucleotide consisting of the nucleotide sequence represented by SEQ ID NO: 1 and the detection performance thereof were described in Table 6 as an example. For example, all of the combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 100% in the validation cohort. Likewise, all of the combinations of two polynucleotides consisting of the nucleotide sequence represented by SEQ ID NO: 1 and a nucleotide sequence represented by any of SEQ ID NOs: 6 to 251 also exhibited sensitivity of 100%. In addition, the combinations of two polynucleotides consisting of the nucleotide sequences except for SEQ ID NO: 1 were described in Table 7 as an example. As the specific combinations of two polynucleotides, for example, the combinations represented by SEQ ID NOs: 3 and 20, SEQ ID NOs: 6 and 20, SEQ ID NOs: 7 and 20, SEQ ID NOs: 10 and 20, SEQ ID NOs: 20 and 22, SEQ ID NOs: 20 and 238, SEQ ID NOs: 20 and 239, SEQ ID NOs: 12 and 24, SEQ ID NOs: 20 and 24, SEQ ID NOs: 24 and 27, SEQ ID NOs: 24 and 33, SEQ ID NOs: 24 and 236, SEQ ID NOs: 24 and 240, SEQ ID NOs: 3 and 26, SEQ ID NOs: 12 and 26, SEQ ID NOs: 13 and 26, SEQ ID NOs: 17 and 26, SEQ ID NOs: 19 and 26, SEQ ID NOs: 3 and 27, SEQ ID NOs: 5 and 27, SEQ ID NOs: 13 and 27, SEQ ID NOs: 20 and 27, SEQ ID NOs: 26 and 27, SEQ ID NOs: 27 and 120, SEQ ID NOs: 27 and 206, SEQ ID NOs: 27 and 237, SEQ ID NOs: 3 and 30, SEQ ID NOs: 17 and 30, SEQ ID NOs: 27 and 30, SEQ ID NOs: 27 and 33, SEQ ID NOs: 30 and 39, SEQ ID NOs: 30 and 117, SEQ ID NOs: 3 and 33, SEQ ID NOs: 7 and 33, SEQ ID NOs: 10 and 33, SEQ ID NOs: 11 and 33, SEQ ID NOs: 13 and 33, SEQ ID NOs: 25 and 33, SEQ ID NOs: 33 and 244, SEQ ID NOs: 3 and 182, SEQ ID NOs: 6 and 182, SEQ ID NOs: 7 and 182, SEQ ID NOs: 12 and 182, SEQ ID NOs: 27 and 182, SEQ ID NOs: 182 and 236, SEQ ID NOs: 2 and 194, SEQ ID NOs: 7 and 194, SEQ ID NOs: 27 and 194, SEQ ID NOs: 194 and 236, SEQ ID NOs: 2 and 206, SEQ ID NOs: 7 and 206, SEQ ID NOs: 206 and 236, SEQ ID NOs: 2 and 208, SEQ ID NOs: 7 and 208, SEQ ID NOs: 13 and 208, SEQ ID NOs: 20 and 208, and SEQ ID NOs: 27 and 208 exhibited accuracy of 96% or higher for discriminating the breast cancer patients from the healthy subjects in both of the training cohort and the validation cohort. Thus, the combinations of two of the polynucleotides consisting of the nucleotide sequences represented by SEQ ID NOs: 1 to 251 also produced excellent detection sensitivity for breast cancer. Markers for the detection of breast cancer with better sensitivity are obtained by further combining 3, 4, 5, 6, 7, 8, 9, 10 or more of the measurement values of the polynucleotides consisting of the nucleotide sequences represented by SEQ ID NOs: 1 to 251. For example, the newly found polynucleotides consisting of the nucleotide sequences represented by SEQ ID NOs: 1 to 235 among the polynucleotides consisting of the nucleotide sequences represented by SEQ ID NOs: 1 to 251 selected in Example 1, were measured to obtain their expression levels between the healthy subject group and the breast cancer group in the validation cohort. All of the polynucleotides were ranked in the descending order of their P values based on the Student's t-test which indicates statistical significance of a difference between groups (i.e., one having the lowest P value was ranked in the first place), and breast cancer detection sensitivity was evaluated using combinations of one or more polynucleotides to which the polynucleotides were added one by one from the top to bottom according to the rank. In short, the order in which the polynucleotides were combined in this evaluation is in reverse in terms of SEQ ID NOs, such as SEQ ID NO: 235 to SEQ ID NOs: 234, 233, . . . shown in Table 2 in order. As a result, the sensitivity in the validation cohort was 38.7% for 1 polynucleotide (SEQ ID NO: 235), 48.4% for 2 polynucleotides (SEQ ID NOs: 234 and 235), 74.2% for 4 polynucleotides (SEQ ID NOs: 232 to 235), 87.1% for 6 polynucleotides (SEQ ID NOs: 230 to 235), 90.3% for 10 polynucleotides (SEQ ID NOs: 226 to 235), 93.5% for 13 polynucleotides (SEQ ID NOs: 223 to 235), 96.8% for 16 polynucleotides (SEQ ID NOs: 220 to 235), 100% for 20 polynucleotides (SEQ ID NOs: 216 to 235), 100% for 30 polynucleotides (SEQ ID NOs: 206 to 235), 100% for 50 polynucleotides (SEQ ID NOs: 186 to 235), 100% for 100 polynucleotides (SEQ ID NOs: 136 to 235), 100% for 200 polynucleotides (SEQ ID NOs: 36 to 235), and 100% for 235 polynucleotides (SEQ ID NOs: 1 to 235).

These results demonstrated that a combination of multiple polynucleotides can produce higher breast cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of breast cancer.

From these results, it can be concluded that all of the polynucleotides consisting of the nucleotide sequences represented by SEQ ID NOs: 1 to 251 serve as excellent markers for breast cancer detection.

TABLE 2

| SEQ ID NO: | Gene name | P value after Bonferroni correction | Expression level in breast cancer patient with respect to healthy subject |
|---|---|---|---|
| 1 | hsa-miR-4783-3p | $1.88 \cdot E{-}98$ | + |
| 2 | hsa-miR-4730 | $1.39 \cdot E{-}95$ | − |
| 3 | hsa-miR-1307-3p | $9.90 \cdot E{-}81$ | + |
| 4 | hsa-miR-4634 | $1.73 \cdot E{-}79$ | − |
| 5 | hsa-miR-663a | $2.71 \cdot E{-}76$ | + |
| 6 | hsa-miR-4532 | $2.24 \cdot E{-}75$ | + |
| 7 | hsa-miR-7704 | $4.18 \cdot E{-}74$ | − |
| 8 | hsa-miR-3178 | $2.19 \cdot E{-}71$ | − |
| 9 | hsa-miR-6729-5p | $1.88 \cdot E{-}69$ | − |
| 10 | hsa-miR-6090 | $2.55 \cdot E{-}68$ | + |
| 11 | hsa-miR-4732-5p | $1.36 \cdot E{-}67$ | + |
| 12 | hsa-miR-3184-5p | $8.11 \cdot E{-}67$ | − |
| 13 | hsa-miR-6727-5p | $3.02 \cdot E{-}64$ | − |
| 14 | hsa-miR-6088 | $3.54 \cdot E{-}64$ | + |
| 15 | hsa-miR-4674 | $9.34 \cdot E{-}64$ | − |
| 16 | hsa-miR-8073 | $1.47 \cdot E{-}63$ | + |
| 17 | hsa-miR-4787-5p | $5.85 \cdot E{-}62$ | − |
| 18 | hsa-miR-1469 | $2.97 \cdot E{-}61$ | + |
| 19 | hsa-miR-125a-3p | $9.95 \cdot E{-}61$ | − |
| 20 | hsa-miR-1233-5p | $2.94 \cdot E{-}60$ | + |
| 21 | hsa-miR-885-3p | $6.54 \cdot E{-}60$ | + |
| 22 | hsa-miR-6802-5p | $4.56 \cdot E{-}59$ | + |
| 23 | hsa-miR-328-5p | $1.83 \cdot E{-}58$ | + |
| 24 | hsa-miR-6787-5p | $5.55 \cdot E{-}58$ | + |
| 25 | hsa-miR-8069 | $2.26 \cdot E{-}57$ | − |
| 26 | hsa-miR-6875-5p | $2.72 \cdot E{-}53$ | − |
| 27 | hsa-miR-1246 | $9.57 \cdot E{-}53$ | + |
| 28 | hsa-miR-4734 | $2.06 \cdot E{-}52$ | + |
| 29 | hsa-miR-6757-5p | $4.71 \cdot E{-}51$ | + |
| 30 | hsa-miR-6756-5p | $5.35 \cdot E{-}51$ | + |
| 31 | hsa-miR-3665 | $1.70 \cdot E{-}50$ | − |
| 32 | hsa-miR-6836-3p | $8.38 \cdot E{-}50$ | − |
| 33 | hsa-miR-6821-5p | $1.19 \cdot E{-}49$ | + |
| 34 | hsa-miR-6805-5p | $3.17 \cdot E{-}49$ | − |
| 35 | hsa-miR-4728-5p | $3.69 \cdot E{-}49$ | + |
| 36 | hsa-miR-6726-5p | $5.62 \cdot E{-}49$ | − |
| 37 | hsa-miR-197-5p | $1.43 \cdot E{-}46$ | + |
| 38 | hsa-miR-149-3p | $3.23 \cdot E{-}46$ | + |
| 39 | hsa-miR-6850-5p | $4.58 \cdot E{-}46$ | − |
| 40 | hsa-miR-4476 | $5.54 \cdot E{-}46$ | − |
| 41 | hsa-miR-6858-5p | $9.61 \cdot E{-}46$ | + |
| 42 | hsa-miR-564 | $1.62 \cdot E{-}44$ | − |
| 43 | hsa-miR-4763-3p | $2.01 \cdot E{-}44$ | + |
| 44 | hsa-miR-575 | $3.61 \cdot E{-}44$ | − |
| 45 | hsa-miR-6771-5p | $2.62 \cdot E{-}43$ | − |
| 46 | hsa-miR-1231 | $7.46 \cdot E{-}43$ | − |
| 47 | hsa-miR-1908-3p | $9.60 \cdot E{-}43$ | − |
| 48 | hsa-miR-150-3p | $2.19 \cdot E{-}42$ | − |
| 49 | hsa-miR-3937 | $9.92 \cdot E{-}42$ | − |
| 50 | hsa-miR-887-3p | $2.38 \cdot E{-}41$ | − |
| 51 | hsa-miR-3940-5p | $3.44 \cdot E{-}41$ | − |
| 52 | hsa-miR-4741 | $4.16 \cdot E{-}41$ | − |
| 53 | hsa-miR-6808-5p | $5.42 \cdot E{-}41$ | + |
| 54 | hsa-miR-6869-5p | $1.03 \cdot E{-}40$ | − |
| 55 | hsa-miR-5090 | $5.03 \cdot E{-}40$ | − |
| 56 | hsa-miR-615-5p | $1.94 \cdot E{-}39$ | − |
| 57 | hsa-miR-8072 | $2.71 \cdot E{-}39$ | + |
| 58 | hsa-miR-128-1-5p | $2.72 \cdot E{-}39$ | − |
| 59 | hsa-miR-1238-5p | $7.46 \cdot E{-}39$ | + |
| 60 | hsa-miR-365a-5p | $9.50 \cdot E{-}39$ | + |
| 61 | hsa-miR-204-3p | $1.32 \cdot E{-}38$ | − |
| 62 | hsa-miR-4492 | $3.33 \cdot E{-}37$ | − |
| 63 | hsa-miR-6785-5p | $4.21 \cdot E{-}37$ | − |

TABLE 2-continued

| SEQ ID NO: | Gene name | P value after Bonferroni correction | Expression level in breast cancer patient with respect to healthy subject |
|---|---|---|---|
| 64 | hsa-miR-6511a-5p | 7.68 · E−37 | + |
| 65 | hsa-miR-4525 | 1.16 · E−36 | − |
| 66 | hsa-miR-1915-5p | 1.34 · E−36 | − |
| 67 | hsa-miR-3180 | 1.07 · E−35 | − |
| 68 | hsa-miR-6879-5p | 1.56 · E−35 | + |
| 69 | hsa-miR-1199-5p | 1.15 · E−34 | − |
| 70 | hsa-miR-6746-5p | 5.65 · E−34 | + |
| 71 | hsa-miR-711 | 5.82 · E−34 | − |
| 72 | hsa-miR-663b | 1.42 · E−33 | − |
| 73 | hsa-miR-4707-3p | 2.19 · E−33 | − |
| 74 | hsa-miR-6893-5p | 6.31 · E−33 | − |
| 75 | hsa-miR-4675 | 6.39 · E−33 | + |
| 76 | hsa-miR-4638-5p | 6.40 · E−33 | − |
| 77 | hsa-miR-4651 | 8.91 · E−33 | − |
| 78 | hsa-miR-6087 | 1.91 · E−32 | + |
| 79 | hsa-miR-4665-5p | 3.57 · E−32 | − |
| 80 | hsa-miR-4758-5p | 4.55 · E−32 | + |
| 81 | hsa-miR-6887-5p | 4.45 · E−31 | + |
| 82 | hsa-miR-3620-5p | 4.64 · E−31 | − |
| 83 | hsa-miR-1909-3p | 5.74 · E−31 | − |
| 84 | hsa-miR-7641 | 8.30 · E−31 | − |
| 85 | hsa-miR-6724-5p | 1.02 · E−30 | + |
| 86 | hsa-miR-1343-3p | 1.19 · E−30 | + |
| 87 | hsa-miR-6780b-5p | 1.22 · E−30 | + |
| 88 | hsa-miR-4484 | 2.77 · E−30 | − |
| 89 | hsa-miR-4690-5p | 3.50 · E−30 | + |
| 90 | hsa-miR-4429 | 2.05 · E−29 | + |
| 91 | hsa-miR-1227-5p | 3.84 · E−29 | + |
| 92 | hsa-miR-4725-3p | 5.39 · E−29 | − |
| 93 | hsa-miR-6861-5p | 5.43 · E−29 | + |
| 94 | hsa-miR-6812-5p | 7.48 · E−29 | + |
| 95 | hsa-miR-3197 | 8.20 · E−29 | + |
| 96 | hsa-miR-8059 | 9.29 · E−29 | + |
| 97 | hsa-miR-3185 | 9.34 · E−29 | + |
| 98 | hsa-miR-4706 | 1.69 · E−28 | + |
| 99 | hsa-miR-4497 | 2.22 · E−28 | − |
| 100 | hsa-miR-3131 | 3.64 · E−28 | + |
| 101 | hsa-miR-6806-5p | 9.04 · E−28 | − |
| 102 | hsa-miR-187-5p | 4.89 · E−27 | − |
| 103 | hsa-miR-3180-3p | 7.10 · E−27 | − |
| 104 | hsa-miR-6848-5p | 7.26 · E−27 | − |
| 105 | hsa-miR-6820-5p | 7.77 · E−27 | − |
| 106 | hsa-miR-6800-5p | 1.80 · E−26 | − |
| 107 | hsa-miR-6717-5p | 1.97 · E−26 | + |
| 108 | hsa-miR-6795-5p | 5.16 · E−26 | + |
| 109 | hsa-miR-4632-5p | 8.43 · E−26 | + |
| 110 | hsa-miR-665 | 2.56 · E−25 | − |
| 111 | hsa-miR-6778-5p | 8.69 · E−25 | − |
| 112 | hsa-miR-3663-3p | 1.09 · E−24 | + |
| 113 | hsa-miR-4689 | 3.36 · E−24 | + |
| 114 | hsa-miR-211-3p | 8.65 · E−24 | + |
| 115 | hsa-miR-6511b-5p | 9.67 · E−24 | + |
| 116 | hsa-miR-4750-5p | 1.07 · E−23 | + |
| 117 | hsa-miR-6126 | 2.06 · E−23 | + |
| 118 | hsa-miR-614 | 2.46 · E−22 | + |
| 119 | hsa-miR-7110-5p | 3.56 · E−22 | − |
| 120 | hsa-miR-744-5p | 5.83 · E−22 | + |
| 121 | hsa-miR-6769a-5p | 1.44 · E−21 | + |
| 122 | hsa-miR-4792 | 2.04 · E−21 | − |
| 123 | hsa-miR-5787 | 3.93 · E−21 | + |
| 124 | hsa-miR-6798-5p | 5.13 · E−21 | − |
| 125 | hsa-miR-6781-5p | 2.43 · E−20 | − |
| 126 | hsa-miR-4419b | 2.59 · E−20 | + |
| 127 | hsa-miR-4446-3p | 7.52 · E−20 | − |
| 128 | hsa-miR-4259 | 8.07 · E−20 | + |
| 129 | hsa-miR-5572 | 1.06 · E−19 | − |
| 130 | hsa-miR-6075 | 1.78 · E−19 | − |
| 131 | hsa-miR-296-3p | 4.75 · E−19 | + |
| 132 | hsa-miR-6891-5p | 8.62 · E−19 | − |
| 133 | hsa-miR-4745-5p | 1.02 · E−18 | − |
| 134 | hsa-miR-6775-5p | 1.17 · E−18 | + |
| 135 | hsa-miR-6870-5p | 1.24 · E−18 | − |
| 136 | hsa-miR-920 | 1.78 · E−18 | + |
| 137 | hsa-miR-4530 | 3.26 · E−18 | − |
| 138 | hsa-miR-6819-5p | 3.67 · E−18 | + |
| 139 | hsa-miR-6825-5p | 5.28 · E−18 | − |
| 140 | hsa-miR-7847-3p | 7.32 · E−18 | + |
| 141 | hsa-miR-6131 | 1.09 · E−17 | + |
| 142 | hsa-miR-4433-3p | 1.35 · E−17 | − |
| 143 | hsa-miR-1228-5p | 9.82 · E−17 | − |
| 144 | hsa-miR-6743-5p | 1.40 · E−16 | + |
| 145 | hsa-miR-1268a | 2.20 · E−16 | − |
| 146 | hsa-miR-3917 | 1.73 · E−15 | + |
| 147 | hsa-miR-6786-5p | 1.89 · E−15 | − |
| 148 | hsa-miR-3154 | 2.12 · E−15 | + |
| 149 | hsa-miR-638 | 2.19 · E−15 | − |
| 150 | hsa-miR-6741-5p | 5.44 · E−15 | + |
| 151 | hsa-miR-6889-5p | 9.29 · E−15 | − |
| 152 | hsa-miR-6840-3p | 1.61 · E−14 | − |
| 153 | hsa-miR-6510-5p | 3.23 · E−14 | − |
| 154 | hsa-miR-3188 | 4.44 · E−14 | + |
| 155 | hsa-miR-551b-5p | 1.71 · E−13 | + |
| 156 | hsa-miR-5001-5p | 2.07 · E−13 | + |
| 157 | hsa-miR-1268b | 2.24 · E−13 | − |
| 158 | hsa-miR-7107-5p | 2.31 · E−13 | − |
| 159 | hsa-miR-6824-5p | 3.30 · E−13 | + |
| 160 | hsa-miR-6732-5p | 3.62 · E−13 | − |
| 161 | hsa-miR-371a-5p | 9.05 · E−13 | + |
| 162 | hsa-miR-6794-5p | 9.74 · E−13 | + |
| 163 | hsa-miR-6779-5p | 1.37 · E−12 | − |
| 164 | hsa-miR-4271 | 1.69 · E−12 | − |
| 165 | hsa-miR-5195-3p | 1.79 · E−12 | + |
| 166 | hsa-miR-6762-5p | 3.61 · E−12 | + |
| 167 | hsa-miR-939-5p | 4.78 · E−12 | − |
| 168 | hsa-miR-1247-3p | 7.37 · E−12 | + |
| 169 | hsa-miR-6777-5p | 9.79 · E−12 | + |
| 170 | hsa-miR-6722-3p | 1.21 · E−11 | + |
| 171 | hsa-miR-3656 | 1.27 · E−11 | + |
| 172 | hsa-miR-4688 | 1.86 · E−11 | + |
| 173 | hsa-miR-3195 | 2.02 · E−11 | − |
| 174 | hsa-miR-6766-5p | 6.97 · E−11 | + |
| 175 | hsa-miR-4447 | 1.08 · E−10 | + |
| 176 | hsa-miR-4656 | 1.12 · E−10 | − |
| 177 | hsa-miR-7108-5p | 1.51 · E−10 | − |
| 178 | hsa-miR-3191-3p | 2.67 · E−10 | + |
| 179 | hsa-miR-1273g-3p | 2.89 · E−10 | − |
| 180 | hsa-miR-4463 | 4.62 · E−10 | + |
| 181 | hsa-miR-2861 | 4.97 · E−10 | + |
| 182 | hsa-miR-3196 | 5.22 · E−10 | − |
| 183 | hsa-miR-6877-5p | 6.47 · E−10 | − |
| 184 | hsa-miR-3679-5p | 1.33 · E−09 | + |
| 185 | hsa-miR-4442 | 1.56 · E−09 | − |
| 186 | hsa-miR-6789-5p | 1.93 · E−09 | − |
| 187 | hsa-miR-6782-5p | 1.97 · E−09 | + |
| 188 | hsa-miR-486-3p | 2.12 · E−09 | − |
| 189 | hsa-miR-6085 | 4.04 · E−09 | + |
| 190 | hsa-miR-4746-3p | 8.57 · E−09 | − |
| 191 | hsa-miR-619-5p | 1.13 · E−08 | − |
| 192 | hsa-miR-937-5p | 1.65 · E−08 | + |
| 193 | hsa-miR-6803-5p | 2.32 · E−08 | + |
| 194 | hsa-miR-4298 | 2.33 · E−08 | + |
| 195 | hsa-miR-4454 | 2.63 · E−08 | + |
| 196 | hsa-miR-4459 | 1.83 · E−07 | + |
| 197 | hsa-miR-7150 | 2.60 · E−07 | + |
| 198 | hsa-miR-6880-5p | 8.86 · E−07 | − |
| 199 | hsa-miR-4449 | 9.44 · E−07 | − |
| 200 | hsa-miR-8063 | 1.05 · E−06 | + |
| 201 | hsa-miR-4695-5p | 1.65 · E−06 | + |
| 202 | hsa-miR-6132 | 1.93 · E−06 | + |
| 203 | hsa-miR-6829-5p | 2.66 · E−06 | + |
| 204 | hsa-miR-4486 | 2.83 · E−06 | − |
| 205 | hsa-miR-6805-3p | 3.24 · E−06 | − |
| 206 | hsa-miR-6826-5p | 4.59 · E−06 | + |
| 207 | hsa-miR-4508 | 6.28 · E−06 | + |
| 208 | hsa-miR-1343-5p | 1.11 · E−05 | − |
| 209 | hsa-miR-7114-5p | 1.35 · E−05 | + |
| 210 | hsa-miR-3622a-5p | 1.53 · E−05 | + |
| 211 | hsa-miR-6765-5p | 1.77 · E−05 | − |
| 212 | hsa-miR-7845-5p | 2.11 · E−05 | − |
| 213 | hsa-miR-3960 | 2.70 · E−05 | − |

TABLE 2-continued

| SEQ ID NO: | Gene name | P value after Bonferroni correction | Expression level in breast cancer patient with respect to healthy subject |
|---|---|---|---|
| 214 | hsa-miR-6749-5p | 4.51 · E−05 | − |
| 215 | hsa-miR-1260b | 4.83 · E−05 | + |
| 216 | hsa-miR-6799-5p | 5.38 · E−05 | + |
| 217 | hsa-miR-4723-5p | 6.54 · E−05 | + |
| 218 | hsa-miR-6784-5p | 7.88 · E−05 | − |
| 219 | hsa-miR-5100 | 8.28 · E−05 | + |
| 220 | hsa-miR-6769b-5p | 9.25 · E−05 | + |
| 221 | hsa-miR-1207-5p | 1.25 · E−04 | + |
| 222 | hsa-miR-642a-3p | 1.38 · E−04 | − |
| 223 | hsa-miR-4505 | 1.49 · E−04 | + |
| 224 | hsa-miR-4270 | 1.79 · E−04 | − |
| 225 | hsa-miR-6721-5p | 3.50 · E−04 | − |
| 226 | hsa-miR-7111-5p | 5.29 · E−04 | − |
| 227 | hsa-miR-6791-5p | 8.34 · E−04 | + |
| 228 | hsa-miR-7109-5p | 1.07 · E−03 | + |
| 229 | hsa-miR-4258 | 1.55 · E−03 | + |
| 230 | hsa-miR-6515-3p | 2.00 · E−03 | + |
| 231 | hsa-miR-6851-5p | 2.15 · E−03 | − |
| 232 | hsa-miR-6125 | 2.94 · E−03 | − |
| 233 | hsa-miR-4749-5p | 3.39 · E−03 | + |
| 234 | hsa-miR-4726-5p | 6.77 · E−03 | + |
| 235 | hsa-miR-4513 | 9.77 · E−03 | + |
| 236 | hsa-miR-760 | 5.40 · E−76 | − |
| 237 | hsa-miR-602 | 3.27 · E−58 | − |
| 238 | hsa-miR-423-5p | 4.16 · E−57 | − |
| 239 | hsa-miR-92a-2-5p | 7.76 · E−55 | − |
| 240 | hsa-miR-16-5p | 7.58 · E−47 | − |
| 241 | hsa-miR-451a | 1.13 · E−36 | − |
| 242 | hsa-miR-135a-3p | 1.83 · E−35 | − |
| 243 | hsa-miR-486-5p | 8.56 · E−34 | − |
| 244 | hsa-miR-4257 | 4.39 · E−31 | + |
| 245 | hsa-miR-92b-5p | 1.67 · E−30 | + |
| 246 | hsa-miR-1915-3p | 3.95 · E−18 | − |
| 247 | hsa-miR-718 | 1.38 · E−15 | − |
| 248 | hsa-miR-940 | 4.63 · E−15 | + |
| 249 | hsa-miR-296-5p | 2.67 · E−10 | + |
| 250 | hsa-miR-23b-3p | 2.43 · E−03 | + |
| 251 | hsa-miR-92a-3p | 3.86 · E−03 | − |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 99.4 | 98.4 | 100 | 100 | 100 | 100 |
| 2 | 99.4 | 98.4 | 100 | 100 | 100 | 100 |
| 3 | 99.4 | 98.4 | 100 | 100 | 100 | 100 |
| 4 | 99.4 | 98.4 | 100 | 96.3 | 90.3 | 100 |
| 5 | 98.8 | 100 | 98 | 98.8 | 96.8 | 100 |
| 6 | 99.4 | 98.4 | 100 | 100 | 100 | 100 |
| 7 | 100 | 100 | 100 | 100 | 100 | 100 |
| 8 | 99.4 | 98.4 | 100 | 98.8 | 96.8 | 100 |
| 9 | 96.9 | 91.9 | 100 | 98.8 | 96.8 | 100 |
| 10 | 98.8 | 96.8 | 100 | 97.5 | 100 | 96 |
| 11 | 99.4 | 98.4 | 100 | 97.5 | 100 | 96 |
| 12 | 100 | 100 | 100 | 100 | 100 | 100 |
| 13 | 99.4 | 98.4 | 100 | 100 | 100 | 100 |
| 14 | 98.1 | 96.8 | 99 | 98.8 | 96.8 | 100 |
| 15 | 96.3 | 90.3 | 100 | 98.8 | 96.8 | 100 |
| 16 | 98.1 | 95.2 | 100 | 98.8 | 100 | 98 |
| 17 | 98.8 | 96.8 | 100 | 100 | 100 | 100 |
| 18 | 98.8 | 96.8 | 100 | 96.3 | 96.8 | 96 |
| 19 | 99.4 | 100 | 99 | 100 | 100 | 100 |
| 20 | 98.8 | 98.4 | 99 | 97.5 | 93.5 | 100 |
| 21 | 98.1 | 98.4 | 98 | 96.3 | 96.8 | 96 |
| 22 | 98.1 | 95.2 | 100 | 98.8 | 96.8 | 100 |
| 23 | 96.9 | 93.5 | 99 | 100 | 100 | 100 |
| 24 | 97.5 | 93.5 | 100 | 98.8 | 96.8 | 100 |
| 25 | 97.5 | 93.5 | 100 | 96.3 | 96.8 | 96 |
| 26 | 96.3 | 90.3 | 100 | 96.3 | 93.5 | 98 |
| 27 | 96.9 | 93.5 | 99 | 96.3 | 96.8 | 96 |
| 28 | 95.7 | 88.7 | 100 | 97.5 | 93.5 | 100 |
| 29 | 96.9 | 95.2 | 98 | 95.1 | 87.1 | 100 |
| 30 | 95.1 | 87.1 | 100 | 91.4 | 83.9 | 96 |
| 31 | 96.9 | 91.9 | 100 | 98.8 | 96.8 | 100 |
| 32 | 95.1 | 88.7 | 99 | 98.8 | 96.8 | 100 |
| 33 | 94.4 | 96.8 | 93 | 98.8 | 96.8 | 100 |
| 34 | 96.9 | 91.9 | 100 | 100 | 100 | 100 |
| 35 | 96.9 | 95.2 | 98 | 88.9 | 80.6 | 94 |
| 36 | 95.1 | 88.7 | 99 | 95.1 | 87.1 | 100 |
| 37 | 96.3 | 91.9 | 99 | 95.1 | 87.1 | 100 |
| 38 | 96.3 | 93.5 | 98 | 100 | 100 | 100 |
| 39 | 95.7 | 91.9 | 98 | 95.1 | 90.3 | 98 |
| 40 | 96.9 | 95.2 | 98 | 95.1 | 90.3 | 98 |
| 41 | 94.4 | 88.7 | 98 | 93.8 | 90.3 | 96 |
| 42 | 97.5 | 98.4 | 97 | 98.8 | 100 | 98 |
| 43 | 98.1 | 98.4 | 98 | 97.5 | 96.8 | 98 |
| 44 | 97.5 | 93.5 | 100 | 100 | 100 | 100 |
| 45 | 94.4 | 88.7 | 98 | 95.1 | 87.1 | 100 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 46 | 96.9 | 91.9 | 100 | 93.8 | 87.1 | 98 |
| 47 | 95.7 | 88.7 | 100 | 98.8 | 96.8 | 100 |
| 48 | 96.9 | 95.2 | 98 | 92.6 | 96.8 | 90 |
| 49 | 95.7 | 93.5 | 97 | 93.8 | 90.3 | 96 |
| 50 | 95.7 | 96.8 | 95 | 97.5 | 96.8 | 98 |
| 51 | 92.6 | 83.9 | 98 | 92.6 | 83.9 | 98 |
| 52 | 93.8 | 93.5 | 94 | 90.1 | 77.4 | 98 |
| 53 | 93.8 | 90.3 | 96 | 91.2 | 90 | 92 |
| 54 | 92.6 | 80.6 | 100 | 93.8 | 83.9 | 100 |
| 55 | 95.7 | 91.8 | 98 | 98.8 | 96.8 | 100 |
| 56 | 97.5 | 95.2 | 99 | 96.3 | 93.5 | 98 |
| 57 | 93.8 | 88.7 | 97 | 86.4 | 80.6 | 90 |
| 58 | 97.5 | 96.8 | 98 | 96.3 | 96.8 | 96 |
| 59 | 95.1 | 90.3 | 98 | 96.3 | 90.3 | 100 |
| 60 | 95.1 | 88.7 | 99 | 95.1 | 93.5 | 96 |
| 61 | 93.8 | 90.3 | 96 | 84 | 90.3 | 80 |
| 62 | 91.3 | 80.3 | 98 | 95.1 | 87.1 | 100 |
| 63 | 93.2 | 95.2 | 92 | 88.9 | 87.1 | 90 |
| 64 | 92.6 | 85.5 | 97 | 98.8 | 96.8 | 100 |
| 65 | 93.2 | 87.1 | 97 | 93.8 | 83.9 | 100 |
| 66 | 93.8 | 87.1 | 98 | 92.6 | 87.1 | 96 |
| 67 | 87.7 | 79 | 93 | 88.9 | 77.4 | 96 |
| 68 | 92.6 | 83.9 | 98 | 96.3 | 90.3 | 100 |
| 69 | 91.4 | 82.3 | 97 | 90.1 | 77.4 | 98 |
| 70 | 93.2 | 87.1 | 97 | 91.4 | 90.3 | 92 |
| 71 | 92.6 | 87.1 | 96 | 93.8 | 83.9 | 100 |
| 72 | 93.8 | 83.9 | 100 | 90.1 | 74.2 | 100 |
| 73 | 95.7 | 91.9 | 98 | 97.5 | 93.5 | 100 |
| 74 | 92.6 | 90.3 | 94 | 87.7 | 87.1 | 88 |
| 75 | 90.1 | 79 | 97 | 96.3 | 93.5 | 98 |
| 76 | 93.8 | 91.9 | 95 | 93.8 | 93.5 | 94 |
| 77 | 93.8 | 87.1 | 98 | 90.1 | 77.4 | 98 |
| 78 | 92.6 | 82.3 | 99 | 91.4 | 90.3 | 92 |
| 79 | 90.7 | 80.6 | 97 | 90.1 | 87.1 | 92 |
| 80 | 90.7 | 75.8 | 100 | 95.1 | 87.1 | 100 |
| 81 | 91.4 | 85.5 | 95 | 87.7 | 83.9 | 90 |
| 82 | 90.7 | 88.7 | 92 | 91.4 | 87.1 | 94 |
| 83 | 93.2 | 83.9 | 99 | 96.3 | 93.5 | 98 |
| 84 | 89.5 | 90.3 | 89 | 84 | 77.4 | 88 |
| 85 | 90.1 | 82.3 | 95 | 93.8 | 93.5 | 94 |
| 86 | 92.6 | 83.9 | 98 | 87.7 | 74.2 | 96 |
| 87 | 88.9 | 79 | 95 | 93.8 | 83.9 | 100 |
| 88 | 92 | 88.7 | 94 | 92.6 | 100 | 88 |
| 89 | 90.7 | 85.5 | 94 | 91.4 | 90.3 | 92 |
| 90 | 92.6 | 90.3 | 94 | 90.1 | 74.2 | 100 |
| 91 | 89.5 | 74.2 | 99 | 92.6 | 83.9 | 98 |
| 92 | 89.5 | 82.3 | 94 | 90.1 | 80.6 | 96 |
| 93 | 89.5 | 79 | 96 | 90.1 | 87.1 | 92 |
| 94 | 89.5 | 80.6 | 95 | 84 | 77.4 | 88 |
| 95 | 89.5 | 91.9 | 88 | 86.4 | 83.9 | 88 |
| 96 | 87.7 | 79 | 93 | 88.9 | 71 | 100 |
| 97 | 90.1 | 88.7 | 91 | 91.4 | 96.8 | 88 |
| 98 | 90.1 | 83.9 | 94 | 86.4 | 77.4 | 92 |
| 99 | 87.6 | 83.6 | 90 | 82.7 | 87.1 | 80 |
| 100 | 88.3 | 80.6 | 93 | 88.9 | 77.4 | 96 |
| 101 | 93.2 | 85.5 | 98 | 88.9 | 71 | 100 |
| 102 | 88.3 | 74.2 | 97 | 95.1 | 90.3 | 98 |
| 103 | 87.7 | 80.6 | 92 | 90.1 | 80.6 | 96 |
| 104 | 87.7 | 77.4 | 94 | 80.2 | 67.7 | 88 |
| 105 | 92 | 88.7 | 94 | 82.7 | 77.4 | 86 |
| 106 | 86.4 | 77.4 | 92 | 93.8 | 87.1 | 98 |
| 107 | 89.5 | 85.5 | 92 | 86.4 | 74.2 | 94 |
| 108 | 88.9 | 80.6 | 94 | 81.5 | 83.9 | 80 |
| 109 | 91.4 | 87.1 | 94 | 87.7 | 77.4 | 94 |
| 110 | 88.3 | 75.8 | 96 | 86.4 | 71 | 96 |
| 111 | 86.4 | 82.3 | 89 | 90.1 | 87.1 | 92 |
| 112 | 86.4 | 67.7 | 98 | 86.4 | 74.2 | 94 |
| 113 | 85.8 | 74.2 | 93 | 95.1 | 90.3 | 98 |
| 114 | 95.1 | 88.7 | 99 | 92.6 | 80.6 | 100 |
| 115 | 90.1 | 82.3 | 95 | 87.7 | 74.2 | 96 |
| 116 | 90.1 | 82.3 | 95 | 88.9 | 83.9 | 92 |
| 117 | 83.3 | 72.6 | 90 | 88.9 | 83.9 | 92 |
| 118 | 86.4 | 83.9 | 88 | 80.2 | 71 | 86 |
| 119 | 86.4 | 80.6 | 90 | 88.9 | 87.1 | 90 |
| 120 | 88.3 | 79 | 94 | 84 | 61.3 | 98 |

TABLE 3-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 121 | 84.6 | 72.6 | 92 | 75.3 | 61.3 | 84 |
| 122 | 84.6 | 74.2 | 91 | 85.2 | 83.9 | 86 |
| 123 | 82.7 | 79 | 85 | 77.8 | 61.3 | 88 |
| 124 | 84.6 | 80.6 | 87 | 85.2 | 90.3 | 82 |
| 125 | 92 | 82.3 | 98 | 91.4 | 80.6 | 98 |
| 126 | 82.7 | 69.4 | 91 | 84 | 61.3 | 98 |
| 127 | 88.9 | 72.6 | 99 | 86.4 | 64.5 | 100 |
| 128 | 88.9 | 83.9 | 92 | 91.4 | 80.6 | 98 |
| 129 | 87 | 82.3 | 90 | 84 | 74.2 | 90 |
| 130 | 84 | 66.1 | 95 | 86.4 | 80.6 | 90 |
| 131 | 79.6 | 69.4 | 86 | 80.2 | 71 | 86 |
| 132 | 84.6 | 71 | 93 | 84 | 71 | 92 |
| 133 | 81.5 | 71 | 88 | 85.2 | 77.4 | 90 |
| 134 | 81.5 | 61.3 | 94 | 81.5 | 64.5 | 92 |
| 135 | 82.1 | 66.1 | 92 | 82.7 | 71 | 90 |
| 136 | 83.3 | 74.2 | 89 | 82.7 | 71 | 90 |
| 137 | 83.3 | 79 | 86 | 77.8 | 83.9 | 74 |
| 138 | 80.2 | 67.7 | 88 | 79 | 74.2 | 82 |
| 139 | 84 | 74.2 | 90 | 86.4 | 83.9 | 88 |
| 140 | 81.5 | 71 | 88 | 85 | 63.3 | 98 |
| 141 | 82.1 | 67.7 | 91 | 82.7 | 64.5 | 94 |
| 142 | 79.6 | 69.4 | 86 | 80.2 | 71 | 86 |
| 143 | 83.3 | 75.8 | 88 | 76.5 | 67.7 | 82 |
| 144 | 87.7 | 74.2 | 96 | 85.2 | 71 | 94 |
| 145 | 83.3 | 79 | 86 | 80.2 | 71 | 86 |
| 146 | 81.5 | 69.4 | 89 | 81.5 | 74.2 | 86 |
| 147 | 84.6 | 69.4 | 94 | 84 | 71 | 92 |
| 148 | 85.8 | 72.6 | 94 | 77.8 | 64.5 | 86 |
| 149 | 85.2 | 66.1 | 97 | 93.8 | 83.9 | 100 |
| 150 | 79.6 | 62.9 | 90 | 80.2 | 71 | 86 |
| 151 | 80.9 | 67.7 | 89 | 86.4 | 83.9 | 88 |
| 152 | 82.7 | 67.7 | 92 | 79 | 61.3 | 90 |
| 153 | 83.3 | 67.7 | 93 | 79 | 61.3 | 90 |
| 154 | 79.6 | 64.5 | 89 | 84 | 67.7 | 94 |
| 155 | 79.6 | 66.1 | 88 | 82.7 | 64.5 | 94 |
| 156 | 78.4 | 59.7 | 90 | 81.5 | 64.5 | 92 |
| 157 | 77.2 | 66.1 | 84 | 71.6 | 54.8 | 82 |
| 158 | 77.8 | 61.3 | 88 | 79 | 64.5 | 88 |
| 159 | 84 | 67.7 | 94 | 85.2 | 74.2 | 92 |
| 160 | 80.2 | 69.4 | 87 | 71.6 | 58.1 | 80 |
| 161 | 77.2 | 56.5 | 90 | 76.5 | 58.1 | 88 |
| 162 | 79 | 61.3 | 90 | 70.4 | 58.1 | 78 |
| 163 | 79.6 | 64.5 | 89 | 81.5 | 58.1 | 96 |
| 164 | 82.1 | 62.9 | 94 | 84 | 61.3 | 98 |
| 165 | 77.8 | 59.7 | 89 | 82.7 | 67.7 | 92 |
| 166 | 82.1 | 56.5 | 98 | 82.7 | 61.3 | 96 |
| 167 | 77.8 | 69.4 | 83 | 79 | 67.7 | 86 |
| 168 | 72.8 | 56.5 | 83 | 70.4 | 58.1 | 78 |
| 169 | 80.2 | 64.5 | 90 | 72.8 | 58.1 | 82 |
| 170 | 80.2 | 53.2 | 97 | 79 | 54.8 | 94 |
| 171 | 83.3 | 74.2 | 89 | 81.5 | 67.7 | 90 |
| 172 | 79 | 69.4 | 85 | 74.1 | 58.1 | 84 |
| 173 | 79.6 | 54.8 | 95 | 84 | 64.5 | 96 |
| 174 | 77.2 | 56.5 | 90 | 80.2 | 61.3 | 92 |
| 175 | 77.2 | 54.8 | 91 | 76.5 | 67.7 | 82 |
| 176 | 83.3 | 72.6 | 90 | 79 | 58.1 | 92 |
| 177 | 77.2 | 59.7 | 88 | 77.8 | 58.1 | 90 |
| 178 | 77.8 | 59.7 | 89 | 77.8 | 48.4 | 96 |
| 179 | 78.4 | 56.5 | 92 | 80.2 | 61.3 | 92 |
| 180 | 72.2 | 45.2 | 89 | 80.2 | 54.8 | 96 |
| 181 | 74.7 | 50 | 90 | 70.4 | 38.7 | 90 |
| 182 | 75.9 | 59.7 | 86 | 61.7 | 35.5 | 78 |
| 183 | 77.2 | 61.3 | 87 | 76.5 | 64.5 | 84 |
| 184 | 75.9 | 58.1 | 87 | 77.8 | 54.8 | 92 |
| 185 | 74.7 | 59.7 | 84 | 75.3 | 64.5 | 82 |
| 186 | 77.8 | 54.8 | 92 | 77.8 | 54.8 | 92 |
| 187 | 77.2 | 64.5 | 85 | 70.4 | 61.3 | 76 |
| 188 | 78.4 | 54.8 | 93 | 74.1 | 35.5 | 98 |
| 189 | 72.8 | 61.3 | 80 | 72.8 | 48.4 | 88 |
| 190 | 77.8 | 54.8 | 92 | 75.3 | 61.3 | 84 |
| 191 | 83.3 | 62.9 | 96 | 81.5 | 61.3 | 94 |
| 192 | 74.7 | 50 | 90 | 80.2 | 54.8 | 96 |
| 193 | 69.8 | 43.5 | 86 | 74.1 | 71 | 76 |
| 194 | 74.7 | 53.2 | 88 | 81.5 | 61.3 | 94 |
| 195 | 75.3 | 54.8 | 88 | 69.1 | 45.2 | 84 |

TABLE 3-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 196 | 74.7 | 56.5 | 86 | 75.3 | 48.4 | 92 |
| 197 | 74.1 | 54.8 | 86 | 69.1 | 29 | 94 |
| 198 | 69.8 | 48.4 | 83 | 72.8 | 54.8 | 84 |
| 199 | 74.1 | 50 | 89 | 72.8 | 41.9 | 92 |
| 200 | 83.3 | 59.7 | 98 | 87.7 | 67.7 | 100 |
| 201 | 68.5 | 41.9 | 85 | 65.4 | 29 | 88 |
| 202 | 75.3 | 45.2 | 94 | 71.6 | 29 | 98 |
| 203 | 71.6 | 38.7 | 92 | 75 | 53.3 | 88 |
| 204 | 71.6 | 53.2 | 83 | 67.9 | 51.6 | 78 |
| 205 | 72.2 | 54.8 | 83 | 69.1 | 45.2 | 84 |
| 206 | 70.4 | 45.2 | 86 | 67.9 | 35.5 | 88 |
| 207 | 72.8 | 48.4 | 88 | 65.4 | 41.9 | 80 |
| 208 | 69.1 | 45.2 | 84 | 67.9 | 41.9 | 84 |
| 209 | 69.1 | 41.9 | 86 | 72.8 | 48.4 | 88 |
| 210 | 74.7 | 51.6 | 89 | 72.8 | 41.9 | 92 |
| 211 | 71 | 53.2 | 82 | 61.7 | 35.5 | 78 |
| 212 | 71 | 45.2 | 87 | 61.7 | 41.9 | 74 |
| 213 | 71 | 24.2 | 100 | 75.3 | 35.5 | 100 |
| 214 | 71 | 45.2 | 87 | 76.5 | 48.4 | 94 |
| 215 | 75.3 | 53.2 | 89 | 65.4 | 32.3 | 86 |
| 216 | 71.6 | 50 | 85 | 71.6 | 41.9 | 90 |
| 217 | 69.8 | 43.5 | 86 | 67.9 | 41.9 | 84 |
| 218 | 71 | 40.3 | 90 | 71.6 | 41.9 | 90 |
| 219 | 71 | 40.3 | 90 | 70.4 | 35.5 | 92 |
| 220 | 73.5 | 45.2 | 91 | 66.7 | 35.5 | 86 |
| 221 | 71.6 | 43.5 | 89 | 72.8 | 41.9 | 92 |
| 222 | 70.4 | 46.8 | 85 | 76.5 | 61.3 | 86 |
| 223 | 77.8 | 46.8 | 97 | 72.8 | 32.3 | 98 |
| 224 | 70.4 | 43.5 | 87 | 72.8 | 45.2 | 90 |
| 225 | 67.3 | 37.1 | 86 | 74.1 | 38.7 | 96 |
| 226 | 67.9 | 37.1 | 87 | 75.3 | 51.6 | 90 |
| 227 | 71 | 41.9 | 89 | 66.7 | 29 | 90 |
| 228 | 69.1 | 40.3 | 87 | 65.4 | 35.5 | 84 |
| 229 | 71.6 | 46.8 | 87 | 65.4 | 38.7 | 82 |
| 230 | 69.1 | 40.3 | 87 | 71.6 | 54.8 | 82 |
| 231 | 71 | 41.9 | 89 | 72.8 | 58.1 | 82 |
| 232 | 71.6 | 41.9 | 90 | 76.5 | 51.6 | 92 |
| 233 | 75.3 | 38.7 | 98 | 72.8 | 29 | 100 |
| 234 | 66 | 33.9 | 86 | 64.2 | 41.9 | 78 |
| 235 | 69.8 | 37.1 | 90 | 67.9 | 38.7 | 86 |
| 236 | 100 | 100 | 100 | 98.8 | 96.8 | 100 |
| 237 | 96.9 | 93.5 | 99 | 98.8 | 96.8 | 100 |
| 238 | 98.8 | 98.4 | 99 | 98.8 | 96.8 | 100 |
| 239 | 96.9 | 95.2 | 98 | 98.8 | 100 | 98 |
| 240 | 95.1 | 93.5 | 96 | 96.3 | 96.8 | 96 |
| 241 | 95 | 91.8 | 97 | 91.4 | 87.1 | 94 |
| 242 | 90.7 | 85.5 | 94 | 91.4 | 80.6 | 98 |
| 243 | 91.4 | 85.5 | 95 | 96.3 | 100 | 94 |
| 244 | 88.9 | 80.6 | 94 | 90.1 | 87.1 | 92 |
| 245 | 94.4 | 87.1 | 99 | 95.1 | 93.5 | 96 |
| 246 | 83.3 | 69.4 | 92 | 81.5 | 67.7 | 90 |
| 247 | 83.3 | 61.3 | 97 | 84 | 67.7 | 94 |
| 248 | 79.6 | 64.5 | 89 | 81.5 | 61.3 | 94 |
| 249 | 75.9 | 56.5 | 88 | 77.8 | 67.7 | 84 |
| 250 | 72.2 | 41.9 | 91 | 70.4 | 38.7 | 90 |
| 251 | 69.1 | 41.9 | 86 | 77.8 | 54.8 | 92 |

TABLE 4

| SEQ ID NO: | Discriminant coefficient | Constant term |
| --- | --- | --- |
| 1 | 2.857 | 18.934 |
| 2 | 2.104 | 18.009 |
| 3 | 2.003 | 12.711 |
| 4 | 3.992 | 34.175 |
| 5 | 3.801 | 39.484 |
| 6 | 2.447 | 30.974 |
| 7 | 4.663 | 59.811 |
| 8 | 5.763 | 63.889 |
| 9 | 5.239 | 59.962 |
| 10 | 6.627 | 84.995 |
| 11 | 1.955 | 14.548 |
| 12 | 2.330 | 14.910 |
| 13 | 4.150 | 48.634 |
| 14 | 3.013 | 32.040 |
| 15 | 2.055 | 18.255 |
| 16 | 2.774 | 19.077 |
| 17 | 5.084 | 64.746 |
| 18 | 4.563 | 46.280 |
| 19 | 1.821 | 9.652 |
| 20 | 2.266 | 26.872 |

TABLE 4-continued

| SEQ ID NO: | Discriminant coefficient | Constant term |
|---|---|---|
| 21 | 2.626 | 14.611 |
| 22 | 3.963 | 34.565 |
| 23 | 4.250 | 47.336 |
| 24 | 3.079 | 27.833 |
| 25 | 6.783 | 80.858 |
| 26 | 3.237 | 25.431 |
| 27 | 1.634 | 14.286 |
| 28 | 2.807 | 33.656 |
| 29 | 2.658 | 20.910 |
| 30 | 4.607 | 39.043 |
| 31 | 5.299 | 67.817 |
| 32 | 2.652 | 19.984 |
| 33 | 4.337 | 38.009 |
| 34 | 4.682 | 48.862 |
| 35 | 5.352 | 38.578 |
| 36 | 2.977 | 26.855 |
| 37 | 2.882 | 21.114 |
| 38 | 5.933 | 55.485 |
| 39 | 5.346 | 55.986 |
| 40 | 1.915 | 11.901 |
| 41 | 4.597 | 34.155 |
| 42 | 2.048 | 10.706 |
| 43 | 4.172 | 34.713 |
| 44 | 1.763 | 9.076 |
| 45 | 5.446 | 45.658 |
| 46 | 2.725 | 15.338 |
| 47 | 1.886 | 10.786 |
| 48 | 2.535 | 15.378 |
| 49 | 4.415 | 34.502 |
| 50 | 2.583 | 15.891 |
| 51 | 3.927 | 44.058 |
| 52 | 3.643 | 32.462 |
| 53 | 6.086 | 41.540 |
| 54 | 3.018 | 38.864 |
| 55 | 3.179 | 22.917 |
| 56 | 2.338 | 13.833 |
| 57 | 5.682 | 67.831 |
| 58 | 2.838 | 18.281 |
| 59 | 2.954 | 19.780 |
| 60 | 3.642 | 21.511 |
| 61 | 1.972 | 23.626 |
| 62 | 4.194 | 40.279 |
| 63 | 3.430 | 28.886 |
| 64 | 3.095 | 19.571 |
| 65 | 2.739 | 17.283 |
| 66 | 1.356 | 7.292 |
| 67 | 4.404 | 35.065 |
| 68 | 3.358 | 27.546 |
| 69 | 2.497 | 15.102 |
| 70 | 3.754 | 25.584 |
| 71 | 3.860 | 28.692 |
| 72 | 2.543 | 20.396 |
| 73 | 2.485 | 13.944 |
| 74 | 2.870 | 22.658 |
| 75 | 2.136 | 17.183 |
| 76 | 2.226 | 12.375 |
| 77 | 4.610 | 47.394 |
| 78 | 3.174 | 36.978 |
| 79 | 2.980 | 26.297 |
| 80 | 3.396 | 29.485 |
| 81 | 3.446 | 23.243 |
| 82 | 4.082 | 29.368 |
| 83 | 3.358 | 28.190 |
| 84 | 1.537 | 10.210 |
| 85 | 4.715 | 45.652 |
| 86 | 2.213 | 17.839 |
| 87 | 3.088 | 27.043 |
| 88 | 2.399 | 24.629 |
| 89 | 4.002 | 24.314 |
| 90 | 2.863 | 17.406 |
| 91 | 4.805 | 44.782 |
| 92 | 3.372 | 29.988 |
| 93 | 4.132 | 30.521 |
| 94 | 3.851 | 23.002 |
| 95 | 3.959 | 36.256 |
| 96 | 2.941 | 23.102 |
| 97 | 3.006 | 20.900 |
| 98 | 3.728 | 29.308 |
| 99 | 2.595 | 30.882 |
| 100 | 2.755 | 20.339 |
| 101 | 3.144 | 19.162 |
| 102 | 1.952 | 17.956 |
| 103 | 4.489 | 37.034 |
| 104 | 4.734 | 32.179 |
| 105 | 3.519 | 24.011 |
| 106 | 4.202 | 32.975 |
| 107 | 2.654 | 17.634 |
| 108 | 4.562 | 28.615 |
| 109 | 4.900 | 37.966 |
| 110 | 2.427 | 15.293 |
| 111 | 2.332 | 16.477 |
| 112 | 2.960 | 35.679 |
| 113 | 2.931 | 27.885 |
| 114 | 2.409 | 15.430 |
| 115 | 2.659 | 15.558 |
| 116 | 2.722 | 15.656 |
| 117 | 3.039 | 32.084 |
| 118 | 2.066 | 14.991 |
| 119 | 2.114 | 14.125 |
| 120 | 2.812 | 19.320 |
| 121 | 4.273 | 28.046 |
| 122 | 1.987 | 11.296 |
| 123 | 4.888 | 61.938 |
| 124 | 3.116 | 29.551 |
| 125 | 3.831 | 36.923 |
| 126 | 3.114 | 20.097 |
| 127 | 1.704 | 11.244 |
| 128 | 2.708 | 16.078 |
| 129 | 2.902 | 17.111 |
| 130 | 3.522 | 27.388 |
| 131 | 2.509 | 16.024 |
| 132 | 3.797 | 26.247 |
| 133 | 2.381 | 26.930 |
| 134 | 5.446 | 44.750 |
| 135 | 2.830 | 18.893 |
| 136 | 2.243 | 13.704 |
| 137 | 2.742 | 24.223 |
| 138 | 5.572 | 41.312 |
| 139 | 2.328 | 13.203 |
| 140 | 4.269 | 27.904 |
| 141 | 1.790 | 19.364 |
| 142 | 3.970 | 28.366 |
| 143 | 3.831 | 42.123 |
| 144 | 2.470 | 23.361 |
| 145 | 3.643 | 37.749 |
| 146 | 3.590 | 21.954 |
| 147 | 6.096 | 72.341 |
| 148 | 4.450 | 26.391 |
| 149 | 2.450 | 28.929 |
| 150 | 3.765 | 26.311 |
| 151 | 3.107 | 20.676 |
| 152 | 3.191 | 26.734 |
| 153 | 2.247 | 12.949 |
| 154 | 3.520 | 21.019 |
| 155 | 1.939 | 10.899 |
| 156 | 3.714 | 28.667 |
| 157 | 3.379 | 30.812 |
| 158 | 3.869 | 28.692 |
| 159 | 4.714 | 30.302 |
| 160 | 3.800 | 29.719 |
| 161 | 3.111 | 23.178 |
| 162 | 4.700 | 38.234 |
| 163 | 5.628 | 38.292 |
| 164 | 2.984 | 23.210 |
| 165 | 2.953 | 20.742 |
| 166 | 2.411 | 18.314 |
| 167 | 2.915 | 19.822 |
| 168 | 4.774 | 29.161 |
| 169 | 3.435 | 22.933 |
| 170 | 4.014 | 33.267 |
| 171 | 4.788 | 52.969 |
| 172 | 4.261 | 30.393 |
| 173 | 2.698 | 20.419 |
| 174 | 3.739 | 22.190 |

TABLE 4-continued

| SEQ ID NO: | Discriminant coefficient | Constant term |
|---|---|---|
| 175 | 3.142 | 19.164 |
| 176 | 3.424 | 23.274 |
| 177 | 4.230 | 35.956 |
| 178 | 3.270 | 18.860 |
| 179 | 2.287 | 16.040 |
| 180 | 3.760 | 39.967 |
| 181 | 5.991 | 71.910 |
| 182 | 6.044 | 68.999 |
| 183 | 4.325 | 29.700 |
| 184 | 3.000 | 19.877 |
| 185 | 3.823 | 34.710 |
| 186 | 3.882 | 35.815 |
| 187 | 3.870 | 23.356 |
| 188 | 2.281 | 17.158 |
| 189 | 5.818 | 59.167 |
| 190 | 2.555 | 15.132 |
| 191 | 1.200 | 8.000 |
| 192 | 4.027 | 33.373 |
| 193 | 6.532 | 69.738 |
| 194 | 3.836 | 23.124 |
| 195 | 2.198 | 25.446 |
| 196 | 3.531 | 27.965 |
| 197 | 3.619 | 27.108 |
| 198 | 2.671 | 18.647 |
| 199 | 3.253 | 19.608 |
| 200 | 1.449 | 12.340 |
| 201 | 4.621 | 33.285 |
| 202 | 3.174 | 24.106 |
| 203 | 3.280 | 19.895 |
| 204 | 3.339 | 22.048 |
| 205 | 2.930 | 20.016 |
| 206 | 2.705 | 17.147 |
| 207 | 5.111 | 63.738 |
| 208 | 4.111 | 39.848 |
| 209 | 4.418 | 30.103 |
| 210 | 3.749 | 22.673 |
| 211 | 4.949 | 48.983 |
| 212 | 3.159 | 19.444 |
| 213 | 3.351 | 49.006 |
| 214 | 4.185 | 40.143 |
| 215 | 2.257 | 19.312 |
| 216 | 4.261 | 34.145 |
| 217 | 2.984 | 26.230 |
| 218 | 3.064 | 35.877 |
| 219 | 2.311 | 23.637 |
| 220 | 4.200 | 26.644 |
| 221 | 3.404 | 21.751 |
| 222 | 3.076 | 22.488 |
| 223 | 3.273 | 26.709 |
| 224 | 5.275 | 40.615 |
| 225 | 3.461 | 24.300 |
| 226 | 5.789 | 41.289 |
| 227 | 4.602 | 40.407 |
| 228 | 5.697 | 41.534 |
| 229 | 2.323 | 20.843 |
| 230 | 3.839 | 25.014 |
| 231 | 3.506 | 21.544 |
| 232 | 4.082 | 45.878 |
| 233 | 3.909 | 30.033 |
| 234 | 4.028 | 26.498 |
| 235 | 4.173 | 25.119 |
| 236 | 3.887 | 30.454 |
| 237 | 2.014 | 10.053 |
| 238 | 2.607 | 16.589 |
| 239 | 1.925 | 14.853 |
| 240 | 1.301 | 6.443 |
| 241 | 1.152 | 8.583 |
| 242 | 1.774 | 11.079 |
| 243 | 2.154 | 13.220 |
| 244 | 3.309 | 23.530 |
| 245 | 3.226 | 25.503 |
| 246 | 3.387 | 34.563 |
| 247 | 2.652 | 16.404 |

TABLE 4-continued

| SEQ ID NO: | Discriminant coefficient | Constant term |
|---|---|---|
| 248 | 3.534 | 22.326 |
| 249 | 3.779 | 28.687 |
| 250 | 1.490 | 9.528 |
| 251 | 2.072 | 13.756 |

TABLE 5-1

Training cohort

| Sample name | Cancer stage | CEA(ng/mL) |
|---|---|---|
| BB001 | IV | 1(−) |
| BB006 | IIIB | 14.4(+) |
| BB007 | IIA | 2.6(−) |
| BB009 | IIIC | 4.9(−) |
| BB010 | IIA | 1.2(−) |
| BB012 | I | 2.7(−) |
| BB013 | I | 14(−) |
| BB014 | IIA | 13.5(+) |
| BB015 | I | 3.5(−) |
| BB017 | IIA | 1.9(−) |
| BB018 | IIA | 2.1(−) |
| BB019 | I | 1.2(−) |
| BB023 | IIA | 2.8(−) |
| BB024 | I | 1.5(−) |
| BB026 | I | 3.8(−) |
| BB027 | IIB | 3.4(−) |
| BB028 | IV | 7.4(+) |
| BB032 | I | 1.7(−) |
| BB033 | IIB | 2.6(−) |
| BB035 | IIA | 2.7(−) |
| BB037 | IIB | 1.2(−) |
| BB038 | IV | 0.8(−) |
| BB039 | IIIA | 4.7(−) |
| BB041 | IIA | 2.1(−) |
| BB042 | IIIB | 1.3(−) |
| BB043 | IIIA | 1.2(−) |
| BB046 | I | 1.7(−) |
| BB047 | I | 1(−) |
| BB048 | I | 1.9(−) |
| BB049 | IIA | 0.6(−) |
| BB051 | IIA | 1(−) |
| BB052 | I | 2.4(−) |
| BB054 | IIA | 1.3(−) |
| BB056 | IIA | 1.9(−) |
| BB057 | IIIB | 3460(+) |
| BB058 | IIA | 0.8(−) |
| BB060 | I | 0.5(−) |
| BB061 | I | 1.4(−) |
| BB064 | IV | 2.4(−) |
| BB065 | IIB | 6.6(+) |
| BB068 | IIA | 0.6(−) |
| BB070 | IIB | 0.7(−) |
| BB071 | IIB | 1.8(−) |
| BB073 | I | 1.1(−) |
| BB076 | I | 2(−) |
| BB077 | IIA | 2.9(−) |
| BB078 | IIA | 2.3(−) |
| BB079 | IIA | 1.1(−) |
| BB082 | I | 1.5(−) |
| BB084 | IV | 435(+) |
| BB085 | IIA | 3.1(−) |
| BB086 | IIA | 1.5(−) |
| BB087 | IIA | 1.7(−) |
| BB089 | I | 2(−) |
| BB092 | I | 3.6(−) |
| BB093 | IIB | 3.7(−) |
| BB094 | I | 6(+) |
| BB095 | IIA | 2.4(−) |
| BB096 | I | 4.6(−) |

TABLE 5-1-continued

| Training cohort | | |
|---|---|---|
| Sample name | Cancer stage | CEA(ng/mL) |
| BB097 | IIA | 1.8(−) |
| BB098 | IIA | 2.6(−) |
| BB099 | IIA | 4.2(−) |
| | Sensitivity (%) | 11.3 |

TABLE 5-2

| Validation cohort | | |
|---|---|---|
| Sample name | Cancer stage | CEA(ng/mL) |
| BB002 | IIIC | 1.3(−) |
| BB005 | IIA | 0.6(−) |
| BB008 | IIA | 0.7(−) |
| BB011 | IIB | 1.4(−) |
| BB016 | I | 2.9(−) |
| BB020 | IIB | 1.5(−) |
| BB021 | IIB | 1.5(−) |
| BB022 | IIA | 0.6(−) |
| BB025 | IIA | 4.1(−) |
| BB029 | IIIA | 2.7(−) |
| BB030 | IIA | 12.7(+) |

TABLE 5-2-continued

| Validation cohort | | |
|---|---|---|
| Sample name | Cancer stage | CEA(ng/mL) |
| BB031 | IIA | 1.4(−) |
| BB034 | IIB | 4.2(−) |
| BB036 | I | 3.5(−) |
| BB040 | IIB | 1.7(−) |
| BB050 | IIIB | 11.1(+) |
| BB053 | I | 0.8(−) |
| BB055 | IIA | 2.8(−) |
| BB059 | IIA | 10.2(+) |
| BB062 | IIA | 5.9(+) |
| BB063 | I | 0.7(−) |
| BB069 | IIA | 0.7(−) |
| BB072 | IIA | 1.1(−) |
| BB074 | IIA | 6.4(+) |
| BB075 | I | 0.5(−) |
| BB080 | IV | 6.6(+) |
| BB081 | I | 0.8(−) |
| BB083 | I | 0.7(−) |
| BB088 | I | 1(−) |
| BB090 | I | 5.4(+) |
| BB091 | IIA | 1.2(−) |
| | Sensitivity (%) | 19.4 |

For CEA, 5 ng/ml or lower was indicated by as "−", while values exceedingthese were indicated as "+"

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 12 | 100 | 100 | 100 | 100 | 100 | 100 |
| 13 | 99.4 | 98.4 | 100 | 100 | 100 | 100 |
| 14 | 100 | 100 | 100 | 100 | 100 | 100 |
| 15 | 99.4 | 98.4 | 100 | 100 | 100 | 100 |
| 16 | 100 | 100 | 100 | 100 | 100 | 100 |
| 17 | 100 | 100 | 100 | 100 | 100 | 100 |
| 18 | 100 | 100 | 100 | 100 | 100 | 100 |
| 19 | 99.4 | 98.4 | 100 | 100 | 100 | 100 |
| 110 | 100 | 100 | 100 | 100 | 100 | 100 |
| 111 | 100 | 100 | 100 | 100 | 100 | 100 |
| 112 | 100 | 100 | 100 | 100 | 100 | 100 |
| 113 | 100 | 100 | 100 | 100 | 100 | 100 |
| 114 | 100 | 100 | 100 | 100 | 100 | 100 |
| 115 | 100 | 100 | 100 | 100 | 100 | 100 |
| 116 | 100 | 100 | 100 | 100 | 100 | 100 |
| 117 | 100 | 100 | 100 | 100 | 100 | 100 |
| 118 | 99.4 | 98.4 | 100 | 100 | 100 | 100 |
| 119 | 100 | 100 | 100 | 100 | 100 | 100 |
| 120 | 100 | 100 | 100 | 100 | 100 | 100 |
| 121 | 99.4 | 98.4 | 100 | 100 | 100 | 100 |
| 122 | 100 | 100 | 100 | 100 | 100 | 100 |
| 123 | 100 | 100 | 100 | 100 | 100 | 100 |
| 124 | 100 | 100 | 100 | 100 | 100 | 100 |
| 125 | 100 | 100 | 100 | 98.8 | 100 | 98 |
| 126 | 100 | 100 | 100 | 100 | 100 | 100 |
| 127 | 100 | 100 | 100 | 100 | 100 | 100 |
| 128 | 99.4 | 98.4 | 100 | 100 | 100 | 100 |
| 129 | 100 | 100 | 100 | 100 | 100 | 100 |
| 130 | 100 | 100 | 100 | 100 | 100 | 100 |
| 131 | 100 | 100 | 100 | 100 | 100 | 100 |
| 132 | 100 | 100 | 100 | 100 | 100 | 100 |
| 133 | 99.4 | 98.4 | 100 | 100 | 100 | 100 |
| 134 | 100 | 100 | 100 | 100 | 100 | 100 |
| 135 | 100 | 100 | 100 | 100 | 100 | 100 |
| 136 | 100 | 100 | 100 | 100 | 100 | 100 |
| 137 | 100 | 100 | 100 | 100 | 100 | 100 |
| 138 | 99.4 | 98.4 | 100 | 100 | 100 | 100 |
| 139 | 100 | 100 | 100 | 100 | 100 | 100 |
| 140 | 100 | 100 | 100 | 100 | 100 | 100 |
| 141 | 100 | 100 | 100 | 100 | 100 | 100 |
| 142 | 100 | 100 | 100 | 100 | 100 | 100 |
| 143 | 99.4 | 98.4 | 100 | 100 | 100 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 144 | 100 | 100 | 100 | 100 | 100 | 100 |
| 145 | 100 | 100 | 100 | 100 | 100 | 100 |
| 146 | 99.4 | 98.4 | 100 | 100 | 100 | 100 |
| 147 | 100 | 100 | 100 | 100 | 100 | 100 |
| 148 | 99.4 | 98.4 | 100 | 100 | 100 | 100 |
| 149 | 99.4 | 98.4 | 100 | 100 | 100 | 100 |
| 150 | 99.4 | 98.4 | 100 | 100 | 100 | 100 |
| 151 | 100 | 100 | 100 | 100 | 100 | 100 |
| 152 | 100 | 100 | 100 | 100 | 100 | 100 |
| 153 | 99.4 | 98.4 | 100 | 100 | 100 | 100 |
| 154 | 99.4 | 98.4 | 100 | 100 | 100 | 100 |
| 155 | 100 | 100 | 100 | 100 | 100 | 100 |
| 156 | 99.4 | 98.4 | 100 | 100 | 100 | 100 |
| 157 | 100 | 100 | 100 | 100 | 100 | 100 |
| 158 | 100 | 100 | 100 | 100 | 100 | 100 |
| 159 | 100 | 100 | 100 | 100 | 100 | 100 |
| 160 | 99.4 | 98.4 | 100 | 100 | 100 | 100 |
| 161 | 99.4 | 98.4 | 100 | 100 | 100 | 100 |
| 162 | 100 | 100 | 100 | 100 | 100 | 100 |
| 163 | 99.4 | 98.4 | 100 | 100 | 100 | 100 |
| 164 | 100 | 100 | 100 | 100 | 100 | 100 |
| 165 | 99.4 | 98.4 | 100 | 100 | 100 | 100 |
| 166 | 99.4 | 98.4 | 100 | 100 | 100 | 100 |
| 167 | 100 | 100 | 100 | 100 | 100 | 100 |
| 168 | 100 | 100 | 100 | 100 | 100 | 100 |
| 169 | 100 | 100 | 100 | 100 | 100 | 100 |
| 170 | 100 | 100 | 100 | 100 | 100 | 100 |
| 171 | 99.4 | 98.4 | 100 | 100 | 100 | 100 |
| 172 | 100 | 100 | 100 | 100 | 100 | 100 |
| 173 | 99.4 | 98.4 | 100 | 100 | 100 | 100 |
| 174 | 99.4 | 98.4 | 100 | 100 | 100 | 100 |
| 175 | 99.4 | 98.4 | 100 | 100 | 100 | 100 |
| 176 | 100 | 100 | 100 | 100 | 100 | 100 |
| 177 | 100 | 100 | 100 | 100 | 100 | 100 |
| 178 | 100 | 100 | 100 | 100 | 100 | 100 |
| 179 | 99.4 | 98.4 | 100 | 100 | 100 | 100 |
| 180 | 100 | 100 | 100 | 100 | 100 | 100 |
| 181 | 100 | 100 | 100 | 100 | 100 | 100 |
| 182 | 99.4 | 98.4 | 100 | 100 | 100 | 100 |
| 183 | 99.4 | 98.4 | 100 | 100 | 100 | 100 |
| 184 | 99.4 | 98.4 | 100 | 100 | 100 | 100 |
| 185 | 99.4 | 98.4 | 100 | 100 | 100 | 100 |
| 186 | 100 | 100 | 100 | 100 | 100 | 100 |
| 187 | 99.4 | 98.4 | 100 | 100 | 100 | 100 |
| 188 | 99.4 | 98.4 | 100 | 100 | 100 | 100 |
| 189 | 99.4 | 98.4 | 100 | 100 | 100 | 100 |
| 190 | 100 | 100 | 100 | 100 | 100 | 100 |
| 191 | 99.4 | 98.4 | 100 | 100 | 100 | 100 |
| 192 | 99.4 | 98.4 | 100 | 100 | 100 | 100 |
| 193 | 99.4 | 98.4 | 100 | 100 | 100 | 100 |
| 194 | 100 | 100 | 100 | 100 | 100 | 100 |
| 195 | 99.4 | 98.4 | 100 | 100 | 100 | 100 |
| 196 | 100 | 100 | 100 | 100 | 100 | 100 |
| 197 | 99.4 | 98.4 | 100 | 100 | 100 | 100 |
| 198 | 99.4 | 98.4 | 100 | 100 | 100 | 100 |
| 199 | 99.4 | 98.4 | 100 | 100 | 100 | 100 |
| 1100 | 100 | 100 | 100 | 100 | 100 | 100 |
| 1101 | 99.4 | 98.4 | 100 | 100 | 100 | 100 |
| 1102 | 100 | 100 | 100 | 100 | 100 | 100 |
| 1103 | 99.4 | 98.4 | 100 | 100 | 100 | 100 |
| 1104 | 100 | 100 | 100 | 100 | 100 | 100 |
| 1105 | 99.4 | 98.4 | 100 | 100 | 100 | 100 |
| 1106 | 100 | 100 | 100 | 100 | 100 | 100 |
| 1107 | 100 | 100 | 100 | 100 | 100 | 100 |
| 1108 | 99.4 | 98.4 | 100 | 100 | 100 | 100 |
| 1109 | 100 | 100 | 100 | 100 | 100 | 100 |
| 1110 | 99.4 | 98.4 | 100 | 100 | 100 | 100 |
| 1111 | 99.4 | 98.4 | 100 | 100 | 100 | 100 |
| 1112 | 100 | 100 | 100 | 100 | 100 | 100 |
| 1113 | 100 | 100 | 100 | 100 | 100 | 100 |
| 1114 | 99.4 | 98.4 | 100 | 100 | 100 | 100 |
| 1115 | 99.4 | 98.4 | 100 | 100 | 100 | 100 |
| 1116 | 99.4 | 98.4 | 100 | 100 | 100 | 100 |
| 1117 | 99.4 | 98.4 | 100 | 100 | 100 | 100 |
| 1118 | 99.4 | 98.4 | 100 | 100 | 100 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1119 | 99.4 | 98.4 | 100 | 100 | 100 | 100 |
| 1120 | 99.4 | 98.4 | 100 | 100 | 100 | 100 |
| 1121 | 100 | 100 | 100 | 100 | 100 | 100 |
| 1122 | 99.4 | 98.4 | 100 | 100 | 100 | 100 |
| 1123 | 99.4 | 98.4 | 100 | 100 | 100 | 100 |
| 1124 | 99.4 | 98.4 | 100 | 100 | 100 | 100 |
| 1125 | 100 | 100 | 100 | 100 | 100 | 100 |
| 1126 | 99.4 | 98.4 | 100 | 100 | 100 | 100 |
| 1127 | 100 | 100 | 100 | 100 | 100 | 100 |
| 1128 | 99.4 | 98.4 | 100 | 100 | 100 | 100 |
| 1129 | 99.4 | 98.4 | 100 | 100 | 100 | 100 |
| 1130 | 99.4 | 98.4 | 100 | 100 | 100 | 100 |
| 1131 | 99.4 | 98.4 | 100 | 100 | 100 | 100 |
| 1132 | 99.4 | 98.4 | 100 | 100 | 100 | 100 |
| 1133 | 99.4 | 98.4 | 100 | 100 | 100 | 100 |
| 1134 | 99.4 | 98.4 | 100 | 100 | 100 | 100 |
| 1135 | 99.4 | 98.4 | 100 | 100 | 100 | 100 |
| 1136 | 99.4 | 98.4 | 100 | 100 | 100 | 100 |
| 1137 | 99.4 | 98.4 | 100 | 100 | 100 | 100 |
| 1138 | 99.4 | 98.4 | 100 | 100 | 100 | 100 |
| 1139 | 99.4 | 98.4 | 100 | 100 | 100 | 100 |
| 1140 | 99.4 | 98.4 | 100 | 100 | 100 | 100 |
| 1141 | 99.4 | 98.4 | 100 | 100 | 100 | 100 |
| 1142 | 99.4 | 98.4 | 100 | 100 | 100 | 100 |
| 1143 | 100 | 100 | 100 | 100 | 100 | 100 |
| 1144 | 99.4 | 98.4 | 100 | 100 | 100 | 100 |
| 1145 | 99.4 | 98.4 | 100 | 100 | 100 | 100 |
| 1146 | 99.4 | 98.4 | 100 | 100 | 100 | 100 |
| 1147 | 99.4 | 98.4 | 100 | 100 | 100 | 100 |
| 1148 | 100 | 100 | 100 | 100 | 100 | 100 |
| 1149 | 99.4 | 98.4 | 100 | 100 | 100 | 100 |
| 1150 | 99.4 | 98.4 | 100 | 100 | 100 | 100 |
| 1151 | 99.4 | 98.4 | 100 | 100 | 100 | 100 |
| 1152 | 100 | 100 | 100 | 100 | 100 | 100 |
| 1153 | 99.4 | 98.4 | 100 | 100 | 100 | 100 |
| 1154 | 99.4 | 98.4 | 100 | 100 | 100 | 100 |
| 1155 | 99.4 | 98.4 | 100 | 100 | 100 | 100 |
| 1156 | 99.4 | 98.4 | 100 | 100 | 100 | 100 |
| 1157 | 100 | 100 | 100 | 100 | 100 | 100 |
| 1158 | 99.4 | 98.4 | 100 | 100 | 100 | 100 |
| 1159 | 99.4 | 98.4 | 100 | 100 | 100 | 100 |
| 1160 | 99.4 | 98.4 | 100 | 100 | 100 | 100 |
| 1161 | 100 | 100 | 100 | 100 | 100 | 100 |
| 1162 | 100 | 100 | 100 | 100 | 100 | 100 |
| 1163 | 99.4 | 98.4 | 100 | 100 | 100 | 100 |
| 1164 | 99.4 | 98.4 | 100 | 100 | 100 | 100 |
| 1165 | 99.4 | 98.4 | 100 | 100 | 100 | 100 |
| 1166 | 99.4 | 98.4 | 100 | 100 | 100 | 100 |
| 1167 | 99.4 | 98.4 | 100 | 100 | 100 | 100 |
| 1168 | 99.4 | 98.4 | 100 | 100 | 100 | 100 |
| 1169 | 100 | 100 | 100 | 100 | 100 | 100 |
| 1170 | 99.4 | 98.4 | 100 | 100 | 100 | 100 |
| 1171 | 99.4 | 98.4 | 100 | 100 | 100 | 100 |
| 1172 | 99.4 | 98.4 | 100 | 100 | 100 | 100 |
| 1173 | 99.4 | 98.4 | 100 | 100 | 100 | 100 |
| 1174 | 99.4 | 98.4 | 100 | 100 | 100 | 100 |
| 1175 | 99.4 | 98.4 | 100 | 100 | 100 | 100 |
| 1176 | 99.4 | 98.4 | 100 | 100 | 100 | 100 |
| 1177 | 99.4 | 98.4 | 100 | 100 | 100 | 100 |
| 1178 | 99.4 | 98.4 | 100 | 100 | 100 | 100 |
| 1179 | 99.4 | 98.4 | 100 | 100 | 100 | 100 |
| 1180 | 99.4 | 98.4 | 100 | 100 | 100 | 100 |
| 1181 | 99.4 | 98.4 | 100 | 100 | 100 | 100 |
| 1182 | 99.4 | 98.4 | 100 | 100 | 100 | 100 |
| 1183 | 99.4 | 98.4 | 100 | 100 | 100 | 100 |
| 1184 | 99.4 | 98.4 | 100 | 100 | 100 | 100 |
| 1185 | 99.4 | 98.4 | 100 | 100 | 100 | 100 |
| 1186 | 100 | 100 | 100 | 100 | 100 | 100 |
| 1187 | 99.4 | 98.4 | 100 | 100 | 100 | 100 |
| 1188 | 100 | 100 | 100 | 100 | 100 | 100 |
| 1189 | 99.4 | 98.4 | 100 | 100 | 100 | 100 |
| 1190 | 99.4 | 98.4 | 100 | 100 | 100 | 100 |
| 1191 | 99.4 | 98.4 | 100 | 100 | 100 | 100 |
| 1192 | 99.4 | 98.4 | 100 | 100 | 100 | 100 |
| 1193 | 99.4 | 98.4 | 100 | 100 | 100 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1194 | 99.4 | 98.4 | 100 | 100 | 100 | 100 |
| 1195 | 100 | 100 | 100 | 100 | 100 | 100 |
| 1196 | 99.4 | 98.4 | 100 | 100 | 100 | 100 |
| 1197 | 99.4 | 98.4 | 100 | 100 | 100 | 100 |
| 1198 | 99.4 | 98.4 | 100 | 100 | 100 | 100 |
| 1199 | 99.4 | 98.4 | 100 | 100 | 100 | 100 |
| 1200 | 99.4 | 98.4 | 100 | 100 | 100 | 100 |
| 1201 | 99.4 | 98.4 | 100 | 100 | 100 | 100 |
| 1202 | 99.4 | 98.4 | 100 | 100 | 100 | 100 |
| 1203 | 99.4 | 98.4 | 100 | 100 | 100 | 100 |
| 1204 | 99.4 | 98.4 | 100 | 100 | 100 | 100 |
| 1205 | 99.4 | 98.4 | 100 | 100 | 100 | 100 |
| 1206 | 99.4 | 98.4 | 100 | 100 | 100 | 100 |
| 1207 | 99.4 | 98.4 | 100 | 100 | 100 | 100 |
| 1208 | 99.4 | 98.4 | 100 | 100 | 100 | 100 |
| 1209 | 99.4 | 98.4 | 100 | 100 | 100 | 100 |
| 1210 | 99.4 | 98.4 | 100 | 100 | 100 | 100 |
| 1211 | 99.4 | 98.4 | 100 | 100 | 100 | 100 |
| 1212 | 99.4 | 98.4 | 100 | 100 | 100 | 100 |
| 1213 | 99.4 | 98.4 | 100 | 100 | 100 | 100 |
| 1214 | 100 | 100 | 100 | 100 | 100 | 100 |
| 1215 | 100 | 100 | 100 | 100 | 100 | 100 |
| 1216 | 99.4 | 98.4 | 100 | 100 | 100 | 100 |
| 1217 | 99.4 | 98.4 | 100 | 100 | 100 | 100 |
| 1218 | 99.4 | 98.4 | 100 | 100 | 100 | 100 |
| 1219 | 100 | 100 | 100 | 100 | 100 | 100 |
| 1220 | 100 | 100 | 100 | 100 | 100 | 100 |
| 1221 | 99.4 | 98.4 | 100 | 100 | 100 | 100 |
| 1222 | 99.4 | 98.4 | 100 | 100 | 100 | 100 |
| 1223 | 99.4 | 98.4 | 100 | 100 | 100 | 100 |
| 1224 | 99.4 | 98.4 | 100 | 100 | 100 | 100 |
| 1225 | 100 | 100 | 100 | 100 | 100 | 100 |
| 1226 | 99.4 | 98.4 | 100 | 100 | 100 | 100 |
| 1227 | 99.4 | 98.4 | 100 | 100 | 100 | 100 |
| 1228 | 99.4 | 98.4 | 100 | 100 | 100 | 100 |
| 1229 | 99.4 | 98.4 | 100 | 100 | 100 | 100 |
| 1230 | 99.4 | 98.4 | 100 | 100 | 100 | 100 |
| 1231 | 99.4 | 98.4 | 100 | 100 | 100 | 100 |
| 1232 | 99.4 | 98.4 | 100 | 100 | 100 | 100 |
| 1233 | 99.4 | 98.4 | 100 | 100 | 100 | 100 |
| 1234 | 99.4 | 98.4 | 100 | 100 | 100 | 100 |
| 1235 | 99.4 | 98.4 | 100 | 100 | 100 | 100 |
| 1236 | 100 | 100 | 100 | 100 | 100 | 100 |
| 1237 | 100 | 100 | 100 | 100 | 100 | 100 |
| 1238 | 100 | 100 | 100 | 100 | 100 | 100 |
| 1239 | 100 | 100 | 100 | 100 | 100 | 100 |
| 1240 | 100 | 100 | 100 | 100 | 100 | 100 |
| 1241 | 100 | 100 | 100 | 100 | 100 | 100 |
| 1242 | 100 | 100 | 100 | 100 | 100 | 100 |
| 1243 | 100 | 100 | 100 | 100 | 100 | 100 |
| 1244 | 100 | 100 | 100 | 100 | 100 | 100 |
| 1245 | 99.4 | 98.4 | 100 | 100 | 100 | 100 |
| 1246 | 99.4 | 98.4 | 100 | 100 | 100 | 100 |
| 1247 | 99.4 | 98.4 | 100 | 100 | 100 | 100 |
| 1248 | 99.4 | 98.4 | 100 | 100 | 100 | 100 |
| 1249 | 99.4 | 98.4 | 100 | 100 | 100 | 100 |
| 1250 | 99.4 | 98.4 | 100 | 100 | 100 | 100 |
| 1251 | 99.4 | 98.4 | 100 | 100 | 100 | 100 |

TABLE 7

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 3_20 | 100 | 100 | 100 | 100 | 100 | 100 |
| 6_20 | 100 | 100 | 100 | 100 | 100 | 100 |
| 7_20 | 100 | 100 | 100 | 100 | 100 | 100 |
| 10_20 | 100 | 100 | 100 | 100 | 100 | 100 |
| 20_22 | 98.8 | 96.7 | 100 | 98.8 | 96.8 | 100 |
| 20_238 | 98.8 | 96.7 | 100 | 98.8 | 96.8 | 100 |

TABLE 7-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 20_239 | 100 | 100 | 100 | 100 | 100 | 100 |
| 12_24 | 100 | 100 | 100 | 98.8 | 96.8 | 100 |
| 20_24 | 100 | 100 | 100 | 98.8 | 96.8 | 100 |
| 24_27 | 98.8 | 96.8 | 100 | 98.8 | 96.8 | 100 |
| 24_33 | 100 | 100 | 100 | 100 | 100 | 100 |
| 24_236 | 100 | 100 | 100 | 98.8 | 96.8 | 100 |
| 24_240 | 100 | 100 | 100 | 100 | 100 | 100 |
| 3_26 | 100 | 100 | 100 | 100 | 100 | 100 |
| 12_26 | 100 | 100 | 100 | 98.8 | 96.8 | 100 |
| 13_26 | 100 | 100 | 100 | 98.8 | 96.8 | 100 |
| 17_26 | 100 | 100 | 100 | 98.8 | 100 | 98 |
| 19_26 | 100 | 100 | 100 | 98.8 | 100 | 98 |
| 3_27 | 100 | 100 | 100 | 100 | 100 | 100 |
| 5_27 | 100 | 100 | 100 | 100 | 100 | 100 |
| 13_27 | 99.4 | 98.4 | 100 | 100 | 100 | 100 |
| 20_27 | 98.1 | 96.7 | 99 | 100 | 100 | 100 |
| 26_27 | 99.4 | 98.4 | 100 | 96.3 | 93.5 | 98 |
| 27_120 | 98.8 | 98.4 | 99 | 100 | 100 | 100 |
| 27_206 | 98.1 | 95.2 | 100 | 97.5 | 96.8 | 98 |
| 27_237 | 99.4 | 98.4 | 100 | 100 | 100 | 100 |
| 3_30 | 100 | 100 | 100 | 100 | 100 | 100 |
| 17_30 | 99.4 | 98.4 | 100 | 100 | 100 | 100 |
| 27_30 | 100 | 100 | 100 | 98.8 | 96.8 | 100 |
| 27_33 | 98.8 | 98.4 | 99 | 100 | 100 | 100 |
| 30_39 | 99.4 | 98.4 | 100 | 100 | 100 | 100 |
| 30_117 | 99.4 | 98.4 | 100 | 98.8 | 96.8 | 100 |
| 3_33 | 99.4 | 98.4 | 100 | 100 | 100 | 100 |
| 7_33 | 100 | 100 | 100 | 100 | 100 | 100 |
| 10_33 | 100 | 100 | 100 | 100 | 100 | 100 |
| 11_33 | 100 | 100 | 100 | 98.8 | 100 | 98 |
| 13_33 | 100 | 100 | 100 | 100 | 100 | 100 |
| 25_33 | 100 | 100 | 100 | 98.8 | 100 | 98 |
| 33_244 | 100 | 100 | 100 | 100 | 100 | 100 |
| 3_182 | 99.4 | 98.4 | 100 | 100 | 100 | 100 |
| 6_182 | 99.4 | 98.4 | 100 | 100 | 100 | 100 |
| 7_182 | 100 | 100 | 100 | 100 | 100 | 100 |
| 12_182 | 100 | 100 | 100 | 100 | 100 | 100 |
| 27_182 | 98.1 | 96.8 | 99 | 97.5 | 96.8 | 98 |
| 182_236 | 100 | 100 | 100 | 98.8 | 96.8 | 100 |
| 2_194 | 99.4 | 98.4 | 100 | 100 | 100 | 100 |
| 7_194 | 100 | 100 | 100 | 100 | 100 | 100 |
| 27_194 | 98.1 | 95.2 | 100 | 97.5 | 96.8 | 98 |
| 194_236 | 100 | 100 | 100 | 98.8 | 96.8 | 100 |
| 2_206 | 99.4 | 98.4 | 100 | 100 | 100 | 100 |
| 7_206 | 100 | 100 | 100 | 100 | 100 | 100 |
| 206_236 | 100 | 100 | 100 | 98.8 | 96.8 | 100 |
| 2_208 | 99.4 | 98.4 | 100 | 100 | 100 | 100 |
| 7_208 | 100 | 100 | 100 | 100 | 100 | 100 |
| 13_208 | 99.4 | 98.4 | 100 | 100 | 100 | 100 |
| 20_208 | 98.1 | 96.7 | 99 | 97.5 | 93.5 | 100 |
| 27_208 | 98.1 | 95.2 | 100 | 98.8 | 96.8 | 100 |

Example 3

<Selection of Gene Markers Using all Samples and Method for Evaluating Breast Cancer Discriminant Performance of Acquired Gene Markers>

In this Example, the samples of the training cohort and the validation cohort used in Examples 1 and 2 were integrated, and selection of a gene marker and evaluation of its breast cancer discriminant performance were conducted using all of the samples.

Specifically, the miRNA expression levels in the sera of the 93 breast cancer patients and the 150 healthy subjects obtained in the preceding Reference Examples were normalized by quantile normalization. In order to acquire diagnostic markers with higher reliability, only genes having a gene expression level of $2^6$ or higher in 50% or more of the samples in either of the breast cancer patient group or the healthy subject group, were selected in the gene marker selection. In order to further acquire statistical significance for discriminating a breast cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant. The obtained genes are described in Table 7. In this way, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5ph and hsa-miR-6763-5p genes, and the nucleotide sequences of SEQ ID NOs: 252 to 269 related thereto were found in addition to the genes described in Table 2. As with the nucleotide sequences of SEQ ID NOs: 1 to 251, the results obtained about the polynucleotides represented by the nucleotide sequences of SEQ ID NOs: 252 to 269 also showed that the measurement values were significantly lower (−) or higher (+) in the breast cancer patient group than in the healthy subject group (Table 8). These results were able to be validated in the validation cohort. Thus, the presence or absence of breast cancer in the newly obtained samples can be determined by the methods described in Examples 1 and 2 by using the gene expression level measurement values described in Table 8 either alone or in combination with the gene expression level measurement values described in Table 2

TABLE 8

| SEQ ID NO: | Gene name | P value after Bonferroni correction | Expression level in breast cancer patient with respect to healthy subject |
|---|---|---|---|
| 1 | hsa-miR-4783-3p | 1.81 · E−151 | + |
| 2 | hsa-miR-4730 | 1.00 · E−148 | − |
| 3 | hsa-miR-1307-3p | 5.85 · E−126 | + |
| 4 | hsa-miR-4634 | 9.92 · E−114 | − |
| 5 | hsa-miR-663a | 2.55 · E−112 | − |
| 6 | hsa-miR-4532 | 8.96 · E−113 | + |
| 7 | hsa-miR-7704 | 4.82 · E−114 | + |
| 8 | hsa-miR-3178 | 5.69 · E−112 | − |
| 9 | hsa-miR-6729-5p | 3.52 · E−112 | − |
| 10 | hsa-miR-6090 | 1.64 · E−100 | − |
| 11 | hsa-miR-4732-5p | 7.04 · E−96 | − |
| 12 | hsa-miR-3184-5p | 2.08 · E−103 | + |
| 13 | hsa-miR-6727-5p | 3.11 · E−99 | + |
| 14 | hsa-miR-6088 | 4.52 · E−100 | − |
| 15 | hsa-miR-4674 | 2.03 · E−94 | + |
| 16 | hsa-miR-8073 | 5.49 · E−98 | − |
| 17 | hsa-miR-4787-5p | 1.53 · E−96 | + |
| 18 | hsa-miR-1469 | 3.95 · E−87 | + |
| 19 | hsa-miR-125a-3p | 3.12 · E−91 | − |
| 20 | hsa-miR-1233-5p | 2.43 · E−93 | + |
| 21 | hsa-miR-885-3p | 4.92 · E−87 | − |
| 22 | hsa-miR-6802-5p | 5.06 · E−87 | − |
| 23 | hsa-miR-328-5p | 6.06 · E−96 | + |
| 24 | hsa-miR-6787-5p | 2.26 · E−85 | + |
| 25 | hsa-miR-8069 | 5.26 · E−78 | + |
| 26 | hsa-miR-6875-5p | 2.38 · E−74 | + |
| 27 | hsa-miR-1246 | 1.05 · E−75 | + |
| 28 | hsa-miR-4734 | 6.82 · E−87 | − |
| 29 | hsa-miR-6757-5p | 9.57 · E−75 | + |
| 30 | hsa-miR-6756-5p | 4.28 · E−70 | − |
| 31 | hsa-miR-3665 | 5.78 · E−78 | − |
| 32 | hsa-miR-6836-3p | 7.87 · E−76 | − |
| 33 | hsa-miR-6821-5p | 1.18 · E−80 | − |
| 34 | hsa-miR-6805-5p | 3.26 · E−79 | − |
| 35 | hsa-miR-4728-5p | 9.76 · E−65 | + |
| 36 | hsa-miR-6726-5p | 4.07 · E−72 | + |
| 37 | hsa-miR-197-5p | 5.63 · E−71 | − |
| 38 | hsa-miR-149-3p | 3.94 · E−70 | + |
| 39 | hsa-miR-6850-5p | 2.45 · E−70 | − |
| 40 | hsa-miR-4476 | 8.32 · E−64 | + |
| 41 | hsa-miR-6858-5p | 4.09 · E−67 | − |
| 42 | hsa-miR-564 | 5.81 · E−69 | + |
| 43 | hsa-miR-4763-3p | 2.83 · E−72 | + |
| 44 | hsa-miR-575 | 1.96 · E−69 | − |
| 45 | hsa-miR-6771-5p | 1.90 · E−65 | − |
| 46 | hsa-miR-1231 | 8.50 · E−61 | − |
| 47 | hsa-miR-1908-3p | 3.70 · E−64 | + |
| 48 | hsa-miR-150-3p | 2.41 · E−58 | − |
| 49 | hsa-miR-3937 | 5.29 · E−66 | − |
| 50 | hsa-miR-887-3p | 1.78 · E−64 | − |
| 51 | hsa-miR-3940-5p | 2.92 · E−65 | − |
| 52 | hsa-miR-4741 | 1.21 · E−57 | + |
| 53 | hsa-miR-6808-5p | 5.95 · E−62 | − |
| 54 | hsa-miR-6869-5p | 9.36 · E−66 | − |
| 55 | hsa-miR-5090 | 2.20 · E−62 | − |
| 56 | hsa-miR-615-5p | 1.59 · E−59 | − |
| 57 | hsa-miR-8072 | 1.93 · E−53 | + |
| 58 | hsa-miR-128-1-5p | 2.45 · E−57 | + |
| 59 | hsa-miR-1238-5p | 3.00 · E−60 | − |
| 60 | hsa-miR-365a-5p | 5.03 · E−59 | + |
| 61 | hsa-miR-204-3p | 1.93 · E−49 | − |
| 62 | hsa-miR-4492 | 6.71 · E−60 | − |
| 63 | hsa-miR-6785-5p | 3.81 · E−56 | + |
| 64 | hsa-miR-6511a-5p | 6.21 · E−62 | + |
| 65 | hsa-miR-4525 | 2.38 · E−55 | − |
| 66 | hsa-miR-1915-5p | 8.81 · E−57 | − |
| 67 | hsa-miR-3180 | 1.19 · E−50 | − |
| 68 | hsa-miR-6879-5p | 2.38 · E−58 | − |
| 69 | hsa-miR-1199-5p | 7.83 · E−51 | − |
| 70 | hsa-miR-6746-5p | 9.76 · E−50 | − |
| 71 | hsa-miR-711 | 1.44 · E−49 | + |
| 72 | hsa-miR-663b | 4.49 · E−49 | − |
| 73 | hsa-miR-4707-3p | 2.18 · E−52 | + |
| 74 | hsa-miR-6893-5p | 2.49 · E−43 | − |
| 75 | hsa-miR-4675 | 5.39 · E−56 | + |
| 76 | hsa-miR-4638-5p | 1.64 · E−51 | + |
| 77 | hsa-miR-4651 | 6.25 · E−50 | − |
| 78 | hsa-miR-6087 | 6.15 · E−53 | − |
| 79 | hsa-miR-4665-5p | 3.35 · E−48 | − |
| 80 | hsa-miR-4758-5p | 1.52 · E−54 | − |
| 81 | hsa-miR-6887-5p | 8.54 · E−46 | − |
| 82 | hsa-miR-3620-5p | 4.32 · E−42 | − |
| 83 | hsa-miR-1909-3p | 6.17 · E−53 | + |
| 84 | hsa-miR-7641 | 2.63 · E−43 | − |
| 85 | hsa-miR-6724-5p | 3.58 · E−49 | + |
| 86 | hsa-miR-1343-3p | 1.04 · E−45 | − |
| 87 | hsa-miR-6780b-5p | 5.24 · E−50 | − |
| 88 | hsa-miR-4484 | 5.63 · E−49 | + |
| 89 | hsa-miR-4690-5p | 2.68 · E−43 | − |
| 90 | hsa-miR-4429 | 7.93 · E−44 | − |
| 91 | hsa-miR-1227-5p | 1.26 · E−46 | − |
| 92 | hsa-miR-4725-3p | 3.25 · E−44 | + |
| 93 | hsa-miR-6861-5p | 2.28 · E−46 | + |
| 94 | hsa-miR-6812-5p | 3.34 · E−37 | + |
| 95 | hsa-miR-3197 | 8.32 · E−45 | + |
| 96 | hsa-miR-8059 | 6.38 · E−41 | + |
| 97 | hsa-miR-3185 | 7.20 · E−46 | + |
| 98 | hsa-miR-4706 | 4.07 · E−39 | + |
| 99 | hsa-miR-4497 | 7.65 · E−39 | + |
| 100 | hsa-miR-3131 | 4.60 · E−42 | − |
| 101 | hsa-miR-6806-5p | 8.93 · E−34 | + |
| 102 | hsa-miR-187-5p | 5.69 · E−42 | + |
| 103 | hsa-miR-3180-3p | 1.37 · E−41 | − |
| 104 | hsa-miR-6848-5p | 9.99 · E−33 | − |
| 105 | hsa-miR-6820-5p | 2.48 · E−37 | + |
| 106 | hsa-miR-6800-5p | 2.58 · E−42 | + |
| 107 | hsa-miR-6717-5p | 2.75 · E−37 | − |
| 108 | hsa-miR-6795-5p | 2.83 · E−36 | − |
| 109 | hsa-miR-4632-5p | 1.50 · E−40 | + |
| 110 | hsa-miR-665 | 3.04 · E−37 | − |
| 111 | hsa-miR-6778-5p | 3.57 · E−36 | − |
| 112 | hsa-miR-3663-3p | 2.48 · E−39 | + |
| 113 | hsa-miR-4689 | 1.46 · E−43 | + |
| 114 | hsa-miR-211-3p | 1.36 · E−39 | + |
| 115 | hsa-miR-6511b-5p | 4.55 · E−39 | + |
| 116 | hsa-miR-4750-5p | 1.70 · E−32 | + |
| 117 | hsa-miR-6126 | 6.52 · E−41 | + |
| 118 | hsa-miR-614 | 1.36 · E−31 | + |
| 119 | hsa-miR-7110-5p | 2.57 · E−36 | − |
| 120 | hsa-miR-744-5p | 1.36 · E−32 | − |
| 121 | hsa-miR-6769a-5p | 2.68 · E−28 | + |
| 122 | hsa-miR-4792 | 3.78 · E−29 | − |
| 123 | hsa-miR-5787 | 5.62 · E−30 | + |
| 124 | hsa-miR-6798-5p | 8.69 · E−34 | − |
| 125 | hsa-miR-6781-5p | 1.34 · E−35 | + |
| 126 | hsa-miR-4419b | 3.49 · E−28 | − |
| 127 | hsa-miR-4446-3p | 2.83 · E−32 | − |
| 128 | hsa-miR-4259 | 9.25 · E−30 | − |
| 129 | hsa-miR-5572 | 7.92 · E−32 | − |
| 130 | hsa-miR-6075 | 1.06 · E−34 | − |
| 131 | hsa-miR-296-3p | 7.28 · E−27 | − |
| 132 | hsa-miR-6891-5p | 1.19 · E−28 | + |
| 133 | hsa-miR-4745-5p | 1.47 · E−30 | + |
| 134 | hsa-miR-6775-5p | 1.24 · E−28 | − |
| 135 | hsa-miR-6870-5p | 1.50 · E−29 | − |
| 136 | hsa-miR-920 | 2.07 · E−27 | + |

TABLE 8-continued

| SEQ ID NO: | Gene name | P value after Bonferroni correction | Expression level in breast cancer patient with respect to healthy subject |
|---|---|---|---|
| 137 | hsa-miR-4530 | 4.79 · E−26 | + |
| 138 | hsa-miR-6819-5p | 4.33 · E−27 | − |
| 139 | hsa-miR-6825-5p | 3.99 · E−29 | + |
| 140 | hsa-miR-7847-3p | 1.49 · E−26 | + |
| 141 | hsa-miR-6131 | 3.83 · E−28 | − |
| 142 | hsa-miR-4433-3p | 8.75 · E−27 | − |
| 143 | hsa-miR-1228-5p | 4.12 · E−20 | − |
| 144 | hsa-miR-6743-5p | 4.05 · E−31 | − |
| 145 | hsa-miR-1268a | 1.93 · E−25 | + |
| 146 | hsa-miR-3917 | 3.71 · E−24 | − |
| 147 | hsa-miR-6786-5p | 3.71 · E−27 | + |
| 148 | hsa-miR-3154 | 1.49 · E−21 | + |
| 149 | hsa-miR-638 | 2.61 · E−28 | + |
| 150 | hsa-miR-6741-5p | 2.54 · E−24 | − |
| 151 | hsa-miR-6889-5p | 3.14 · E−26 | + |
| 152 | hsa-miR-6840-3p | 4.16 · E−20 | − |
| 153 | hsa-miR-6510-5p | 2.15 · E−19 | + |
| 154 | hsa-miR-3188 | 3.01 · E−21 | + |
| 156 | hsa-miR-5001-5p | 1.47 · E−22 | − |
| 157 | hsa-miR-1268b | 1.93 · E−20 | + |
| 158 | hsa-miR-7107-5p | 6.37 · E−21 | − |
| 159 | hsa-miR-6824-5p | 9.39 · E−21 | − |
| 160 | hsa-miR-6732-5p | 3.49 · E−17 | − |
| 161 | hsa-miR-371a-5p | 1.21 · E−19 | − |
| 162 | hsa-miR-6794-5p | 1.02 · E−15 | + |
| 163 | hsa-miR-6779-5p | 6.91 · E−17 | + |
| 164 | hsa-miR-4271 | 2.14 · E−22 | + |
| 165 | hsa-miR-5195-3p | 1.17 · E−19 | − |
| 166 | hsa-miR-6762-5p | 5.65 · E−18 | + |
| 167 | hsa-miR-939-5p | 4.70 · E−21 | + |
| 168 | hsa-miR-1247-3p | 4.05 · E−14 | + |
| 169 | hsa-miR-6777-5p | 4.37 · E−16 | − |
| 170 | hsa-miR-6722-3p | 9.50 · E−18 | − |
| 171 | hsa-miR-3656 | 1.77 · E−21 | + |
| 172 | hsa-miR-4688 | 4.75 · E−17 | − |
| 173 | hsa-miR-3195 | 3.33 · E−18 | − |
| 174 | hsa-miR-6766-5p | 1.29 · E−18 | − |
| 175 | hsa-miR-4447 | 1.50 · E−14 | + |
| 176 | hsa-miR-4656 | 7.31 · E−14 | + |
| 177 | hsa-miR-7108-5p | 1.06 · E−16 | − |
| 179 | hsa-miR-1273g-3p | 3.79 · E−17 | + |
| 180 | hsa-miR-4463 | 4.63 · E−18 | − |
| 181 | hsa-miR-2861 | 2.60 · E−15 | + |
| 182 | hsa-miR-3196 | 6.55 · E−12 | + |
| 183 | hsa-miR-6877-5p | 2.44 · E−17 | + |
| 184 | hsa-miR-3679-5p | 6.45 · E−18 | + |
| 185 | hsa-miR-4442 | 3.11 · E−15 | − |
| 186 | hsa-miR-6789-5p | 1.50 · E−14 | − |
| 187 | hsa-miR-6782-5p | 1.14 · E−13 | − |
| 188 | hsa-miR-486-3p | 8.80 · E−15 | + |
| 189 | hsa-miR-6085 | 3.88 · E−15 | + |
| 190 | hsa-miR-4746-3p | 2.87 · E−13 | − |
| 191 | hsa-miR-619-5p | 2.89 · E−12 | + |
| 192 | hsa-miR-937-5p | 2.36 · E−13 | + |
| 193 | hsa-miR-6803-5p | 2.14 · E−12 | + |
| 194 | hsa-miR-4298 | 1.25 · E−14 | + |
| 195 | hsa-miR-4454 | 9.63 · E−11 | + |
| 196 | hsa-miR-4459 | 3.66 · E−13 | − |
| 197 | hsa-miR-7150 | 1.76 · E−10 | + |
| 198 | hsa-miR-6880-5p | 3.57 · E−11 | − |
| 199 | hsa-miR-4449 | 4.62 · E−11 | + |
| 200 | hsa-miR-8063 | 4.89 · E−13 | + |
| 201 | hsa-miR-4695-5p | 5.30 · E−09 | − |
| 202 | hsa-miR-6132 | 2.15 · E−10 | + |
| 203 | hsa-miR-6829-5p | 3.96 · E−09 | − |
| 204 | hsa-miR-4486 | 2.13 · E−07 | + |
| 205 | hsa-miR-6805-3p | 8.96 · E−10 | + |
| 206 | hsa-miR-6826-5p | 7.62 · E−08 | − |
| 207 | hsa-miR-4508 | 6.79 · E−08 | + |
| 208 | hsa-miR-1343-5p | 8.96 · E−07 | + |
| 209 | hsa-miR-7114-5p | 1.55 · E−09 | + |
| 210 | hsa-miR-3622a-5p | 2.52 · E−08 | − |
| 211 | hsa-miR-6765-5p | 6.46 · E−07 | + |
| 212 | hsa-miR-7845-5p | 1.78 · E−04 | − |
| 213 | hsa-miR-3960 | 2.10 · E−10 | − |
| 214 | hsa-miR-6749-5p | 1.32 · E−07 | − |
| 215 | hsa-miR-1260b | 1.44 · E−04 | + |
| 216 | hsa-miR-6799-5p | 1.14 · E−07 | + |
| 217 | hsa-miR-4723-5p | 6.30 · E−07 | − |
| 218 | hsa-miR-6784-5p | 4.08 · E−08 | + |
| 219 | hsa-miR-5100 | 1.78 · E−06 | − |
| 220 | hsa-miR-6769b-5p | 6.44 · E−06 | + |
| 221 | hsa-miR-1207-5p | 8.21 · E−07 | − |
| 222 | hsa-miR-642a-3p | 2.06 · E−09 | − |
| 223 | hsa-miR-4505 | 3.06 · E−06 | + |
| 224 | hsa-miR-4270 | 9.73 · E−07 | + |
| 225 | hsa-miR-6721-5p | 1.84 · E−08 | − |
| 226 | hsa-miR-7111-5p | 3.24 · E−09 | + |
| 227 | hsa-miR-6791-5p | 2.88 · E−06 | − |
| 228 | hsa-miR-7109-5p | 7.96 · E−05 | + |
| 229 | hsa-miR-4258 | 1.36 · E−05 | + |
| 230 | hsa-miR-6515-3p | 3.81 · E−03 | + |
| 231 | hsa-miR-6851-5p | 1.63 · E−06 | − |
| 232 | hsa-miR-6125 | 1.36 · E−05 | − |
| 233 | hsa-miR-4749-5p | 7.65 · E−05 | − |
| 234 | hsa-miR-4726-5p | 5.88 · E−04 | + |
| 235 | hsa-miR-4513 | 4.79 · E−06 | − |
| 236 | hsa-miR-760 | 1.45 · E−111 | + |
| 237 | hsa-miR-602 | 1.06 · E−88 | − |
| 238 | hsa-miR-423-5p | 9.24 · E−79 | − |
| 239 | hsa-miR-92a-2-5p | 2.54 · E−85 | − |
| 240 | hsa-miR-16-5p | 1.34 · E−69 | + |
| 241 | hsa-miR-451a | 5.22 · E−54 | + |
| 242 | hsa-miR-135a-3p | 8.02 · E−58 | + |
| 243 | hsa-miR-486-5p | 8.22 · E−52 | + |
| 244 | hsa-miR-4257 | 4.02 · E−46 | + |
| 245 | hsa-miR-92b-5p | 1.86 · E−45 | − |
| 246 | hsa-miR-1915-3p | 4.13 · E−28 | − |
| 247 | hsa-miR-718 | 1.29 · E−25 | + |
| 248 | hsa-miR-940 | 5.23 · E−17 | − |
| 249 | hsa-miR-296-5p | 3.77 · E−16 | − |
| 250 | hsa-miR-23b-3p | 1.91 · E−04 | + |
| 251 | hsa-miR-92a-3p | 3.74 · E−07 | + |
| 252 | hsa-miR-658 | 4.76 · E−43 | + |
| 253 | hsa-miR-6842-5p | 3.63 · E−12 | − |
| 254 | hsa-miR-6124 | 8.99 · E−06 | + |
| 255 | hsa-miR-6765-3p | 2.30 · E−05 | − |
| 256 | hsa-miR-7106-5p | 4.48 · E−05 | − |
| 257 | hsa-miR-4534 | 2.10 · E−04 | − |
| 258 | hsa-miR-92b-3p | 2.53 · E−04 | − |
| 259 | hsa-miR-3135b | 3.35 · E−04 | + |
| 260 | hsa-miR-4687-3p | 3.90 · E−04 | + |
| 261 | hsa-miR-762 | 4.64 · E−04 | − |
| 262 | hsa-miR-3619-3p | 1.13 · E−03 | + |
| 263 | hsa-miR-4467 | 1.30 · E−03 | − |
| 264 | hsa-miR-557 | 1.49 · E−03 | + |
| 265 | hsa-miR-1237-5p | 1.57 · E−03 | + |
| 266 | hsa-miR-1908-5p | 4.45 · E−03 | − |
| 267 | hsa-miR-4286 | 5.37 · E−03 | − |
| 268 | hsa-miR-6885-5p | 7.57 · E−03 | + |
| 269 | hsa-miR-6763-5p | 9.02 · E−03 | + |

Example 4

<Method for Evaluating Breast Cancer-Specific Discriminant Performance by Combination of Multiple Gene Markers Using Samples in the Validation Cohort>

In this Example, gene expression levels of miRNAs in sera were compared between breast cancer patients and a control group consisting of healthy subjects and prostate cancer patients in the same way as the method described in Example 1 using the gene markers selected in Example 1 with respect to the training cohort described in Reference Example 2, to select a gene marker for diagnosis. The polynucleotides consisting of the nucleotide sequences represented by SEQ ID NOs: 851 to 856 thus newly selected were further combined with the polynucleotides consisting of the nucleotide sequences represented by SEQ ID NOs: 1 to 269 to study a method for evaluating breast cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 2 measurement values that comprise at least one of the measurement values of the polynucleotides consisting of the nucleotide sequences represented by SEQ ID NOs: 1 to 269, and 851 to 856 to construct a discriminant for determining the presence or absence of breast cancer. Next, accuracy, sensitivity, and specificity in the validation cohort were calculated using the discriminant thus prepared, with a positive sample group that is the breast cancer patient group and a negative sample group that is a combination of the healthy subject group and the prostate cancer patient group. The discriminant performance of the selected polynucleotides was validated using independent samples.

Most of polynucleotides consisting of the nucleotide sequences represented by these SEQ ID NOs (SEQ ID NOs: 1 to 269, and 851 to 856 corresponding to the miRNA markers of Table 1) or complementary sequences thereof mentioned above were able to provide relatively high accuracy, sensitivity, and specificity in the determination of the presence or absence of breast cancer, and furthermore, were able to specifically discriminate breast cancer from the other cancers.

At least one polynucleotide selected from the group consisting of polynucleotides consisting of the nucleotide sequences represented by SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 53, 54, 55, 58, 59, 60, 62, 63, 64, 65, 67, 68, 69, 70, 71, 72, 73, 75, 77, 79, 80, 81, 82, 83, 86, 88, 89, 90, 92, 93, 94, 96, 98, 99, 100, 103, 104, 106, 107, 108, 110, 111, 113, 114, 115, 116, 118, 119, 121, 122, 124, 125, 126, 127, 128, 129, 130, 131, 132, 133, 135, 136, 139, 140, 143, 145, 146, 147, 149, 150, 155, 157, 160, 161, 165, 167, 171, 173, 174, 175, 177, 178, 181, 182, 186, 190, 193, 194, 199, 204, 205, 206, 208, 211, 218, 225, 232, 236, 237, 238, 239, 242, 243, 244, 246, 247, 252, 260, 265, 266, 851, 852, 853, 854, 855 and 856, or complementary sequences thereof (the cancer type-specific polynucleotide group 1) was capable of specifically binding to the target marker. Among the combinations of multiple polynucleotides selected from the cancer type-specific polynucleotide group 1, particularly, combinations comprising at least one polynucleotide selected from the group consisting of polynucleotides consisting of the nucleotide sequences represented by SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 54, 55, 58, 59, 60, 62, 63, 64, 65, 67, 68, 69, 71, 72, 73, 75, 77, 79, 80, 82, 83, 86, 88, 92, 93, 96, 99, 103, 104, 106, 110, 111, 114, 116, 118, 119, 122, 124, 125, 127, 130, 132, 133, 135, 139, 143, 145, 147, 149, 157, 160, 173, 177, 181, 182, 186, 211, 218, 232, 236, 237, 238, 239, 242, 243, 246, 247, 260, 266, 851, 852, 853 and 854, or complementary sequences thereof (the cancer type-specific polynucleotide group 2) were able to specifically discriminate breast cancer from the other cancer with high accuracy.

The number of the polynucleotides with cancer type specificity in the combination mentioned above can be 1, 2, 3, 4, 5, 6, 7, 8, 9, 10 or more for the combination. The combinations of 2 or more of these polynucleotides were able to exhibit discriminant accuracy of 95% or higher.

Specifically, the discriminant accuracy of the measurement using combinations of one or two polynucleotide(s) that consists of a nucleotide sequence represented by any of SEQ ID NOs: 1 to 269 and 851 to 856 or a complementary sequence thereof is shown in Table 9.

For example, the combinations of SEQ ID NOs: 2 and 1, SEQ ID NOs: 2 and 237, SEQ ID NOs: 2 and 4, SEQ ID NOs: 2 and 3, SEQ ID NOs: 2 and 51, SEQ ID NOs: 1 and 237, SEQ ID NOs: 1 and 4, SEQ ID NOs: 1 and 3, SEQ ID NOs: 1 and 51, SEQ ID NOs: 1 and 6, SEQ ID NOs: 4 and 237, SEQ ID NOs: 3 and 237, SEQ ID NOs: 51 and 237, SEQ ID NOs: 237 and 6, SEQ ID NOs: 237 and 12, SEQ ID NOs: 3 and 4, SEQ ID NOs: 4 and 51, SEQ ID NOs: 4 and 6, SEQ ID NOs: 4 and 12, SEQ ID NOs: 4 and 15, SEQ ID NOs: 3 and 51, SEQ ID NOs: 3 and 6, SEQ ID NOs: 3 and 12, SEQ ID NOs: 3 and 15, SEQ ID NOs: 3 and 8, SEQ ID NOs: 51 and 6, SEQ ID NOs: 51 and 12, SEQ ID NOs: 51 and 15, SEQ ID NOs: 51 and 8, SEQ ID NOs: 51 and 34, SEQ ID NOs: 2 and 6, SEQ ID NOs: 12 and 6, SEQ ID NOs: 15 and 6, SEQ ID NOs: 8 and 6, SEQ ID NOs: 6 and 34, SEQ ID NOs: 2 and 12, SEQ ID NOs: 1 and 12, SEQ ID NOs: 12 and 15, SEQ ID NOs: 8 and 12, SEQ ID NOs: 12 and 34, SEQ ID NOs: 2 and 15, SEQ ID NOs: 1 and 15, SEQ ID NOs: 237 and 15, SEQ ID NOs: 8 and 15, SEQ ID NOs: 15 and 34, SEQ ID NOs: 2 and 8, SEQ ID NOs: 1 and 8, SEQ ID NOs: 237 and 8, SEQ ID NOs: 4 and 8, SEQ ID NOs: 8 and 34, SEQ ID NOs: 2 and 34, SEQ ID NOs: 1 and 34, SEQ ID NOs: 237 and 34, SEQ ID NOs: 4 and 34, SEQ ID NOs: 3 and 34, SEQ ID NOs: 2 and 9, SEQ ID NOs: 1 and 9, SEQ ID NOs: 9 and 237, SEQ ID NOs: 4 and 9, SEQ ID NOs: 3 and 9, SEQ ID NOs: 2 and 143, SEQ ID NOs: 1 and 143, SEQ ID NOs: 237 and 143, SEQ ID NOs: 4 and 143, SEQ ID NOs: 3 and 143, SEQ ID NOs: 2 and 13, SEQ ID NOs: 1 and 13, SEQ ID NOs: 237 and 13, SEQ ID NOs: 4 and 13, SEQ ID NOs: 3 and 13, SEQ ID NOs: 2 and 125, SEQ ID NOs: 1 and 125, SEQ ID NOs: 237 and 125, SEQ ID NOs: 4 and 125, SEQ ID NOs: 3 and 125, SEQ ID NOs: 2 and 236, SEQ ID NOs: 1 and 236, SEQ ID NOs: 237 and 236, SEQ ID NOs: 4 and 236, SEQ ID NOs: 3 and 236, SEQ ID NOs: 2 and 46, SEQ ID NOs: 1 and 46, SEQ ID NOs: 237 and 46, SEQ ID NOs: 4 and 46, SEQ ID NOs: 3 and 46, SEQ ID NOs: 2 and 32, SEQ ID NOs: 1 and 32, SEQ ID NOs: 237 and 32, SEQ ID NOs: 4 and 32, SEQ ID NOs: 3 and 32, SEQ ID NOs: 2 and 62, SEQ ID NOs: 1 and 62, SEQ ID NOs: 237 and 62, SEQ ID NOs: 4 and 62, SEQ ID NOs: 3 and 62, SEQ ID NOs: 2 and 88, SEQ ID NOs: 1 and 88, SEQ ID NOs: 237 and 88, SEQ ID NOs: 4 and 88, SEQ ID NOs: 3 and 88, SEQ ID NOs: 2 and 52, SEQ ID NOs: 1 and 52, SEQ ID NOs: 237 and 52, SEQ ID NOs: 4 and 52, SEQ ID NOs: 3 and 52, SEQ ID NOs: 2 and 7, SEQ ID NOs: 1 and 7, SEQ ID NOs: 237 and 7, SEQ ID NOs: 4 and 7, SEQ ID NOs: 3 and 7, SEQ ID NOs: 2 and 26, SEQ ID NOs: 1 and 26, SEQ ID NOs: 237 and 26, SEQ ID NOs: 4 and 26, SEQ ID NOs: 3 and 26, SEQ ID NOs: 2 and 25, SEQ ID NOs: 1 and 25, SEQ ID NOs: 237 and 25, SEQ ID NOs: 4 and 25, SEQ ID NOs: 3 and 25, SEQ ID NOs: 2 and 54, SEQ ID NOs: 1 and 54, SEQ ID NOs: 237 and 54, SEQ ID NOs: 4 and 54, SEQ ID NOs: 3 and 54, SEQ ID NOs: 2 and 92, SEQ ID NOs: 1 and 92, SEQ ID NOs: 237 and 92, SEQ ID NOs: 4 and 92, SEQ ID NOs: 3 and 92, SEQ ID NOs: 2 and 14, SEQ ID NOs: 1 and 14, SEQ ID NOs: 237 and 14, SEQ ID NOs: 4 and 14, SEQ ID NOs: 3 and 14, SEQ ID NOs: 2 and 242, SEQ ID NOs: 1 and 242, SEQ ID NOs: 237 and 242, SEQ ID NOs: 4 and 242, SEQ ID NOs: 3 and 242, SEQ ID NOs: 2 and 47, SEQ ID NOs: 1 and 47, SEQ ID NOs: 237 and 47, SEQ ID NOs: 4 and 47, SEQ ID NOs:

3 and 47, SEQ ID NOs: 2 and 45, SEQ ID NOs: 1 and 45, SEQ ID NOs: 237 and 45, SEQ ID NOs: 4 and 45, SEQ ID NOs: 3 and 45, SEQ ID NOs: 2 and 39, SEQ ID NOs: 1 and 39, SEQ ID NOs: 237 and 39, SEQ ID NOs: 4 and 39, SEQ ID NOs: 3 and 39, SEQ ID NOs: 2 and 21, SEQ ID NOs: 1 and 21, SEQ ID NOs: 237 and 21, SEQ ID NOs: 4 and 21, SEQ ID NOs: 3 and 21, SEQ ID NOs: 2 and 17, SEQ ID NOs: 1 and 17, SEQ ID NOs: 237 and 17, SEQ ID NOs: 4 and 17, SEQ ID NOs: 3 and 17, SEQ ID NOs: 2 and 83, SEQ ID NOs: 1 and 83, SEQ ID NOs: 237 and 83, SEQ ID NOs: 4 and 83, SEQ ID NOs: 3 and 83, SEQ ID NOs: 2 and 149, SEQ ID NOs: 1 and 149, SEQ ID NOs: 237 and 149, SEQ ID NOs: 4 and 149, SEQ ID NOs: 3 and 149, SEQ ID NOs: 2 and 246, SEQ ID NOs: 1 and 246, SEQ ID NOs: 237 and 246, SEQ ID NOs: 4 and 246, SEQ ID NOs: 3 and 246, SEQ ID NOs: 2 and 22, SEQ ID NOs: 1 and 22, SEQ ID NOs: 237 and 22, SEQ ID NOs: 4 and 22, SEQ ID NOs: 3 and 22, SEQ ID NOs: 2 and 55, SEQ ID NOs: 1 and 55, SEQ ID NOs: 237 and 55, SEQ ID NOs: 4 and 55, SEQ ID NOs: 3 and 55, SEQ ID NOs: 2 and 182, SEQ ID NOs: 1 and 182, SEQ ID NOs: 237 and 182, SEQ ID NOs: 4 and 182, SEQ ID NOs: 3 and 182, SEQ ID NOs: 2 and 73, SEQ ID NOs: 1 and 73, SEQ ID NOs: 237 and 73, SEQ ID NOs: 4 and 73, SEQ ID NOs: 3 and 73, SEQ ID NOs: 2 and 77, SEQ ID NOs: 1 and 77, SEQ ID NOs: 237 and 77, SEQ ID NOs: 4 and 77, SEQ ID NOs: 3 and 77, SEQ ID NOs: 2 and 24, SEQ ID NOs: 1 and 24, SEQ ID NOs: 237 and 24, SEQ ID NOs: 4 and 24, SEQ ID NOs: 3 and 24, SEQ ID NOs: 2 and 103, SEQ ID NOs: 1 and 103, SEQ ID NOs: 237 and 103, SEQ ID NOs: 4 and 103, SEQ ID NOs: 3 and 103, SEQ ID NOs: 2 and 49, SEQ ID NOs: 1 and 49, SEQ ID NOs: 237 and 49, SEQ ID NOs: 4 and 49, SEQ ID NOs: 3 and 49, SEQ ID NOs: 2 and 239, SEQ ID NOs: 1 and 239, SEQ ID NOs: 237 and 239, SEQ ID NOs: 4 and 239, SEQ ID NOs: 3 and 239, SEQ ID NOs: 2 and 23, SEQ ID NOs: 1 and 23, SEQ ID NOs: 237 and 23, SEQ ID NOs: 4 and 23, SEQ ID NOs: 3 and 23, SEQ ID NOs: 2 and 58, SEQ ID NOs: 1 and 58, SEQ ID NOs: 237 and 58, SEQ ID NOs: 4 and 58, SEQ ID NOs: 3 and 58, SEQ ID NOs: 2 and 211, SEQ ID NOs: 1 and 211, SEQ ID NOs: 237 and 211, SEQ ID NOs: 4 and 211, SEQ ID NOs: 3 and 211, SEQ ID NOs: 2 and 147, SEQ ID NOs: 1 and 147, SEQ ID NOs: 237 and 147, SEQ ID NOs: 4 and 147, SEQ ID NOs: 3 and 147, SEQ ID NOs: 2 and 65, SEQ ID NOs: 1 and 65, SEQ ID NOs: 237 and 65, SEQ ID NOs: 4 and 65, SEQ ID NOs: 3 and 65, SEQ ID NOs: 2 and 31, SEQ ID NOs: 1 and 31, SEQ ID NOs: 237 and 31, SEQ ID NOs: 4 and 31, SEQ ID NOs: 3 and 31, SEQ ID NOs: 2 and 72, SEQ ID NOs: 1 and 72, SEQ ID NOs: 237 and 72, SEQ ID NOs: 4 and 72, SEQ ID NOs: 3 and 72, SEQ ID NOs: 2 and 63, SEQ ID NOs: 1 and 63, SEQ ID NOs: 237 and 63, SEQ ID NOs: 4 and 63, SEQ ID NOs: 3 and 63, SEQ ID NOs: 2 and 80, SEQ ID NOs: 1 and 80, SEQ ID NOs: 237 and 80, SEQ ID NOs: 4 and 80, SEQ ID NOs: 3 and 80, SEQ ID NOs: 2 and 37, SEQ ID NOs: 1 and 37, SEQ ID NOs: 237 and 37, SEQ ID NOs: 4 and 37, SEQ ID NOs: 3 and 37, SEQ ID NOs: 2 and 67, SEQ ID NOs: 1 and 67, SEQ ID NOs: 237 and 67, SEQ ID NOs: 4 and 67, SEQ ID NOs: 3 and 67, SEQ ID NOs: 2 and 232, SEQ ID NOs: 1 and 232, SEQ ID NOs: 237 and 232, SEQ ID NOs: 4 and 232, SEQ ID NOs: 3 and 232, SEQ ID NOs: 2 and 127, SEQ ID NOs: 1 and 127, SEQ ID NOs: 237 and 127, SEQ ID NOs: 4 and 127, SEQ ID NOs: 3 and 127, SEQ ID NOs: 2 and 145, SEQ ID NOs: 1 and 145, SEQ ID NOs: 237 and 145, SEQ ID NOs: 4 and 145, SEQ ID NOs: 3 and 145, SEQ ID NOs: 2 and 16, SEQ ID NOs: 1 and 16, SEQ ID NOs: 237 and 16, SEQ ID NOs: 4 and 16, SEQ ID NOs: 3 and 16, SEQ ID NOs: 2 and 11, SEQ ID NOs: 1 and 11, SEQ ID NOs: 237 and 11, SEQ ID NOs: 4 and 11, SEQ ID NOs: 3 and 11, SEQ ID NOs: 2 and 186, SEQ ID NOs: 1 and 186, SEQ ID NOs: 237 and 186, SEQ ID NOs: 4 and 186, SEQ ID NOs: 3 and 186, SEQ ID NOs: 2 and 50, SEQ ID NOs: 1 and 50, SEQ ID NOs: 237 and 50, SEQ ID NOs: 4 and 50, SEQ ID NOs: 3 and 50, SEQ ID NOs: 2 and 69, SEQ ID NOs: 1 and 69, SEQ ID NOs: 237 and 69, SEQ ID NOs: 4 and 69, SEQ ID NOs: 3 and 69, SEQ ID NOs: 2 and 33, SEQ ID NOs: 1 and 33, SEQ ID NOs: 237 and 33, SEQ ID NOs: 4 and 33, SEQ ID NOs: 3 and 33, SEQ ID NOs: 2 and 247, SEQ ID NOs: 1 and 247, SEQ ID NOs: 237 and 247, SEQ ID NOs: 4 and 247, SEQ ID NOs: 3 and 247, SEQ ID NOs: 2 and 36, SEQ ID NOs: 1 and 36, SEQ ID NOs: 237 and 36, SEQ ID NOs: 4 and 36, SEQ ID NOs: 3 and 36, SEQ ID NOs: 2 and 218, SEQ ID NOs: 1 and 218, SEQ ID NOs: 237 and 218, SEQ ID NOs: 4 and 218, SEQ ID NOs: 3 and 218, SEQ ID NOs: 2 and 43, SEQ ID NOs: 1 and 43, SEQ ID NOs: 237 and 43, SEQ ID NOs: 4 and 43, SEQ ID NOs: 3 and 43, SEQ ID NOs: 2 and 29, SEQ ID NOs: 1 and 29, SEQ ID NOs: 237 and 29, SEQ ID NOs: 4 and 29, SEQ ID NOs: 3 and 29, SEQ ID NOs: 2 and 110, SEQ ID NOs: 1 and 110, SEQ ID NOs: 237 and 110, SEQ ID NOs: 4 and 110, SEQ ID NOs: 3 and 110, SEQ ID NOs: 2 and 20, SEQ ID NOs: 1 and 20, SEQ ID NOs: 237 and 20, SEQ ID NOs: 4 and 20, SEQ ID NOs: 3 and 20, SEQ ID NOs: 2 and 157, SEQ ID NOs: 1 and 157, SEQ ID NOs: 237 and 157, SEQ ID NOs: 4 and 157, SEQ ID NOs: 3 and 157, SEQ ID NOs: 2 and 75, SEQ ID NOs: 1 and 75, SEQ ID NOs: 237 and 75, SEQ ID NOs: 4 and 75, SEQ ID NOs: 3 and 75, SEQ ID NOs: 2 and 82, SEQ ID NOs: 1 and 82, SEQ ID NOs: 237 and 82, SEQ ID NOs: 4 and 82, SEQ ID NOs: 3 and 82, SEQ ID NOs: 2 and 106, SEQ ID NOs: 1 and 106, SEQ ID NOs: 237 and 106, SEQ ID NOs: 4 and 106, SEQ ID NOs: 3 and 106, SEQ ID NOs: 2 and 111, SEQ ID NOs: 1 and 111, SEQ ID NOs: 237 and 111, SEQ ID NOs: 4 and 111, SEQ ID NOs: 3 and 111, SEQ ID NOs: 2 and 96, SEQ ID NOs: 1 and 96, SEQ ID NOs: 237 and 96, SEQ ID NOs: 4 and 96, SEQ ID NOs: 3 and 96, SEQ ID NOs: 2 and 266, SEQ ID NOs: 1 and 266, SEQ ID NOs: 237 and 266, SEQ ID NOs: 4 and 266, SEQ ID NOs: 3 and 266, SEQ ID NOs: 2 and 124, SEQ ID NOs: 1 and 124, SEQ ID NOs: 237 and 124, SEQ ID NOs: 4 and 124, SEQ ID NOs: 3 and 124, SEQ ID NOs: 2 and 68, SEQ ID NOs: 1 and 68, SEQ ID NOs: 237 and 68, SEQ ID NOs: 4 and 68, SEQ ID NOs: 3 and 68, SEQ ID NOs: 2 and 71, SEQ ID NOs: 1 and 71, SEQ ID NOs: 237 and 71, SEQ ID NOs: 4 and 71, SEQ ID NOs: 3 and 71, SEQ ID NOs: 2 and 35, SEQ ID NOs: 1 and 35, SEQ ID NOs: 237 and 35, SEQ ID NOs: 4 and 35, SEQ ID NOs: 3 and 35, SEQ ID NOs: 2 and 173, SEQ ID NOs: 1 and 173, SEQ ID NOs: 237 and 173, SEQ ID NOs: 4 and 173, SEQ ID NOs: 3 and 173, SEQ ID NOs: 2 and 5, SEQ ID NOs: 1 and 5, SEQ ID NOs: 237 and 5, SEQ ID NOs: 4 and 5, SEQ ID NOs: 3 and 5, SEQ ID NOs: 2 and 851, SEQ ID NOs: 1 and 851, SEQ ID NOs: 237 and 851, SEQ ID NOs: 4 and 851, SEQ ID NOs: 3 and 851, SEQ ID NOs: 2 and 852, SEQ ID NOs: 1 and 852, SEQ ID NOs: 237 and 852, SEQ ID NOs: 4 and 852, SEQ ID NOs: 3 and 852, SEQ ID NOs: 2 and 30, SEQ ID NOs: 1 and 30, SEQ ID NOs: 237 and 30, SEQ ID NOs: 4 and 30, SEQ ID NOs: 3 and 30, SEQ ID NOs: 2 and 93, SEQ ID NOs: 1 and 93, SEQ ID NOs: 237 and 93, SEQ ID NOs: 4 and 93, SEQ ID NOs: 3 and 93, SEQ ID NOs: 2 and 27, SEQ ID NOs: 1 and 27, SEQ ID NOs: 237 and 27, SEQ ID NOs: 4 and 27, SEQ ID NOs: 3 and 27, SEQ ID NOs: 2 and 853, SEQ ID NOs: 1 and 853, SEQ ID NOs: 237 and 853, SEQ ID NOs: 4 and 853, SEQ ID NOs: 3 and 853, SEQ ID NOs: 2 and 238, SEQ ID NOs: 1 and 238, SEQ ID NOs: 237 and 238, SEQ ID NOs: 4 and 238, SEQ ID NOs: 3 and 238, SEQ ID NOs: 2 and 130, SEQ ID NOs: 1 and 130, SEQ ID NOs: 237 and 130, SEQ ID NOs: 4 and 130, SEQ ID NOs: 3 and 130, SEQ ID NOs: 2 and 177, SEQ ID NOs: 1 and 177, SEQ ID NOs: 237 and 177, SEQ ID NOs: 4 and 177, SEQ ID NOs: 3 and 177, SEQ ID NOs: 2 and 64, SEQ ID NOs: 1 and 64, SEQ ID NOs: 237 and 64, SEQ ID NOs: 4 and 64, SEQ ID NOs: 3 and 64, SEQ ID NOs: 2 and 114, SEQ ID NOs: 1 and 114, SEQ ID NOs: 237 and 114, SEQ ID NOs: 4 and 114, SEQ ID NOs: 3 and 114, SEQ ID NOs: 2 and 119, SEQ ID NOs: 1 and 119, SEQ ID NOs: 237 and 119, SEQ ID NOs: 4 and 119, SEQ ID NOs: 3 and 119, SEQ ID NOs: 2 and 135, SEQ ID NOs: 1 and 135, SEQ ID NOs: 237 and 135, SEQ ID NOs: 4 and 135, SEQ ID NOs: 3 and 135, SEQ ID NOs: 2 and 243, SEQ ID NOs: 1 and 243, SEQ ID NOs: 237 and 243, SEQ ID NOs: 4 and 243, SEQ ID NOs: 3 and 243, SEQ ID NOs: 2 and 122, SEQ ID NOs: 1 and 122, SEQ ID NOs: 237 and 122, SEQ ID NOs: 4 and 122, SEQ ID NOs: 3 and 122, SEQ ID NOs: 2 and 260, SEQ ID NOs: 1 and 260, SEQ ID NOs: 237 and 260, SEQ ID NOs: 4 and 260, SEQ ID NOs: 3 and 260, SEQ ID NOs: 2 and 59, SEQ ID NOs: 1 and 59, SEQ ID NOs: 237 and 59, SEQ ID NOs: 4 and 59, SEQ ID NOs: 3 and 59, SEQ ID NOs: 2 and 854, SEQ ID NOs: 1 and 854, SEQ ID NOs: 237 and 854, SEQ ID NOs: 4 and 854, SEQ ID NOs: 3 and 854, SEQ ID NOs: 2 and 132, SEQ ID NOs: 1 and 132, SEQ ID NOs: 237 and 132, SEQ ID NOs: 4 and 132, SEQ ID NOs: 3 and 132, SEQ ID NOs: 2 and 181, SEQ ID NOs: 1 and 181, SEQ ID NOs: 237 and 181, SEQ ID NOs: 4 and 181, SEQ ID NOs: 3 and 181, SEQ ID NOs: 2 and 79, SEQ ID NOs: 1 and 79, SEQ ID NOs: 237 and 79, SEQ ID NOs: 4 and 79, SEQ ID NOs: 3 and 79, SEQ ID NOs: 2 and 133, SEQ ID NOs: 1 and 133, SEQ ID NOs: 237 and 133, SEQ ID NOs: 4 and 133, SEQ ID NOs: 3 and 133, SEQ ID NOs: 2 and 41, SEQ ID NOs: 1 and 41, SEQ ID NOs: 237 and 41, SEQ ID NOs: 4 and 41, SEQ ID NOs: 3 and 41, SEQ ID NOs: 2 and 139, SEQ ID NOs: 1 and 139, SEQ ID NOs: 237 and 139, SEQ ID NOs: 4 and 139, SEQ ID NOs: 3 and 139, SEQ ID NOs: 2 and 118, SEQ ID NOs: 1 and 118, SEQ ID NOs: 237 and 118, SEQ ID NOs: 4 and 118, SEQ ID NOs: 3 and 118, SEQ ID NOs: 2 and 86, SEQ ID NOs: 1 and 86, SEQ ID NOs: 237 and 86, SEQ ID NOs: 4 and 86, SEQ ID NOs: 3 and 86, SEQ ID NOs: 2 and 60, SEQ ID NOs: 1 and 60, SEQ ID NOs: 237 and 60, SEQ ID NOs: 4 and 60, SEQ ID NOs: 3 and 60, SEQ ID NOs: 2 and 116, SEQ ID NOs: 1 and 116, SEQ ID NOs: 237 and 116, SEQ ID NOs: 4 and 116, SEQ ID NOs: 3 and 116, SEQ ID NOs: 2 and 160, SEQ ID NOs: 1 and 160, SEQ ID NOs: 237 and 160, SEQ ID NOs: 4 and 160, SEQ ID NOs: 3 and 160, SEQ ID NOs: 2 and 38, SEQ ID NOs: 1 and 38, SEQ ID NOs: 237 and 38, SEQ ID NOs: 4 and 38, SEQ ID NOs: 3 and 38, SEQ ID NOs: 2 and 99, SEQ ID NOs: 1 and 99, SEQ ID NOs: 237 and 99, SEQ ID NOs: 4 and 99, SEQ ID NOs: 3 and 99, SEQ ID NOs: 2 and 104, SEQ ID NOs: 1 and 104, SEQ ID NOs: 237 and 104, SEQ ID NOs: 4 and 104, and SEQ ID NOs: 3 and 104 were able to produce breast cancer discriminant accuracy of 95% or higher.

Figure 4:
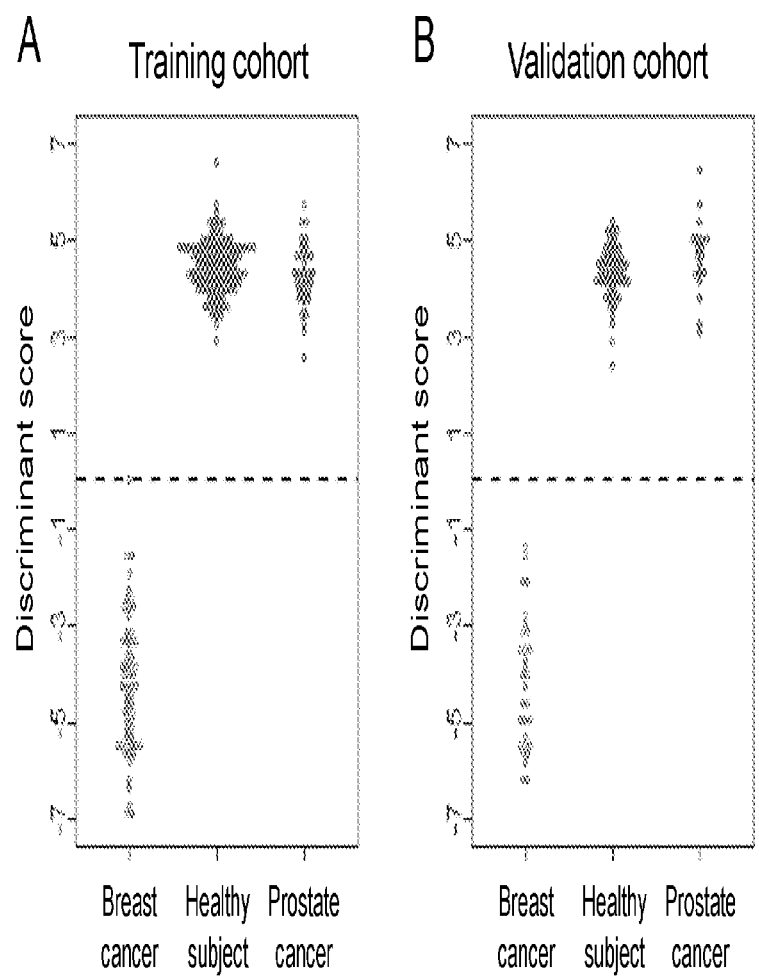
FIG. 4 Upper diagram: a discriminant (1.87×hsa-miR-4730+0.42×hsa-miR-602−18.58) was prepared by use of Fisher's discriminant analysis from the expression level measurement values of hsa-miR-602 (SEQ ID NO: 237) and hsa-miR-4730 (SEQ ID NO: 2) in 62 breast cancer patients, 102 healthy subjects, and 33 prostate cancer patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared for the training cohort as to the expression level measurement values of hsa-miR-602 (SEQ ID NO: 237) and hsa-miR-4730 (SEQ ID NO: 2) in 31 breast cancer patients, 48 healthy subjects, and 19 prostate cancer patients selected as a validation cohort were plotted on the ordinate against the sample groups on the abscissa. The dotted line in the diagram depicts the discriminant boundary that offered a discriminant score of 0 and discriminated between the two groups.

The measurement values of the nucleotide sequences represented by SEQ ID NOs: 2 and 237 were further compared among 62 breast cancer patients, 102 healthy subjects, and 33 prostate cancer patients in the training cohort. As a result, a scatter diagram that significantly separated the discriminant scores of the breast cancer patient group from those of the other groups was obtained in the training cohort (see FIG. 4A). These results were also reproducible for the validation cohort (see FIG. 4B).

TABLE 9

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 2 | 99.5 | 99.5 | 99.5 | 99.5 | 99.5 | 99.5 |
| 2_1 | 100 | 100 | 100 | 100 | 100 | 100 |
| 2_237 | 99.5 | 98.4 | 100 | 100 | 100 | 100 |
| 2_4 | 99.5 | 98.4 | 100 | 100 | 100 | 100 |
| 2_3 | 100 | 100 | 100 | 100 | 100 | 100 |
| 2_51 | 99.5 | 98.4 | 100 | 100 | 100 | 100 |
| 1 | 99.5 | 99.5 | 99.5 | 99.5 | 99.5 | 99.5 |
| 1_237 | 100 | 100 | 100 | 100 | 100 | 100 |
| 1_4 | 100 | 100 | 100 | 100 | 100 | 100 |
| 1_3 | 99.5 | 98.4 | 100 | 100 | 100 | 100 |
| 1_51 | 100 | 100 | 100 | 100 | 100 | 100 |
| 1_6 | 99.5 | 98.4 | 100 | 100 | 100 | 100 |
| 237 | 98.5 | 98.5 | 98.5 | 98.5 | 98.5 | 98.5 |
| 4_237 | 99.5 | 98.4 | 100 | 99 | 96.8 | 100 |
| 3_237 | 100 | 100 | 100 | 100 | 100 | 100 |
| 51_237 | 99 | 96.8 | 100 | 100 | 100 | 100 |
| 237_6 | 100 | 100 | 100 | 100 | 100 | 100 |
| 237_12 | 100 | 100 | 100 | 99 | 96.8 | 100 |
| 4 | 99 | 99 | 99 | 99 | 99 | 99 |
| 3_4 | 100 | 100 | 100 | 100 | 100 | 100 |
| 4_51 | 99.5 | 98.4 | 100 | 100 | 100 | 100 |
| 4_6 | 100 | 100 | 100 | 100 | 100 | 100 |
| 4_12 | 100 | 100 | 100 | 99 | 96.8 | 100 |
| 4_15 | 99.5 | 98.4 | 100 | 99 | 96.8 | 100 |
| 3 | 99.5 | 99.5 | 99.5 | 99.5 | 99.5 | 99.5 |
| 3_51 | 100 | 100 | 100 | 100 | 100 | 100 |
| 3_6 | 99 | 96.8 | 100 | 100 | 100 | 100 |
| 3_12 | 100 | 100 | 100 | 100 | 100 | 100 |
| 3_15 | 100 | 100 | 100 | 100 | 100 | 100 |
| 3_8 | 100 | 100 | 100 | 100 | 100 | 100 |
| 51 | 99 | 99 | 99 | 99 | 99 | 99 |
| 51_6 | 99.5 | 100 | 99.3 | 100 | 100 | 100 |
| 51_12 | 100 | 100 | 100 | 100 | 100 | 100 |
| 51_15 | 99.5 | 98.4 | 100 | 100 | 100 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 51_8 | 100 | 100 | 100 | 100 | 100 | 100 |
| 51_34 | 99.5 | 98.4 | 100 | 100 | 100 | 100 |
| 6 | 98.5 | 98.5 | 98.5 | 98.5 | 98.5 | 98.5 |
| 2_6 | 100 | 100 | 100 | 100 | 100 | 100 |
| 12_6 | 100 | 100 | 100 | 100 | 100 | 100 |
| 15_6 | 100 | 100 | 100 | 100 | 100 | 100 |
| 8_6 | 100 | 100 | 100 | 100 | 100 | 100 |
| 6_34 | 100 | 100 | 100 | 100 | 100 | 100 |
| 12 | 100 | 100 | 100 | 100 | 100 | 100 |
| 2_12 | 100 | 100 | 100 | 100 | 100 | 100 |
| 1_12 | 100 | 100 | 100 | 100 | 100 | 100 |
| 12_15 | 100 | 100 | 100 | 99 | 96.8 | 100 |
| 8_12 | 100 | 100 | 100 | 100 | 100 | 100 |
| 12_34 | 100 | 100 | 100 | 100 | 100 | 100 |
| 15 | 98.5 | 98.5 | 98.5 | 98.5 | 98.5 | 98.5 |
| 2_15 | 99.5 | 98.4 | 100 | 100 | 100 | 100 |
| 1_15 | 100 | 100 | 100 | 100 | 100 | 100 |
| 237_15 | 99 | 96.8 | 100 | 99 | 96.8 | 100 |
| 8_15 | 99.5 | 98.4 | 100 | 100 | 100 | 100 |
| 15_34 | 99 | 96.8 | 100 | 100 | 100 | 100 |
| 8 | 99.5 | 99.5 | 99.5 | 99.5 | 99.5 | 99.5 |
| 2_8 | 99.5 | 98.4 | 100 | 100 | 100 | 100 |
| 1_8 | 100 | 100 | 100 | 100 | 100 | 100 |
| 237_8 | 100 | 100 | 100 | 100 | 100 | 100 |
| 4_8 | 100 | 100 | 100 | 100 | 100 | 100 |
| 8_34 | 99.5 | 98.4 | 100 | 99 | 100 | 98.5 |
| 34 | 99 | 99 | 99 | 99 | 99 | 99 |
| 2_34 | 99.5 | 98.4 | 100 | 100 | 100 | 100 |
| 1_34 | 100 | 100 | 100 | 100 | 100 | 100 |
| 237_34 | 100 | 100 | 100 | 99 | 96.8 | 100 |
| 4_34 | 100 | 100 | 100 | 100 | 100 | 100 |
| 3_34 | 100 | 100 | 100 | 100 | 100 | 100 |
| 9 | 99.5 | 99.5 | 99.5 | 99.5 | 99.5 | 99.5 |
| 2_9 | 100 | 100 | 100 | 100 | 100 | 100 |
| 1_9 | 99.5 | 98.4 | 100 | 100 | 100 | 100 |
| 9_237 | 100 | 100 | 100 | 100 | 100 | 100 |
| 4_9 | 100 | 100 | 100 | 100 | 100 | 100 |
| 3_9 | 100 | 100 | 100 | 100 | 100 | 100 |
| 143 | 98 | 98 | 98 | 98 | 98 | 98 |
| 2_143 | 100 | 100 | 100 | 100 | 100 | 100 |
| 1_143 | 100 | 100 | 100 | 100 | 100 | 100 |
| 237_143 | 100 | 100 | 100 | 99 | 96.8 | 100 |
| 4_143 | 100 | 100 | 100 | 100 | 100 | 100 |
| 3_143 | 100 | 100 | 100 | 100 | 100 | 100 |
| 13 | 99 | 99 | 99 | 99 | 99 | 99 |
| 2_13 | 99.5 | 98.4 | 100 | 100 | 100 | 100 |
| 1_13 | 99.5 | 98.4 | 100 | 100 | 100 | 100 |
| 237_13 | 100 | 100 | 100 | 100 | 100 | 100 |
| 4_13 | 99.5 | 98.4 | 100 | 100 | 100 | 100 |
| 3_13 | 100 | 100 | 100 | 100 | 100 | 100 |
| 125 | 98 | 98 | 98 | 98 | 98 | 98 |
| 2_125 | 99.5 | 98.4 | 100 | 100 | 100 | 100 |
| 1_125 | 100 | 100 | 100 | 100 | 100 | 100 |
| 237_125 | 99 | 96.8 | 100 | 99 | 96.8 | 100 |
| 4_125 | 99.5 | 98.4 | 100 | 99 | 96.8 | 100 |
| 3_125 | 99.5 | 98.4 | 100 | 100 | 100 | 100 |
| 236 | 100 | 100 | 100 | 100 | 100 | 100 |
| 2_236 | 100 | 100 | 100 | 100 | 100 | 100 |
| 1_236 | 100 | 100 | 100 | 100 | 100 | 100 |
| 237_236 | 99.5 | 98.4 | 100 | 99 | 96.8 | 100 |
| 4_236 | 100 | 100 | 100 | 99 | 96.8 | 100 |
| 3_236 | 100 | 100 | 100 | 100 | 100 | 100 |
| 46 | 95.4 | 95.4 | 95.4 | 95.4 | 95.4 | 95.4 |
| 2_46 | 99.5 | 98.4 | 100 | 100 | 100 | 100 |
| 1_46 | 99.5 | 98.4 | 100 | 100 | 100 | 100 |
| 237_46 | 99.5 | 98.4 | 100 | 98 | 93.5 | 100 |
| 4_46 | 100 | 100 | 100 | 99 | 96.8 | 100 |
| 3_46 | 100 | 100 | 100 | 100 | 100 | 100 |
| 32 | 97.5 | 97.5 | 97.5 | 97.5 | 97.5 | 97.5 |
| 2_32 | 99.5 | 98.4 | 100 | 100 | 100 | 100 |
| 1_32 | 100 | 100 | 100 | 100 | 100 | 100 |
| 237_32 | 99 | 96.8 | 100 | 99 | 96.8 | 100 |
| 4_32 | 99 | 96.8 | 100 | 98 | 93.5 | 100 |
| 3_32 | 100 | 100 | 100 | 100 | 100 | 100 |
| 62 | 95.4 | 95.4 | 95.4 | 95.4 | 95.4 | 95.4 |

TABLE 9-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2_62 | 99.5 | 98.4 | 100 | 100 | 100 | 100 |
| 162 | 99.5 | 98.4 | 100 | 100 | 100 | 100 |
| 237_62 | 99 | 96.7 | 100 | 99 | 96.8 | 100 |
| 4_62 | 99 | 96.7 | 100 | 98 | 93.5 | 100 |
| 3_62 | 100 | 100 | 100 | 99 | 96.8 | 100 |
| 88 | 94.9 | 94.9 | 94.9 | 94.9 | 94.9 | 94.9 |
| 2_88 | 100 | 100 | 100 | 100 | 100 | 100 |
| 1_88 | 99.5 | 98.4 | 100 | 100 | 100 | 100 |
| 237_88 | 100 | 100 | 100 | 99 | 96.8 | 100 |
| 4_88 | 100 | 100 | 100 | 100 | 100 | 100 |
| 3_88 | 100 | 100 | 100 | 100 | 100 | 100 |
| 52 | 95.4 | 95.4 | 95.4 | 95.4 | 95.4 | 95.4 |
| 2_52 | 100 | 100 | 100 | 100 | 100 | 100 |
| 1_52 | 100 | 100 | 100 | 100 | 100 | 100 |
| 237_52 | 100 | 100 | 100 | 99 | 96.8 | 100 |
| 4_52 | 99 | 96.8 | 100 | 99 | 96.8 | 100 |
| 3_52 | 100 | 100 | 100 | 100 | 100 | 100 |
| 7 | 98.5 | 98.5 | 98.5 | 98.5 | 98.5 | 98.5 |
| 2_7 | 99.5 | 98.4 | 100 | 100 | 100 | 100 |
| 1_7 | 99.5 | 98.4 | 100 | 100 | 100 | 100 |
| 237_7 | 99.5 | 98.4 | 100 | 100 | 100 | 100 |
| 4_7 | 99.5 | 98.4 | 100 | 99 | 96.8 | 100 |
| 3_7 | 100 | 100 | 100 | 100 | 100 | 100 |
| 26 | 94.4 | 94.4 | 94.4 | 94.4 | 94.4 | 94.4 |
| 2_26 | 99.5 | 98.4 | 100 | 100 | 100 | 100 |
| 1_26 | 100 | 100 | 100 | 100 | 100 | 100 |
| 237_26 | 99.5 | 98.4 | 100 | 99 | 96.8 | 100 |
| 4_26 | 100 | 100 | 100 | 99 | 96.8 | 100 |
| 3_26 | 100 | 100 | 100 | 100 | 100 | 100 |
| 25 | 99 | 99 | 99 | 99 | 99 | 99 |
| 2_25 | 99.5 | 98.4 | 100 | 100 | 100 | 100 |
| 1_25 | 100 | 100 | 100 | 100 | 100 | 100 |
| 237_25 | 99.5 | 98.4 | 100 | 100 | 100 | 100 |
| 4_25 | 100 | 100 | 100 | 100 | 100 | 100 |
| 3_25 | 100 | 100 | 100 | 100 | 100 | 100 |
| 54 | 95.9 | 95.9 | 95.9 | 95.9 | 95.9 | 95.9 |
| 2_54 | 100 | 100 | 100 | 100 | 100 | 100 |
| 1_54 | 99.5 | 98.4 | 100 | 100 | 100 | 100 |
| 237_54 | 99 | 96.8 | 100 | 99 | 96.8 | 100 |
| 4_54 | 99.5 | 98.4 | 100 | 99 | 96.8 | 100 |
| 3_54 | 99.5 | 98.4 | 100 | 100 | 100 | 100 |
| 92 | 94.4 | 94.4 | 94.4 | 94.4 | 94.4 | 94.4 |
| 2_92 | 100 | 100 | 100 | 100 | 100 | 100 |
| 1_92 | 99.5 | 98.4 | 100 | 100 | 100 | 100 |
| 237_92 | 99.5 | 98.4 | 100 | 98 | 93.5 | 100 |
| 4_92 | 99 | 96.8 | 100 | 99 | 96.8 | 100 |
| 3_92 | 99.5 | 98.4 | 100 | 100 | 100 | 100 |
| 14 | 96.4 | 96.4 | 96.4 | 96.4 | 96.4 | 96.4 |
| 2_14 | 100 | 100 | 100 | 100 | 100 | 100 |
| 1_14 | 100 | 100 | 100 | 100 | 100 | 100 |
| 237_14 | 100 | 100 | 100 | 100 | 100 | 100 |
| 4_14 | 100 | 100 | 100 | 100 | 100 | 100 |
| 3_14 | 100 | 100 | 100 | 100 | 100 | 100 |
| 242 | 95.4 | 95.4 | 95.4 | 95.4 | 95.4 | 95.4 |
| 2_242 | 99.5 | 98.4 | 100 | 100 | 100 | 100 |
| 1_242 | 100 | 100 | 100 | 100 | 100 | 100 |
| 237_242 | 98.5 | 95.2 | 100 | 99 | 96.8 | 100 |
| 4_242 | 99.5 | 98.4 | 100 | 99 | 96.8 | 100 |
| 3_242 | 99.5 | 98.4 | 100 | 100 | 100 | 100 |
| 47 | 97 | 97 | 97 | 97 | 97 | 97 |
| 2_47 | 99.5 | 98.4 | 100 | 100 | 100 | 100 |
| 1_47 | 100 | 100 | 100 | 100 | 100 | 100 |
| 237_47 | 98.5 | 95.2 | 100 | 98 | 93.5 | 100 |
| 4_47 | 99 | 96.8 | 100 | 98 | 93.5 | 100 |
| 3_47 | 100 | 100 | 100 | 100 | 100 | 100 |
| 45 | 95.9 | 95.9 | 95.9 | 95.9 | 95.9 | 95.9 |
| 2_45 | 100 | 100 | 100 | 100 | 100 | 100 |
| 1_45 | 100 | 100 | 100 | 100 | 100 | 100 |
| 237_45 | 99 | 96.8 | 100 | 98 | 93.5 | 100 |
| 4_45 | 100 | 100 | 100 | 99 | 96.8 | 100 |
| 3_45 | 100 | 100 | 100 | 100 | 100 | 100 |
| 39 | 98.5 | 98.5 | 98.5 | 98.5 | 98.5 | 98.5 |
| 2_39 | 99.5 | 98.4 | 100 | 100 | 100 | 100 |
| 1_39 | 99.5 | 98.4 | 100 | 100 | 100 | 100 |
| 237_39 | 99 | 96.8 | 100 | 100 | 100 | 100 |

TABLE 9-continued

| | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 4_39 | 99 | 96.8 | 100 | 100 | 100 | 100 |
| 3_39 | 100 | 100 | 100 | 100 | 100 | 100 |
| 21 | 95.9 | 95.9 | 95.9 | 95.9 | 95.9 | 95.9 |
| 2_21 | 100 | 100 | 100 | 100 | 100 | 100 |
| 1_21 | 99.5 | 98.4 | 100 | 100 | 100 | 100 |
| 237_21 | 99.5 | 100 | 99.3 | 100 | 100 | 100 |
| 4_21 | 99.5 | 100 | 99.3 | 100 | 100 | 100 |
| 3_21 | 99.5 | 98.4 | 100 | 100 | 100 | 100 |
| 17 | 98 | 98 | 98 | 98 | 98 | 98 |
| 2_17 | 99.5 | 98.4 | 100 | 100 | 100 | 100 |
| 1_17 | 99.5 | 98.4 | 100 | 100 | 100 | 100 |
| 237_17 | 99.5 | 98.4 | 100 | 100 | 100 | 100 |
| 4_17 | 99.5 | 98.4 | 100 | 100 | 100 | 100 |
| 3_17 | 99.5 | 98.4 | 100 | 100 | 100 | 100 |
| 83 | 96.4 | 96.4 | 96.4 | 96.4 | 96.4 | 96.4 |
| 2_83 | 99.5 | 98.4 | 100 | 100 | 100 | 100 |
| 1_83 | 99.5 | 98.4 | 100 | 100 | 100 | 100 |
| 237_83 | 99.5 | 98.4 | 100 | 99 | 96.8 | 100 |
| 4_83 | 100 | 100 | 100 | 100 | 100 | 100 |
| 3_83 | 99.5 | 98.4 | 100 | 100 | 100 | 100 |
| 149 | 94.9 | 94.9 | 94.9 | 94.9 | 94.9 | 94.9 |
| 2_149 | 99.5 | 98.4 | 100 | 100 | 100 | 100 |
| 1_149 | 99.5 | 98.4 | 100 | 100 | 100 | 100 |
| 237_149 | 99.5 | 98.4 | 100 | 99 | 96.8 | 100 |
| 4_149 | 99.5 | 98.4 | 100 | 99 | 96.8 | 100 |
| 3_149 | 99.5 | 98.4 | 100 | 100 | 100 | 100 |
| 246 | 94.4 | 94.4 | 94.4 | 94.4 | 94.4 | 94.4 |
| 2_246 | 99.5 | 98.4 | 100 | 100 | 100 | 100 |
| 1_246 | 99.5 | 98.4 | 100 | 100 | 100 | 100 |
| 237_246 | 98.5 | 95.2 | 100 | 98 | 93.5 | 100 |
| 4_246 | 99 | 96.8 | 100 | 98 | 93.5 | 100 |
| 3_246 | 100 | 100 | 100 | 100 | 100 | 100 |
| 22 | 94.9 | 94.9 | 94.9 | 94.9 | 94.9 | 94.9 |
| 2_22 | 100 | 100 | 100 | 100 | 100 | 100 |
| 1_22 | 99.5 | 98.4 | 100 | 100 | 100 | 100 |
| 237_22 | 99.5 | 98.4 | 100 | 100 | 100 | 100 |
| 4_22 | 99.5 | 98.4 | 100 | 99 | 96.8 | 100 |
| 3_22 | 100 | 100 | 100 | 100 | 100 | 100 |
| 55 | 98.5 | 98.5 | 98.5 | 98.5 | 98.5 | 98.5 |
| 2_55 | 99.5 | 98.4 | 100 | 100 | 100 | 100 |
| 1_55 | 100 | 100 | 100 | 100 | 100 | 100 |
| 237_55 | 99 | 96.8 | 100 | 100 | 100 | 100 |
| 4_55 | 99 | 96.8 | 100 | 100 | 100 | 100 |
| 3_55 | 100 | 100 | 100 | 100 | 100 | 100 |
| 1_82 | 97 | 97 | 97 | 97 | 97 | 97 |
| 2_182 | 99.5 | 98.4 | 100 | 100 | 100 | 100 |
| 1_182 | 99.5 | 98.4 | 100 | 100 | 100 | 100 |
| 237_182 | 100 | 100 | 100 | 100 | 100 | 100 |
| 4_182 | 100 | 100 | 100 | 100 | 100 | 100 |
| 3_182 | 100 | 100 | 100 | 100 | 100 | 100 |
| 73 | 98 | 98 | 98 | 98 | 98 | 98 |
| 2_73 | 99.5 | 98.4 | 100 | 100 | 100 | 100 |
| 1_73 | 100 | 100 | 100 | 100 | 100 | 100 |
| 237_73 | 99 | 96.8 | 100 | 99 | 96.8 | 100 |
| 4_73 | 99.5 | 98.4 | 100 | 99 | 96.8 | 100 |
| 3_73 | 100 | 100 | 100 | 100 | 100 | 100 |
| 77 | 93.9 | 93.9 | 93.9 | 93.9 | 93.9 | 93.9 |
| 2_77 | 99.5 | 98.4 | 100 | 100 | 100 | 100 |
| 1_77 | 99.5 | 98.4 | 100 | 100 | 100 | 100 |
| 237_77 | 99.5 | 98.4 | 100 | 99 | 96.8 | 100 |
| 4_77 | 99 | 96.8 | 100 | 98 | 93.5 | 100 |
| 3_77 | 100 | 100 | 100 | 100 | 100 | 100 |
| 24 | 94.4 | 94.4 | 94.4 | 94.4 | 94.4 | 94.4 |
| 2_24 | 100 | 100 | 100 | 100 | 100 | 100 |
| 1_24 | 99.5 | 98.4 | 100 | 100 | 100 | 100 |
| 237_24 | 100 | 100 | 100 | 100 | 100 | 100 |
| 4_24 | 100 | 100 | 100 | 100 | 100 | 100 |
| 3_24 | 99.5 | 98.4 | 100 | 99 | 96.8 | 100 |
| 103 | 92.4 | 92.4 | 92.4 | 92.4 | 92.4 | 92.4 |
| 2_103 | 100 | 100 | 100 | 100 | 100 | 100 |
| 1_103 | 100 | 100 | 100 | 100 | 100 | 100 |
| 237_103 | 99 | 96.8 | 100 | 98 | 93.5 | 100 |
| 4_103 | 99 | 96.8 | 100 | 99 | 96.8 | 100 |
| 3_103 | 100 | 100 | 100 | 100 | 100 | 100 |
| 49 | 94.4 | 94.4 | 94.4 | 94.4 | 94.4 | 94.4 |

TABLE 9-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 2_49 | 100 | 100 | 100 | 100 | 100 | 100 |
| 1_49 | 100 | 100 | 100 | 100 | 100 | 100 |
| 237_49 | 99.5 | 98.4 | 100 | 98 | 93.5 | 100 |
| 4_49 | 100 | 100 | 100 | 99 | 96.8 | 100 |
| 3_49 | 100 | 100 | 100 | 100 | 100 | 100 |
| 239 | 98 | 98 | 98 | 98 | 98 | 98 |
| 2_239 | 100 | 100 | 100 | 100 | 100 | 100 |
| 1_239 | 100 | 100 | 100 | 100 | 100 | 100 |
| 237_239 | 100 | 100 | 100 | 100 | 100 | 100 |
| 4_239 | 100 | 100 | 100 | 100 | 100 | 100 |
| 3_239 | 100 | 100 | 100 | 100 | 100 | 100 |
| 23 | 89.3 | 89.3 | 89.3 | 89.3 | 89.3 | 89.3 |
| 2_23 | 100 | 100 | 100 | 100 | 100 | 100 |
| 1_23 | 100 | 100 | 100 | 100 | 100 | 100 |
| 237_23 | 99.5 | 98.4 | 100 | 100 | 100 | 100 |
| 4_23 | 100 | 100 | 100 | 100 | 100 | 100 |
| 3_23 | 100 | 100 | 100 | 100 | 100 | 100 |
| 58 | 94.4 | 94.4 | 94.4 | 94.4 | 94.4 | 94.4 |
| 2_58 | 99.5 | 98.4 | 100 | 100 | 100 | 100 |
| 1_58 | 100 | 100 | 100 | 100 | 100 | 100 |
| 237_58 | 100 | 100 | 100 | 99 | 96.8 | 100 |
| 4_58 | 100 | 100 | 100 | 99 | 96.8 | 100 |
| 3_58 | 100 | 100 | 100 | 100 | 100 | 100 |
| 211 | 93.4 | 93.4 | 93.4 | 93.4 | 93.4 | 93.4 |
| 2_211 | 99.5 | 98.4 | 100 | 100 | 100 | 100 |
| 1_211 | 99.5 | 98.4 | 100 | 100 | 100 | 100 |
| 237_211 | 100 | 100 | 100 | 96.9 | 90.3 | 100 |
| 4_211 | 99.5 | 98.4 | 100 | 99 | 96.8 | 100 |
| 3_211 | 99.5 | 98.4 | 100 | 100 | 100 | 100 |
| 147 | 93.4 | 93.4 | 93.4 | 93.4 | 93.4 | 93.4 |
| 2_147 | 100 | 100 | 100 | 100 | 100 | 100 |
| 1_147 | 99.5 | 98.4 | 100 | 100 | 100 | 100 |
| 237_147 | 100 | 100 | 100 | 100 | 100 | 100 |
| 4_147 | 99.5 | 98.4 | 100 | 100 | 100 | 100 |
| 3_147 | 99.5 | 98.4 | 100 | 100 | 100 | 100 |
| 65 | 90.9 | 90.9 | 90.9 | 90.9 | 90.9 | 90.9 |
| 2_65 | 99.5 | 98.4 | 100 | 100 | 100 | 100 |
| 1_65 | 99.5 | 98.4 | 100 | 100 | 100 | 100 |
| 237_65 | 99 | 96.8 | 100 | 98 | 93.5 | 100 |
| 4_65 | 99 | 96.8 | 100 | 98 | 93.5 | 100 |
| 3_65 | 99.5 | 98.4 | 100 | 100 | 100 | 100 |
| 31 | 91.9 | 91.9 | 91.9 | 91.9 | 91.9 | 91.9 |
| 2_31 | 99.5 | 98.4 | 100 | 100 | 100 | 100 |
| 1_31 | 99.5 | 98.4 | 100 | 100 | 100 | 100 |
| 237_31 | 99.5 | 98.4 | 100 | 99 | 96.8 | 100 |
| 4_31 | 99 | 96.8 | 100 | 99 | 96.8 | 100 |
| 3_31 | 99.5 | 98.4 | 100 | 100 | 100 | 100 |
| 72 | 90.4 | 90.4 | 90.4 | 90.4 | 90.4 | 90.4 |
| 2_72 | 99.5 | 98.4 | 100 | 100 | 100 | 100 |
| 1_72 | 100 | 100 | 100 | 100 | 100 | 100 |
| 237_72 | 98.5 | 95.2 | 100 | 100 | 100 | 100 |
| 4_72 | 99.5 | 98.4 | 100 | 100 | 100 | 100 |
| 3_72 | 100 | 100 | 100 | 100 | 100 | 100 |
| 63 | 87.8 | 87.8 | 87.8 | 87.8 | 87.8 | 87.8 |
| 2_63 | 100 | 100 | 100 | 100 | 100 | 100 |
| 1_63 | 99.5 | 98.4 | 100 | 100 | 100 | 100 |
| 237_63 | 99.5 | 98.4 | 100 | 98 | 93.5 | 100 |
| 4_63 | 99.5 | 98.4 | 100 | 99 | 96.8 | 100 |
| 3_63 | 99.5 | 98.4 | 100 | 100 | 100 | 100 |
| 80 | 88.3 | 88.3 | 88.3 | 88.3 | 88.3 | 88.3 |
| 2_80 | 100 | 100 | 100 | 100 | 100 | 100 |
| 1_80 | 99.5 | 98.4 | 100 | 100 | 100 | 100 |
| 237_80 | 100 | 100 | 100 | 100 | 100 | 100 |
| 4_80 | 100 | 100 | 100 | 99 | 96.8 | 100 |
| 3_80 | 99.5 | 98.4 | 100 | 100 | 100 | 100 |
| 37 | 97 | 97 | 97 | 97 | 97 | 97 |
| 2_37 | 99.5 | 98.4 | 100 | 100 | 100 | 100 |
| 1_37 | 99.5 | 98.4 | 100 | 100 | 100 | 100 |
| 237_37 | 99.5 | 98.4 | 100 | 100 | 100 | 100 |
| 4_37 | 99.5 | 98.4 | 100 | 99 | 96.8 | 100 |
| 3_37 | 100 | 100 | 100 | 100 | 100 | 100 |
| 67 | 92.4 | 92.4 | 92.4 | 92.4 | 92.4 | 92.4 |
| 2_67 | 99.5 | 98.4 | 100 | 100 | 100 | 100 |
| 1_67 | 100 | 100 | 100 | 100 | 100 | 100 |
| 237_67 | 98.5 | 95.2 | 100 | 99 | 96.8 | 100 |

TABLE 9-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 4_67 | 99 | 96.8 | 100 | 99 | 96.8 | 100 |
| 3_67 | 100 | 100 | 100 | 100 | 100 | 100 |
| 232 | 90.9 | 90.9 | 90.9 | 90.9 | 90.9 | 90.9 |
| 2_232 | 99.5 | 98.4 | 100 | 100 | 100 | 100 |
| 1_232 | 99.5 | 98.4 | 100 | 100 | 100 | 100 |
| 237_232 | 99.5 | 98.4 | 100 | 98 | 93.5 | 100 |
| 4_232 | 99 | 96.8 | 100 | 99 | 96.8 | 100 |
| 3_232 | 99.5 | 98.4 | 100 | 100 | 100 | 100 |
| 127 | 83.8 | 83.8 | 83.8 | 83.8 | 83.8 | 83.8 |
| 2_127 | 99.5 | 98.4 | 100 | 100 | 100 | 100 |
| 1_127 | 100 | 100 | 100 | 100 | 100 | 100 |
| 237_127 | 98.5 | 95.2 | 100 | 98 | 93.5 | 100 |
| 4_127 | 99 | 96.8 | 100 | 98 | 93.5 | 100 |
| 3_127 | 100 | 100 | 100 | 99 | 96.8 | 100 |
| 145 | 91.9 | 91.9 | 91.9 | 91.9 | 91.9 | 91.9 |
| 2_145 | 100 | 100 | 100 | 100 | 100 | 100 |
| 1_145 | 99.5 | 98.4 | 100 | 100 | 100 | 100 |
| 237_145 | 100 | 100 | 100 | 99 | 96.8 | 100 |
| 4_145 | 99.5 | 98.4 | 100 | 100 | 100 | 100 |
| 3_145 | 100 | 100 | 100 | 100 | 100 | 100 |
| 16 | 98.5 | 98.5 | 98.5 | 98.5 | 98.5 | 98.5 |
| 2_16 | 100 | 100 | 100 | 100 | 100 | 100 |
| 1_16 | 99.5 | 98.4 | 100 | 100 | 100 | 100 |
| 237_16 | 100 | 100 | 100 | 100 | 100 | 100 |
| 4_16 | 100 | 100 | 100 | 99 | 96.8 | 100 |
| 3_16 | 99.5 | 98.4 | 100 | 99 | 96.8 | 100 |
| 11 | 99.5 | 99.5 | 99.5 | 99.5 | 99.5 | 99.5 |
| 2_11 | 100 | 100 | 100 | 100 | 100 | 100 |
| 1_11 | 99.5 | 98.4 | 100 | 100 | 100 | 100 |
| 237_11 | 100 | 100 | 100 | 100 | 100 | 100 |
| 4_11 | 100 | 100 | 100 | 100 | 100 | 100 |
| 3_11 | 100 | 100 | 100 | 100 | 100 | 100 |
| 186 | 87.3 | 87.3 | 87.3 | 87.3 | 87.3 | 87.3 |
| 2_186 | 99.5 | 98.4 | 100 | 100 | 100 | 100 |
| 1_186 | 99.5 | 98.4 | 100 | 100 | 100 | 100 |
| 237_186 | 98.5 | 95.2 | 100 | 96.9 | 90.3 | 100 |
| 4_186 | 99.5 | 98.4 | 100 | 99 | 96.8 | 100 |
| 3_186 | 100 | 100 | 100 | 100 | 100 | 100 |
| 50 | 98.5 | 98.5 | 98.5 | 98.5 | 98.5 | 98.5 |
| 2_50 | 100 | 100 | 100 | 100 | 100 | 100 |
| 1_50 | 99.5 | 98.4 | 100 | 100 | 100 | 100 |
| 237_50 | 100 | 100 | 100 | 100 | 100 | 100 |
| 4_50 | 100 | 100 | 100 | 100 | 100 | 100 |
| 3_50 | 100 | 100 | 100 | 100 | 100 | 100 |
| 69 | 90.9 | 90.9 | 90.9 | 90.9 | 90.9 | 90.9 |
| 2_69 | 99.5 | 98.4 | 100 | 100 | 100 | 100 |
| 1_69 | 99.5 | 98.4 | 100 | 100 | 100 | 100 |
| 237_69 | 98.5 | 95.2 | 100 | 98 | 93.5 | 100 |
| 4_69 | 99 | 96.8 | 100 | 98 | 93.5 | 100 |
| 3_69 | 100 | 100 | 100 | 100 | 100 | 100 |
| 33 | 81.2 | 81.2 | 81.2 | 81.2 | 81.2 | 81.2 |
| 2_33 | 100 | 100 | 100 | 100 | 100 | 100 |
| 1_33 | 99.5 | 98.4 | 100 | 100 | 100 | 100 |
| 237_33 | 100 | 100 | 100 | 100 | 100 | 100 |
| 4_33 | 100 | 100 | 100 | 100 | 100 | 100 |
| 3_33 | 99.5 | 98.4 | 100 | 100 | 100 | 100 |
| 247 | 89.3 | 89.3 | 89.3 | 89.3 | 89.3 | 89.3 |
| 2_247 | 100 | 100 | 100 | 100 | 100 | 100 |
| 1_247 | 100 | 100 | 100 | 100 | 100 | 100 |
| 237_247 | 98.5 | 95.2 | 100 | 98 | 93.5 | 100 |
| 4_247 | 99 | 96.8 | 100 | 99 | 96.8 | 100 |
| 3_247 | 100 | 100 | 100 | 100 | 100 | 100 |
| 36 | 93.9 | 93.9 | 93.9 | 93.9 | 93.9 | 93.9 |
| 2_36 | 99.5 | 98.4 | 100 | 100 | 100 | 100 |
| 1_36 | 99.5 | 98.4 | 100 | 100 | 100 | 100 |
| 237_36 | 100 | 100 | 100 | 99 | 96.8 | 100 |
| 4_36 | 99 | 96.8 | 100 | 98 | 93.5 | 100 |
| 3_36 | 100 | 100 | 100 | 100 | 100 | 100 |
| 218 | 89.3 | 89.3 | 89.3 | 89.3 | 89.3 | 89.3 |
| 2_218 | 99.5 | 98.4 | 100 | 100 | 100 | 100 |
| 1_218 | 99.5 | 98.4 | 100 | 100 | 100 | 100 |
| 237_218 | 99 | 96.8 | 100 | 100 | 100 | 100 |
| 4_218 | 99 | 96.8 | 100 | 99 | 96.8 | 100 |
| 3_218 | 100 | 100 | 100 | 100 | 100 | 100 |
| 43 | 82.7 | 82.7 | 82.7 | 82.7 | 82.7 | 82.7 |

TABLE 9-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 2_43 | 99.5 | 98.4 | 100 | 100 | 100 | 100 |
| 1_43 | 99.5 | 98.4 | 100 | 100 | 100 | 100 |
| 237_43 | 100 | 100 | 100 | 99 | 96.8 | 100 |
| 4_43 | 99.5 | 98.4 | 100 | 99 | 96.8 | 100 |
| 3_43 | 99.5 | 98.4 | 100 | 100 | 100 | 100 |
| 29 | 96.4 | 96.4 | 96.4 | 96.4 | 96.4 | 96.4 |
| 2_29 | 99.5 | 98.4 | 100 | 100 | 100 | 100 |
| 1_29 | 99.5 | 98.4 | 100 | 100 | 100 | 100 |
| 237_29 | 98.5 | 95.2 | 100 | 100 | 100 | 100 |
| 4_29 | 99.5 | 98.4 | 100 | 100 | 100 | 100 |
| 3_29 | 100 | 100 | 100 | 100 | 100 | 100 |
| 110 | 83.8 | 83.8 | 83.8 | 83.8 | 83.8 | 83.8 |
| 2_110 | 99.5 | 98.4 | 100 | 100 | 100 | 100 |
| 1_110 | 99.5 | 98.4 | 100 | 100 | 100 | 100 |
| 237_110 | 99 | 96.8 | 100 | 96.9 | 90.3 | 100 |
| 4_110 | 99 | 96.8 | 100 | 99 | 96.8 | 100 |
| 3_110 | 99.5 | 98.4 | 100 | 99 | 96.8 | 100 |
| 20 | 95.9 | 95.9 | 95.9 | 95.9 | 95.9 | 95.9 |
| 2_20 | 100 | 100 | 100 | 100 | 100 | 100 |
| 1_20 | 100 | 100 | 100 | 100 | 100 | 100 |
| 237_20 | 99 | 96.7 | 100 | 99 | 96.8 | 100 |
| 4_20 | 99.5 | 98.4 | 100 | 98 | 93.5 | 100 |
| 3_20 | 100 | 100 | 100 | 100 | 100 | 100 |
| 157 | 89.3 | 89.3 | 89.3 | 89.3 | 89.3 | 89.3 |
| 2_157 | 100 | 100 | 100 | 100 | 100 | 100 |
| 1_157 | 99.5 | 98.4 | 100 | 100 | 100 | 100 |
| 237_157 | 100 | 100 | 100 | 98 | 93.5 | 100 |
| 4_157 | 99 | 96.8 | 100 | 99 | 96.8 | 100 |
| 3_157 | 100 | 100 | 100 | 100 | 100 | 100 |
| 75 | 90.9 | 90.9 | 90.9 | 90.9 | 90.9 | 90.9 |
| 2_75 | 100 | 100 | 100 | 100 | 100 | 100 |
| 1_75 | 99.5 | 98.4 | 100 | 100 | 100 | 100 |
| 237_75 | 99.5 | 98.4 | 100 | 100 | 100 | 100 |
| 4_75 | 100 | 100 | 100 | 100 | 100 | 100 |
| 3_75 | 99.5 | 98.4 | 100 | 100 | 100 | 100 |
| 82 | 89.3 | 89.3 | 89.3 | 89.3 | 89.3 | 89.3 |
| 2_82 | 100 | 100 | 100 | 100 | 100 | 100 |
| 1_82 | 99.5 | 98.4 | 100 | 100 | 100 | 100 |
| 237_82 | 99 | 96.8 | 100 | 98 | 93.5 | 100 |
| 4_82 | 100 | 100 | 100 | 99 | 96.8 | 100 |
| 3_82 | 100 | 100 | 100 | 100 | 100 | 100 |
| 106 | 89.3 | 89.3 | 89.3 | 89.3 | 89.3 | 89.3 |
| 2_106 | 99.5 | 98.4 | 100 | 100 | 100 | 100 |
| 1_106 | 100 | 100 | 100 | 100 | 100 | 100 |
| 237_106 | 99 | 96.8 | 100 | 99 | 96.8 | 100 |
| 4_106 | 99.5 | 98.4 | 100 | 100 | 100 | 100 |
| 3_106 | 100 | 100 | 100 | 100 | 100 | 100 |
| 111 | 81.7 | 81.7 | 81.7 | 81.7 | 81.7 | 81.7 |
| 2_111 | 99.5 | 98.4 | 100 | 100 | 100 | 100 |
| 1_111 | 99.5 | 98.4 | 100 | 100 | 100 | 100 |
| 237_111 | 98.5 | 95.2 | 100 | 98 | 93.5 | 100 |
| 4_111 | 99 | 96.8 | 100 | 99 | 96.8 | 100 |
| 3_111 | 99.5 | 98.4 | 100 | 100 | 100 | 100 |
| 96 | 86.3 | 86.3 | 86.3 | 86.3 | 86.3 | 86.3 |
| 2_96 | 99.5 | 98.4 | 100 | 100 | 100 | 100 |
| 1_96 | 99.5 | 98.4 | 100 | 100 | 100 | 100 |
| 237_96 | 99 | 96.8 | 100 | 99 | 96.8 | 100 |
| 4_96 | 99 | 96.8 | 100 | 99 | 96.8 | 100 |
| 3_96 | 99.5 | 98.4 | 100 | 100 | 100 | 100 |
| 266 | 87.8 | 87.8 | 87.8 | 87.8 | 87.8 | 87.8 |
| 2_266 | 99.5 | 98.4 | 100 | 100 | 100 | 100 |
| 1_266 | 99.5 | 98.4 | 100 | 100 | 100 | 100 |
| 237_266 | 99 | 96.8 | 100 | 98 | 93.5 | 100 |
| 4_266 | 99.5 | 98.4 | 100 | 99 | 96.8 | 100 |
| 3_266 | 99.5 | 98.4 | 100 | 99 | 96.8 | 100 |
| 124 | 91.9 | 91.9 | 91.9 | 91.9 | 91.9 | 91.9 |
| 2_124 | 100 | 100 | 100 | 100 | 100 | 100 |
| 1_124 | 99.5 | 98.4 | 100 | 100 | 100 | 100 |
| 237_124 | 100 | 100 | 100 | 100 | 100 | 100 |
| 4_124 | 100 | 100 | 100 | 100 | 100 | 100 |
| 3_124 | 99.5 | 98.4 | 100 | 100 | 100 | 100 |
| 68 | 81.2 | 81.2 | 81.2 | 81.2 | 81.2 | 81.2 |
| 2_68 | 99.5 | 98.4 | 100 | 100 | 100 | 100 |
| 1_68 | 99.5 | 98.4 | 100 | 100 | 100 | 100 |
| 237_68 | 99 | 96.8 | 100 | 99 | 96.8 | 100 |

TABLE 9-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 4_68 | 99 | 96.8 | 100 | 99 | 96.8 | 100 |
| 3_68 | 99.5 | 98.4 | 100 | 100 | 100 | 100 |
| 71 | 86.8 | 86.8 | 86.8 | 86.8 | 86.8 | 86.8 |
| 2_71 | 100 | 100 | 100 | 100 | 100 | 100 |
| 1_71 | 99.5 | 98.4 | 100 | 100 | 100 | 100 |
| 237_71 | 99 | 96.8 | 100 | 96.9 | 90.3 | 100 |
| 4_71 | 99 | 96.8 | 100 | 99 | 96.8 | 100 |
| 3_71 | 100 | 100 | 100 | 99 | 96.8 | 100 |
| 35 | 90.4 | 90.4 | 90.4 | 90.4 | 90.4 | 90.4 |
| 2_35 | 99.5 | 98.4 | 100 | 100 | 100 | 100 |
| 1_35 | 99.5 | 98.4 | 100 | 100 | 100 | 100 |
| 237_35 | 99.5 | 98.4 | 100 | 100 | 100 | 100 |
| 4_35 | 99.5 | 98.4 | 100 | 100 | 100 | 100 |
| 3_35 | 99.5 | 98.4 | 100 | 100 | 100 | 100 |
| 173 | 82.2 | 82.2 | 82.2 | 82.2 | 82.2 | 82.2 |
| 2_173 | 99.5 | 98.4 | 100 | 100 | 100 | 100 |
| 1_173 | 99.5 | 98.4 | 100 | 100 | 100 | 100 |
| 237_173 | 98.5 | 95.2 | 100 | 98 | 93.5 | 100 |
| 4_173 | 99 | 96.8 | 100 | 98 | 93.5 | 100 |
| 3_173 | 99.5 | 98.4 | 100 | 100 | 100 | 100 |
| 5 | 94.4 | 94.4 | 94.4 | 94.4 | 94.4 | 94.4 |
| 2_5 | 100 | 100 | 100 | 100 | 100 | 100 |
| 1_5 | 99.5 | 98.4 | 100 | 100 | 100 | 100 |
| 237_5 | 100 | 100 | 100 | 100 | 100 | 100 |
| 4_5 | 100 | 100 | 100 | 100 | 100 | 100 |
| 3_5 | 99.5 | 98.4 | 100 | 100 | 100 | 100 |
| 851 | 81.7 | 81.7 | 81.7 | 81.7 | 81.7 | 81.7 |
| 2_851 | 99.5 | 98.4 | 100 | 100 | 100 | 100 |
| 1_851 | 99.5 | 98.4 | 100 | 100 | 100 | 100 |
| 237_851 | 99 | 96.8 | 100 | 98 | 93.5 | 100 |
| 4_851 | 99 | 96.8 | 100 | 99 | 96.8 | 100 |
| 3_851 | 99.5 | 98.4 | 100 | 100 | 100 | 100 |
| 852 | 85.8 | 85.8 | 85.8 | 85.8 | 85.8 | 85.8 |
| 2_852 | 100 | 100 | 100 | 100 | 100 | 100 |
| 1_852 | 99.5 | 98.4 | 100 | 100 | 100 | 100 |
| 237_852 | 99 | 96.8 | 100 | 98 | 93.5 | 100 |
| 4_852 | 99 | 96.8 | 100 | 99 | 96.8 | 100 |
| 3_852 | 100 | 100 | 100 | 100 | 100 | 100 |
| 30 | 93.4 | 93.4 | 93.4 | 93.4 | 93.4 | 93.4 |
| 2_30 | 100 | 100 | 100 | 100 | 100 | 100 |
| 1_30 | 99.5 | 98.4 | 100 | 100 | 100 | 100 |
| 237_30 | 99 | 96.8 | 100 | 100 | 100 | 100 |
| 4_30 | 99.5 | 98.4 | 100 | 99 | 96.8 | 100 |
| 3_30 | 99.5 | 98.4 | 100 | 100 | 100 | 100 |
| 93 | 88.8 | 88.8 | 88.8 | 88.8 | 88.8 | 88.8 |
| 2_93 | 99.5 | 98.4 | 100 | 100 | 100 | 100 |
| 1_93 | 99.5 | 98.4 | 100 | 100 | 100 | 100 |
| 237_93 | 99.5 | 98.4 | 100 | 100 | 100 | 100 |
| 4_93 | 100 | 100 | 100 | 100 | 100 | 100 |
| 3_93 | 99.5 | 98.4 | 100 | 100 | 100 | 100 |
| 27 | 98.5 | 98.5 | 98.5 | 98.5 | 98.5 | 98.5 |
| 2_27 | 100 | 100 | 100 | 100 | 100 | 100 |
| 1_27 | 99.5 | 98.4 | 100 | 100 | 100 | 100 |
| 237_27 | 100 | 100 | 100 | 100 | 100 | 100 |
| 4_27 | 99.5 | 98.4 | 100 | 99 | 96.8 | 100 |
| 27_208 | 99 | 98.4 | 99.3 | 98 | 96.8 | 98.5 |
| 853 | 79.2 | 79.2 | 79.2 | 79.2 | 79.2 | 79.2 |
| 2_853 | 99.5 | 98.4 | 100 | 100 | 100 | 100 |
| 1_853 | 99.5 | 98.4 | 100 | 100 | 100 | 100 |
| 237_853 | 98.5 | 95.2 | 100 | 98 | 93.5 | 100 |
| 4_853 | 99 | 96.8 | 100 | 99 | 96.8 | 100 |
| 3_853 | 99.5 | 98.4 | 100 | 100 | 100 | 100 |
| 238 | 97.5 | 97.5 | 97.5 | 97.5 | 97.5 | 97.5 |
| 2_238 | 100 | 100 | 100 | 100 | 100 | 100 |
| 1_238 | 100 | 100 | 100 | 100 | 100 | 100 |
| 237_238 | 99 | 96.8 | 100 | 99 | 96.8 | 100 |
| 4_238 | 99 | 96.8 | 100 | 99 | 96.8 | 100 |
| 3_238 | 100 | 100 | 100 | 100 | 100 | 100 |
| 130 | 80.7 | 80.7 | 80.7 | 80.7 | 80.7 | 80.7 |
| 2_130 | 100 | 100 | 100 | 100 | 100 | 100 |
| 1_130 | 99.5 | 98.4 | 100 | 100 | 100 | 100 |
| 237_130 | 99 | 96.8 | 100 | 99 | 96.8 | 100 |
| 4_130 | 99 | 96.8 | 100 | 99 | 96.8 | 100 |
| 3_130 | 99.5 | 98.4 | 100 | 100 | 100 | 100 |
| 177 | 81.7 | 81.7 | 81.7 | 81.7 | 81.7 | 81.7 |

TABLE 9-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 2_177 | 100 | 100 | 100 | 100 | 100 | 100 |
| 1_177 | 99.5 | 98.4 | 100 | 100 | 100 | 100 |
| 237_177 | 99 | 96.8 | 100 | 99 | 96.8 | 100 |
| 4_177 | 99.5 | 98.4 | 100 | 99 | 96.8 | 100 |
| 3_177 | 99.5 | 98.4 | 100 | 99 | 96.8 | 100 |
| 64 | 87.3 | 87.3 | 87.3 | 87.3 | 87.3 | 87.3 |
| 2_64 | 99.5 | 98.4 | 100 | 100 | 100 | 100 |
| 1_64 | 99.5 | 98.4 | 100 | 100 | 100 | 100 |
| 237_64 | 99.5 | 98.4 | 100 | 100 | 100 | 100 |
| 4_64 | 99.5 | 98.4 | 100 | 100 | 100 | 100 |
| 3_64 | 99.5 | 98.4 | 100 | 100 | 100 | 100 |
| 114 | 95.4 | 95.4 | 95.4 | 95.4 | 95.4 | 95.4 |
| 2_114 | 100 | 100 | 100 | 99 | 100 | 98.5 |
| 1_114 | 99.5 | 98.4 | 100 | 99 | 100 | 98.5 |
| 237_114 | 99.5 | 98.4 | 100 | 99 | 100 | 98.5 |
| 4_114 | 100 | 100 | 100 | 99 | 100 | 98.5 |
| 3_114 | 99.5 | 98.4 | 100 | 99 | 100 | 98.5 |
| 119 | 92.4 | 92.4 | 92.4 | 92.4 | 92.4 | 92.4 |
| 2_119 | 100 | 100 | 100 | 100 | 100 | 100 |
| 1_119 | 99.5 | 98.4 | 100 | 100 | 100 | 100 |
| 237_119 | 100 | 100 | 100 | 99 | 96.8 | 100 |
| 4_119 | 100 | 100 | 100 | 100 | 100 | 100 |
| 3_119 | 99.5 | 98.4 | 100 | 100 | 100 | 100 |
| 135 | 87.8 | 87.8 | 87.8 | 87.8 | 87.8 | 87.8 |
| 2_135 | 99.5 | 98.4 | 100 | 100 | 100 | 100 |
| 1_135 | 99.5 | 98.4 | 100 | 100 | 100 | 100 |
| 237_135 | 99.5 | 98.4 | 100 | 96.9 | 90.3 | 100 |
| 4_135 | 99.5 | 98.4 | 100 | 99 | 96.8 | 100 |
| 3_135 | 99.5 | 98.4 | 100 | 99 | 96.8 | 100 |
| 243 | 93.9 | 93.9 | 93.9 | 93.9 | 93.9 | 93.9 |
| 2_243 | 99.5 | 98.4 | 100 | 100 | 100 | 100 |
| 1_243 | 99.5 | 98.4 | 100 | 100 | 100 | 100 |
| 237_243 | 99.5 | 98.4 | 100 | 99 | 96.8 | 100 |
| 4_243 | 99.5 | 98.4 | 100 | 100 | 100 | 100 |
| 3_243 | 100 | 100 | 100 | 100 | 100 | 100 |
| 122 | 87.8 | 87.8 | 87.8 | 87.8 | 87.8 | 87.8 |
| 2_122 | 99.5 | 98.4 | 100 | 100 | 100 | 100 |
| 1_122 | 99.5 | 98.4 | 100 | 100 | 100 | 100 |
| 237_122 | 98.5 | 95.2 | 100 | 96.9 | 90.3 | 100 |
| 4_122 | 99 | 96.8 | 100 | 99 | 96.8 | 100 |
| 3_122 | 100 | 100 | 100 | 100 | 100 | 100 |
| 260 | 90.9 | 90.9 | 90.9 | 90.9 | 90.9 | 90.9 |
| 2_260 | 99.5 | 98.4 | 100 | 100 | 100 | 100 |
| 1_260 | 99.5 | 98.4 | 100 | 100 | 100 | 100 |
| 237_260 | 99.5 | 98.4 | 100 | 96.9 | 90.3 | 100 |
| 4_260 | 99.5 | 98.4 | 100 | 99 | 96.8 | 100 |
| 3_260 | 99.5 | 98.4 | 100 | 99 | 96.8 | 100 |
| 59 | 91.9 | 91.9 | 91.9 | 91.9 | 91.9 | 91.9 |
| 2_59 | 99.5 | 98.4 | 100 | 100 | 100 | 100 |
| 1_59 | 99.5 | 98.4 | 100 | 100 | 100 | 100 |
| 237_59 | 99.5 | 98.4 | 100 | 100 | 100 | 100 |
| 4_59 | 99 | 96.8 | 100 | 99 | 96.8 | 100 |
| 3_59 | 99.5 | 98.4 | 100 | 100 | 100 | 100 |
| 854 | 77.7 | 77.7 | 77.7 | 77.7 | 77.7 | 77.7 |
| 2_854 | 99.5 | 98.4 | 100 | 100 | 100 | 100 |
| 1_854 | 99.5 | 98.4 | 100 | 100 | 100 | 100 |
| 237_854 | 99.5 | 98.4 | 100 | 99 | 96.8 | 100 |
| 4_854 | 99 | 96.8 | 100 | 99 | 96.8 | 100 |
| 3_854 | 99.5 | 98.4 | 100 | 100 | 100 | 100 |
| 132 | 91.4 | 91.4 | 91.4 | 91.4 | 91.4 | 91.4 |
| 2_132 | 100 | 100 | 100 | 100 | 100 | 100 |
| 1_132 | 99.5 | 98.4 | 100 | 100 | 100 | 100 |
| 237_132 | 99.5 | 98.4 | 100 | 98 | 93.5 | 100 |
| 4_132 | 99.5 | 98.4 | 100 | 99 | 96.8 | 100 |
| 3_132 | 99.5 | 98.4 | 100 | 99 | 96.8 | 100 |
| 181 | 79.2 | 79.2 | 79.2 | 79.2 | 79.2 | 79.2 |
| 2_181 | 99.5 | 98.4 | 100 | 100 | 100 | 100 |
| 1_181 | 99.5 | 98.4 | 100 | 100 | 100 | 100 |
| 237181 | 99 | 96.8 | 100 | 99 | 96.8 | 100 |
| 4_181 | 99 | 96.8 | 100 | 98 | 93.5 | 100 |
| 3_181 | 99.5 | 98.4 | 100 | 100 | 100 | 100 |
| 79 | 92.4 | 92.4 | 92.4 | 92.4 | 92.4 | 92.4 |
| 2_79 | 100 | 100 | 100 | 100 | 100 | 100 |
| 1_79 | 99.5 | 98.4 | 100 | 100 | 100 | 100 |
| 237_79 | 99.5 | 98.4 | 100 | 98 | 93.5 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 4_79 | 99.5 | 98.4 | 100 | 99 | 96.8 | 100 |
| 3_79 | 99.5 | 98.4 | 100 | 100 | 100 | 100 |
| 133 | 79.7 | 79.7 | 79.7 | 79.7 | 79.7 | 79.7 |
| 2_133 | 99.5 | 98.4 | 100 | 100 | 100 | 100 |
| 1_133 | 99.5 | 98.4 | 100 | 100 | 100 | 100 |
| 237_133 | 98.5 | 95.2 | 100 | 99 | 96.8 | 100 |
| 4_133 | 99 | 96.8 | 100 | 99 | 96.8 | 100 |
| 3_133 | 99.5 | 98.4 | 100 | 100 | 100 | 100 |
| 41 | 91.4 | 91.4 | 91.4 | 91.4 | 91.4 | 91.4 |
| 2_41 | 99.5 | 98.4 | 100 | 100 | 100 | 100 |
| 1_41 | 99.5 | 98.4 | 100 | 100 | 100 | 100 |
| 237_41 | 99 | 96.8 | 100 | 99 | 96.8 | 100 |
| 4_41 | 99.5 | 98.4 | 100 | 99 | 96.8 | 100 |
| 3_41 | 99.5 | 98.4 | 100 | 100 | 100 | 100 |
| 139 | 88.3 | 88.3 | 88.3 | 88.3 | 88.3 | 88.3 |
| 2_139 | 100 | 100 | 100 | 100 | 100 | 100 |
| 1_139 | 99.5 | 98.4 | 100 | 100 | 100 | 100 |
| 237_139 | 100 | 100 | 100 | 98 | 93.5 | 100 |
| 4_139 | 100 | 100 | 100 | 99 | 96.8 | 100 |
| 3_139 | 99.5 | 98.4 | 100 | 100 | 100 | 100 |
| 118 | 87.8 | 87.8 | 87.8 | 87.8 | 87.8 | 87.8 |
| 2_118 | 99.5 | 98.4 | 100 | 100 | 100 | 100 |
| 1_118 | 99.5 | 98.4 | 100 | 100 | 100 | 100 |
| 237_118 | 99 | 96.8 | 100 | 100 | 100 | 100 |
| 4_118 | 99.5 | 98.4 | 100 | 100 | 100 | 100 |
| 3_118 | 99.5 | 98.4 | 100 | 100 | 100 | 100 |
| 86 | 85.3 | 85.3 | 85.3 | 85.3 | 85.3 | 85.3 |
| 2_86 | 99.5 | 98.4 | 100 | 100 | 100 | 100 |
| 1_86 | 99.5 | 98.4 | 100 | 100 | 100 | 100 |
| 237_86 | 99 | 96.8 | 100 | 100 | 100 | 100 |
| 4_86 | 99 | 96.8 | 100 | 100 | 100 | 100 |
| 3_86 | 99.5 | 98.4 | 100 | 99 | 96.8 | 100 |
| 60 | 84.8 | 84.8 | 84.8 | 84.8 | 84.8 | 84.8 |
| 2_60 | 99.5 | 98.4 | 100 | 100 | 100 | 100 |
| 1_60 | 99.5 | 98.4 | 100 | 100 | 100 | 100 |
| 237_60 | 99 | 96.8 | 100 | 99 | 96.8 | 100 |
| 4_60 | 99.5 | 98.4 | 100 | 99 | 96.8 | 100 |
| 3_60 | 99.5 | 98.4 | 100 | 100 | 100 | 100 |
| 116 | 80.2 | 80.2 | 80.2 | 80.2 | 80.2 | 80.2 |
| 2_116 | 100 | 100 | 100 | 100 | 100 | 100 |
| 1_116 | 99.5 | 98.4 | 100 | 100 | 100 | 100 |
| 237_116 | 99.5 | 98.4 | 100 | 100 | 100 | 100 |
| 4_116 | 99.5 | 98.4 | 100 | 99 | 96.8 | 100 |
| 3_116 | 99.5 | 98.4 | 100 | 100 | 100 | 100 |
| 160 | 80.2 | 80.2 | 80.2 | 80.2 | 80.2 | 80.2 |
| 2_160 | 99.5 | 98.4 | 100 | 100 | 100 | 100 |
| 1_160 | 99.5 | 98.4 | 100 | 100 | 100 | 100 |
| 237_160 | 99.5 | 98.4 | 100 | 98 | 93.5 | 100 |
| 4_160 | 99 | 96.8 | 100 | 99 | 96.8 | 100 |
| 3_160 | 99.5 | 98.4 | 100 | 100 | 100 | 100 |
| 38 | 79.2 | 79.2 | 79.2 | 79.2 | 79.2 | 79.2 |
| 2_38 | 99.5 | 98.4 | 100 | 100 | 100 | 100 |
| 1_38 | 99.5 | 98.4 | 100 | 100 | 100 | 100 |
| 237_38 | 98.5 | 95.2 | 100 | 100 | 100 | 100 |
| 4_38 | 99 | 96.8 | 100 | 99 | 96.8 | 100 |
| 3_38 | 99.5 | 98.4 | 100 | 99 | 96.8 | 100 |
| 99 | 86.2 | 86.2 | 86.2 | 86.2 | 86.2 | 86.2 |
| 2_99 | 99.5 | 98.4 | 100 | 100 | 100 | 100 |
| 1_99 | 99.5 | 98.4 | 100 | 100 | 100 | 100 |
| 237_99 | 99 | 96.7 | 100 | 99 | 96.8 | 100 |
| 4_99 | 99 | 96.7 | 100 | 98 | 93.5 | 100 |
| 3_99 | 99.5 | 98.4 | 100 | 100 | 100 | 100 |
| 104 | 86.3 | 86.3 | 86.3 | 86.3 | 86.3 | 86.3 |
| 2_104 | 99.5 | 98.4 | 100 | 100 | 100 | 100 |
| 1_104 | 100 | 100 | 100 | 100 | 100 | 100 |
| 237_104 | 98.5 | 95.2 | 100 | 98 | 93.5 | 100 |
| 4_104 | 99 | 96.8 | 100 | 99 | 96.8 | 100 |
| 3_104 | 100 | 100 | 100 | 100 | 100 | 100 |

201

Comparative Example 1

<Breast Cancer Discriminant Performance of an Existing Tumor Marker in Blood>

The concentrations of the existing tumor marker CEA in blood were measured in the training cohort and the validation cohort obtained in the preceding Reference Examples. When the concentrations of these tumor markers in blood are higher than the reference values described in Non-Patent Literature 3 above (CEA: 5 ng/mL), subjects are usually suspected of having cancer. Thus, whether or not the concentration of CEA in blood exceeded its reference value was confirmed for each sample, and the results were assessed for the ability of the tumor marker to detect cancer in breast cancer patients. The sensitivity of the existing marker in the training cohort and the validation cohort was calculated. The results are shown in Table 5. The sensitivity of CEA was as low as 11.3% in the training cohort and 19.4% in the validation cohort, demonstrating that the marker is not useful in the detection of breast cancer (Table 5).

On the other hand, as shown above in Tables 3 and 6 of Examples 1 and 2, it can be concluded that in all of the polynucleotides consisting of the nucleotide sequences represented by SEQ ID NOs: 1 to 251, combinations of 1 or 2 polynucleotides exhibiting sensitivity beyond the existing breast cancer markers are present, and thus such polynucleotides serve as excellent diagnosis markers.

As shown in these Examples and Comparative Example, the kit, etc., and the method of the present invention can detect breast cancer with higher sensitivity than the existing tumor marker and therefore permit early detection and treatment of breast cancer. As a result, improvement in the survival rate because of the reduced risk of recurrence, and breast conservation therapy as a therapeutic option can also be provided.

INDUSTRIAL APPLICABILITY

According to the present invention, breast cancer can be effectively detected by a simple and inexpensive method. This enables early detection, diagnosis and treatment of breast cancer. The method of the present invention can detect breast cancer with limited invasiveness using the blood of a patient and therefore allows breast cancer to be detected conveniently and rapidly. All publications, patents, and patent applications cited herein are incorporated herein by reference in their entirety.

The invention claimed is:

1. A method for detecting breast cancer in a human subject, comprising:
   measuring expression level of miR-6757-5p in a blood, serum or plasma sample from the subject,
   comparing the measured expression level of hsa-miR-6757-5p to a control expression level for a healthy subject;
   detecting an increased level of hsa-miR-6757-5p in the sample from the subject as compared to the control expression level from the sample from the healthy subject;
   wherein the increased level of hsa-miR-6757-5p indicates that the subject has breast cancer; and
   wherein the method further comprises treating the subject for the breast cancer or performing a diagnostic procedure on the subject with the breast cancer;
   wherein the treatment comprises surgery, radiotherapy, chemotherapy or a combination thereof; and
   wherein the diagnostic procedure comprises mammography, ultrasonography, CT, MRI, abdominal ultrasonography, bone scintigraphy, PET, pathological examination which involves analyzing a lesion tissue under a microscope, or a combination thereof.

2. The method according to claim 1, wherein the expression level of hsa-miR-6757-5p in the sample is measured by using a kit comprising a nucleic acid(s) that specifically binds to hsa-miR-6757-5p.

3. The method according to claim 2, wherein the kit further comprises at least one nucleic acid capable of specifically binding to at least one polynucleotide selected from the group consisting of other breast cancer markers: miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-885-3p, miR-6802-5p, miR-328-5p, miR-6787-5p, miR-8069, miR-6875-5p, miR-1246, miR-4734, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-5p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739, and/or miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p, miR-92a-3p, miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

4. The method according to claim 1, comprising performing the diagnostic procedure on the subject.

5. The method according to claim 1, wherein the expression level of hsa-miR-6757-5p in the sample is measured by using a device comprising a nucleic acid(s) that specifically binds to hsa-miR-6757-5p.

6. The method according to claim 5, wherein the device further comprises at least one nucleic acid capable of specifically binding to at least one polynucleotide selected from the group consisting of other breast cancer markers: miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-885-3p, miR-6802-5p, miR-328-5p, miR-6787-5p, miR-8069, miR-6875-5p, miR-1246, miR-4734, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739, and/or miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p, miR-92a-3p, miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

* * * * *